US012766198B2

(12) United States Patent
Getts et al.

(10) Patent No.: US 12,766,198 B2
(45) Date of Patent: Oct. 20, 2026

(54) METHODS AND COMPOSITIONS FOR GENOMIC INTEGRATION

(71) Applicant: CREATE Medicines, Inc., Cambridge, MA (US)

(72) Inventors: Daniel Getts, Medfield, MA (US); Yuxiao Wang, Belmont, MA (US); Namita Bisaria, Somerville, MA (US)

(73) Assignee: CREATE Medicines, Inc., Cambridge, MA (US)

( * ) Notice: Subject to any disclaimer, the term of this patent is extended or adjusted under 35 U.S.C. 154(b) by 1048 days.

(21) Appl. No.: 17/687,395

(22) Filed: Mar. 4, 2022

(65) Prior Publication Data

US 2022/0184230 A1 Jun. 16, 2022

Related U.S. Application Data

(63) Continuation of application No. PCT/US2020/049240, filed on Sep. 3, 2020.

(60) Provisional application No. 63/039,261, filed on Jun. 15, 2020, provisional application No. 62/908,800, filed on Oct. 1, 2019, provisional application No. 62/895,441, filed on Sep. 3, 2019.

(51) Int. Cl.

| | |
|---|---|
| ***A61K 48/00*** | (2006.01) |
| ***A61K 31/711*** | (2006.01) |
| ***A61K 31/713*** | (2006.01) |
| ***A61K 38/17*** | (2006.01) |
| ***A61K 38/45*** | (2006.01) |
| ***A61K 38/46*** | (2006.01) |
| ***A61K 39/395*** | (2006.01) |
| ***C07K 14/705*** | (2006.01) |
| ***C07K 14/725*** | (2006.01) |
| ***C07K 16/32*** | (2006.01) |
| ***C12N 9/12*** | (2006.01) |
| ***C12N 9/22*** | (2006.01) |
| ***C12N 15/11*** | (2006.01) |
| ***C12N 15/113*** | (2010.01) |
| ***C12N 15/85*** | (2006.01) |
| ***C12N 15/90*** | (2006.01) |

(52) U.S. Cl.

CPC .......... *A61K 48/005* (2013.01); *A61K 31/711* (2013.01); *A61K 31/713* (2013.01); *A61K 38/1774* (2013.01); *A61K 38/45* (2013.01); *A61K 38/465* (2013.01); *A61K 39/39558* (2013.01); *C07K 14/7051* (2013.01); *C07K 16/32* (2013.01); *C12N 9/1276* (2013.01); *C12N 9/22* (2013.01); *C12N 15/11* (2013.01); *C12N 15/113* (2013.01); *C12N 15/85* (2013.01); *C12N 15/90* (2013.01); *C12N 15/907* (2013.01); *C12Y 207/07049* (2013.01); *A61K 48/00* (2013.01); *C07K 2319/03* (2013.01); *C07K 2319/09* (2013.01); *C07K 2319/30* (2013.01); *C07K 2319/33* (2013.01); *C12N 2310/14* (2013.01); *C12N 2310/20* (2017.05); *C12N 2320/31* (2013.01); *C12N 2800/80* (2013.01); *C12N 2800/90* (2013.01); *C12N 2830/50* (2013.01); *C12N 2840/203* (2013.01)

(58) Field of Classification Search

CPC ........... C12Y 207/07049; C12N 15/90; C12N 2840/203; C12N 2320/31; C07K 2319/33

See application file for complete search history.

(56) References Cited

U.S. PATENT DOCUMENTS

| | | | |
|---|---|---|---|
| 4,470,461 | A | 9/1984 | Stapp |
| 4,522,811 | A | 6/1985 | Eppstein et al. |
| 5,122,464 | A | 6/1992 | Wilson et al. |
| 5,225,539 | A | 7/1993 | Winter |
| 5,571,894 | A | 11/1996 | Wels et al. |
| 5,580,859 | A | 12/1996 | Felgner et al. |
| 5,585,089 | A | 12/1996 | Queen et al. |
| 5,587,458 | A | 12/1996 | King et al. |
| 5,591,828 | A | 1/1997 | Bosslet et al. |
| 5,633,234 | A | 5/1997 | August et al. |
| 5,639,642 | A | 6/1997 | Kjeldsen et al. |
| 5,641,870 | A | 6/1997 | Rinderknecht et al. |
| 5,693,761 | A | 12/1997 | Queen et al. |
| 5,766,903 | A | 6/1998 | Sarnow et al. |
| 5,773,244 | A | 6/1998 | Ares, Jr. et al. |
| 5,776,910 | A | 7/1998 | Schreiber et al. |
| 5,869,046 | A | 2/1999 | Presta et al. |
| 6,150,160 | A | 11/2000 | Kazazian, Jr. et al. |
| 6,210,931 | B1 | 4/2001 | Feldstein et al. |
| 6,210,963 | B1 | 4/2001 | Haddada et al. |

(Continued)

FOREIGN PATENT DOCUMENTS

| | | |
|---|---|---|
| CA | 2850380 C | 8/2015 |
| CN | 1951499 A | 4/2007 |

(Continued)

OTHER PUBLICATIONS

Ade CM, Derbes RS, Wagstaff BJ, et al. Evaluating different DNA binding domains to modulate L1 ORF2p-driven site-specific retrotransposition events in human cells. Gene. Feb. 2018;642:188-198. DOI: 10.1016/j.gene.2017.11.033. PMID: 29154869; PMCID: PMC5734997. (Year: 2018).*

(Continued)

*Primary Examiner* — Jennifer Dunston
*Assistant Examiner* — Alexandra Rose Lippolis
(74) *Attorney, Agent, or Firm* — Wilson Sonsini Goodrich & Rosati

(57) ABSTRACT

Methods and composition for modulating a target genome and stable integration of a transgene of interest into the genome of a cell are disclosed.

16 Claims, 31 Drawing Sheets

Specification includes a Sequence Listing.

(56) References Cited

U.S. PATENT DOCUMENTS 6,248,516 B1 6/2001 Winter et al.
6,455,299 B1 9/2002 Steinman et al.
6,468,798 B1 10/2002 Debs et al.
6,602,709 B1 8/2003 Albert et al.
6,734,014 B1 5/2004 Hwu et al.
6,806,080 B2 10/2004 Kasahara et al.
6,936,468 B2 8/2005 Robbins et al.
7,833,789 B2 11/2010 Naldini et al.
7,926,300 B2 4/2011 Roberts et al.
8,198,020 B2 6/2012 Francois et al.
8,709,412 B2 4/2014 Jones et al.
8,932,860 B2 1/2015 Rozwadowski et al.
9,045,541 B2 6/2015 Eckelman et al.
9,149,519 B2 10/2015 Landau et al.
9,206,479 B2 12/2015 Maquat et al.
9,221,908 B2 12/2015 Frazier et al.
9,353,370 B2 5/2016 Carninci et al.
9,428,569 B2 8/2016 Spencer et al.
9,481,892 B2 11/2016 Schumann et al.
9,518,116 B2 12/2016 Frazier et al.
9,663,575 B2 5/2017 Eckelman et al.
9,745,368 B2 8/2017 Milone et al.
9,820,350 B2 11/2017 Pyshos et al.
9,845,345 B2 12/2017 Ring et al.
9,850,312 B2 12/2017 Agatsuma et al.
9,913,920 B2 3/2018 Movahedi et al.
10,034,900 B2 7/2018 Senju
10,081,680 B2 9/2018 Weiskopf et al.
10,106,609 B2 10/2018 Yang et al.
10,125,193 B2 11/2018 Cooper et al.
10,155,038 B2 12/2018 Rabinovich et al.
10,166,255 B2 1/2019 Moriarity et al.
10,172,880 B2 1/2019 Osborn et al.
10,174,095 B2 1/2019 Brogdon et al.
10,174,309 B2 1/2019 Grawunder
10,184,122 B2 1/2019 Grunenwald et al.
10,189,903 B2 1/2019 Jensen
10,214,591 B1 2/2019 Spadafora et al.
10,259,859 B2 4/2019 Pons et al.
10,259,873 B2 4/2019 Frazier et al.
10,299,335 B2 5/2019 Pyshos et al.
10,415,017 B2 9/2019 O'Neill
10,428,143 B2 10/2019 Krummel et al.
10,602,584 B2 3/2020 Pyshos et al.
10,617,749 B1 4/2020 Hanks et al.
10,774,125 B2 9/2020 Ring et al.
10,925,944 B2 2/2021 De Vries et al.
10,980,836 B1 4/2021 Getts et al.
11,013,764 B2 5/2021 Getts et al.
11,026,973 B2 6/2021 Getts et al.
11,034,749 B2 6/2021 Gill et al.
11,041,023 B2 6/2021 Vale et al.
11,517,589 B2 12/2022 Wagner et al.
11,572,557 B2 2/2023 Velema et al.
11,672,874 B2 6/2023 Getts et al.
12,319,925 B2 6/2025 Getts et al.
12,599,678 B2 4/2026 Getts et al.
2002/0103152 A1 8/2002 Kay et al.
2002/0132224 A1 9/2002 Poznansky et al.
2003/0121063 A1 6/2003 Kazazian, Jr. et al.
2003/0130496 A1 7/2003 Winter et al.
2004/0053873 A1 3/2004 Barman et al.
2005/0031628 A1 2/2005 George et al.
2006/0018889 A1 1/2006 Li et al.
2006/0183226 A1 8/2006 Fujiwara et al.
2006/0188891 A1 8/2006 Bickmore, Jr. et al.
2007/0037759 A1 2/2007 Deininger et al.
2008/0254027 A1 10/2008 Bernett et al.
2011/0045591 A1 2/2011 Schumann et al.
2011/0171729 A1 7/2011 Wang et al.
2011/0250203 A1 10/2011 Klitgaard et al.
2011/0287038 A1 11/2011 Slawin et al.
2011/0293603 A1 12/2011 Saraiva et al.
2012/0045389 A1 2/2012 Gassull Duro et al.
2013/0280285 A1 10/2013 Schonfeld et al.
2014/0037606 A1 2/2014 Amiel
2014/0134142 A1 5/2014 Smith et al.
2014/0140989 A1 5/2014 Eckelman et al.
2014/0141046 A1 5/2014 Karlsson-Parra et al.
2014/0161805 A1 6/2014 Jamieson et al.
2014/0242701 A1 8/2014 Shiku et al.
2015/0057161 A1 2/2015 Schultze et al.
2015/0274826 A1 10/2015 Frazier et al.
2016/0038541 A1 2/2016 Stripecke et al.
2016/0045551 A1 2/2016 Brentjens et al.
2016/0137733 A1 5/2016 Frazier et al.
2016/0145348 A1 5/2016 Stephan
2016/0250258 A1 9/2016 Delaney et al.
2016/0251435 A1 9/2016 Eckelman et al.
2017/0087185 A1 3/2017 Crane et al.
2017/0151281 A1 6/2017 Wagner et al.
2017/0151282 A1 6/2017 Discher et al.
2017/0166657 A1 6/2017 O'Neill et al.
2017/0204422 A1 7/2017 Nelson et al.
2017/0226183 A1 8/2017 Schiffer-Mannioui
2017/0233452 A1 8/2017 Mcivor et al.
2017/0246278 A1 8/2017 Vera Valdes et al.
2017/0275665 A1 9/2017 Silas et al.
2017/0283498 A1 10/2017 Frazier et al.
2017/0292118 A1 10/2017 Duchateau et al.
2017/0369890 A1 12/2017 Henriksen
2018/0000899 A1 1/2018 Francois et al.
2018/0030553 A1 2/2018 Tang et al.
2018/0057592 A1 3/2018 Frazier et al.
2018/0104308 A1 4/2018 Mamonkin et al.
2018/0105600 A1 4/2018 Pons et al.
2018/0133252 A9 5/2018 Wilson et al.
2018/0135032 A1 5/2018 Izsvak et al.
2018/0142019 A1 5/2018 Manning et al.
2018/0155405 A1 6/2018 Ring et al.
2018/0171021 A1 6/2018 Karlsson et al.
2018/0186855 A1 7/2018 Rosenthal
2018/0186878 A1 7/2018 Rosenthal
2018/0221503 A1 8/2018 Kadiyala et al.
2018/0244748 A1 8/2018 Gill et al.
2018/0250395 A1 9/2018 Pietsch et al.
2018/0265890 A1 9/2018 Qian et al.
2018/0319883 A1 11/2018 Weiskopf et al.
2018/0325953 A1 11/2018 Poznansky et al.
2018/0334653 A1 11/2018 O'Neill
2018/0355011 A1 12/2018 Lim et al.
2019/0008897 A1 1/2019 Scatena et al.
2019/0010219 A1 1/2019 Short
2019/0023761 A1 1/2019 Pule et al.
2019/0038671 A1 2/2019 Fan et al.
2019/0040453 A1 2/2019 Bibillo et al.
2019/0055297 A1 2/2019 Zhao et al.
2019/0062450 A1 2/2019 De Palma et al.
2019/0070277 A1 3/2019 O'Neill et al.
2019/0112373 A1 4/2019 Manning et al.
2019/0119379 A1 4/2019 Gottschalk et al.
2019/0119396 A1 4/2019 Liu et al.
2019/0144522 A1 5/2019 Bari et al.
2019/0144863 A1 5/2019 Lee et al.
2019/0169266 A1 6/2019 Pons et al.
2019/0169637 A1 6/2019 Hudecek et al.
2019/0169638 A1 6/2019 Izsvák et al.
2019/0185880 A1 6/2019 Shedlock et al.
2019/0233496 A1 8/2019 Rosenthal
2019/0240343 A1 8/2019 Ahmed et al.
2019/0248892 A1 8/2019 Frazier et al.
2019/0263928 A1 8/2019 Watanabe et al.
2019/0275150 A1 9/2019 Pincetic et al.
2019/0323037 A1 10/2019 Buerckstuemmer et al.
2019/0336615 A1 11/2019 Thompson et al.
2019/0345217 A1 11/2019 Ma et al.
2019/0381158 A1 12/2019 Gunn
2020/0101147 A1 4/2020 Zeng
2020/0109398 A1 4/2020 Rubens et al.
2020/0239592 A1 7/2020 Vale et al.
2020/0247870 A1 8/2020 Gill et al.
2020/0345773 A1 11/2020 Getts et al.
2020/0345774 A1 11/2020 Getts et al.
2020/0390072 A1 12/2020 Kotin et al.

(56) References Cited

U.S. PATENT DOCUMENTS

2021/0002377 A1 1/2021 Brogdon et al.
2021/0038702 A1 2/2021 De Vries et al.
2021/0046110 A1 2/2021 Gill et al.
2021/0095001 A1 4/2021 Gill et al.
2021/0222163 A1 7/2021 Wu et al.
2021/0252053 A1 8/2021 Wagner et al.
2021/0277140 A1 9/2021 Vale et al.
2021/0285009 A1 9/2021 Schaffer et al.
2021/0299172 A1 9/2021 Getts et al.
2021/0361703 A1 11/2021 Getts et al.
2022/0000917 A1 1/2022 Klichinsky et al.
2022/0000918 A1 1/2022 Klichinsky et al.
2022/0001021 A1 1/2022 Uhl et al.
2022/0001031 A1 1/2022 Getts et al.
2022/0002375 A1 1/2022 Gill et al.
2022/0002376 A1 1/2022 Gill et al.
2022/0002377 A1 1/2022 Gill et al.
2022/0002675 A1 1/2022 Klichinsky et al.
2022/0033465 A1 2/2022 Gill et al.
2022/0033466 A1 2/2022 Gill et al.
2022/0033467 A1 2/2022 Gill et al.
2022/0033468 A1 2/2022 Gill et al.
2022/0041688 A1 2/2022 Gill et al.
2022/0073639 A1 3/2022 Ruella et al.
2022/0098273 A1 3/2022 Corey
2022/0118010 A1 4/2022 Wagner et al.
2022/0145293 A1 5/2022 Abudayyeh et al.
2022/0152199 A1 5/2022 Getts et al.
2022/0154224 A1 5/2022 Abudayyeh et al.
2022/0175830 A1 6/2022 Wagner et al.
2022/0175831 A1 6/2022 Wagner et al.
2022/0202856 A1 6/2022 Wagner et al.
2022/0233586 A1 7/2022 Wagner et al.
2022/0241428 A1 8/2022 Getts et al.
2022/0364110 A1 11/2022 Getts et al.
2022/0378824 A1 12/2022 Getts et al.
2022/0411817 A1 12/2022 Getts et al.
2023/0046472 A1 2/2023 Getts et al.
2023/0141052 A1 5/2023 Getts et al.
2023/0277659 A1 9/2023 Getts et al.
2023/0364265 A1 11/2023 Getts et al.
2023/0364266 A1 11/2023 Getts et al.
2024/0327482 A1 10/2024 Getts et al.
2025/0250584 A1 8/2025 Getts et al.

FOREIGN PATENT DOCUMENTS

EP 0404097 A2 12/1990
EP 0338841 B1 3/1995
EP 2205750 B1 3/2012
EP 2626415 A2 8/2013
EP 2953643 A1 12/2015
EP 2242512 B1 4/2016
EP 3197495 A1 8/2017
EP 3328402 A1 6/2018
EP 3350335 A1 7/2018
EP 2956343 B1 12/2018
EP 3414333 A1 12/2018
EP 3504244 A1 7/2019
EP 3519441 A1 8/2019
EP 3574018 A2 12/2019
EP 4025686 A2 7/2022
EP 4337268 A1 3/2024
GB 2572005 A 9/2019
JP 2015513916 A 5/2015
JP 2022546592 A 11/2022
WO WO-9201813 A1 2/1992
WO WO-9301161 A1 1/1993
WO WO-9425591 A1 11/1994
WO WO-9505835 A1 3/1995
WO WO-1995005835 A1 3/1995
WO WO-02077029 A2 10/2002
WO WO-2004050855 A2 6/2004
WO WO-2004072290 A1 8/2004
WO WO-2006069812 A2 7/2006
WO WO-2007113572 A1 10/2007
WO WO-2008011599 A2 1/2008
WO WO-2009056321 A1 5/2009
WO WO-2011028554 A1 3/2011
WO WO-2012005763 A1 1/2012
WO WO-2012045389 A1 4/2012
WO WO-2012170930 A1 12/2012
WO WO-2013123088 A1 8/2013
WO WO-2013151736 A2 10/2013
WO WO-2013185552 A1 12/2013
WO WO-2014055668 A1 4/2014
WO WO-2014123580 A1 8/2014
WO WO-2014153114 A1 9/2014
WO WO-2016030501 A1 3/2016
WO WO-2016033331 A1 3/2016
WO WO-2016040441 A1 3/2016
WO WO-2016049641 A1 3/2016
WO WO-2016070136 A1 5/2016
WO WO-2016126213 A1 8/2016
WO WO-2016126608 A1 8/2016
WO WO-2016138491 A1 9/2016
WO WO-2016149254 A1 9/2016
WO WO-2016172606 A1 10/2016
WO WO-2016205749 A1 12/2016
WO WO-2017019848 A1 2/2017
WO WO-2017025944 A2 2/2017
WO WO-2017044487 A1 3/2017
WO WO-2017050884 A1 3/2017
WO WO-2017136633 A1 8/2017
WO WO-2017172981 A2 10/2017
WO WO-2017219027 A1 12/2017
WO WO-2017219934 A1 12/2017
WO WO-2018038684 A1 3/2018
WO WO-2018064076 A1 4/2018
WO WO-2018073394 A1 4/2018
WO WO-2018083126 A1 5/2018
WO WO-2018107129 A1 6/2018
WO WO-2018140831 A3 8/2018
WO WO-2018169948 A1 9/2018
WO WO-2018170340 A1 9/2018
WO WO-2018231871 A1 12/2018
WO WO-2019005641 A1 1/2019
WO WO-2019010551 A1 1/2019
WO WO-2019020089 A1 1/2019
WO WO-2019020090 A1 1/2019
WO WO-2019023164 A1 1/2019
WO WO-2019032624 A1 2/2019
WO WO-2019050948 A1 3/2019
WO WO-2019051424 A2 3/2019
WO WO-2019055946 A1 3/2019
WO WO-2019067328 A1 4/2019
WO WO-2019070704 A1 4/2019
WO WO-2019070843 A1 4/2019
WO WO-2019079215 A1 4/2019
WO WO-2019086512 A1 5/2019
WO WO-2019090175 A1 5/2019
WO WO-2019129146 A1 7/2019
WO WO-2019191332 A1 10/2019
WO WO-2019191334 A1 10/2019
WO WO-2019191340 A1 10/2019
WO WO-2019201995 A1 10/2019
WO WO-2020006049 A1 1/2020
WO WO-2020047124 A1 3/2020
WO WO-2020095044 A1 5/2020
WO WO-2020097193 A1 5/2020
WO WO-2020131662 A1 6/2020
WO WO-2020131862 A1 6/2020
WO WO-2020150534 A9 8/2020
WO WO-2020191234 A1 9/2020
WO WO-2020223550 A1 11/2020
WO WO-2020252208 A2 12/2020
WO WO-2020257727 A1 12/2020
WO WO-2021016075 A1 1/2021
WO WO-2021046243 A2 3/2021
WO WO-2021102042 A1 5/2021
WO WO-2021119538 A1 6/2021
WO WO-2021178709 A1 9/2021
WO WO-2021178717 A2 9/2021
WO WO-2021178720 A2 9/2021

(56) References Cited

FOREIGN PATENT DOCUMENTS

| | | | |
|---|---|---|---|
| WO | WO-2021178898 | A1 | 9/2021 |
| WO | WO-2021263152 | A1 | 12/2021 |
| WO | WO-2022036265 | A1 | 2/2022 |
| WO | WO-2022067033 | A1 | 3/2022 |
| WO | WO-2022087235 | A1 | 4/2022 |
| WO | WO-2022241029 | A1 | 11/2022 |
| WO | WO-2025128722 | A2 | 6/2025 |

OTHER PUBLICATIONS

Manoj, F., Tai, L.W., Wang, K.S.M. et al. Targeted insertion of large genetic payloads using cas directed LINE-1 reverse transcriptase. Sci Rep 11, 23625 (2021). https://doi.org/10.1038/s41598-021-03130-0 (Year: 2021).*

Wang et al. CRISPR-Enabled Autonomous Transposable Element (CREATE) for RNA-based gene editing and delivery. EMBO Rep. Feb. 2025;26(4):1062-1083. doi: 10.1038/s44319-024-00364-7. Epub Jan. 9, 2025. PMID: 39789389; PMCID: PMC11850887. (Year: 2025).*

1-(3,4-dichlorophenyl)-3-(4-methoxyphenyl)-4-(4-morpholinyl)-1H-pyrrole-2,5-dione (CAS 1417162) 1 page, Retrieved URL https://www.caymanchem.com/product/18397/ri-2.

6-hydroxyDL-dopa (CAS 21373-30-8). 3 Pages. Retrived URL: https://www.rndsystems.com/products/6-hydroxy-dl-dopa_5740.

B02 (Cas 1290541-46-6). 4 Pages. Retrived URL: https://www.rndsystems.com/products/b02_6392.

Benzamide for synthesis. CAS No. 55-21-0, EC No. 200-227-7. 3 Pages. Retrived URL: https://www.merckmillipore.com/IN/en/product/Benzamide,MDA_CHEM-802191.

Camptothecin (CPT) (CAS 7689-03-4). 8 Pages. Retrived URL: https://www.tcichemicals.com/IN/en/p/C1495.

DIDS (CAS 67483-13-0). 4 Pages. Retrived URL: https://www.tocris.com/products/dids_4523.

Final Office Action issued in counterpart U.S. Appl. No. 17/499,232 dated Dec. 8, 2022.

Final Office Action issued in counterpart U.S. Appl. No. 17/499,232 dated Jul. 7, 2022.

GenBank Accession No. AAC51261. Version No. AAC51261.1. Putative p150 [*Homo sapiens*]. 2 pages. Retrieved from URL: https://www.ncbi.nlm.nih.gov/protein/AAC51261.

GenBank Accession No. AAC51262. Version No. AAC51262.1. p40 [*Homo sapiens*]. 2 pages. Retrieved from URL: https://www.ncbi.nlm.nih.gov/protein/AAC51262.

GenBank Accession No. AAC51263. Version No. AAC51263.1. Putative p150 [*Homo sapiens*]. 2 pages. Retrieved from URL: https://www.ncbi.nlm.nih.gov/protein/AAC51263.

GenBank Accession No. AAC51264. Version No. AAC51264.1. Putative p150 [*Homo sapiens*]. 2 pages. Retrieved from URL: https://www.ncbi.nlm.nih.gov/protein/AAC51264.

GenBank Accession No. AAC51265. Version No. AAC51265.1. p40 [*Homo sapiens*]. 2 pages. Retrieved from URL: https://www.ncbi.nlm.nih.gov/protein/AAC51265.

GenBank Accession No. AAC51266. Version No. AAC51266.1. p40 [*Homo sapiens*]. 2 pages. Retrieved from URL: https://www.ncbi.nlm.nih.gov/protein/AAC51266.

GenBank Accession No. AAC51267. Version No. AAC51267.1. Putative p150 [*Homo sapiens*]. 2 pages. Retrieved from URL: https://www.ncbi.nlm.nih.gov/protein/AAC51267.

GenBank Accession No. AAC51268. Version No. AAC51268.1. p40 [*Homo sapiens*]. 2 pages. Retrieved from URL: https://www.ncbi.nlm.nih.gov/protein/AAC51268.

GenBank Accession No. AAC51269. Version No. AAC51269.1. Putative p150 [*Homo sapiens*]. 2 pages. Retrieved from URL: https://www.ncbi.nlm.nih.gov/protein/AAC51269.

GenBank Accession No. AAC51270. Version No. AAC51270.1. p40 [*Homo sapiens*]. 2 pages. Retrieved from URL: https://www.ncbi.nlm.nih.gov/protein/AAC51270.

GenBank Accession No. AAC51271. Version No. AAC51271.1. Putative p150 [*Homo sapiens*]. 2 page. Retrieved from URL: https://www.ncbi.nlm.nih.gov/protein/AAC51271.

GenBank Accession No. AAC51272. Version No. AAC51272.1. p40 [*Homo sapiens*]. 1 page. Retrieved from URL: https://www.ncbi.nlm.nih.gov/protein/AAC51272.

GenBank Accession No. AAC51273. Version No. AAC51273.1. Putative p150 [*Homo sapiens*]. 2 page. Retrieved from URL: https://www.ncbi.nlm.nih.gov/protein/AAC51273.

GenBank Accession No. AAC51274. Version No. AAC51274.1. p40 [*Homo sapiens*]. 2 page. Retrieved from URL: https://www.ncbi.nlm.nih.gov/protein/AAC51274.

GenBank Accession No. AAC51275. Version No. AAC51275.1. p40 [*Homo sapiens*]. 1 page. Retrieved from URL: https://www.ncbi.nlm.nih.gov/protein/AAC51275.

GenBank Accession No. AAC51276. Version No. AAC51276.1. Putative p150 [*Homo sapiens*]. 2 page. Retrieved from URL: https://www.ncbi.nlm.nih.gov/protein/AAC51276.

GenBank Accession No. AAC51277. Version No. AAC51277.1. p40 [*Homo sapiens*]. 2 page. Retrieved from URL: https://www.ncbi.nlm.nih.gov/protein/AAC51277.

GenBank Accession No. AAC51278. Version No. AAC51278.1. p40 [*Homo sapiens*]. 2 page. Retrieved from URL: https://www.ncbi.nlm.nih.gov/protein/AAC51278.

GenBank Accession No. AAC51279. Version No. AAC51279.1. Putative p150 [*Homo sapiens*]. 2 page. Retrieved from URL: https://www.ncbi.nlm.nih.gov/protein/AAC51279.

Irinotecan (CAS 100286-90-6). 7 Pages. Retrived URL: https://www.sigmaaldrich.com/IN/en/product/sigma/i1406.

ML216 (Cas 1430213-30-1). 2 Pages. Retrived URL: https://www.scbt.com/p/ml-216-1430213-30-1.

Niraparib (MK-827 Tesaro) CAS 1038915-60-4). 2 Pages. Retrived URL: https://www.bldpharm.com/products/1038915-60-4.html.

Non-Final Office Action issued in counterpart U.S. Appl. No. 17/499,232 dated May 4. 2022.

Non-Final Office Action issued in counterpart U.S. Appl. No. 17/499,232 dated Sep. 26. 2022.

Non-Final Office Action issued in counterpart U.S. Appl. No. 17/855,230 dated Oct. 26, 2022.

Non-Final Office Action issued in counterpart U.S. Appl. No. 17/855,423 dated Nov. 7, 2022.

NSC 19630 (CAS 72835-26-8). 2 Pages. Retrived URL: https://www.merckmillipore.com/IN/en/product/WRN-Helicase-Inhibitor-NSC-19630-CAS-72835-26-8-Calbiochem,EMD_BIO-681647.

NSC 617145 (CAS 203115-63-3). 3 Pages. Retrived URL: https://www.rndsystems.com/products/nsc-617145_5340.

Olaparib (Lynparza) (CAS 763113-22-0). 54 Pages. Retrived URL: https://pubchem.ncbi.nlm.nih.gov/compound/Olaparib.

PCT/US2022/028831 International Search Report and Written Opinion dated Sep. 2, 2022.

PF-01367338 Pfizer. 3 Pages. Retrived URL: https://www.pfizer.com/news/press-release/press-release-detail/clovis-oncology-inc-receives-license-worldwide-development.

RI-1 (Cas 415713-60-9). 3 Pages. Retrived URL: https://www.rndsystems.com/products/ri-1_6168.

Sambrook, Joseph et al. Molecular Cloning: A Laboratory Manual, 2nd Edition. Cold Spring Harbor Laboratory Press : pp. 1-30 (1989).

Streptonigrin (SN) (CAS 3930-19-6). 2 Pages. Retrived URL: https://medkoo.com/products/15240.

Topotecan (Hycamtin® GlaxoSmithKline) (CAS 123948-87-8). 2 Pages. Retrived URL: https://www.scbt.com/p/topotecan-123948-87-8.

U.S. Appl. No. 18/313,087 Office Action dated Jun. 27, 2024.

U.S. Appl. No. 18/313,126 Office Action dated May 31, 2024.

U.S. Appl. No. 18/157,052 Office Action dated May 15, 2024.

U.S. Appl. No. 18/313,087 Office Action dated Feb. 12, 2024.

U.S. Appl. No. 18/313,126 Office Action dated Feb. 1, 2024.

Veliparib (ABT-888 Abbvie) (CAS 912444-00-9). 4 Pages. Retrived URL: https://www.selleckchem.com/products/ABT-888.html.

www.kazusa.orjp/codon.

Christian Cm et al., Involvement of Conserved Amino Acids in the C-Terminal Region of LINE-1 ORF2p in Retrotransposition. Genetics. Mar. 2017;205(3):1139-1149. Epub Jan. 18, 2017.

(56) References Cited

OTHER PUBLICATIONS

Khazina E and Weichenrieder O. Human LINE-1 retrotransposition requires a metastable coiled coil and a positively charged N-terminus in L1ORF1p. eLIFE. Mar. 22, 2018;7:e34960.
Kines KJ. et al., The endonuclease domain of the LINE-1 ORF2 protein can tolerate multiple mutations. Mob DNA. Apr. 19, 2016;7:8.
Chen, Peter J. et al.: Enhanced prime editing systems by manipulating cellular determinants of editing outcomes. Cell 184:5635-565 (2021). https://doi.org/10.1016/j.cell.2021.09.018.
Goodwin, Timothy J.D. et al.: A yeast model for target-primed (non-LTR) retro transposition. BMC Genomics 8(1):263 (2007). DOI:10.1186/1471-2164-8-263.
Jiang, Kaiyi et al.: Programmable RNA-guided DNA endonucleases are widespread in eukaryotes and their viruses. Science Advances 9(eadk0171):1-14 (2023). https://www.science.org/doi/pdf/10.1126/sciadv.adk0171.
Kaur, Davneet et al.: IS200/IS605 Family-Associated TnpB Increases Transposon Activity and Retention. doi: https://doi.org/10.1101/2022.10.12.511977.
Kim, Sun Chang et al.: Modifications of mRNA vaccine structural elements for improving mRNA stability and translation efficiency. Molecular & Cellular Toxicology 18:1-8 (2022). https://doi.org/10.1007/s13273-021-00171-4.
Kuroki-Kami, Azusa et al.: Targeted gene knockin in zebrafish using the 28S rDNA-specific non-LTR retrotransposon R2Ol. Mobile DNA 10:23 (2019).
Li, Xiaoyi et al.: The MOV10 Helicase Inhibits LINE-1 Mobility. Journal of Biological Chemistry 288(29):21148-21160 (2013).
Nigumann, Pilvi et al.: Many human genes are transcribed from the antisense promoter of L1 retrotransposon. Genomics 79(5):628-34 (2002). doi: 10.1006/geno.2002.6758 (Abstract).
Pavani, Giulia et al.: Targeted Gene Delivery: Where to Land. Frontier in Genome Editing 2:609650 (2021). doi: 10.3389/fgeed.2020.609650.
U.S. Appl. No. 18/313,087 Office Action dated Dec. 23, 2024.
U.S. Appl. No. 18/313,126 Office Action dated Dec. 17, 2024.
Wang; Yuxiao et al.: CRISPR-Enabled Autonomous Transposable Element (CREATE) for RNA-based gene editing and delivery. Cold Spring Harbor Laboratory May 4, 2024. bioRxiv preprint doi: https://doi.org/10.1101/2024.01.29.577809.
Wilkinson, Max E. et al.: Structure of the R2 non-LTR retrotransposon initiating target-primed reverse transcription. Science 380(6642):301-308 (2023). DOI: 10.1126/science.adg7883.
Xiao, Qingquan et al.: Engineered IscB-wRNA system with expanded target range for base editing. Nature Chemical Biology 21:100-108 (2025). https://www.nature.com/articles/s41589-024-01706-1.
Xie, Kabin et al.: Boosting CRISPR/Cas9 multiplex editing capability with the endogenous tRNA-processing system. PNAS 112(11):3570-3575 (2015). https://www.pnas.org/doi/10.1073/pnas.1420294112.
Yin, Shuming et al.: Engineering of efficiency-enhanced Cas9 and base editors with improved gene therapy efficacies. Mol. Ther. 31(3):744-759 (2022). doi: 10.1016/j.ymthe.2022.11.014.
Zhao, Zhihan et al.: Prime editing: advances and therapeutic applications. Trends in Biotechnology 41(8):1000-1012 https://www.cell.com/trends/biotechnology/pdf/S0167-7799(23)00085-9.
Meyer, Thomas J. et al. Heads or tails: L1 insertion-associated 5' homopolymeric sequences. Mob DNA 1(1):7 (2010).
U.S. Appl. No. 18/157,052 Office Action dated Sep. 5, 2024.
Ade et al.: Evaluating different DNA binding domains to modulate L1 ORF2p-driven site-specific retrotransposition events in human cells. Gene. (2018); 642:188-198. Epub (2018).
Ahl et al.: Retrotransposition and Crystal Structure of an Alu RNP in the Ribosome-Stalling Conformation. Mol Cell. 60(5):715-727 doi:10.1016/j.molcel.2015.10.003 (2015).
Ali et al.: Induction of neoantigen-reactive T cells from healthy donors. Nature Protocols (2019).
Altschul et al.: Basic Local Alignment Search Tool. J Mol Biol 215(3):403-410 (1990).
Alvey el al.: SIRPA-Inhibited, Marrow-Derived macrophages engorge, accumulate, and differentiate in Antibody-Targeted regression of solid tumors. Current Biology 27:2065-2077 (2017).
Alvey et al. Engineering macrophages to eat Cancer: from “marker of self” CD47 and phagocytosis to differentiation. Journal of Leukocyte Biology 102:31-40 (2017).
Ancuta et al.: (BMC Genomics 10:403, pp. 1-19 (2009 )).
Andreesen et al.: Adoptive transfer of tumor cytotoxic macrophages generated in vitro from circulating blood monocytes: a new approach to Cancer immunotherapy. Cancer Research 50:7450-7456 (1990).
Andreu el al.: Primary macrophages and J774 cells respond differently to infection with *Mycobacterium tuberculosis*. Scientific Reports 7:42225 (2017).
Auffray et al.: Blood monocytes: development, heterogeneity, and relationship with dendritic cells, Annual Rev. Immunol. 27:669-92 (2009).
Batista et al.: B cells acquire antigen from target cells after synapse formation. Nature 411:489-494 (2001).
Baxter et al.: Engineering domain fusion chimeras from I-OnuI family LAGLIDADG homing endonucleases.Nucleic Acids Res. 40(16):7985-8000 doi:10.1093/nar/gks502 (2012).
Beck et al.: LINE-1 Elements in Structural Variation and Disease. Annual Review of Genomics and Human Genetics vol. 12:187-215 (Volume publication date Sep. 2011). https://doi.org/10.1146/annurev-genom-082509-141802.
Beningo et al.: Fc-receptor-mediated phagocytosis is regulated by mechanical properties of the target. Journal of Cell Science 115:849-856 (2002).
Benton et al.: Screening lambdagt recombinant clones by hybridization to single plaques in situ. Science. 196(4286):80-182 (1977).
Berger et al.: Efficient Elutriation of monocytes within a closed system (Elutra™). Journal of Immunological Methods 298:61-72 (2005).
Bhattacharjee et al.: Monocytes isolated by positive and negative magnetic sorting techniques show different molecular characteristics and immunophenotypic behaviour. F100Research p. 1-13 (2018).
Biglari et al.: Human monocytes expressing a CEA-specific chimeric CD64 receptor specifically target CEA-expressing tumour cells in vitro and in vivo. Gene Therapy 13, 602-610 (2006).
Blumenthal et al.: Development and Characterization of Chimeric Antigen Receptor Monocytes (CAR Mono), a Novel Cell Therapy Platform for Solid Tumor Immunotherapy. Poster Presentation. Society for Immunotherapy of Cancer (SITC) Meeting, Washington, DC, United States (2021). https://secureservercdn.net/45.40.149.113/74d.fcf.myftpupload.com/wp-content/uploads/2021/11/Poster-104-Daniel-Blumenthal-Carisma-Therapeutics.pdf.
Blumenthal et al.: Pre-clinical development of CAR Monocytes (CAR Mono) for solid tumor immunotherapy. Poster Presentation. The American Association for Cancer Research (AACR) Annual Meeting, New Orleans, LA, United States (2022) https://secureservercdn.net/45.40.149.113/74d.fcf.myftpupload.com/wp-content/uploads/2022/07/Poster-5000-Daniel-Blumenthal-Carisma-Therapeutics.pdf.
Bournazos et al.: The Role and Function of Fcγ Receptors on Myeloid Cells. Microbiol Spectr 4(6) (2016).
Brooks et al.: Binding of cytoplasmic proteins to the CD19 intracellular domain is high affinity, competitive, and multimeric. The Journal of Immunology 172:7556-7564 (2004).
Bu el al.: Analysis of the interaction of ZAP-70 and syk protein-tyrosine kinases with the T-cell antigen receptor by plasmon resonance. PNAS 92:5106-5110 (1995).
Bucheton et al.: The Molecular basis of I-R Hybrid Dysgenesis in *Drosophila melanogaster*: Identification, Cloning, and Properties of the I Factor. Cell 38:153-163 (1984).
Burgueño-Bucio E. et al.: The multiple faces of CD5. J Leukoc Biol. 105(5):891-904. Epub (2019).
Calderwood, David: Integrin Activation. Journal of Cell Science 117:657-666 (2004).
Callahan et al.: Polymerization and nucleic acid-binding properties of human L1 ORF1 protein. Nucleic Acids Research 40(2):813-827 (2012).
Carisma Therapeutics. “Carisma Therapeutics Corporate Overview.” Nov. 2018.

(56) References Cited

OTHER PUBLICATIONS

Cebrian-Serrano et al.: CRISPR-Cas orthologues and variants: optimizing the repertoire, specificity and delivery of genome engineering tools. Mammalian Genome 28:247-261 (2017).
Chadwick et al.: Safety of a single aerosol administration of escalating doses of the cationic lipid GL-67/DOPE/EMPE-PEG 5000 formulation to the lungs of normal volunteers. Gene Therapy 4:937-942 (1997).
Chao et al.: Anti-CD47 antibody synergizes with rituximab to promote phagocytosis and eradicate non-Hodgkin lymphoma. Cell 142:699-713 (2010).
Chen et al.: Functional Interrogation of Primary Human T Cells via CRISPR Genetic Editing. The Journal of Immunology 201:1586-1598 (2018).
Chen et al.: SLAMF7 is critical for phagocytosis of haematopoietic tumour cells via Mac-1 integrin. Nature 544:493-497 (2017).
Corresponding PCT Application No. PCT/US2019/060052, filed Nov. 6, 2019.
Cros et al.: Human CD14dim) Monocytes Patrol and Sense Nucleic Acids and viruses via TLR7 and TLR8 Receptors. Immunity 33:375-386, (2010).
Cross et al.: Nanomechanical analysis of cells from cancer patients. Nature Nanotechnology 2:780-783 (2007).
Daeron et al.: Fc Receptors. Current Topics in Microbiology and Immunology, vol. 382 (2014).
Davis et al.: The kinetic-segregation model: TCR triggering and beyond. Nature Immunology 7:803-809 (2006).
De Kleer et al.: Ontogeny of myeloid cells. frontiers in Immunology 5(423):1-11 (2014).
De Koning et al.: Repetitive Elements May Comprise Over two= Thirds of the Human Genome. PLoS 7(2) 1-12 (2011).
De Oliveria et al.: Modification of Hematopoietic Stem/Progenitor Cells with CD19-Specific Chimeric Antigen Receptros as a Novel Approach for Cancer Immunotherapy. Human Gene Therapy 24:824-839 (2013).
Deininger: Alu elements: know the SINEs. Genome Biol. 12(12):236, pp. 1-21 doi:10.1186/GB-2011-12-12-236 (2011).
Devereux et al., "A Comprehensive Set of Sequence Analysis Programs for the VAX," Nucleic Acids Research 11:12(1 Pt 1):387-395 (Jan. 1984).
Dewannieux et al.: Endogenous retroviruses: acquisition, amplification and taming of genome invaders. Science Direct, Current Opinion in Virology 3:646-656 (2013).
Dewannieux et al.: L1-mediated Retrotransposition of Murine B1 and B2 SINEs Recapitulated in Cultured Cells. J. Mol. Bio. 349:241-247 (2005).
Dewannieux et al.: LINE-mediated retrotransposition of marked Alu sequences. Nature Genetics 35(1):41-48 (2003).
Dong et al.: LINE-Like Retrotransposition in *Saccharomyces cerevsiae*. The Genetics Society of America (2008). DOI: 10.1534/genetics.108.096636.
Dotti et al. Design and Development of Therapies using Chimeric Antigen Receptor-Expressing T cells. Immunol Rev. 257(1):35 pgs (2014).
Doucet et al.: A 3' Poly(A) Tract Is Required for LINE-1 Retrotransposition. Mol Cell 60(5):728-741 doi:10.1016/j.molcel.2015.10.012 (2015).
Douse et al.: TASOR is a pseudo-PARP that directs HUSH complex assembly and epigenetic transposon control. Nature Communications 11(4940):1-16 (2020).
Edelstein et al.: Computer control of microscopes using mmanager. Current Protocols in Molecular Biology 14:14.20 (2010).
Eickbush et al.: Evolution of the R2 Retrotransposon Ribozyme and Its self-Cleavage Site. PLoS 8(9): 1-16 (2013).
Engel et al.: Abnormal B lymphocyte development, activation, and differentiation in mice that lack or overexpress the CD19 signal transduction molecule. Immunity 3:39-50 (1995).
EP20861388 European Extended Search Report dated Aug. 11, 2023.
European Patent Application No. 20861388.5 Extended European Search Report dated Aug. 11, 2023.
Faulkner et al.: L1 retrotransposition in the soma: a field jumping ahead. Mob DNA 9:22, pp. 1-18 doi:10.1186/s13100-018-0128-1 (2018).
Fesnak et al.: Engineered T cells: the promise and challenges of cancer immunotherapy. Nature Reviews Cancer 16:566-581 (2016).
Fingl et al.: Chapter 1: General Principles. The Pharmacological Basis of Therapeutics (49 pgs) (1975).
Floor et al.: Get in LINE: Competition for Newly Minted Retrotransposon Proteins at the Ribosome. Molecular Cell 60(5):712-714 http://dx.doi.org/10.1016/j.molcel.2015.11.014 (2015).
Flynn et al.: Mammalian Y RNAs are modified at discrete guanosine residues with N-glycans. bioRxiv 787614 doi:https://doi.org/10.1101/787614 [1-31] (2019).
Fraser et al.: Development, functional characterization and validation of methodology for GMP-compliant manufacture of phagocytic macrophages: A novel cellular therapeutic for liver cirrhosis. Cyotherapy ISSN 1465-3249 (2017).
Frassinelli et al.: The RNA editing enzyme ADAR2 restricts L1 mobility. RNA Biol, pp. 1-13 doi:10.1080/15476286.2021.1940020 (2021).
Freeman et al.: Integrins Form an Expanding Diffusional Barrier that Coordinates Phagocytosis. Cell 164:128-140 (2016).
Freeman et al.: Phagocytosis: receptors, signal integration, and the cytoskeleton. Immunological Reviews 262:193-215 (2014).
Fujiwara et al.: Site-specific non-LTR retrotransposons. Microbiology Spectrum, p. 1-16 (2014).
Gabitova et al.: Anti-HER2 CAR monocytes demonstrate targeted anti-tumor activity and enable a single day cell manufacturing process. Poster Presentation. The American Association for Cancer Research (AACR) Annual Meeting, Philadelphia, PA, United States (2021). https://secureservercdn.net/45.40.149.113/74d.fcf.myftpupload.com/wp-content/uploads/2021/09/Anti-HER2-CAR-monocytes_AACR2021.pdf.
Gao et al.: Cationic liposome-medicated gene transfer. Gene Therapy (2): 710-722 (1995).
Gardai et al.: Cell-surface calreticulin initiates clearance of viable or apoptotic cells through trans-activation of LRP on the phagocyte. Cell 123:321-334 (2005).
Geissmann et al.: Blood Monocytes Consist of Two Principal Subsets with Distinct Migratory Properties. Immunity (19):71-82 (2003).
Getts et al.: Harnessing nanoparticles for immune modulation. Trends Immunol 36(7):419-427 (2015).
Getts et al.: Microparticles bearing encephalitogenic peptides induce T-cell tolerance and ameliorate experimental autoimmune encephalomyelitis. Nat Biotechnol 30(12):1217-1224 (2012).
Gokhale et al.: Antisense raf oligodeoxyribonucleotide is protected by liposomal encapsulation and inhibits Raf-1 protein expression in vitro and in vivo: implication for gene therapy of radioresitant cancer. Gene Therapy 4:1289-1299 (1997).
Goodard et al.: A second dose of CFTR cDNA-liposome complex is as effective as the first does in restoring cAMP-dependent chloride secretion to nullCF mice trachea. Gene Therapy 4:1231-1236 (1997).
GORDON: Phagocytosis: An Immunobiologic Process. Immunity 44 (2016).
Gordon, S., Phagocytosis an immunobiologic process. Immunity 44, Mar. 15, 2016 p. 463-475.
Gorman et al.: Efficient in vivo delivery of DNA to pulmonary cells using the novel lipid EDMPC. Gene Therapy 4:953-992 (1997).
Goudot et al.: Aryl Hydrocarbon Receptro Controls Monocyte Differentiation into Dendritic Cells versus Macrophages. Immunity 47: 582-596 (2017).
Great Britain Patent Application No. GB2203647.9 Examination Report dated Jan. 24, 2024.
Grechishnikova et al.: Conserved 3' UTR stem-loop structure in L1 and Alu transposons in human genome: possible role in retrotransposition. BMC Genomics 17(1):992, pp. 1-17 doi:10.1186/s12864-016-3344-4 (2016).
Grunstein et al.: Colony hybridization: a method for the isolation of cloned DNAs that contain a specific gene. Proc Natl Acad Sci 72, (10):3961-3965 (1975).

(56) References Cited

OTHER PUBLICATIONS

Guatelli et al.: Isothermal, in vitro amplification of nucleic acids by a multienzyme reaction modeled after retroviral replication. Proc Natl Acad. Sci. 87(5)1874-1878 (1990).
Hackett et al.: A Transposon and Transposase System for Human Application. Mol Ther. 18(4):674-683 doi:10.1038/mt.2010.2 (2010).
Han et al.: Development of miniature base editors using engineered IscB nickase. Nature Methods (2022). https://doi.org/10.1038/s41592-023-0189809.
Harburger et al.: Integrin signalling at a glance. Journal of Cell Sciences 122 (2009).
Harland et al.: Stability of RNA in developing Xenopus embryos and identification of a destabilizing sequence in TFIIIA messenger RNA. Development 102(4):837-852 (1988).
Harshyne et al.: A Role for Class A Scavenger Receptor in Dendritic Cell Nibbling from Live Cells. The Journal of Immunology 170:2302-2309 (2003).
Harshyne et al.: Dendritic cells acquire antigens from live cells for Cross-Presentation to CTL. The Journal of Immunology 166:3717-3723 (2001).
Haso et al.: Anti-CD22-chimeric antigen receptors targeting B-cell precursor acute lymphoblastic leukemia. Blood 121:1165-1174 (2013).
Holliger et al., "Diabodies": Small Bivalent and Bispecific Antibody Fragments. PNAS USA 90:6444-6448 (Jul. 1993).
Hsu et al.: Electron microscopic evidence for the circular form of RNA in the cytoplasm of eukaryotic cells. Nature 280:339-340 (1979).
Huang et al.: Antigen-loaded monocyte administration induces potent therapeutic antitumor T cell responses, The Journal of Clinical Investigation, p. 1-15 (2020).
Hudson et al.: Engineered antibodies. Nature Medicine 9(1):129-134 (2003).
Hui et al.: In vitro membrane reconstitution of the T-cell receptor proximal signaling network. Nature Structural & Molecular Biology 21:133-142 (2014).
Hui et al.: T cell constimulatory receptor CD28 is a primary target for PD-1-mediated inhibition. Science 355(6332):1428-1433 (2017).
Ingersoll et al.: Brief Report: Pilot Randomized Controlled Trial of Reciprocal Imitation Training for Teaching Elicited and Spontaneous Imitation to Children with Autism, J Autism Dev Disord 40(9):1154-1160 (2010).
International Search Report and Written Opinion for PCT/US2020/030837 issued Oct. 1, 2020.
International Search Report for PCT/US2020/037312 issued Nov. 30, 2020.
Italiani et al.: From Monocytes to M1/M2 Macrophages: Phenotypical vs. Functional Differentiation. Front Immunol 17(5):514 (2014).
Ivancevic et al.: LINEs between Species: Evolutionary Dynamics of LINE-1 Retrotransposons across the Eukaryotic Tree of Life. Genome Biol Evol. 8(11):3301-3322 doi:10.1093/gbe/evw243 (2016).
Ivic et al.: Molecular Reconstruction of Sleeping Beauty, a Tc1-like Transposon from Fish, and Its Transposition in Human Cells. Cell 91:501-510 (1997).
Ivics et al.: Transposon-medicated Genome Manipulations in Vertebrates. Nat Methods 6(6):415-422 (2009).
Jadus et al.: Macrophages can recognize and kill tumor cells bearing the membrane isoform of macrophage colony-stimulating factor. Blood 87:5232-5241 (1996).
Jaeger et al.: TectoRNA: modular assembly units for the construction of RNA nano-objects. Nucleic Acids Res. 29(2):455-463 doi:10.1093/nar/29.2.455 (2001).
Jaiswal et al.: CD47 is upregulated on circulating hematopoietic stem cells and leukemia cells to avoid phagocytosis. Cell 138:271-285 (2009).
Jamburuthugoda et al.: Identification of RNA binding motifs in the R2 retrotransposon-encoded reverse transcriptase. Nucleic Acids Res. 42(13):8405-8415 doi:10.1093/nar/gku514 (2014).
James et al.: Biophysical mechanism of T-cell receptor triggering in a reconstituted system. Nature 487:64-69 (2012).
Jarrosson-Wuilleme et al.: Transduction of nondividing human macrophages with gammaretrovirus-derived vectors. J Virol. 80(3):1152-1159 doi:10.1128/JVI.80.3.1152-1159.2006 (2006).
Jeck et al.: Circular RNAs are abundant, conserved, and associated with ALU repeats. RNA 19:41-157 (2013).
Joly et al.: What is trogocytosis and what is its purpose? Nature Immunology 4:815 (2003).
Kamber et al.: Inter-cellular CRISPR screens reveal regulators of cancer cell phagocytosis. Nature 597(7877):549-554 doi:10.1038/s41586-021-03879-4 (2021).
Kao et al.: The role of the laminin beta subunit in laminin heterotrimer assembly and basement membrane function and development in C. elegans. Developmental Biology 290:211-219 (2006).
Kapitonov et al.: ISC, a Novel Group of Bacterial and Archaeal DNA Transposons That Encode Cas9 Homologs. Journal of Bacteriology, American Society for Microbiology 198:5 (2022). DOI: https://doi.org/10.1128/jb.00783-15.
Kievits et al.: NASBATM isothermal enzymatic in vitro nucleic acid amplification optimized for the diagnosis of HIV-1 infection. J. Virol. Methods 35:273-286 (1991).
Kim et al.: Monocyte Enrichment from Leukapheresis products by using the Elutra cell separator. Transfusion 47:2290-2296 (2007).
Kimmel et al.: Preparation of cDNA and the generation of cDNA libraries: overview. Methods Enzymol 152:307-316 (1987).
Kinsey, J. A.: Tad, a LINE-Like Transposable Element of Neurospora, Can Transpose Between Nuclei in Heterokaryons. Genetics 126:317-326 (1990).
Klichinsky et al.: Human chimeric antigen receptor macrophages for cancer immunotherapy. Nat Biotechnol. 38(8):947-953 (2020); Epub (2020).
Klichinsky M. et al., "CAR-Macrophage for Cancer Immunotherapy: Latest Findings from the CT-0508 Clinical Trial" YouTube, https://youtu.be/2Ag7SVM-fPg, published Jun. 27, 2022, https://carismatx.com/programs/ct-0508/.
Kochenderfer et al.: Construction and preclinical evaluation of an anti-CD19 chimeric antigen receptor. Journal of Immunotherapy 32:689-702 (2009).
Kowalski et al.: Delivering the Messenger: Advances in Technologies for Therapeutic mRNA Delivery. Mol. Ther 27(4):710-728 (2019).
Kwoh et al.: Transcription-based amplification system and detection of amplified human immunodeficiency virus type 1 with a bead-based sandwich hybridization format. Proc Natl Acad Sci 86(4):1173-1177 (1989).
Laborde, Rebecca R et al.: Cancer Vaccines in the World of Immune Suppressive Monocytes (CD14+HLA-DRIo/neg Cells): The Gateway to Improved Responses. Frontiers in Immunology vol. 5 (2014). https://doi.org/10.3389/fimmu.2014.00147.
Lacerna et al.: Adoptive cancer immunotherapy utilizing lymphokine activated killer cells and gamma interferon activated killer monocytes. Pharmacology & Therapeutics 38:453-465 (1988).
Laird et al.: (J. Leukocyte Biology 85: 966-977 (2009)).
Larson et al.: Spliced integrated retrotransposed element (SpIRE) formation in the human genome. PLoS Biology 16(3):e2003067, pp. 1-37 (2018).
Lee et al.: Macrophage-based cell therapies: the long and winding road. Journal of Controlled Release 240:527-540 (2016).
Levine et al.: Global Manufacturing of Car T Cell Therapy. Mol Ther Methods Clin Dev. 4:92-101 (2016).
Li et al.: The dicistronic RNA from the mouse LINE-1 retrotransposon contains an internal ribosome entry site upstream of each ORF: implications for retrotransposition. Nucleic Acids Research 34(3):853-864 (2006).
Lim, et al., "Antisense oligonucleotide modulation of non-productive alternative splicing upregulates gene expression" (2020) Nature Communication.
Lim et al.: The Principles of Engineering Immune Cells to Treat Cancer. Cell 168:724-740 (2017).
Liu et al.: CD47 blockade triggers T cell-mediated destruction of immunogenic tumors. Nature Medicine 21:1209-1215 (2015).

(56) References Cited

OTHER PUBLICATIONS

Liu et al.: Ouroboros resembling competitive endogenous loop (ORCEL) in revealed through transcriptome sequencing dataset analysis. BMC Genomics 19(Suppl 2):171, pp. 87-95 doi:10.1186/s12864-018-4456-9 (2018).
Liu Q et al.: Nuclear localization of the ORF2 protein encoded by porcine circovirus type 2. Virology 285(1):91-9 (2001).
Lloyd et al., "Modelling the Human Immune Response: Performance of a 10" Human Antibody Repertoire Against a Broad Panel of Therapeutically Relevant Antigens," Protein Engineering Design & Selection 22(3):159-168 (2009) (Published online Oct. 29, 2008).
Loannidi et al.: Drag-and-drop genome insertion without DNA cleavage with CRISPR-directed integrases. bioRxiv (2021). doi: https://doi.org/10.1101/2021.11.01.466786.
Luan et al.: Reverse Transcription of R2Bm RNA Is Primed by a Nick at the Chromosomal Target Site: A Mechanism for Non-LTR Retrotransposition Cell 72:595-605 (1993).
Macia et al.: Engineered LINE-1 retrotransposition in nondividing human neurons. Genome Res. 27(3):335-348 doi:10.1101/gr.206805.116 (2017).
Majeti et al.: CD47 is an adverse prognostic factor and therapeutic antibody target on human acute myeloid leukemia stem cells. Cell 138:286-299 (2009).
Manoj et al.: Targeted insertion of large genetic payloads using ca directed LINE-1 reverse transcriptase. Scientific Reports—Nature Portfolio p. 1-9 (2021).
Matsuyoshi et al.: Enchanced Priming of Antigen-Specific CTL's In Vivo by Embryonic Stem Cell-Derived Dendritic Cells Expressing Chemokine Along with Antigenic Protein: Application to Antitumor Vaccination. The Journal of Immunology 172:776-786 (2004).
Mayordomo et al.: Bone marrow-derived dendritic cells pulsed with synthetic tumour peptides elicit protective and therapeutic antitumour immunity. Nature Medicine 1:1297-1302 (1995).
Mccaffrey et al.: RNA Interference in Adult Mice. Nature 418:38-39 (2002).
Mcever et al.: Selectins: initiators of leucocyte adhesion and signalling at the vascular wall. Cardovascular Research 107:331-339 (2015).
Medzihradszky, K.F.: Lessons in de novo peptide sequencing by tandem mass spectrometry. Mass Spectrom Rev 34(1):43-63 (2015).
Memczak et al.: Circular RNAs are a large class of animal RNAs with regulatory potency. Nature 495:333-338 (2013).
Mildner et al.: Distinct and Non-Redundant Roles of Microglia and Myeloid Subsets in Mouse Models of Alzheimer's Disease. Neurobiology of Disease, J. Neurosci. 31(31):11159-11171 (2011).
Mita et al.: BRCA1 and S phase DNA repair pathways restrict LINE-1 retrotransposition in human cells. Nat Struct Mol Biol. 27(2):179-191 doi:10.1038/s41594-020-0374-z (2020).
Monahan et al.: Direct intramuscular injection with recombinant AAV vectors results in sustained expression in a dog model of hemophilia. Gene Therapy 5:40-49 (1998).
Morrissey et al.: Chimeric antigen receptors that trigger phagocytosis. eLife p. 1-21 (2018).
Muckenfuss et al.: APOBEC3 proteins inhibit human LINE-1 retrotransposition. J Biol Chem. 281(31):22161-22172 doi:10.1074/jbc.M601716200 (2006).
Mukherjee et al.: Non-Classical monocytes display inflammatory features: Validation in Sepsis and Systemic Lupus Erythematous. Scientific Reports p. 1-14 (2015).
Murshid et al.: Hsp90-peptide complexes stimulate antigen presentation through the class II pathway after binding scavenger receptor SREC-1. Immunobiology 219(12):924-931 (2014).
Nakamizo et al.: Single-cell analysis of human skin identifies CD14+ type 3 dendritic cells co-producing IL1B and IL23A in psoriasis. J Exp Med 218(9):e20202345 (2021). https://doi.org/10.1084/jem.20202345.
Ni et al.: Transposon tools hopping in vertebrates. Briefings in Functional Genomics and proteomics 7(6):444-453 (2008).
Novikova et al.: Engineering cooperative tecto-RNA complexes having programmable stoichiometries. Nucleic Acids Res. 39(7):2903-2917 doi:10.1093/nar/gkq1231 (2011).
Oates et al.: Characterizing the polarization continuum of macrophage subtypes M1, M2a and M2c. bioRxiv (2022). doi: https://doi.org/10.1101/2022.06.13.495868.
Office Action dated Dec. 8, 2022 issued in U.S. Appl. No. 17/499,232.
Office Action dated Oct. 26, 2022 issued in U.S. Appl. No. 17/855,230.
Office Action dated Oct. 7, 2022 issued in U.S. Appl. No. 17/855,423.
Olingy et al.: Monocyte heterogeneity and functions in cancer. J Leukoc Biol. 106(2):309-322 (2019). doi: 10.1002/JLB.4RI0818-311R. Epub (2019).
Onodera et al.: Successful Peripheral T-Lymphocyte-Directed Gene Transfer for a Patient With Severe Combined Immune Deficiency Caused by Adenosine Deaminase Deficiency. Blood 91(1):30-36 (1998).
Orecchioni et al.: Macrophage Polarization: Different Gene Signatures in M1(LPS+) vs. Classically and M2(LPS−) vs. Alternatively Activated Macrophages. Front Immunol. (2019);10:1084. Erratum in: Front Immunol. 25;11:234 (2020).
Orechini et al.: ADAR1 restricts LINE-1 retrotransposition. Nucleic Acids Res. 45(1):155-168 doi:10.1093/nar/gkw834 (2017).
Oshi et al.: M1 Macrophage and M1/M2 ratio defined by transcriptomic signatures resemble only part of their conventional clinical characteristics in breast cancer. Sci Rep. 10(1):16554 (2020).
Oviedo-Boyso et al.: The Phosphoinositide-3-Kinase-Akt Signaling Pathway Is Important for *Staphylococcus aureus* Internalization by Endothelial Cells Infection and Immunity 79(11):4569-4577 (2011).
Oviedo-Boyso J., The Phosphoinositide-3-Kinase-Akt Signaling Pathway Is Important for *Staphylococcus aureus* Internalization by Endothelial Cells, Infection and Immunity, Nov. 2011, p. 4569-4577.
Ozcan et al.: Programmable RNA targeting with the single-protein CRISPR effector Cas7-11. Nature 597(7878):720-725 doi: 10.1038/s41586-021-03886-5 (2021).
Pascolo S.: Messenger RNA-based vaccines. Expert Opin Biol Ther. 4(8):1285-94 (2004).
Passlick et al.: Identification and Characterization of a Novel Monocyte Subpopulation in Human Peripheral Blood. Article in Blood 74:2527-2534 (1989).
Patel et al.: The fate and lifespan of human monocyte subsets in steady state and systemic inflammation. J. Exp. Med. 214(7):1913-1923 (2017).
PCT/US2019/060052 International Preliminary Report on Patentability May 11, 2021.
PCT/US2019/060052 International Search Report and Written Opinion dated Apr. 30, 2020.
PCT/US2020/030837 International Search Report and Written Opinion dated Sep. 1, 2020.
PCT/US2020/037312 International Search Report dated Nov. 30, 2020.
PCT/US2020/049240 International Search Report and Written Opinion dated Mar. 26, 2021.
PCT/US2020/049240 International Search Report dated Mar. 26, 2021.
PCT/US2020/064686 International Preliminary Report on Patentability mailed Jun. 23, 2022.
PCT/US2020/064686 International Search Report and Written Opinion dated Apr. 6, 2021.
Penberthy et al.: Apoptotic cell recognition receptors and scavenger receptors. Immunological Reviews 269:44-59 (2016).
Pierini et al.: Chimeric antigen receptor macrophages (CAR-M) elicit a systemic anti-tumor immune response and synergize with PD-1 blockade in immunocompetent mouse models of HER2+ solid tumors. Poster Presentation. Society for Immunotherapy of Cancer (SITC) Meeting, Virtual (2020). https://secureservercdn.net/45.40.149.113/74d.fcf.myftpupload.com/wp-content/uploads/2021/09/CAR-M-syngeneic-model_SITC2020.pdf.
Pierini et al.: Chimeric antigen receptor macrophages (CAR-M) sensitize solid tumors to anti-PD1 immunotherapy. Poster Presentation. The American Association for Cancer Research (AACR) Annual Meeting, New Orleans, LA, United States (2022). https://

(56) References Cited

OTHER PUBLICATIONS secureservercdn.net/45.40.149.113/74d.fcf.myftpupload.com/wp-content/uploads/2022/07/AACR2022_CARMaPD11.pdf.
Piskareva et al.: The carboxy-terminal segment of the human LINE-1 ORF2 protein is involved in RNA binding. FEBS Open Bio. 3:433-437 (2013).
Pluckthun et al.: The Pharmacology of Monoclonal Antibodies. Springer-Verlag 11:69-315 (1994).
Putnam. Antisense strategies and therapeutic applications. Am. J. Health Syst. Pharm. 53:151-160 (1996), erratum at Am. J. Health Syst. Pharm. 53:325 (1996).
Ralston et al.: Trogocytosis by Entamoeba histolytica contributes to cell killing and tissue invasion. Nature 508:526-530 (2014).
Reiss et al.: A Phase 1, First-In-Human (FIH) Study of the Anti-HER2 CAR Macrophage CT-0508 in Participants with HER2 Overexpressing Solid Tumors. Poster Presentation. American Society of Clinical Oncology (ASCO) Annual Meeting, New Chicago, IL, United States (2022). https://secureservercdn.net/45.40.149.113/74d.fcf.myftpupload.com/wp-content/uploads/2022/07/ASCO-Data-In-Person-2022.final_.pdf.
Reiss et al.: LBA (951): A Phase 1 first in human study of adenovirally transduced anti-HER2 CAR Macrophages in subjects with HER2 overexpressing solid tumors: preliminary safety, pharmacokinetics, and TME reprogramming data. Poster Presentation. Society for Immunotherapy of Cancer (SITC) Meeting, Washington, DC, United States (2021). https://secureservercdn.net/45.40.149.113/74d.fcf.myftpupload.com/wp-content/uploads/2021/11/Poster-LBA951-CT-0508-Study-101-SITC-FINAL.pdf.
Richardson et al.: The Influence of LINE-1 and SINE Retrotransposons on Mammalian Genomes. Microbiol Spectr. 3(2):MDNA3-0061-2014, pp. 1-63 doi:10.1128/microbiolspec.MDNA3-0061-2014 (2015).
Roberts et al.: Antigen-Specific Cytolysis by Neutrophils and NK Cells Expressing Chimeric Immune Receptros Bearing xx Signaling Domains. J Immunol 161:375-384 (1998).
Roberts et al.: Critical Role for CD103(+)/CD141(+) Dendritic Cells Bearing CCR7 for Tumor Antigen Trafficking and Priming of T Cell Immunity in Melanoma. Cancer Cell 30:324-336 (2016).
Rosales et al: Phagocytosis: A Fundamental Process in Immunity. BioMed Research International, Article ID 9042851 (2017).
Ruiz-Aguilar et al.: Human CD16+ and CD16+ monocyte subsets display unique effector properties in inflammatory conditions in vivo. Journal of Leukocyte Biology 90:1119-1131 (2011).
Russell, D.G.: *Mycobacterium tuberculosis* and the intimate discourse of a chronic infection. Immunol Rev 240(1):252-268 (2011).
Scherberich et al.: CD14++ monocytes, CD14+/CD16+ subset and soluble CD14 as biological markers of inflammatory systemic diseases and monitoring immunosuppressive therapy. Clin Chem Lab Med. 37(3):209-13 (1999).
Schlam et al.: Phosphoinositide 3-kinase enables phagocytosis of large particles by terminating actin assembly through Rac/Cdc42 GTPase-activating proteins. Nature Communications 6:8623 (2015).
Schroers R, et al. Transduction of human PBMC-derived dendritic cells and macrophages by an HIV-1-based lentiviral vector system. Mol Ther. Feb. 2000;1(2):171-9.
Segel et al.: Mammalian retrovirus-like protein PEG10 packages its own mRNA and can be pseudotyped for mRNA delivery. Science 373(6557):882-889 (2021).
Senju et al.: Generation and genetic modification of dendritic cells derived from mouse embryonic stem cells derived from mouse embryonics stem cells. Blood 101(9):3501-3508 (2003).
Senju et al.: Generation of dendritic cells and macrophages from human induced pluripotent stem cells aiming at cell therapy. Gene Therapy 18:874-883 (2011).
Shein et al.: Recognition of 3'-end L1, Alu, processed pseudogenes, and mRNA stem-loops in the human genome using sequence-based and structure-based machine-learning models. Sci Rep. 9(1):7211, pp. 1-16 doi:10.1038/s41598-019-43403-3 (2019).
Shumann et al.: The impact of transposable element activity on therapeutically relevant human stem cells. Mob DNA 10:9, pp. 1-23 doi:10.1186/s13100-019-0151-x (2019).
Sica, F., Fingolimod Immune Effects Beyond Its Sequestration Ability, Neurol Ther (2019) 8:231-240.
Silverstein RL., Mechanisms of Cell Signaling by the Scavenger Receptor CD36: Implications in Atherosclerosis and Thrombosis, Transactions of the American Clinical and Climatological Association, vol. 121, 2010.
Sloas et al.: SIRPα-Deficient CAR-Macrophages Exhibit Enhanced Anti-Tumor Function and Bypass the CD47 Immune Checkpoint. Poster Presentation. Society for Immunotherapy of Cancer (SITC) Meeting, Washington, DC, United States (2021). https://secureservercdn.net/45.40.149.113/74d.fcf.myftpupload.com/wp-content/uploads/2021/11/CRISPR_CAR-M_Poster_101721_share-Read-Only.pdf.
Soderberg et al. (J. Virology 67(6): 3166-3175 (1993)).
Strauss et al.: The immunophenotype of antigen presenting cells of the mononuclear phagocyte system in a normal human liver—A systematic review. Journal of Hepatology 62:458-468 (2015).
Su et al.: Phase separation of signaling molecules promotes T cell receptor signal transduction. Science 352(6285):595-599 (2016).
Supplementary European Search Report dated Dec. 16, 2022 issued in European Patent Application 20798060.
Takahashi et al.: A new family of site-specific retrotransposons, SART1, is inserted into telomeric repeats of the silkworm, Bombyx mori. Nucleic acids Research 25(8):1-7 (1997).
Taylor, et al., A DNA-Based T Cell Receptor Reveals a Role for Receptor Clustering in Ligand Discrimination. Cell 169(1):108-19 e20 (2017).
Tippet et al.: (J. Leukocyte Biology 93:913-920 (2013)).
Tristan-Ramos et al.: The tumor suppressor microRNA let-7 inhibits human LINE-1 retrotransposition. Nat Commun. 11(1):5712 doi:10.1038/s41467-020-19430-4 [1-14] (2020).
Tseng et al.: Anti-CD47 antibody-mediated phagocytosis of cancer by macrophages primes an effective antitumor T-cell response. PNAS 110:11103-11108 (2013).
Tsutsui et al. The use of microbubbles to target drug delivery. Cardiovascular Ultrasound 2:23 (2004).
Tuveson et al.: CD19 of B cells as a surrogate kinase insert region to bindphosphatidylinositol 3-kinase. Science 260:986-989 (1993).
Villanueva MT. Macrophages get a CAR. Nat Rev Drug Discov. 19(5):308 (2020).
Wahl et al.: Molecular hybridization of immobilized nucleic acids: theoretical concepts and practical considerations. Methods Enzymol 152:399-407 (1987).
Walker et al.: Strand displacement amplification-an isothermal, in vitro DNA amplification technique. Nucleic Acids Res 20(7):1691-1696 (1992).
Wei et al.: Human L1 retrotransposition: cis preference versus trans complementation. Mol Cell Biol. 21(4):1429-1439 doi:10.1128/MCB.21.4.1429-1439.2001 (2001).
Weischenfeldt et al.: Bone Marrow-Derived Macrophages (BMM): Isolation and Applications. Cold Spring Harbor Protocols 2008:pdb.prot5080.
Wilkinson et al. (Med. Microbio. Immunol. 204:273-284 (2015)).
Wong et al.: The three human monocyte subsets: implications for health and disease. Immunol Res. 2012; 53(1-3):41-57. Epub (2012).
Xia et al.: siRNA-mediated gene silencing in vitro and in vivo. Nat Biotechnol. 20:1006-1010 (2002).
Xiao et al.: Electrophysiological Characteristics of Primary Afferent Fibers After Systemic Administration of Anti-GC2 Ganglioside Antibody, Pain69: 145-151 (1997).
Xiao et al.: Identification and characterization of fully human anti-CD22 monoclonal antibodies. mAbs 1:297-303 (2009).
Yarnall et al.: Drag-and-drop genome insertion of large sequences without double-strand DNA cleavage using CRISPR-directed integrases. nature biotechnology (2022). https://doi.org/10.1038/s41587-022-01527-4.
Yeh et al.: In vivo base editing of post-mitotic sensory cells. Nat Commun. 9(1):2184, pp. 1-10 doi:10.1038/s41467-018-04580-3 (2018).
Yesselman et al.: RNA tertiary structure energetics predicted by an ensemble model of the RNA double helix.bioRxiv 341107, pp. 1-31 DOI:10.1101/341107 (2018).

(56) References Cited

OTHER PUBLICATIONS

Yong et al.: A role for multiple chimeric antigen receptor-expressing leukocytes in antigen-specific responses to cancer. Oncotarget 7(23):34582-34598 (2016).
Yong et al.: Using electroporation to determine function of a chimeric antigen receptor in T cell and macrophage cell lines. The Open Gene Therapy Journal 23:5(1) (2013).
Zhang et al.: Homologous 2',5'-phosphodiesterases from disparate RNA viruses antagonize antiviral innate immunity. PNAS USA 110(32):13114-13119 doi:10.1073/pnas.1306917110 (2013).
Zhang et al.: The structure and retrotransposition mechanism of LTR-retrotransposons in the asexual yeast *Candida albicans*. Virulence 5(6):655-664 doi:10.4161/viru.32180 (2014).
Boross, P. et al.: Anti-tumor activity of human IgG1 anti-gp75 TA99 mAb against B16F10 melanoma in human FcgammaRI transgenic mice. Immunol. Lett. 2014 160:151-157. (Abstract).
Jain et al.: Preclinical pharmacologic evaluation of pralatrexate and romidepsin confirms potent synergy of the combination in a murine model of human T-cell lymphoma. Clin Cancer Res. 21(9):2096-2106 (2015).
Mantovani et al.: Tumour-associated macrophages as treatment targets in oncology. Nat Rev Clin Oncol. 14(7):399-416 (2017).
Pathria et al.: Targeting Tumor-Associated Macrophages in Cancer. Trends Immunol. 40(4):310-327 (2019).
Studnicka, Gary M. et al. Human-engineered Monoclonal Antibodies Retain Full Specific Binding Activity by Preserving non-CDR Complementarity-modulating Residues. Protein Eng. 7(6):805-814 (1994).
Takechi et al.: A melanosomal membrane protein is a cell surface target for melanoma therapy. Clin Cancer Res. 2(11):1837-1842 (1996).
U.S. Appl. No. 18/157,052 Notice of Allowance dated Jan. 29, 2025.
Wagstaff, Bradley et al.: Rescuing Alu: Recovery of New Inserts Shows LINE-1Preserves Alu Activity through A-Tail Expansion. PLOS Genetics 8(8):e1002842. doi:10.1371/journal.pgen.1002842.t004.
Extended European Search Report dated May 7, 2025 issued in European Patent Application No. EP22808288.9.
Han, Jeffrey et al.: A highly active synthetic mammalian retrotransposon. Nature 429:314-318 (2004).
U.S. Appl. No. 18/313,087 Office Action dated Jun. 9, 2025.
U.S. Appl. No. 18/313,126 Office Action dated Jun. 16, 2025.
Wang, Yuxiao et al.: CRISPR-Enabled Autonomous Transposable Element (CREATE) for RNA-based gene editing and delivery. EMBO Reports 26:1062-1083 (2025).
Zheng, Feiyang et al.: LINE-1 vectors mediate recombinant antibody gene transfer by retrotransposition in Chinese hamster ovary cells. Biotechnology Journal vol. 16, No. 7 (2021). Abstract.
Adikusuma, Fatwa et al.: Versatile single-step-assembly CRISPR/Cas9 vectors for dual gRNA expression. Plos One 12(12):e0187236 (2017). https://doi.org/10.1371/journal.pone.0187236.
Beucher, Anthony et al.: One-step dual CRISPR/Cas9 guide RNA cloning protocol. Imperial College London, posted Jun. 26, 2019. DOI: https://doi.org/10.21203/rs.2.1831/v1.
Garfinkel, David J et al.: Ty element transposition: reverse transcriptase and virus-like particles. Cell 42(2):507-517 (1985). https://doi.org/10.1016/0092-8674(85)90108-4.
U.S. Appl. No. 18/313,087 Office Action dated Apr. 9, 2026.
U.S. Serial No. 18/313, 126 Notice of Allowance dated Feb. 6, 2026.
Yates, John L et al.: Stable replication of plasmids derived from EpsteinBarr virus in various mammalian cell. Nature 313:812-815 (1985) - Abstract.

* cited by examiner

METHODS AND COMPOSITIONS FOR GENOMIC INTEGRATION

CROSS REFERENCE

This Application is a continuation of PCT/US2020/049240 filed on Sep. 3, 2020, which claims the benefit of U.S. Provisional Application No. 62/895,441, filed on Sep. 3, 2019, U.S. Provisional Application No. 62/908,800, filed on Oct. 1, 2019, and U.S. Provisional Application No. 63/039,261, filed on Jun. 15, 2020, each of which is incorporated herein by reference in its entirety.

SEQUENCE LISTING

The instant application contains a Sequence Listing which has been filed electronically in ASCII format and is hereby incorporated by reference in its entirety. Said ASCII Sequence Listing copy was created on Oct. 13, 2020, named 56371-706_601_SL.txt and is 363,857 bytes in size. No new matter is added.

BACKGROUND

Cell therapy is a rapidly developing field for addressing difficult to treat diseases, such as cancer, persistent infections and certain diseases that are refractory to other forms of treatment. Cell therapy often utilizes cells that are engineered ex vivo and administered to an organism to correct deficiencies within the body. An effective and reliable system for manipulation of a cell's genome is crucial, in the sense that when the engineered cell is administered into an organism, it functions optimally and with prolonged efficacy. Likewise, reliable mechanisms of genetic manipulation form the cornerstone in the success of gene therapy. However, severe deficiencies exist in methods for delivering nucleic acid cargo (e.g., large cargo) in a therapeutically safe and effective manner. Viral delivery mechanisms are frequently used to deliver large nucleic acid cargo in a cell but are tied to safety issues and cannot be used to express the cargo in some cell types. Additionally, subjecting a cell to repeated gene manipulation can affect cell health, induce alterations of cell cycle and render the cell unsuitable for therapeutic use. Advancements are continually sought in the area for efficacious delivery and stabilization of an exogenously introduced genetic material for therapeutic purposes.

SUMMARY

Provided herein are compositions and methods for stable, non-viral transfer and integration of genetic material into a cell. In one aspect, the genetic material is a self-integrating polynucleotide. The genetic material can be stably integrated in the genome of the cell. The cell may be a human cell. The method is designed for a safe and reliable integration of a genetic material into the genome of a cell.

In one aspect, provided herein are compositions and methods that allow integration of genetic material into the genome of a cell, wherein the genetic material that can be integrated is not specifically restricted by size. In some aspects, the method described herein provides a one-step, single polynucleotide-mediated delivery and integration of genetic "cargo" in the genome of a cell. The genetic material may comprise a coding sequence, e.g., a sequence encoding a transgene, a peptide, a recombinant protein, or an antibody or fragments thereof, wherein the method and compositions ensure stable expression of the transcribed product encoded by the coding sequence. The genetic material may comprise a non-coding sequence, for example, a regulatory RNA sequences, e.g., a regulatory small inhibitory RNA (siRNA), microRNA (miRNA), long non-coding RNA (lncRNA), or one or more transcription regulators such as a promoter and/or an enhancer, and may also include, but not limited to structural biomolecules such as ribosomal RNA (rRNA), transfer RNA (tRNA) or a fragment thereof or a combination thereof.

In another aspect, provided herein are methods and compositions for site-specific integration of a genetic material that may not be specifically restricted by size, into the genome of a cell via a non-viral delivery that ensures both safety and efficacy of the transfer. Provided methods and compositions may be particularly useful in developing a therapeutic, such as a therapeutic comprising a polynucleotide comprising a genetic material and a machinery that allows transfer into a cell and stable integration into the genome of the cell into which the polynucleotide or an mRNA encoding the polynucleotide is transferred. In some embodiments, the therapeutic may be a cell that comprises a polynucleotide that has been stably integrated into the genome of the cell using the methods and compositions described herein.

In one aspect, the present disclosure provides compositions and methods for stable gene transfer into a cell. In some embodiments, the compositions and methods are for stable gene transfer into an immune cell. In some cases, the immune cell is a myeloid cell. In some cases, the methods described herein relate to development of myeloid cells for immunotherapy.

Immunotherapy using phagocytic cells involves making and using engineered myeloid cells, such as macrophages or other phagocytic cells that attack and kill diseased cells, such as cancer cells, or infected cells. Engineered myeloid cells, such as macrophages and other phagocytic cells are prepared by incorporating in them via recombinant nucleic acid technology, a synthetic, recombinant nucleic acid encoding an engineered protein, such as a chimeric antigen receptor, that comprises a targeted antigen binding extracellular domain that is designed to bind to specific antigens on the surface of a target, such as a target cell, such as a cancer cell. Binding of the engineered chimeric receptor to an antigen on a target, such as cancer antigen (or likewise, a disease target), initiates phagocytosis of the target. This triggers two fold action: one, phagocytic engulfment and lysis of the target destroys the target and eliminates it as a first line of immune defense; two, antigens from the target are digested in the phagolysosome of the myeloid cell, are presented on the surface of the myeloid cell, which then leads to activation of T cells and further activation of the immune response and development of immunological memory. Chimeric receptors are engineered for enhanced phagocytosis and immune activation of the myeloid cell in which it is incorporated and expressed. Chimeric antigen receptors of the disclosure are variously termed herein as a chimeric fusion protein, CFP, phagocytic receptor (PR) fusion protein (PFP), or chimeric antigen receptor for phagocytosis (CAR-P), while each term is directed to the concept of a recombinant chimeric and/or fusion receptor protein. In some embodiments, genes encoding non-receptor proteins are also co-expressed in the myeloid cells, typically for an augmentation of the chimeric antigen receptor function. In summary, contemplated herein are various engineered receptor and non-receptor recombinant proteins that are designed to augment phagocytosis and or immune response of a myeloid cell against a disease target, and methods and compositions for creating and incorporating recombinant nucleic acids that encode the engineered receptors or non-receptor recombinant protein, such that the methods and compositions are suitable for creating an engineered myeloid cell for immunotherapy.

In one aspect, the present disclosure provides compositions and methods for stable gene transfer into a cell, where the cell can be any somatic cell. In some embodiments the compositions and methods are designed for cell-specific or tissue-specific delivery. In some cases, the methods described herein relate to supplying a functional protein or a fragment thereof to compensate for an absent or defective (mutated) protein in vivo, e.g., for a protein replacement therapy.

Incorporation of a recombinant nucleic acid in a cell can be accomplished by one or more gene transfer techniques that are available in the state of the art. However, incorporation of exogenous genetic (e.g., nucleic acid) elements into the genome for therapeutic purposes still faces several challenges. Achieving stable integration in a safe and dependable manner, and efficient and prolonged expression are a few among them. Most of the successful gene transfer systems aimed at genomic integration of the cargo nucleic acid sequence rely on viral delivery mechanisms, which have some inherent safety and efficacy issues. Delivery and integration of long nucleic acid sequences cannot be achieved by current gene editing systems.

Little attention has so far been devoted to making and using engineered myeloid cells for stable long-term gene transfer and expression of the transgene. For example, gene transfer to differentiated mammalian cells ex vivo for cell therapy can be accomplished via viral gene transfer mechanisms. However, there are several strategic disadvantages associated with the use of viral gene-transfer vectors, including an undesired potential for transgene silencing over time, the preferential integration into transcriptionally active sites of the genome with associated undesired activation of other genes (e.g. oncogenes) and genotoxicity. In addition to the safety issues increased expense and cumbersome effort of manufacturing, storing and handling integrating viruses often stand in the way of large-scale use of viral vector mediated of gene-modified cells in therapeutic applications. These persistent concerns associated with viral vectors regarding safety, as well as cost and scale of vector production necessitates alternative methods for effective therapy.

Integration of a transgene into the genome of a cell to be used for an immunotherapy can be advantageous in the sense that it is stable and a lower number of cells is required for delivery during the therapy. On the other hand, integrating a transgene in a non-dividing cell can be challenging in both affecting the health and function of the cell as well as the ultimate lifespan of the cell in vivo, and therefore affects its overall utility as the therapeutic. In some embodiments, the methods described herein for generating a myeloid cell for immunotherapy can be a cumulative product of a number of steps and compositions involving but not limited to, for example, selecting a myeloid cell for modifying; method and compositions for incorporating a recombinant nucleic acid in a myeloid cell; methods and compositions for enhancing expression of the recombinant nucleic acid; methods and compositions for selecting and modifying vectors; methods of preparing a recombinant nucleic acid suitable for in vivo administration for uptake and incorporation of the recombinant nucleic acid by a myeloid cell in vivo and therefore generating a myeloid cell for therapy. In some aspects, one or more embodiments of the various inventions described herein are transferrable among each other, and one of skill in the art is expected to use them in alternatives, combinations or interchangeably without the necessity of undue experimentation. All such variations of the disclosed elements are contemplated and fully encompassed herein.

In one aspect, transposons, or transposable elements (TEs) are considered herein, for means of incorporating a heterologous, synthetic or recombinant nucleic acid encoding a transgene of interest in a myeloid cell. Transposon, or transposable elements are genetic elements that have the capability to transpose fragments of genetic material into the genome by use of an enzyme known as transposase. Mammalian genomes contain a high number of transposable element (TE)-derived sequences, and up to 70% of our genome represents TE-derived sequences (de Koning et al. 2011; Richardson et al. 2015). These elements could be exploited to introduce genetic material into the genome of a cell. The TE elements are capable of mobilization, often termed as "jumping" genetic material within the genome. TEs generally exist in eukaryotic genomes in a reversibly inactive, epigenetically silenced form. In the present disclosure methods and compositions for efficient and stable integration of transgenes into macrophages and other phagocytic cells. The method is based on use of a transposase and transposable elements mRNA-encoded transposase. In some embodiments, Long Interspersed Element-1 (L1) RNAs are used for stable integration and/or retrotransposition of the transgene into a cell (e.g., a macrophage or phagocytic cell.

Contemplated herein are methods for retrotransposon mediated stable integration of an exogenous nucleic acid sequence into the genome of a cell. The method may take advantage of the random genomic integration machinery of the retrotransposon into the cell without creating an adverse effect. Methods described herein can be used for robust and versatile incorporation of an exogenous nucleic acid sequence into a cell, such that the exogenous nucleic acid is incorporated at a safe locus within the genome and is expressed without being silenced by the cell's inherent defense mechanism. The method described herein can be used to incorporate an exogenous nucleic acid that is about 1 kb, about 2 kb, about 3 kb, about 4 kb, about 5 kb, about 6 kb, about 7 kb about 8 kb, about 9 kb, about 10 kb, or more in size. In some embodiments, the exogenous nucleic acid is not incorporated within a ribosomal locus. In some embodiments, the exogenous nucleic acid is not incorporated within a ROSA26 locus, or another safe harbor locus. In some embodiments, the methods and compositions described herein can incorporate an exogenous nucleic acid sequence anywhere within the genome of the cell. Furthermore, contemplated herein is a retrotransposition system that is developed to incorporate an exogenous nucleic acid sequence into a specific predetermined site within the genome of a cell, without creating an adverse effect. The disclosed methods and compositions incorporate several mechanisms of engineering the retrotransposons for highly specific incorporation of the exogenous nucleic acid into a cell with high fidelity. Retrotransposons chosen for this purpose may be a human retrotransposon.

Methods and compositions described herein represent a salient breakthrough in the molecular systems and mechanisms for manipulating the genome of a cell. Shown here for the first time is a method that exploits a human retrotransposon system into non-virally delivering and stably integrating a large fragment of exogenous nucleic acid sequence (at least greater than 100 nucleobases, at least greater than 1 kb, at least greater than 2 kb, at least greater than 3 kb, etc.) into a non-conserved region of the genome that is not an rDNA or a ribosomal locus or a designated safe-harbor locus such as the ROSA 26 locus.

In some embodiments, a retrotransposable system is used to stably incorporate into the genome and express a non-endogenous nucleic acid, where the non-endogenous nucleic acid comprises retrotransposable elements within the nucleic acid sequence. In some embodiments, a cell's endogenous retrotransposable system (e.g., proteins and enzymes) is used to stably express a non-endogenous nucleic acid in the cell. In some embodiments, a cell's endogenous retrotransposable system (e.g., proteins and enzymes, such as a LINE-1 retrotransposition system) is used, but may further express one or more components of the retrotransposable system to stably express a non-endogenous nucleic acid in the cell.

In some embodiments, a synthetic nucleic acid is provided herein, the synthetic nucleic acid encoding a transgene, and encoding one or more components for genomic integration and/or retrotransposition.

In one aspect, provided herein is a method of integrating a nucleic acid sequence into a genome of a cell, the method comprising introducing a recombinant mRNA or a vector encoding an mRNA into the cell, wherein the mRNA comprises: an insert sequence, wherein the insert sequence comprises an exogenous sequence, or a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell. In some embodiments, the 5' UTR sequence or the 3' UTR sequence comprises a binding site for human ORF2p.

In one aspect, provided herein is a method for integrating a nucleic acid sequence into the genome of an immune cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the transgene sequence is integrated into the genome of the immune cell.

In one aspect, provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence. In some embodiments, the sequence of a human retrotransposon is upstream of the 3' UTR sequence. In some embodiments, the polynucleotide sequence that is desired to be transferred and incorporated into the genome of a cell (e.g., the insert) is inserted at a site 3' to the sequence encoding ORF1 in a recombinant nucleic acid construct. In some embodiments, the polynucleotide sequence that is desired to be transferred and incorporated into the genome of a cell is inserted at a site 3' to the sequence encoding ORF2 in a recombinant nucleic acid construct. In some embodiments the sequence that is desired to be transferred and incorporated into the genome of a cell is inserted within the 3'-UTR of ORF1 or ORF2, or both. In some embodiments, the polynucleotide sequence that is sequence that is desired to be transferred and incorporated into the genome of a cell is inserted upstream of the poly A tail of ORF2 in a recombinant nucleic acid construct.

In some embodiments, the sequence of a human retrotransposon encodes for two proteins that are translated from a single RNA containing two ORFs. In some embodiments, the two ORFs are non-overlapping ORFs. In some embodiments, the two ORFs are ORF1 and ORF2. In some embodiments, the ORF1 encodes ORF1p and ORF2 encodes ORF2p.

In some embodiments, the sequence of a human retrotransposon comprises a sequence of a non-LTR retrotransposon. In some embodiments, the sequence of a human retrotransposon comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase. In some embodiments, the endonuclease and/or a reverse transcriptase is ORF2p. In some embodiments, the reverse transcriptase is a group II intron reverse transcriptase domain. In some embodiments, the endonuclease and/or a reverse transcriptase is a minke whale endonuclease and/or a reverse transcriptase. In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA.

In some embodiments, provided herein is a polynucleotide construct comprising an mRNA wherein the mRNA comprises a sequence encoding a human retrotransposon, wherein, (i) the sequence of a human retrotransposon comprises a sequence encoding ORF1p, (ii) the mRNA does not comprise a sequence encoding ORF1p, or (iii) the mRNA comprises a replacement of the sequence encoding ORF1p with a 5' UTR sequence from the complement gene. In some embodiments, the mRNA comprises a first mRNA molecule encoding ORF1p, and a second mRNA molecule encoding an endonuclease and/or a reverse transcriptase. In some embodiments, the mRNA is an mRNA molecule comprising a first sequence encoding ORF1p, and a second sequence encoding an endonuclease and/or a reverse transcriptase. In some embodiments, the first sequence encoding ORF1p and the second sequence encoding an endonuclease and/or a reverse transcriptase are separated by a linker sequence.

In some embodiments, the linker sequence comprises an internal ribosome entry sequence (IRES). In some embodiments, the IRES is an IRES from CVB3 or EV71. In some embodiments, the linker sequence encodes a self-cleaving peptide sequence. In some embodiments, the linker sequence encodes a T2A, a E2A or a P2A sequence In some embodiments, the sequence of a human retrotransposon comprises a sequence that encodes ORF1p fused to an additional protein sequence and/or a sequence that encodes ORF2p fused to an additional protein sequence. In some embodiments, the ORF1p and/or the ORF2p is fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences. In some embodiments, the 5' UTR sequence or the 3' UTR sequence comprises a sequence that promotes or enhances interaction of a poly A tail of the mRNA with the endonuclease and/or a reverse transcriptase. In some embodiments, the 5' UTR sequence or the 3' UTR sequence comprises a sequence that promotes or enhances interaction of a poly-A-binding proteins (e.g., PABP) with the endonuclease and/or a reverse transcriptase. In some embodiments, the 5' UTR sequence or the 3' UTR sequence comprises a sequence that increases specificity of the endonuclease and/or a reverse transcriptase to the mRNA relative to another mRNA expressed by the cell. In some embodiments, the 5' UTR sequence or the 3' UTR sequence comprises an Alu element sequence.

In some embodiments, the first sequence encoding ORF1p and the second sequence encoding an endonuclease and/or a reverse transcriptase have the same promoter. In some embodiments, the insert sequence has a promoter that is different from the promoter of the first sequence encoding ORF1p. In some embodiments, the insert sequence has a promoter that is different from the promoter of the second sequence encoding an endonuclease and/or a reverse transcriptase. In some embodiments, the first sequence encoding ORF1p and/or the second sequence encoding an endonuclease and/or a reverse transcriptase have a promoter or transcription initiation site selected from the group consisting of an inducible promoter, a CMV promoter or transcription initiation site, a T7 promoter or transcription initiation site, an EF1a promoter or transcription initiation site and combinations thereof. In some embodiments, the insert sequence has a promoter or transcription initiation site selected from the group consisting of an inducible promoter, a CV promoter or transcription initiation site, a T7 promoter or transcription initiation site, an EF1a promoter or transcription initiation site and combinations thereof.

In some embodiments, the first sequence encoding ORF1p and the second sequence encoding an endonuclease and/or a reverse transcriptase are codon optimized for expression in a human cell.

In some embodiments, the mRNA comprises a WPRE element. In some embodiments, the mRNA comprises a selection marker. In some embodiments, the mRNA comprises a sequence encoding an affinity tag. In some embodiments, the affinity tag is linked to the sequence encoding an endonuclease and/or a reverse transcriptase.

In some embodiments, the 3' UTR comprises a poly A sequence or wherein a poly A sequence is added to the mRNA in vitro. In some embodiments, the poly A sequence is downstream of a sequence encoding an endonuclease and/or a reverse transcriptase. In some embodiments, the insert sequence is upstream of the poly A sequence.

In some embodiments, the 3' UTR sequence comprises the insert sequence. In some embodiments, the insert sequence comprises a sequence that is a reverse complement of the sequence encoding the exogenous polypeptide. In some embodiments, the insert sequence comprises a polyadenylation site. In some embodiments, the insert sequence comprises an SV40 polyadenylation site. In some embodiments, the insert sequence comprises a polyadenylation site upstream of the sequence that is a reverse complement of the sequence encoding the exogenous polypeptide. In some embodiments, the insert sequence is integrated into the genome at a locus that is not a ribosomal locus. In some embodiments, the insert sequence is integrated into the genome at a locus that is not a rDNA locus. In some embodiments, the insert sequence integrates into a gene or regulatory region of a gene, thereby disrupting the gene or downregulating expression of the gene. In some embodiments, the insert sequence integrates into a gene or regulatory region of a gene, thereby upregulating expression of the gene. In some embodiments, the insert sequence integrates into the genome and replaces a gene. In some embodiments, the insert sequence is stably integrated into the genome. In some embodiments, the insert sequence is retrotransposed into the genome. In some embodiments, the insert sequence is integrated into the genome by cleavage of a DNA strand of a target site by an endonuclease encoded by the mRNA. In some embodiments, the insert sequence is integrated into the genome via target-primed reverse transcription (TPRT). In some embodiments, the insert sequence is integrated into the genome via reverse splicing of the mRNA into a DNA target site of the genome.

In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell.

In some embodiments, the mRNA is a self-integrating mRNA. In some embodiments, the method comprises introducing into the cell the mRNA. In some embodiments, the method comprises introducing into the cell the vector encoding the mRNA. In some embodiments, the method comprises introducing the mRNA or the vector encoding the mRNA into a cell ex vivo. In some embodiments, the method further comprises administering the cell to a human subject. In some embodiments, the method comprises administering the mRNA or the vector encoding the mRNA to a human subject. In some embodiments, an immune response is not elicited in the human subject. In some embodiments, the mRNA or the vector is substantially non-immunogenic.

In some embodiments, the vector is a plasmid or a viral vector. In some embodiments, the vector comprises a non-LTR retrotransposon. In some embodiments, the vector comprises a human L1 element. In some embodiments, the vector comprises a L1 retrotransposon ORF1 gene. In some embodiments, the vector comprises a L1 retrotransposon ORF2 gene. In some embodiments, the vector comprises a L1 retrotransposon.

In some embodiments, the mRNA is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases.

In some embodiments, the mRNA comprises a sequence that inhibits or prevents degradation of the mRNA. In some embodiments, the sequence that inhibits or prevents degradation of the mRNA inhibits or prevents degradation of the mRNA by an exonuclease or an RNAse. In some embodiments, the sequence that inhibits or prevents degradation of the mRNA is a G quadruplex, pseudoknot or triplex sequence. In some embodiments, the sequence the sequence that inhibits or prevents degradation of the mRNA is an exoribonuclease-resistant RNA structure from a flaviviral RNA or an ENE element from KSV. In some embodiments, the sequence that inhibits or prevents degradation of the mRNA inhibits or prevents degradation of the mRNA by a deadenylase. In some embodiments, the sequence that inhibits or prevents degradation of the mRNA comprises non-adenosine nucleotides within or at a terminus of a poly A tail of the mRNA. In some embodiments, the sequence that inhibits or prevents degradation of the mRNA increases stability of the mRNA. In some embodiments, the exogenous sequence comprises a sequence encoding an exogenous polypeptide. In some embodiments, the sequence encoding an exogenous polypeptide is not in frame with a sequence encoding an endonuclease and/or a reverse transcriptase. In some embodiments, the sequence encoding an exogenous polypeptide is not in frame with a sequence encoding an endonuclease and/or a reverse transcriptase. In some embodiments, the exogenous sequence does not comprise introns. In some embodiments, the exogenous sequence comprises a sequence encoding an exogenous polypeptide selected from the group consisting of an enzyme, a receptor, a transport protein, a structural protein, a hormone, an antibody, a contractile protein and a storage protein. In some embodiments, the exogenous sequence comprises a sequence encoding an exogenous polypeptide selected from the group consisting of a chimeric antigen receptor (CAR), a ligand, an antibody, a receptor, and an enzyme. In some embodiments, the exogenous sequence comprises a regulatory sequence. In some embodiments, the regulatory sequence comprises a cis-acting regulatory sequence. In some embodiments, the regulatory sequence comprises a cis-acting regulatory sequence selected from the group consisting of an enhancer, a silencer, a promoter or a response element. In some embodiments, the regulatory sequence comprises a trans-acting regulatory sequence. In some embodiments, the regulatory sequence comprises a trans-acting regulatory sequence that encodes a transcription factor.

In some embodiments, integration of the insert sequence does not adversely affect cell health. In some embodiments, the endonuclease, the reverse transcriptase or both are capable of site-specific integration of the insert sequence.

In some embodiments, the mRNA comprises a sequence encoding an additional nuclease domain or a nuclease domain that is not derived from ORF2. In some embodiments, the mRNA comprises a sequence encoding a megaTAL nuclease domain, a TALEN domain, a Cas9 domain, a zinc finger binding domain from an R2 retroelement, or a DNA binding domain that binds to repetitive sequences such as a Rep78 from AAV. In some embodiments, the endonuclease comprises a mutation that reduces activity of the endonuclease compared to the endonuclease without the mutation. In some embodiments, the endonuclease is an ORF2p endonuclease and the mutation is S228P. In some embodiments, the mRNA comprises a sequence encoding a domain that increases fidelity and/or processivity of the reverse transcriptase. In some embodiments, the reverse transcriptase is a reverse transcriptase from a retroelement other than ORF2 or reverse transcriptase that has higher fidelity and/or processivity compared to a reverse transcriptase of ORF2p. In some embodiments, the reverse transcriptase is a group II intron reverse transcriptase. In some embodiments, the group II intron reverse transcriptase is a group IIA intron reverse transcriptase, a group IIB intron reverse transcriptase, or a group IIC intron reverse transcriptase. In some embodiments, the group II intron reverse transcriptase is TGIRT-II or TGIRT-III.

In some embodiments, the mRNA comprises a sequence comprising an Alu element and/or a ribosome binding aptamer. In some embodiments, the mRNA comprises a sequence encoding a polypeptide comprising a DNA binding domain. In some embodiments, the 3' UTR sequence is derived from a viral 3' UTR or a beta-globin 3' UTR.

In one aspect, provided herein is a composition comprising a recombinant mRNA or vector encoding an mRNA, wherein the mRNA comprises a human LINE-1 transposon sequence comprising a human LINE-1 transposon 5' UTR sequence, a sequence encoding ORF1p downstream of the human LINE-1 transposon 5' UTR sequence, an inter-ORF linker sequence downstream of the sequence encoding ORF1p,a sequence encoding ORF2p downstream of the inter-ORF linker sequence, and a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element.

In some embodiments, the insert sequence integrates into the genome of a cell when introduced into the cell. In some embodiments, the insert sequence integrates into a gene associated a condition or disease, thereby disrupting the gene or downregulating expression of the gene. In some embodiments, the insert sequence integrates into a gene, thereby upregulating expression of the gene. In some embodiments, the recombinant mRNA or vector encoding the mRNA is isolated or purified.

In one aspect, provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic.

In some embodiments, the composition comprises human ORF1p and human ORF2p proteins. In some embodiments, the composition comprises a ribonucleoprotein (RNP) comprising human ORF1p and human ORF2p complexed to the nucleic acid. In some embodiments, the nucleic acid is mRNA.

In one aspect, provided herein is a composition comprising a cell comprising a composition described herein. In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell. In some embodiments, the insert sequence is a reverse complement of a sequence encoding an exogenous polypeptide and the exogenous polypeptide is a chimeric antigen receptor (CAR).

In one aspect, provided herein is a pharmaceutical composition comprising a composition described herein, and a pharmaceutically acceptable excipient. In some embodiments, the pharmaceutical composition is for use in gene therapy. In some embodiments, the pharmaceutical composition is for use in the manufacture of a medicament for treating a disease or condition. In some embodiments, the pharmaceutical composition is for use in treating a disease or condition. In one aspect, provided herein is a method of treating a disease in a subject, comprising administering a pharmaceutical composition described herein to a subject with a disease or condition. In some embodiments, the method increases an amount or activity of a protein or functional RNA in the subject. In some embodiments, the subject has a deficient amount or activity of a protein or functional RNA. In some embodiments, the deficient amount or activity of a protein or functional RNA is associated with or causes the disease or condition.

In some embodiments, the method further comprising administering an agent that inhibits human silencing hub (HUSH) complex, an agent that inhibits FAM208A, or an agent that inhibits TRIM28. In some embodiments, the agent that inhibits human silencing hub (HUSH) complex is an agent that inhibits Periphilin, TASOR and/or MPP8. In some embodiments, the agent that inhibits human silencing hub (HUSH) complex inhibits assembly of the HUSH complex. In some embodiments, the agent inhibits the fanconia anemia complex. In some embodiments, the agent inhibits FANCD2-FANC1 heterodimer monoubiquitination. In some embodiments, the agent inhibits FANCD2-FANC1 heterodimer formation. In some embodiments the agent inhibits the Fanconi Anemia (FA) core complex. FA core complex is a component of the fanconi anemia DNA damage repair pathway, e.g., in chemotherapy induced DNA inter-strand crosslinks. The FA core complex comprises two central dimers of the FANCB and FA-associated protein of 100 kDa (FAAP100) subunits, flanked by two copies of the RING finger subunit, FANCL. These two heterotrimers act as a scaffold to assemble the remaining five subunits, resulting in an extended asymmetric structure. Destabilization of the scaffold would disrupt the entire complex, resulting in a non-functional FA pathway. Examples of agents that can inhibit the FA core complex include Bortezomib and curcumin analogs EF24 and 4H-TTD.

Accordingly, it is an object of the present invention to provide novel transposon-based vectors useful in providing gene therapy to an animal. It is an object of the present invention to provide novel transposon-based vectors for use in the preparation of a medicament useful in providing gene therapy to an animal or human. It is another object of the present invention to provide novel transposon-based vectors that encode for the production of desired proteins or peptides in cells. Yet another object of the present invention to provide novel transposon-based vectors that encode for the production of desired nucleic acids in cells. It is a further object of the present invention to provide methods for cell and tissue specific incorporation of transposon-based DNA or RNA constructs comprising targeting a selected gene to a specific cell or tissue of an animal. It is yet another object of the present invention to provide methods for cell and tissue specific expression of transposon-based DNA or RNA constructs comprising designing a DNA or RNA construct with cell specific promoters that enhance stable incorporation of the selected gene by the transposase and expressing the selected gene in the cell. It is an object of the present invention to provide gene therapy for generations through germ line administration of a transposon-based vector. Another object of the present invention is to provide gene therapy in animals through non germ line administration of a transposon-based vector. Another object of the present invention is to provide gene therapy in animals through administration of a transposon-based vector, wherein the animals produce desired proteins, peptides or nucleic acids. Yet another object of the present invention is to provide gene therapy in animals through administration of a transposon-based vector, wherein the animals produce desired proteins or peptides that are recognized by receptors on target cells. Still another object of the present invention is to provide gene therapy in animals through administration of a transposon-based vector, wherein the animals produce desired fusion proteins or fusion peptides, a portion of which are recognized by receptors on target cells, in order to deliver the other protein or peptide component of the fusion protein or fusion peptide to the cell to induce a biological response. Yet another object of the present invention is to provide a method for gene therapy of animals through administration of transposon-based vectors comprising tissue specific promoters and a gene of interest to facilitate tissue specific incorporation and expression of a gene of interest to produce a desired protein, peptide or nucleic acid. Another object of the present invention is to provide a method for gene therapy of animals through administration of transposon-based vectors comprising cell specific promoters and a gene of interest to facilitate cell specific incorporation and expression of a gene of interest to produce a desired protein, peptide or nucleic acid. Still another object of the present invention is to provide a method for gene therapy of animals through administration of transposon-based vectors comprising cell specific promoters and a gene of interest to facilitate cell specific incorporation and expression of a gene of interest to produce a desired protein, peptide or nucleic acid, wherein the desired protein, peptide or nucleic acid has a desired biological effect in the animal.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." herein), of which:

DETAILED DESCRIPTION

Figure 1A:
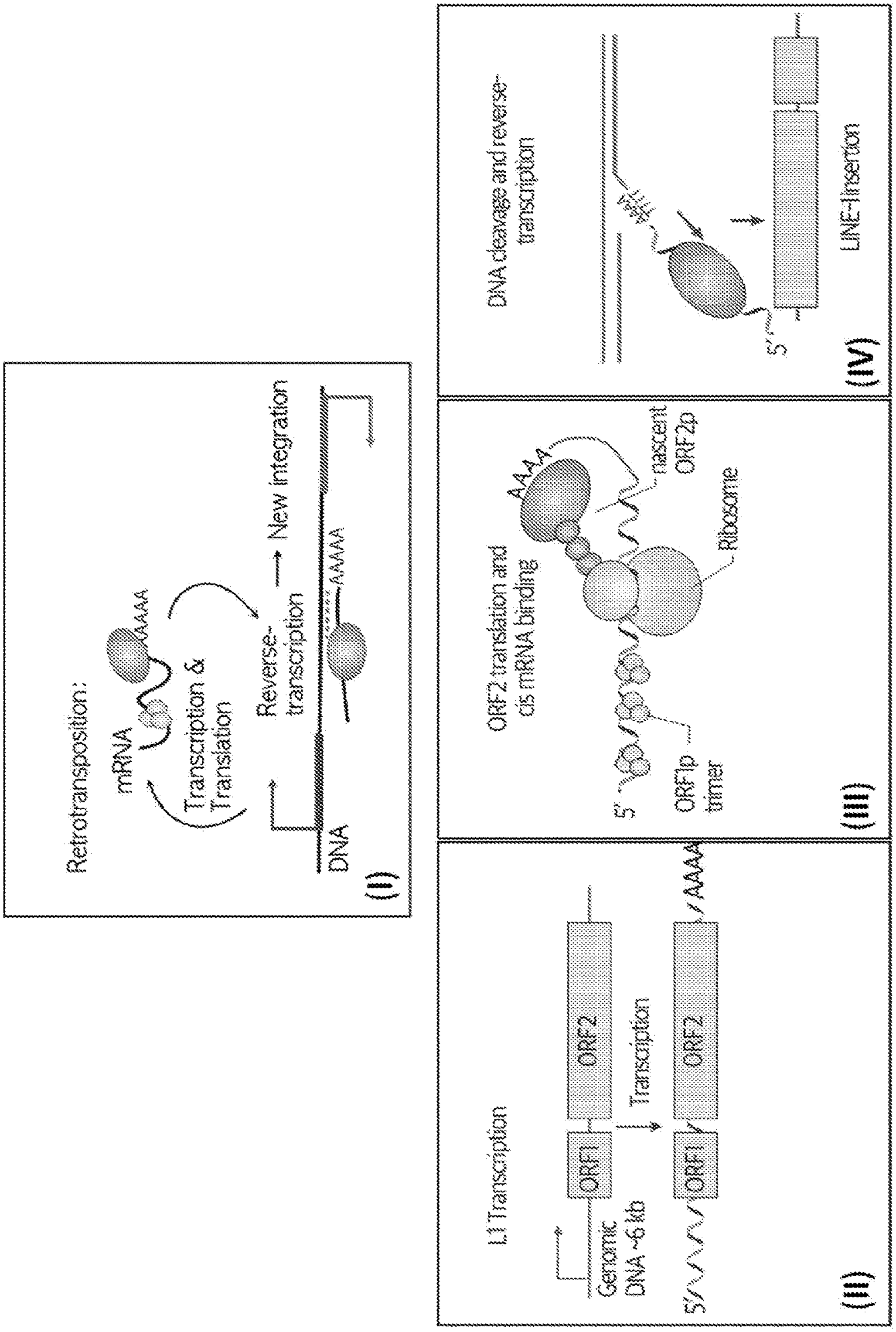
FIG. 1A illustrates a general mechanism of action of retrotransposons. (I) is a schematic representing the overall lifecycle of an autonomous retrotransposon. (II) LINE-1 retrotransposon comprises LINE-1 elements, which encode two proteins ORF1p and ORF2p that are expressed as mRNAs. The bicistronic mRNA is translated into the two proteins, and when ORF2p is translated by a read-through event by the ribosome, it binds the 3'end of its own mRNA through the poly A tail (III). ORF2p cleaves at a consensus sequence TAAAA, where the poly A at the 3' end of the mRNA hybridizes and primes the reverse transcriptase activity of the ORF2 protein. The protein reverse-transcribes the mRNA back into DNA leading to an insertion of the LINE-1 sequence back into a new location in the genome (IV).

The present invention arises in part from the exciting discovery that a polynucleotide could be designed and developed to accomplish transfer and integration of a genetic cargo (e.g., large genetic cargo) into the genome of a cell. In some embodiments, the polynucleotide comprises (i) a genetic material for stable expression, and (ii) a self-integrating genomic integration machinery that allows stable integration of the genetic material into a cell by non-viral means, that is both safe and efficacious. Moreover, the genetic material may be integrated at a locus other than a ribosomal locus; the genetic material may be integrated site-specifically; and/or the integrated genetic material appear to express without triggering a cell's natural silencing machinery.

Clustered Regularly-Interspaced Short Palindromic Repeats (CRISPR) revolutionized the molecular biology field and has developed into a potent gene editing too. It utilizes homology-directed repair (HDR) and can be directed to a genomic site. CRISPR/Cas9 is a naturally occurring RNA-guided endonuclease. While the CRISPR/Cas9 system has demonstrated great promise for site-specific gene editing and other applications, there are several factors that influence its efficacy which must be addressed, especially if it is to be used for in vivo human gene therapy. These factors include target DNA site selection, sgRNA design, off-target cutting, incidence/efficiency of HDR vs. NHEJ, Cas9 activity, and the method of delivery. Delivery remains the major obstacle for use of CRISPR for in vivo applications. Zinc finger nucleases ZFNs are a fusion protein of Cys2-His2 zinc finger proteins (ZFPs) and a non-specific DNA restriction enzyme derived from FokI endonucleases. Challenges with ZFPs include design and engineering of the ZFP for high-affinity binding of the desired sequence, which is non-trivial. Also, not all sequences are available for ZFP binding, so site selection is limited. Another significant challenge is off-target cutting. Transcription activator-like effector nucleases (TALENs) are a fusion protein comprised of a TALE and a FokI nuclease. While off-target cutting remains a concern, TALENs have been shown in one side-by-side comparison study to be more specific and less cytotoxic than ZFNs. However, TALENs are substantially larger, and the cDNA encoding TALEN only is 3 kb. This makes delivery of a pair of TALENs more challenging than a pair of ZFNs due to delivery vehicle cargo size limitations. Further, packaging and delivery of TALENs in some viral vectors may be problematic due to the high level of repetition in the TALENs sequence. A mutant Cas9 system, a fusion protein of inactive dCas9 and a FokI nuclease dimer increase specificity and reduce off-target cutting, the number of potential target sites is lower due to PAM and other sgRNA design constraints.

The present invention addresses the problems described above by providing new, effective and efficient compositions comprising transposon-based vectors for providing therapy, including gene therapy, to animals and humans. The present invention provides methods of using these compositions for providing therapy to animals and humans. These transposon-based vectors can be used in the preparation of a medicament useful for providing a desired effect to a recipient following administration. Gene therapy includes, but is not limited to, introduction of a gene, such as an exogenous gene, into an animal using a transposon-based vector. These genes may serve a variety of functions in the recipient such as coding for the production of nucleic acids, for example RNA, or coding for the production of proteins and peptides. The present invention can facilitate efficient incorporation of the polynucleotide sequences, including the genes of interest, promoters, insertion sequences, poly A and any regulatory sequences. The invention is based on the finding that human LINE-1 elements are capable of retrotransposition in human cells as well as cells of other animal species and can be manipulated in a versatile manner to achieve efficient delivery and integration of a genetic cargo into the genome of a cell. Such LINE-1 elements have a variety of uses in human and animal genetics including, but not limited to, uses in diagnosis and treatment of genetic disorders and in cancer. The LINE-1 elements of the invention are also useful for the treatment of various phenotypic effects of various diseases. For example, LINE-1 elements may be used for transfer of DNA encoding anti-tumorigenic gene products into cancer cells. Other uses of the LINE-1 elements of the invention will become apparent to the skilled artisan upon a reading of the present specification.

In general, a human LINE-1 element comprises a 5' UTR with an internal promoter, two non-overlapping reading frames (ORF1 and ORF2), a 200 bp 3' UTR and a 3' poly A tail. The LINE-1 retrotransposon can also comprise an endonuclease domain at the LINE-1 ORF2 N-terminus. The finding that LINE-1 encodes an endonuclease demonstrates that the element is capable of autonomous retrotransposition. LINE-1 is a modular protein that contains non-overlapping functional domains which mediate its reverse transcription and integration. In some embodiments, the sequence specificity of the LINE-1 endonuclease itself can be altered or the LINE-1 endonuclease can be replaced with another site-specific endonuclease.

The LINE-1 retrotransposon may be manipulated using recombinant DNA technology to comprise and/or be contiguous with, other DNA elements which render the retrotransposon suitable for insertion of substantial lengths (up to 1 kb, or greater than 1 kb) of heterologous or homologous DNA into the genome of a cell. The LINE-1 retrotransposon may also be manipulated using the same type of technology such that insertion of the DNA into the genome of a cell is site-directed (site into which such DNA is inserted is known). Alternatively, the LINE-1 retrotransposon may be manipulated such that the insertion site of the DNA is random. The retrotransposon may also be manipulated to effect insertion of a desired DNA sequence into regions of DNA which are normally transcriptionally silent, wherein the DNA sequence is expressed in a manner such that it does not disrupt the normal expression of genes in the cell. In some embodiments, the integration or retrotransposition is in the trans orientation. In some embodiments, the integration or retrotransposition occurs in the cis orientation.

Since LINE-1 is native to human cells, when the constructs are placed into human cells, they should not be rejected by the immune system as foreign. In addition, the mechanism of LINE-1 retrointegration ensures that only one copy of the gene is integrated at any specific chromosomal location. Accordingly, there is a copy number control built into the system. In contrast, gene transfer procedures using ordinary plasmids offer little or no control regarding copy number and often result in complex arrays of DNA molecules tandemly integrated into the same genomic location.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, may be used interchangeably. These terms may convey that any combination is specifically contemplated. Solely for illustrative purposes, the following phrases "A, B, and/or C" or "A, B, C, or any combination thereof" may mean "A individually; B individually; C individually; A and B; B and C; A and C; and A, B, and C." The term "or" may be used conjunctively or disjunctively, unless the context specifically refers to a disjunctive use.

The term "about" or "approximately" may mean within an acceptable error range for the particular value as determined by one of ordinary skill in the art, which will depend in part on how the value is measured or determined, i.e., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Alternatively, particularly with respect to biological systems or processes, the term may mean within an order of magnitude, within 5-fold, and more preferably within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification may be implemented with respect to any method or composition of the present disclosure, and vice versa. Furthermore, compositions of the present disclosure may be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Applications of the present disclosure encompasses, but are not limited to methods and compositions related to expression of an exogenous nucleic acid in a cell. In some embodiments, the exogenous nucleic acid is configured for stable integration in the genome of a cell, such as a myeloid cell. In some embodiments, the stable integration of the exogenous nucleic acid may be at specific targets within the genome. In some embodiments, the exogenous nucleic acid comprises one or more coding sequences. In some embodiments, the exogenous nucleic acid may comprise one or more coding comprising a nucleic acid sequence encoding an immune receptor. In some embodiments, the present disclosure provides methods and compositions for a stable incorporation of a nucleic acid encoding a transmembrane receptor implicated in an immune response function (e.g. a phagocytic receptor or synthetic chimeric antigen receptor) into human macrophage or dendritic cell or a suitable myeloid cell or a myeloid precursor cell. An exogenous nucleic acid can refer to a nucleic acid that was not originally in a cell and is added from outside the cell, irrespective of whether it comprises a sequence that may already be present in the cell endogenously. An exogenous nucleic acid may be a DNA or an RNA molecule. An exogenous nucleic acid may comprise a sequence encoding a transgene. An exogenous nucleic acid may encode a recombinant protein, such as a recombinant receptor, or a chimeric antigen receptor (CAR). An exogenous nucleic acid may be referred to as a "genetic cargo" in the context of the exogenous nucleic acid being delivered inside a cell. The genetic cargo may be a DNA or an RNA. Genetic material can generally be delivered inside a cell ex vivo by a few different known techniques using either chemical ($CaCl_2$— medicated transfection), or physical (electroporation), or biological (e.g. viral infection or transduction) means.

In one aspect, provided herein are methods and compositions for delivery inside a cell, for example a myeloid cell and stable incorporation of one or more nucleic acids, comprising nucleic acid sequences encoding one or more proteins, wherein the stable incorporation may be via non-viral mechanisms. In some embodiments, the delivery of a nucleic acid composition into a myeloid cell is via a non-viral mechanism. In some embodiments, the delivery of the nucleic acids may further bypass plasmid mediated delivery. A "plasmid," as used herein, refers to a non-viral expression vector, e.g., a nucleic acid molecule that encodes for genes and/or regulatory elements necessary for the expression of genes. A "viral vector," as used herein, refers to a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

In some embodiments, provided herein is a method of delivering a composition inside a cell, such as in a myeloid cell, the composition comprising one or more nucleic acid sequences encoding one or more proteins, wherein the one or more nucleic acid sequences is an RNA. In some embodiments, the RNA is mRNA. In some embodiments, one or more mRNA comprising one or more nucleic acid sequences are delivered. In some embodiments, the one or more mRNA may comprise at least one modified nucleotide. The term "nucleotide," as used herein, refers to a base-sugar-phosphate combination. A nucleotide may comprise a synthetic nucleotide. A nucleotide may comprise a synthetic nucleotide analog. Nucleotides may be monomeric units of a nucleic acid sequence (e.g. deoxyribonucleic acid (DNA) and ribonucleic acid (RNA)). The term nucleotide may include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, or derivatives thereof. Such derivatives may include, for example, [aS]dATP, 7-deaza-dGTP and 7-deaza-dATP, and nucleotide derivatives that confer nuclease resistance on the nucleic acid molecule containing them. The term nucleotide as used herein may refer to dideoxyribonucleoside triphosphates (ddNTPs) and their derivatives. Illustrative examples of dideoxyribonucleoside triphosphates may include, but are not limited to, ddATP, ddCTP, ddGTP, ddITP, and ddTTP. A nucleotide may be unlabeled or detectably labeled by well-known techniques. Labeling may also be carried out with quantum dots. Detectable labels may include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,NcN'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides may include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAN1RA] ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, TR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-1 4-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides may also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-cICTP, biotin-14-dCTP), and biotin-dUTP (e.g. biotin-11-dUTP, biotin-1.6-dUTP, biotin-20-dUTP).

The terms “polynucleotide,” “oligonucleotide,” and “nucleic acid” are used interchangeably to refer to a polymeric form of nucleotides of any length, either deoxyribonucleotides or ribonucleotides, or analogs thereof, either in single-, double-, or multi-stranded form. A polynucleotide may be exogenous or endogenous to a cell. A polynucleotide may exist in a cell-free environment. A polynucleotide may be a gene or fragment thereof. A polynucleotide may be DNA. A polynucleotide may be RNA. A polynucleotide may have any three-dimensional structure, and may perform any function, known or unknown. A polynucleotide may comprise one or more analogs (e.g. altered backbone, sugar, or nucleobase). If present, modifications to the nucleotide structure may be imparted before or after assembly of the polymer. Some non-limiting examples of modified nucleotides or analogs include: pseudouridine, 5-bromouracil, 5-methylcytosine, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, eDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides may be interrupted by non-nucleotide components.

In some embodiments, the nucleic acid composition may comprise one or more mRNA, comprising at least one mRNA encoding a transmembrane receptor implicated in an immune response function (e.g. a phagocytic receptor or synthetic chimeric antigen receptor) into human macrophage or dendritic cell or a suitable myeloid cell or a myeloid precursor cell. In some embodiments, the nucleic acid composition comprises one or more mRNA, and one or more lipids for delivery of the nucleic acid into a cell of hematopoietic origin, such as a myeloid cell or a myeloid cell precursor cell. In some embodiments, the one or more lipids may form a liposomal complex.

As used herein, the composition described herein may be used for delivery inside a cell. A cell may originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, pumpkin, hay, potatoes, cotton, *Cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. Agardh*, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell may not be originating from a natural organism (e.g. a cell may be a synthetically made, sometimes termed an artificial cell). In some embodiments, the cell referred to herein is a mammalian cell. In some embodiments, the cell is a human cell. The methods and compositions described herein relates to incorporating a genetic material in a cell, more specifically a human cell, wherein the human cell can be any human cell. As used herein, a human cell may be of any origin, for example, a somatic cell, a neuron, a fibroblast, a muscle cell, an epithelial cell, a cardiac cell, or a hematopoietic cell. The methods and compositions described herein can also be applicable to and useful for incorporating exogenous nucleic acid in hard-to-transfect human cell. The methods are simple and universally applicable, once a suitable exogenous nucleic acid construct has been designed and developed. The methods and compositions described herein are applicable to incorporate an exogenous nucleic acid in a cell ex vivo. In some embodiments, the compositions may be applicable for systemic administration in an organism, where the nucleic acid material in the composition may be taken up by a cell in vivo, whereupon it is incorporated in cell in vivo.

In some embodiments, the methods and compositions described herein may be directed to incorporating an exogenous nucleic acid in a human hematopoietic cell, for example, a human cell of hematopoietic origin, such as a human myeloid cell or a myeloid cell precursor. However, the methods and compositions described herein can be used or made suitable for use in any biological cell with minimum modifications. Therefore, a cell as may refer to any cell that is a basic structural, functional and/or biological unit of a living organism.

In one aspect, provided herein are methods and compositions for utilizing transposable elements for stable incorporation of one or more nucleic acids into the genome of a cell, where the cell is a member of a hematopoietic cells, for example a myeloid cell. In some embodiments, the one or more nucleic acids comprise at least one nucleic acid sequence encoding a transmembrane receptor protein having a role in immune response. In some embodiments, the methods and compositions are directed to using a retrotransposable element for incorporating one or more nucleic acid sequences into a myeloid cell. The nucleic acid composition may comprise one or more nucleic sequences, such as a gene, where the gene is a transgene. The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and may include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene may refer to an "endogenous gene" or a native gene in its natural location in the genome of an organism. A gene may refer to an "exogenous gene" or a non-native gene. A non-native gene may refer to a gene not normally found in the host organism, but which is introduced into the host organism by gene transfer. A non-native gene may also refer to a gene not in its natural location in the genome of an organism. A non-native gene may also refer to a naturally occurring nucleic acid or polypeptide sequence that comprises mutations, insertions and/or deletions (e.g., non-native sequence).

The term "transgene" refers to any nucleic acid molecule that is introduced into a cell, that may be intermittently termed herein as a recipient cell. The resultant cell after receiving a transgene may be referred to a transgenic cell. A transgene may include a gene that is partly or entirely heterologous (i.e., foreign) to the transgenic organism or cell, or may represent a gene homologous to an endogenous gene of the organism or cell. In some cases, transgenes include any polynucleotide, such as a gene that encodes a polypeptide or protein, a polynucleotide that is transcribed into an inhibitory polynucleotide, or a polynucleotide that is not transcribed (e.g., lacks an expression control element, such as a promoter that drives transcription). Transcripts and encoded polypeptides may be collectively referred to as "gene product." If the polynucleotide is derived from genomic DNA, expression may include splicing of the mRNA in a eukaryotic cell. "Up-regulated," with reference to expression, refers to an increased expression level of a polynucleotide (e.g., RNA such as mRNA) and/or polypeptide sequence relative to its expression level in a wild-type state while "down-regulated" refers to a decreased expression level of a polynucleotide (e.g., RNA such as mRNA) and/or polypeptide sequence relative to its expression in a wild-type state. Expression of a transfected gene may occur transiently or stably in a cell. During "transient expression" the transfected gene is not transferred to the daughter cell during cell division. Since its expression is restricted to the transfected cell, expression of the gene is lost over time. In contrast, stable expression of a transfected gene may occur when the gene is co-transfected with another gene that confers a selection advantage to the transfected cell. Such a selection advantage may be a resistance towards a certain toxin that is presented to the cell. Where a transfected gene is required to be expressed, the application envisages the use of codon-optimized sequences. An example of a codon optimized sequence may be a sequence optimized for expression in a eukaryote, e.g., humans (i.e. being optimized for expression in humans), or for another eukaryote, animal or mammal. Codon optimization for a host species other than human, or for codon optimization for specific organs is known. In some embodiments, the coding sequence encoding a protein may be codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. Codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell may generally reflect the codons used most frequently in peptide synthesis. Accordingly, genes may be tailored for optimal gene expression in a given organism based on codon optimization. Codon usage tables are readily available, for example, at the "Codon Usage Database" available at www.kazusa.orjp/codon/and these tables may be adapted in a number of ways. Computer algorithms for codon optimizing a particular sequence for expression in a particular host cell are also available, such as Gene Forge (Aptagen; Jacobus, PA), are also available.

A "multicistronic transcript" as used herein refers to an mRNA molecule that contains more than one protein coding region, or cistron. A mRNA comprising two coding regions is denoted a "bicistronic transcript." The "5'-proximal" coding region or cistron is the coding region whose translation initiation codon (usually AUG) is closest to the 5' end of a multicistronic mRNA molecule. A "5'-distal" coding region or cistron is one whose translation initiation codon (usually AUG) is not the closest initiation codon to the 5' end of the mRNA.

The terms "transfection" or "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The term "promoter," as used herein, refers to a polynucleotide sequence capable of driving transcription of a coding sequence in a cell. Thus, promoters used in the polynucleotide constructs of the disclosure include cis-acting transcriptional control elements and regulatory sequences that are involved in regulating or modulating the timing and/or rate of transcription of a gene. For example, a promoter may be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions, developmental conditions, or drug or chemical conditions. Exemplary inducible promoter may be a doxycycline or a tetracycline inducible promoter. Tetracycline regulated promoters may be both tetracycline inducible or tetracycline repressible, called the tet-on and tet-off systems. The tet regulated systems rely on two components, i.e., a tetracycline-controlled regulator (also referred to as transactivator) (tTA or rtTA) and a tTA/rtTA-dependent promoter that controls expression of a downstream cDNA, in a tetracycline-dependent manner. tTA is a fusion protein containing the repressor of the Tn10 tetracycline-resistance operon of *Escherichia coli* and a carboxyl-terminal portion of protein 16 of herpes simplex virus (VP16). The tTA-dependent promoter consists of a minimal RNA polymerase II promoter fused to tet operator (tetO) sequences (an array of seven cognate operator sequences). This fusion converts the tet repressor into a strong transcriptional activator in eukaryotic cells. In the absence of tetracycline or its derivatives (such as doxycycline), tTA binds to the tetO sequences, allowing transcriptional activation of the tTA-dependent promoter. However, in the presence of doxycycline, tTA cannot interact with its target and transcription does not occur. The tet system that uses tTA is termed tet-OFF, because tetracycline or doxycycline allows transcriptional down-regulation. In contrast, in the tet-ON system, a mutant form of tTA, termed rtTA, has been isolated using random mutagenesis. In contrast to tTA, rtTA is not functional in the absence of doxycycline but requires the presence of the ligand for transactivation. The term "exon" refers to a nucleic acid sequence found in genomic DNA that is bioinformatically predicted and/or experimentally confirmed to contribute contiguous sequence to a mature mRNA transcript. The term "intron" refers to a sequence present in genomic DNA that is bioinformatically predicted and/or experimentally confirmed to not encode part of or all of an expressed protein, and which, in endogenous conditions, is transcribed into RNA (e.g. pre-mRNA) molecules, but which is spliced out of the endogenous RNA (e.g. the pre-mRNA) before the RNA is translated into a protein.

The term "splice acceptor site" refers to a sequence present in genomic DNA that is bioinformatically predicted and/or experimentally confirmed to be the acceptor site during splicing of pre-mRNA, which may include identified and unidentified natural and artificially derived or derivable splice acceptor sites.

An "internal ribosome entry site" or "IRES" refers to a nucleotide sequence that allows for 5'-end/cap-independent initiation of translation and thereby raises the possibility to express 2 proteins from a single messenger RNA (mRNA) molecule. IRESs are commonly located in the 5' UTR of positive-stranded RNA viruses with uncapped genomes. Another means to express 2 proteins from a single mRNA molecule is by insertion of a 2A peptide(-like) sequence in between their coding sequence. 2A peptide(-like) sequences mediate self-processing of primary translation products by a process variously referred to as "ribosome skipping", "stop-go" translation and "stop carry-on" translation. 2A peptide (-like) sequences are present in various groups of positive- and double-stranded RNA viruses including Picornaviridae, Flaviviridae, Tetraviridae, Dicistroviridae, Reoviridae and Totiviridae.

The term "2A peptide" refers to a class of 18-22 amino-acid (AA)-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (*Thosea asigna* virus 2A) were also identified. The mechanism of 2A-mediated "self-cleavage" is believed to be ribosome skipping the formation of a glycyl-prolyl peptide bond at the C-terminus of the 2A sequence. 2A peptide(-like) sequences mediate self-processing of primary translation products by a process variously referred to as "ribosome skipping", "stop-go" translation and "stop carry-on" translation. 2A peptide(-like) sequences are present in various groups of positive- and double-stranded RNA viruses including Picornaviridae, Flaviviridae, Tetraviridae, Dicistroviridae, Reoviridae and Totiviridae.

As used herein, the term "operably linked" refers to a functional relationship between two or more segments, such as nucleic acid segments or polypeptide segments. Typically, it refers to the functional relationship of a transcriptional regulatory sequence to a transcribed sequence.

The term "termination sequence" refers to a nucleic acid sequence which is recognized by the polymerase of a host cell and results in the termination of transcription. The termination sequence is a sequence of DNA that, at the 3' end of a natural or synthetic gene, provides for termination of mRNA transcription or both mRNA transcription and ribosomal translation of an upstream open reading frame. Prokaryotic termination sequences commonly comprise a GC-rich region that has a two-fold symmetry followed by an AT-rich sequence. A commonly used termination sequence is the T7 termination sequence. A variety of termination sequences are known in the art and may be employed in the nucleic acid constructs of the present invention, including the TINT3, TL13, TL2, TR1, TR2, and T6S termination signals derived from the bacteriophage lambda, and termination signals derived from bacterial genes, such as the trp gene of *E. coli.*

The terms "polyadenylation sequence" (also referred to as a "poly A site" or "poly A sequence") refers to a DNA sequence which directs both the termination and polyadenylation of the nascent RNA transcript. Efficient polyadenylation of the recombinant transcript is desirable, as transcripts lacking a poly A tail are typically unstable and rapidly degraded. The poly A signal utilized in an expression vector may be "heterologous" or "endogenous". An endogenous poly A signal is one that is found naturally at the 3' end of the coding region of a given gene in the genome. A heterologous poly A signal is one which is isolated from one gene and placed 3' of another gene, e.g., coding sequence for a protein. A commonly used heterologous poly A signal is the SV40 poly A signal. The SV40 poly A signal is contained on a 237 bp BamHI/BclI restriction fragment and directs both termination and polyadenylation; numerous vectors contain the SV40 poly A signal. Another commonly used heterologous poly A signal is derived from the bovine growth hormone (BGH) gene; the BGH poly A signal is also available on a number of commercially available vectors. The poly A signal from the Herpes simplex virus thymidine kinase (HSV tk) gene is also used as a poly A signal on a number of commercial expression vectors. The polyadenylation signal facilitates the transportation of the RNA from within the cell nucleus into the cytosol as well as increases cellular half-life of such an RNA. The polyadenylation signal is present at the 3'-end of an mRNA.

The terms "complement," "complements," "complementary," and "complementarity," as used herein, refer to a sequence that is complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/embossneedle/nucleotide.html), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.ukaools/psa/emboss_water/nucleotide.html, optionally with default settings). Optimal alignment can be assessed using any suitable parameters of a chosen algorithm, including default parameters.

Complementarity may be perfect or substantial/sufficient. Perfect complementarity between two nucleic acids may mean that the two nucleic acids may form a duplex in which every base in the duplex is bonded to a complementary base by Watson-Crick pairing. Substantial or sufficient complementary may mean that, a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions may be predicted by using the sequences and standard mathematical calculations to predict the melting temperature ($T_m$) of hybridized strands, or by empirical determination of $T_m$ by using routine methods.

"Transposons" as used herein are segments within the chromosome that can translocate within the genome, also known as "jumping gene". There are two different classes of transposons: class 1, or retrotransposons, that mobilize via an RNA intermediate and a "copy-and-paste" mechanism, and class II, or DNA transposons, that mobilize via excision integration, or a "cut-and-paste" mechanism (Ivics Nat Methods 2009). Bacterial, lower eukaryotic (e.g. yeast) and invertebrate transposons appear to be largely species specific, and cannot be used for efficient transposition of DNA in vertebrate cells. "Sleeping Beauty" (Ivics Cell 1997), was the first active transposon that was artificially reconstructed by sequence shuffling of inactive TEs from fish. This made it possible to successfully achieve DNA integration by transposition into vertebrate cells, including human cells. Sleeping Beauty is a class II DNA transposon belonging to the Tcl/mariner family of transposons (Ni Genomics Proteomics 2008). In the meantime, additional functional transposons have been identified or reconstructed from different species, including *Drosophila*, frog and even human genomes, that all have been shown to allow DNA transposition into vertebrate and also human host cell genomes. Each of these transposons have advantages and disadvantages that are related to transposition efficiency, stability of expression, genetic payload capacity etc. Exemplary class II transposases that have been created include Sleeping Beauty, PiggyBac, Frog Prince, Himar1, Passport, Minos, hAT, Tol1, Tol2, AciDs, PIF, Harbinger, Harbinger3-DR, and Hsmar1.

"Heterologous" as used herein, includes molecules such as DNA and RNA which may not naturally be found in the cell into which it is inserted. For example, when mouse or bacterial DNA is inserted into the genome of a human cell, such DNA is referred to herein as heterologous DNA. In contrast, the term "homologous" as used herein, denotes molecules such as DNA and RNA that are found naturally in the cell into which it is inserted. For example, the insertion of mouse DNA into the genome of a mouse cell constitutes insertion of homologous DNA into that cell. In the latter case, it is not necessary that the homologous DNA be inserted into a site in the cell genome in which it is naturally found; rather, homologous DNA may be inserted at sites other than where it is naturally found, thereby creating a genetic alteration (a mutation) in the inserted site.

A "transposase" is an enzyme that is capable of forming a functional complex with a transposon end-containing composition (e.g., transposons, transposon ends), and catalyze insertion or transposition of the transposon end-containing composition into double stranded DNA which is incubated with an in vitro transposon reaction. The term "transposon end" means a double-stranded DNA that contains the nucleotide sequences (the "transposon end sequences") necessary to form the complex with the transposase or integrase enzyme that is functional in an in vitro transposition reaction.

A transposon end forms a complex or a synaptic complex or a transposon complex or a transposon composition with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a transferred transposon end sequence or transferred strand and a non-transferred transposon end sequence, or non-transferred strand For example, one transposon end that forms a complex with a hyperactive Tn5 transposase that is active in an in vitro transposition reaction comprises a transferred strand that exhibits a transferred transposon end sequence as follows: 5' AGATGTGTATAAGAGACAG 3' (SEQ ID NO: 51), and a non-transferred strand that exhibits a "non-transferred transposon end sequence" as follows: (5' CTGTCTCTTATACACATCT 3' (SEQ ID NO: 52). The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure. As used herein an "cleavage domain" refers to a nucleic acid sequence that is susceptible A "restriction site domain" means a tag domain that exhibits a sequence for the purpose of facilitating cleavage using a restriction endonuclease. For example, in some embodiments, the restriction site domain is used to generate di-tagged linear ssDNA fragments. In some embodiments, the restriction site domain is used to generate a compatible double-stranded 5'-end in the tag domain so that this end can be ligated to another DNA molecule using a template-dependent DNA ligase. In some embodiments, the restriction site domain in the tag exhibits the sequence of a restriction site that is present only rarely, if at all, in the target DNA (e.g., a restriction site for a rare-cutting restriction endonuclease such as NotI or AscI).

As used herein, the term "recombinant nucleic acid molecule" refers to a recombinant DNA molecule or a recombinant RNA molecule. A recombinant nucleic acid molecule is any nucleic acid molecule containing joined nucleic acid molecules from different original sources and not naturally attached together. Recombinant RNA molecules include RNA molecules transcribed from recombinant DNA molecules. A recombinant nucleic acid may be synthesized in the laboratory. A recombinant nucleic acid can be prepared by using recombinant DNA technology by using enzymatic modification of DNA, such as enzymatic restriction digestion, ligation, and DNA cloning. A recombinant DNA may be transcribed in vitro, to generate a messenger RNA (mRNA), the recombinant mRNA may be isolated, purified and used to transfect a cell. A recombinant nucleic acid may encode a protein or a polypeptide. A recombinant nucleic acid, under suitable conditions, can be incorporated into a living cell, and can be expressed inside the living cell. As used herein, "expression" of a nucleic acid usually refers to transcription and/or translation of the nucleic acid. The product of a nucleic acid expression is usually a protein but can also be an mRNA. Detection of an mRNA encoded by a recombinant nucleic acid in a cell that has incorporated the recombinant nucleic acid, is considered positive proof that the nucleic acid is "expressed" in the cell. The process of inserting or incorporating a nucleic acid into a cell can be via transformation, transfection or transduction. Transformation is the process of uptake of foreign nucleic acid by a bacterial cell. This process is adapted for propagation of plasmid DNA, protein production, and other applications. Transformation introduces recombinant plasmid DNA into competent bacterial cells that take up extracellular DNA from the environment. Some bacterial species are naturally competent under certain environmental conditions, but competence is artificially induced in a laboratory setting. Transfection is the forced introduction of small molecules such as DNA, RNA, or antibodies into eukaryotic cells. Just to make life confusing, 'transfection' also refers to the introduction of bacteriophage into bacterial cells. 'Transduction' is mostly used to describe the introduction of recombinant viral vector particles into target cells, while 'infection' refers to natural infections of humans or animals with wild-type viruses.

A "stem-loop" sequence refers to a nucleic acid sequence (e.g., RNA sequence) with sufficient self-complementarity to hybridize and form a stem and the regions of non-complementarity that bulges into a loop. The stem may comprise mismatches or bulges.

The term "vector" refers to a nucleic acid molecule capable of transporting or mediating expression of a heterologous nucleic acid. A "vector sequence" as used herein, refers to a sequence of nucleic acid comprising at least one origin of replication and at least one selectable marker gene. Vectors capable of directing the expression of genes and/or nucleic acid sequence to which they are operatively linked are referred to herein as "expression vectors".

A plasmid is a species of the genus encompassed by the term "vector." In general, expression vectors of utility are often in the form of "plasmids" which refer to circular double stranded DNA molecules which, in their vector form are not bound to the chromosome, and typically comprise entities for stable or transient expression of the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the cell. A vector can be a DNA or RNA vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked. A safe harbor locus is a region within the genome where additional exogenous or heterologous nucleic acid sequence can be inserted, and the host genome is able to accommodate the inserted genetic material. Exemplary safe harbor sites include but are not limited to: AAVS1 site, GGTA1 site, CMAH site, B4GALNT2 site, B2M site, ROSA26 site, COLA1 site, and TIGRE site. For example, the heterologous nucleic acid described in this disclosure may be integrated at one or more sites in the genome of the cell, wherein the one or more locations is selected from the group consisting of: AAVS1 site, GGTA1 site, CMAH site, B4GALNT2 site, B2M site, ROSA26 site, COLA1 site, and TIGRE site. In some embodiments, the nucleic acid cargo comprising the transgene may be delivered to a R2D locus.

In some embodiments, the nucleic acid cargo comprising the transgene may be delivered to the genome in an intergenic or intragenic region. In some embodiments the nucleic acid cargo comprising the transgene is integrated into the genome 5' or 3' within 0.1 kb, 0.25 kb, 0.5 kb, 0.75, kb, 1 kb, 2 kb, 3 kb, 4 kb, 5 kb, 7.5 kb, 10 kb, 15 kb, 20 kb, 25 kb, 50, 75 kb, or 100 kb of an endogenous active gene. In some embodiments the nucleic acid cargo comprising the transgene is integrated into the genome 5' or 3' within 0.1 kb, 0.25 kb, 0.5 kb, 0.75, kb, 1 kb, 2 kb, 3 kb, 4 kb, 5 kb, 7.5 kb, 10 kb, 15 kb, 20 kb, 25 kb, 50, 75 kb, or 100 kb of an endogenous promoter or enhancer. In some embodiments the nucleic acid cargo comprising the transgene is 50-50,000 base pairs, e.g., between 50-40,000 bp, between 500-30,000 bp between 500-20,000 bp, between 100-15,000 bp, between 500-10,000 bp, between 50-10,000 bp, between 50-5,000 bp. In some embodiments the nucleic acid cargo comprising the transgene is less than 1,000, 1,300, 1500, 2,000, 3,000, 4,000, 5,000, or 7,500 nucleotides in length.

L1 and Non-L1 Retrotransposon Systems

Retrotransposons can contain transposable elements that are active participants in reorganizing their resident genomes. Broadly, retrotransposons can refer to DNA sequences that are transcribed into RNA and translated into protein and have the ability to reverse-transcribe themselves back into DNA. Approximately 45% of the human genome is comprised of sequences that result from transposition events. Retrotransposition occasionally generates target site deletions or adds non-retrotransposon DNA to the genome by processes termed 5'- and 3'-transduction. Recombination between non-homologous retrotransposons causes deletions, duplications or rearrangements of gene sequence. Ongoing retrotransposition can generate novel splice sites, polyadenylation signals and promoters, and so builds new transcription modules.

Generally, retrotransposons may be grouped into two classes, the retrovirus-like LTR retrotransposons, and the non-LTR elements such as human L1 elements, *Neurospora* TAD elements (Kinsey, 1990, Genetics 126:317-326), I factors from *Drosophila* (Bucheton et al., 1984, Cell 38:153-163), and R2Bm from *Bombyx mori* (Luan et al., 1993, Cell 72: 595-605). These two types of retrotransposons are structurally different and also retrotranspose using radically different mechanisms. Exemplary, non-limiting examples of LINE-encoded polypeptides are found in GenBank Accession Nos. AAC51261, AAC51262, AAC51263, AAC51264, AAC51265, AAC51266, AAC51267, AAC51268, AAC51269, AAC51270, AAC51271, AAC51272, AAC51273, AAC51274, AAC51275, AAC51276, AAC51277, AAC51278 and AAC51279.

The decision to focus on LINE-1 to develop into a system as described in the disclosure for a number of reasons at least some of which are exemplified below: (a) LINE-1 (or L1-) elements are autonomous as they encode all of the machinery alone to complete this reverse transcription and integration process; (b) L1 elements are abundant in the human genome, such that these elements may be considered as a naturalized element of the genome; (c) L1 retrotransposon retrotransposes its own mRNA with high degree of specificity, compared to other mRNAs floating around in the cells.

The L1 expresses a 6-kb bicistronic RNA that encodes the 40 kDa Open Reading Frame-1 RNA-binding protein (ORF1p) of essential but uncertain function, and a 150 kDa ORF2 protein with endonuclease and reverse transcriptase (RT) activities. L1 retrotransposition is a complex process involving transcription of the L1, transport of its RNA to the cytoplasm, translation of the bicistronic RNA, formation of a ribonucleoprotein (RNP) particle, its re-import to the nucleus and target-primed reverse transcription at the integration site. A few transcription factors that interact with L Is have been identified. Transcribed L1 RNA forms an RNP in cis with the proteins that are translated from the transcript. L1 integrates into genomic DNA by target-site primer reverse transcription (TPRT) by ORF2p cleavage at the 5'-TTTT-3' where a poly A sequence of L1 RNA anneals and primes reverse transcriptase (RT) activity to make L1 cDNA.

Other mobile elements of the genome can "hijack" the L1 ORF for retrotransposition. For example, Alu elements are such mobile DNA elements that belong to the class of short interspersed elements (SINEs) that are non-autonomous retrotransposons and acquire trans-factors to integrate. Alu elements and SINE-1 elements can associate with the L1 ribonucleoproteins in trans to be also retrotransposed by ORF1p and ORF2p. Somewhat similar to the L1 RNA, the Alu element ends with a long A-run, often referred to as the A-tail, and it also has a smaller A-rich region (indicated by AA) separating the two halves of a diverged dimer structure. Alu elements are likely to have the internal components of an RNA polymerase III promoter (such as, commonly designated as an A box and a B box promoters), but they do not encode a terminator for RNA polymerase III. They may utilize a stretch of T nucleotides at various distances downstream of the Alu element to terminate a transcription. A typical Alu transcript encompasses the entire Alu, including the A-tail, and has a 3' region that is unique for each locus. The Alu RNA folds into separate structures for each monomer unit. The RNA has been shown to bind the 7SL RNA SRP9 and 14 heterodimer, as well as poly A-binding protein (PABP). The poly A tail of Alu primes with T rich (TTTT) region of the genome and attracts ORF2p to bind to the primed region and cleaves at the T rich region via its endonuclease activity. The T-rich region primes reverse transcription by ORF2p on the 3' A-tail region of the Alu element. This creates a cDNA copy of the body of the Alu element. A nick occurs by an unknown mechanism on the second strand and second-strand synthesis is primed. The new Alu element is then flanked by short direct repeats that are duplicates of the DNA sequence between the first and second nicks. Alu elements are extremely prevalent within RNA molecules, owing to their preference for gene-rich regions. A full-length Alu (~300 bp) is derived from the signal recognition particle RNA 7SL and consists of two similar monomers with an A-rich linker in-between, A- and B-boxes present in the 5' monomer, and a poly-A tail lacking the preceding polyadenylation signal resulting in an elongated tail (up to 100 bp in length). Alus can be transcribed by RNA polymerase III using the internal promoters within the A- and B-boxes; however, Alus contain no ORFs and therefore do not encode for protein products.

Other non-L1 transposons include SVAs and HERV-Ks. A full-length SVA (SINE-VNTR-Alu) element (~2-3 kb) is a composite unit that contains a CCCTCT repeat, two Alu-like sequences, a VNTR, a SINE-R region with env (envelope) gene, the 3' LTR of HERV-K10, and a polyadenylation signal followed by a poly-A tail. It is most likely that SVAs are transcribed by RNA polymerase II, although it is unknown whether SVA elements carry an internal promoter.

A full-length HERV-K element (~9-10 kb) is comprised of ancient remnants of endogenous retroviral sequences and includes two flanking LTR regions surrounding three retroviral ORFs: (1) gag encoding the structural proteins of a retroviral capsid; (2) pol-pro encoding the enzymes: protease, RT, and integrase; and (3) env encoding proteins allowing for horizontal transfer. The LTR of HERV-K contains an internal, bidirectional promoter that appears to be under the transcriptional control of RNA polymerase II.

L1 retrotransposition and RNA binding can take place at or near poly-A tail. The 3'-UTR plays a role in the recognition of stringent-type LINE RNA of ORF1 protein (ORF1p). Stringent-type LINEs can contain a stem-loop structure located at the end of the 3'UTR. Branched molecules consisting of junctions between transposon 3'-end cDNA and the target DNA, as well as specific positioning of L1 RNA within ORF2 protein (ORF2p), were detected during initial stages of L1 retrotransposition in vitro. Secondary or tertiary RNA structure shared by L1 and Alu are likely to be responsible for recognition by and binding of ORF2, possibly along with a poly-A tail. In some embodiments, the stem-loop structure located downstream of the poly-A sequence correlates with cleavage intensity.

Mechanisms for restricting or resolving L1 integration have also evolved for the sake of maintaining genetic integrity and stability of the genome. Non-homologous end-joining repair proteins, such as XRCC1, Ku70 and DNA-PK, have been implicated in resolution of the L1 integrate at the time of insertion. In addition, the cell has evolved a number of proteins that stand against unrestricted retrotransposition, including the APOBEC3 family of cytosine deaminases, adenosine deaminase ADAR1, chromatin-remodeling factors and members of the piRNA pathway for post-transcription gene silencing that functions in the male germ line.

I. Compositions Comprising Nucleic Acid Constructs and Methods Involved for Stable Expression of Encoded Protein Provided herein is a recombinant nucleic acid encoding one or more proteins for expression in a cell, such as a myeloid cell. In one embodiment, the recombinant nucleic acid is designed for stable expression of the one or more proteins or polypeptides encoded by the recombinant nucleic acid. In some embodiments, the stable expression is achieved by incorporation of recombinant nucleic acid within the genome of the cell.

It can be easily understood by one of skill in the art that the compositions and methods described herein can be utilized to design products in which the recombinant nucleic acid may comprise one or more sequences that do not translate as a protein or a polypeptide component, but may encode an oligonucleotide that can be a regulatory nucleic acid, such as an inhibitor oligonucleotide product, such as an activator oligonucleotide.

In one aspect, provided herein is a composition comprising a synthetic nucleic acid, comprising a nucleic acid sequence encoding a gene of interest and one or more retrotransposable elements to stably incorporate a non-endogenous nucleic acid into a cell. In some embodiments, the cell is a hematopoietic cell. In some embodiments, the cell is a myeloid cell. In some embodiments, the cell is a precursor cell. In some embodiments, the cell is undifferentiated. In some embodiments, the cell has further differentiation potential. In some embodiments, the cell is not a stem cell.

A. LINE/Alu Retrotransposon Construct

In some embodiments, the present disclosure may utilize a retrotransposable system to stably incorporate into the genome and express a non-endogenous nucleic acid, where the non-endogenous nucleic acid comprises retrotransposable elements within the nucleic acid sequence. In some embodiments, the present disclosure may utilize a cell's endogenous retrotransposable system (e.g., proteins and enzymes), to stably express a non-endogenous nucleic acid in the cell. In some embodiments, the present disclosure may utilize a cell's endogenous retrotransposable system (e.g., proteins and enzymes, such as a LINE1 retrotransposition system), but may further express one or more components of the retrotransposable system to stably express a non-endogenous nucleic acid in the cell.

In some embodiments, a synthetic nucleic acid is provided herein, the synthetic nucleic acid encoding a transgene, and encoding one or more components for retrotransposition. The synthetic nucleic acid described herein is interchangeably termed as a nucleic acid construct, transgene or the exogenous nucleic acid.

In one aspect, provided herein is a method of integrating a nucleic acid sequence into a genome of a cell, the method comprising introducing a recombinant mRNA or a vector encoding an mRNA into the cell, wherein the mRNA comprises: an insert sequence, wherein the insert sequence comprises an exogenous sequence, or a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell.

In some embodiments, the 5' UTR sequence or the 3' UTR sequence comprises a binding site for human ORF2p.

In one aspect, provided herein is a method for integrating a nucleic acid sequence into the genome of an immune cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the transgene sequence is integrated into the genome of the immune cell.

In one aspect, provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence. In some embodiments, the sequence of a human retrotransposon is upstream of the 3' UTR sequence.

In some embodiments, the sequence of a human retrotransposon encodes for two proteins that are translated from a single RNA containing two ORFs. In some embodiments, the two ORFs are non-overlapping ORFs. In some embodiments, the two ORFs are ORF1 and ORF2. In some embodiments, the ORF1 encodes ORF1p and ORF2 encodes ORF2p.

In some embodiments, the sequence of a human retrotransposon comprises a sequence of a non-LTR retrotransposon. In some embodiments, the sequence of a human retrotransposon encodes comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase. In some embodiments, the endonuclease and/or a reverse transcriptase is ORF2p. In some embodiments, the reverse transcriptase is a group II intron reverse transcriptase domain. In some embodiments, the endonuclease and/or a reverse transcriptase is a minke whale endonuclease and/or a reverse transcriptase. In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA.

In some embodiments, (i) the sequence of a human retrotransposon comprises a sequence encoding ORF1p, (ii) the mRNA does not comprise a sequence encoding ORF1p, or (iii) the mRNA comprises a replacement of the sequence encoding ORF1p with a 5' UTR sequence from the complement gene. In some embodiments, the mRNA comprises a first mRNA molecule encoding ORF1p, and a second mRNA molecule encoding an endonuclease and/or a reverse transcriptase. In some embodiments, the mRNA is an mRNA molecule comprising a first sequence encoding ORF1p, and a second sequence encoding an endonuclease and/or a reverse transcriptase. In some embodiments, the first sequence encoding ORF1p and the second sequence encoding an endonuclease and/or a reverse transcriptase are separated by a linker sequence.

In some embodiments, the linker sequence comprises an internal ribosome entry sequence (IRES). In some embodiments, the IRES is an IRES from CVB3 or EV71. In some embodiments, the linker sequence encodes a self-cleaving peptide sequence. In some embodiments, the linker sequence encodes a T2A, a E2A or a P2A sequence In some embodiments, the sequence of a human retrotransposon comprises a sequence that encodes ORF1p fused to an additional protein sequence and/or a sequence that encodes ORF2p fused to an additional protein sequence. In some embodiments, the ORF1p and/or the ORF2p is fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences. In some embodiments, the 5' UTR sequence or the 3' UTR sequence comprises a sequence that promotes or enhances interaction of a poly A tail of the mRNA with the endonuclease and/or a reverse transcriptase. In some embodiments, the 5' UTR sequence or the 3' UTR sequence comprises a sequence that promotes or enhances interaction of a poly-A-binding protein (PABP) with the endonuclease and/or a reverse transcriptase. In some embodiments, the 5' UTR sequence or the 3' UTR sequence comprises a sequence that increases specificity of the endonuclease and/or a reverse transcriptase to the mRNA relative to another mRNA expressed by the cell. In some embodiments, the 5' UTR sequence or the 3' UTR sequence comprises an Alu element sequence.

In some embodiments, the first sequence encoding ORF1p and the second sequence encoding an endonuclease and/or a reverse transcriptase have the same promoter. In some embodiments, the insert sequence has a promoter that is different from the promoter of the first sequence encoding ORF1p. In some embodiments, the insert sequence has a promoter that is different from the promoter of the second sequence encoding an endonuclease and/or a reverse transcriptase. In some embodiments, the first sequence encoding ORF1p and/or the second sequence encoding an endonuclease and/or a reverse transcriptase have a promoter or transcription initiation site selected from the group consisting of an inducible promoter, a CMV promoter or transcription initiation site, a T7 promoter or transcription initiation site, an EF1a promoter or transcription initiation site and combinations thereof. In some embodiments, the insert sequence has a promoter or transcription initiation site selected from the group consisting of an inducible promoter, a CMV promoter or transcription initiation site, a T7 promoter or transcription initiation site, an EF1a promoter or transcription initiation site and combinations thereof.

In some embodiments, the first sequence encoding ORF1p and the second sequence encoding an endonuclease and/or a reverse transcriptase are codon optimized for expression in a human cell.

In some embodiments, the mRNA comprises a WPRE element. In some embodiments, the mRNA comprises a selection marker. In some embodiments, the mRNA comprises a sequence encoding an affinity tag. In some embodiments, the affinity tag is linked to the sequence encoding an endonuclease and/or a reverse transcriptase.

In some embodiments, the 3' UTR comprises a poly A sequence or wherein a poly A sequence is added to the mRNA in vitro. In some embodiments, the poly A sequence is downstream of a sequence encoding an endonuclease and/or a reverse transcriptase. In some embodiments, the insert sequence is upstream of the poly A sequence.

In some embodiments, the 3' UTR sequence comprises the insert sequence. In some embodiments, the insert sequence comprises a sequence that is a reverse complement of the sequence encoding the exogenous polypeptide. In some embodiments, the insert sequence comprises a polyadenylation site. In some embodiments, the insert sequence comprises an SV40 polyadenylation site. In some embodiments, the insert sequence comprises a polyadenylation site upstream of the sequence that is a reverse complement of the sequence encoding the exogenous polypeptide. In some embodiments, the insert sequence is integrated into the genome at a locus that is not a ribosomal locus. In some embodiments, the insert sequence integrates into a gene or regulatory region of a gene, thereby disrupting the gene or downregulating expression of the gene. In some embodiments, the insert sequence integrates into a gene or regulatory region of a gene, thereby upregulating expression of the gene. In some embodiments, the insert sequence integrates into the genome and replaces a gene. In some embodiments, the insert sequence is stably integrated into the genome. In some embodiments, the insert sequence is retrotransposed into the genome. In some embodiments, the insert sequence is integrated into the genome by cleavage of a DNA strand of a target site by an endonuclease encoded by the mRNA. In some embodiments, the insert sequence is integrated into the genome via target-primed reverse transcription (TPRT). In some embodiments, the insert sequence is integrated into the genome via reverse splicing of the mRNA into a DNA target site of the genome.

In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell.

In some embodiments, the mRNA is a self-integrating mRNA. In some embodiments, the method comprises introducing into the cell the mRNA. In some embodiments, the method comprises introducing into the cell the vector encoding the mRNA. In some embodiments, the method comprises introducing the mRNA or the vector encoding the mRNA into a cell ex vivo. In some embodiments, the method further comprises administering the cell to a human subject. In some embodiments, the method comprises administering the mRNA or the vector encoding the mRNA to a human subject. In some embodiments, an immune response is not elicited in the human subject. In some embodiments, the mRNA or the vector is substantially non-immunogenic.

In some embodiments, the vector is a plasmid or a viral vector. In some embodiments, the vector comprises a non-LTR retrotransposon. In some embodiments, the vector comprises a human L1 element. In some embodiments, the vector comprises a L1 retrotransposon ORF1 gene. In some embodiments, the vector comprises a L1 retrotransposon ORF2 gene. In some embodiments, the vector comprises a L1 retrotransposon.

In some embodiments, the mRNA is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases.

In some embodiments, the mRNA comprises a sequence that inhibits or prevents degradation of the mRNA. In some embodiments, the sequence that inhibits or prevents degradation of the mRNA inhibits or prevents degradation of the mRNA by an exonuclease or an RNAse. In some embodiments, the sequence that inhibits or prevents degradation of the mRNA is a G quadruplex, pseudoknot or triplex sequence. In some embodiments, the sequence the sequence that inhibits or prevents degradation of the mRNA is an exoribonuclease-resistant RNA structure from a flaviviral RNA or an ENE element from KSV. In some embodiments, the sequence that inhibits or prevents degradation of the mRNA inhibits or prevents degradation of the mRNA by a deadenylase. In some embodiments, the sequence that inhibits or prevents degradation of the mRNA comprises non-adenosine nucleotides within or at a terminus of a poly A tail of the mRNA. In some embodiments, the sequence that inhibits or prevents degradation of the mRNA increases stability of the mRNA. In some embodiments, the exogenous sequence comprises a sequence encoding an exogenous polypeptide. In some embodiments, the sequence encoding an exogenous polypeptide is not in frame with a sequence encoding an endonuclease and/or a reverse transcriptase. In some embodiments, the sequence encoding an exogenous polypeptide is not in frame with a sequence encoding an endonuclease and/or a reverse transcriptase. In some embodiments, the exogenous sequence does not comprise introns. In some embodiments, the exogenous sequence comprises a sequence encoding an exogenous polypeptide selected from the group consisting of an enzyme, a receptor, a transport protein, a structural protein, a hormone, an antibody, a contractile protein and a storage protein. In some embodiments, the exogenous sequence comprises a sequence encoding an exogenous polypeptide selected from the group consisting of a chimeric antigen receptor (CAR), a ligand, an antibody, a receptor, and an enzyme. In some embodiments, the exogenous sequence comprises a regulatory sequence. In some embodiments, the regulatory sequence comprises a cis-acting regulatory sequence. In some embodiments, the regulatory sequence comprises a cis-acting regulatory sequence selected from the group consisting of an enhancer, a silencer, a promoter or a response element. In some embodiments, the regulatory sequence comprises a trans-acting regulatory sequence. In some embodiments, the regulatory sequence comprises a trans-acting regulatory sequence that encodes a transcription factor.

In some embodiments, integration of the insert sequence does not adversely affect cell health. In some embodiments, the endonuclease, the reverse transcriptase or both are capable of site-specific integration of the insert sequence.

In some embodiments, the mRNA comprises a sequence encoding an additional nuclease domain or a nuclease domain that is not derived from ORF2. In some embodiments, the mRNA comprises a sequence encoding a megaTAL nuclease domain, a TALEN domain, a Cas9 domain, a zinc finger binding domain from an R2 retroelement, or a DNA binding domain that binds to repetitive sequences such as a Rep78 from AAV. In some embodiments, the endonuclease comprises a mutation that reduces activity of the endonuclease compared to the endonuclease without the mutation. In some embodiments, the endonuclease is an ORF2p endonuclease and the mutation is S228P. In some embodiments, the mRNA comprises a sequence encoding a domain that increases fidelity and/or processivity of the reverse transcriptase. In some embodiments, the reverse transcriptase is a reverse transcriptase from a retroelement other than ORF2 or reverse transcriptase that has higher fidelity and/or processivity compared to a reverse transcriptase of ORF2p. In some embodiments, the reverse transcriptase is a group II intron reverse transcriptase. In some embodiments, the group II intron reverse transcriptase is a group IIA intron reverse transcriptase, a group IIB intron reverse transcriptase, or a group IIC intron reverse transcriptase. In some embodiments, the group II intron reverse transcriptase is TGIRT-II or TGIRT-III.

In some embodiments, the mRNA comprises a sequence comprising an Alu element and/or a ribosome binding aptamer. In some embodiments, the mRNA comprises a sequence encoding a polypeptide comprising a DNA binding domain. In some embodiments, the 3' UTR sequence is derived from a viral 3' UTR or a beta-globin 3' UTR.

In one aspect, provided herein is a composition comprising a recombinant mRNA or vector encoding an mRNA, wherein the mRNA comprises a human LINE-1 transposon sequence comprising a human LINE-1 transposon 5' UTR sequence, a sequence encoding ORF1p downstream of the human LINE-1 transposon 5' UTR sequence, an inter-ORF linker sequence downstream of the sequence encoding ORF1p,a sequence encoding ORF2p downstream of the inter-ORF linker sequence, and a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element.

In some embodiments, the insert sequence integrates into the genome of a cell when introduced into the cell. In some embodiments, the insert sequence integrates into a gene associated a condition or disease, thereby disrupting the gene or downregulating expression of the gene. In some embodiments, the insert sequence integrates into a gene, thereby upregulating expression of the gene. In some embodiments, the recombinant mRNA or vector encoding the mRNA is isolated or purified.

In one aspect, provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic.

In some embodiments, the composition comprises human ORF1p and human ORF2p proteins. In some embodiments, the composition comprises a ribonucleoprotein (RNP) comprising human ORF1p and human ORF2p complexed to the nucleic acid. In some embodiments, the nucleic acid is mRNA.

In one aspect, provided herein is a composition comprising a cell comprising a composition described herein. In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell. In some embodiments, the insert sequence is a reverse complement of a sequence encoding an exogenous polypeptide and the exogenous polypeptide is a chimeric antigen receptor (CAR).

In one aspect, provided herein is a pharmaceutical composition comprising a composition described herein, and a pharmaceutically acceptable excipient. In some embodiments, the pharmaceutical composition is for use in gene therapy. In some embodiments, the pharmaceutical composition is for use in the manufacture of a medicament for treating a disease or condition. In some embodiments, the pharmaceutical composition is for use in treating a disease or condition. In one aspect, provided herein is a method of treating a disease in a subject, comprising administering a pharmaceutical composition described herein to a subject with a disease or condition. In some embodiments, the method increases an amount or activity of a protein or functional RNA in the subject. In some embodiments, the subject has a deficient amount or activity of a protein or functional RNA. In some embodiments, the deficient amount or activity of a protein or functional RNA is associated with or causes the disease or condition.

In some embodiments, the method further comprising administering an agent that inhibits human silencing hub (HUSH) complex, an agent that inhibits FAM208A, or an agent that inhibits TRIM28. In some embodiments, the agent that inhibits human silencing hub (HUSH) complex is an agent that inhibits Periphilin, TASOR and/or MPP8. In some embodiments, the agent that inhibits human silencing hub (HUSH) complex inhibits assembly of the HUSH complex.

In some embodiments, the agent inhibits the fanconia anemia complex. In some embodiments, the agent inhibits FANCD2-FANC1 heterodimer monoubiquitination. In some embodiments, the agent inhibits FANCD2-FANC1 heterodimer formation. In some embodiments the agent inhibits the Fanconi Anemia (FA) core complex. FA core complex is a component of the fanconi anemia DNA damage repair pathway, e.g., in chemotherapy induced DNA inter-strand crosslinks. The FA core complex comprises two central dimers of the FANCB and FA-associated protein of 100 kDa (FAAP100) subunits, flanked by two copies of the RING finger subunit, FANCL. These two heterotrimers act as a scaffold to assemble the remaining five subunits, resulting in an extended asymmetric structure. Destabilization of the scaffold would disrupt the entire complex, resulting in a non-functional FA pathway. Examples of agents that can inhibit the FA core complex include Bortezomib and curcumin analogs EF24 and 4H-TTD.

In some embodiments, the sequences to be inserted may be placed under the control of tissue-specific elements, such that the entire inserted DNA is only functional in those cells in which the tissue-specific element is active.

In one aspect, provided herein are method and compositions for stable gene transfer to a cell by introducing to the cell a heterologous nucleic acid or gene of interest (e.g., a transgene, a regulatory sequence, for example, a sequence for an inhibitory nucleic acid, an siRNA, a miRNA), flanked by sequences that cause retrotransposition of the heterologous nucleic acid sequence into the genome of the cell. In some embodiments, the heterologous nucleic acid is termed insert for the purpose of the description in this document, where the insert is the nucleic acid sequence that will be reverse transcribed and inserted into the genome of the cell by the intended design of the constructs described herein. In some embodiments, the heterologous nucleic acid is also termed the cargo, or cargo sequence for the purpose of the description in this document. The cargo can comprise the sequence of the heterologous nucleic acid that that is inserted in the genome. In some embodiments, the cell may be a cell mammalian cell. The mammalian cell may be of epithelial, mesothelial or endothelial origin. In some embodiments, the cell may be a stem cell. In some embodiments, the cell may be a precursor cell. In some embodiments, the cell may be a cell that is terminally differentiated. In some embodiments, the cell may be a muscle cell, a cardiac cell, an epithelial cell, a hematopoietic cell, a mucous cell, an epidermal cell, a squamous cell, a cartilage cell, a bone cell, or any cell of mammalian origin. In some embodiments, the cell is of hematopoietic lineage. In some embodiments, he cell is of myeloid lineage, or a phagocytic cell, for example a monocyte, macrophage, a dendritic cell or a myeloid precursor cell. In some embodiments, the nucleic acid encoding the transgene is an mRNA.

In some embodiments, the retrotransposable elements may be derived from a non-LTR retrotransposon.

Provided herein is a method of integrating a nucleic acid sequence into a genome of a cell, the method comprising introducing a recombinant mRNA or a vector encoding an mRNA into the cell, wherein the mRNA comprises an insert sequence and wherein the insert sequence is integrated into the genome of the cell. In some embodiments, the insert sequence comprises (i) an exogenous sequence, or (ii) a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein. In some embodiments, the ORF protein is a human LINE 1 ORF2 protein. In some embodiments, the ORF protein is a non-human ORF protein. In some embodiments, the ORF protein is a chimeric protein, a recombinant protein or an engineered protein.

Provided herein is a method for integrating a nucleic acid sequence into the genome of an immune cell, the method comprising introducing a recombinant mRNA or a vector encoding an mRNA, wherein the mRNA comprises, (a) an insert sequence, wherein the insert sequence comprises (i) an exogenous sequence or (ii) a sequence that is a reverse complement of the exogenous sequence; (b) 5' UTR sequence and a 3' UTR sequence downstream of the 5' UTR sequence, wherein the 5' UTR sequence or the 3' UTR sequence comprises an endonuclease binding site and a reverse transcriptase binding site, and wherein the transgene sequence is integrated into the genome of the immune cell.

In some embodiments, the structural elements that mediate RNA integration or transposition may be encoded in a synthetic construct and are relied upon to deliver a heterologous gene of interest to the cell. In some embodiments, the synthetic construct may comprise a nucleic acid encoding the heterologous gene of interest and the structural elements that cause integration or retrotransposition of a heterologous gene of interest into the genome. In some embodiments, the structural elements that cause integration or retrotransposition may include a 5' L1 RNA region, and a 3'-L1 region, the latter comprising a poly A 3' region for priming. In some embodiments, the 5' L1 RNA region may comprise one or more stem loop regions. In some embodiments, the L1-3' region may comprise one or more stem loop regions. In some embodiments, the 5'- and 3' L1 regions are constructed as flanking the nucleic acid sequence encoding the heterologous gene of interest (the transgene). In some embodiments, the structural elements may include a region from an L1 or an Alu RNA comprising the hairpin loop structure that includes the A-Box and the B-Box elements that are ribosomal binding sites In some embodiments, the synthetic nucleic acid may comprise a L1-Ta promoter.

There may be two types of LINE RNA recognition by ORF2p—the stringent and the relaxed. In the stringent type RT recognizes its own 3'UTR tail, and in the relaxed type RT does not require any specific recognition except for the poly-A tail. Division into the stringent and the relaxed type came from the observation that some LINE/SINE pairs share the same 3'-end. For the stringent type, the experimental studies showed that a 3'UTR stem-loop promotes retrotransposition. The 5'-UTR of the LINE retrotransposition sequences have been shown to contain three conserved stem loop regions.

In some embodiments, the transgene, or transcript of interest may be flanked by transposable elements from a L1 or an Alu sequence at the 5' and the 3' end. In some embodiments, the 5' region of a retrotransposon comprises an Alu sequence. In some embodiments, the 3' region of a retrotransposon comprises an Alu sequence. In some embodiments, the 5' region of a retrotransposon comprises an L1 sequence. In some embodiments, the 3' region of a retrotransposon comprises an L1 sequence. In some embodiments, the transgene or transcript of interest is flanked by an SVA transposon sequence.

In some embodiments, the transcript of interest may comprise an L1 or an Alu sequence, encoding the binding regions for ORF2p and the 3'-poly A priming regions. In some embodiments, the heterologous nucleic acid encoding the transgene of interest may be flanked by an L1 or an Alu sequence, encoding the binding regions for ORF1p and the 3'-poly A priming regions. The 3'-region may comprise one or more stem loop structures. In some embodiments, the transcript of interest is structured for cis integration or retrotransposition. In some embodiments, the transcript of interest is structured for trans integration or retrotransposition.

In some embodiments, the retrotransposon is a human retrotransposon. The sequence of a human retrotransposon can comprise a sequence encoding an endonuclease and/or a reverse transcriptase. The sequence of a human retrotransposon can encode for two proteins that are translated from a single RNA containing two non-overlapping ORFs. In some embodiments, the two ORFs are ORF1 and ORF2.

Accordingly, provided herein is a method for stably integrating a heterologous nucleic acid encoding a transgene into the genome of a cell, such as a myeloid cell, the method comprising introducing to the cell a nucleic acid encoding: the transgene; one or more 5'nucleic acid sequences flanking the region encoding the transgene, comprising a 5' region of a retrotransposon; and one or more 3' nucleic acid sequence flanking the region encoding the transgene, comprising a 3' region of a retrotransposon, wherein the 3' region of the retrotransposon comprises a genomic DNA priming sequence and a LINE transposase binding sequence, having the respective endonuclease and reverse transcriptase (RT) activity.

Provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; (b) a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and a reverse transcriptase binding site, and wherein the sequence of a human retrotransposon encodes for two proteins that are translated from a single RNA containing two ORFs, and wherein the insert sequence is integrated into the genome of the cell.

In some embodiments, the method comprising using a single nucleic acid molecule for delivering and integrating the insert sequence into the genome of a cell. The single nucleic acid molecule may be a plasmid vector. The single nucleic acid may be DNA or an RNA molecule. The single nucleic acid may be an mRNA.

In some embodiments, the method comprises introducing into a cell one or more polynucleotides comprising the human retrotransposon and a heterologous nucleic acid sequence. In some embodiments, the one or more polynucleotides comprises (i) a first nucleic acid molecule encoding an ORF1p; (ii) a second nucleic acid molecule encoding an ORF2p and a sequence encoding a cargo. In some embodiments, the first nucleic acid and the second nucleic acid are mRNA. In some embodiments, the first nucleic acid and the second nucleic acid are DNA, e.g., encoded in separate plasmid vectors.

Provided herein is a self-integrating polynucleotide that comprises a sequence which is inserted into the genome of a cell, and insert is stably integrated into the genome by the self-integrating naked polynucleotide. In some embodiments, the polynucleotide is an RNA. In some embodiments, the polynucleotide is an mRNA. In some embodiments, the polynucleotide is an mRNA that has modifications. In some embodiments, the modifications ensure protection against RNases in the intracellular milieu. In some embodiments, the modifications include substituted modified nucleotides, e.g., 5-methylcytidine, pseudouridine or 2-thiouridine.

In some embodiments, a single polynucleotide is used for delivery and genomic integration of the insert (or cargo) nucleic acid. In some embodiments, the single polynucleotide is bicistronic. In some embodiments, the single polynucleotide is tricistronic. In some embodiments, the single polynucleotide is multi-cistronic. In some embodiments, a two or more polynucleotide molecules are used for delivery and genomic integration of the insert (or cargo) nucleic acid.

In some embodiments, a retrotransposable genetic element may be generated, the retrotransposable genetic element comprising (i) a heterologous nucleic acid encoding a transgene or a non-coding sequence to be inserted into the genome of a cell (the insert); (ii) a nucleic sequence encoding one or more retrotransposon ORF-encoding sequences; (iii) one or more UTR regions of the ORF-coding sequences, such that the heterologous nucleic acid encoding a transgene or a non-coding sequence to be inserted is comprised within the UTR sequences; wherein the 3' region of the retrotransposon ORF-encoding sequences comprises a genomic DNA priming sequence.

In some embodiments, the retrotransposable genetic element may be introduced into a cell for stably integrating the transgene into the genomic DNA. In some embodiments, the retrotransposable genetic element comprises (a) a retrotransposon protein coding sequence, and a 3' UTR; and (b) a sequence comprising a heterologous nucleic acid that is to be inserted (e.g, integrated) within the genome of a cell. The retrotransposon protein coding sequence, and the 3' UTR may be a complete and sufficient unit for delivering the heterologous nucleic acid sequence within the genome of the cell, and comprise the retrotransposable elements, such as an endonuclease, a reverse transcriptase, a sequence in the 3' UTR for binding to and priming the genomic DNA at the region cleaved by the endonuclease to start reverse transcribing and incorporating the heterologous nucleic acid.

In some embodiments, the coding sequence of the insert is in forward orientation with respect to the coding sequence of the one or more ORFs. In some embodiments, the coding sequence of the insert is in reverse orientation with respect to the coding sequence of the one or more ORFs. The coding sequence of the insert and the coding sequence of the one or more ORFs may comprise distinct regulatory elements, including 5' UTR, 3' UTR, promoter, enhancer, etc. In some embodiments, the 3' UTR or the 5'-UTR of the insert may comprise the coding sequence of the one or more ORFs, and likewise, the coding sequence of the insert may be situated within in the 3' UTR of the coding sequence of the one or more ORFs.

In some embodiments, a retrotransposable genetic element may be generated, the retrotransposable genetic element comprising: (a) an insert sequence, comprising (i) an exogenous sequence, a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein.

In some embodiments, the retrotransposon may comprise a SINE or LINE element. In some embodiments, the retrotransposon comprises a SINE or LINE stem loop structure, such as an Alu element.

In some embodiments, the retrotransposon is a LINE-1 (L1) retrotransposon. In some embodiments, the retrotransposon is human LINE-1. Human LINE-1 sequences are abundant in the human genome. There are approximately 13,224 total human L1s, of which 480 are active, which make up about 3.6%. Therefore, human L1 proteins are well tolerated and non-immunogenic in humans. Moreover, a tight regulation of random transposition in human ensures that random transposase activity will not be triggered by introduction of the L1 system as described herein. In addition, the retrotransposable constructs designed herein may comprise targeted and specific incorporation of the insert sequence. In some embodiments, the retrotransposable genetic element may comprise designs intended to overcome the silencing machinery actively prevalent in human cells, while being careful that random integration resulting in genomic instability is not initiated.

Accordingly, the retrotransposable constructs may comprise a sequence encoding a human LINE-1 ORF1 protein; and a human LINE-1 ORF2 protein. In some embodiments, the construct comprises a nucleic acid sequence encoding an ORF1p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to MGKKQNRKTGNSKTQSASPPPK-ERSSSPATEQSWMENDFDELREEGFRRSNYSEL-REDIQTKGK EVENFEKNLEECITRITNTEKCLKEL MELKTKARELREECRSLRSRCDQLEERVSAMEDEM-NEM KREGKFREKRIKRNEQSLQEIWDYVKRP NLRLIGVPESDVENGTKLENTLQDIIQENFPNLARQA NVQIQEIQRTPQRYSSRRATPRHIIVRFTKVEMKEK MLRAAREKGRVTLKGKPIRLTVDLSAETL QAR-REWGPIFNILKEKNFQPRISYPAKLSFISEGEIKY-FIDKQMLRDFVTTRPALKELLKEALNME RNN-RYQPLQNHAKM (SEQ ID NO: 53). In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to

```
                                        (SEQ ID NO: 54)
atgggcaagaagcaaaatcgcaagacggggaattccaagacacaatccgc
tagcccaccacctaaagagcgttctagctcccctgctactgagcagtcct
ggatggaaaacgacttcgatgaactccgggaagagggatttaggcgatcc
aactattcagaactccgcgaagatatccagacaaaggggaaggaagtcga
gaatttcgagaagaacctcgaggagtgcatcacccgtatcacaaacactg
agaaatgtctcaaagaactcatggaacttaagacaaaagccagggagctt
cgagaggagtgtcggagtctgagatccaggtgtgaccagctcgaggagcg
cgtgagcgcgatggaagacgagatgaacgagatgaaaagagagggcaaat
tcagggagaagcgcattaagaggaacgaacagagtctgcaggagatttgg
gattacgtcaagaggcctaacctgcggttgatcggcgtccccgagagcga
cgtagaaaacgggactaaactggagaatacacttcaagacatcattcaag
aaaattttccaaacctggctcggcaagctaatgtgcaaatccaagagatc
caacgcacaccccagcggtatagctctcggcgtgccacccctaggcatat
tatcgtgcgctttactaaggtggagatgaaagagaagatgctgcgagccg
ctcgggaaaagggaagggtgactttgaagggcaaacctattcggctgacg
gttgaccttagcgccgagacactccaggcacgccgggaatggggccccat
ctttaatatcctgaaggagaagaacttccagccacgaatctcttaccctg
caaagttgagttttatctccgagggtgagattaagtatttcatcgataaa
cagatgctgcgagacttcgtgacaactcgcccagctctcaaggaactgct
caaagaggctcttaatatggagcgcaataatagatatcaacccttgcaga
accacgcaaagatgtga.
```

In some embodiments, the construct comprises a nucleic acid sequence encoding an ORF2p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to MTGSNSHIT-ILTLNINGLNSAIKRHRLASWIKSQDPSVCCIQETHLT-CRDTHRLKIKGWRKIYQAN GKQKKAGVAIL-VSDKTDFKPTKIKRDKEGHYIMVKGSIQQEELTILNI YAPNTGAPRFIKQVLSDL QRDLDSHTLIMGDFNTPL-STLDRSTRQKVNKDTQELNSALHQAD-LIDIYRTLHPKSTEYTFFSAP HHTYSKIDHIVGSKALL-SKCKRTEIITNYLSDHSAIKLELRIKNLTQSRSTTWKL NNLLLNDYWV HNEMKAEIKMFFETNENKDT-TYQNLWDAFKAVCRGKFIALNAYKRKQERSKIDTLT-SQLKELE KQEQTHSKASRRQEITKIRAELKEI-ETQKTLQKINESRSWFFERINKIDRPLARLIKKKREK NQIDTI KNDKGDITTDPTEIQTTIREYYKHLYAN-KLENLEEMDTFLDTYTLPRLNQEEVESLNRPITGSEIV AIINSLPTKKSPGPDGFTAEFYQRYMEELVP-FLLKLFQSIEKEGILPNSFYEASIILIPKPGRDTTKKE NFRPISLMNIDAKILNKILANRIQQHIKKLIHHDQVG-FIPGMQGWFNIRKSINVIQHINRAKDKNH MIISI-DAEKAFDKIQQPFMLKTLNKLGIDGTYFKII-RAIYDKPTANIILNGQKLEAFPLKTGTRQGC PLSPLLFNIVLEVLARAIRQEKEIKGIQLGKEEVKLSL-FADDMIVYLENPIVSAQNLLKLISNFSKV SGYK-INVQKSQAFLYTNNRQTESQIMGELPFVIASKRI-KYLGIQLTRDVKDLFKENYKPLLKEIKE DTNKWKNIPCSWVGRINIVKMAILPKVIYRFNAIP-IKLPMTFFTELEKTTLKFIWNQKRARIAKSIL SQKNK-AGGITLPDFKLYYKATVTKTAWYWYQNR-DIDQWNRTEPSEIMPHIYNYLIFDKPEKNK QWGKDSLFNKWCWENWLAICRKLKLDPFLTPYT-KINSRWIKDLNVKPKTIKTLEENLGITIQDIG VGKDFMSKTPKAMATKDKIDKWDLIKLKSFCTA-KETTIRVNRQPTTWEKIFATYSSDKGLISRIY NELKQIYKKKTNNPIKKWAKDMNRHFSKEDI-YAAKKHMKKCSSSLAIREMQIKTTMRYHLTPV RMAIIKKSGNNRCWRGCGEIGTLLHCWWDCK-LVQPLWKSVWRFLRDLELEIPFDPAIPLLGIYP NEYKSCCYKDTCTRMFIAALFTIAKTWNQPKCPT-MIDWIKKMWHIYTMEYYAAIKNDEFISFVG TWMKLETIILSKLSQEQKTKHRIFSLIGGN (SEQ ID NO: 55). In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to (SEQ ID NO: 56)

```
atgaccggctctaactcacatatcaccatccttacacttaacattaacgg
cctcaactcagctatcaagcgccatcggctggccagctggatcaaatcac
aggatccaagcgtttgttgcatccaagagacccacctgacctgtagagat
actcaccgcctcaagatcaagggatggcgaaagatttatcaggcgaacgg
taagcagaagaaagccggagtcgcaattctggtctcagacaagacggatt
tcaagcccaccaaaattaagcgtgataaggaaggtcactatattatggtg
aaaggcagcatacagcaggaagaacttaccatattgaacatctacgcgcc
```

-continued

```
aaacaccggcgcacctcgctttatcaaacaggtcctgtccgatctgcagc
gagatctggattctcatacgttgattatgggtgatttcaatacaccattg
agcaccctggatcgcagcaccaggcaaaaggtaaataaagacacgcaaga
gctcaatagcgcactgcatcaggcagatctcattgatatttatcgcactc
ttcatcctaagagtaccgagtacacattcttcagcgccccacatcataca
tactcaaagatcgatcatatcgtcggctcaaaggctctgctgtcaaagtg
caagcgcacagagataattacaaattacctgtcagatcatagcgcgatca
agctcgagctgagaatcaagaacctgacccagagccggagtaccacttgg
aagcttaataacctgctgctcaacgattattgggtccacaatgagatgaa
ggcagagattaaaatgttcttcgaaacaaatgagaataaggatactacct
atcaaaacctttgggatgcctttaaggccgtctgcagaggcaagttcatc
gccctcaacgcctataaaagaaaacaagagagatctaagatcgatactct
cacctctcagctgaaggagttggagaaacaggaacagacccactccaagg
cgtcaagacggcaggagatcacaaagattcgcgccgagttgaaagagatc
gaaacccaaaagactcttcagaaaattaacgagtctcgtagttggttctt
cgagcggattaataagatagacagacctctggcacgactgattaagaaga
agcgcgaaaagaaccagattgataccatcaagaacgacaagggcgacatc
actactgacccgaccgagatccagaccactattcgggagtattataagca
tttgtatgctaacaagcttgagaacctggaagagatggacacttttctgg
atacctatactctgccacggcttaatcaagaggaagtcgagtccctcaac
cgcccaattacaggaagcgagattgtggccataattaactccctgccgac
aaagaaatctcctggtccggacgggtttacagctgagttttatcaacggt
atatggaagagcttgtaccgtttctgctcaagctctttcagtctatagaa
aaggaaggcatcttgcccaattccttctacgaagcttctataatacttat
tcccaaaccaggacgcgataccacaaagaaggaaaacttccggcccatta
gtctcatgaatatcgacgctaaaatattgaacaagattctcgccaacaga
atccaacaacatattaagaaattgatacatcacgaccaggtggggtttat
acctggcatgcagggctggtttaacatccggaagagtattaacgtcattc
aacacattaatagagctaaggataagaatcatatgatcatctctatagac
gcggaaaaggcattcgataagattcagcagccatttatgctcaagactct
gaacaaactcggcatcgacggaacatattttaagattattcgcgcaattt
acgataagccgactgctaacattatccttaacggccaaaagctcgaggcc
tttccgctcaagactggaacccgccaaggctgtcccctctccccgctttt
gtttaatattgtactcgaggtgctggctagggctattcgtcaagagaaag
agattaaagggatacagctcgggaaggaagaggtcaagctttccttgttc
gccgatgatatgattgtgtacctggagaatcctattgtgtctgctcagaa
ccttcttaaacttatttctaactttagcaaggtcagcggctataagatta
acgtccagaaatctcaggcctttctgtacacaaataatcgacagaccgaa
tcccagataatgggtgagcttccgtttgtcatagccagcaaaaggataaa
gtatctcggaatccagctgacacgagacgttaaagatttgtttaaggaaa
attacaagcctctcctgaaagagattaaggaagatactaataagtggaag
```

-continued

```
aatatcccctgttcatgggttggcagaatcaacatagtgaagatggcaat
acttcctaaagtgatatatcgctttaacgccatcccaattaaactgccta
tgaccttctttacggagctcgagaaaacaacccttaaatttatatggaat
caaaagagagcaagaatagcgaagtccatcttgagccagaagaataaggc
cggtgggattactttgcctgattttaagttgtattataaagccacagtaa
ctaagacagcctggtattggtatcagaatagagacatcgaccagtggaat
cggaccgaaccatcagagataatgccccacatctataattaccttatatt
cgataagccagaaaagaataaacagtggggcaaagacagcctcttcaaca
agtggtgttgggagaattggctggccatatgccggaaactcaagctcgac
ccctttcttacaccctacactaaaatcaacagtaggtggatcaaggactt
gaatgtcaagccaaagactataaagacactggaagagaatcttgggatca
caatacaagatataggcgtcggcaaagattttatgtcaaagacgcccaag
gccatggccactaaggataagattgataagtgggaccttattaagctcaa
aagcttctgtactgccaaggagaccacgatcagagttaataggcagccca
ctacatgggaaaagatttcgccacttattcatcagataaggggttgata
agcagaatatataacgagctgaagcagatctacaagaagaaaacgaataa
tcccatcaagaagtgggcaaaagatatgaacaggcattttagcaaagagg
atatctacgccgcgaagaagcatatgaagaagtgtagttcaagcttggcc
attcgtgagatgcagattaagacgaccatgcgataccaccttaccccagt
gaggatggcaattatcaagaaatctggcaataatagatgttggcggggct
gtggcgagattggcaccctgctccattgctggtgggattgcaagctggtg
cagccgctttggaaatcagtctggcgctttctgagggacctcgagcttga
gattcccttcgatcccgcaattcccttgctcggaatctatcctaacgaat
acaagagctgttgttacaaggatacgtgtacccggatgttcatcgcggcc
ttgtttacgatagctaagacgtggaatcagcctaagtgccccacaatgat
cgattggatcaagaaaatgtggcatatttataccatggagtattacgcag
caattaagaatgacgaatttatttccttcgttgggacctggatgaagctg
gagactattattctgagcaagctgtctcaggagcaaaagacaaagcatag
aatcttctctctcattggtggtaactaa.
```

In some embodiments, the construct comprises a nucleic acid sequence encoding an ORF2p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to MVIGTYISIITLNVNGLNAPTKRHRLAEWIQKQDPYICCLQETHFRPRDTYRLKVRGWKKIFHAN GNQKKAGVAILISDKIDFKIKNVTRDKEGHYIMIQGSIQEEDI TIINIYAPNIGAPQYIRQLLTAIKE EIDSNTIIVGDFNTSLTPMDRSSKMKINKETEALNDTIDQIDLIDIYRTFHPKTADYTFFSSAHGTFS RIDHILGHKSSLSKFKKIEIISSIFSDHNAMRLEMNHREKNVKKTNTWR LNNTLLNNQEITEEIKQ EIKKYLETNDNENTTTQNLWDAAKAVLRGKFIAIQAYLKKQEKSQVNNLTLHLKKLEKEEQTK PKVSRRKEIIKIRAEINEIETKKTIAKINKTKSWFFEKINKIDKPLARLIKKKRERTQINKIRNEKGE VTTDTAEIQNILRDYYKQLYANKMDNLEEMDKFLERYNLPRLNQEETENINRPITS NEIETVIKNL PTNKSPGPDGFTGEFYQTFREELTPILLKLFQKIAEEGTLPNSFYEATITLIPKPDKDTTKKENYRPI SLMNIDAKILNKILANRIQQHIKRIIHHDQVGFIPGMQGFFNIRKSINVIHHINK LKKKNHMIISIDA EKAFDKIQHPFMIKTLQKVGIEGTYLNIIKAIYDKPTANIILNGEKLKAFPLRSGTRQGCPLSPLLF NIVLEVLATAIREEKEIKGIQIGKEEVKLSLFADDMILYIENPKT ATRKLLELINEYGKVAGYKINA QKSLAFLYTNDEKSEREIMETLPFTIATKRIKYLGINLPKETKDLYAENYKTLMKEIKDDTNRWR DIPCSWIGRINIVKMSILPKAIYRFNAIPIKLPMAFFTELEQIILKFVWRHKRP RIAKAVLRQKNGA GGIRLPDFRLYYKATVIKTIWYWHKNRNIDQWNKIESPEINPRTYGQLIYDKGGKDIQWRKDSLF NKWCWENWTATCKRMKLEYSLTPYTKINSKWIRDLNIRLD TIKLLEENIGRTLFDINHSKIFFDPP PRVMEIKTKINKWDLMKLQSFCTAKETINKTKRQPSEWEKIFANESTDKGLISKIYKQLIQLNIKE TNTPIQKWAEDLNRHFSKEDIQTATKHMKRCSTSLIIREMQIKTTMR YHLTPVRMGIIRKSTNNK CWRGCGEKGTLLHCWWECKLIQPLWRTIWRFLKKLKIELPYDPAIPLLGIYPEKTVIQKDTCTR MFIAALFTIARSWKQPKCPSTDEWIKKMWYIYTMEYYSAIKRNEIGSFLETWMDLETVIQSE VSQ KEKNKYRILTHICGTWKNGTDEPVCRTEIETQM (SEQ ID NO: 57). In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to (SEQ ID NO: 58)

```
atggtcataggaacatacatatcgataattaccttaaacgtgaatggatt
aaatgccccaaccaaaagacatagactggctgaatggatacaaaaacaag
acccatatatatgctgtctacaagagacccacttcagacctagggacaca
tacagactgaaagtgaggggatggaaaaagatattccatgcaaatggaaa
tcaaaagaaagctggagtagctatactcatatcagataaaatagacttta
aaataaagaatgttacaagagacaaggaaggacactacataatgatccag
ggatcaatccaagaagaagatataacaattataaatatatatgcacccaa
cataggagcacctcaatacataaggcaactgctaacagctataaaagagg
aaatcgacagtaacacaataatagtggggggactttaacacctcacttaca
ccaatggacagatcatccaaaatgaaaataaataaggaaacagaagcttt
aaatgacacaatagaccagatagatttaattgatatatataggacattcc
atccaaaaacagcagattacacgttcttctcaagtgcgcacggaacattc
tccaggatagatcacatcttgggtcacaaatcaagcctcagtaaatttaa
gaaaattgaaatcatatcaagcatcttttctgaccacaacgctatgagat
tagaaatgaatcacagggaaaaaaacgtaaaaaagacaaacacatggagg
ctaaacaatacgttactaaataaccaagagatcactgaagaaatcaaaca
```

-continued ggaaataaaaaaatacctagagacaaatgacaatgaaaacacgacgaccc aaaacctatgggatgcagcaaaagcggttctaagagggaagtttatagct atacaagcctacctaaagaaacaagaaaaatctcaagtaaacaatctaac cttacacctaaagaaactagagaaagaagaacaaacaaaacccaaagtta gcagaaggaaagaaatcataaagatcagagcagaaataaatgaaatagaa acaaagaaaacaatagcaaagatcaataaaactaaaagttggttctttga gaagataaacaaaattgataagccattagccagactcatcaagaaaaaga gggagaggactcaaatcaataaaatcagaaatgaaaaaggagaagttaca acagacaccgcagaaatacaaaacatcctaagagactactacaagcaact ttatgccaataaaatggacaacctggaagaaatggacaaattcttagaaa ggtataaccttccaagactgaaccaggaagaaacagaaaatatcaacaga ccaatcacaagtaatgaaattgaaactgtgattaaaaatcttccaacaaa caaaagtccaggaccagatggcttcacaggtgaattctatcaaacattta gagaagagctaacacccatccttctcaaactcttccaaaaaattgcagaa gaaggaacactcccaaactcattctatgaggccaccatcaccctgatacc aaaaccagacaaagacactacaaaaaaagaaaattacagaccaatatcac tgatgaatatagatgcaaaaatcctcaacaaaatactagcaaacagaatc caacaacacattaaaaggatcatacaccacgatcaagtgggatttatccc agggatgcaaggattcttcaatatacgcaaatcaatcaatgtgatacacc atattaacaaattgaagaagaaaaaccatatgatcatctcaatagatgca gaaaaagcttttgacaaaattcaacacccatttatgataaaaactctcca gaaagtgggcatagagggaacctacctcaacataataaaggccatatatg acaaacccacagcaaacatcattctcaatggtgaaaaactgaaagcattt cctctaagatcaggaacgagacaaggatgtccactctcaccactattatt caacatagttctggaagtcctagccacggcaatcagagaagaaaaagaaa taaaaggaatacaaattggaaaagaagaagtaaaactgtcactgtttgcg gatgacatgatactatacatagagaatcctaaaactgccaccagaaaact gctagagctaattaatgaatatggtaaagttgcaggttacaaaattaatg cacagaaatctcttgcattcctatacactaatgatgaaaaatctgaaaga gaaattatggaaacactcccatttaccattgcaacaaaaagaataaaata cctaggaataaacctacctaaggagacaaaagacctgtatgcagaaaact ataagacactgatgaaagaaattaaagatgataccaacagatggagagat ataccatgttcttggattggaagaatcaacattgtgaaaatgagtatact acccaaagcaatctacagattcaatgcaatccctatcaaattaccaatgg catttttttacggagctagaacaaatcatcttaaaatttgtatggagacac aaaagaccccgaatagccaaagcagtcttgaggcaaaaaaatggagctgg aggaatcagactccctgacttcagactatactacaaagctacagtaatca agacaatatggtactggcacaaaaacagaaacatagatcaatggaacaag atagaaagcccagagattaacccacgcacctatggtcaactaatctatga caaaggaggcaaagatatacaatggagaaaagacagtctcttcaataagt ggtgctgggaaaactggacagccacatgtaaaagaatgaaattagaatac -continued tccctaacaccatacacaaaaataaactcaaaatggattagagacctaaa tataagactggacactataaaactcttagaggaaaacataggaagaacac tctttgacataaatcacagcaagatctttttcgatccacctcctagagta atggaaataaaaacaaaaataaacaagtgggacctaatgaaacttcaaag cttttgcacagcaaaggaaaccataaacaagacgaaaagacaaccctcag aatgggagaaaatatttgcaaatgaatcaacggacaaaggattaatctcc aaaatatataaacagctcattcagctcaatatcaaagaaacaaacacccc aatccaaaaatgggcagaagacctaaatagacatttctccaaagaagaca tacagacggccacgaagcacatgaaaagatgctcaacatcactaattatt agagaaatgcaaatcaaaactacaatgaggtatcacctcactcctgttag aatgggcatcatcagaaaatctacaaacaacaaatgctggagagggtgtg gagaaaagggaaccctcttgcactgttggtgggaatgtaaattgatacag ccactatggagaacaatatggaggttccttaaaaaactaaaaatagaatt accatatgacccagcaatcccactactgggcatatacccagagaaaaccg taattcaaaaagacacatgcacccgaatgttcattgcagcactatttaca atagccaggtcatggaagcaacctaaatgcccatcgacagacgaatggat aaagaagatgtggtacatatatacaatggaatattactcagccataaaaa ggaacgaaattgggtcatttttagagacgtggatggatctagagactgtc atacagagtgaagtaagtcagaaagagaaaaacaaatatcgtatattaac gcatatatgtggaacctggaaaaatggtacagatgaaccggtctgcagga cagaaattgagacacaaatgtaa.

In some embodiments, the construct comprises a nucleic acid sequence encoding a nuclear localization sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to PAAKRVKLD (SEQ ID NO: 59). In some embodiments, the nuclear localization sequence is fused to the ORF2p sequence. In some embodiments, the construct comprises a nucleic acid sequence encoding a flag tag having the sequence DYKDDDDK (SEQ ID NO: 60). In some embodiments, the flag tag is fused to the ORF2p sequence. In some embodiments, the flag tag is fused to the nuclear localization sequence.

In some embodiments, the construct comprises a nucleic acid sequence encoding an MS2 coat protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to ASNFTQFVLVDNGGTGDVTVAPSNFANGIAEWISSN-SRSQAYKVTCSVRQSSAQNRKYTIKVEV PKGAWR-SYLNMELTIPIFATNSDCELIVKAMQGLLKDGNPIP-SAIAANSGIYAMASNFTQFVLVD NGGTGDVTVAPSNFANGIAEWISSNSR-SQAYKVTCSVRQSSAQNRKYTIKVEVPKGAWRSYLN MELTIPIFATNSDCELIVKAMQGLLKDGNPIPSA-IAANSGIY (SEQ ID NO: 61). In some embodiments, the MS2 coat protein sequence is fused to the ORF2p sequence.

In some embodiments, the transgene may comprise a flanking sequence which comprises an Alu ORF2p recognition sequence.

In some embodiments, additional elements may be introduced into the mRNA. In some embodiments, the additional elements may be an IRES element or a T2A element. In some embodiments, the mRNA transcript comprises one, two, three or more stop codons at the 3'-end.

In some embodiments, the one, two, three or more stop codons are designed to be in tandem. In some embodiments, the one, two, three or more stop codons are designed to be in all three reading frames. In some embodiments, the one, two, three or more stop codons may be designed to be both in multiple reading frames and in tandem.

In some embodiments, one or more target specific nucleotides may be added at the priming end of the L1 or the Alu RNA priming region.

In some embodiments, the 5' UTR sequence or the 3' UTR sequence in addition to be able to bind the ORF protein may also be capable of binding to one or more endogenous proteins that regulate gene retrotransposition and/or stable integration. In some embodiments, the flanking sequence is capable of binding to a PABP protein.

In some embodiments, the 5'region flanking the transcript may comprise a strong promoter. In some embodiments, the promoter is a CMV promoter.

In some embodiments, an additional nucleic encoding L1 ORF2p is introduced into the cell. In some embodiments, the sequence encoding L1 ORF1 is omitted, and only L1-ORF2 is included. In some embodiments, the nucleic acid encoding the transgene with the flanking elements is mRNA. In some embodiments, the endogenous L1-ORF1p function may be suppressed or inhibited.

In some embodiments, the nucleic acid encoding the transgene with the retrotransposition flanking elements comprise one or more nucleic acid modifications. In some embodiments, the nucleic acid encoding the transgene with the retrotransposition flanking elements comprises one or more nucleic acid modifications in the transgene. In some embodiments, the modifications comprise codon optimization of the transgene sequence. In some embodiments, the codon optimization is for more efficient recognition by the human translational machinery, leading to more efficient expression in a human cell. In some embodiments, the one or more nucleic acid modification is performed in the 5'-flanking sequence or the 3'-flanking sequence including one or more stem-loop regions. the nucleic acid encoding the transgene with the retrotransposition flanking elements comprise one, two, three, four, five, six, seven eight, nine, ten or more nucleic acid modifications.

In some embodiments, the retrotransposed transgene is stably expressed for the life of the cell. In some embodiments, the cell is a myeloid cell. In some embodiments, the myeloid cell is a monocyte precursor cell. In some embodiments, the myeloid cell is an immature monocyte. In some embodiments, the monocyte is an undifferentiated monocyte. In some embodiments, the myeloid cell is a CD14+ cell. In some embodiments, the myeloid cell does not express CD16 marker. In some embodiments, the myeloid cell is capable of remaining functionally active for a desired period of greater than 3 days, greater than 4 days, greater than 5 days, greater than 6 days, greater than 7 days, greater than 8 days, greater than 9 days, greater than 10 days, greater than 11 days, greater than 12 days, greater than 13 days, greater than 14 days or more under suitable conditions. A suitable condition may denote an in vitro condition, or an in vivo condition or a combination of both.

In some embodiments, the retrotransposed transgene may be stably expressed in the cell for about 2 days, about 3 days, about 4 days, about 5 days, about 6 days, about 7 days, about 8 days, about 9 days or about 10 days. In some embodiments, the retrotransposed transgene is stably expressed in the cell for more than 10 days. In some embodiments, the retrotransposed transgene is stably expressed in the cell for more than 2 weeks. In some embodiments, the retrotransposed transgene is stably expressed in the cell for about 1 month.

In some embodiments, the retrotransposed transgene may be modified for stable expression. In some embodiments, the retrotransposed transgene may be modified for resistant to in vivo silencing.

In some embodiments, the expression of the retrotransposed transgene may be controlled by a strong promoter. In some embodiments, the expression of the retrotransposed transgene may be controlled by a moderately strong promoter. In some embodiments, the expression of the retrotransposed transgene may be controlled by a strong promoter that can be regulated in an in vivo environment. In some embodiments, the promoter is a CMV promoter. In some embodiments, the promoter is a L1-Ta promoter.

In some embodiments, the ORF1p may be overexpressed. In some embodiments, the ORF2 may be overexpressed. In some embodiments, the ORF1p or ORF2p or both are overexpressed. In some embodiments, upon overexpression of an ORF1, ORF1p is at least 1.1 fold, 1.5 fold, 2 fold, 3 fold, 4 fold, 5 fold, 6 fold, 7 fold, 8 fold, 9 fold, 10 fold, 12 fold, 14 fold, 16 fold, 18 fold, 20 fold, 30 fold, 40 fold, 50 fold, 60 fold, 70 fold, 80 fold, 90 fold, or at least 100 fold higher than a cell not overexpressing and ORF1.

In some embodiments, upon overexpression of an ORF2 sequence, ORF2p is at least 1.1 fold, 1.5 fold, 2 fold, 3 fold, 4 fold, 5 fold, 6 fold, 7 fold, 8 fold, 9 fold, 10 fold, 12 fold, 14 fold, 16 fold, 18 fold, 20 fold, 30 fold, 40 fold, 50 fold, 60 fold, 70 fold, 80 fold, 90 fold, or at least 100 fold higher than a cell not overexpressing and ORF2p.

Retrotransposition Fidelity and Target Specificity

The LINE-1 elements can bind to their own mRNA poly A tail to initiate retrotransposition. LINE-1 elements preferably retrotranspose their own mRNA over random mRNAs (Dewannieux et al., 2013, 3,000-fold higher LINE-1 retrotransposition as compared to random mRNAs). In addition, LINE-1 elements can also integrate non-specific poly-A sequences within a genome.

In one aspect, provided herein are retrotransposition compositions and methods of using the same with increased retrotransposition specificity. For example, retrotransposition compositions with high specificity may be used for highly specific and efficient reverse transcription and subsequently, integration into genome of a target cell, e.g., a myeloid cell. In some embodiments, a retrotransposition composition provided herein comprises a retrotransposition cassette that comprises one or more additional components that increases integration or retrotransposing specificity. For example, the retrotransposon cassette may encode one or more additional elements that allows for high affinity RNA-protein interaction to out compete non-specific binding between poly-A sequences and ORF2.

Accordingly, several measures are disclosed herein for enhancing integration or retrotransposition efficiency.

One exemplary measure for enhancing integration or retrotransposition efficiency is external manipulation of the cells. The endonuclease function of the retrotransposition machinery delivered in a cell may likely be subject to inhibition by the cell's transposition silencing machinery, such as DNA repair pathways. For example, small molecules can be used to modulate or inhibit DNA repair pathways in the cells prior to introducing the nucleic acid. For example, cell sorting and/or synchronization can be used prior to introducing the nucleic acid, such as by electroporation, as cell cycle synchronized cell populations were shown to increase gene transfer to the cells. Cell sorting may be utilized to synchronize or homogenize the cell types and increase uniform transfer and expression of the exogenous nucleic acid. Uniformity may be achieved sorting stem cells from non-stem cells. Another exemplary measure for enhancing integration or retrotransposition efficiency is to enhance biochemical activity. For example, this may be achieved by increasing reverse-transcriptase processivity or DNA cleavage (endonuclease) activity. Another exemplary measure for enhancing integration or retrotransposition efficiency is to subvert endogenous silencing mechanisms. For example, this may be achieved by replacing entire LINE-1 sequence with a different organisms' LINE-1. Another exemplary measure for enhancing integration or retrotransposition efficiency is to enhance translation and ribosome binding. For example, this may be achieved by increasing expression of LINE-1 proteins, increasing LINE protein binding LINE-1 mRNA, or increasing LINE-1 complex binding to ribosomes. Another exemplary measure for enhancing integration or retrotransposition efficiency is to increase nuclear import or retention. For example, this may be achieved by fusing the LINE-1 sequence to a nuclear retention signal sequence. Another exemplary measure for enhancing integration or retrotransposition efficiency is to enhance specific-specific insertion. For example, this may be achieved by fusing a targeting domain to ORF2 to increase sequence specific retrotransposition.

In one embodiment, the method encompasses enhancing the retrotransposon for increasing specificity and robustness of expression of the cargo by modifying the UTR sequence of the LINE-1 ORFs. In some embodiments, the 5'UTR upstream of ORF1 or ORF2 encoding sequence may be further modified to comprise a sequence that is complementary to the sequence of a target region within the genome that helps in homologous recombination at the specific site where the ORF nuclease can act and the retrotransposition can take place. In some embodiments, the sequence that can bind to a target sequence by homology is between 2-15 nucleotides long. In some embodiments, the sequence having homology to a genomic target that is included in the 5'UTR of an ORF1 mRNA may be about 3 nucleotides, about 4 nucleotides, about 5 nucleotides, about 6 nucleotides, about 7 nucleotides, about 8 nucleotides, about 9 nucleotides or about 10 nucleotides long. In some embodiments, the sequence having homology to a genomic target is about 12 or about 15 nucleotides long. In some embodiments, the sequence having homology to a genomic target comprises about 2-5, about 2-6, about 2-8 or about 2-10, or about 2-12 contiguous nucleotides that share complementarity with the respective target region within the genome.

In some embodiments, an ORF2 is associated with or fused to an additional protein domain that comprises RNA binding activity. In some embodiments, the retrotransposon cassette comprises a cognate RNA sequence that comprises affinity with the additional protein domain associated with or fused to the ORF2. In some embodiments, the ORF2 is associated with or fused to a MS2-MCP coat protein. In some embodiments, the retrotransposon cassette further comprises a MS2 hairpin RNA sequence in the 3' or 5' UTR sequence that interacts with the MS2-MCP coat protein. In some embodiments, the ORF2 is associated with or fused to a PP7 coat protein. In some embodiments, the retrotransposon cassette further comprises a PP7 hairpin RNA sequence in the 3' or 5' UTR sequence that interacts with the MS2-MCP coat protein. In some embodiments, the one or more additional elements increases retrotransposition specificity by at least 1.5 fold, at least 2 fold, at least 3 fold, at least 4 fold, at least 5 fold, at least 10 fold, at least 20 fold, at least 30 fold, at least 50 fold, at least 100 fold, at least 200 fold, at least 300 fold, at least 500 fold, at least 1000 fold, at least 1500 fold, at least 2000 fold, at least 3000 fold, at least 5000 fold or more as compared to a retrotransposon cassette without the one or more additional elements.

The DNA endonuclease domain appears to have specificity for a series of purines 3' of the target site followed by a series of pyrimidines $(Py)_n\downarrow(Pu)_n$. An exemplary sequence may be $(\text{Adenosine})_n\downarrow(\text{Thymidine})_n$.

In one aspect, provided herein are methods of using retrotransposition having high target specificity. Consequently, provided herein is a method and compositions for stable incorporation of a transgene into the genome of a myeloid cell, such as a monocyte or macrophage, wherein the method comprises incorporating the transgene using a non-LTR retrotransposon system, wherein the retrotransposition occurs at a specific genomic locus with a target specificity, high precision and fidelity. Therefore, in some embodiments, the method comprises administration to the cell a composition comprising a system having at least one transgene, flanked with one or more retrotransposable elements, and one or more nucleic acids encoding one or more proteins for increasing the transposition specificity, and/or further comprising modifying one or more genes associated with the retrotransposition.

The nucleic acid comprising the transgene, situated in UTR region of the retrotransposable elements is often referred to as a retrotransposition cassette. Accordingly, in some embodiments, the retrotransposition cassette comprises the nucleic acid encoding the transgene and flanking Alu transposable elements. The retrotransposable elements comprise a sequence for binding the retrotransposons, for example, L1-transposons, such as L1-ORF proteins, ORF1p and ORF2p. ORF proteins are known to bind to their own mRNA sequence for retrotransposition. Therefore, the retrotransposition cassette comprises the nucleic acid encoding the transgene; a flanking L1-ORF2p binding sequence, and/or a L1-ORF1p binding sequence, comprising a sequence encoding a L1-ORF1p encoding sequence and a L1-ORF2p encoding sequence outside the transgene sequence. In some embodiments, the L1-ORF1 and L1-ORF2 are interspersed by a spacer region, also termed as an ORF1-ORF2 inter-region. In some embodiments, the L1-ORF1 and L1-ORF2 coding sequences are in an opposite orientation with respect to the coding region of the transgene. The retrotransposition cassette can comprise a poly A region downstream of the L1-ORF2-coding sequence and the transgene sequence is placed downstream of the poly A sequence. The L1-ORF2 comprises a nucleic acid sequence that encodes an endonuclease (EN) and a reverse transcriptase (RT) followed by the poly A sequence. In some embodiments, the L1-ORF2 sequence in the retrotransposition cassette described herein is a complete (intact) sequence, that is, encodes the full length native (WT) L1-ORF2 sequence. In some embodiments, the L1-ORF2 sequence in the retrotransposition cassette described herein comprises a partial or modified sequence.

The system described herein can comprise a promoter for expressing the L1-ORF1p and L1-ORF2p. In some embodiments, the transgene expression is driven by a separate promoter. In some embodiments, the transgene and the ORFs are in tandem orientation. In some embodiments, the transgene and the ORFs are in opposite orientation.

In some embodiments, the method comprises incorporating one or more elements in addition to the retrotransposon cassette. In some embodiments, the one or more additional elements comprise a nucleic acid sequence encoding one or more domains of a heterologous protein. The heterologous protein may be a sequence specific nucleic acid binding protein, for example, a sequence specific DNA binding protein domain (DBD). In some embodiments, the heterologous protein is a nuclease or a fragment thereof. In some embodiments, the additional elements comprise a nucleic acid sequence encoding one or more nuclease domains or fragments thereof from a heterologous protein. In some embodiments, the heterologous nuclease domain has reduced nuclease activity. In some embodiments, the heterologous nuclease domain is rendered inactive. In some embodiments, the ORF2 nuclease is rendered inactive; whereas one or more nuclease domains from the heterologous protein is configured to render specificity to the retrotransposition. In some embodiments, one or more nuclease domains or fragments thereof from the heterologous protein targets a specific desired polynucleotide within the genome where retrotransposition and incorporation of the polynucleotide of interest is to be incorporated. In some embodiments, the one or more nuclease domains from the heterologous protein comprise a mega-TAL nuclease domain, TALENs, or a zinc finger nuclease domain, for example, a mega-TAL, a TALE, or a zinc finger domain fused to or associated with a nuclease domain, e.g., a FokI nuclease domain. In some embodiments, the one or more nuclease domains from the heterologous protein comprise a CRISPR-Cas protein domain loaded with a specific guide nucleic acid, e.g., a guide RNA (gRNA) for a specific target locus. In some embodiments, the CRISPR-Cas protein is a Cas9, a Cas12a, a Cas12b, a Cas13, a CasX, or a CasY protein domain. In some embodiments, the one or more nuclease domains from the heterologous protein has target specificity.

In some embodiments, the additional nuclease domain may be incorporated into the ORF2 domain. In some embodiments, the additional nuclease may be fused with the ORF2p domain. In some embodiments, the additional nuclease domain may be fused to an ORF2p, wherein the ORF2p includes a mutation in the ORF2p endonuclease domain. In some embodiments, the mutation inactivates the ORF2p endonuclease domain. In some embodiments, the mutation is a point mutation. In some embodiments, the mutation is a deletion. In some embodiments, the mutation is an insertion. In some embodiments, the mutation abrogates the ORF2 endonuclease (nickase) activity. In some embodiments, a mutation inactivates the DNA target recognition of ORF2p endonuclease. In some embodiments, the mutation covers a region associated with ORF2p nuclease-DNA recognition. In some embodiments, a mutation reduces the DNA target recognition of ORF2p endonuclease. In some embodiments, the ORF2p endonuclease domain mutation is in the N-terminal region of the protein. In some embodiments, the ORF2p endonuclease domain mutation is in a conserved region of the protein. In some embodiments, the ORF2p endonuclease domain mutation is in the conserved N-terminal region of the protein. In some embodiments, the mutation comprises the N14 amino acid within L1 endonuclease domain. In some embodiments, the mutation comprises 2, 3, 4, 5, 6, 7, 8, 9, 10, 11, 12, 13, 14, 15, 16, 17, 18, 19, 20 or more consecutive amino acids including the N14 amino acid within L1 endonuclease domain. In some embodiments, the mutation comprises the comprises the E43 amino acid within L1 endonuclease. In some embodiments, the mutation comprises 2, 3, 4, 5, 6, 7, 8, 9, 10, 11, 12, 13, 14, 15, 16, 17, 18, 19, 20 or more consecutive amino acids including the E43 amino acid within L1 endonuclease domain. In some embodiments, the mutation comprises 2 or more amino acids in the L1 endonuclease domain including N14, or E43 or a combination thereof. In some embodiments, the mutation comprises D145 of the L1 endonuclease domain. In some embodiments, the mutation may be D145A. In some embodiments, the may be a comprise D205 of the L1 endonuclease domain. In some embodiments, the mutation may be D205G. In some embodiments, the mutation may comprise H230 of L1 endonuclease domain. In some embodiments, the may be a comprise S228 of the L1 endonuclease domain. In some embodiments, the mutation may be S228P.

In some embodiments, a mutation reduces the DNA target recognition of ORF2p endonuclease by at least 50%. In some embodiments, a mutation reduces the DNA target recognition of ORF2p endonuclease by at least 60%. In some embodiments, a mutation reduces the DNA target recognition of ORF2p endonuclease by at least 70%. In some embodiments, a mutation reduces the DNA target recognition of ORF2p endonuclease 80%. In some embodiments, a mutation reduces the DNA target recognition of ORF2p endonuclease 90%. In some embodiments, a mutation reduces the DNA target recognition of ORF2p by 95%. In some embodiments, a mutation reduces the DNA target recognition of ORF2p by 100%.

In some embodiments, the mutation is a deletion. In some embodiments, the deletion is complete, i.e., 100% of the L1 endonuclease domain is deleted. In some embodiments, the deletion is partial. In some embodiments, the about 98%, about 95%, about 94%, about 93%, about 92% about 91%, about 90%, about 85%, about 80%, about 75%, about 70%, about 65%, about 60%, or about 50% of the ORF2 endonuclease domain is deleted.

In some embodiments, an additional nuclease domain is inserted into the ORF2 protein sequence. In some embodiments, ORF2 endonuclease domain is deleted, and is replaced with an endonuclease domain from a heterologous protein. In some embodiments, the ORF2 endonuclease is partially deleted and replaced with an endonuclease domain from a heterologous protein. The endonuclease domain from a heterologous protein may be a mega-TAL nuclease domain. The endonuclease domain from a heterologous protein may be a TALENs. The endonuclease domain from a heterologous protein may be a Cas9 loaded with a specific gRNA for a locus.

In some embodiments, the endonuclease is an endonuclease that has (i) a specific target on the genome and (ii) it creates a 5'-P and a 3'-OH terminus at the cleavage site.

In some embodiments, the additional endonuclease domain from a heterologous protein is an endonuclease domain from a related retrotransposon.

In some embodiments, the endonuclease domain from a heterologous protein may comprise a bacterial endonuclease engineered for targeting a specific site. In some embodiments, the endonuclease domain from a heterologous protein may comprise a domain of a homing endonuclease or a fragment thereof. In some embodiments, the endonuclease is a homing endonuclease. In some embodiments, the homing endonuclease is an engineered LAGLIDADG (SEQ ID NO: 62) homing endonucleases ("LAGLIDADG" disclosed as (LHEs) or a fragment thereof. In some embodiments, additional endonucleases may be a restriction endonuclease, Cre, Cas TAL or fragments thereof. In some embodiments, the endonuclease may comprise a Group II intron encoded protein (ribozyme) or a fragment thereof.

An engineered or modified L1-ORF2p as discussed in the preceding paragraphs, that is endowed with specific DNA targeting capability due to the additional/heterologous endonuclease is expected to be highly advantageous in driving targeted stable integration of a transgene into the genome. The engineered L1-ORF2p can generate much reduced off-target effects when expressed in a cell than using a native, non-engineered L1-ORF2p. In some embodiments, the engineered L1-ORF2p generates no off-target effect.

In some embodiments, the engineered or modified L1-ORF2p targets a recognition site that is other than the usual $(Py)_n\downarrow(Pu)_n$ site. In some embodiments, engineered L1-ORF2p targets a recognition site that comprises the $(Py)_n\downarrow(Pu)_n$ site, for example, TTTT/AA site, such as a hybrid target site. In some embodiments, the engineered L1-ORF2p targets a recognition site having at least one nucleotide in addition to the conventional L1-ORF2 $(Py)_n\downarrow(Pu)_n$ site, for example TTTT/AAG, or TTTT/AAC, or TTTT/AAT, TTTT/AAA, GTTTT/AA, CTTTT/AA, ATTTT/AA, or TTTTT/AA. In some embodiments, the engineered L1-ORF2p targets a recognition site that is in addition to the conventional L1-ORF2p $(Py)_n\downarrow(Pu)_n$ site. In some embodiments, the engineered L1-ORF2p targets a recognition site that is other than to the conventional L1-ORF2p $(Py)_n\downarrow(Pu)_n$ site. In some embodiments, the engineered L1-ORF2p targets a recognition site that is 4, 5, 6, 7, 8, 9, 10 or more nucleotides long. In some embodiments, the engineered or modified L1-ORF2p recognition site may be 11, 12, 13, 14, 15, 16, 17, 18, 19, 20 or more nucleotides.

The engineered L1-ORF2p can be engineered to retain its ability to bind to its own mRNA after translation and reverse transcribe with high efficiency. In some embodiments, the engineered L1-ORF2p has enhanced efficiency of reverse transcription compared to a native (WT) L1-ORF2p.

In some embodiments, the system comprising a retrotransposable element further comprises a gene modification that reduces non-specific retrotransposition. In some embodiments, the gene modification may comprise a sequence encoding the L1-ORF2p. In some embodiments, the modification may comprise mutation of one or more amino acids that are essential for binding to a protein that helps ORF2p binding to the target genomic DNA. A protein that helps ORF2p binding to the target genomic DNA may be part of the chromatin-ORF interactome. In some embodiments, the modification may comprise one or more amino acids that are essential for binding to a protein that helps ORF2p DNA endonuclease activity. In some embodiments, the modification may comprise one or more amino acids that are essential for binding to a protein that helps ORF2p RT activity. In some embodiments, the modification may comprise at a protein binding site on ORF2p such that the association of a protein with ORF2p is altered, wherein binding of the protein to ORF2p is required for binding to chromatin. In some embodiments, the modification may comprise at a protein binding site on ORF2p such that the association of the protein with ORF2p is more stringent and/or specific than in absence of the modification. In some embodiments, as a consequence of altered association of ORF2p with the protein owing to the modification of ORF2p coding sequence at the protein binding site, the binding of ORF2p to the target DNA has increased specificity. In some embodiments, the modification may reduce binding of ORF2 to one or more proteins that are part of the ORF2p chromatin interactome.

In some embodiments, the gene modification may be in the PIP domain of ORF2p.

In some embodiments, the gene modification may be in one or more genes encoding a protein that binds to an ORF2p and helps in the recognition, binding, endonuclease or RT activity of ORF2p. In some embodiments, the gene modification may be in one or more genes encoding PCNA, PARP1, PABP, MCM, TOP1, RPA, PURA, PURB, RUVBL2, NAP1, ZCCHC3, UPF1 or MOV10 proteins at an ORF2p interacting site for each protein or at a site that affects the protein's interaction with ORF2p or the interaction of ORF2p with target DNA. In some embodiments, the modification may be on an ORF2p binding domain of PCNA at an ORF2p interacting site or at a site that affects the protein's interaction with ORF2p or the interaction of ORF2p with target DNA. In some embodiments, the modification may be on an ORF2p binding domain of TOP1. In some embodiments, the modification may be on an ORF2p binding domain of RPA. In some embodiments, the modification may be on an ORF2p binding domain of PARP1 at an ORF2p interacting site or at a site that affects the protein's interaction with ORF2p or the interaction of ORF2p with target DNA. In some embodiments, the modification may be on an ORF2p binding domain of PABP (e.g., PABPC1) at an ORF2p interacting site or at a site that affects the protein's interaction with ORF2p or the interaction of ORF2p with target DNA. In some embodiments, the gene modification may be on an MCM gene. In some embodiments, the gene modification may be on a gene encoding MCM3 protein at an ORF2p interacting site or at a site that affects the protein's interaction with ORF2p or the interaction of ORF2p with target DNA. In some embodiments, the gene modification may be on a gene encoding MCM5 protein at an ORF2p interacting site or at a site that affects the protein's interaction with ORF2p or the interaction of ORF2p with target DNA. In some embodiments, the gene modification may be on a gene encoding MCM6 protein at an ORF2p interacting site or at a site that affects the protein's interaction with ORF2p or the interaction of ORF2p with target DNA. In some embodiments, the gene modification may be on a gene encoding MEPCE protein at an ORF2p interacting site or at a site that affects the protein's interaction with ORF2p or the interaction of ORF2p with target DNA. In some embodiments, the gene modification may be on a gene encoding on a gene encoding RUVBL1 or RUVBL2 protein at an ORF2p interacting site or at a site that affects the protein's interaction with ORF2p or the interaction of ORF2p with target DNA. In some embodiments, the gene modification may be on a gene encoding on a gene encoding TROVE protein at an ORF2p interacting site or at a site that affects the protein's interaction with ORF2p or the interaction of ORF2p with target DNA.

In some embodiments, the retrotransposition system disclosed herein comprises one or more elements that increase the fidelity of reverse transcription.

In some embodiments, the L1-ORF2 RT domain is modified. In some embodiments, the modification includes one or more of: increasing fidelity, increasing processivity, increasing DNA-RNA substrate affinity; or inactivating RNase H activity.

In some embodiments, the modification comprises introducing one or more mutations in the RT domain of the L1-ORF2, such that the fidelity of the RT is increased. In some embodiments, the mutation comprises a point mutation. In some embodiments, the mutation comprises alteration, such as substitution of one, two three, four, five, six or more amino acids in the L1-ORF2p RT domain. In some embodiments, the mutation comprises deletion of one or more amino acids, for example, one, two, three, four, five, six, seven, eight, nine, ten or more amino acids in the L1-ORF2p RT domain. In some embodiments, the mutation may comprise an in-del mutation. In some embodiments, the mutation may comprise a frame-shift mutation.

In some embodiments, the modification may comprise inclusion of an additional RT domain or fragment thereof from a second protein. In some embodiments, the second protein is a viral reverse transcriptase. In some embodiments, the second protein is a non-viral reverse transcriptase. In some embodiments, the second protein is a retrotransposable element. In some embodiments, the second protein is a non-LTR retrotransposable element. In some embodiments, the second protein is a group II intron protein. In some embodiments, the group II intron is as TGIRTII. In some embodiments, the second protein is a Cas nickase, wherein the retrotransposable system further comprises introducing a guide RNA. In some embodiments, the second protein is a Cas9 endonuclease, wherein the retrotransposable system further comprises introducing a guide RNA. In some embodiments, the second protein or fragment thereof is fused to the N-terminus of the L1-ORF2 RT domain or the modified L1-ORF2 RT domain. In some embodiments, the second protein or fragment thereof is fused to the C-terminus of the L1-ORF2 RT domain or the modified L1-ORF2 RT domain.

In some embodiments, the additional RT domain or fragment thereof from the second protein is incorporated in the retrotransposition system in addition to the full-length WT L1-ORF2p RT domain. In some embodiments, the additional RT domain or fragment thereof from the second protein is incorporated in presence of a modified (engineered) L1-ORF2p RT domain or a fragment thereof, where the modification (or engineering) may comprise a mutation for enhancement of the L1-ORF2p RT processivity, stability and/or fidelity of the modified L1-ORF2p RT compared to the native or WT ORF2p.

In some embodiments, the reverse transcriptase domain could be replaced with other more highly processive and high-fidelity RT domains from other retroelements or group II introns, such as TGIRTII.

In some embodiments, the modification may comprise a fusion with an additional RT domain or fragment thereof from a second protein. In some embodiments, the second protein may comprise a retroelement. The additional RT domain or fragment thereof from a second protein is configured to increase the fidelity of reverse transcription of the fused L1-ORF2p RT domain. In some embodiments, the nucleic acid encoding the additional RT domain or fragment thereof is fused to a native or WT L1-ORF2 encoding sequence. In some embodiments, the nucleic acid encoding the additional RT domain or fragment thereof from a second protein is fused to a modified L1-ORF2 encoding sequence. In some embodiments, the modification comprises introducing one or more mutations in the RT domain of the L1-ORF2 or fragment thereof, such that the fidelity of the fused RT is increased. In some embodiments, the mutation in the RT domain of the L1-ORF2 or fragment thereof comprises a point mutation. In some embodiments, the mutation comprises alteration, such as substitution of one, two three, four, five, six or more amino acids in the L1-ORF2p RT domain. In some embodiments, the mutation comprises deletion of one or more amino acids, for example, one, two, three, four, five, six, seven, eight, nine, ten or more amino acids in the L1-ORF2p RT domain. In some embodiments, the mutation may comprise an in-del mutation. In some embodiments, the mutation may comprise a frame-shift mutation.

In some embodiments, the modified L1-ORF2p RT domain has increased processivity than the WT L1-ORF2p RT domain.

In some embodiments, the modified L1-ORF2p RT domain has at least 10% higher processivity and/or fidelity over the WT L1-ORF2p RT domain. In some embodiments, the modified L1-ORF2p RT domain has at least 20%, 30%, 40%, 50%, 60%, 70%, 80%, 90%, 100%, 110%, 120%, 150%, 200%, 300%, 400%, 500%, 1000% or higher processivity and/or fidelity over the WT L1-ORF2p RT domain. In some embodiments, the modified RT can process greater than 6 kb nucleic acid stretch. In some embodiments, the modified RT can process greater than 7 kb nucleic acid stretch. In some embodiments, the modified RT can process greater than 8 kb nucleic acid stretch. In some embodiments, the modified RT can process greater than 9 kb nucleic acid stretch. In some embodiments, the modified RT can process greater than 10 kb nucleic acid stretch.

B. Group II Introns and Ribozymes

Group II enzymes are mobile ribozymes that self-splice precursor RNAs, yielding excised intron lariat RNAs. The introns encode a reverse transcriptase. The reverse transcriptase may stabilize the RNA for forward and reverse splicing, and later in converting the integrated intron RNA to DNA.

Group II RNAs are characterized by a conserved secondary structure spanning 400-800b nucleotides. The secondary structure is formed by six domains DI-VI, and is organized in a structure resembling a wheel, where the domains radiate from a central point. The domains interact to form a conserved tertiary structure that brings together distant sequences to form an active site. The active site binds the splice sites and branch point residue nucleotide and in association of Mg2+ cations, activate catalysis of splicing. The DV domain is within the active site, which has the conserved catalytic AGC and an AY bulge and both these regions bind Mg2+ ions necessary for the catalysis. DI is the largest domain with upper and lower halves separated by kappa and zeta motifs. The lower half contains the □' motif, which is associated with an active site. The upper half contains sequence elements that bind to the 5' and 3' exons at the active sites. DIV encodes the intron-encoded protein (IEP) with subdomain IVa near the 5'-end containing the high affinity binding site for IEP. Group II introns have conserved 5'- and 3'-end sequences, GUGYG and AY respectively.

Group II RNA introns can be utilized to retrotranspose a sequence of interest into DNA via target primed reverse transcription. This process of transposition by Group II RNA introns is often referred to as retrohoming. Group II introns recognize DNA target sites by base pairing of the intron RNA to the DNA target sequence, they can be modified to retarget a specific sequence carried within the intron to a desired DNA site.

In some embodiments, the method and compositions for retrotransposition described herein may comprise a Group II intron sequence, a modified Group II intron sequence or a fragment thereof. Exemplary Group II IEPs (maturase) include but are not limited to bacterial, fungal, yeast IEPs, that are functional in human cells. In particular, the nuclease leaves a 3'-OH at the cleavage site of the DNA which can be utilized by another RT for priming and reverse transcription.

An exemplary Group II maturase may be TGIRT (thermally stable group II intron maturase).

In one or more embodiments of several aspects described herein, the nucleic acid construct comprises an RNA. In one or more embodiments of several aspects of the disclosure, the nucleic acid construct is an RNA. In one or more embodiments of several aspects of the disclosure, the nucleic acid construct is an mRNA. In one aspect, the mRNA comprises a sequence of a heterologous gene or portion thereof, wherein the heterologous gene or portion thereof encodes a polypeptide or protein. In some embodiments, the mRNA comprises a sequence encoding a fusion protein. In some embodiments, the mRNA comprises a sequence encoding a recombinant protein. In some embodiments, the mRNA comprises a sequence encoding a synthetic protein. In some embodiments, the nucleic acid comprises one or more sequences, wherein the one or more sequences encode on or more heterologous proteins, one or more recombinant proteins, or one or more synthetic proteins or a combination thereof. In some embodiments, the nucleic acid comprises one or more sequences, wherein the one or more sequences encode on or more heterologous proteins comprising a synthetic protein or a recombinant protein. In some embodiments, the synthetic or recombinant protein is a recombinant fusion protein.

In one or more of embodiments of several aspects of the disclosure, the nucleic acid construct is developed for expressing in a eukaryotic cell. In some embodiments, the nucleic acid construct is developed for expressing in a human cell. In some embodiments, the nucleic acid construct is developed for expressing in a hematopoietic cell. In some embodiments, the nucleic acid construct is developed for expressing in a myeloid cell. In some embodiments, the myeloid cell is a human cell.

II. Modifications in Nucleic Acid Constructs for Methods of Enhancement of Expression of Encoded Protein In some aspects of the disclosure, the recombinant nucleic acid is modified for enhanced expression of the protein encoded by a sequence of the nucleic acid. Enhanced expression of the protein encoded therein can be a function of the nucleic acid stability, translation efficiency and the stability of the translated protein. A number of modifications are contemplated herein for incorporation in the design of the nucleic acid construct that can confer nucleic acid stability, such as stability of the messenger RNA encoding the exogenous or heterologous protein, which may be a synthetic recombinant protein or a fragment thereof.

In some embodiments, the nucleic acid is mRNA, comprising one or more sequences, wherein the one or more sequences encode one or more heterologous proteins comprising a synthetic or a recombinant fusion protein.

In some embodiments, one or more modifications are made in the mRNA comprising a sequence encoding a recombinant or fusion protein to increase the mRNA half-life.

Structural Elements to Block 5'-3' Degradations by Exonucleases: 5'-Cap and 3' UTR Modifications A proper 5'-cap structure is important in the synthesis of functional messenger RNA. In some embodiments, the 5'-cap comprises a guanosine triphosphate arranged as GpppG at the 5'terminus of the nucleic acid. In some embodiments, the mRNA comprises a 5' 7-methylguanosine cap, m7-GpppG. A 5' 7-methylguanosine cap increases mRNA translational efficiency and prevents degradation of mRNA 5'-3'exonucleases. In some embodiments, the mRNA comprises "anti-reverse" cap analog (ARCA, $m^{7,3'}$-*o*GpppG). Translational efficiency however, can be markedly increased by usage of the ARCA. In some embodiments, the guanosine cap is a Cap 0 structure. In some embodiments, the guanosine cap is a Cap 1 structure. In addition to its essential role of cap-dependent initiation of protein synthesis, the mRNA cap also functions as a protective group from 5' to 3' exonuclease cleavage and a unique identifier for recruiting protein factors for pre-mRNA splicing, polyadenylation and nuclear export. It acts as the anchor for the recruitment of initiation factors that initiate protein synthesis and the 5' to 3' looping of mRNA during translation. Three enzymatic activities are required to generate the Cap 0 structure, namely, RNA triphosphatase (TPase), RNA guanylyltransferase (GTase) and guanine-N7 methyltransferase (guanine-N7 MTase). Each of these enzyme activities carries out an essential step in the conversion of the 5' triphosphate of nascent RNA to the Cap 0 structure. RNA TPase removes the γ-phosphate from the 5' triphosphate to generate 5' diphosphate RNA. GTase transfers a GMP group from GTP to the 5' diphosphate via a lysine-GMP covalent intermediate. The guanine-N7 MTase then adds a methyl group to the N7 amine of the guanine cap to form the cap 0 structure. For Cap 1 structure, m7G-specific 2'O methyltransferase (2'O MTase) methylates the +1 ribonucleotide at the 2'O position of the ribose to generate the cap 1 structure. The nuclear RNA capping enzyme interacts with the polymerase subunit of RNA polymerase II complex at phosphorylated Ser5 of the C-terminal heptad repeats. RNA guanine-N7 methyltransferase also interacts with the RNA polymerase II phosphorylated heptad repeats. In some embodiments, the cap is a G-quadruplex cap.

In some embodiments, the mRNA is synthesized by in vitro transcription (IVT). In some embodiments, mRNA synthesis and capping may be performed in one step. Capping may occur in the same reaction mixture as IVT. In some embodiments, mRNA synthesis and capping may be performed in separate steps. mRNA thus formed by IVT is purified and then capped.

In some embodiments, the nucleic acid construct, e.g., the mRNA construct, comprises one or more sequences encoding a protein or a polypeptide of interest can be designed to comprise elements that protect, prevent, inhibit or reduce degradation of the mRNA by endogenous 5'-3' exoribonucleases, for example, Xml. Xml is a cellular enzyme in the normal RNA decay pathways that degrades 5' monophosphorylated RNAs. However, some viral RNA structural elements are found to be particularly resistant to such RNases, for example, the Xml-resistant structure in flaviviral sfRNAs, called the 'xrRNA'. For example, the mosquito-borne flaviviruses (MBFV) genomes contain discrete RNA structures in their 3'-untranslated region (UTR) that block the progression of Xrn1. These RNA elements are sufficient to block Xrn1 without the use of accessory proteins. xrRNAs halt the enzyme at a defined location such that the viral RNA located downstream of the xrRNAs is protected from degradation. The xrRNAs from Zikavirus or Murray Valley encephalitis virus, for example, comprise three-way junction and multiple pseudoknot interactions that create an unusual and complex fold that requires a set of nucleotides conserved across the MBFVs structure. xrRNAs halt the enzyme at a defined location such that the viral RNA located downstream of the xrRNAs is protected from degradation. The 5'-end of the RNA passes through a ring-like structure of the fold and is believed to remain protected from the Xrn1-like exonuclease.

In some embodiments, the nucleic acid construct comprising the one or more sequences that encode a protein of interest may comprise one or more xrRNA structures incorporated therein. In some embodiments, the xrRNA is a stretch of nucleotides having the conserved regions of the 3' UTR of one or more viral xrRNA sequences. In some embodiments, 1, 2, 3, 4, 5, 6, 7, 8, 9, 10 or more xrRNA elements are incorporated within the nucleic acid construct. In some embodiments, 2 or more xrRNA elements are incorporated in tandem within the nucleic acid construct. In some embodiments, the xrRNA comprise one or more regions comprising conserved sequences or fragments thereof or modifications thereof. In some embodiments, the xrRNA is placed at the 3'UTR of a retrotransposon element. In some embodiments, the xrRNA is placed at upstream of the sequences encoding the one or more proteins or polypeptides. In some embodiments, the xrRNA is placed in the 3'UTR of a retrotransposon element, such as an ORF2 sequence, and upstream of the sequences encoding the one or more proteins or polypeptides.

In some embodiments, the xrRNA structure comprises a MBFV xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a xrRNA sequence from a member of no known arthropod vector flaviviruses (NKVFVs), or a sequence that is at least 90% identical thereof. In some embodiments, the xrRNA structure comprises a xrRNA sequence from a member of insect-specific flaviviruses (ISFVs), or a sequence that is at least 90% identical thereof. In some embodiments, the xrRNA structure comprises a Zikavirus xrRNA sequence, or a sequence that is at least 90% identical thereof. It is hereby contemplated that any known xrRNA structural elements or conceivable non-obvious variations thereof may be used for the purpose described herein.

Several messenger RNAs from different organisms exhibit one or more pseudoknot structures that exhibits resistance from 5'-3' exonuclease. A pseudoknot is a RNA structure that is minimally composed of two helical segments connected by single-stranded regions or loops. Although several distinct folding topologies of pseudoknots exist.

Poly A Tail Modifications

The poly A structure in the 3'UTR of an mRNA is an important regulator of mRNA half-life. Exosomal deadenylation at the poly A tail initiates mRNA body degradation. In some embodiments, the length of the poly A tail of the mRNA construct is taken into critical consideration and designed for maximizing the expression of the protein encoded by the mRNA coding region, and the mRNA stability. In some embodiments, the nucleic acid construct comprises one or more poly A sequences. In some embodiments, the poly A sequence at the 3'UTR of the sequences encoding the one or more proteins or polypeptides comprise 20-200 adenosine nucleobases. In some embodiments, the poly A sequence comprises 30-200 adenosine nucleobases. In some embodiments, the poly A sequence comprises 50-200 adenosine nucleobases. In some embodiments, the poly A sequence comprises 80-200 adenosine nucleobases. In some embodiments, the mRNA segment comprising the sequences that encode one or more proteins or polypeptides comprises a 3'-UTR having a poly-A tail comprising about 180 adenosine nucleobases, or about 140 adenosine nucleobases, or about 120 adenosine nucleobases. In some embodiments, the poly A tail comprises about 122 adenosine nucleobases. In some embodiments, the poly A sequence comprises 50 adenosine nucleobases. In some embodiments, the poly A sequence comprises 30 adenosine nucleobases. In some embodiments, the adenosine nucleobases in the poly A tail are placed in tandem, with or without intervening non-adenosine bases. In some embodiments, one or more non-adenosine nucleobases are incorporated in the poly A tail, which confer further resistance to certain exonucleases.

In some embodiments, the stretch of adenosines in poly A tail of the construct comprises one or more non-adenosine (A) nucleobase. In some embodiments, the non-A nucleobase is present at −3, −2, −1, and/or +1 position at the poly A 3'-terminal region. In some embodiments, the non-A bases comprise a guanosine (G) or a cytosine (C) or an uracil base (U). In some embodiments, the non-A base is a G. In some embodiments, the non-A base more than one, in tandem, for example, GG. In some embodiments, the modification at the 3' end of the poly A tail with one or more non-A base is directed at disrupting the A base stacking at the poly A tail. The poly A base stacking is effective for deadenylation by various deadenylating enzymes, and therefore 3'end of poly ending in -AAAG, -AAAGA, or -AAAGGA are effective in conferring stability against deadenylation. In some organisms, a GC sequence intervening a poly A sequence is shown to effectively show down 3'-5' exonuclease mediated decay. A modification contemplated herein comprises an intervening non-A residue, or a non-A residue duplex intervening a poly A stretch at the 3'end.

In some embodiments, a triplex structure is introduced in the 3' UTR which effectively stalls or slows down exonuclease activity involving the 3'-end.

In some embodiments, the mRNA with the modifications described above has an extended half-life and demonstrates stable expression over a longer period than the unmodified mRNA. In some embodiments, the mRNA stably expresses for greater than 2 days, 3 days, 4 days, 5 days, 6 days, 7 days, 8 days 9 days or 10 days or more, and the mRNA or its protein product is detectable in vivo. In some embodiments, the mRNA is detected up to 3 days, 4 days, 5 days, 6 days, 7 days, 8 days, 9 days, 10 days, 11 days, 12 days, 13 days, 14 days or 15 days in vivo. In some embodiments, a protein product of the mRNA is detected up to 3 days, 4 days, 5 days, 6 days, 7 days, 8 days, 9 days, 10 days, 11 days, 12 days, 13 days, 14 days, 15 days, 16 days, 17 days, 18 days, 20 days, 25 days or 30 days in vivo.

CircRNA and tectoRNA

Figure 3A:
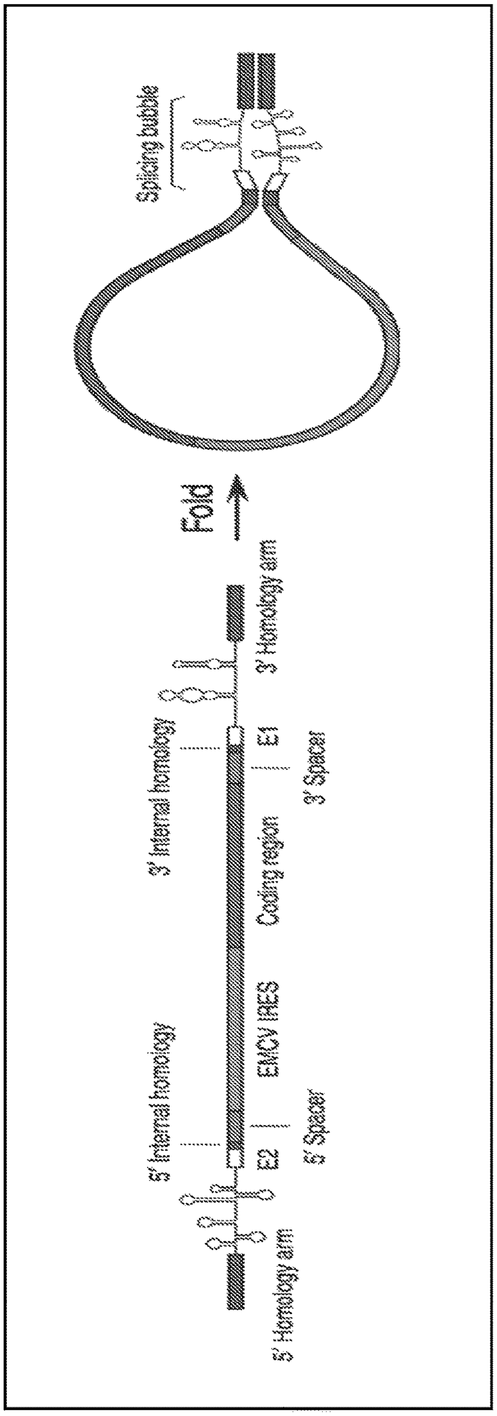
FIG. 3A illustrates an exemplary diagram of conventional circRNA structure and formation.

Circular RNA is useful in the design and production of stable form of RNA used as a messenger RNA to direct synthesis protein chains, such as long, multiply repeating protein chains. There are few methods to make circular RNA (circRNA). They include protein-mediated ligation of RNA ends using RNA ligase and using a split self-splicing intron, such that if the two halves of the intron are located and the ends of a transcribed mRNA, the intron will splice itself out and leave a ligated product (FIG. 3A). Another technique relies on the ability of T4 DNA ligase to act as an RNA ligase when the RNA ends to be ligated are held together by an oligonucleotide. Both these techniques suffer from inefficiency and require a large amount of enzyme. A third technique uses the cyclization or circularization activity of group I introns where most of the intron sequences that carry out the reaction must remain a part of the circle. Group I introns share a complex set of secondary and tertiary structures containing a series of conserved RNA stem loops which form the catalytic core. Many of these introns are self-splicing in vitro and can splice and form two ligated exons as RNA with no accessory protein factors. The products created by the group I autocatalytic reaction are (1) an upstream exon ligated at the 5' splice site to the 3' splice site of a downstream exon and (2) a linear intron that can undergo further reversible auto-catalysis to form a circular intron. The presence of such a large highly structured nucleic acid sequence severely limits the types of RNA sequences that can be made circular by that technique. In addition, the catalytic activity of the intron may remain and interfere with structure and function of the circular RNA.

It is useful to increase the rate of the reaction, and thus the overall efficiency, by bringing the ends of the RNA in closer proximity. Previous work has achieved this by including complementary RNA sequences 3' and 5' to the ends of the mRNA such that upon hybridization of these sequences, the ends of the mRNA are in closer proximity such that it can undergo the ligation or self-splicing reaction with an overall faster rate compared to without the complementary sequences. These are called homology arms (FIG. 3A) of the self-splicing version of the circularization reaction. A major issue with such hybridization strategy is that if there are complementary sequences within the coding region to either of the homology arms, hybridization would actually inhibit the splicing reaction and the arms would need to be optimized for each new coding region. An alternative to this strategy described herein is the use of RNA sequences that fold a three-dimensional structure to form a stable binding interaction that is independent of sequence.

Non-Watson-Crick RNA tertiary interactions can be exploited to construct 'tectoRNA' molecular units, defined as RNA molecules capable of self-assembly. The use of such type of tertiary interactions allows one to control and modulate the assembly process by manipulating cation concentration (e.g. $Mg^{2+}$), and/or suitable temperature and employing modularly designed 'selector' RNA molecules. For the self-assembly of one-dimensional arrays, a basic modular unit was designed that comprises a 4-way junction with an interacting module on each helical arm. In some embodiments, the interacting module is a GAAA loop or a specific GAAA loop receptor. Each tectoRNA can interact with two other tectoRNAs via the formation of four loop-receptor interactions, two with each partner molecule.

In some embodiments, the tectoRNA structures are suitably selected, and integrated in the RNA comprising the exon and intron to form a circRNA. In some embodiments, the integration is done by well-known molecular biology techniques such as ligation. In some embodiments, the tectoRNA forms a stable structure at high temperatures. The tectoRNA structure do not compete with internal RNA sequences, thereby creating high efficiency circularization and splicing.

The circRNA can comprise a coding sequence described in any of the preceding sections. For example, it can comprise a sequence encoding fusion protein comprising a tethering or a receptor molecule. The receptor can be a phagocytic receptor fusion protein.

In some embodiments, the intron is a self-splicing intron.

In some embodiments, the terminal regions having the tertiary structures, also termed scaffolding regions for the circRNA, are about 30 nucleotides to about 100 nucleotides long. In some embodiments, the tertiary structure motif is about 45 nucleotides, about 50 nucleotides, about 55 nucleotides, about 60 nucleotides, about 65 nucleotides, about 70 nucleotides or about 75 nucleotides long. In some embodiments, the tertiary motifs are formed at high temperatures. In some embodiments, the tertiary motifs are stable.

In some embodiments, the nucleic acid construct having the one or more modifications as described herein and comprising one or more sequences encoding one or more proteins or polypeptides, is stable when administered in vivo. In some embodiments, the nucleic acid is an mRNA. In some embodiments, the mRNA comprising one or more sequences encoding one or more proteins or polypeptides is stable in vivo for more than 2 days, for more than 3 days, more than 4 days, more than 5 days, more than 6 days, more than 7 days, more than 8 days, more than 9 days, more than 10 days, more than 11 days, more than 12 days, more than 13 days, more than 14 days, more than 15 days, more than 16 days, more than 17 days, more than 18 days, more than 19 days, or more than 20 days. In some embodiments, the protein encoded by the sequences in the mRNA can be detected in vivo at greater than 3 days, 4 days, 5 days, 6 days, 7 days, 8 days, 9 days, 10 days, 11 days, 12 days, 13 days, 14 days, 15 days, 16 days, 17 days, 18 days, 19 days, or 20 days. In some embodiments, the protein encoded by the sequences in the mRNA can be detected in vivo for about 7 days after the mRNA is administered. In some embodiments, the protein encoded by the sequences in the mRNA can be detected in vivo for about 14 days after the mRNA is administered. In some embodiments, the protein encoded by the sequences in the mRNA can be detected in vivo for about 21 days after the mRNA is administered. In some embodiments, the protein encoded by the sequences in the mRNA can be detected in vivo for about 30 days after the mRNA is administered. In some embodiments, the protein encoded by the sequences in the mRNA can be detected in vivo for more than about 30 days after the mRNA is administered.

In some aspects, enhancing nucleic acid uptake or incorporation within the cell is contemplated for enhancing expression of the retrotransposition. One of the methods include obtaining a homogenous population of cells to initiate incorporation of the nucleic acid, e.g. via transfection, in case of plasmid vector constructs, or via electroporation or any other means that may be used suitably to deliver a nucleic acid molecule into the cell. In some embodiments, cell cycle synchronization may be sought. Cell cycle synchronization may be accomplished by sorting cells for a certain common phenotype. In some embodiments, the cell population may be subjected to a treatment with a reagent that can stall cell cycle progression of all cells at a certain stage. Exemplary reagents can be found in commercial databases, such as www.tocris.com/cell-biology/cell-cycle-inhibitors, or www.scbt.com/browse/chemicals-Other-Chemicals-cell-cycle-arresting-compounds. For example, itraconazole or nocodazole inhibits cell cycle at G1 phase, or reagents that arrest cell cycle at G0/G1 phase, for example, 5-[(4-Ethylphenyl)methylene]-2-thioxo-4-thiazolidinone (compound 10058-F4) (Tocris Bioscience); or a G2M cell cycle blocker, such as AZD 5438 (chemical name, 4-[2-Methyl-1-(1-methylethyl)-1H-imidazol-5-yl]-N-[4-(methylsulfonyl)phenyl]-2-pyrimidinamine) which blocks cell cycle at G2M, G1 or S phases, to name a few. Cyclosporin, hydroxyurea, thymidine, are well known reagents that can cause cell cycle arrests. Some reagents may irreversibly alter a cell state or may be toxic for the cells. Serum deprivation of cells for about 2-16 hours prior to electroporation or transfection, depending on the cell type, may also be an easy and reversible strategy for cell synchronization.

In some embodiments, retrotransposition efficiency may be increased by encouraging generation of DNA double stranded breaks to a cell that has been transfected with or electroporated with the retrotransposition constructs as described herein and/or modulating the DNA repair machinery. Application of these techniques may be limited depending on end uses of the cell that would undergo the genetic manipulation ex vivo for stable incorporation of a nucleic acid sequence by this method. In some cases, use of such techniques may be contemplated where robust expression of the protein or transcript encoded by the incorporated nucleic acid is expected as an outcome for a determined period of time. Method of introducing double stranded breaks in a cell include subjecting the cell to controlled ionizing radiation of about 0.1 Gy or less for a short period.

In some embodiments, efficiency of LINE-1 mediated retrotransposition may be increased by treating the cell with small molecule inhibitors of DNA repair proteins to increase the window for the reverse transcriptase to act. Exemplary small molecule inhibitors of DNA repair proteins may be Benzamide (CAS 55-21-0), Olaparib (Lynparza) (CAS 763113-22-0), Rucaparib (Clovis-AG014699, PF-01367338 Pfizer), Niraparib (MK-827 Tesaro) CAS 1038915-60-4); Veliparib (ABT-888 Abbvie) (CAS 912444-00-9); Camptothecin (CPT) (CAS 7689-03-4); Irinotecan (CAS 100286-90-6); Topotecan (Hycamtin® GlaxoSmithKline) (CAS 123948-87-8); NSC 19630 (CAS 72835-26-8); NSC 617145 (CAS 203115-63-3); ML216 (CAS 1430213-30-1); 6-hydroxyDL-dopa (CAS 21373-30-8); D-103; D-G23; DIDS (CAS 67483-13-0); B02 (CAS 1290541-46-6); RI-1 (CAS 415713-60-9); RI-2 (CAS 1417162-36-7); Streptonigrin (SN) (CAS 3930-19-6).

III. Nucleic Acid Cargo:

A. Transgene

In one aspect the transgene or noncoding sequence that is the heterologous nucleic acid sequence to be inserted within the genome of a cell is delivered as an mRNA. The mRNA may comprise greater than about 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000 bases. In some embodiments, the mRNA may be more than 10,000 bases long. In some embodiments, the mRNA may be about 11,000 bases long. In some embodiments, the mRNA may be about 12,000 bases long. In some embodiments, the mRNA comprises a transgene sequence that encodes a fusion protein. In some embodiments, the nucleic acid is delivered as a plasmid.

In some embodiments, the nucleic acid is delivered in the cell by transfection. In some embodiments, the nucleic acid is delivered in the cell by electroporation. In some embodiments, the transfection or electroporation is repeated more than once to enhance incorporation of the nucleic acid into the cell.

Contemplated herein are retrotransposon mediated stable integration of a recombinant nucleic acid encoding a phagocytic or tethering receptor (PR) fusion protein (CFP). In some embodiments, the CFPs comprise: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked.

In some embodiments, the nucleic acid comprises a sequence encoding a chimeric fusion protein (CFP), the CFP comprising an extracellular domain comprising a CD5 binding domain, and a transmembrane domain operatively linked to the extracellular domain. In some embodiments, the CD5 binding domain is a CD5 binding protein, such as an antigen binding fragment of an antibody, a Fab fragment, an scFv domain or an sdAb domain. In some embodiments, wherein the CD5 binding domain comprises an scFv comprising (i) a variable heavy chain (VH) sequence with at least 90% sequence identity to EIQLVQSGGGLVKPGGSVRISCAASGYTFTNYGMNWVRQAPGKGLEWMGWINTHTGEPTYAD SFKGRFTFSLDDSKNTAYLQINSLRAEDTAVYFCTRRGYDWYFDVWGQGTTVTV (SEQ ID NO: 63); and (ii) a variable light chain (VL) sequence with at least 90% sequence identity to DIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIK (SEQ ID NO: 64). In some embodiments, the CFP further comprises an intracellular domain, wherein the intracellular domain comprises one or more intracellular signaling domains, and wherein a wild-type protein comprising the intracellular domain does not comprise the extracellular domain. In some embodiments, the one or more intracellular signaling domains comprises a phagocytic signaling domain. In some embodiments, the phagocytosis signaling domain comprises an intracellular signaling domain derived from a receptor other than Megf10, MerTk, FcαR, and Bai1. In some embodiments, the phagocytosis signaling domain comprises an intracellular signaling domain derived from FcγR, FcαR or FcεR. In some embodiments, the phagocytosis signaling domain comprises an intracellular signaling domain with at least 90% sequence identity to LYCRRLKIQVRKAAITSYEKSDGVYTGLSTRNQETYETLKHEKPP (SEQ ID NO: 65). In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence with at least 90% sequence identity to YEDMRGILYAAPQLRSIRGQPGPNHEEDADSYENM (SEQ ID NO: 66). In some embodiments, the proinflammatory signaling domain is derived from an intracellular signaling domain of CD40. In some embodiments, the proinflammatory signaling domain comprises a sequence with at least 90% sequence identity to KVAKKPTNKAPHPKQEPQEINFPDDLPGSNTAAPVQETLHGCQPVTQEDGKESRISVQERQ (SEQ ID NO: 67). In some embodiments, the transmembrane domain comprises a CD8 transmembrane domain. In some embodiments, the transmembrane domain comprises a sequence with at least 90% sequence identity to IYIWAPLAGTCGVLLLSLVIT (SEQ ID NO: 68). In some embodiments, the extracellular domain further comprises a hinge domain derived from CD8, wherein the hinge domain is operatively linked to the transmembrane domain and the CD5 binding domain. In some embodiments, the extracellular domain comprises a sequence with at least 90% sequence identity to ALSNSIMYFSHFVPVFLPAKPTTTPAPRPPTPAPTIASQPLSLRPEACRPAAGGAVHTRGLD (SEQ ID NO: 69). In some embodiments, the CFP comprises an extracellular domain comprising a scFv that specifically binds CD5, and a hinge domain derived from CD8; a hinge domain derived from CD28 or at least a portion of an extracellular domain from CD68; a CD8 transmembrane domain, a CD28 transmembrane domain or a CD68 transmembrane domain; and an intracellular domain comprising at least two intracellular signaling domains, wherein the at least two intracellular signaling domains comprise: a first intracellular signaling domain derived from FcγR or FcεR, and a second intracellular signaling domain comprising a PI3K recruitment domain, or derived from CD40. In some embodiments, the recombinant polynucleic acid is an mRNA or circRNA. In some embodiments, the nucleic acid is delivered into a myeloid cell. In some embodiments, the nucleic acid is delivered into a CD14+ cell, a CD14+CD16− cell, an M0 macrophage, an M2 macrophage, an M1 macrophage or a mosaic myeloid cell/macrophage. In some embodiments, the fusion protein comprises a sequence with at least 90% sequence identity to EIQLVQSGGGLVKPGGSVRISCAASGYTFTNYGMNWVRQAPGKGLEWMGWINTHTGEPTYAD SFKGRFTFSLDDSKNTAYLQINSLRAEDTAVYFCTRRGYDWYFDVWGQGT TVTVSSGGGGSGG GGSGGGGSDIQMTQSPSSLSASVGDRVTITCRASQDINSYLSWFQQKPGKAPKTLI YRANRLESG VPSRFSGSGSGTDYTLTISSLQYE DFGIYYCQQYDESPWTFGGGTKLEIKSGGGGSGALSNSIMYF SHFVPVFLPAKPTTTPAPRPPTPAPTIASQPLSLRPEACRPAAGGAVHTRGLDIYIWAPLAGTCGV LLLSLVITLYCRRLKIQVRKAAITSYEKSDGVYTGLSTRNQETYETLKHEKPPQGSGSYEDMRGI LYAAPQLRSIRGQPGPNHEEDADSYENM (SEQ ID NO: 70). In some embodiments, the fusion protein comprises a sequence with at least 90% sequence identity to

```
                                       (SEQ ID NO: 71)
EIQLVQSGGGLVKPGGSVRISCAASGYTFTNYGMNWVRQAPGKGLEWMGW

INTHTGEPTYADSFKGRFTFSLDDSKNTAYLQINSLRAEDTAVYFCTRRG

YDWYFDVWGQGTTVTVSSGGGGSGGGGSGGGGSDIQMTQSPSSLSASVGD

RVTITCRASQDINSYLSWFQQKPGKAPKTLIYRANRLESGVPSRFSGSGS

GTDYTLTISSLQYEDFGIYYCQQYDESPWTFGGGTKLEIKSGGGGSGALS

NSIMYFSHFVPVFLPAKPTTTPAPRPPTPAPTIASQPLSLRPEACRPAAG

GAVHTRGLDIYIWAPLAGTCGVLLLSLVITLYCRLKIQVRKAAITSYEKS

DGVYTGLSTRNQETYETLKHEKPPQKKVAKKPTNKAPHPKQEPQEINFPD

DLPGSNTAAPVQETLHGCQPVTQEDGKESRISVQERQ
or

                                       (SEQ ID NO: 72)
EIQLVQSGGGLVKPGGSVRISCAASGYTFTNYGMNWVRQAPGKGLEWMGW

INTHTGEPTYADSFKGRFTFSLDDSKNTAYLQINSLRAEDTAVYFCTRRG

YDWYFDVWGQGTTVTVSSGGGGSGGGGSGGGGSDIQMTQSPSSLSASVGD

RVTITCRASQDINSYLSWFQQKPGKAPKTLIYRANRLESGVPSRFSGSGS

GTDYTLTISSLQYEDFGIYYCQQYDESPWTFGGGTKLEIKSGGGGSGALS

NSIMYFSHFVPVFLPAKPTTTPAPRPPTPAPTIASQPLSLRPEACRPAAG

GAVHTRGLDIYIWAPLAGTCGVLLLSLVITLYCRRLKIQVRKAAITSYEK

SDGVYTGLSTRNQETYETLKHEKPPQKKVAKKPTNKAPHPKQEPQEINFP

DDLPGSNTAAPVQETLHGCQPVTQEDGKESRISVQERQ.
```

In some embodiments, the fusion protein is a transmembrane protein, an intracellular protein or an intracellular protein. In one embodiment the fusion protein is directed to enhancing the function of an immune cell, e.g., a myeloid cell, selected from monocyte, macrophages dendritic cells or precursors thereof. In one embodiment the fusion protein augments a cellular function of an immune cell, such as phagocytosis. The disclosure is not limited by the transgenes that can be expressed using the methods and compositions described. The transgenes indicated in this section are exemplary.

Provided herein are exemplary transgene candidates, for stable integration into the genome of a phagocytic cell. In one embodiment the transgene is a recombinant nucleic acid encoding a phagocytic receptor (PR) fusion protein (CFP). The recombinant nucleic acid has a PR subunit comprising: (i) a transmembrane domain, and (ii) an intracellular domain comprising a phagocytic receptor intracellular signaling domain; and an extracellular antigen binding domain specific to an antigen of a target cell; wherein the transmembrane domain and the extracellular antigen binding domain are operatively linked such that antigen binding to the target by the extracellular antigen binding domain of the fused receptor activated in the intracellular signaling domain of the phagocytic receptor. In some embodiments, the recombinant nucleic acid encodes a chimeric antigen receptor. In some embodiments, the chimeric antigen receptor is a chimeric antigen receptor (phagocytosis) (CAR-P). In some embodiments, the fusion protein is a recombinant protein for locking anti-phagocytic signals. In some embodiments, the fusion protein is a phagocytosis enhancing chimeric protein. In some embodiments, the chimeric protein has intracellular domains comprising active phagocytosis signal transduction domains. In some embodiments, the chimeric protein enhances the phagocytic potential by enhancing the inflammatory potential of the phagocytic cell in which it expresses. In some embodiments, the transgene is designed to express a chimeric protein which is activated by contact with an antigen in a target cell, whereupon the phagocytic cell phagocytoses the target cell and kills the target cell.

The terms "spacer" or "linker" as used in reference to a fusion protein refers to a peptide sequence that joins the protein domains of a fusion protein. Generally, a spacer has no specific biological activity other than to join or to preserve some minimum distance or other spatial relationship between the proteins or RNA sequences. However, in some embodiments, the constituent amino acids of a spacer can be selected to influence some property of the molecule such as the folding, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. The linker is used to separate two antigenic peptides by a distance sufficient to ensure that, in some embodiments, each antigenic peptide properly folds. Exemplary peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also can be used in the linker sequence.

The various exemplary proteins encoded by a transgene that can be expressed for enhancing the immune potential of a phagocytic cell are described below. This is not an exhaustive list but serves as an exemplary list for transgene design within the scope of the present disclosure.

In some embodiments, the PSP subunit comprises a transmembrane (TM) domain of a phagocytic receptor.

In some embodiments, the PSP subunit comprises an ICD domain of a phagocytic receptor.

In some embodiments, the ICD encoded by the recombinant nucleic acid comprises a domain selected from the group consisting of lectin, dectin 1, mannose receptor (CD206), scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), and CD169 receptor.

In some embodiments, the ICD comprises the signaling domain derived from any one or more of: lectin, dectin 1, mannose receptor (CD206), scavenger receptor A1 (SRA1), MARCO (Macrophage Receptor with Collagenous Structure, aliases: SRA6, SCARA2), CD36 (Thrombospondin receptor, aliases: Scavenger Receptor class B, member 3), CD163 (Scavenger receptor, cysteine rich-type 1), MSR1, SCARA3, COLEC12 (aliases: Scavenger Receptor With C-Type Lectin, SCARA4, or Collectin 12), SCARA5, SCARB1, SCARB2, CD68 (SCARD, microsialin), OLR1 (Oxidized Low Density Lipoprotem Receptor 1, LOX1, or C-Type Lectin Domain Family 8 Member A), SCARF1, SCARF2, SRCRB4D, SSC5D, and CD169 (aliases, Sialoadhesin receptor, SIGLEC1).

In some embodiments, the recombinant nucleic acid encodes, for example, an intracellular domain of human MARCO. The PSR subunit comprises an intracellular domain having a 44 amino acid ICD of human MARCO having an amino acid sequence: MRNKKILKEDELLSETQQAAFHQIAMEPFEINVPKPKRRNGVNF (SEQ ID NO: 73). In some embodiments, the PSR subunit comprises a variant which is at least 70%, 75%, 80%, 85%, 90% or 95% identical to the intracellular domain of MARCO.

In some embodiments, for example, the PSR (phagocytic scavenger receptor) comprises a transmembrane region of human MARCO.

In some embodiments, the recombinant nucleic acid encodes an intracellular domain of human SRA1. The PSR subunit comprises an intracellular domain having a 50 amino acid ICD of human SRA1 having an amino acid sequence: MEQWDHFHNQQEDTDSCSESVKFDARSMTA LLPPNPKNSPSLQEKLKSFK (SEQ ID NO: 74). In some embodiments, the PSR subunit comprises a variant which is at least 70%, 75%, 80%, 85%, 90% or 95% identical to the intracellular domain of human SRA1. The intracellular region of SRA has a phosphorylation site.

In some embodiments, the PSR comprises a transmembrane region of human SRA1.

In some embodiments, for example, the recombinant nucleic acid comprises an intracellular domain of CD36. In some embodiments, the recombinant nucleic acid comprises a TM domain of CD36. Naturally occurring full length CD36 has two TM domains and two short intracellular domains, and an extracellular domain of CD36 binds to oxidized LDL. Both of the intracellular domains contain pairs of cysteines that are fatty acid acylated. It lacks known signaling domains (e.g. kinase, phosphatase, g-protein binding, or scaffolding domains). N-terminal cytoplasmic domain is extremely short (5-7 amino acid residues) and is closely associated with the internal leaflet of the plasma membrane. The carboxy-terminal domain contains 13 amino acids, containing a CXCX5K motif homologous to a region in the intracellular domain of CD4 and CD8 that is known to interact with signaling molecules. The intracellular domain of CD36 is capable of assembling a signaling complex that activates lyn kinases, MAP kinases and Focal Adhesion Kinases (FAK), and inactivation of src homology 2-containing phosphotyrosine phosphatase (SHP-2). Members of the guanine nucleotide exchange factors (GEFs) have been identified as potential key signaling intermediates.

In some embodiments, the recombinant nucleic acid encodes for example, an intracellular domain of human SCARA3. In some embodiments, the PSR subunit comprises a variant which is at least 70%, 75%, 80%, 85%, 90% or 95% identical to the intracellular domain of human SCARA3. In some embodiments, the PSR comprises the TM domain of SCARA3. In some embodiments, the TM domains are about 20-30 amino acids long.

Scavenger receptors may occur as homo or hetero dimers. MARCO, for example occurs as a homo trimer.

In some embodiments, the TM domain or the ICD domain of the PSP is not derived from FcR, Megf10, Bail or MerTK. In some embodiments, the ICD of the PSR does not comprise a CD3 zeta intracellular domain.

In some embodiments, the intracellular domain and transmembrane domains are derived from FcR beta.

In one aspect the recombinant nucleic acid encodes a chimeric antigenic receptor for enhanced phagocytosis (CAR-P), which is a phagocytic scavenger receptor (PSR) fusion protein (CFP) comprising: (a) an extracellular domain comprising an extracellular antigen binding domain specific to an antigen of a target cell, (b) a transmembrane domain, and (c) a recombinant PSR intracellular signaling domain, wherein the recombinant PSR intracellular signaling domain comprises a first portion derived from a phagocytic and a second portion derived from non-phagocytic receptor.

In some embodiments, the second portion is not a PI3K recruitment domain. In some embodiments, the second portion is a PI3K recruitment domain.

The second portion derived from non-phagocytic receptor may comprise an intracellular signaling domain that enhances phagocytosis, and/or inflammatory potential of the engineered phagocytic cells expressing the recombinant nucleic acid. In some embodiments, the second portion derived from non-phagocytic receptor comprises more than one intracellular domain (ICD). In some embodiments, the second portion derived from non-phagocytic receptor comprises a second ICD. In some embodiments, the second portion derived from non-phagocytic receptor comprises a second and a third ICD. In some embodiments, the second portion derived from non-phagocytic receptor comprises a second, a third and a fourth ICD, wherein the second portion is encoded by the recombinant nucleic acid. The respective second portions comprising a second, or third or fourth ICD derived from non-phagocytic receptor are described as follows.

Chimeric Antigen Receptors for Enhancing Intracellular Signaling and Inflammation Activation In one aspect, the recombinant nucleic acid encodes a second intracellular domain in addition to the phagocytic ICD, which confers capability of potent pro-inflammatory immune activation, such as when macrophages engage in fighting infection. The second intracellular domain (second ICD) is fused to the cytoplasmic terminus of the first phagocytic ICD. The second intracellular domain provides a second signal is necessary to trigger inflammasomes and pro-inflammatory signals. Nod-like receptors (NLRs) are a subset of receptors that are activated in innate immune response, and oligomerize to form multi-protein complexes that serve as platforms to recruit proinflammatory caspases and induce their cleavage and activation. This leads to direct activation of ROS, and often result in a violent cell death known as pyroptosis. There are four inflammasome complexes, NLRP1m, NLRP3, IPAF and AIM2.

The tumor microenvironment (TME) constitutes an immunosuppressive environment. Influence of IL-10, glucocorticoid hormones, apoptotic cells, and immune complexes can interfere with innate immune cell function. Immune cells, including phagocytic cells settle into a tolerogenic phenotype. In macrophages, this phenotype, commonly known as the M2 phenotype is distinct from the M1 phenotype, where the macrophages are potent and capable of killing pathogens. Macrophages exposed to LPS or IFN-gamma, for example, can polarize towards an M1 phenotype, whereas macrophages exposed to IL-4 or IL-13 will polarize towards an M2 phenotype. LPS or IFN-gamma can interact with Toll-like receptor 4 (TLR4) on the surface of macrophages inducing the Trif and MyD88 pathways, inducing the activation of transcription factors IRF3, AP-1, and NFKB and thus activating TNFs genes, interferon genes, CXCL10, NOS2, IL-12, etc., which are necessary in a pro-inflammatory M1 macrophage response. Similarly, IL-4 and IL-13 bind to IL-4R, activation the Jak/Stat6 pathway, which regulates the expression of CCL17, ARG1, IRF4, IL-10, SOCS3, etc., which are genes associated with an anti-inflammatory response (M2 response). Expression of CD14, CD80, D206 and low expression of CD163 are indicators of macrophage polarization towards the M1 phenotype.

In some embodiments, the recombinant nucleic acid encodes one or more additional intracellular domains, comprising a cytoplasmic domain for inflammatory response. In some embodiments, expression of the recombinant nucleic acid encoding the phagocytic receptor (PR) fusion protein (CFP) comprising the cytoplasmic domain for inflammatory response in the engineered macrophages confers potent pro-inflammatory response similar to the M1 phenotype.

In some embodiments, the cytoplasmic domain for inflammatory response can be the signal transducing domains or regions of TLR3, 4, 9, MYD88, TRIF, RIG-1, MDA5, CD40, IFN receptor, NLRP-1-14, NOD1, NOD2, Pyrin, AIM2, NLRC4, CD40.

In some embodiments, the expression of the recombinant nucleic acid encoding the phagocytic scavenger receptor (PSR) fusion protein (CFP) comprises a pro-inflammatory cytoplasmic domain for activation of IL-1 signaling cascade.

In some embodiments, the cytoplasmic portion of the chimeric receptor (for example, phagocytic receptor (PR) fusion protein (CFP)) comprises a cytoplasmic domain from a toll-like receptor, such as the intracellular signaling domains of toll-like receptor 3 (TLR3), toll-like receptor 4 (TLR4), toll-like receptor 7 (TLR7), toll-like receptor 8 (TLR8), toll-like receptor 9 (TLR9). In some embodiments, the cytoplasmic portion of the chimeric receptor comprises a suitable region from interleukin-1 receptor-associated kinase 1 (IRAK1). In some embodiments, the cytoplasmic portion of the chimeric receptor comprises a suitable region from differentiation primary response protein (MYD88). In some embodiments, the cytoplasmic portion of the chimeric receptor comprises a suitable region from myelin and lymphocyte protein (MAL). In some embodiments, the cytoplasmic portion of the chimeric receptor comprises a suitable region from retinoic acid inducible gene (RIG-1).

In some embodiments, the transmembrane domain of the PSR comprises the transmembrane domain of any one of MYD88, TLR3, TLR4, TLR7, TLR8, TLR9, MAL, IRAK1, proteins.

In some embodiments, the recombinant PSR intracellular signaling domain comprises a first portion derived from a phagocytic and a second portion derived from non-phagocytic receptor wherein the second portion derived from non-phagocytic receptor comprises a phosphorylation site. In some embodiments, the phosphorylation site comprises amino acid sequences suitable for an autophosphorylation site. In some embodiments, the phosphorylation site comprises amino acid sequences suitable phosphorylation by Src family kinases. In some embodiments, the phosphorylation site comprises amino acid sequences, which upon phosphorylation are capable of binding to SH2 domains in a kinase. In some embodiments, a receptor tyrosine kinase domain is fused at the cytoplasmic end of the CFP in addition to the first cytoplasmic portion. In some embodiments, the phosphorylation is a tyrosine phosphorylation.

In some embodiments, the second intracellular domain is an Immune receptor Tyrosine Activation Motif (ITAM). The ITAM motif is present in mammalian α and β immunoglobulin proteins, TCR γ receptors, FCR γ receptors subunits, CD3 chains receptors and NFAT activation molecule.

In some embodiments, the CFP intracellular domain comprises one ITAM motif. In some embodiments, the CFP intracellular domain comprises more than one ITAM motifs. In some embodiments, the CFP intracellular domain comprises two or more ITAM motifs. In some embodiments, the CFP intracellular domain comprises three or more ITAM motifs. In some embodiments, the CFP intracellular domain comprises four or more ITAM motifs. In some embodiments, the CFP intracellular domain comprises five or more ITAM motifs. In some embodiments, the CFP intracellular domain comprises six or more ITAM motifs. In some embodiments, the CFP intracellular domain comprises seven or more ITAM motifs. In some embodiments, the CFP intracellular domain comprises eight or more ITAM motifs. In some embodiments, the CFP intracellular domain comprises nine or more ITAM motifs. In some embodiments, the CFP intracellular domain comprises ten or more ITAM motifs.

In some embodiments, one or more domains in the first phagocytic ICD comprises a mutation.

In some embodiments, one or more domains in the second ICD comprises a mutation to enhance a kinase binding domain, to generate a phosphorylation site, to generate an SH2 docking site or a combination thereof.

Co-Expression of an Inflammatory Gene

In one aspect, the recombinant nucleic acid comprises a coding sequence for a pro-inflammatory gene, which is co-expressed with the CFP in the engineered cell. In some embodiments, the pro-inflammatory gene is a cytokine. Examples include but not limited to TNF-α, IL-1α, IL-1β, IL-6, CSF, GMCSF, or IL-12 or interferons.

The recombinant nucleic acid encoding the proinflammatory gene can be monocistronic, wherein the two coding sequences for (a) the PSP and (b) the proinflammatory gene are post-transcriptionally or post-translationally cleaved for independent expression.

In some embodiments, the two coding sequences comprise a self-cleavage domain, encoding a P2A sequence, for example.

In some embodiments, the two coding regions are separated by an IRES site.

In some embodiments, the two coding sequences are encoded by a bicistronic genetic element. The coding regions for (a) the PSP and (b) the proinflammatory gene can be unidirectional, where each is under a separate regulatory control. In some embodiments, the coding regions for both are bidirectional and drive in opposite directions. Each coding sequence is under a separate regulatory control.

Coexpression of the proinflammatory gene is designed to confer strong inflammatory stimulation of the macrophage and activate the surrounding tissue for inflammation.

Integrin Activation Domains

Cell-cell and cell-substratum adhesion is mediated by the binding of integrin extracellular domains to diverse protein ligands; however, cellular control of these adhesive interactions and their translation into dynamic cellular responses, such as cell spreading or migration, requires the integrin cytoplasmic tails. These short tails bind to intracellular ligands that connect the receptors to signaling pathways and cytoskeletal networks (Calderwood D A, 2004, Integrin Activation, Journal of Cell Science 117, 657-666). Integrins are heterodimeric adhesion receptors formed by the non-covalent association of α and β subunits. Each subunit is a type I transmembrane glycoprotein that has relatively large extracellular domains and, with the exception of the β4 subunit, a short cytoplasmic tail. Individual integrin family members have the ability to recognize multiple ligands. Integrins can bind to a large number of extracellular matrix proteins (bone matrix proteins, collagens, fibronectins, fibrinogen, laminins, thrombospondins, vitronectin, and von Willebrand factor), reflecting the primary function of integrins in cell adhesion to extracellular matrices. Many "counter-receptors" are ligands, reflecting the role of integrins in mediating cell-cell interactions. Integrins undergo conformational changes to increase ligand affinity.

The Integrin $\beta_2$ subfamily consists of four different integrin receptors, $\alpha_M\beta_2$ (CD11b/CD18, Mac-1, CR3, Mo-1), $\alpha_L\beta_2$ (CD11a/CD18, LFA-1), $\alpha_x\beta_2$ (CD11c/CD18), and $\alpha_D\beta_2$ (CD11d/CD18). These leukocyte integrins are involved in virtually every aspect of leukocyte function, including the immune response, adhesion to and transmigration through the endothelium, phagocytosis of pathogens, and leukocyte activation.

The α subunits of all $\beta_2$ integrins contain an inserted region of ~200 amino acids, termed the I or A domain. Highly conserved I domains are found in several other integrin α subunits and other proteins, such as certain coagulation and complement proteins. I domains mediate protein-protein interactions, and in integrins, they are integrally involved in the binding of protein ligands. Although the I domains dominate the ligand binding functions of their integrins, other regions of the α subunits do influence ligand recognition. As examples, in $\alpha_M\beta_2$ a mAb (OKM1) recognizing an epitope outside the I domain but in the $\alpha_M$ subunit inhibits ligand binding; and the EF-hand regions in $\alpha_L\beta 2$ and $\alpha_2\beta_1$, integrins with I domains in their α subunits, contribute to ligand recognition. The $\alpha_M$ subunit, and perhaps other α subunits, contains a lectin-like domain, which is involved in engagement of non-protein ligands, and occupancy may modulate the function of the I domain.

As integrins lack enzymatic activity, signaling is instead induced by the assembly of signaling complexes on the cytoplasmic face of the plasma membrane. Formation of these complexes is achieved in two ways; first, by receptor clustering, which increases the avidity of molecular interactions thereby increasing the on-rate of binding of effector molecules, and second, by induction of conformational changes in receptors that creates or exposes effector binding sites. Within the ECM, integrins have the ability to bind fibronectin, laminins, collagens, tenascin, vitronectin and thrombospondin. Clusters of integrin/ECM interactions form focal adhesions, concentrating cytoskeletal components and signaling molecules within the cell. The cytoplasmic tail of integrins serve as a binding site for α-actinin and talin which then recruit vinculin, a protein involved in anchoring F-actin to the membrane. Talin is activated by kinases such as protein kinase C (PKCα).

Integrins are activated by selectins. Leucocytes express L-selectin, activated platelets express P-selectin, and activated endothelial cells express E- and P-selectin. P-selectin-mediated adhesion enables chemokine- or platelet-activating factor-triggered activation of β2 integrins, which stabilizes adhesion. It also facilitates release of chemokines from adherent leucocytes. The cytoplasmic domain of P-selectin glycoprotein ligand 1 formed a constitutive complex with Nef-associated factor 1. After binding of P-selectin, Src kinases phosphorylated Nef-associated factor 1, which recruit the phosphoinositide-3-OH kinase p85-p110δ heterodimer and result in activation of leukocyte integrins. E-selectin ligands transduce signals that also affect β2 integrin function. Selectins trigger activation of Src family kinases. SFKs activated by selectin engagement phosphorylate the immunoreceptor tyrosine-based activation motifs (ITAMs) in the cytoplasmic domains of DAP12 and FcRγ. In some respects, CD44 is sufficient to transduce signals from E-selectin. CD44 triggers the inside-out signaling of integrins. A final common step in integrin activation is binding of talin to the cytoplasmic tail of the β subunit. Kindlins, another group of cytoplasmic adaptors, bind to a different region of integrin β tails. Kindlins increase the clustering of talin-activated integrins. Kindlins are responsive to selectin signaling, however, kindlins are found mostly in hematopoietic cells, such as neutrophils. Selectin signaling as well as signaling upon integrin activation by chemokines components have shared components, including SFKs, Syk, and SLP-76.

In some embodiments, the intracellular domain of the recombinant PSR fusion protein comprises an integrin activation domain. The integrin activation domain comprises an intracellular domain of a selectin, for example, a P-selectin, L-selectin or E-selectin.

In some embodiments, the intracellular domain of the recombinant PSR fusion protein comprises an integrin activation domain of laminin.

In some embodiments, the intracellular domain of the recombinant PSR fusion protein comprises an integrin activation domain for activation of Talin.

In some embodiments, the intracellular domain of the recombinant PSR fusion protein comprises an integrin activation domain fused to the cytoplasmic end of the phagocytic receptor ICD domain.

Chimeric Receptor for Enhancing Antigen Cross Presentation

In some embodiments, the recombinant nucleic acid encodes a domain capable of enabling cross presentation of antigens. In general, MHC class I molecules present self- or pathogen-derived antigens that are synthesized within the cell, whereas exogenous antigens derived via endocytic uptake are loaded onto MHC class II molecules for presentation to CD4+ T cells. MHC I-restricted presentation of endogenous antigens, in which peptides are generated by the proteasome. However, in some cases, DC can process exogenous antigens into the MHC-I pathway for presentation to CD8+ T cells. This is referred to as cross presentation of antigens. Soluble or exogenous antigenic components may get degraded by lysosomal proteases in the vacuoles and cross presented by DCs, instead of following the endocytotic pathway. In some instances, chaperones, such as heat shock protein 90 (Hsp90) have shown to help cross present antigens by certain APCs. HSP-peptide complexes are known to be internalized by a distinct group of receptors compared to free polypeptides. These receptors are from the scavenger receptor families and included LOX-1, SREC-I/SCARF-I, and FEEL 1/Stabilin-1. Both SREC-I and LOX-1 have been shown to mediate the cross presentation of molecular chaperone bound antigens and lead to activation of CD8+ T lymphocytes.

SREC-1 (scavenger receptor expressed by endothelial cells) has no significant homology to other types of scavenger receptors but has unique domain structures. It contains 10 repeats of EGF-like cysteine-rich motifs in the extracellular domain. Recently, the structure of SREC-I was shown to be similar to that of a transmembrane protein with 16 EGF-like repeats encoded by the *Caenorhabditis elegans* gene ced-I, which functions as a cell surface phagocytic receptor that recognizes apoptotic cells.

Cross presentation of cancer antigens through the Class-I MHC pathway results in enhanced CD8+ T cell response, which is associated with cytotoxicity and therefore beneficial in tumor regression. In some embodiments, the intracellular domain of the CFP comprises a SREC1 intracellular domain. In some embodiments, the intracellular domain of the CFP comprises a SRECII intracellular domain.

In some embodiments, the PSR subunit comprises: an intracellular domain comprising a PSR intracellular signaling domain from SREC1 or SRECII.

In some embodiments, the PSR subunit comprises: (i) a transmembrane domain, and (ii) an intracellular domain comprising a PSR intracellular signaling domain from SREC1 or SRECII.

In some embodiments, the PSR subunit comprises: (i) a transmembrane domain, (ii) an intracellular domain comprising a PSR intracellular signaling domain, and (iii) an extracellular domain from SREC1 or SRECII.

Transmembrane Domain of a CFP Fusion Protein

In some embodiments, the TM encoded by the recombinant nucleic acid comprises a domain of a scavenger receptor (SR). In some embodiments, the TM can be the TM domain of or derived from any one or more of: lectin, dectin 1, mannose receptor (CD206), SRA1, MARCO, CD36, CD163, MSR1, SCARA3, COLEC12, SCARA5, SCARB1, SCARB2, CD68, OLR1, SCARF1, SCARF2, SRCRB4D, SSC5D, and CD169.

In some embodiments, the TM domains are about 20-30 amino acids long. TM domains of SRs are about 20-30 amino acids long.

The TM domain or the ICD domain of the PSP is not derived from Megf10, Bai1 or MerTK. The ICD of the PSR does not comprise a CD3 zeta intracellular domain.

In some embodiments, the TM is derived from the same phagocytic receptor as the ICD.

In some embodiments, the TM region is derived from a plasma membrane protein. The TM can be selected from an Fc receptor (FcR). In some embodiments, nucleic acid sequence encoding domains from specific FcRs are used for cell-specific expression of a recombinant construct. An FCR-alpha region comprising the TM domain may be used for macrophage specific expression of the construct. FcRβ recombinant protein expresses in mast cells.

In some embodiments, the CFP comprises the TM of an FCR-beta (FcRβ).

In some embodiments, the CFP comprises both the FcRβ TM and ICD domains.

In some embodiments, the TM domain is derived from CD8.

In some embodiments, the TM is derived from CD2.

In some embodiments, the TM is derived from FCR alpha.

Extracellular Domain of a CFP Fusion Protein

The extracellular domain comprises an antigen binding domain that binds to one or more target antigens on a target cell. The target binding domain is specific for the target. The extracellular domain can include an antibody or an antigen-binding domain selected from intrabodies, peptibodies, nanobodies, single domain antibodies. SMIPs, and multi-specific antibodies.

In some embodiments, the extracellular domain includes a Fab binding domain. In yet other such embodiments, the extracellular domain includes a scFv.

In some embodiments, the chimeric antigen receptor comprises an extracellular antigen binding domain is derived from the group consisting of an antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof. In some embodiments, the antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof specifically bind to one or more antigens.

In some embodiments, the antigens are cancer antigens, and the target cell is a target cancer cell. In some embodiments, the antigen for a target cancer cell is selected from the group consisting of CD3, CD4, CD5, CD7, CD19, CCR2, CCR4, CD30, CD37, TCRB1/2, TCR □□, TCR □□. CD22, HER2 (ERBB2/neu), Mesothelin, PSCA, CD123, CD30, CD171, CD138, CS-1, CLECL1, CD33, CD79b, EGFRvIII, GD2, GD3, BCMA, PSMA, ROR1, FLT3, TAG72, CD38, CD44v6, CEA, EPCAM, B7H3 (CD276), KIT (CD 117), CD213A2, IL-1 IRa, PRSS21, VEGFR2, CD24, MUC-16, PDGFR-beta, SSEA-4, CD20, MUC1, EGFR, NCAM, Prostase, PAP, ELF2M, Ephrin B2, FAP, EphA2, GM3, TEM1/CD248, TEM7R, CLDN6, TSHR, GPRC5D, CD97, CD179a, ALK, and IGLL1.

Various cancer antigen targets can be selected from cancer antigens known to one of skill in the art. Depending on the cancer and the cell type involved cancer antigens are mutated native proteins. The antigen binding domains are screened for specificity towards mutated/cancer antigens and not the native antigens.

In some embodiments, for example, the cancer antigen for a target cancer cell can be one or more of the mutated/cancer antigens: MUC16, CCAT2, CTAG1A, CTAG1B, MAGE A1, MAGEA2, MAGEA3, MAGE A4, MAGEA6, PRAME, PCA3, MAGE C1, MAGEC2, MAGED2, AFP, MAGEA8, MAGE9, MAGEA11, MAGEA12, IL13RA2, PLAC1, SDCCAG8, LSP1, CT45A1, CT45A2, CT45A3, CT45A5, CT45A6, CT45A8, CT45A10, CT47A1, CT47A2, CT47A3, CT47A4, CT47A5, CT47A6, CT47A8, CT47A9, CT47A10, CT47A11, CT47A12, CT47B1, SAGE1, and CT55.

In some embodiments, for example, the cancer antigen for a target cancer cell can be one or more of the mutated/cancer antigens: CD2, CD3, CD4, CD5, CD7, CD8, CD20, CD30, CD45, CD56, where the cancer is a T cell lymphoma.

In some embodiments, for example, the cancer antigen for a target cancer cell can be one or more of the mutated/cancer antigens: IDH1, ATRX, PRL3, or ETBR, where the cancer is a glioblastoma.

In some embodiments, for example, the cancer antigen for a target cancer cell can be one or more of the mutated/cancer antigens: CA125, beta-hCG, urinary gonadotropin fragment, AFP, CEA, SCC, inhibin or extradiol, where the cancer is ovarian cancer.

In some embodiments, the cancer antigen for a target cancer cell may be HER2.

In some embodiments, the cancer antigen for a target cancer cell may be EGFR Variant III.

In some embodiments, the cancer antigen for a target cancer cell may be CD19.

In some embodiments, the SR subunit region comprises an extracellular domain (ECD) of the scavenger receptor. In some embodiments, the ECD of the scavenger receptor comprises an ECD domain of the SR comprising the ICD and the TM domains. In some embodiments, the SR-ECD contributes to the binding of the phagocyte to the target cell, and in turn is activated, and activates the phagocytosis of the target cell.

In some embodiments, the PSR domain optionally comprises the ECD domain or portion thereof of the respective scavenger receptor the ICD and TM domains of which is incorporated in the PSR. Therefore, in some embodiments, In some embodiments, the ECD encoded by the recombinant nucleic acid comprises a domain selected from the group consisting of lectin, dectin 1, mannose receptor (CD206), scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), and CD169 receptor. The extracellular domains of most macrophage scavenger receptors contain scavenger receptors with a broad binding specificity that may be used to discriminate between self and non-self in the nonspecific antibody-independent recognition of foreign substances. The type I and II class A scavenger receptors (SR-AI1 and SR-AII) are trimeric membrane glycoproteins with a small NH2-terminal intracellular domain, and an extracellular portion containing a short spacer domain, an a-helical coiled-coil domain, and a triple-helical collagenous domain. The type I receptor additionally contains a cysteine-rich COOH-terminal (SRCR) domain. These receptors are present in macrophages in diverse tissues throughout the body and exhibit an unusually broad ligand binding specificity. They bind a wide variety of polyanions, including chemically modified proteins, such as modified LDL, and they have been implicated in cholesterol deposition during atherogenesis. They may also play a role in cell adhesion processes in macrophage-associated host defense and inflammatory conditions.

In some embodiments, the SR ECD is designed to bind to pro-apoptotic cells. In some embodiments, the scavenger receptor ECD comprises a binding domain for a cell surface molecule of a cancer cell or an infected cell.

In some embodiments, the extracellular domain of the PR subunit is linked by a linker to a target cell binding domain, such as an antibody or part thereof, specific for a cancer antigen.

In some embodiments, the extracellular antigen binding domain comprises one antigen binding domain. In some embodiments, the extracellular antigen binding domain comprises more than one binding domain. In some embodiments, the binding domain is an scFv. In some embodiments, the binding domain is an single domain antibody (sdAb). In some embodiments, the binding domain is fused to the recombinant PR at the extracellular domain. In some embodiments, the binding domain (e.g., scFv) and the extracellular domain of the PR are linked via a linker.

In some embodiments, the ECD antigen binding domain can bind to an intracellular antigen. In some embodiments, the intracellular antigen is a cancer antigen.

In some embodiments, the extracellular antigen binding domain binds to the target ligand with an affinity of less than 1000 nM. In some embodiments, the extracellular antigen binding domain binds to the target ligand with an affinity of less than 500 nM. In some embodiments, the extracellular antigen binding domain binds to the target ligand with an affinity of less than 450 nM. In some embodiments, the extracellular antigen binding domain binds to the target ligand with an affinity of less than 400 nM. In some embodiments, the extracellular antigen binding domain binds to the target ligand with an affinity of less than 350 nM. In some embodiments, the extracellular antigen binding domain binds to the target ligand with an affinity of less than 250 nM. In some embodiments, the extracellular antigen binding domain binds to the target ligand with an affinity of less than 200 nM. In some embodiments, the extracellular antigen binding domain binds to the target ligand with an affinity of less than 100 nM. In some embodiments, the extracellular antigen binding domain binds to the target ligand with an affinity ranging between than 200 nM to 1000 nM. In some embodiments, the extracellular antigen binding domain binds to the target ligand with an affinity ranging between than 300 nM to 1.5 mM. In some embodiments, the antigen binding domain binds to the target ligand with an affinity >200 nM, >300 nM or >500 nM.

Peptide Linker

In some embodiments, the extracellular antigen binding domains, scfvs are linked to the TM domain or other extracellular domains by a linker. In some embodiments, where there are more than one scfv at the extracellular antigen binding domain the more than scfvs are linked with each other by linkers.

In some embodiments, the linkers are flexible. In some embodiments, the linkers comprise a hinge region. Linkers are usually short peptide sequences. In some embodiments, the linkers are stretches of Glycine and one or more Serine residues. Other amino acids preferred for short peptide linkers include but are not limited to threonine (Thr), serine (Ser), proline (Pro), glycine (Gly), aspartic acid (Asp), lysine (Lys), glutamine (Gln), asparagine (Asn), and alanine (Ala) arginine (Arg), phenylalanine (Phe), glutamic acid (Glu). Of these Pro, Thr, and Gln are frequently used amino acids for natural linkers. Pro is a unique amino acid with a cyclic side chain which causes a very restricted conformation. Pro-rich sequences are used as interdomain linkers, including the linker between the lipoyl and E3 binding domain in pyruvate dehydrogenase ($GA_2PA_3PAKQEA_3PAPA_2KAEAPA_3PA_2KA$ (SEQ ID NO: 75)). For the purpose of the disclosure, the empirical linkers may be flexible linkers, rigid linkers, and cleavable linkers. Sequences such as (G4S)x (SEQ ID NO: 76) (where x is multiple copies of the moiety, designated as 1, 2, 3, 4, and so on) comprise a flexible linker sequence. Other flexible sequences used herein include several repeats of glycine, e.g., (Gly)6 (SEQ ID NO: 77) or (Gly)8 (SEQ ID NO: 78). On the other hand, a rigid linker may be used, for example, a linker (EAAAK)x, where x is an integer, 1, 2, 3, 4 etc. (SEQ ID NO: 79) gives rise to a rigid linker.

In some embodiments, the linker comprises at least 2, or at least 3 amino acids. In some embodiments, the linker comprises 4 amino acids. In some embodiments, the linker comprises 5 amino acids. In some embodiments, the linker comprises 6 amino acids. In some embodiments, the linker comprises 7 amino acids. In some embodiments, the linker comprises 8 amino acids. In some embodiments, the linker comprises 9 amino acids. In some embodiments, the linker comprises 8 amino acids. In some embodiments, the linker comprises 10 amino acids. In some embodiments, the linker comprises 11 amino acids. In some embodiments, the linker comprises 12 amino acids. In some embodiments, the linker comprises 13 amino acids. In some embodiments, the linker comprises 14 amino acids. In some embodiments, the linker comprises 15 amino acids. In some embodiments, the linker comprises 16 amino acids. In some embodiments, the linker comprises 17 amino acids. In some embodiments, the linker comprises 18 amino acids. In some embodiments, the linker comprises 19 amino acids. In some embodiments, the linker comprises 20 amino acids.

As contemplated herein, any suitable ECD, TM or ICD domain can be cloned interchangeably in the suitable portion of any one of the CARP receptors described in the disclosure to obtain a protein with enhanced phagocytosis compared to an endogenous receptor.

Characteristics of the Fusion Proteins:

The CFP can structurally incorporates into the cell membrane of the cell in which it is expressed. Specific leader sequences in the nucleic acid construct, such as the signal peptide can be used to direct plasma membrane expression of the encoded protein. The transmembrane domain encoded by the construct can incorporate the expressed protein in the plasma membrane of the cell.

In some embodiments, the transmembrane domain comprises a TM domain of an FcRalpha receptor, which dimerizes with endogenous FcR-gamma receptors in the macrophages, ensuring macrophage specific expression.

The CFP can render the cell that expresses it as potently phagocytic. When the recombinant nucleic acid encoding the CFP is expressed in a cell, the cell can exhibit an increased phagocytosis of a target cell having the antigen of a target cell, compared to a cell not expressing the recombinant nucleic acid. When the recombinant nucleic acid is expressed in a cell, the cell can exhibit an increased phagocytosis of a target cell having the antigen of a target cell, compared to a cell not expressing the recombinant nucleic acid. In some embodiments, the recombinant nucleic acid when expressed in a cell, the cell exhibits at least 2-fold increased phagocytosis of a target cell having the antigen of a target cell, compared to a cell not expressing the recombinant nucleic acid. In some embodiments, the recombinant nucleic acid when expressed in a cell, the cell exhibits at least 3-fold, 4-fold, 5-fold, 6-fold, 7-fold, 8-fold, 9-fold, 10-fold, 20-fold 30-fold or at least 5-fold increased phagocytosis of a target cell having the antigen of a target cell, compared to a cell not expressing the recombinant nucleic acid.

In some embodiments, expression of SIRP-ΔICD enhances phagocytosis of the cell expressing it by 1.1 fold or more, 1.2 fold or more, 1.3 fold or more, q.4 fold or more, 1.5 fold or more, by 1.6 fold or more, 1.7 fold or more, 1.8 fold or more, 1.9 fold or more, 2 fold or more, 3 fold or more, 4 fold or more, 5 fold or more, 8 fold or more, 10 fold or more, 15 fold or more, 20 fold or more, 30 fold or more, 40 fold or more, 50 fold or more, 60 fold or more, 70 fold or more 80 fold or more, 90 fold or more, 100 fold or more, compared to a cell not expressing SIRP-ΔICD.

In some embodiments, the cells co-expressing SIRP-ΔICD and a CFP encoding a phagocytic receptor as described herein exhibits an augmented phagocytosis compared to a cell that does not express either of the proteins. In some embodiments, co-expressing SIRP-ΔICD and a CFP encoding a phagocytic receptor as described herein exhibits more than 2-fold, more than 3-fold, more than 4-fold, more than 5-fold, more than 6-fold, more than 7-fold, more than 8-fold, more than 9-fold, more than 10-fold, more than 20-fold, more than 30-fold, more than 40-fold, more than 50-fold, more than 60-fold, more than 70-fold, more than 80-fold, more than 90-fold, more than 100-fold, or more than 150-fold or more than 200-fold increase in phagocytic potential (measured in fold change of phagocytic index) compared to a cell that does not express either the SIRP-ΔICD or the CFP encoding a phagocytic receptor.

In some embodiments, expression of the any one of a CFP expressing a CD47 blocking extracellular domain of SIRPα and an intracellular domain of a phagocytic receptor augments phagocytic activity of a cell expressing it by at least 1.5 fold or more, 1.6 fold or more, 1.7 fold or more, 1.8 fold or more, 1.9 fold or more, 2 fold or more, 3 fold or more, 4 fold or more, 5 fold or more, 8 fold or more, 10 fold or more, 15 fold or more, 20 fold or more, 30 fold or more, 40 fold or more, 50 fold or more, 60 fold or more, 70 fold or more 80 fold or more, 90 fold or more, 100 fold or more, compared to a cell not expressing the CFP, or compared to a cell expressing SIRP-ΔICD.

In some embodiments, the enhancement in phagocytosis of target cells by a cell expressing either SIRP-ΔICD is highly increased compared to a phagocytic cell not expressing SIRP-ΔICD.

In some embodiments, the enhancement in phagocytosis of target cells by a cell expressing a CFP comprising a CD47 blocking extracellular domain of SIRPα and an intracellular domain of a phagocytic receptor is highly increased compared to a control phagocytic cell not expressing the fusion protein or a control phagocytic cell expressing the SIRP-ΔICD.

In some embodiments, when the recombinant nucleic acid described herein is expressed in a cell, the cell exhibits an increased cytokine production. The cytokine can comprise any one of: IL-1, IL-6, IL-12, IL-23, TNF, CXCL9, CXCL10, CXCL11, IL-18, IL-23, IL-27 and interferons.

In some embodiments, when the recombinant nucleic acid described herein is expressed in a cell, the cell exhibits an increased cell migration.

In some embodiments, when the recombinant nucleic acid described herein is expressed in a cell, the cell exhibits an increased immune activity. In some embodiments, when the recombinant nucleic acid is expressed in a cell, the cell exhibits an increased expression of MHC II. In some embodiments, when the recombinant nucleic acid is expressed in a cell, the cell exhibits an increased expression of CD80. In some embodiments, when the recombinant nucleic acid is expressed in a cell, the cell exhibits an increased expression of CD86. In some embodiments, when the recombinant nucleic acid is expressed in a cell, the cell exhibits an increased iNOS production.

In some embodiments, when the recombinant nucleic acid is expressed in a cell, the cell exhibits decreased trogocytosis of a target cell expressing the antigen of a target cell compared to a cell not expressing the recombinant nucleic acid.

In embodiments, the chimeric receptors may be glycosylated, pegylated, and/or otherwise post-translationally modified. In further embodiments, glycosylation, pegylation, and/or other posttranslational modifications may occur in vivo or in vitro and/or may be performed using chemical techniques. In additional embodiments, any glycosylation, pegylation and/or other posttranslational modifications may be N-linked or O-linked. In embodiments any one of the chimeric receptors may be enzymatically or functionally active such that, when the extracellular domain is bound by a ligand, a signal is transduced to polarize a macrophage.

In some embodiments, the chimeric fusion protein (CFP) comprises an extracellular domain (ECD) targeted to bind to CD5 (CD5 binding domain), for example, comprising a heavy chain variable region (VH) having an amino acid sequence as set forth in SEQ ID NO: 1. In some embodiments, the chimeric CFP comprises a CD5 binding heavy chain variable domain comprising an amino acid sequence that has at least 80%, 85%, 90%, 95%, 96%, 97%, 98%, 99% sequence identity to SEQ ID NO: 1. In some embodiments, the extracellular domain (ECD) targeted to bind to CD5 (CD5 binding domain) comprises a light chain variable domain (VL) having an amino acid sequence as set forth in SEQ ID NO: 2. In some embodiments, the chimeric CFP comprises a CD5 binding light chain variable domain comprising an amino acid sequence that has at least 80%, 85%, 90%, 95%, 96%, 97%, 98%, 99% sequence identity to SEQ ID NO: 2.

In some embodiments, the CFP comprises an extracellular domain targeted to bind to HER2 (HER2 binding domain) having for example a heavy chain variable domain amino acid sequence as set forth in SEQ ID NO: 8 and a light chain variable domain amino acid sequence as set forth in SEQ ID NO: 9. In some embodiments, the CFP comprises a HER2 binding heavy chain variable domain comprising an amino acid sequence that has at least 80%, 85%, 90%, 95%, 96%, 97%, 98%, 99% sequence identity to SEQ ID NO: 8. In some embodiments, the CFP comprises a HER2 binding light chain variable domain comprising an amino acid sequence that has at least 80%, 85%, 90%, 95%, 96%, 97%, 98%, 99% sequence identity to SEQ ID NO: 9.

In some embodiments, the CFP comprises a hinge connecting the ECD to the transmembrane (TM). In some embodiments the hinge comprises the amino acid sequence of the hinge region of a CD8 receptor. In some embodiments, the CFP may comprise a hinge having the amino acid sequence set forth in SEQ ID NO: 7 (CD8a chain hinge domain). In some embodiments, the PFP hinge region comprises an amino acid sequence that is at least 80%, 85%, 90%, 95%, 96%, 97%, 98%, 99% sequence identity to SEQ ID NO: 7.

In some embodiments, the CFP comprises a CD8 transmembrane region, for example having an amino acid sequence set forth in SEQ ID NO: 6. In some embodiments, the CFP TM region comprises an amino acid sequence that is at least 80%, 85%, 90%, 95%, 96%, 97%, 98%, 99% sequence identity to SEQ ID NO: 6.

In some embodiments, the CFP comprises an intracellular domain having an FcR domain. In some embodiments, the CFP comprises an FcR domain intracellular domain comprises an amino acid sequence set forth in SEQ ID NO: 3, or at least a sequence having 80%, 85%, 90%, 95%, 96%, 97%, 98%, 99% sequence identity to SEQ ID NO: 3.

In some embodiments, the CFP comprises an intracellular domain having a PI3K recruitment domain. In some embodiments the PI3K recruitment domain comprises an amino sequence set forth in SEQ ID NO: 4. In some embodiments the PI3K recruitment domain comprises an amino acid sequence that has at least 80%, 85%, 90%, 95%, 96%, 97%, 98%, 99% sequence identity to SEQ ID NO: 4.

In some embodiments, the CFP comprises an intracellular domain having a CD40 intracellular domain. In some embodiments the CD40 ICD comprises an amino sequence set forth in SEQ ID NO: 5. In some embodiments the CD40 ICD comprises an amino acid sequence that has at least 80%, 85%, 90%, 95%, 96%, 97%, 98%, 99% sequence identity to SEQ ID NO: 5.

In some embodiments, the CD5 binding domain comprises an scFv comprising: (i) a variable heavy chain ($V_H$) sequence of SEQ ID NO: 1 or with at least 90% sequence identity to SEQ ID NO: 1; and (ii) a variable light chain ($V_L$) sequence of SEQ ID NO: 2 or with at least 70%, 75%, 80%, 85%, 90%, 91%, 92%, 93%, 94%, 95%, 96%, 97%, 98% or 99% sequence identity to SEQ ID NO: 2. In some embodiments, the CD5 binding domain comprises an scFv comprising SEQ ID NO: 33 or with at least 70%, 75%, 80%, 85%, 90%, 91%, 92%, 93%, 94%, 95%, 96%, 97%, 98% or 99% sequence identity to SEQ ID NO: 33. In some embodiments, the HER2 binding domain comprises an scFv comprising: (i) a variable heavy chain ($V_H$) sequence of SEQ ID NO: 8 or with at least 70%, 75%, 80%, 85%, 90%, 91%, 92%, 93%, 94%, 95%, 96%, 97%, 98% or 99% sequence identity to SEQ ID NO: 8; and (ii) a variable light chain ($V_L$) sequence of SEQ ID NO: 9 or with at least 70%, 75%, 80%, 85%, 90%, 91%, 92%, 93%, 94%, 95%, 96%, 97%, 98% or 99% sequence identity to SEQ ID NO: 9. In some embodiments, the CD5 binding domain comprises an scFv comprising SEQ ID NO: 32 or with at least 70%, 75%, 80%, 85%, 90%, 91%, 92%, 93%, 94%, 95%, 96%, 97%, 98% or 99% sequence identity to SEQ ID NO: 32. In some embodiments, the CFP further comprises an intracellular domain, wherein the intracellular domain comprises one or more intracellular signaling domains, and wherein a wild-type protein comprising the intracellular domain does not comprise the extracellular domain.

In some embodiments, the extracellular domain further comprises a hinge domain derived from CD8, wherein the hinge domain is operatively linked to the transmembrane domain and the anti-CD5 binding domain. In some embodiments, the extracellular hinge domain comprises a sequence of SEQ ID NO: 7 or with at least 70%, 75%, 80%, 85%, 90%, 91%, 92%, 93%, 94%, 95%, 96%, 97%, 98% or 99% sequence identity to SEQ ID NO: 7.

In some embodiments, the CFP comprises an extracellular domain fused to a transmembrane domain of SEQ ID NO: 30 or with at least 70%, 75%, 80%, 85%, 90%, 91%, 92%, 93%, 94%, 95%, 96%, 97%, 98% or 99% sequence identity to SEQ ID NO: 30. In some embodiments, the CFP comprises an extracellular domain fused to a transmembrane domain of SEQ ID NO: 31 or with at least 70%, 75%, 80%, 85%, 90%, 91%, 92%, 93%, 94%, 95%, 96%, 97%, 98% or 99% sequence identity to SEQ ID NO: 31.

In some embodiments, the transmembrane domain comprises a CD8 transmembrane domain. In some embodiments, the transmembrane domain comprises a sequence of SEQ ID NO: 6 or 29 or with at least 70%, 75%, 80%, 85%, 90%, 91%, 92%, 93%, 94%, 95%, 96%, 97%, 98% or 99% sequence identity to SEQ ID NO: 6 or 29. In some embodiments, the transmembrane domain comprises a sequence of SEQ ID NO: 18 or with at least 70%, 75%, 80%, 85%, 90%, 91%, 92%, 93%, 94%, 95%, 96%, 97%, 98% or 99% sequence identity to SEQ ID NO: 18. In some embodiments, the transmembrane domain comprises a sequence of SEQ ID NO: 34 or with at least 70%, 75%, 80%, 85%, 90%, 91%, 92%, 93%, 94%, 95%, 96%, 97%, 98% or 99% sequence identity to SEQ ID NO: 34. In some embodiments, the transmembrane domain comprises a sequence of SEQ ID NO: 19 or with at least 70%, 75%, 80%, 85%, 90%, 91%, 92%, 93%, 94%, 95%, 96%, 97%, 98% or 99% sequence identity to SEQ ID NO: 19.

In some embodiments, the CFP comprises one or more intracellular signaling domains that comprise a phagocytic signaling domain. In some embodiments, the phagocytosis signaling domain comprises an intracellular signaling domain derived from a receptor other than Megf10, MerTk, FcRα, and Bai1. In some embodiments, the phagocytosis signaling domain comprises an intracellular signaling domain derived from a receptor other than Megf10, MerTk, an FcR, and Bai1. In some embodiments, the phagocytosis signaling domain comprises an intracellular signaling domain derived from a receptor other than CD3ζ. In some embodiments, the phagocytosis signaling domain comprises an intracellular signaling domain derived from FcRγ, FcRα or FcRε. In some embodiments, the phagocytosis signaling domain comprises an intracellular signaling domain derived from CD3ζ. In some embodiments, the CFP comprises an intracellular signaling domain of any one of SEQ ID NOs: 3, 20, 27 and 28 or with at least 70%, 75%, 80%, 85%, 90%, 91%, 92%, 93%, 94%, 95%, 96%, 97%, 98% or 99% sequence identity to any one of SEQ ID NOs: 3, 20, 27 and 28. In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence of SEQ ID NO: 4 or with at least 70%, 75%, 80%, 85%, 90%, 91%, 92%, 93%, 94%, 95%, 96%, 97%, 98% or 99% sequence identity to SEQ ID NO: 4. In some embodiments, the proinflammatory signaling domain is derived from an intracellular signaling domain of CD40. In some embodiments, the proinflammatory signaling domain comprises a sequence of SEQ ID NO: 5 or with at least 70%, 75%, 80%, 85%, 90%, 91%, 92%, 93%, 94%, 95%, 96%, 97%, 98% or 99% sequence identity to SEQ ID NO: 5. In some embodiments, the CFP comprises an intracellular signaling domain of SEQ ID NO: 21 or with at least 70%, 75%, 80%, 85%, 90%, 91%, 92%, 93%, 94%, 95%, 96%, 97%, 98% or 99% sequence identity to SEQ ID NO: 21. In some embodiments, the CFP comprises an intracellular signaling domain of SEQ ID NO: 23 or with at least 70%, 75%, 80%, 85%, 90%, 91%, 92%, 93%, 94%, 95%, 96%, 97%, 98% or 99% sequence identity to SEQ ID NO: 23.

In some embodiments, the CFP comprises a sequence of SEQ ID NO: 14 or with at least 70%, 75%, 80%, 85%, 90%, 91%, 92%, 93%, 94%, 95%, 96%, 97%, 98% or 99% sequence identity to SEQ ID NO: 14. In some embodiments, the CFP comprises a sequence of SEQ ID NO: 15 or with at least 70%, 75%, 80%, 85%, 90%, 91%, 92%, 93%, 94%, 95%, 96%, 97%, 98% or 99% sequence identity to SEQ ID NO: 15. In some embodiments, the CFP comprises a sequence of SEQ ID NO: 16 or with at least 70%, 75%, 80%, 85%, 90%, 91%, 92%, 93%, 94%, 95%, 96%, 97%, 98% or 99% sequence identity to SEQ ID NO: 16. In some embodiments, the CFP comprises a sequence of SEQ ID NO: 24 or with at least 70%, 75%, 80%, 85%, 90%, 91%, 92%, 93%, 94%, 95%, 96%, 97%, 98% or 99% sequence identity to SEQ ID NO: 24. In some embodiments, the CFP comprises a sequence of SEQ ID NO:25 or with at least 70%, 75%, 80%, 85%, 70%, 75%, 80%, 85%, 90%, 91%, 92%, 93%, 94%, 95%, 96%, 97%, 98% or 99%, 91%, 92%, 93%, 94%, 95%, 96%, 97%, 98% or 99% sequence identity to SEQ ID NO: 25.

In some embodiments, the CFP comprises: (a) an extracellular domain comprising: (i) a scFv that specifically binds CD5, and (ii) a hinge domain derived from CD8; a hinge domain derived from CD28 or at least a portion of an extracellular domain from CD68; (b) a CD8 transmembrane domain, a CD28 transmembrane domain, a CD2 transmembrane domain or a CD68 transmembrane domain; and (c) an intracellular domain comprising at least two intracellular signaling domains, wherein the at least two intracellular signaling domains comprise: (i) a first intracellular signaling domain derived from FcRα, FcRγ or FcRε, and (ii) a second intracellular signaling domain: (A) comprising a PI3K recruitment domain, or (B) derived from CD40. In some embodiments, the CFP comprises as an alternative (c) to the above: an intracellular domain comprising at least two intracellular signaling domains, wherein the at least two intracellular signaling domains comprise: (i) a first intracellular signaling domain derived from a phagocytic receptor intracellular domain, and (ii) a second intracellular signaling domain derived from a scavenger receptor phagocytic receptor intracellular domain comprising: (A) comprising a PI3K recruitment domain, or (B) derived from CD40. Exemplary scavenger receptors from which an intracellular signaling domain may be derived may be found in Table 2. In some embodiments, the CFP comprises and intracellular signaling domain derived from an intracellular signaling domain of an innate immune receptor.

In some embodiments, the recombinant polynucleic acid is an mRNA. In some embodiments, the recombinant polynucleic acid is a circRNA. In some embodiments, the recombinant polynucleic acid is a viral vector. In some embodiments, the recombinant polynucleic acid is delivered via a viral vector.

In some embodiments, the myeloid cell is a CD14+ cell, a CD14+/CD16− cell, a CD14+/CD16+ cell, a CD14−/CD16+ cell, CD14−/CD16− cell, a dendritic cell, an M0 macrophage, an M2 macrophage, an M1 macrophage or a mosaic myeloid cell/macrophage/dendritic cell.

In one aspect, provided herein is a method of treating cancer in a human subject in need thereof comprising administering a pharmaceutical composition to the human subject, the pharmaceutical composition comprising: (a) a myeloid cell comprising a recombinant polynucleic acid sequence, wherein the polynucleic acid sequence comprises a sequence encoding a chimeric fusion protein (CFP), the CFP comprising: (i) an extracellular domain comprising an anti-CD5 binding domain, and (ii) a transmembrane domain operatively linked to the extracellular domain; and (b) a pharmaceutically acceptable carrier; wherein the myeloid cell expresses the CFP.

In some embodiments, upon binding of the CFP to CD5 expressed by a target cancer cell of the subject killing or phagocytosis activity of the myeloid cell is increased by greater than 20% compared to a myeloid cell not expressing the CFP. In some embodiments, growth of a tumor is inhibited in the human subject.

In some embodiments, the cancer is a CD5+ cancer. In some embodiments, the cancer is leukemia, T cell lymphoma, or B cell lymphoma. In some embodiments, the CFP comprises one or more sequences shown in Table A and/or Table B below.

TABLE A

Exemplary sequences of CFPs and domains thereof

| SEQ ID NO | PFP/Domain | Sequence |
|---|---|---|
| 1 | Anti-CD5 heavy chain variable domain | EIQLVQSGGGLVKPGGSVRISCAASGYTFTNYGMNWVRQA PGKGLEWMGWINTHTGEPTYADSFKGRFTFSLDDSKNTAY LQINSLRAEDTAVYFCTRRGYDWYFDVWGQGTTVTV |

TABLE A-continued

| Exemplary sequences of CFPs and domains thereof | | |
|---|---|---|
| SEQ ID NO | PFP/Domain | Sequence |
| 2 | Anti-CD5 light chain variable domain | DIQMTQSPSSLSASVGDRVTITCRASQDINSYLSWFQQKPG KAPKTLIYRANRLESGVPSRFSGSGSGTDYTLTISSLQYEDF GIYYCQQYDESPWTFGGGTKLEIK |
| 33 | Anti-CD5 scFv | EIQLVQSGGGLVKPGGSVRISCAASGYTFTNYGMNWVRQA PGKGLEWMGWINTHTGEPTYADSFKGRFTFSLDDSKNTAY LQINSLRAEDTAVYFCTRRGYDWYFDVWGQGTTVTV*SSGG GGSGGGGSGGGGS*DIQMTQSPSSLSASVGDRVTITCRASQDI NSYLSWFQQKPGKAPKTLIYRANRLESGVPSRFSGSGSGTD YTLTISSLQYEDFGIYYCQQYDESPWTFGGGTKLEIK |
| 3 | FcRγ-chain intracellular signaling domain | LYCRRLKIQVRKAAITSYEKSDGVYTGLSTRNQETYETLKH EKPPQ |
| 20 | FcRγ-chain intracellular signaling domain | LYCRLKIQVRKAAITSYEKSDGVYTGLSTRNQETYETLKHE KPPQ |
| 27 | FcRγ-chain intracellular signaling domain | RLKIQVRKAAITSYEKSDGVYTGLSTRNQETYETLKHEKPP Q |
| 28 | FcRγ-chain intracellular signaling domain | RLKIQVRKAAITSYEKSDGVYTGLSTRNQETYETLKHEKPP Q |
| 4 | PI3K recruitment domain | YEDMRGILYAAPQLRSIRGQPGPNHEEDADSYENM |
| 5 | CD40 intracellular domain | KKVAKKPTNKAPHPKQEPQEINFPDDLPGSNTAAPVQETLH GCQPVTQEDGKESRISVQERQ |
| 6 | CD8α chain transmembrane domain | IYIWAPLAGTCGVLLLSLVIT |
| 29 | CD8α chain transmembrane domain | IYIWAPLAGTCGVLLLSLVITLYC |
| 7 | CD8α chain hinge domain | ALSNSIMYFSHFVPVFLPAKPTTTPAPRPPTPAPTIASQPLSL RPEACRPAAGGAVHTRGLD |
| 8 | Anti-HER2 heavy chain variable domain | DIQMTQSPSSLSASVGDRVTITCRASQDVNTAVAWYQQKP GKAPKLLIYSASFLYSGVPSRFSGSRSGTDFTLTISSLQPEDF ATYYCQQHYTTPPTFGQGTKVEIKRTGSTSGSGKPGSGEGS EVQLVE |
| 9 | Anti-HER2 light chain variable domain | LVQPGGSLRLSCAASGFNIKDTYIHWVRQAPGKGLEWVAR IYPTNGYTRYADSVKGRFTISADTSKNTAYLQMNSLRAEDT AVYYCSRWGGDGFYAMDVWGQGTLVTV |
| 32 | Anti-HER2 scFv | DIQMTQSPSSLSASVGDRVTITCRASQDVNTAVAWYQQKP GKAPKLLIYSASFLYSGVPSRFSGSRSGTDFTLTISSLQPEDF ATYYCQQHYTTPPTFGQGTKVEIKRTGSTSGSGKPGSGEGS EVQLVE*SSGGGGSGGGGSGGGGS*LVQPGGSLRLSCAASGFN IKDTYIHWVRQAPGKGLEWVARIYPTNGYTRYADSVKGRF TISADTSKNTAYLQMNSLRAEDTAVYYCSRWGGDGFYAM DVWGQGTLVTV |
| 17 | GMCSF Signal peptide | MWLQSLLLLGTVACSIS |
| 18 | CD28 transmembrane domain | FWVLVVVGGVLACYSLLVTVAFIIFWV |
| 34 | CD2 Transmembrane domain | IYLIIGICGGGSLLMVFVALLVFYIT |

TABLE A-continued

Exemplary sequences of CFPs and domains thereof

| SEQ ID NO | PFP/Domain | Sequence |
|---|---|---|
| 19 | CD68 transmembrane domain | ILLPLIIGLILLGLLALVLIAFCII |
| 21 | TNFR1 intracellular domain | QRWKSKLYSIVCGKSTPEKEGELEGTTTKPLAPNPSFSPTPG FTPTLGFSPVPSSTFTSSSTYTPGDCPNFAAPRREVAPPYQG ADPILATALASDPIPNPLQKWEDSAHKPQSLDTDDPATLYA VVENVPPLRWKEFVRRLGLSDHEIDRLELQNGRCLREAQY SMLATWRRRTPRREATLELLGRVLRDMDLLGCLEDIEEAL CGPAALPPAPSLLR |
| 22 | TNFR2 intracellular domain | PLCLQREAKVPHLPADKARGTQGPEQQHLLITAPSSSSSSLE SSASALDRRAPTRNQPQAPGVEASGAGEARASTGSSDSSPG GHGTQVNVTCIVNVCSSSDHSSQCSSQASSTMGDTDSSPSE SPKDEQVPFSKEECAFRSQLETPETLLGSTEEKPLPLGVPDA GMKPS |
| 23 | MDA5 intracellular domain | MSNGYSTDENFRYLISCFRARVKMYIQVEPVLDYLTFLPAE VKEQIQRTVATSGNMQAVELLLSTLEKGVWHLGWTREFVE ALRRTGSPLAARYMNPELTDLPSPSFENAHDEYLQLLNLLQ PTLVDKLLVRDVLDKCMEEELLTIEDRNRIAAAENNGNESG VRELLKRIVQKENWFSAFLNVLRQTGNNELVQELTGSDCSE SNAEIEN |
| 30 | CD8α chain hinge domain + transmembrane domain | ALSNSIMYFSHFVPVFLPAKPTTTPAPRPPTPAPTIASQPLSL RPEACRPAAGGAVHTRGLDIYIWAPLAGTCGVLLLSLVITL YC |
| 31 | CD8α chain hinge domain + transmembrane domain | ALSNSIMYFSHFVPVFLPAKPTTTPAPRPPTPAPTIASQPLSL RPEACRPAAGGAVHTRGLDIYIWAPLAGTCGVLLLSLVIT |
| 14 | CD5-FcRγ-PI3K | MWLQSLLLLGTVACSISEIQLVQSGGGLVKPGGSVRISCAA SGYTFTNYGMNWVRQAPGKGLEWMGWINTHTGEPTYAD SFKGRFTFSLDDSKNTAYLQINSLRAEDTAVYFCTRRGYDW YFDVWGQGTTVTV*SSGGGGSGGGGSGGGGS*DIQMTQSPSS LSASVGDRVTITCRASQDINSYLSWFQQKPGKAPKTLIYRA NRLESGVPSRF*SGSGSG*TDYTLTISSLQYEDFGIYYCQQYDE SPWTFGGGTKLEIK*SGGGGSG*ALSNSIMYFSHFVPVFLPAKP TTTPAPRPPTPAPTIASQPLSLRPEACRPAAGGAVHTRGLDI YIWAPLAGTCGVLLLSLVITLYCRRLKIQVRKAAITSYEKSD GVYTGLSTRNQETYETLKHEKPPQ*GSGS*YEDMRGILYAAPQ LRSIRGQPGPNHEEDADSYENM |
| 15 | HER2-FcRγ-PI3K | MWLQSLLLLGTVACSISDIQMTQSPSSLSASVGDRVTITCRA SQDVNTAVAWYQQKPGKAPKLLIYSASFLYSGVPSRFSGSR SGTDFTLTISSLQPEDFATYYCQQHYTTPPTFGQGTKVEIKR TGSTSGSGKPGSGEGSEVQLVE*SGGG*LVQPGGSLRLSCAAS GFNIKDTYIHWVRQAPGKGLEWVARIYPTNGYTRYADSVK GRFTISADTSKNTAYLQMNSLRAEDTAVYYCSRWGGDGFY AMDVWGQGTLVTV*SSSGGGGSG*ALSNSIMYFSHFVPVFLP AKPTTTPAPRPPTPAPTIASQPLSLRPEACRPAAGGAVHTRG LDIYIWAPLAGTCGVLLLSLVITLYCRRLKIQVRKAAITSYE KSDGVYTGLSTRNQETYETLKHEKPPQ*GSGS*YEDMRGILYA APQLRSIRGQPGPNHEEDADSYENM |
| 16 | CD5-FcRγ-CD40 | MWLQSLLLLGTVACSISEIQLVQSGGGLVKPGGSVRISCAA SGYTFTNYGMNWVRQAPGKGLEWMGWINTHTGEPTYAD SFKGRFTFSLDDSKNTAYLQINSLRAEDTAVYFCTRRGYDW YFDVWGQGTTVTV*SSGGGGSGGGGSGGGGS*DIQMTQSPSS LSASVGDRVTITCRASQDINSYLSWFQQKPGKAPKTLIYRA NRLESGVPSRFSGSGSGTDYTLTISSLQYEDFGIYYCQQYDE SPWTFGGGTKLEIK*SGGGGSG*ALSNSIMYFSHFVPVFLPAKP TTTPAPRPPTPAPTIASQPLSLRPEACRPAAGGAVHTRGLDI YIWAPLAGTCGVLLLSLVITLYCRLKIQVRKAAITSYEKSDG VYTGLSTRNQETYETLKHEKPPQKKVAKKPTNKAPHPKQE PQEINFPDDLPGSNTAAPVQETLHGCQPVTQEDGKESRISVQ ERQ |
| 24 | CD5-FcRγ-MDA5 | MWLQSLLLLGTVACSISEIQLVQSGGGLVKPGGSVRISCAA SGYTFTNYGMNWVRQAPGKGLEWMGWINTHTGEPTYAD SFKGRFTFSLDDSKNTAYLQINSLRAEDTAVYFCTRRGYDW |

TABLE A-continued

Exemplary sequences of CFPs and domains thereof

| SEQ ID NO | PFP/Domain | Sequence |
|---|---|---|
| | | YFDVWGQGTTVTVSSGGGGSGGGGSGGGGSDIQMTQSPSS<br>LSASVGDRVTITCRASQDINSYLSWFQQKPGKAPKTLIYRA<br>NRLESGVPSRFSGSGSGTDYTLTISSLQYEDFGIYYCQQYDE<br>SPWTFGGGTKLEIKSGGGGSGALSNSIMYFSHFVPVFLPAKP<br>TTTPAPRPPTPAPTIASQPLSLRPEACRPAAGGAVHTRGLDI<br>YIWAPLAGTCGVLLLSLVITLYCRLKIQVRKAAITSYEKSDG<br>VYTGLSTRNQETYETLKHEKPPQGSGSMSNGYSTDENFRY<br>LISCFRARVKMYIQVEPVLDYLTFLPAEVKEQIQRTVATSG<br>NMQAVELLLSTLEKGVWHLGWTREFVEALRRTGSPLAAR<br>YMNPELTDLPSPSFENAHDEYLQLLNLLQPTLVDKLLVRDV<br>LDKCMEEELLTIEDRNRIAAAENNGNESGVRELLKRIVQKE<br>NWFSAFLNVLRQTGNNELVQELTGSDCSESNAEIEN |
| 25 | CD5-FcRγ-TNFR1 | MWLQSLLLLGTVACSISEIQLVQSGGGLVKPGGSVRISCAA<br>SGYTFTNYGMNWVRQAPGKGLEWMGWINTHTGEPTYAD<br>SFKGRFTFSLDDSKNTAYLQINSLRAEDTAVYFCTRRGYDW<br>YFDVWGQGTTVTVSSGGGGSGGGGSGGGGSDIQMTQSPSS<br>LSASVGDRVTITCRASQDINSYLSWFQQKPGKAPKTLIYRA<br>NRLESGVPSRFSGSGSGTDYTLTISSLQYEDFGIYYCQQYDE<br>SPWTFGGGTKLEIKSGGGGSGALSNSIMYFSHFVPVFLPAKP<br>TTTPAPRPPTPAPTIASQPLSLRPEACRPAAGGAVHTRGLDI<br>YIWAPLAGTCGVLLLSLVITLYCRLKIQVRKAAITSYEKSDG<br>VYTGLSTRNQETYETLKHEKPPQGSGSQRWKSKLYSIVCG<br>KSTPEKEGELEGTTTKPLAPNPSFSPTPGFTPTLGFSPVPSSTF<br>TSSSTYTPGDCPNFAAPRREVAPPYQGADPILATALASDPIP<br>NPLQKWEDSAHKPQSLDTDDPATLYAVVENVPPLRWKEFV<br>RRLGLSDHEIDRLELQNGRCLREAQYSMLATWRRRTPRRE<br>ATLELLGRVLRDMDLLGCLEDIEEALCGPAALPPAPSLLR |
| 26 | CD5-FcRγ-TNFR2 | MWLQSLLLLGTVACSISEIQLVQSGGGLVKPGGSVRISCAA<br>SGYTFTNYGMNWVRQAPGKGLEWMGWINTHTGEPTYAD<br>SFKGRFTFSLDDSKNTAYLQINSLRAEDTAVYFCTRRGYDW<br>YFDVWGQGTTVTVSSGGGGSGGGGSGGGGSDIQMTQSPSS<br>LSASVGDRVTITCRASQDINSYLSWFQQKPGKAPKTLIYRA<br>NRLESGVPSRFSGSGSGTDYTLTISSLQYEDFGIYYCQQYDE<br>SPWTFGGGTKLEIKSGGGGSGALSNSIMYFSHFVPVFLPAKP<br>TTTPAPRPPTPAPTIASQPLSLRPEACRPAAGGAVHTRGLDI<br>YIWAPLAGTCGVLLLSLVITLYCRLKIQVRKAAITSYEKSDG<br>VYTGLSTRNQETYETLKHEKPPQGSGSPLCLQREAKVPHLP<br>ADKARGTQGPEQQHLLITAPSSSSSSLESSASALDRRAPTRN<br>QPQAPGVEASGAGEARASTGSSDSSPGGHGTQVNVTCIVN<br>VCSSSDHSSQCSSQASSTMGDTDSSPSESPKDEQVPFSKEEC<br>AFRSQLETPETLLGSTEEKPLPLGVPDAGMKPS |

TABLE B

Linker sequences

| SEQ ID | Sequence |
|---|---|
| 10 | SSGGGGSGGGGSGGGGS |
| 11 | SGGGGSG |
| 12 | SGGG |
| 13 | GSGS |

IV. Noncoding Exogenous Sequence for Delivery and Incorporation into the Genome of a Cell A noncoding sequence may be delivered into the cell and designed to be incorporated in the genome of the cell. The noncoding sequence as used herein, is a sequence that does not result in a translated protein product, but may have regulatory elements, such as transcribed products, such as inhibitory RNA. In some embodiments, such a sequence may be a miRNA sequence. In some embodiments, the sequence may be a sequence for siRNA generation. In some embodiments, the sequence may comprise an intronic sequence, or a binding site created, such that one or more DNA binding proteins can dock on the site and influence the nature and behavior of the adjoining regions. In some embodiments, the sequence may be a transcription factor binding site. In some embodiments, the sequence may comprise an enhancer binding site. In some embodiments, the sequence may comprise a binding site for topoisomerase, gyrase, reverse transcriptase, polymerase, poly A binding protein, guanylyl cyclase, ligase, restriction enzymes, DNA methylase, HDAC enzymes, and many others. In some embodiments, the noncoding sequence may be directed to manipulating heterochromatin. A noncoding insert sequence, as it may also be referred to here, may be a few nucleotides to 5 kB in length.

V. Plasmid Design and Recombinant Nucleic Acid Design Comprising an Insert Sequence The nucleic acid construct comprising one or more sequences encoding one or more proteins or polypeptides is incorporated in a plasmid for transcription and generating an mRNA. mRNA can be transcribed in an in vitro system using synthetic system of cell extracts. Alternatively, mRNA can be generated in a cell and harvested. The cell can be a prokaryotic cell, such as a bacterial cell. In some embodiments, the cell is a eukaryotic cell. In some embodiments, the transcription occurs in a synthetic system. Provided herein are exemplary plasmid design.

In some embodiments, of the various aspects of the disclosure, a plasmid is designed for expression of the mRNA molecule comprising a heterologous sequence of interest that encodes a protein or a polypeptide. The plasmid comprises, inter alia, the sequences for genomic integration elements for integration of the heterologous sequence of interest that encodes a protein or a polypeptide; the sequence comprising the transgene or fragment thereof, operably linked to its separate promoter and regulatory elements that are required for its expression in the host following integration in the host genome, (such as, the subject who is administered the mRNA); one or more regulatory elements for transcription and generation of the mRNA including a promoter for expression of the mRNA, e.g. in a bacterial cell or cell extract, and 3' stabilizing elements; sequences for one or more detection marker and/or selection markers.

As is known to one of skill in the art, a plasmid backbone can be an available vector, such as an in-house or commercially developed vector, that can be improved in various ways for best expression of the transcribed sequences, for example, (but not limited to), by introducing one or more desirable restriction digestion sites in the MCS (multiple cloning site), introducing a desired promoter for overall mRNA transcription, such as the T7 promoter, exchanging an existing sequence within the plasmid vector for one or more desired sequences, or introducing one or more desired segments, such as a selection marker sequence.

The plasmid comprises transcription regulatory elements, such as a promoter at the 5' region, and a 3'-stabilizing element. In some embodiments, the promoter is chosen for enhanced mRNA transcription in the desired cell, such as an *E coli* bacterial cell. In some embodiments, the promoter for transcription of the plasmid is selected from a T7 promoter, a Sp6 promoter, pL (lambda) promoter, T3 promoter, trp promoter, araBad promoter, lac promoter or a Ptac promoter. In some embodiments, the promoter is a T7 promoter. T7 or Sp6 promoters are constitutive promoters and are useful for high level transcription or in vitro transcription. In some embodiments, the 3' stabilizing element is a sequence from BGH 3' element, WPRE 3' element, SV40 element, hGH element and other elements. The 3' element comprises the necessary poly A and transcription termination sequences.

Exemplary selection markers include antibiotic selection marker and/or expression detection marker. Antibiotic selection markers include but are not limited to ampicillin resistance gene sequence (beta lactamase gene or fragment thereof) conferring resistance to ampicillin, for example G418 selection marker, tetracycline resistance gene sequence conferring resistance to tetracycline, kanamycin resistance gene sequence conferring resistance to kanamycin, erythromycin resistance gene sequence conferring resistance to erythromycin, chloramphenicol resistance gene sequence conferring resistance to chloramphenicol, neomycin resistant gene sequence conferring resistance to neomycin, and others. Exemplary expression detection marker include FLAG, HA, GFP and others.

In some embodiments, the and other tags that can be fused to one or more coding sequences to function as a surrogate for the expression of the desired protein or peptide to which it is fused.

In some embodiments, the plasmid is less than 20 kb in length. In some embodiments, the plasmid is less than 19 kb in length. In some embodiments, the plasmid is less than 20 kb in length. In some embodiments, the plasmid is less than 18 kb in length. In some embodiments, the plasmid is less than 20 kb in length. In some embodiments, the plasmid is less than 17 kb in length. In some embodiments, the plasmid is less than 20 kb in length. In some embodiments, the plasmid is less than 16 kb in length. In some embodiments, the plasmid is less than 15 kb in length. In some embodiments, the plasmid is less than 14 kb in length. In some embodiments, the plasmid is less than 13 kb in length. In some embodiments, the plasmid is less than 12 kb in length. In some embodiments, the plasmid is about 15 kb, about 14 kb, about 13 kb, about 12 kb or about 10 kb in length.

In some embodiments, the codon is optimized for maximized transcription suitable for the transcription system.

VI. Features Related to the Expression of the Transgene In Vivo

Transcription Regulatory Elements in the Recombinant Nucleic Acid Construct (Transgene)

In some embodiments, the recombinant nucleic comprises one or more regulatory elements within the noncoding regions that can be manipulated for desired expression profiles of the encoded proteins. In some embodiments, the noncoding region may comprise suitable enhancer. In some embodiments, the enhancer comprises a binding region for a regulator protein or peptide may be added to the cell or the system comprising the cell, for commencement of expression of the protein encoded under the influence of the enhancer. Conversely, a regulatory element may comprise a protein binding domain that remains bound with the cognate protein and continue to inhibit transcription and/or translation of recombinant protein until an extracellular signal is provided for the protein to decouple from the bound position to allow commencement of the protein synthesis. Examples include but are not limited to Tetracycline-inducible (Tet-Inducible or Tet-on) and Tetracycline repressible (Tet-off) systems known to one of skill in the art.

Construct comprising metabolic switch: In some embodiments, the 5' and 3' untranslated regions flanking the coding regions of the construct may be manipulated for regulation of expression of the recombinant protein encoded by the nucleic acid constructs described above. For instance, the 3'UTR may comprise one or more elements that are inserted for stabilizing the mRNA. In some embodiments, AU-Rich Elements (ARE) sequences are inserted in the 3' UTR that result in binding of RNA binding proteins that stabilize or destabilize the mRNA, allowing control of the mRNA half-life.

In some embodiments, the 3'UTR may comprise a conserved region for RNA binding proteins (e.g. GAPDH) binding to mature mRNA strand preventing translation. In some embodiments, glycolysis results in the uncoupling of the RNA binding proteins (e.g. GAPDH) allowing for mRNA strand translation. The principle of the metabolic switch is to trigger expression of target genes when a cell enters a certain metabolic state. In resting cells, for example, GAPDH is an RNA binding protein (RBP). It binds to ARE sequences in the 3'UTR, preventing translation of mRNA. When the cell enters glycolysis, GAPDH is required to convert glucose into ATP, coming off the mRNA allowing for translation of the protein to occur. In some embodiments, the environment in which the cell comprising the recombinant nucleic acid is present, provides the metabolic switch to the gene expression. For example, hypoxic condition can trigger the metabolic switch inducing the disengaging of GAPDH from the mRNA. The expression of the mRNA therefore can be induced only when the macrophage leaves the circulation and enters into a tumor environment, which is hypoxic. This allows for systemic administration of the nucleic acid or a cell comprising the nucleic acid, but ensures a local expression, specifically targeting the tumor environment.

In some embodiments, the nucleic acid construct can be a split construct, for example, allowing a portion of the construct to be expressed under the control of a constitutive expression system whereas another portion of the nucleic acid is expressed under control of a metabolic switch, as described above. In some embodiments, the nucleic acid may be under bicistronic control. In some embodiments, the bicistronic vector comprises a first coding sequence under a first regulatory control, comprising the coding sequence of a target recognition moiety which may be under constitutive control; and a second coding sequence encoding an inflammatory gene expression which may be under the metabolic switch. In some embodiments, the bicistronic vector may be unidirectional. In some embodiments, the bicistronic vector may be bidirectional.

In some embodiments, the ARE sequences comprise protein binding motifs for binding ARE sequence that bind to ADK, ALDH18A1, ALDH6A1, ALDOA, ASS1, CCBL2, CS, DUT, ENO1, FASN, FDPS, GOT2, HADHB, HK2, HSD17B10, MDH2, NME1, NQO1, PKM2, PPP1CC, SUCLG1, TP11, GAPDH, or LDH.

Pharmaceutical Compositions and Immunotherapy

In one aspect provided herein is a pharmaceutical composition comprising (i) the nucleic acid encoding the transgene is incorporated in a transpositioning or retrotranspositioning system comprising the transgene, the 5'- and 3'-flanking transposition or retrotranspositioning elements, the expression regulation elements, such as promoters, introns; and a nucleic acid encoding the transposase or retrotransposase, (ii) a nucleic acid delivery vehicle and a pharmaceutically acceptable salt or excipient.

In some embodiments, the pharmaceutical composition comprises cells comprising the nucleic acid encoding the transgene that is stably integrated in the genome of the cell and a pharmaceutically acceptable excipient. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995), using viral vectors (Monahan, et al, Gene Therapy 4:40-49, 1997; Onodera, et al, Blood 91:30-36, 1998), by uptake of "naked DNA", and the like. Techniques well known in the art for the transformation of cells (see discussion above) can be used for the ex vivo administration of nucleic acid constructs. The exact formulation, route of administration and dosage can be chosen empirically. (See e.g. Fingl et al., 1975, in "The Pharmacological Basis of Therapeutics", Ch. 1 pl).

In some embodiments, the nucleic acid comprising the transgene and the transposable elements is introduced or incorporated in the cell by known methods of nucleic acid transfer inside a cell, such as using lipofectamine, or calcium phosphate, or via physical means such as electroporation or nucleofection. In some embodiments, the nucleic acid is encapsulated in liposomes or lipid nanoparticles. LNPs are 100-300 nm in diameter provide efficient means of mRNA delivery to various cell types, including macrophages. In some embodiments, the nucleic acid is transferred by other nanoparticles. In some embodiments, the vector for expression of the CFP is of a viral origin, namely a lentiviral vector or an adenoviral vector. In some embodiments, the nucleic acid encoding the recombinant nucleic acid is encoded by a lentiviral vector. In some embodiments, the lentiviral vector is prepared in-house and manufactured in large scale for the purpose. In some embodiments, commercially available lentiviral vectors are utilized, as is known to one of skill in the art.

In some embodiments, the viral vector is an Adeno-Associated Virus (AAV) vector.

The methods find use in a variety of applications in which it is desired to introduce an exogenous nucleic acid into a target cell and are particularly of interest where it is desired to express a protein encoded by an expression cassette in a target cell, where the target cell or cells are part of a multicellular organism. The transposase system may be administered to the organism or host in a manner such that the targeting construct is able to enter the target cell(s), e.g., via an in vivo or ex vivo protocol. Such cells or organs are typically returned to a living body.

In some embodiments, the transgene encoding a fusion protein related to immune function is stably integrated in a living cell of a subject ex vivo, following which the cell comprising the transgene is returned to the subject. Of exemplary importance, the CFP transgene (phagocytic receptor fusion protein) is intended for expression in an immune cell, such as a myeloid cell, a phagocytic cell, a macrophage, a monocyte or a cell of dendritic cell lineage is contacted ex vivo with the recombinant nucleic acids for stable transfer of the transgene and re-introduced in the same subject for combating a disease of the subject. The diseases contemplated comprises infectious diseases, cancer and autoimmune diseases. The nucleic acid encoding the PSR subunit comprising fusion protein (CFP) described herein is used to generate engineered phagocytic cells for treating cancer.

Cancers include, but are not limited to T cell lymphoma, cutaneous lymphoma, B cell cancer (e.g., multiple myeloma, Waldenstrom's macroglobulinemia), the heavy chain diseases (such as, for example, alpha chain disease, gamma chain disease, and mu chain disease), benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

In general, cellular immunotherapy comprises providing the patient a medicament comprising live cells, which should be HLA matched for compatibility with the subject, and such that the cells do not lead to graft versus Host Disease, GVHD. A subject arriving at the clinic for personalized medicine and immunotherapy as described above, is routinely HLA typed for determining the HLA antigens expressed by the subject.

EXAMPLES

It should be appreciated that the invention should not be construed to be limited to the examples which are now described; rather, the invention should be construed to include any and all applications provided herein and all equivalent variations within the skill of the ordinary artisan.

Example 1. Exemplary Retrotransposon Designs Constructs

Figure 1B:
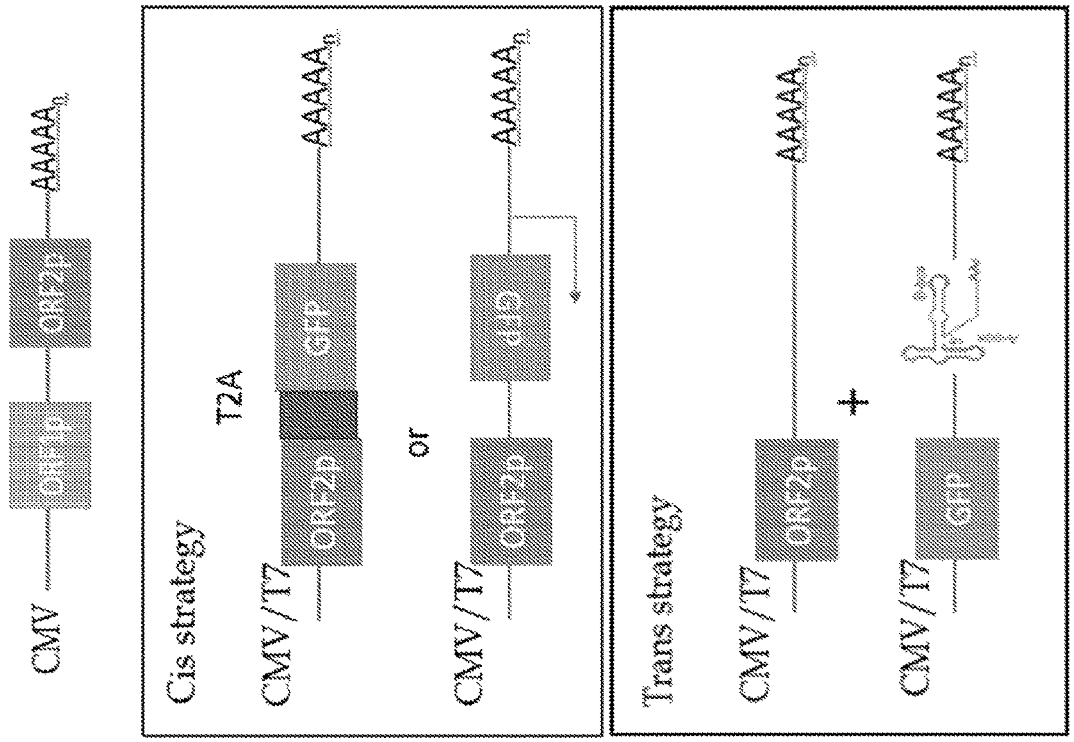
FIG. 1B illustrates various exemplary designs for integrating an mRNA encoding a transgene into the genome of a cell. GFP shown here in a box is an exemplary transgene.
Figure 1C:
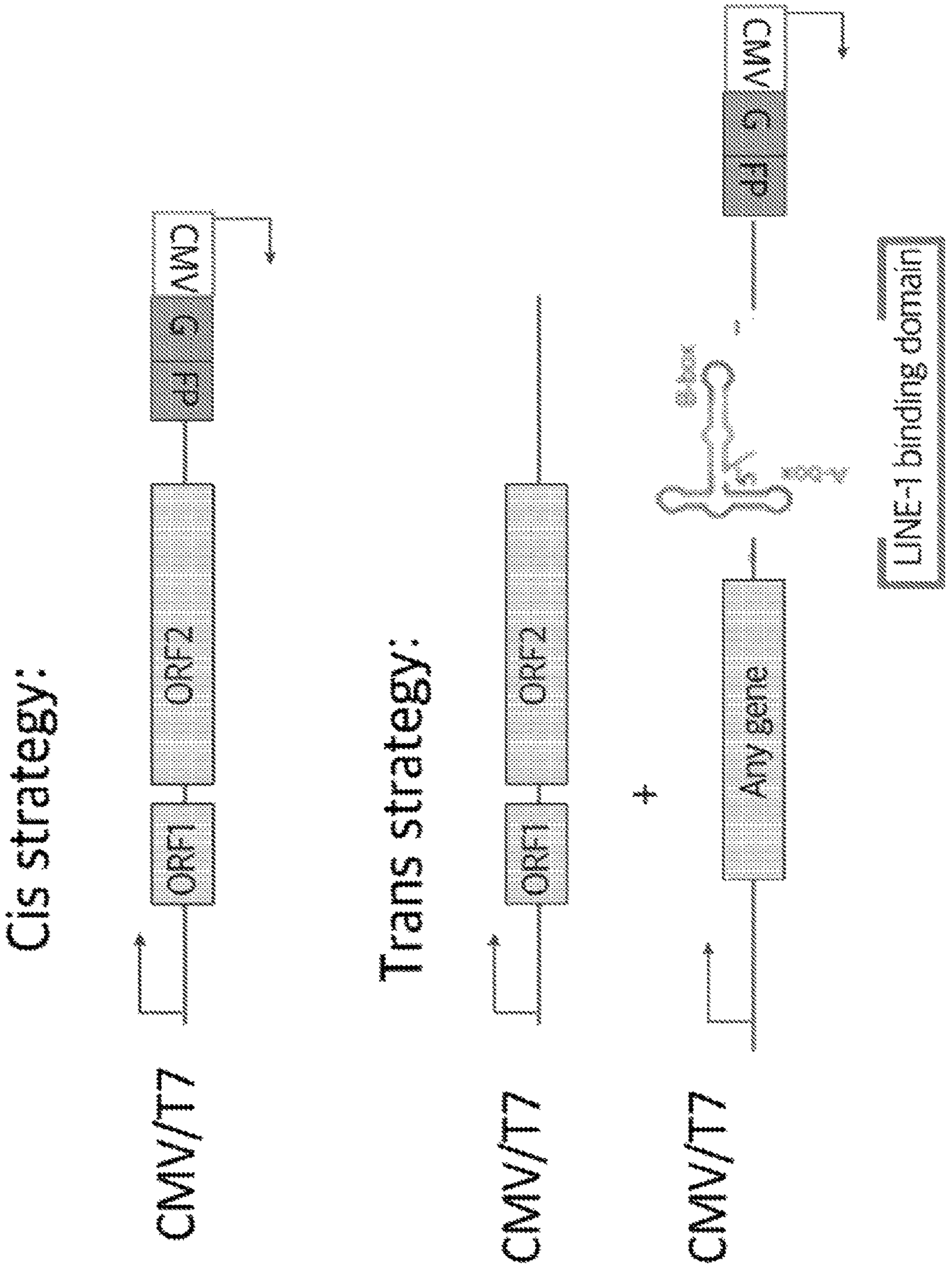
FIG. 1C illustrates various exemplary designs for integrating an mRNA encoding a transgene into the genome of a cell. GFP shown here in a box is an exemplary transgene.

Provided here are exemplary strategies of designing retrotransposon constructs for incorporating into the genome of a cell and expressing an exemplary transgene. FIG. 1B and FIG. 1C illustrates various strategic designs for integrating an mRNA encoding transgene into the genome of a cell. GFP shown here in a box is an exemplary transgene. The mRNA encoding the transgene (e.g., GFP) can be co-expressed with a nucleic acid sequence encoding an ORF2p protein, in either sense or antisense orientation; the respective coding sequences may be in a monocistronic or bicistronic construct shown under exemplary Cis-strategies (FIG. 1B and FIG. 1C). CMV/T7 are promoters.

Figure 2A:
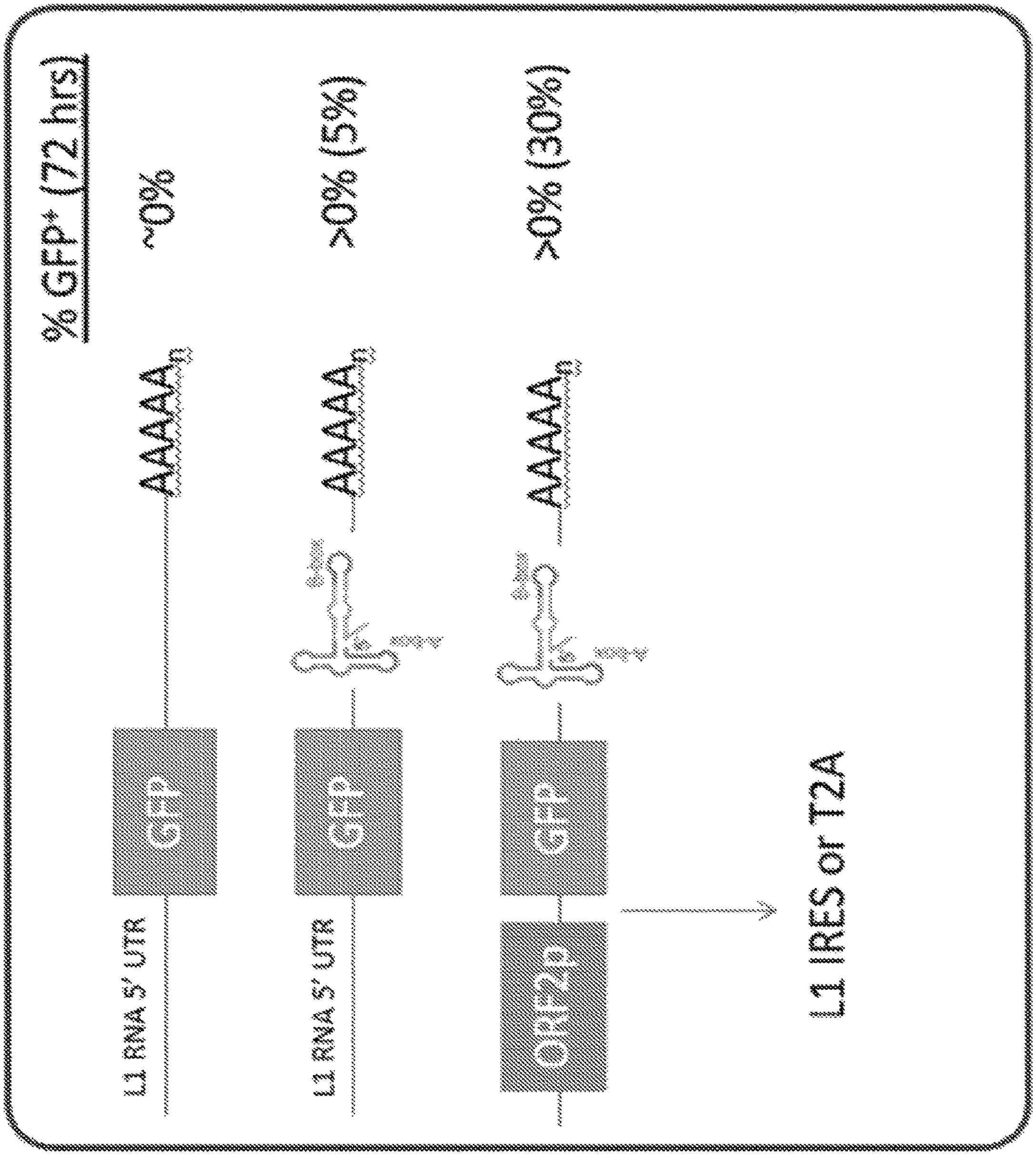
FIG. 2A illustrates three exemplary designs for expressing an exemplary transgene GFP by stably incorporating the sequence encoding GFP using the constructs. Expected GFP expression levels at 72 hours are shown on the right side.
Figure 2B:
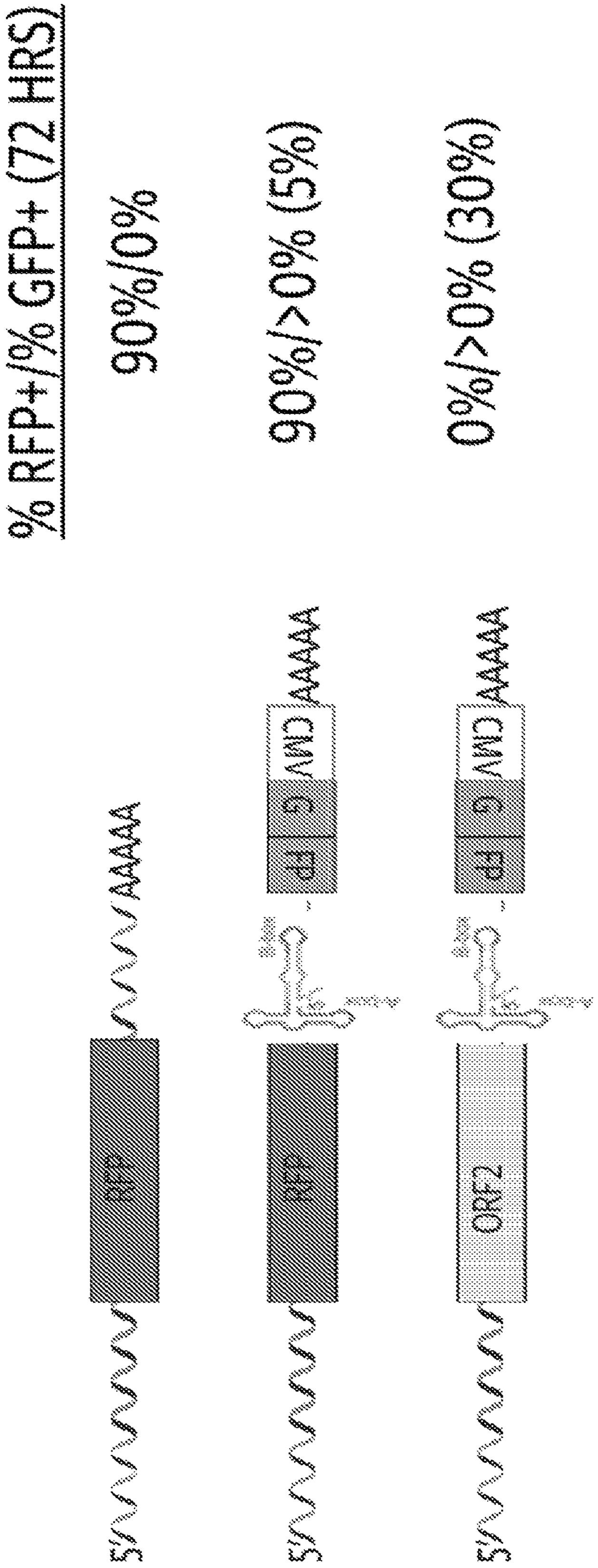
FIG. 2B illustrates three exemplary designs for expressing an exemplary transgene GFP by stably incorporating the sequence encoding RFP, RFP and GFP or ORF2p and GFP using the constructs. Expected GFP and RFP expression levels at 72 hours are shown on the right side.

On the other hand, the same could be directed to be expressed in a trans manner. The trans-strategy can include a sequence encoding an ORF2p protein or both ORF1p and ORF2p proteins from a bicistronic sequence and an mRNA encoding a GFP in a sense or antisense direction in the 3'UTR of any gene. The transgene is flanked by a retrotransposing sequence comprising transposase binding sequences, an A-box and B-box, and a poly A tail. FIG. 2A illustrates three exemplary designs for expressing an exemplary transgene GFP by stably incorporating the sequence encoding GFP using the constructs. The first construct comprises a sequence encoding GFP, flanked by L1 5'-UTR; and a poly A sequence at the 3' UTR, in absence of any transposase binding elements. The second and the third constructs comprise a sequence encoding GFP, a 3'UTR an A Box and a B-box, and a poly A sequence at the 3' UTR. The third construct comprises an additional sequence encoding ORF2p. Expected GFP expression levels at 72 hours are shown on the right side. FIG. 2B illustrates three exemplary designs for expressing an exemplary transgene GFP in an mRNA that either encodes RFP or ORF2p by stably incorporating the sequence encoding GFP using the constructs. The first construct comprises a sequence encoding RFP, and a poly A sequence at the 3' UTR, in absence of any L1 elements. The second and the third constructs comprise a 3'UTR comprising an A Box and a B-box, and a poly A sequence at the 3' UTR. The second construct comprises a sequence encoding RFP and the third construct comprises a sequence encoding ORF2p. Expected RFP and GFP expression levels at 72 hours are shown on the right side.

Example 2. Exemplary circRNA Designs Constructs

In this example, modular designs for circRNA are demonstrated, which incorporate a stretch of about 50 nucleotide long RNA having naturally occurring tertiary structures in order to prepare a circRNA. Use of the tertiary-structure forming RNA makes the circRNA formation process independent of sequence mediated hybridization for circularization. These RNA motifs having tertiary structures can be incorporated in the desired RNA having an exon and an intron in place of the 5' and 3' homology arms, thereby forming the terminal RNA scaffolds for circularization.

Figure 3B:
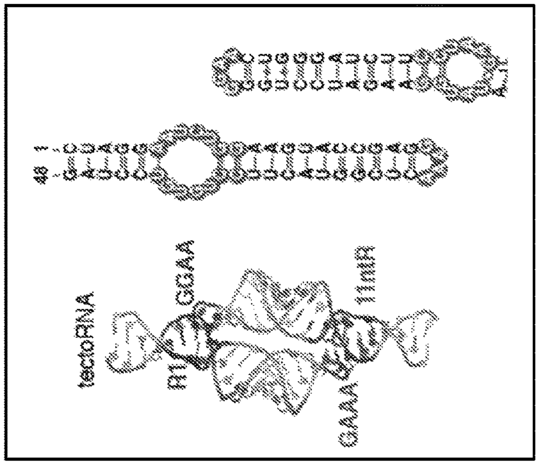
FIG. 3B illustrates two views of an exemplary RL-GAAA tectoRNA motif designs (SEQ ID NOS 80-81, respectively, in order of appearance).
Figure 3C:
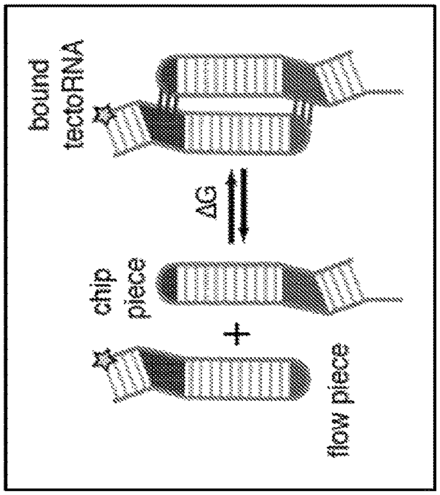
FIG. 3C illustrates exemplary structures of chip-flow piece RNAs as platforms for testing potential tectoRNA.

TectoRNA: RNA-RNA binding interfaces are constructed by combining pairs of GNRA loop/loop-receptor interaction motifs, yielding high affinity, high specificity tertiary structures. (FIG. 3B). Pairs of GNRA loop/loop-receptor interaction motifs are fused using the four-way junction from the hairpin ribozyme to create divalent, self-assembling scaffolding units ('tectoRNA') which help form a closed cooperatively assembling ring-shaped complexes. Using two orthogonal loop/loop-receptor interaction motifs, RNA monomers are designed that are capable of directional assembly in either the parallel ('up-up') or anti-parallel ('up-down') assembly modes. In anti-parallel assembly of interacting molecules, each incorporated monomer switches the directionality of the growing chain and thus compensates for its intrinsic bending, producing long, relatively straight multi-unit chains. For selecting a tectoRNA scaffolds having minimum occurrences of alternative secondary structures, sequences are checked by submitting them to the RNA folding program Mfold (bioinfo.math.rpi.edu/~zukerm/ma/mfold) which predicts the thermodynamically favored secondary structure of a given RNA sequence. A thermodynamically favored structure is selected for scaffolding that has minimum alternative secondary structures (typically but not exclusively, no other secondary structure is closer than 15% in energy to the lowest energy structure). RNA molecule is prepared by conventional methods, such as in vitro run-off transcription using T7 RNA polymerase. FIG. 3B shows a RL-GAAA loop structure. In order to profile tectoRNA heterodimers a fluorescence-based chip-flow piece testing method is utilized. In this method, a library of potential variants of the structured RNA (chip piece) is synthesized as DNA templates and amplified to include sequencing adapters and regions for RNAP initiation. Each DNA variant is transcribed in situ into RNA, enabling display of sequence-identified clusters of RNA on the surface of the sequencing chip. The fluorescently-labeled tectoRNA binding partner, the "flow piece", is introduced to the sequencing chip flow cell at increasing concentrations, allowing quantification of bound fluorescence to each cluster of RNA after equilibration. These fluorescence values are used to derive the affinity of the flow piece to each chip piece variant (FIG. 3C), in terms of the dissociation constant ($K_d$) and binding free energy, ($\Delta G=RT\log(K_d)$).

The selected terminal RNA scaffold segments comprising the tertiary structures are incorporated using T7 transcription or ligated at the 5' and 3' ends of the desired RNA to be circularized; or are incorporated in the desired RNA by any known molecular biology techniques.

Example 3: Exemplary Retrotransposon Designs with Enhanced Specificity

In this example, designs for a nucleic acid construct for L1-mediated retrotransposon for enhanced target specificity is demonstrated. An mRNA is designed comprising ORF2 encoding sequence and a sequence encoding a gene of interest, to incorporate the gene of interest into the genome of a cell using ORF2. In one exemplary design, the construct comprises an ORF2 that is further modified.

Figure 4A:
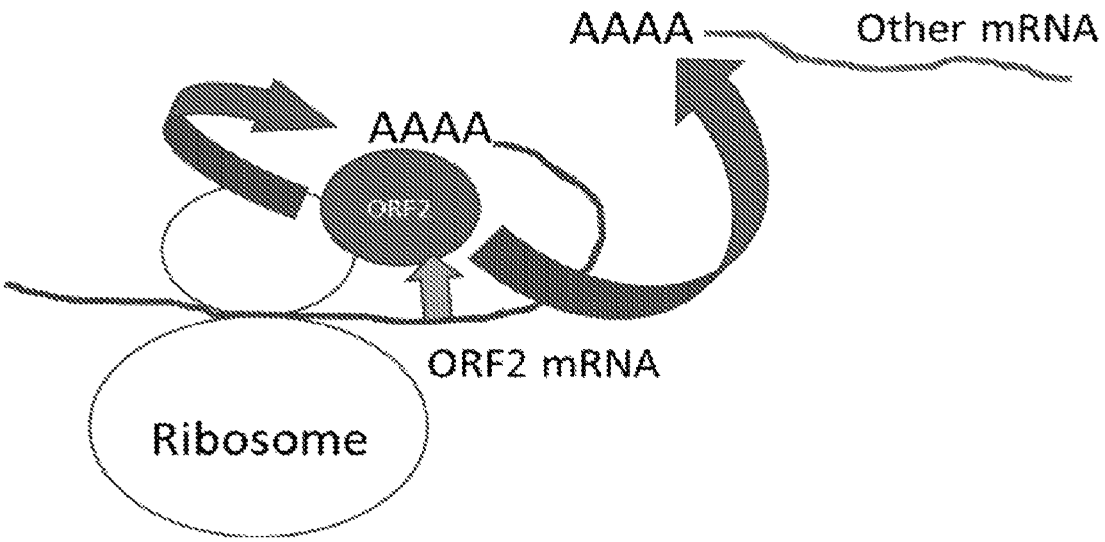
FIG. 4A illustrates an exemplary schematic showing ORF2p binding to an ORF2 poly A region.

As shown in FIG. 4A, ORF2 protein initiates retrotransposition by binding to its own poly A sequence. However, because poly A is abundantly present in mRNAs, a non-specific binding and integration becomes a possibility. To increase the specificity, a recombinant ORF2 is designed comprising an mRNA-binding domain of a heterologous protein, and the cognate mRNA sequence for the heterologous mRNA-binding domain is inserted near the poly A sequence in the 3'-UTR and the ORF2 poly A binding site.

Figure 4B:
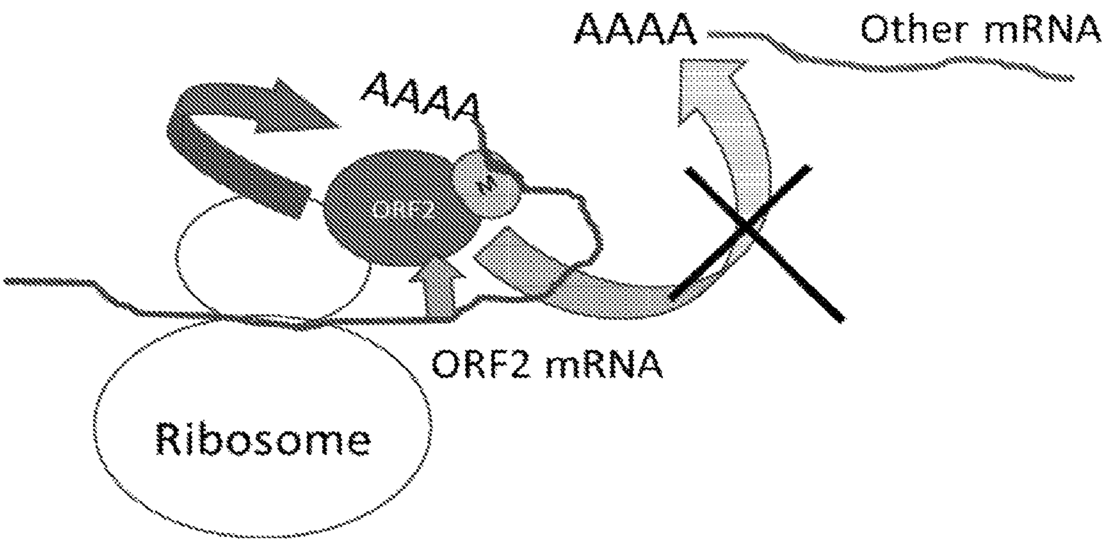
FIG. 4B illustrates an exemplary schematic showing how a fusion of ORF2p with an MS2 RNA binding domain binds to an MS2 binding RNA sequence in the 3'UTR of an mRNA encoding the ORF2 an increase specificity.

A chimeric ORF2 is thereby generated as shown in (FIG. 4B), in which a high affinity RNA-binding domain of a heterologous protein encoding sequence is incorporated or fused to the ORF2 sequence and cognate RNA sequences corresponding to the high affinity RNA-binding protein is incorporated in the 3'UTR region of the mRNA, proximal to the poly A region. In this example the heterologous high affinity RNA-binding domain is derived from MCP coat protein MS2 (shown as M in the figure), is incorporated within the ORF2 sequence and the cognate sequence, the MS2 hairpin, is included in the 3' UTR sequence of the mRNA (FIG. 4B). The MS2 binds to the cognate sequence, increasing the specificity of the chimeric ORF2 to its own mRNA for reverse transcribing and incorporating the respective sequence associated with the ORF2 mRNA in the mammalian cell genome (FIG. 4B).

Figure 4C:
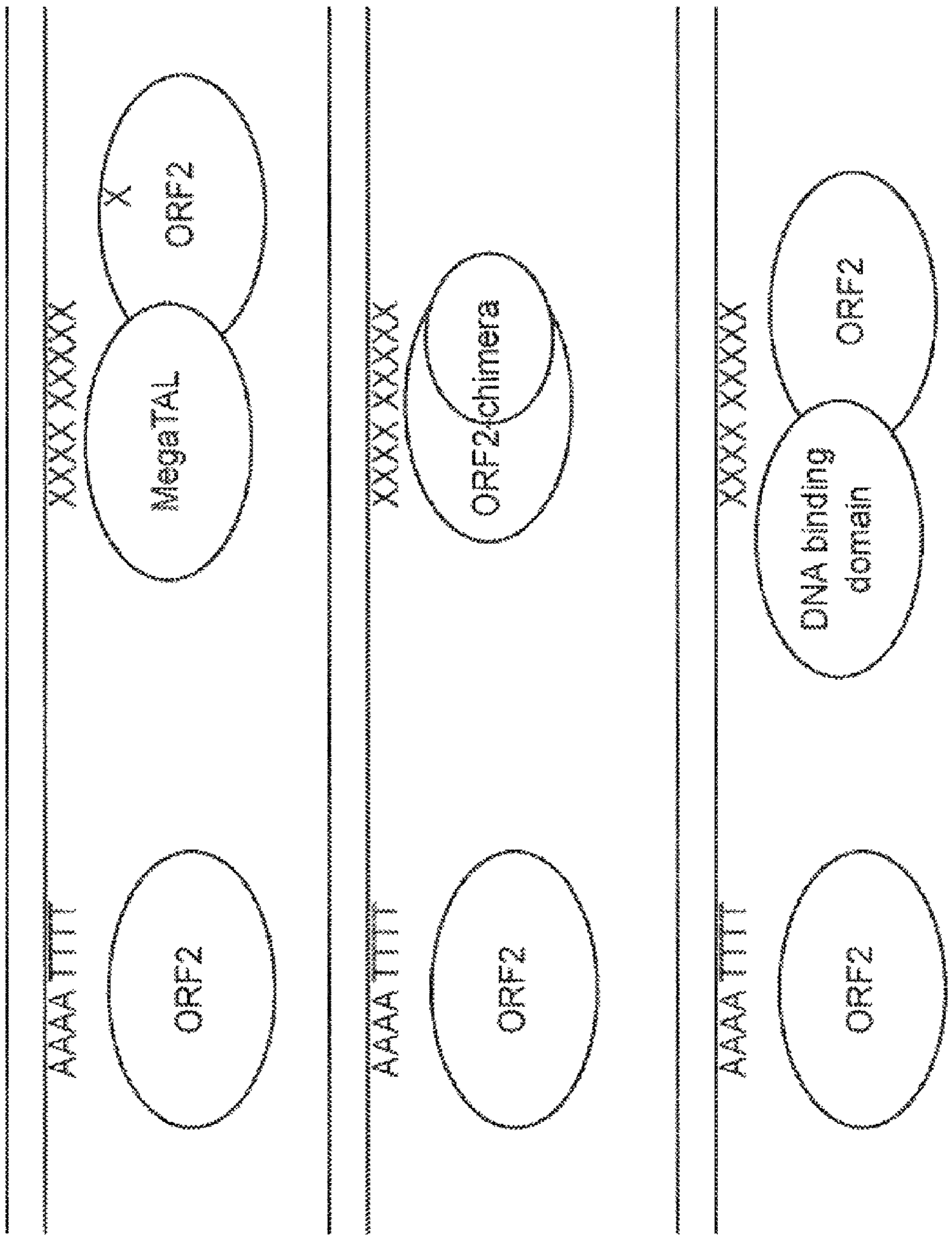
FIG. 4C illustrates exemplary designs of retrotransposon systems for stably integrating a nucleic acid into the genome of a cell at specific sites. The upper panel shows a design using an ORFp2-MegaTAL DNA binding domain fusion where the DNA binding and endonuclease activity of ORF2p is mutated to be inactive. The middle panel shows a chimeric ORF2p where the endonuclease domain has been replaced with a high specificity and high-fidelity nuclease domain of another protein. The lower panel shows a fusion of a DNA binding domain of a heterologous protein with ORF2p such that the fusion protein binds to ORF2 binding site as well additional DNA sequences in the vicinity of the ORF2 site.

In other exemplary designs, attempts to increase specificity of integration of the transgene by the ORF2 within the genome of a target cell is undertaken. In one exemplary design, Mega TAL encoding sequence fused to an ORF2 as shown in FIG. 4C (upper panel). Along with that, the ORF2 is mutated to remove its ability to recognize and bind to RNA sequence that has less specificity. The fused protein is directed to the TAL binding sequence incorporated within the 3'UTR and perform endonuclease function. The Mega TAL DNA binding sequence is targeted by the fusion protein. Likewise, other chimera (FIG. 4C (middle panel)) and fusion protein with a specific DNA binding domain FIG. 4C (lower panel) are designed.

Example 4. Exemplary Plasmid Design and Developments for LINE-1 Mediated Retrotransposition of an Exogenous Nucleic Acid Sequence In this example plasmid vectors are generated for delivery and incorporation of a recombinant LINE-1 construct comprising an ORF2 transposon element operably linked to a transgene transposable into a mammalian cell, and regulatory elements for mRNA transcription and stabilization. The mRNA can be transcribed in a bacterial host cell, which can be further processed and/or purified for introduction into a mammalian cell in vitro or administration in an organism, such as a mammal, a rodent, sheep, pig or a human.

Any suitable vector backbone is used for incorporating the recombinant nucleic acid sequence as insert and transcribing in a bacterial system for mRNA generation; or in vitro transcription system may be utilized to generate an mRNA comprising the recombinant nucleic acid sequence. Several features are added to the plasmid. Upon successful scalable mRNA production, and purification, the mRNA may be introduced in a mammalian cell of interest, such as a myeloid cell.

Plasmids traditionally used in the field of study for retrotransposition lack designer genes, gene blocks, and Gibson assembly methods were used regularly to insert different features. A new vector that takes features from the old vectors but has flexibility to insert new features can be beneficial both for the study and optimization of LINE-1 elements as a gene delivery system. Below is an outline of base features and additional features that can increase retrotransposition frequency, both using the plasmid alone or the mRNA transcribed from the plasmid. In an exemplary plasmid design shown graphically in FIG. 5(I), which contains the natural LINE-1 sequence with the original 5'UTR, 3'UTR and interORF sequence with no restriction sites to swap out any of these features. New optimized plasmid Removed Dox inducible promoter, replaced with CMV or EIF1a or EF1a promoter
Added a T7 site to make mRNA
Codon optimized ORF1 and ORF2
Added a WPRE element to stabilize mRNA
Added FLAG tag to ORF2 to help with protein detection
Decreased size from 18 kb to 14 kb
Added blunt restriction sites (dotted lines with blunt arrows) at each feature to facilitate insertions
Includes a G418 selection marker
The plasmid is shown in FIG. 5 (II).

Figure 5:
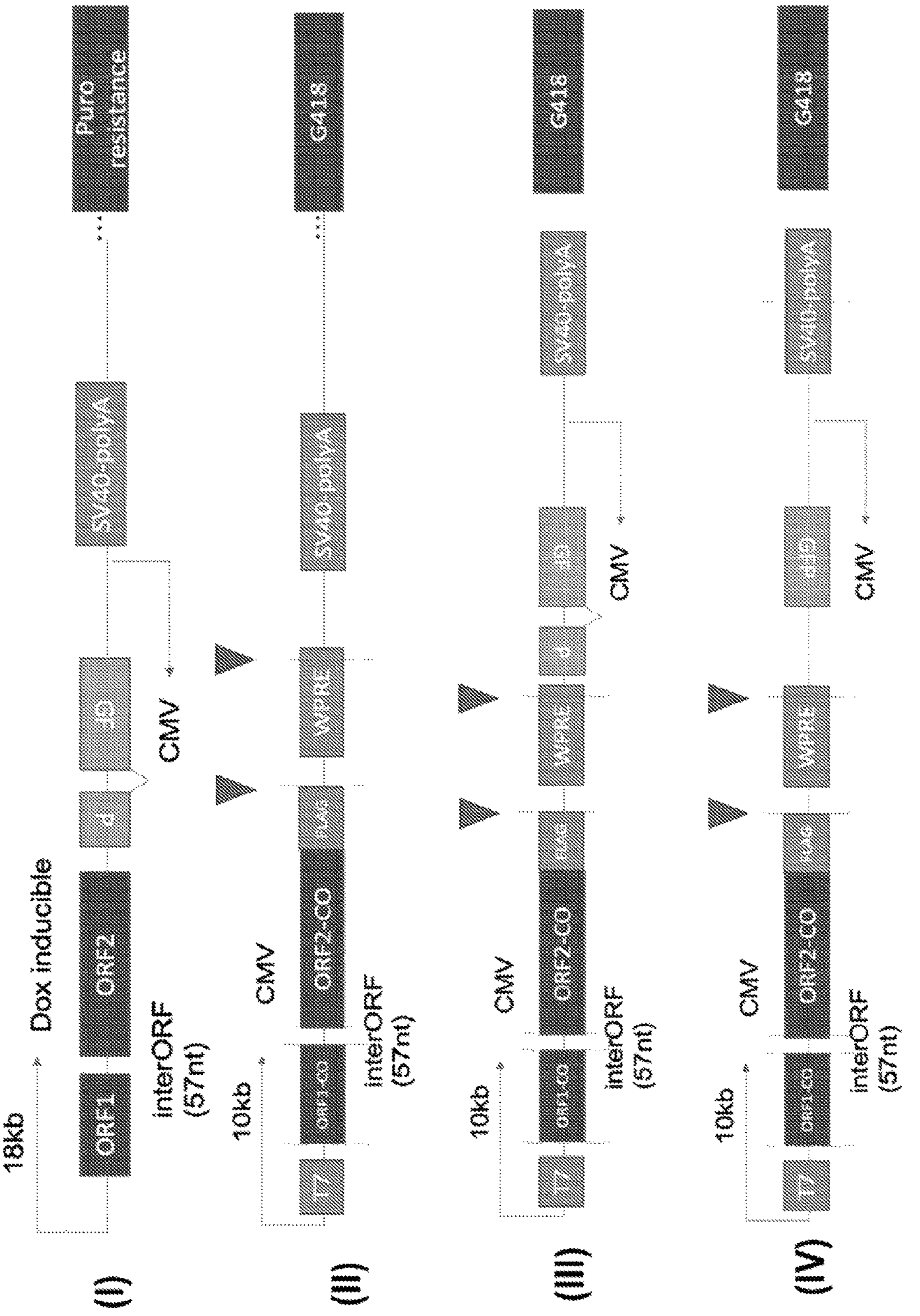
FIG. 5 illustrates exemplary constructs for integrating an mRNA encoding a transgene into the genome of a cell.
Figure 5:
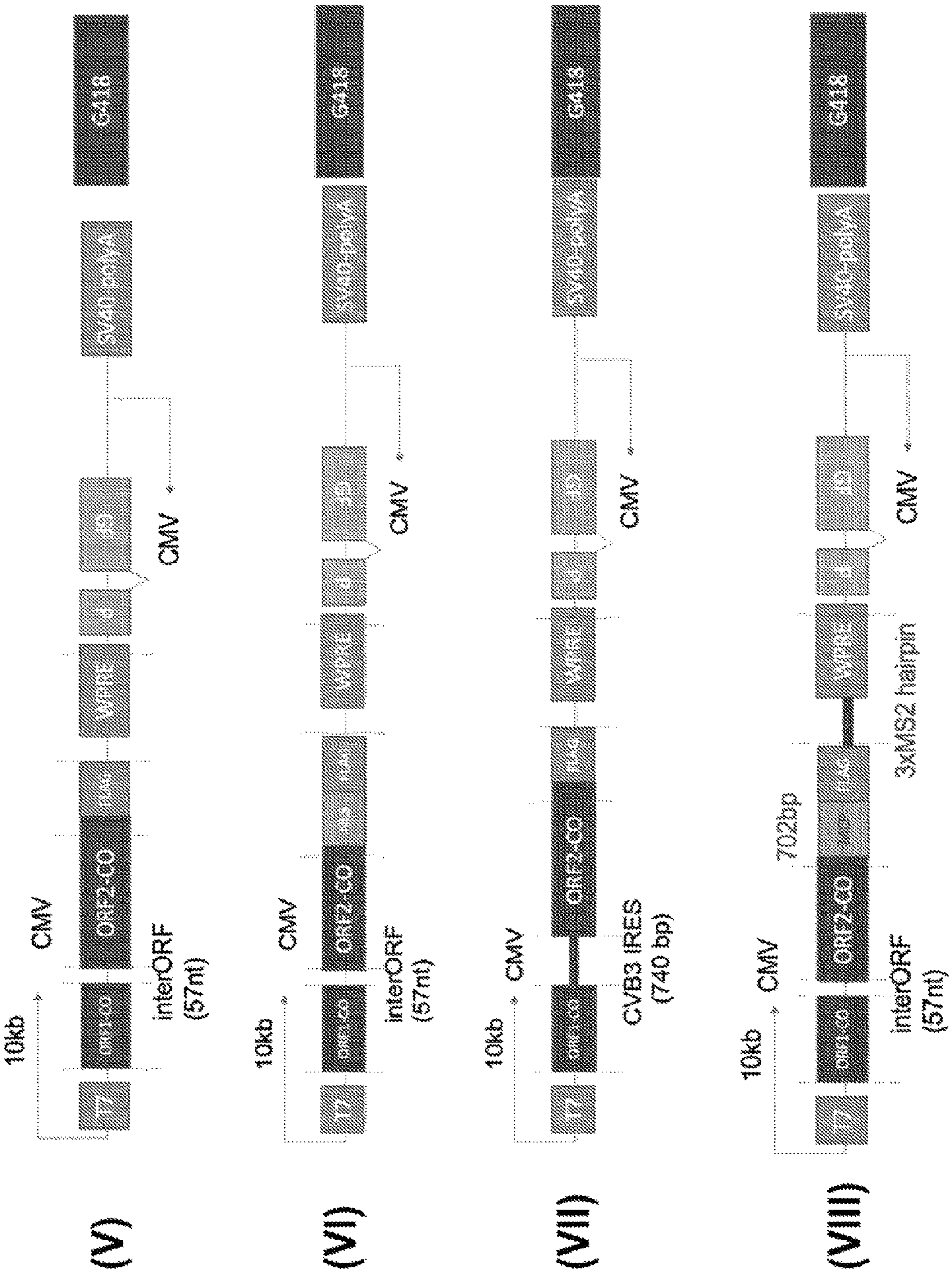
Figure 5:
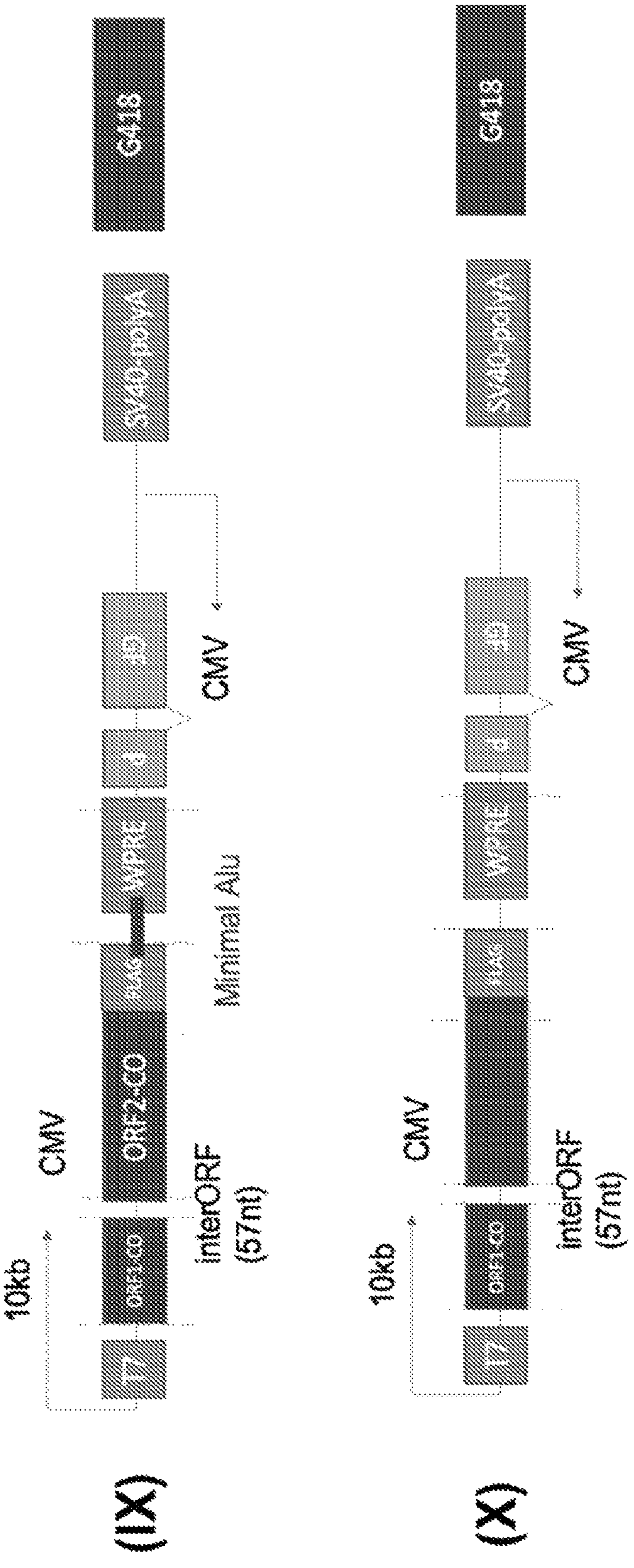

With Gibson a reverse split GFP is inserted for plasmid reporter gene as shown in FIG. 5 (III). A complete reverse GFP for the mRNA reporter is inserted as in FIG. 5 (IV).

Using the plasmid construct in FIG. 5 (V) as parent, a nuclear localization sequence (NLS) is inserted at the N terminus of ORF2 to help with nuclear import (FIG. 5 (VI)). An IRES or another termination/promoter sequence is inserted to increase expression of ORF2 (FIG. 5 (VII)). To facilitate stronger interactions between ORF2 and the mRNA, MS2 hairpins are inserted in the 3'UTR and a MS2 coat protein sequence in the N terminus of the ORF2 protein (FIG. 5 (VIII)). A corresponding exemplary ORF2 with enhanced specificity and its mechanism of action is disclosed in the preceding example and in FIG. 4B. To facilitate stronger interactions of the mRNA with the translating ribosome and to stall translation so that nascent ORF2 will more likely bind the mRNA, an Alu element is inserted in the 3'UTR of the mRNA (FIG. 5 (IX)). To potentially use a more active ORF2 protein, the ORF2's RT domain is replaced with the Group II intron's reverse transcriptase domain (FIG. 5 (X)). Additionally, the minke whale genome has the highest number and percentage of active LINE elements (~5,000 with 60% active compared to humans that have 480 with 3.6% active). The two sequences are 67% identical and the whale sequence has the active endonuclease and reverse-transcriptase residues. The respective minke whale domains can be used to replace native ORF2 endonuclease and/or RT domains or design a chimera domain.

Figure 6A:
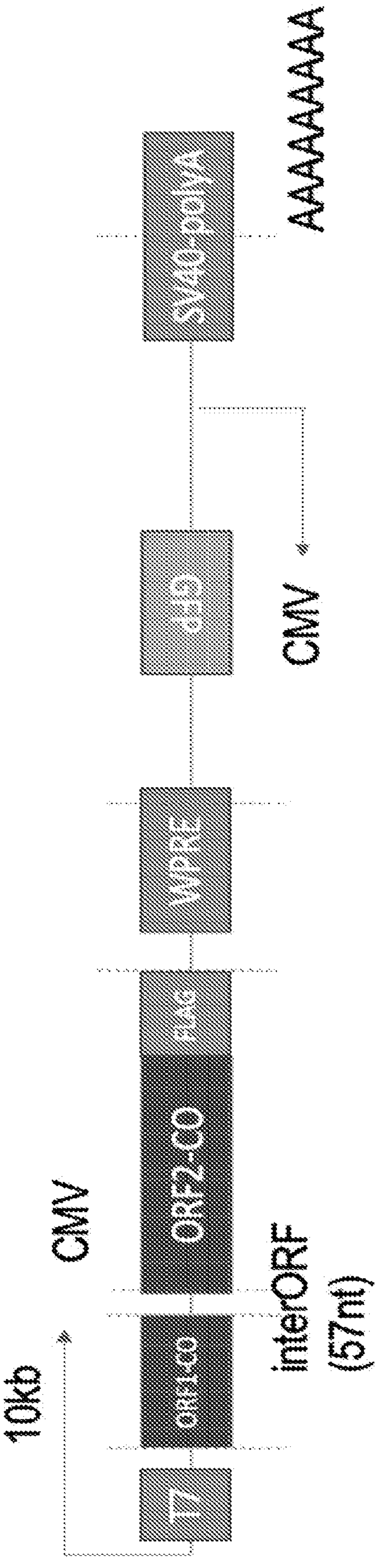
FIG. 6A illustrates an exemplary construct with a sequence encoding ORF1p for integrating an mRNA encoding a transgene into the genome of a cell.
Figure 6B:
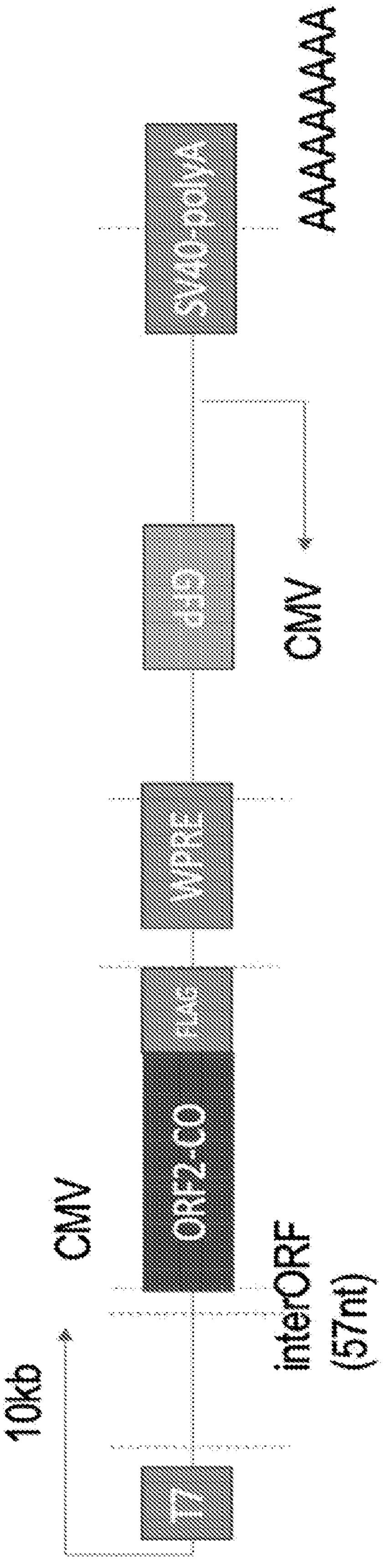
FIG. 6B illustrates an exemplary construct without a sequence encoding ORF1p for integrating an mRNA encoding a transgene into the genome of a cell.

Example 5. MRNA Design Synthetic mRNA Generation mRNA can be strategically designed for synthetic production by oligosynthesis and or ligation of oligonucleotides. Additionally, such designs are useful for in vitro transcription (IVT) mediated mRNA generation. The mRNA strategy can include the same variants as the plasmid strategy discussed in the previous example. The main differences are that the reporter GFP sequence does not include an intron (FIG. 6A) and that the constructs can be delivered without the ORF1 coding region (FIG. 6B).

Example 6. Structural Features for Increased mRNA Half-Life

Figure 7A:
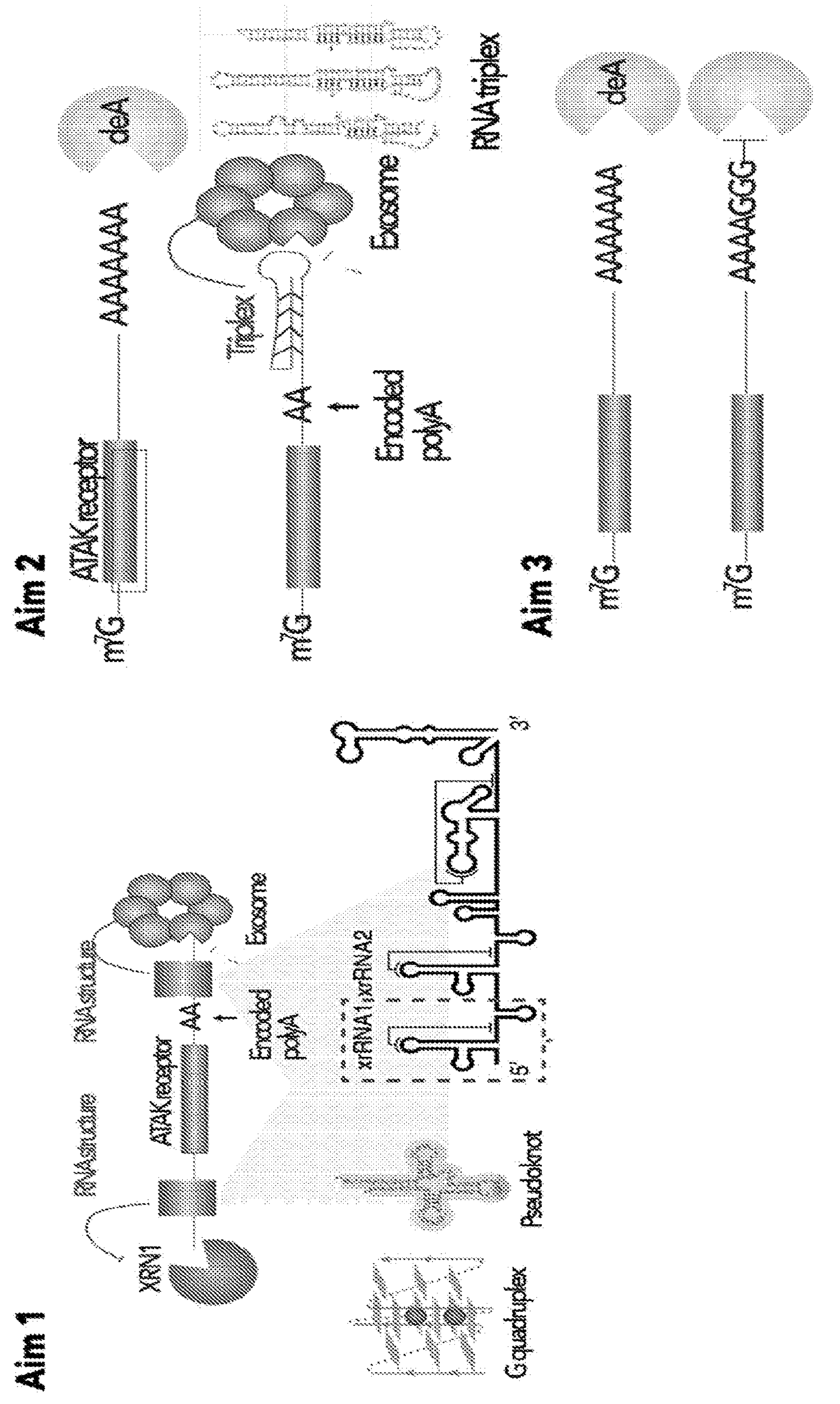
FIG. 7A illustrates exemplary methods of improving mRNA half-life by inhibiting degradation by 5'-3' exonucleases, such as XRN1, or 3'-5' exosomal degradation, by introducing structures corresponding to a G-quadruplex, or, a pseudoknot (SEQ ID NO: 82) in the 5'UTR; and/or xrRNAs, a triplex motifs (SEQ ID NOS 83-85, respectively, in order of appearance) and/or a non-A nucleotide residues in the 3'UTR.
Figure 7C:
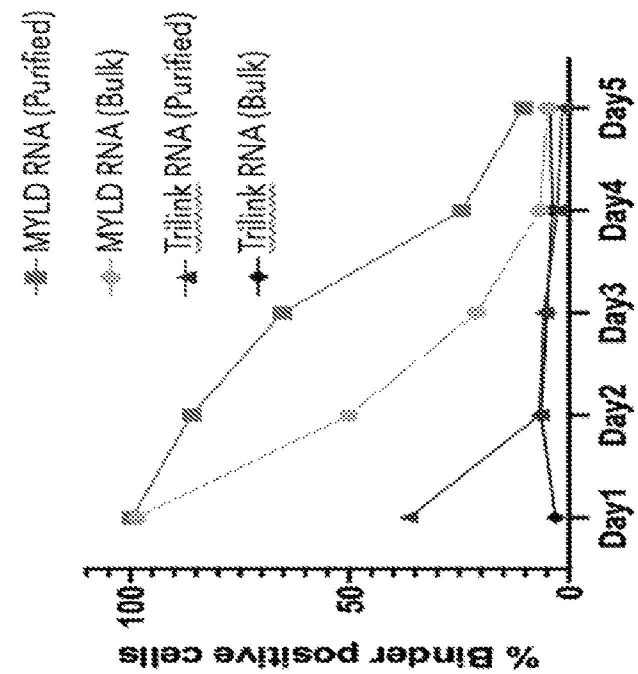
FIG. 7C shows expected results of introducing bulk or purified RNA encoding a chimeric receptor that binds a cancer cell as described in FIG. 7B on increased and prolonged expression of the chimeric receptors.
Figure 7B:
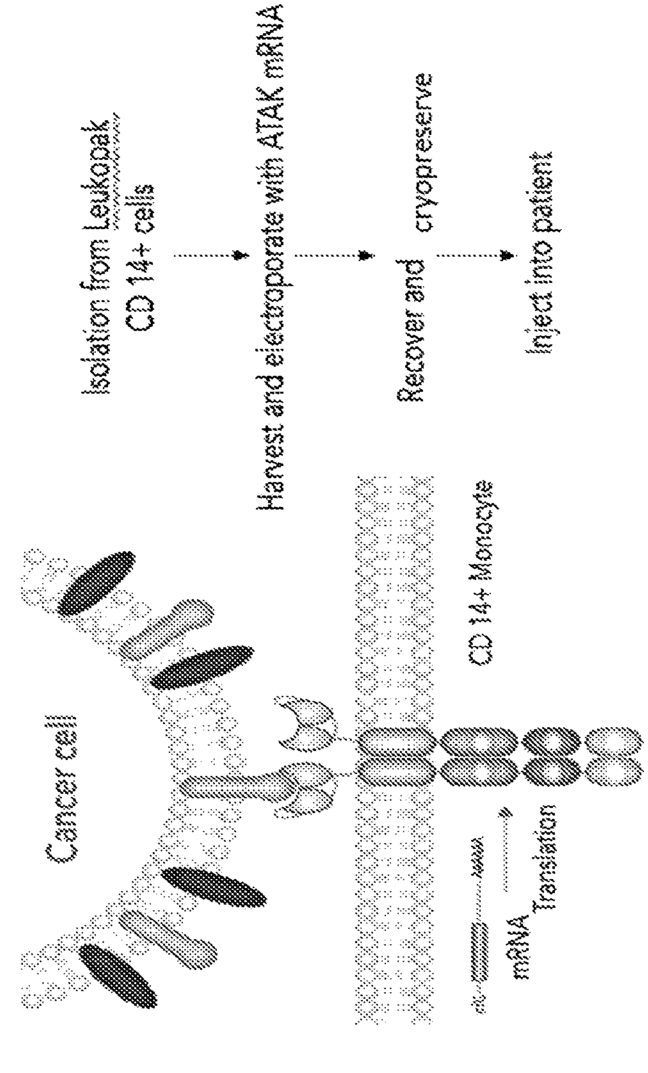
FIG. 7B illustrates an exemplary schematic of a myeloid cell expressing a transgene encoding a chimeric receptor that binds a cancer cell and induces anti-cancer activity.

In this example, structural features are introduced in the mRNA comprising the retrotransposition elements and/or the transgene for increasing the mRNA half-life. The goal is to increase the duration of protein expression from the mRNA in primary monocytes from three days to at least 5 days with an ultimate goal of 10 days. As shown in FIG. 7B (left), the mRNA comprising a sequence encoding the transgene when introduced into a CD14+ myeloid cell (monocyte), is translated and expresses a chimeric receptor (an ATAK construct) capable of binding to an antigen on a cancer cell.

A number of mRNA designs are generated by synthesizing various gene blocks comprising singly, or combinations of one or more of: (i) a G-quadruplex, (ii) a viral pseudoknot structure in the 5' UTR; and/or (iii) one or (iv) more xrRNA loop structures in the 3' UTR (v) a triplex RNA structure as shown in FIG. 7A; and cloned into the transcription vector at the respective UTRs adjoining the coding sequence of the transgene. These constructs are individually prepared by an off-site vendor and tested in-house for determining stability of the mRNA, as measured by the expression of the chimeric receptor (An exemplary receptor and its function is depicted graphically in FIG. 7B (left). The process flow chart is shown on FIG. 7B (right). In short, constructs are cloned into plasmids, with encoded or modified poly A tails. The mRNA was transcribed at 100 ug scale and purified with ethanol precipitation (Aldevron). Meanwhile, frozen monocytes are thawed and harvested. Harvested cells were electroporated with the purified mRNA (5-10 ug), and cultured for 1, 2, 3, 5 days. Cells positive for the chimeric receptor (binder positive cells), are detected by means of their ability to bind to a target cell or a substrate coated with the target antigen. The expected results are shown in FIG. 7C. Bulk or purified mRNA expressing one or more of the structural features outlined in (i)-(v) (data denoted by solid squares) or a combination thereof outperforms the commercially available counterparts that do not contain any of the features outlined in (i)-(v) (data denoted by triangles).

Example 7. LINE-1 Retrotransposon Plasmid Mediated Delivery of GFP Gene

Figure 8A:
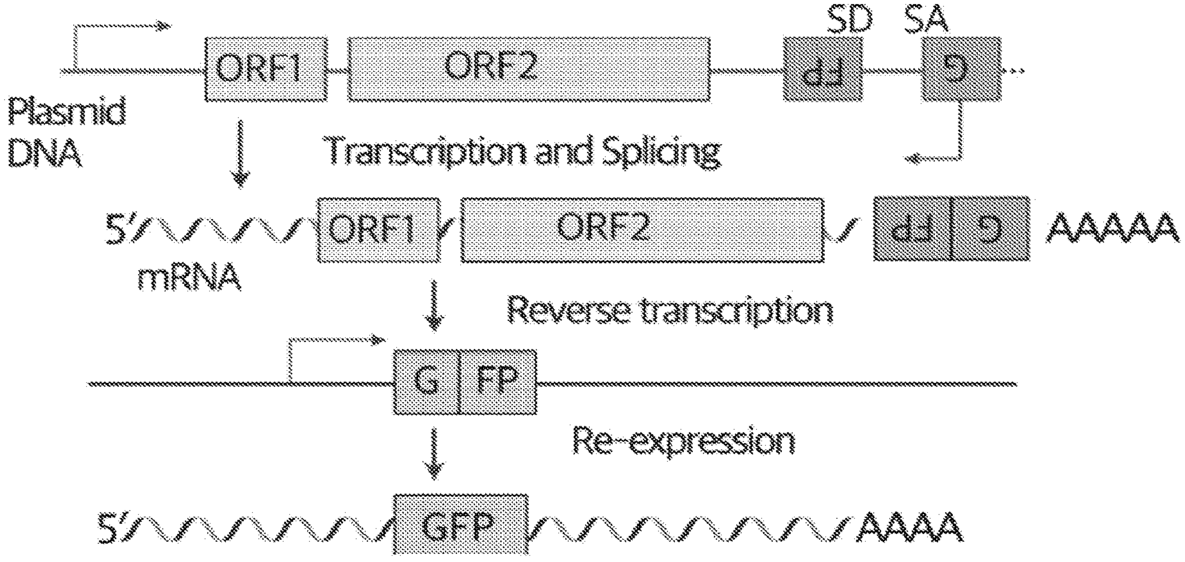
FIG. 8A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding GFP, where the coding sequence of GFP is interrupted with an intron. The GFP is not expressed until the sequence is integrated in the genome and the intron is spliced.
Figure 8B:
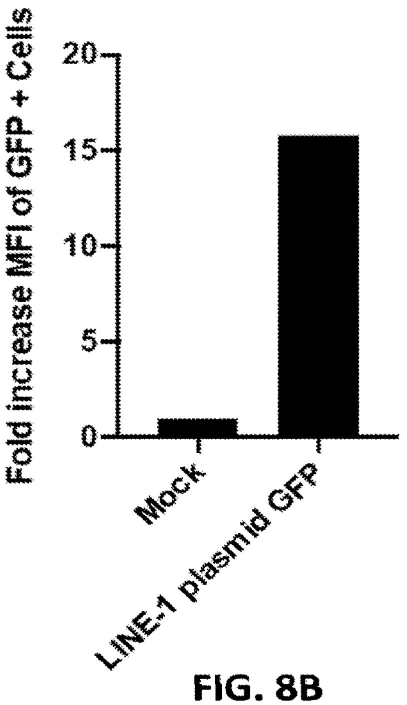
FIG. 8B shows exemplary results showing successful integration of the mRNA transcript encoded by the plasmid shown in FIG. 8A and expression of GFP relative to mock-transfected cells (fold increase in mean fluorescence intensity of GFP positive cells is shown). Mock transfected cells were transfected by the vector lacking the GFP cargo sequence.
Figure 8C:
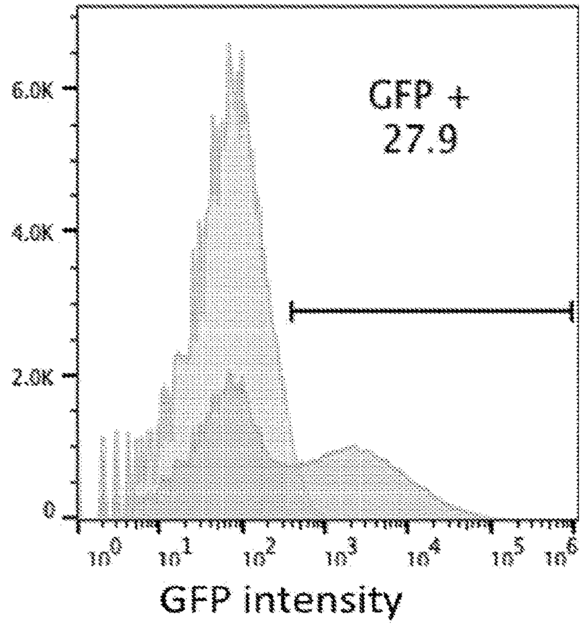
FIG. 8C shows exemplary flow cytometry results from the results shown in FIG. 8B.

In this test run, genomic integration of a GFP cargo and expression the GFP protein using a LINE-1 retrotransposon system was verified. The LINE-1-GFP construct (LINE-1 plasmid GFP) is exemplified in FIG. 8A: A plasmid construct having a LINE-1 sequence encoding ORF1p (ORF1), a sequence encoding ORF2p (ORF2), and a CMV promoter driven split GFP gene situated in the 3'UTR of the LINE-1 in reverse orientation with respect to the ORFs. The split GFP is designed to have an intronic sequence inserted in between a splice donor and acceptor sites, which ensures that the GFP is expressed only after integration and splicing mediated removal of the noncoding sequence in the middle of the coding sequence. In this case the cargo is 2.1 kb. HEK293T cells were transfected with the plasmid using Fugene reagent, and plasmid positive cells were selected by puromycin. The mRNA generated from a genome integrated GFP successfully translates and is measured by flow cytometry, as indicated as change in mean fluorescence intensity (MFI) (FIG. 8B) and fraction of cells with GFP fluorescence intensity compared to mock transfected cells (FIG. 8C). Mock transfected cells received the plasmid that lack the GFP sequence.

Figure 9A:
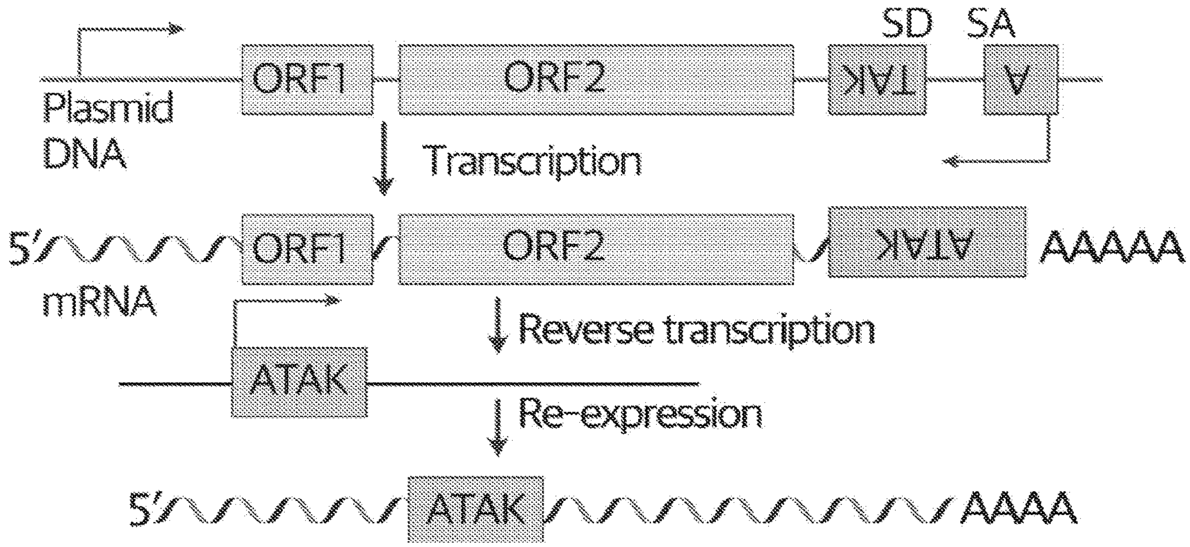
FIG. 9A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) that has extracellular region capable of binding to CD5 and an intracellular region comprising an FCR intracellular domain and a PI3 kinase recruitment domain. The coding sequence of the ATAK receptor is interrupted with an intron.
Figure 9B:
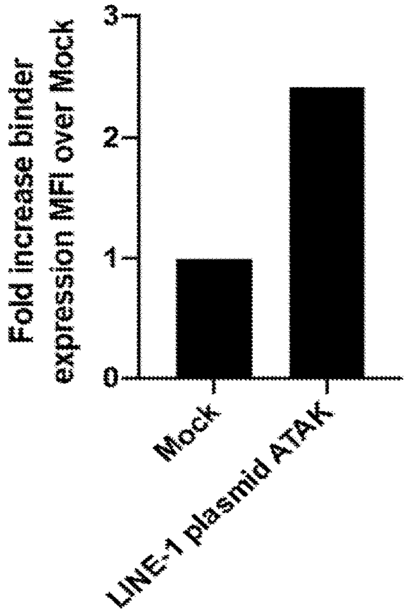
FIG. 9B shows exemplary results showing successful integration of the mRNA transcript encoded by the plasmid shown in FIG. 9A and expression of ATAK relative to mock-transfected cells (fold increase in mean fluorescence intensity of ATAK positive cells is shown). Mock transfected cells were transfected by the vector lacking the ATAK cargo sequence. Expression of ATAK receptor protein was detected by binding with a labeled CD5 antibody.
Figure 9C:
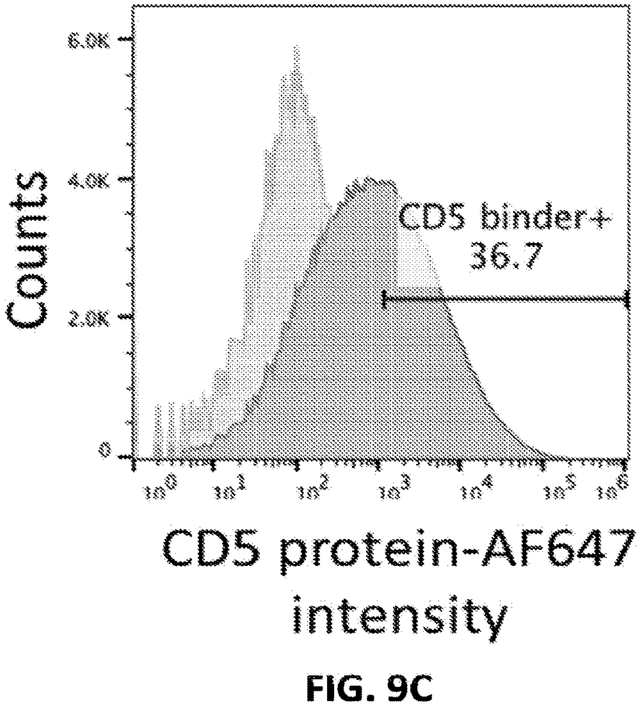
FIG. 9C shows exemplary flow cytometry results from the results shown in FIG. 9B.

Example 8. LINE-1 Retrotransposon Plasmid Mediated Delivery of a Chimeric Receptor Gene This example demonstrates that a recombinant gene can be successfully expressed using the LINE-1 sequence in a cell. HEK 293 cells were transfected with a plasmid having the LINE-1 elements, with a 3 kb cargo sequence encoding recombinant receptor protein CD5-intron-fcr-PI3K (ATAK) that is interrupted by an intron sequence in the CD5 binding domain. The cargo is a chimeric receptor that has a CD5 binding extracellular domain, a FCRγ transmembrane domain, and an intracellular domain having a PI3-kinase recruitment domain. The schematic representation of the retrotransposon plasmid is shown in FIG. 9A. As in the design of the experiment above, the ATAK receptor cannot express unless it is integrated in the genome and the intron is spliced off. Following transfection in HEK293T cells, the receptor expression is detected using labeled CD5 as bait for the CD5 binding extracellular domain. Results shown in FIGS. 9B and 9C show successful integration and expression of the receptor. 36.5% cells were ATAK (CD5 binder) positive (FIG. 9C).

Figure 10A:
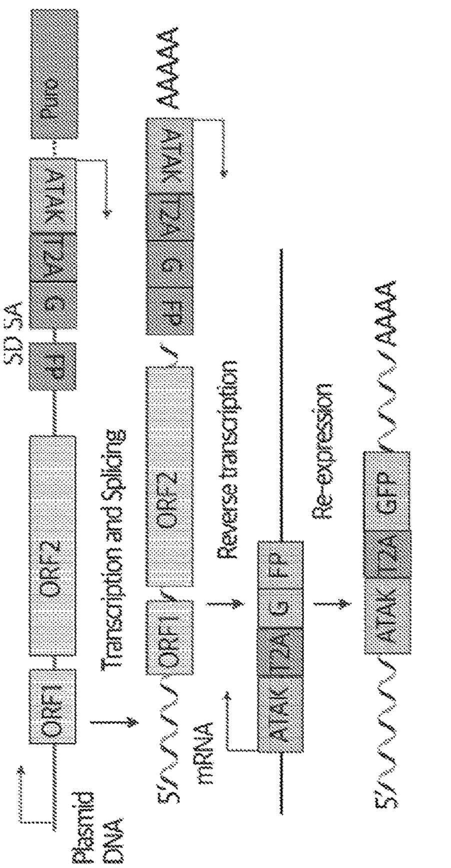
FIG. 10A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) followed by a T2A self-cleavage sequence followed by a split GFP sequence (all in a reverse orientation relative to the LINE-1 sequence). The coding sequence of the GFP is interrupted with an intron. Expected mRNA after reverse transcription and integration of the cargo are depicted.
Figure 10B:
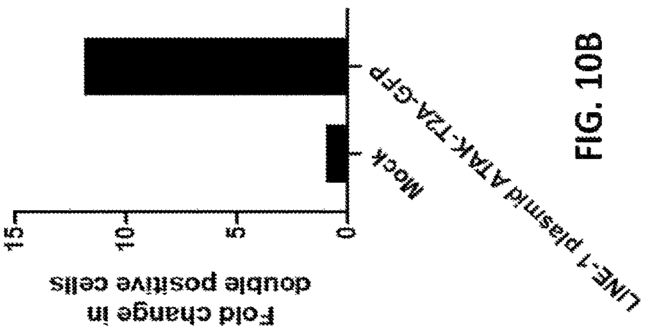
FIG. 10B shows exemplary results showing successful integration of the mRNA transcript encoded by the plasmid shown in FIG. 10A and expression of ATAK-T2A-GFP relative to mock-transfected cells (fold change in GFP and ATAK double positive cells is shown). Mock transfected cells were transfected by the vector lacking the ATAK cargo sequence. Expression of ATAK receptor protein was detected by binding with a labeled CD5 antibody.
Figure 10C:
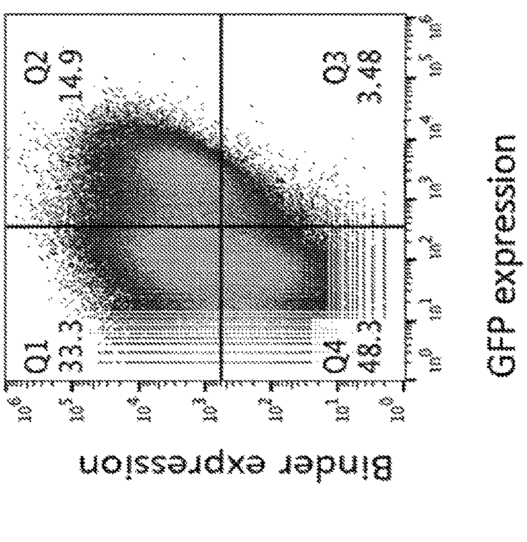
FIG. 10C shows representative flow cytometry data from two separate experimental runs for expression of both GFP and CD5 binder (ATAK) using the experimental setup shown in FIG. 10A.
Figure 10D:
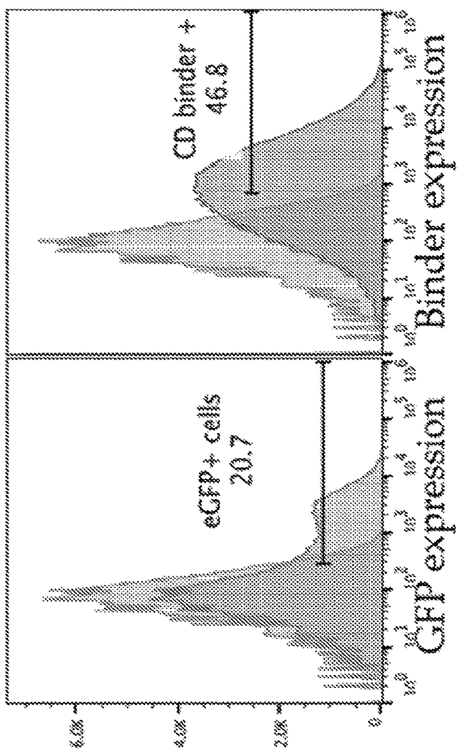
FIG. 10D shows representative flow cytometry data from two separate experimental runs for expression of both GFP and CD5 binder (ATAK) using the experimental setup shown in FIG. 10A.

In a further modification, a LINE-1 construct (LINE-1plasmid-cd5_fcr-pi3k_t2a_GFPintron) with a longer 3.7 kb cargo sequence encoding a non-interrupted recombinant receptor protein CD5-intron-fcr-PI3K and an interrupted GFP sequence with a T2A sequence between receptor and the GFP sequences (FIG. 10A). Normalized against mock-transfected cells, there was a greater than 10-fold increase of the ATAK receptor and GFP double-positive cells was noted (FIG. 10B). Exemplary fluorescence identification of GFP and fluorescent tagged CD5 binding and gating quantitation for experimental runs are shown in FIG. 10C and FIG. 10D.

Example 9. MRNA Encoding LINE-1 Retrotransposon for Delivery of a Cargo Gene

Figure 11A:
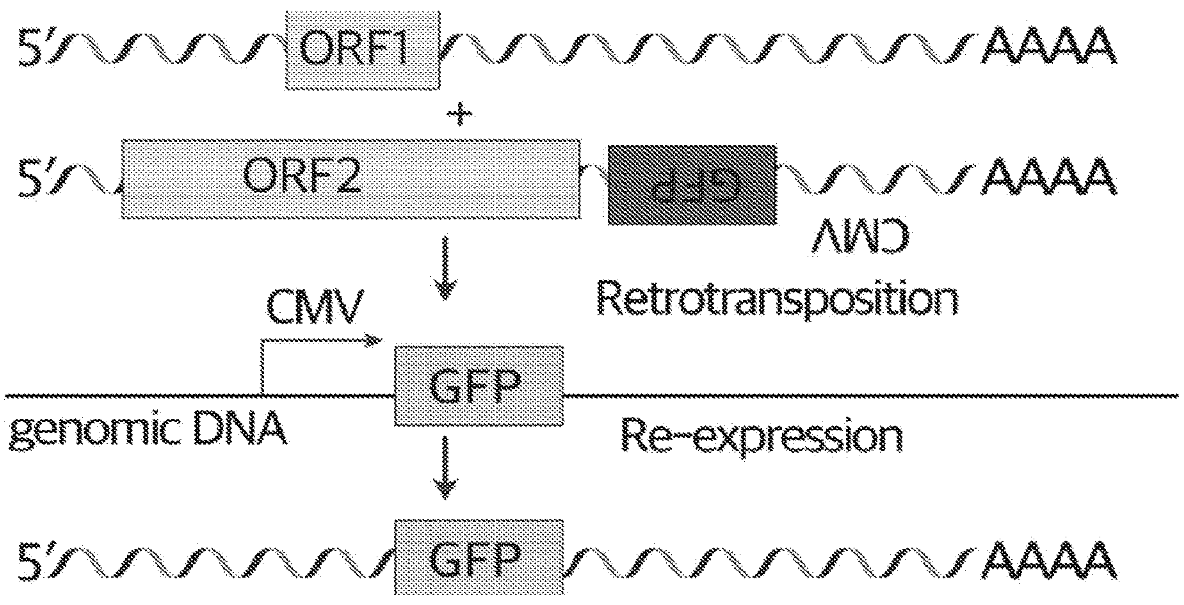
FIG. 11A shows exemplary mRNA constructs for retrotransposition-based gene delivery. The ORF1 and ORF2 sequences are in two difference mRNA molecules. The ORF2p (ORF2) coding mRNA comprises and inverted GFP coding sequence.
Figure 11B:
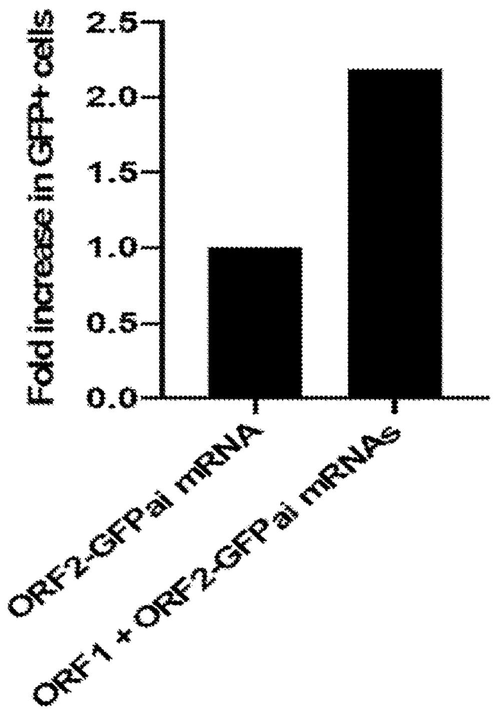
FIG. 11B depicts exemplary data showing expression of GFP (fold increase in mean fluorescence intensity of GFP positive cells is shown) upon electroporating both ORF1-mRNA and ORF2-FLAG-GFPai mRNA normalized to electroporation of ORF2-FLAG-GFPai mRNA only.

In this assay, capability of delivering and expressing a LINE-1 retrotransposable gene sequence as an mRNA was tested. An mRNA encoding an ORF1 (ORF1-FLAG-mRNA), and an mRNA encoding ORF2 and GFP in the antisense direction with a CMV promoter sequence (ORF2-FLAG-GFPai) are designed as shown in FIG. 11A. The cargo size in this assay was 2.4 kb, and GFP is in antisense orientation with respect to ORF2 sequence. The mRNAs were electroporated in 293T cells and the reporter genes expression was demonstrated as shown in FIG. 11B. This experimental set up demonstrated that no ORF1-read-through is necessary for the expression of the ORF2p, and expression of ORF2p from a different mRNA molecule can allow higher expression of ORF2p and GFP. With these results, a successful delivery of the LINE-1 and cargo in the form of mRNA was achieved.

Figure 12A:
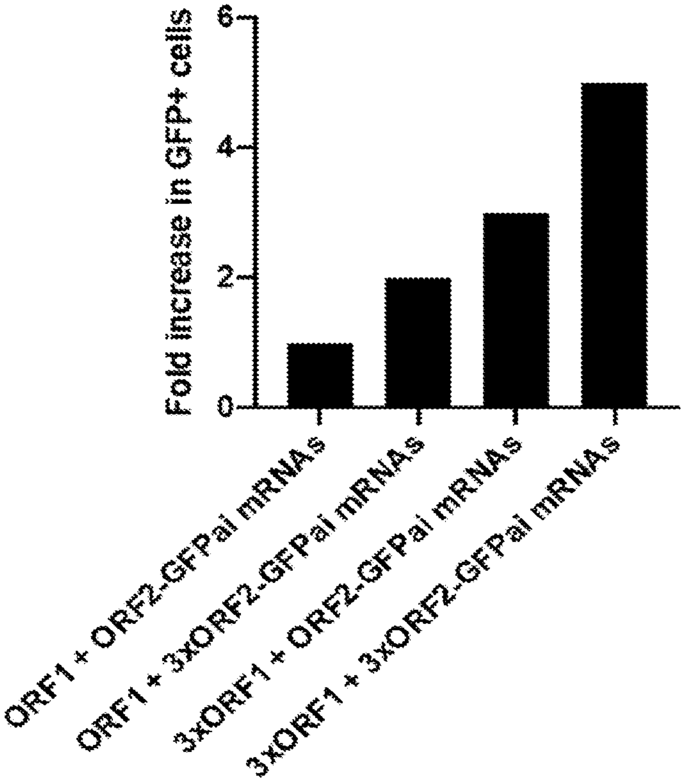
FIG. 12A depicts exemplary data showing expression of GFP (fold increase in mean fluorescence intensity of GFP positive cells is shown) upon electroporating ORF1-mRNA and ORF2-FLAG-GFPai mRNA at different amounts. Fold increase is relative to 1× ORF2-GFPao and 1× ORF1 mRNA.
Figure 12B:
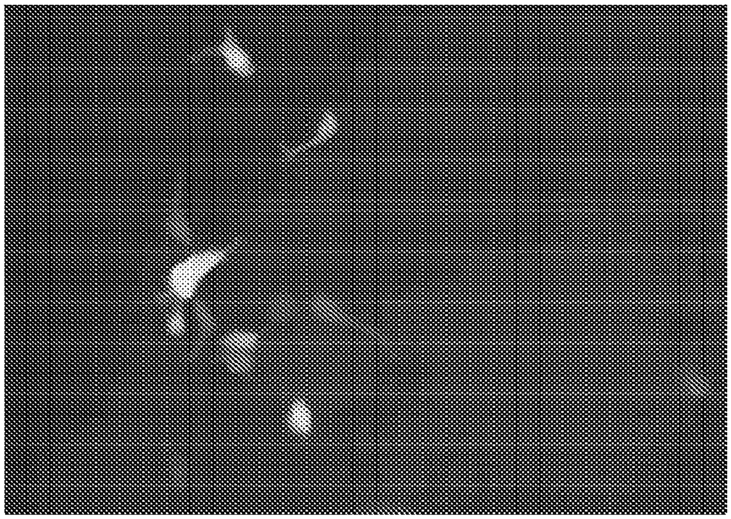
FIG. 12B shows an exemplary fluorescent microscopy image of GFP+ cells following electroporation of the mRNA depicted in FIG. 11A.
Figure 13B:
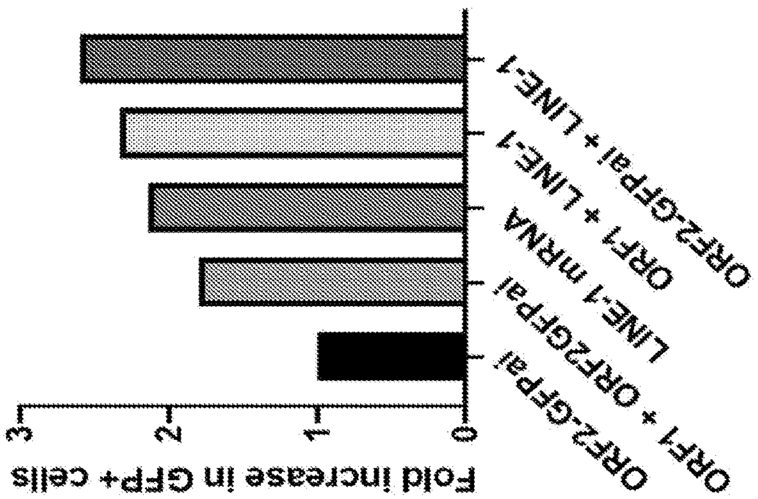
FIG. 13B depicts exemplary data showing expression of GFP (fold increase in mean fluorescence intensity of GFP positive cells is shown) upon electroporating the constructs depicted in FIG. 13A.
Figure 13A:
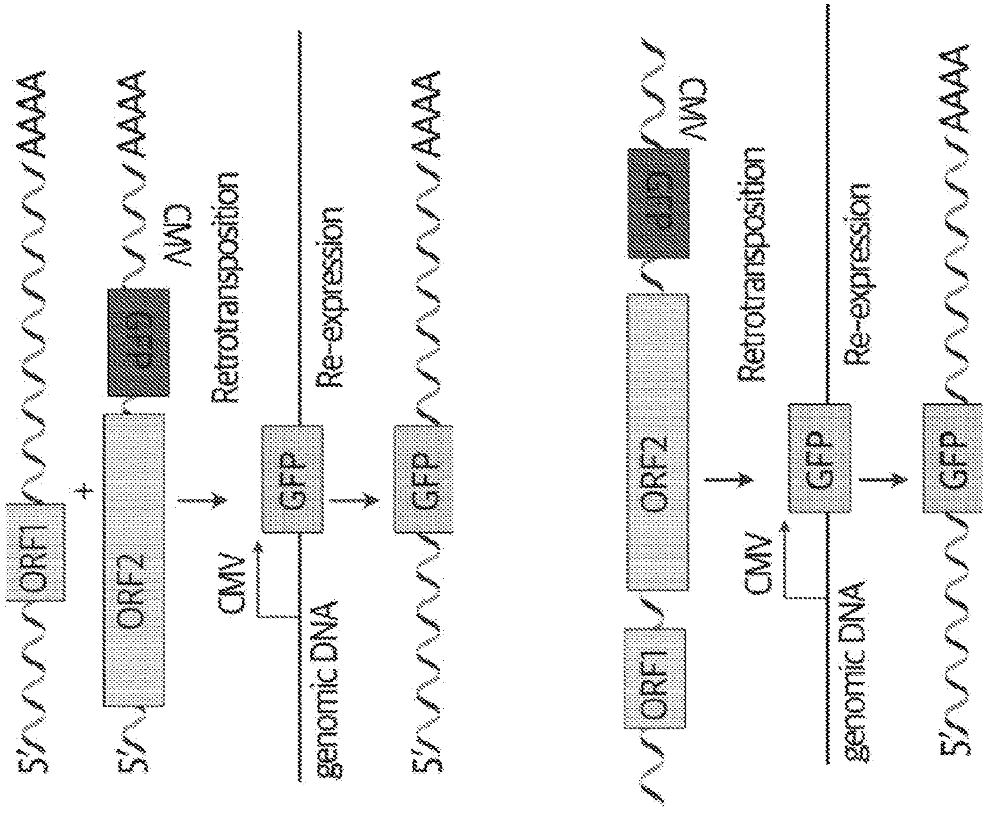
FIG. 13A shows exemplary mRNA constructs where the ORF1 and ORF2 sequences are in two difference mRNA molecules (top panel) and a LINE-1 mRNA transcript comprising ORF1 and ORF2 protein encoding sequences on a single mRNA molecule (bottom panel) for gene delivery. mRNA contains the bicistronic ORF1 and ORF2 sequence with a CMV-GFP sequence in the 3'UTR going from 3'-5'. Upon retrotransposition of the delivered ORF2-cmv-GFP antisense (LINE-1 mRNA), cells are expected to express GFP.

In order to determine whether the relative levels of ORF1 and ORF2 mRNA affected GFP expression an experiment was set up to test the varying amounts of ORF1 and ORF2 mRNAs (FIG. 11A). 3× the amount of each and together is tested for increases in GFP+ cells and results are shown in FIG. 12A. Fold increase is relative to 1× ORF2-GFP and 1× ORF1 mRNA. GFP expression was higher when 3× ORF1 was used with 1× ORF2, but not the reverse; whereas having both 3× ORF1 and 3× ORF2 showed the maximum level of GFP expression in the sets compared. The cargo size here is 2.4 kb. FIG. 12B shows fluorescent microscopy image of GFP+ cells following retrotransposon mRNA electroporation. A complete LINE-1 mRNA encoding both ORF1 and ORF2 in a single mRNA molecule (LINE 1-GFP mRNA construct) was tested for delivery and genomic integration in a cell. mRNA contains the bicistronic ORF1 and ORF2 sequence with a CMV-GFP sequence in the 3'UTR going from 3'-5' (FIG. 13A). In this study the cargo size is 2.4 kb. As shown in FIG. 13B, upon retrotransposition of the delivered ORF2-cmv-GFP antisense (LINE-1 mRNA), third bar from left, cells expressed higher GFP compared to ORF1 and ORF2 being on separate mRNA molecules (graph bar 1, 2). Inclusion of ORF1 in a separate mRNA in addition to LINE-1 complete mRNA increased GFP expression over LINE-1 alone. Inclusion of ORF2+ GFP expectantly showed higher GFP which could be the contribution of the additional ORF2 with the GFP cargo encoding mRNA.

Figure 14B:
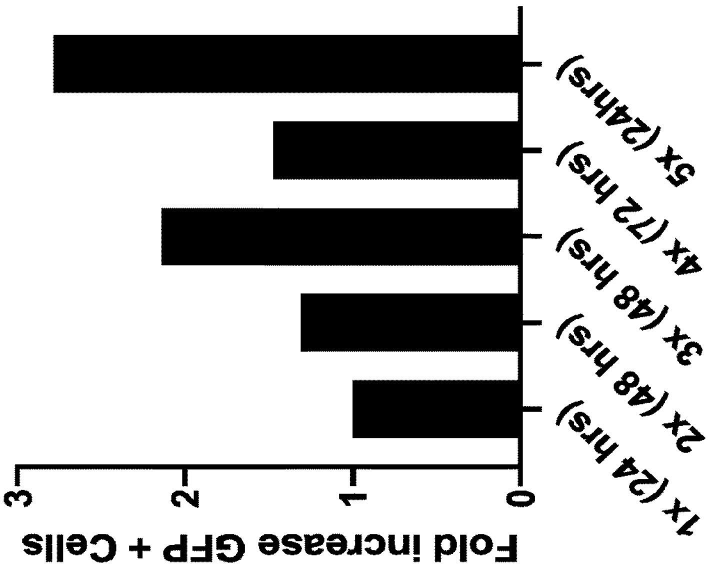
FIG. 14B depicts exemplary data showing expression of GFP at the indicated times (fold increase in mean fluorescence intensity of GFP positive cells is shown) upon electroporating 1-5 times according to FIG. 14A.
Figure 14A:
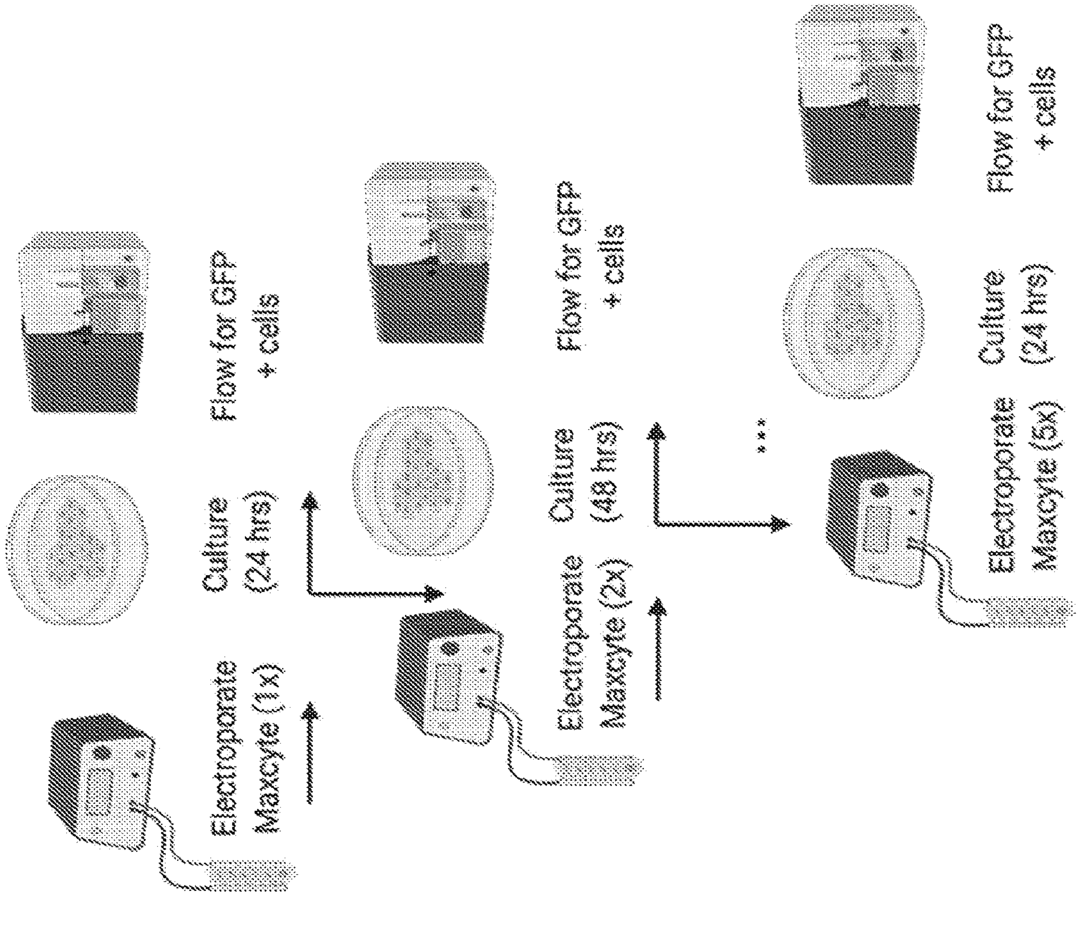
FIG. 14A shows an exemplary experimental design for testing whether multiple electroporations increases retrotransposition efficiency. HEK293T cells were electroporated every 48 hours with the Maxcyte system and assessed for GFP positive cells using flow after culturing for 24-72 hrs.

To test whether subsequent electroporation increases retrotransposition efficiency, cells were electroporation every 48 hours. GFP positive cells were assessed using flow after culturing for 24-72 hrs. The fluorescence data were normalized to the values in the set with a single electroporation event. As shown in FIGS. 14A and 14B, multiple electroporation led to an upward trend in the expression of the transposed gene, but the changes were modest.

Figure 15A:
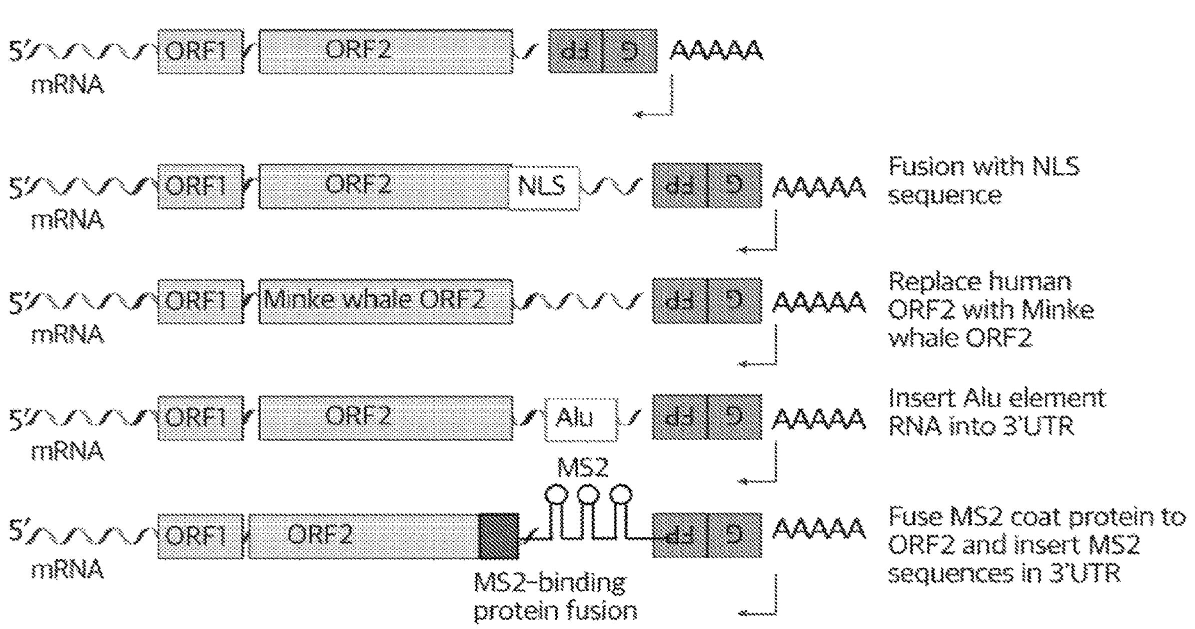
FIG. 15A depicts exemplary constructs to enhance retrotransposition via mRNA delivery. In one construct a nuclear localization signal (NLS) sequence is fused to the C terminus of the ORF2 sequence (ORF2-NLS fusion). In one construct a Minke whale ORF2 sequence was used in place of the human ORF2. In one construct a minimal sequence of the Alu element (AJL-H33delta) is inserted in the 3'UTR of the LINE-1 sequence. In one construct MS2 hairpins are inserted in the 3'UTR of the LINE-1 sequence and an MS2 hairpin binding protein (MCP) sequence is fused to the ORF2 sequence.

Example 10. Modifications to the ORF2 Protein Sequence to Enhance Retrotransposition by mRNA Modification of the LINE-1 sequence to enhance retrotransposition via mRNA delivery were tested using GFP reporter as readout. The experiment was performed as follows. All modifications were in the context of the bicistronic ORF1 and ORF2 sequence. (i) ORF2-NLS fusion was created by inserting C-terminal NLS sequence to the ORF2 sequence. (ii) Human ORF2 was replaced with Minke whale ORF2; (Ivancevic et al., 2016). (iii) Incorporation of an Alu element in the 3'UTR: Using a minimal sequence of the Alu element (AJL-H33A; Ahl et al., 2015) in the 3'UTR of the LINE-1. (iv) MS2-hairpin in the 3'UTR+ORF2-MCP fusion: MS2 hairpins in the 3'UTR of the LINE-1 sequence and a MS2 hairpin binding protein (MCP) fused to the ORF2 sequence (FIG. 15A). The mock construct had the wild-type human ORF2 sequence.

Figure 15B:
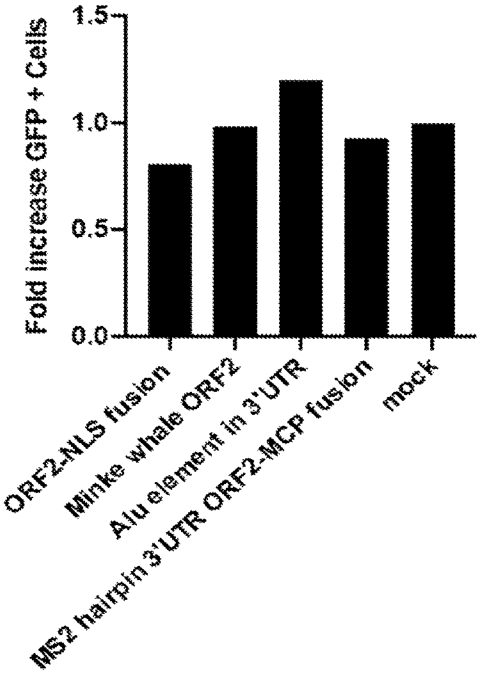
FIG. 15B depicts exemplary data showing expression of GFP (fold increase in mean fluorescence intensity of GFP positive cells is shown) using the constructs depicted in FIG. 15A.

Quantification of the fold increase in the fraction of GFP positive cells relative to mock construct electroporated cells are shown in FIG. 15B.

Example 11. Retrotransposition in an Immune Cell

Figure 16B:
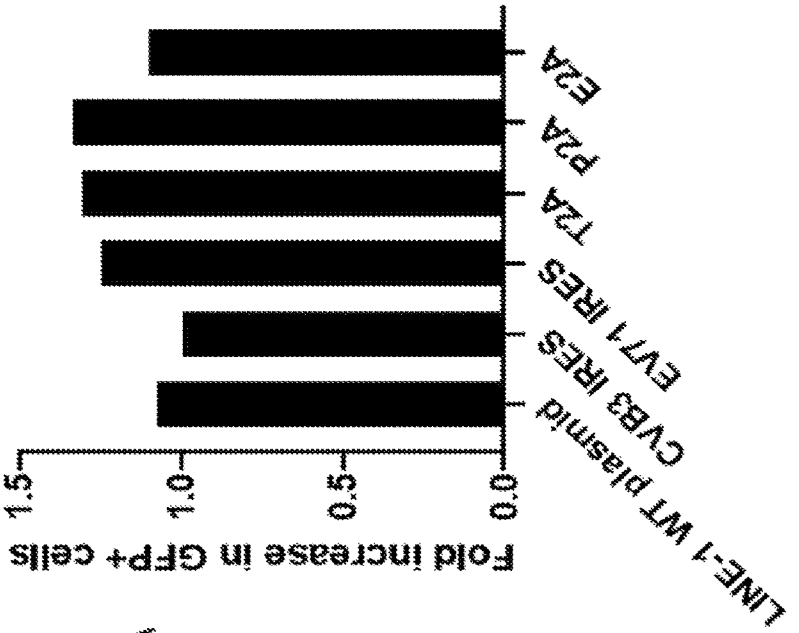
FIG. 16B depicts exemplary data showing expression of GFP (fold increase in mean fluorescence intensity of GFP positive cells is shown) using the constructs depicted in FIG. 16A.
Figure 16A:
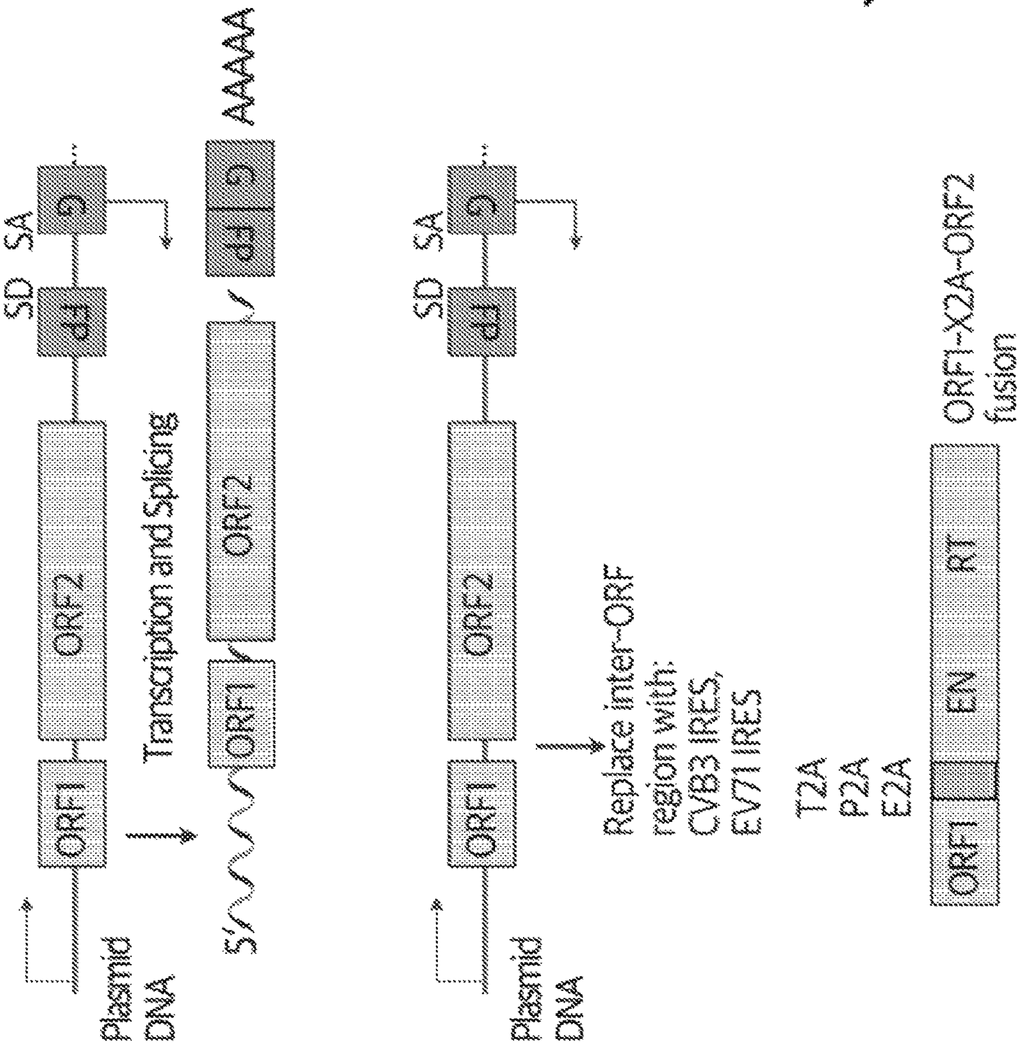
FIG. 16A shows exemplary plasmid constructs where the ORF1 and ORF2 sequences are in two difference plasmid molecules (top panel) and a plasmid encoding a LINE-1 mRNA transcript comprising ORF1 and ORF2 protein encoding sequences on a single mRNA molecule with various replacements of the inter-ORF sequence between ORF1 and ORF2 (bottom panel) for gene delivery.

In this experiment, the inter-ORF region is further manipulated to determine if any of the changes improve GFP expression after transfection of the HEK cells. Taking LINE-1plasmid GFP, the inter-ORF region is manipulated as follows: (a) In one construct the inter-ORF region is replaced with an IRES from CVB3; (b) In another construct, the inter-ORF region is replaced with an IRES from EV71; (c) In three separate constructs, an E2A or P2A or T2A self-cleavage sequence is intercalated in the inter-ORF region. Result are as shown in FIG. 16. Compared to the LINE-1 plasmid GFP (LINE-1 wild type plasmid) led to only modest changes in the GFP readout, especially with T2A sequence insertion. Insertion of EV71 IRES sequence improved GFP expression, while CVB3 IRES did not show any improvement.

Example 12. Retrotransposition in an Immune Cell

Figure 17B:
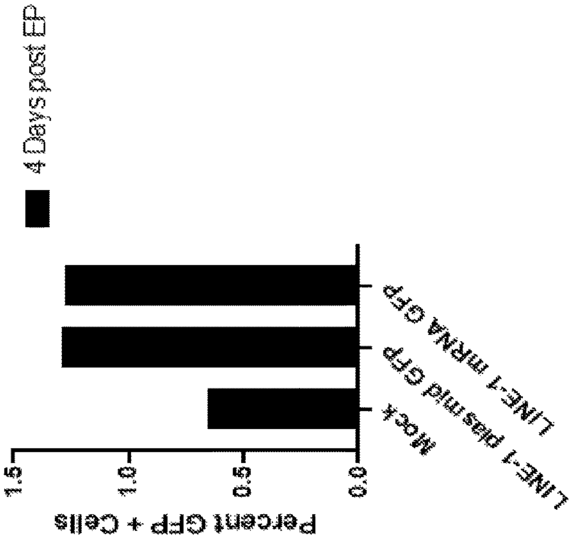
FIG. 17B depicts exemplary data showing expression of GFP (fold increase in mean fluorescence intensity of GFP positive cells is shown) in Jurkat cells using the constructs depicted in FIG. 17A. The plasmid construct was transfected, and the mRNA construct was electroporated.
Figure 17A:
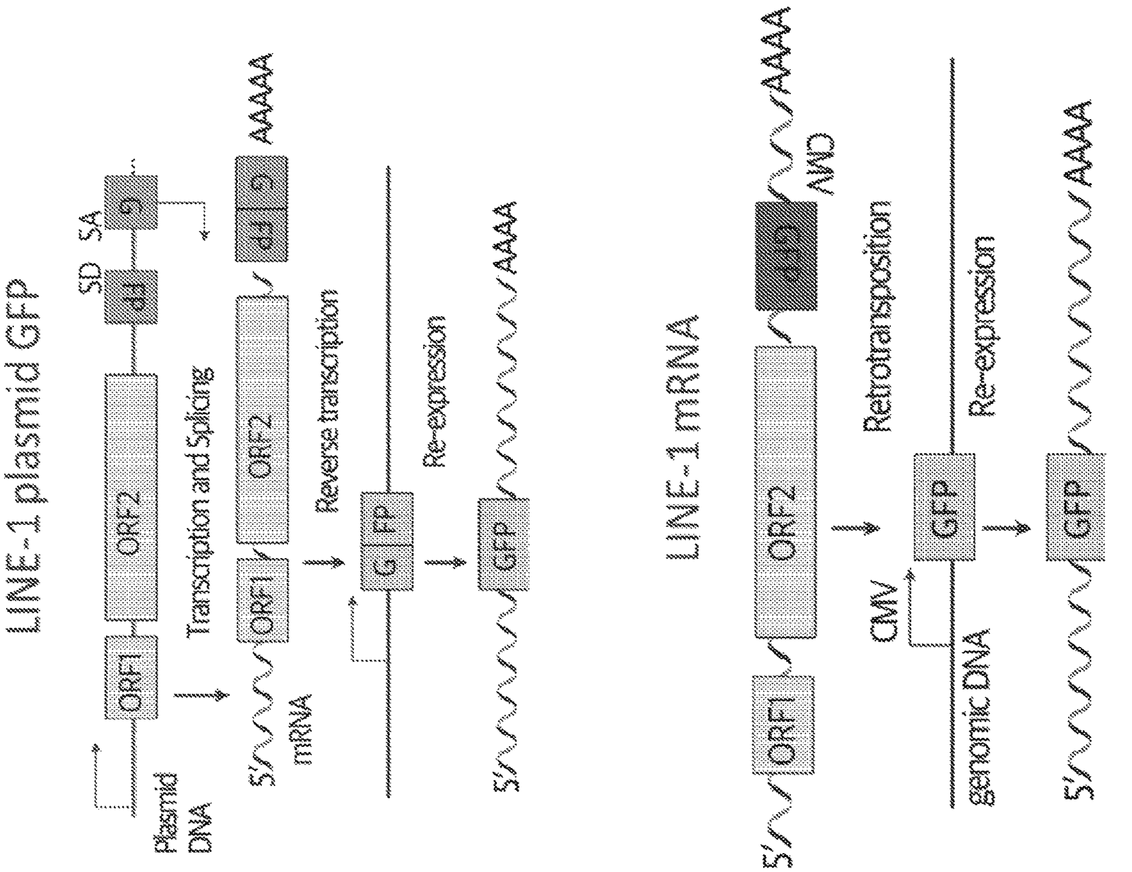
FIG. 17A depicts an exemplary plasmid construct encoding a LINE-1 mRNA transcript comprising ORF1 and ORF2 protein encoding sequences on a single mRNA molecule with a GFP sequence (top panel) and an exemplary LINE-1 mRNA transcript comprising ORF1 and ORF2 protein encoding sequences on a single mRNA molecule with a GFP sequence.

To test retrotransposition in immune cells, LINE-1 plasmid and mRNA were tested with the CMV-GFP antisense reporter cargo by electroporating into Jurkat cells, which is a T cell lymphoma line (FIG. 17A-FIG. 17B). Mock set were electroporated with a plasmid with no GFP sequence. GFP expression in the transfected cells was assessed, representative data at 4 days post electroporation is shown in FIG. 17B. Fold increase is reported relative to mock transfected cells. Both plasmid and mRNA delivery modes resulted in successful GFP expression.

Figure 18A:
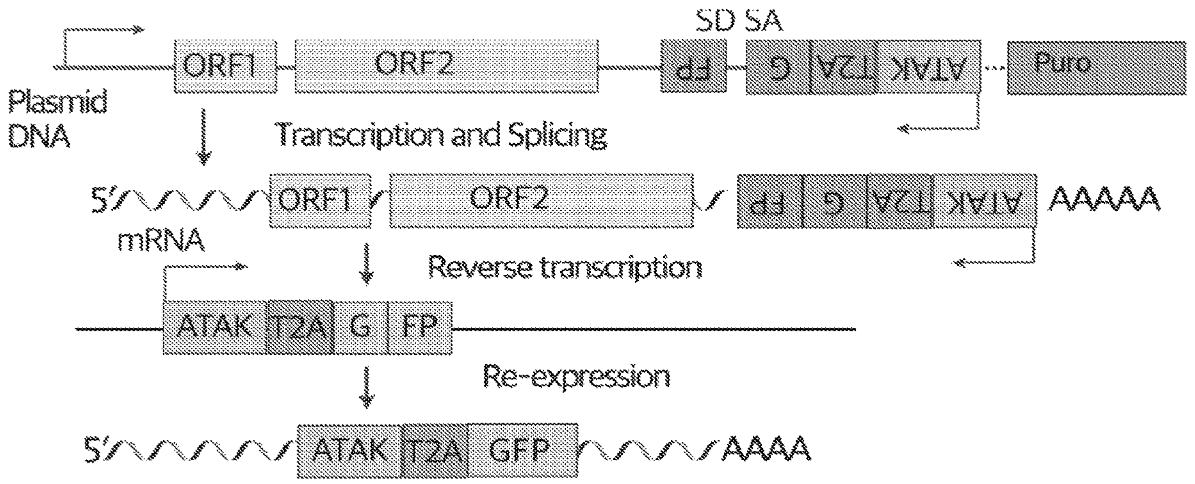
FIG. 18A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) followed by a T2A self-cleavage sequence followed by a split GFP sequence (all in a reverse orientation relative to the LINE-1 sequence). The coding sequence of the GFP is interrupted with an intron. Expected mRNA after reverse transcription and integration of the cargo are depicted.
Figure 18B:
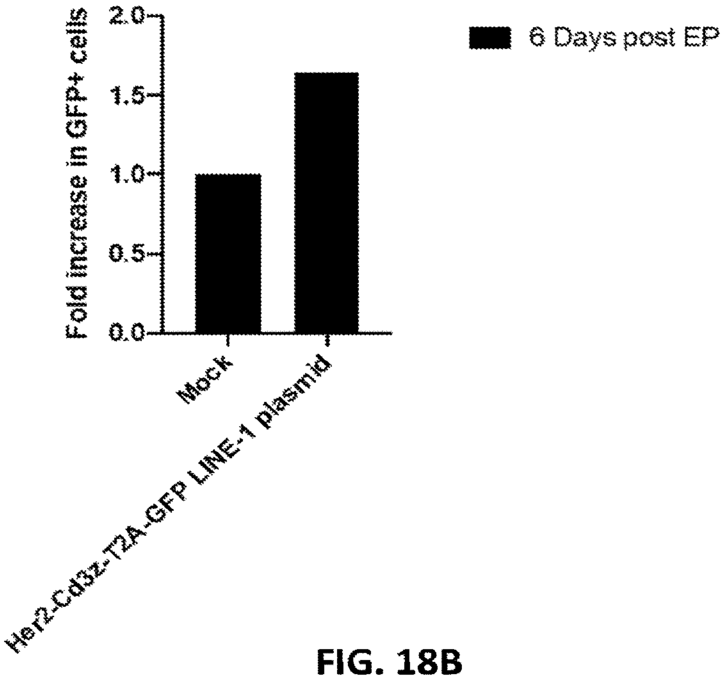
FIG. 18B shows exemplary results showing successful integration of the mRNA transcript encoded by the plasmid shown in FIG. 10A and expression of ATAK-T2A-GFP relative to mock-transfected cells (fold change in GFP and ATAK double positive cells is shown) in a myeloid cell line (THP-1). Data represents expression at 6 days post transfection, normalized over mock plasmid transfected cells wherein the mock plasmid does not have GFP coding sequence.

Next, THP-1 cells (a myeloid, monocytic cell line) were electroporated with a plasmid having LINE-1 sequences and a 3.7 kb cargo encoding a chimeric HER-2 binding receptor, and a split GFP (LINE-1 plasmid Her2-Cd3z-T2A-GFPintron) (FIG. 18A). The cargo is a chimeric receptor that comprises a HER2 binding extracellular domain, a CD3z transmembrane domain, and split GFP reporter. The plasmid was successfully integrated into the genome and showed prolonged expression, as demonstrated in FIG. 18B. Representative expression at day 6 post transfection is shown in the figure. From these studies, it was demonstrated that LINE-1 mediated gene delivery can result in successful stable genomic integration in various cell types, including epithelial cell types (HEK-293T cells); T cells (e.g., Jurkat cells); and cells of myeloid lineage (e.g., THP-1 cells) and results in prolonged expression. Moreover, unlike CRISPR dependent technologies such as Prime editing, retrotransposition can result in integration of large genetic cargo, and, these can be delivered as a single nucleic acid construct.

Example 13. External Methods for Further Enhancing Efficiency of LINE-1 Mediated Retrotransposition of the Cargo Sequences In this section, methods for further enhancing the efficiency of retrotransposition of cargo sequences into the genome of cells are detailed.

Figure 19:
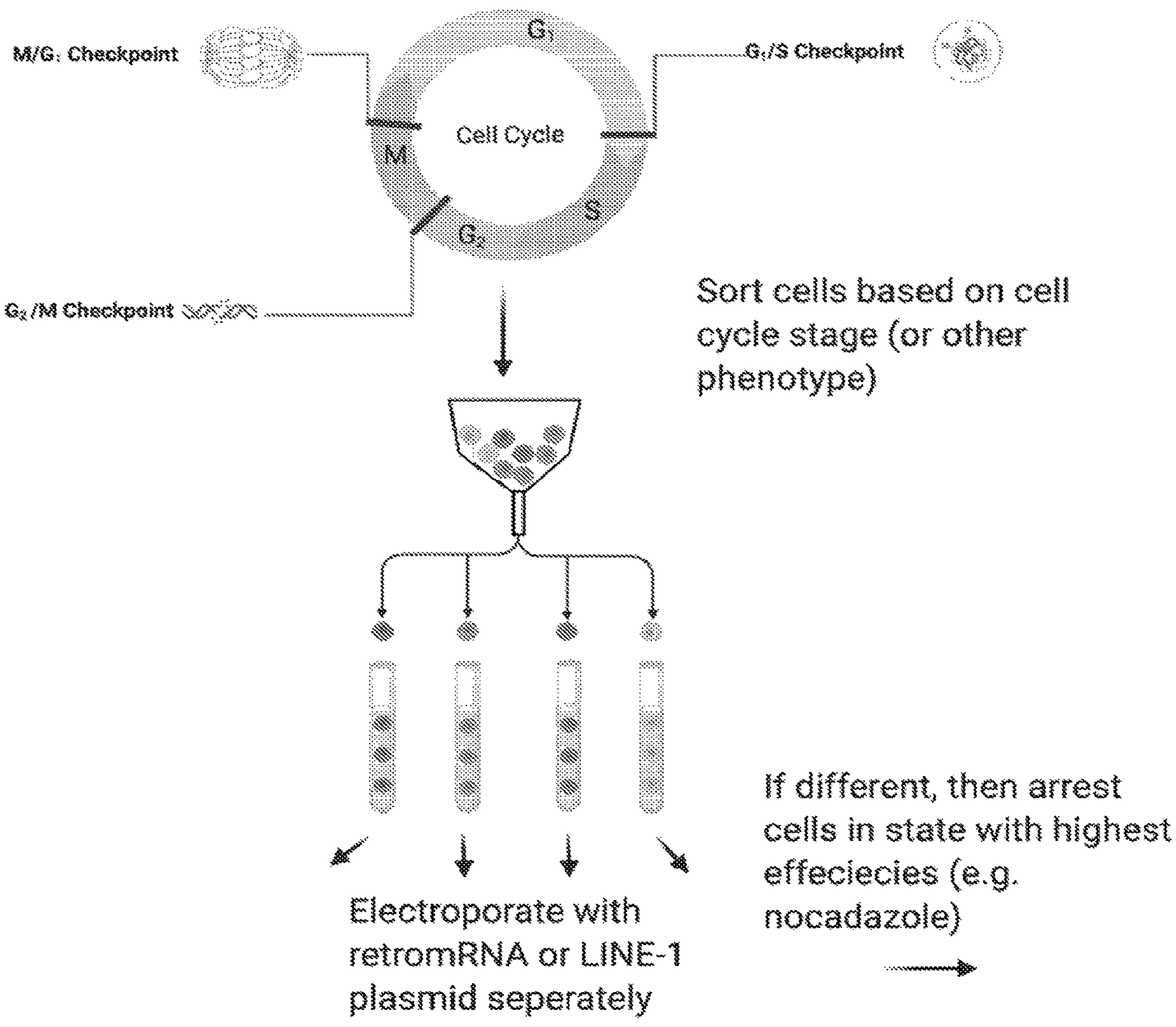
FIG. 19 illustrates an exemplary experimental set up for cell synchronization. A heterogenous cell population is sorted based on cell cycle stage, prior to delivery of an exogenous nucleic acid. Cell cycle synchronization is expected to result in higher expression and stabilization of the exogenous nucleic acid delivered. If cells are not homogeneous after cell sorting, then cells can be further incubated with a suitable agent that arrests cell cycle at a stage.

Cell cycle synchronization by selection of cells in a population that are in a certain stage of cell cycle or G1 arrest by a suitable agent can lead to higher nucleic acid uptake efficiency, e.g., plasmid vector transfection efficiency or electroporation efficiency. In this assay, cells are pre-sorted and each group is separately electroporated to ensure uniform electroporation. The efficiencies of electroporation are compared between these groups and a cell cycle stage that results in highest efficiency as determined by the expression of the GFP test plasmid or mRNA is selected (FIG. 19).

In another variation of this experiment, cells are synchronized with or without sorting by treating the cells, with a cell cycle arrest reagent for a few hours prior to electroporation. An exemplary list of cell cycle arrest reagents is provided in Table 1. The list is non-exhaustive, and is inclusive of reagents that can be proapoptotic, and hence careful selection suitable for the purpose and dose and time of incubation is optimized for use in the particular context.

TABLE 1

Exemplary non-exhaustive list of small molecule reagents that are used for inhibiting cell cycle

| Agent | Cell cycle | Mechanism |
|---|---|---|
| 5-[(4-Ethylphenyl)methylene]-2-thioxo-4-thiazolidinone | Arrests cell cycle at G0-G1 | Inhibits c-Myc-Max dimerization |
| Itraconazole | Inhibits cell cycle at G1 | SMO antagonist |
| ABT 751 (Tocris Bioscience, cat #4138) | Blocks cell cycle at G2M | Inhibits microtubule proliferation |
| Artesunate | Arrests cell cycle at G2M | Suppresses ROS-induced NLRP3 |
| AZD 5438 | Blocks cell cycle at G2M, M, S and G1 phases | Inhibits Cdk |
| Baicalein | Arrests cell cycle at G1 and G2 phases | Inhibits lipoxygenases |
| CPI 203 (alternative name: TEN 101) | Arrests cell cycle at G1 phase | BET bromodomain inhibitor |
| Diadzein | Arrests cell cycle at G1 | Estrogen receptor agonist |
| DIM | Blocks cell cycle at G2M | Induces EGFR activation |
| Epothilone B | Arrests cell cycle at G2M | Inhibits tubulin proliferation |
| Indirubin-3'-oxime | Antiproliferative | Inhibits GSK3b |
| MPC 6827 hydrochloride | Cell cycle arrest | Inhibits microtubule proliferation |
| Pladienolide | Inhibits G1 and G2/M | Decreases mRNA splicing |
| Plumbagin | Induces G2/M arrest | Inhibits TOR signaling and others |
| Temsirolimus | Induces G1/S | mTOR inhibitor |
| Toceranib | Cell cycle arrest | Inhibits PDGFR and VEGFR |
| WYE 687 dihydrochloride | Induces G1 arrest | mTOR inhibitor |
| YC1 | Induces G1 arrest | Guanylyl cyclase activator |

Figure 20:
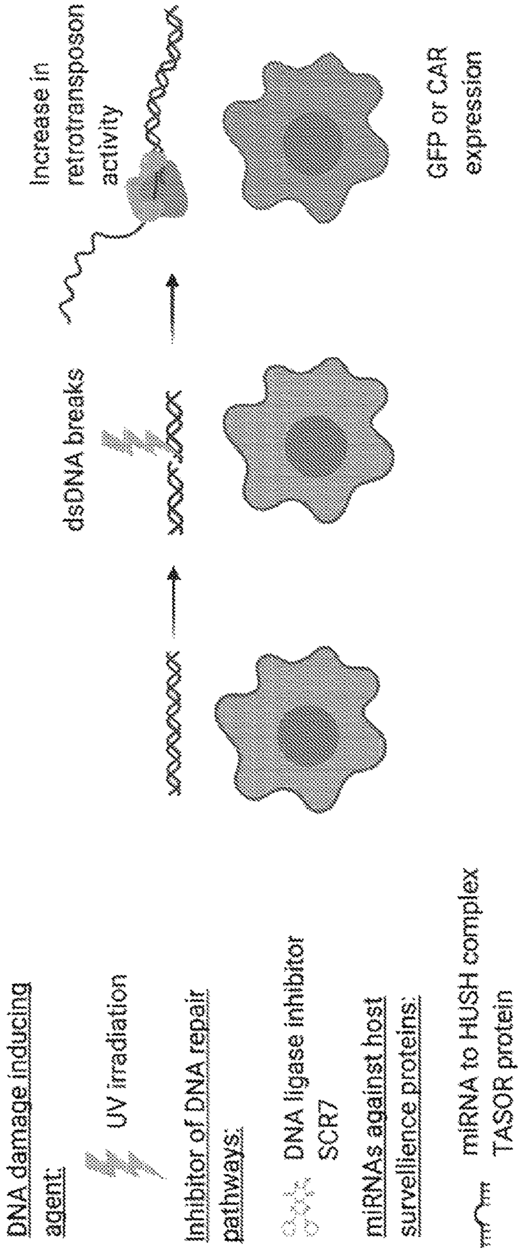
FIG. 20 illustrates an exemplary method for increasing retrotransposon efficiency by inducing DNA double stranded breaks, with or without inhibiting DNA repair pathways, such as by inducing DNA ligase inhibitor SCR7 or inhibiting host surveillance proteins, for example, using miRNA to HUSH complex TASOR protein.

For certain ex vivo usages, retrotransposition is enhanced by inducing DNA double stranded breaks (DSB) in a cell that expresses a retrotransposition machinery as described in any of the examples above by controlled irradiation, which create opportunities for the homologous recombination and priming for the reverse transcriptase (FIG. 20). In another example, cells transfected with LINE-1 plasmid GFP construct and subjected to an irradiation pulse. GFP expression is monitored. The intensity and time of irradiation is optimized for obtaining the maximum benefit, as indicated by higher GFP expression.

In another example, cells transfected with LINE-1 plasmid GFP were divided into experimental sets that are treated as follows (i) irradiation in order to induce DSB (as described above); (ii) treat cells in this set with a small molecule, such as SCR7, that blocks DNA ligase and therefore inhibits the DNA damage repair machinery. Preventing protective repair mechanism from inhibiting the progress of the retrotransposition is expected to enhance GFP expression: (iii) irradiate the cells then treat the cells with SCR7, combination of the two is expected to show a more robust effect. GFP expression is monitored over a period of 6 days, and the set that shows maximum GFP fluorescence over the longest period indicates a condition that is adopted in further studies.

Figure 21:
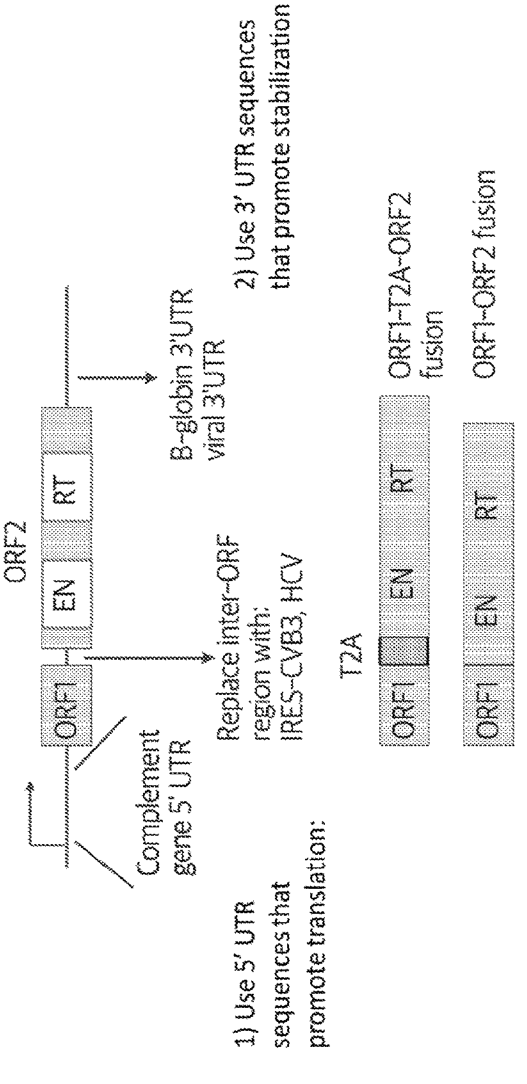
FIG. 21 illustrates exemplary constructs for integrating an mRNA encoding a transgene into the genome of a cell.

Example 14. Enhancing Efficiency of LINE-1 Mediated Retrotransposition of the Cargo Sequences by Further Modification of the Construct Enhancing non-coding regions of the construct to offer stability and higher expression. In this example a LINE-1 plasmid-GFP is further modified to test for increased GFP expression as follows: (a) In one construct, the 5'UTR is replaced with an UTR of a complement gene; (b) In another construct, the 3' UTR is replaced with the UTR sequence of B-globin gene for increased stability; (c) In another construct the inter-ORF region is replaced with an IRES from CVB3; (d) In another construct, the inter-ORF region is replaced with an IRES from EV71 (e) In three separate constructs, an E2A or P2A or T2A self-cleavage sequence is intercalated in the inter-ORF region as shown in a diagrammatic representation in FIG. 21. In addition to the above, various combinations of (a)-(e) and additional combinations listed in Table 2 are tested using the same set-up as above. GFP expressions are monitored after transfection of the constructs in parallel test sets into HEK293T cells to see if any of these constructs increased GFP expression compared to the LINE-1 plasmid GFP alone. The combinations that show improvement are adopted.

TABLE 2

Exemplary combinations of 5' and 3' UTR and inter-ORF insertion elements for inclusion in the LINE-1 construct for increase in retrotransposition efficiency.

| 5'-UTR sequences selected from sequences | 3'-UTR sequences | Inter-ORF sequences |
|---|---|---|
| Complement 5'UTR | WPRE | T2A, E2A, P2A |
| Covid-19 5' leader sequence | B-globin 3'UTR | CVB3 IRES |
| CYBA 5'UTR | RSV RSE | EV71 IRES |
| CYP2E1 5' UTR | AREs | EMCV IRES |
| | RNA zipcodes for the ER | PV IRES |
| | mtRNR1-AES | CSFV IRES |
| | | HRV2 IRES |
| | | AAA (tri alanine fusion or any fusion-linker sequence) |

Figure 22:
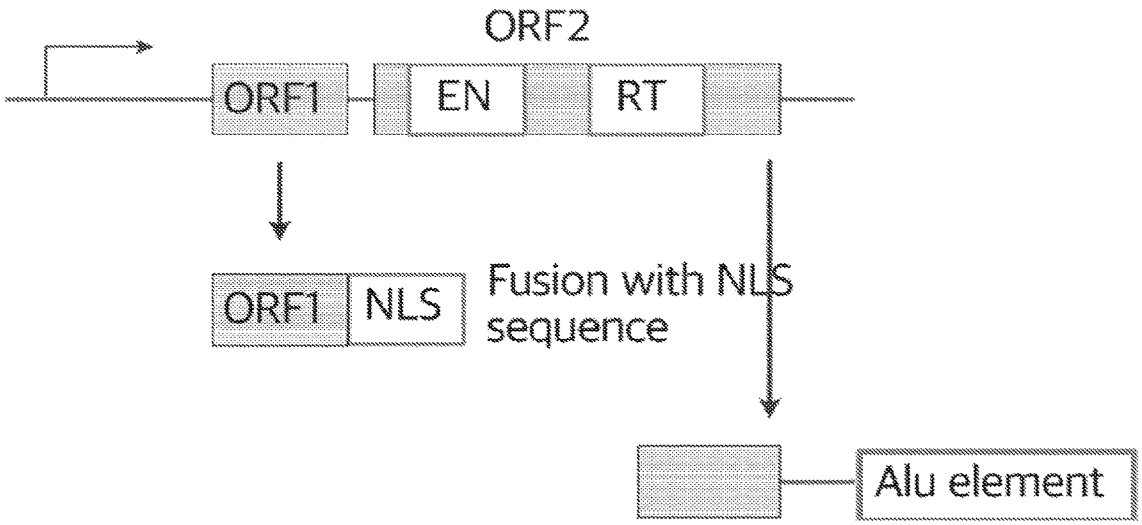
FIG. 22 illustrates exemplary constructs for integrating an mRNA encoding a transgene into the genome of a cell.

II. Enhancing localization and retention of the ORFs in the nucleus. In this example, LINE-1 plasmid-GFP is further modified to test for increased GFP expression as follows: (a) the ORF2 encoding sequence is fused with a nuclear localization sequence (NLS) (graphically represented in FIG. 15A second construct from top). (b) the ORF1 encoding sequence is fused with a nuclear localization sequence (NLS), graphically represented in FIG. 22; and (c) An Alu binding sequence is inserted 3' of the sequence encoding ORF2 reverse transcriptase (graphically represented in FIG. 15A, fourth construct from the top; (d) Both (a) and (c) together (not shown); (e) Both (b) and (c) together, the NLS sequence is fused to the ORF1 N-terminus, and an Alu binding sequence is inserted 3' of the sequence encoding ORF2 reverse transcriptase (FIG. 22) and (f) Integrating a SINE-derived nuclear RNA LOcalizatIoN (SIRLOIN) sequence in LINE-1 3' UTR. HEK-293T cells were transfected with constructs (a)-(f) and the LINE-plasmid GFP construct in parallel. GFP expression is monitored after transfection into HEK293T cells. The set that shows maximum GFP fluorescence over the longest period is adopted.

Figure 23:
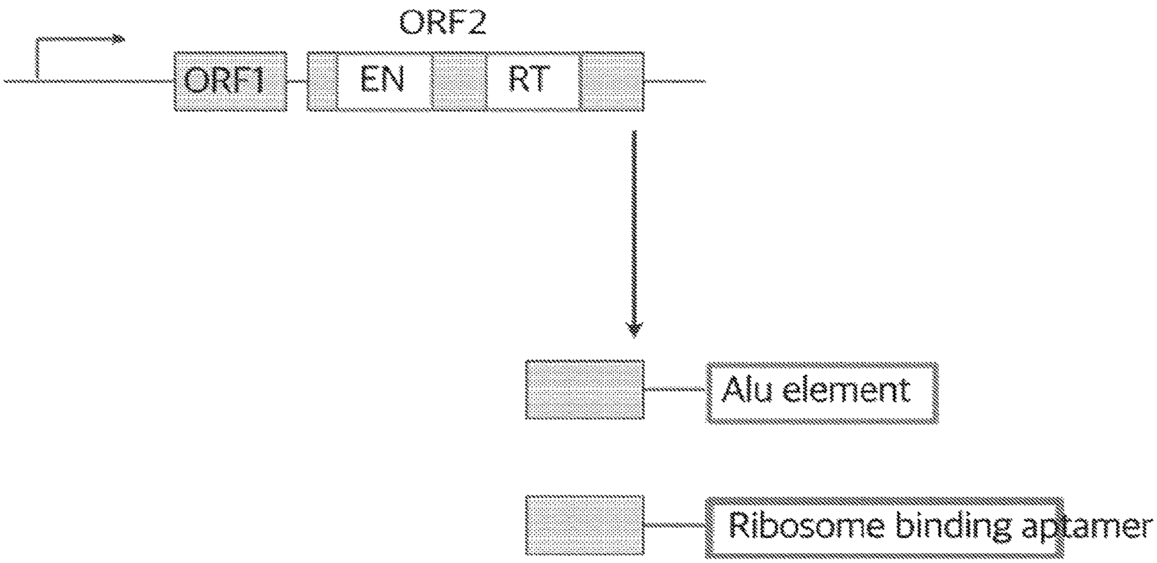
FIG. 23 illustrates exemplary constructs for integrating an mRNA encoding a transgene into the genome of a cell.

III. Modifying construct to increase LINE-1-protein-RNA complex binding to the ribosome. In this example, an additional sequence is inserted in the 3'UTR of the LINE-1 construct to increase association of the LINE-1 protein RNA construct to the ribosomes, the sequence is an Alu element, or a ribosome binding aptamer (FIG. 23).

For enhancing LINE-1 protein-RNA complex binding to the ribosome, insertion of the following elements in the 3' UTR of the mRNA is done and tested similar to the experiments above. Insertion of Alu elements is described above. In separate constructs, Alu element truncations, Ribosome binding aptamers (109.2-3) and Ribosome expansion segments (ES9S) binding sequence are inserted and each tested for increase in GFP expression.

Figure 24:
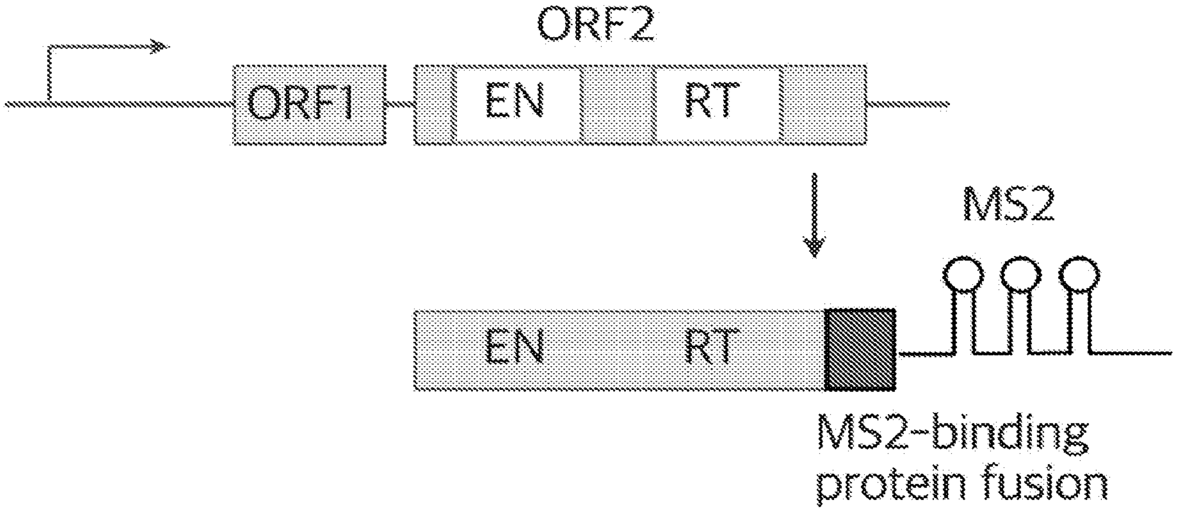
FIG. 24 illustrates exemplary constructs for integrating an mRNA encoding a transgene into the genome of a cell.

IV. Enhancing binding of ORF2 to its own mRNA for retrotransposition. In this example, a sequence containing MS2 binding loop structure is introduced into the 3'UTR of the LINE-1, and a sequence encoding MS2 RNA binding domain is fused to the RNA binding domain of the ORF2p-RT (graphically represented in FIGS. 4A and 4B, and FIG. 24, an exemplary construct SEQ ID NO:49). The fused protein will specifically attach to the MS2-binding structural motif in the 3' UTR, and therefore any non-specific binding and retrotransposition is minimized (FIG. 24). GFP expression is monitored after transfection into HEK293T cells. Following a similar design, the ORF is fused with the protein binding sequences shown in left column of Table 3 below, combined with a cognate sequence inserted in the 3'UTR region of the ORF2 shown in the corresponding right column in the same row.

TABLE 3

Exemplary list of elements to enhance translation efficiency and stability of the LINE-1 proteins and increased expression of LINE-1 proteins.

| Elements to be fused with the LINE-1 ORF2 | 3' UTR sequence recognizable by the element |
|---|---|
| PP7 coat protein | PP7 |
| Streptavidin | S1m aptamer |
| Tobramycin | Tobramycin aptamer |

Figure 25:
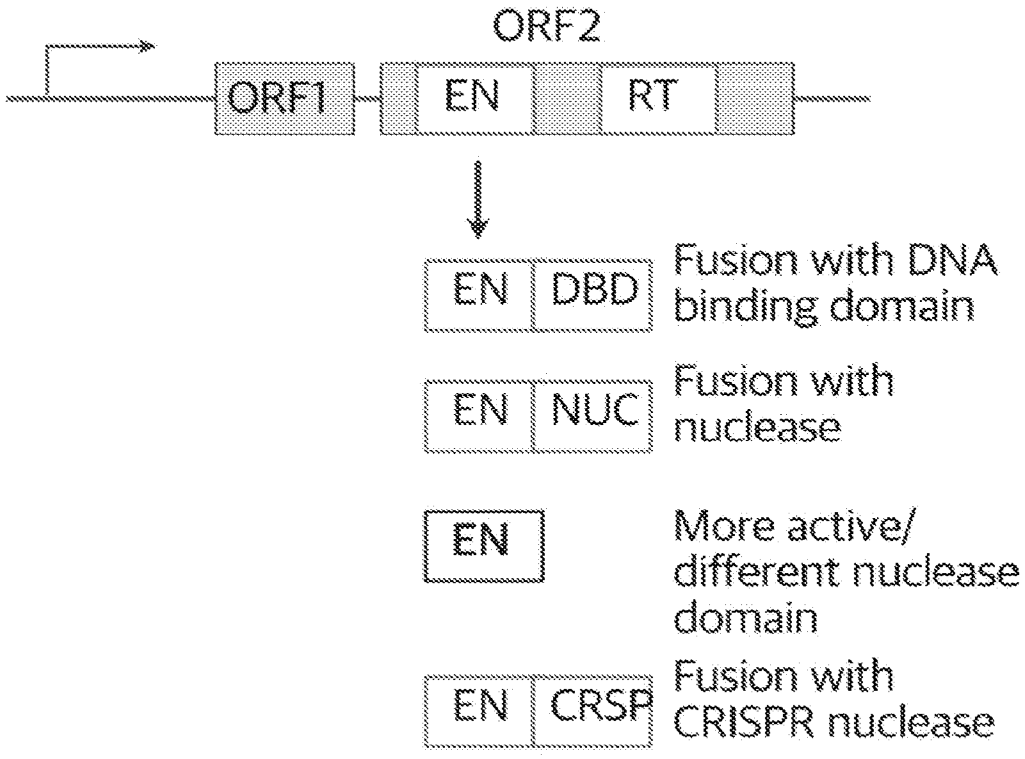
FIG. 25 illustrates exemplary constructs for integrating an mRNA encoding a transgene into the genome of a cell.

V. Modifying the endonuclease function of the retrotransposon. In this example, the constructs are modified to test increase in GFP expression as follows. In a first experimental set, the LINE-1 plasmid GFP is cut at the 3'end of the endonuclease coding sequence of ORF2, and a sequence encoding the DNA binding domain (DBD) of a heterologous zinc finger protein (ZFP) is inserted. In another experimental set, the endonuclease domain is fused with a CRISPR nuclease. A variety of nucleases can be tested by modifying the LINE-1 plasmid GFP ORF by creating a fusion protein using DNA binding domains and cleavage domain as shown in a non-exhaustive list in Table 4, In addition, two ORF-2 domains are encoded in one set to facilitate dimerization. The construct that has higher GFP expression than the ORF2 endonuclease can be further selected. The plasmid designs are graphically represented in FIG. 25. GFP expression is monitored after transfection of the plasmids into HEK293T cells, and the set that yielded best.

TABLE 4

Exemplary non-exhaustive list of additional DNA cleavage domains/enzymes that can be fused to or inserted in place of LINE-1 endonuclease.

| Gene/Enzyme | Description |
|---|---|
| Fokl | Class II endonuclease from Flavobacterium okeanokoites, recognition and cleavage sequence are separated by a few nucleotides; recognizes DNA sequence 5-GGATG-3' |
| Restriction enzymes, | e.g., HindII, EcoR1, BamH1 |
| LAGLIDADG (SEQ ID NO: 62) family nuclease A | Intron encoded homing proteins found in various genera including bacteria |
| GIY-YIG | This domain is found in the amino terminal region of excinuclease abc subunit c (uvrC), bacteriophage T4, endonuclease segA, segB, seg C, seg D, and seg E and group I introns of fungi and phage. |

TABLE 4-continued

Exemplary non-exhaustive list of additional DNA cleavage domains/enzymes that can be fused to or inserted in place of LINE-1 endonuclease.

| Gene/Enzyme | Description |
|---|---|
| His-Cys box | Homing endonucleases containing two clusters of conserved histidine and cysteine residues over a 100 amino acid region. |
| H-N-H | Widely present nuclease in phage DNA. Crucial component of the terminase packaging reaction of *E. coli* phage HK97. |
| PD-(D/E)xK | Phosphodiesterases, present in a large number of proteins, e.g., DUF4420, DUF3883, DUF4263, COG5482, COG1395, Tsp45I, HaeII, Eco47II, ScaI, HpaII. |
| Vsr-like/EDxHD | C-terminal nuclease domain that displays recognizable homology to bacterial Very short repair (Vsr) endonucleases |

Figure 26:
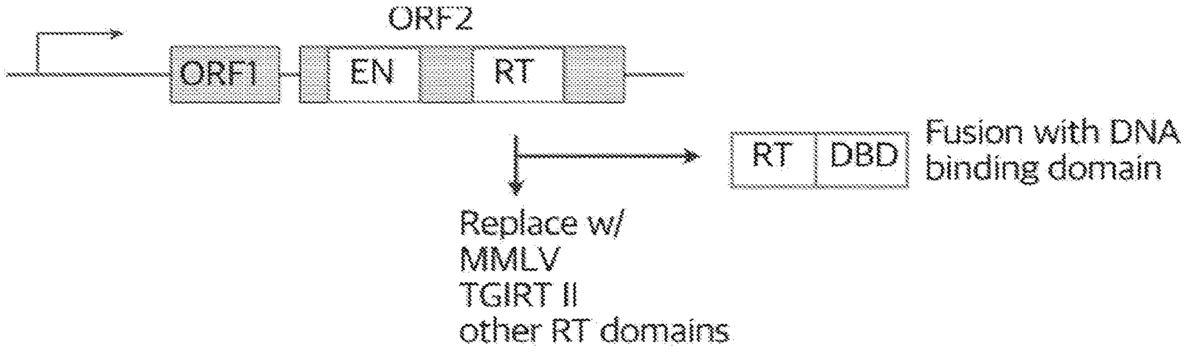
FIG. 26 illustrates exemplary constructs for integrating an mRNA encoding a transgene into the genome of a cell.

VI. Modifying the reverse transcriptase function of the retrotransposon. In this example, the reverse transcriptase domain of ORF2 is modified for increasing its efficiency. In one experimental set, the sequence encoding the human ORF2 in LINE-1plasmid GFP is excised and replaced with a sequence encoding MMLV or TGIRTII. In another experimental set, the ORF2 reverse transcriptase domain is fused with a DNA binding domain of a heterologous protein. The reverse transcriptase domains and/or the DNA binding domains can be selected from a non-exhaustive list provided in Table 5A-Table 5B. The constructs are graphically exemplified in FIG. 26. GFP expression is monitored after transfection into HEK293T cells.

TABLE 5A

Selected non-exhaustive list of reverse transcriptase for replacing the LINE-1 RT for higher efficiency

| Reverse Transcriptase | Description |
|---|---|
| M-MLV-RT | Murine leukemia virus |
| TGIRT-II | Thermostable group II intron reverse transcriptase with high fidelity and processivity |
| AMV-RT | Avian Myeloblastosis Virus reverse transcriptase |
| Group II intron maturase RT | Derived from *Eubacterium rectale* |
| HIV-RT | Efficient RT derived from HIV |
| TERT | Catalyzes the RNA-dependent extension of 3'-chromosomal termini with the 6-nucleotide telomeric repeat unit, 5'-TTAGGG-3'. |

TABLE 5B

Selected non-exhaustive list of DNA-binding domains for fusing to a RT for higher efficiency

| DNA binding domains (DBD) |
|---|
| Zinc finger domains |
| Leucine zipper (bZip) |
| Helix-turn-helix domain |
| HMG-box |
| R2 retroelement DBD |
| Sso7d |
| Protein A (ssDNA) |
| OB-fold (ssDNA) |

Figure 27:
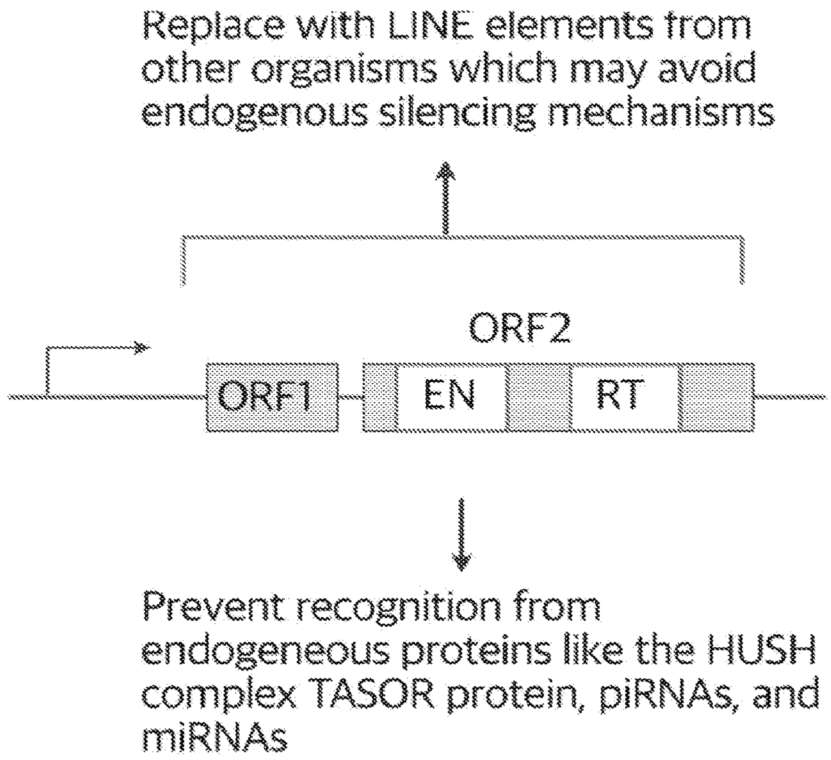
FIG. 27 illustrates exemplary constructs for integrating an mRNA encoding a transgene into the genome of a cell.

VII. Replacing human LINE-1 with LINE-1 from other organisms. In this example, the sequence encoding human LINE-1 is replaced by a LINE-1 from a different organism. In one example, the human LINE-1 construct is compared with a construct where the human LINE-1 is replaced by a minke whale LINE-1 sequence (FIG. 27). Using the same experimental framework, a number of ORFs are tested. An exemplary non-exhaustive list is provided in Table 6 below. A further comprehensive list is available in Ivancevic A. et al., Genome Biol Evol 8(ii):3301-3322.

TABLE 6

Exemplary LINE-1 elements from organism for use in replacement of the human LINE-1

| Species Name | No of total LINE-1/No active/percent active |
|---|---|
| *Balaenoptera acutorostrata scammoni* | 8,012/5,006/62.4% |
| *Rhinopithecus roxellana* | 11,115/2,954/26.5% |
| *Mus musculus* | 18,280/4,143/22.66% |
| *Aedes aegypti* | 519/184/35.4% |
| *Zea mays* | 744/165/22.17% |
| *Brassica napus* | 1,929/565/29.2% |
| *Brassica rapa* | 543/228/41.9% |
| *Danio rerio* | 590/268/45.4% |

In another set, human LINE-1 is retained as in the GFP plasmid, but an inhibitor of human LINE-1 silencer is utilized to prevent recognition by endogenous proteins like HUSH complex TASOR protein. In this case, the TASOR inhibitor is an inhibitory RNA, such as a miRNA.

Figure 28:
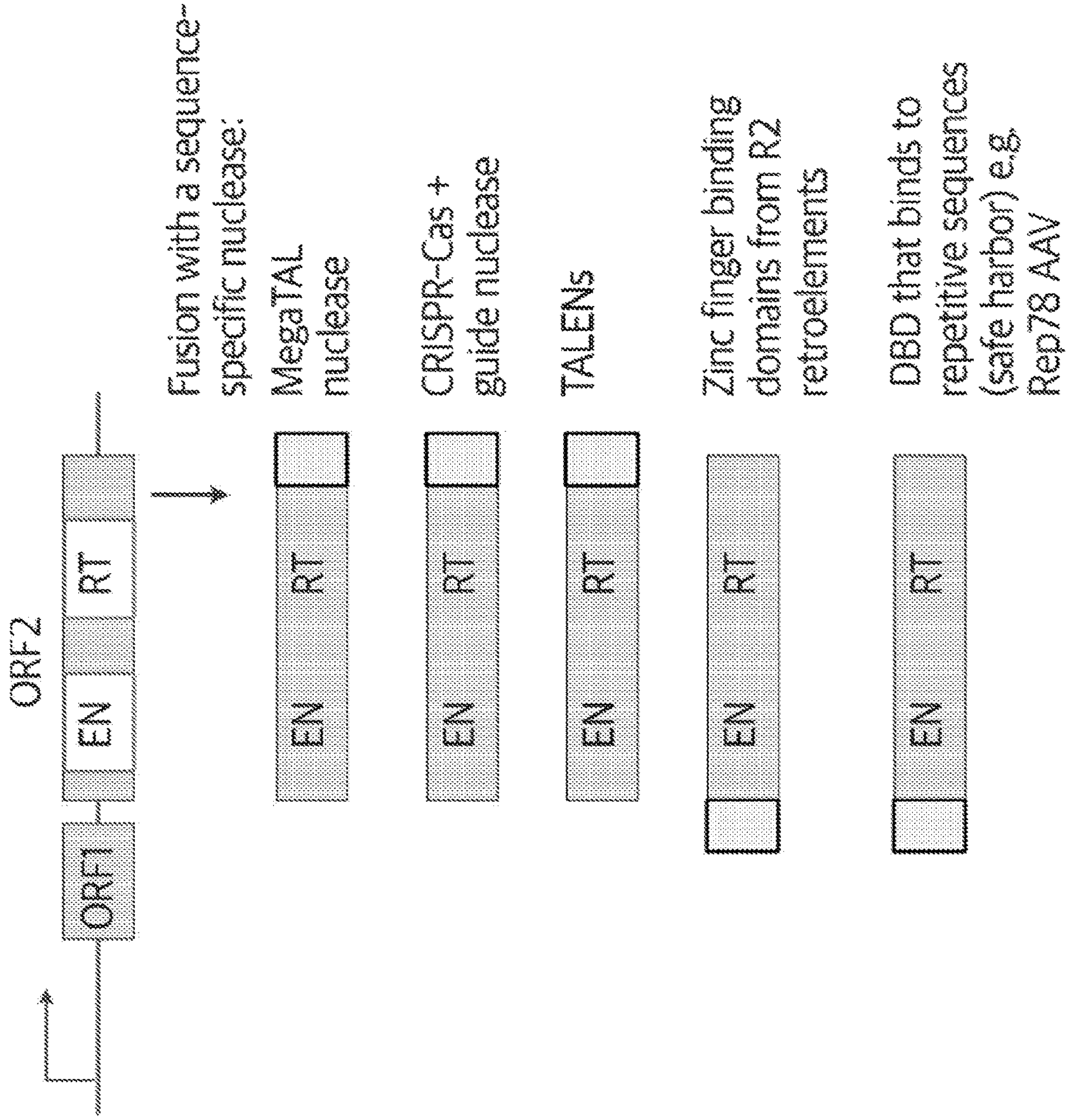
FIG. 28 illustrates exemplary constructs for integrating an mRNA encoding a transgene into the genome of a cell.

VIII. LINE-1 fusion proteins for target specificity. In this example, the LINE-1 plasmid GFP ORF2 is fused with a domain of a MegaTAL nuclease, a CRISPR-CAS nuclease, a TALEN, R2 retroelement binding zinc finger binding domain, or a DNA binding domain that can bind to repetitive elements such as Rep78 AAV. FIG. 28 exemplifies the deigns. Table 7 provides a list of the different elements that can be fused to increase sequence specific retrotransposition.

TABLE 7

Exemplary proteins with DNA binding domains to be fused to ORF2 for increasing retrotransposition specificity,

| Elements |
|---|
| Transcription Factors |
| MegaTAL nucleases |
| TALENs |
| Zinc finger binding domains from other retroelements |
| Safe harbor binding proteins |
| Cfp1 |

Each plasmid is transfected into HEK293 cells and GFP expression is monitored.

The modifications described in this section under (I)-(VIII) are designed to test for increase in retrotransposition efficiency, using GFP as readout. Following this, a number of useful modifications from (I)-(VIII) are incorporated into a single retrotransposition construct, tested with GFP as insert for the outcome, and the GFP sequence is replaced by the desired insert sequence Sequences Following are exemplary sequences of the constructs used in the examples. These sequences are for reference exemplary purposes and sequence variations and optimizations that are conceivable by one of skill in the art without undue experimentation are contemplated and encompassed by the disclosure. Where mRNA sequences are referred in the sequence title, the construct recites nucleotides of a DNA template and one of skill in the art can easily derive the corresponding mRNA sequence.

TABLE 8

| Plasmid and mRNA construct sequences |
|---|
| ORF1-FLAG- mRNA (Codon Optimized human ORF1 coding sequence-FLAG)(SEQ ID NO: 35): |
| 1 TAATACGACT CACTATAGGG AGAAAGACGC CACCATGGGC AAGAAGCAAA ATCGCAAGAC |
| 61 GGGGAATTCC AAGACACAAT CCGCTAGCCC ACCACCTAAA GAGCGTTCTA GCTCCCCTGC |
| 121 TACTGAGCAG TCCTGGATGG AAAACGACTT CGATGAACTC CGGGAAGAGG GATTTAGGCG |
| 181 ATCCAACTAT TCAGAACTCC GCGAAGATAT CCAGACAAAG GGGAAGGAAG TCGAGAATTT |
| 241 CGAGAAGAAC CTCGAGGAGT GCATCACCCG TATCACAAAC ACTGAGAAAT GTCTCAAAGA |
| 301 ACTCATGGAA CTTAAGACAA AAGCCAGGGA GCTTCGAGAG GAGTGTCGGA GTCTGAGATC |
| 361 CAGGTGTGAC CAGCTCGAGG AGCGCGTGAG CGCGATGGAA GACGAGATGA ACGAGATGAA |
| 421 AAGAGAGGGC AAATTCAGGG AGAAGCGCAT TAAGAGGAAC GAACAGAGTC TGCAGGAGAT |
| 481 TTGGGATTAC GTCAAGAGGC CTAACCTGCG GTTGATCGGC GTCCCCGAGA GCGACGTAGA |
| 541 AAACGGGACT AAACTGGAGA ATACACTTCA AGACATCATT CAAGAAAATT TTCCAAACCT |
| 601 GGCTCGGCAA GCTAATGTGC AAATCCAAGA GATCCAACGC ACACCCCAGC GGTATAGCTC |
| 661 TCGGCGTGCC ACCCCTAGGC ATATTATCGT GCGCTTTACT AAGGTGGAGA TGAAAGAGAA |
| 721 GATGCTGCGA GCCGCTCGGG AAAAGGGAAG GGTGACTTTG AAGGGCAAAC CTATTCGGCT |
| 781 GACGGTTGAC CTTAGCGCCG AGACACTCCA GGCACGCCGG GAATGGGGCC CCATCTTTAA |
| 841 TATCCTGAAG GAGAAGAACT TCCAGCCACG AATCTCTTAC CCTGCAAAGT TGAGTTTTAT |
| 901 CTCCGAGGGT GAGATTAAGT ATTTCATCGA TAAACAGATG CTGCGAGACT TCGTGACAAC |
| 961 TCGCCCAGCT CTCAAGGAAC TGCTCAAAGA GGCTCTTAAT ATGGAGCGCA ATAATAGATA |
| 1021 TCAACCCTTG CAGAACCACG CAAAGATGGA TTATAAGGAT GACGATGATA AATGA |
| (SEQ ID NO: 35) |
| ORF2-FLAG-GFPai mRNA (Codon Optimized human ORF2 coding sequence)(SEQ ID NO: 36) |
| 1 TAATACGACT CACTATAGGG AGAAAGACGC CACCATGACA GGTTCAAATA GTCACATTAC |
| 61 GATTCTCACT CTGAATATAA ATGGGCTGAA TTCTGCAATT AAACGGCACA GGCTTGCTTC |
| 121 CTGGATAAAG TCTCAAGACC CCTCAGTGTG CTGTATTCAG GAAACGCATC TCACGTGCAG |
| 181 GGACACCCAT CGGCTGAAAA TAAAAGGCTG GCGGAAGATC TACCAAGCCA ATGGAAAACA |
| 241 AAAGAAGGCT GGGGTGGCGA TACTTGTAAG CGATAAAACA GACTTTAAAC CAACTAAGAT |
| 301 CAAACGGGAC AAAGAGGGCC ATTACATCAT GGTAAAGGGT AGTATTCAAC AAGAGGAGCT |
| 361 GACTATCCTG AATATTTATG CACCTAATAC TGGAGCCCCC AGATTCATAA AGCAAGTGTT |
| 421 GAGTGACCTT CAACGCGACC TCGACTCCCA CACTCTGATC ATGGGAGACT TTAACACCCC |
| 481 GCTGTCCACT CTCGACAGAT CTACTAGACA GAAAGTCAAC AAGGATACAC AGGAACTGAA |
| 541 CAGTGCTCTC CACCAAGCGG ACCTTATCGA CATCTACAGA ACACTCCACC CCAAAAGCAC |
| 601 AGAATATACC TTCTTTTCAG CCCCTCACCA CACCTATTCC AAAATTGACC ACATTGTGGG |
| 661 GAGTAAAGCC CTTCTCTCCA AATGTAAACG GACCGAAATT ATCACTAACT ATCTCTCCGA |
| 721 CCACAGTGCA ATAAAACTTG AATTGCGAAT TAAGAATCTC ACTCAAAGTA GATCCACGAC |
| 781 ATGGAAACTG AACAATCTCC TCTTGAATGA CTACTGGGTG CATAACGAAA TGAAGGCTGA |
| 841 AATAAAGATG TTCTTTGAGA CCAACGAAAA CAAAGACACC ACGTACCAGA ATCTCTGGGA |
| 901 CGCTTTCAAA GCAGTGTGTC GAGGAAAATT TATTGCACTG AATGCTTACA AGCGGAAGCA |
| 961 GGAAAGATCC AAAATAGACA CCCTGACTAG CCAACTTAAA GAACTGGAAA AGCAAGAGCA |
| 1021 AACTCATAGC AAAGCTAGCC GTCGCCAAGA AATTACGAAA ATCAGAGCTG AACTGAAGGA |
| 1081 AATTGAGACA CAGAAAACCC TGCAAAAGAT AAATGAAAGC CGCAGCTGGT TCTTTGAACG |
| 1141 CATCAACAAA ATCGATAGGC CACTTGCTCG CCTTATCAAG AAGAAAAGGG AGAAGAATCA |
| 1201 AATCGACACT ATAAAGAATG ATAAAGGCGA TATAACCACC GATCCCACAG AAATTCAAAC |
| 1261 AACCATACGC GAATACTACA AACACCTCTA CGCCAATAAA CTCGAAAATC TCGAGGAAAT |
| 1321 GGATACATTC CTCGACACGT ACACCCTTCC CAGGCTGAAC CAGGAAGAAG TTGAATCACT |
| 1381 GAATCGGCCT ATCACGGGGA GTGAAATAGT AGCTATCATC AATTCACTCC CTACCAAGAA |
| 1441 GTCACCCGGA CCTGATGGAT TCACCGCCGA ATTCTACCAG AGATACATGG AAGAACTGGT |
| 1501 GCCCTTCTTG CTGAAACTTT TCCAAAGTAT TGAGAAAGAG GGAATACTTC CAAACTCATT |
| 1561 TTATGAGGCA TCCATCATTC TGATCCCGAA GCCCGGCAGG GACACGACCA AGAAAGAGAA |
| 1621 TTTTCGACCA ATCTCATTGA TGAACATTGA TGCAAAGATC CTCAATAAAA TACTGGCAAA |
| 1681 TCGGATTCAG CAGCACATAA AGAAGCTGAT CCACCATGAT CAAGTAGGCT TCATCCCCGG |
| 1741 TATGCAAGGT TGGTTCAATA TACGAAAATC AATCAATGTT ATCCAGCATA TAAACCGGGC |
| 1801 CAAAGACAAG AACCACATGA TTATTAGTAT CGATGCTGAG AAAGCCTTTG ACAAAATACA |
| 1861 ACAACCCTTC ATGCTGAAAA CATTGAATAA GCTGGGAATT GATGGCACCT ACTTCAAAAT |
| 1921 CATCAGAGCC ATATATGACA AACCAACAGC AAATATCATT CTGAATGGTC AGAAATTGGA |
| 1981 AGCATTCCCC TTGAAAACCG GCACACGGCA GGGTTGCCCT CTGTCACCAC TCCTCTTCAA |
| 2041 CATCGTGTTG GAAGTTCTTG CCCGCGCAAT CCGGCAGGAA AAGGAAATCA AGGGCATTCA |
| 2101 ACTGGGCAAA GAGGAAGTTA AATTGAGCCT GTTTGCAGAC GACATGATCG TCTATTTGGA |
| 2161 AAACCCCATA GTTAGTGCAC AAAATCTGCT GAAGTTGATC AGTAATTTCT CCAAAGTGAG |
| 2221 TGGGTACAAA ATCAATGTGC AAAAGAGCCA AGCTTTCTTG TACACCAACA ACAGGCAAAC |
| 2281 TGAGTCTCAA ATCATGGGCG AACTCCCCTT CGTGATTGCA TCCAAGCGGA TCAAATACCT |
| 2341 GGGGATTCAA TTGACTCGTG ATGTGAAGGA CCTCTTCAAG GAGAACTACA AACCCCTGCT |
| 2401 CAAGGAAATC AAAGAGGACA CAAACAAATG GAAGAACATT CCATGCTCTT GGGTGGGAAG |
| 2461 GATCAATATC GTCAAAATGG CCATCCTGCC CAAGGTAATT TACAGGTTCA ATGCTATACC |
| 2521 CATCAAGCTC CCCATGACAT TCTTCACAGA ACTTGAAAAG ACGACGCTGA AGTTCATTTG |
| 2581 GAACCAGAAA CGTGCCAGGA TTGCTAAATC TATTCTCTCC CAAAAGAACA AAGCTGGCGG |
| 2641 AATCACACTC CCAGACTTCA AACTTTACTA CAAGGCGACC GTGACGAAAA CGGCTTGGTA |
| 2701 CTGGTACCAA AACAGGGATA TAGATCAATG GAACCGAACG GAGCCCAGCG AAATTATGCC |
| 2761 TCATATATAC AACTATCTGA TCTTTGACAA ACCGGAGAAG AACAAGCAAT GGGGAAAGGA |
| 2821 TAGTCTGTTT AATAAATGGT GCTGGGAAAA CTGGCTCGCA ATCTGTAGGA AGCTGAAACT |
| 2881 GGATCCATTC TTGACGCCTT ATACAAAGAT AAATTCCCGA TGGATTAAAG ATCTCAACGT |

TABLE 8-continued

Plasmid and mRNA construct sequences

2941 GAAACCCAAA ACAATTAAAA CCCTCGAGGA AAACCTGGGT ATTACGATTC AGGACATTGG
3001 GGTGGGAAAG GACTTCATGT CCAAAACCCC AAAAGCGATG GCAACCAAAG ACAAAATCGA
3061 CAAATGGGAT CTCATAAAAC TTAAGTCATT TTGCACAGCT AAAGAAACGA CAATTAGGGT
3121 GAACCGACAA CCGACCACTT GGGAGAAAAT CTTCGCAACA TACAGTTCTG ACAAAGGCCT
3181 GATTTCCAGG ATCTACAATG AATTGAAACA AATTTACAAG AAGAAGACGA ACAACCCTAT
3241 AAAGAAATGG GCCAAGGACA TGAACAGACA CTTCTCTAAG GAAGACATTT ATGCAGCCAA
3301 GAAACACATG AAGAAATGCA GCTCTTCACT GGCAATCAGG GAAATGCAAA TCAAAACAAC
3361 AATGAGATAT CATCTCACAC CCGTCAGAAT GGCCATCATT AAGAAGAGCG GAAACAACCG
3421 GTGCTGGCGT GGTTGCGGAG AAATCGGTAC TCTCCTTCAC TGTTGGTGGG ACTGTAAACT
3481 CGTTCAACCA CTGTGGAAGT CTGTGTGGCG GTTCCTCAGA GATCTGGAAC TCGAAATCCC
3541 ATTTGACCCA GCCATCCCTC TCCTGGGTAT ATACCCGAAT GAGTATAAAT CCTGCTGCTA
3601 TAAAGACACC TGCACAAGGA TGTTTATTGC AGCTCTCTTC ACAATCGCGA AGACGTGGAA
3661 CCAACCCAAA TGTCCGACTA TGATTGACTG GATTAAGAAG ATGTGGCACA TATACACTAT
3721 GGAATACTAT GCTGCGATCA AGAACGATGA GTTCATATCA TTTGTGGGCA CATGGATGAA
3781 ACTCGAAACC ATCATACTCT CTAAATTGAG TCAAGAACAG AAAACTAAAC ACCGTATATT
3841 TTCCCTGATC GGTGGGAATT AGCTACAAAG ACGATGACGA CAAGGACCAT GGAGACGGTG
3901 AGAGACACAA AAAATTCCAA CACACTATTG CAATGAAAAT AAATTTCCTT TATTAGCCAG
3961 AAGTCAGATG CTCAAGGGGC TTCATGATGT CCCCATAATT TTTGGCAGAG GGAAAAAGAT
4021 CTCAGTGGTA TTTGTGAGCC AGGGCATTGG CCTTCTGATA GGCAGCCTGC ACCTGAGGAG
4081 TGCGGCCGCT TTACTTGTAC AGCTCGTCCA TGCCGAGAGT GATCCCGGCG GCGGTCACGA
4141 ACTCCAGCAG GACCATGTGA TCGCGCTTCT CGTTGGGGTC TTTGCTCAGG GCGGACTGGG
4201 TGCTCAGGTA GTGGTTGTCG GGCAGCAGCA CGGGGCCGTC GCCGATGGGG GTGTTCTGCT
4261 GGTAGTGGTC GGCGAGCTGC ACGCTGCCGT CCTCGATGTT GTGGCGGATC TTGAAGTTCA
4321 CCTTGATGCC GTTCTTCTGC TTGTCGGCCA TGATATAGAC GTTGTGGCTG TTGTAGTTGT
4381 ACTCCAGCTT GTGCCCCAGG ATGTTGCCGT CCTCCTTGAA GTCGATGCCC TTCAGCTCGA
4441 TGCGGTTCAC CAGGGTGTCG CCCTCGAACT TCACCTCGGC GCGGGTCTTG TAGTTGCCGT
4501 CGTCCTTGAA GAAGATGGTG CGCTCCTGGA CGTAGCCTTC GGGCATGGCG GACTTGAAGA
4561 AGTCGTGCTG CTTCATGTGG TCGGGGTAGC GGCTGAAGCA CTGCACGCCG TAGGTCAGGG
4621 TGGTCACGAG GGTGGGCCAG GGCACGGGCA GCTTGCCGGT GGTGCAGATG AACTTCAGGG
4681 TCAGCTTGCC GTAGGTGGCA TCGCCCTCGC CCTCGCCGGA CACGCTGAAC TTGTGGCCGT
4741 TTACGTCGCC GTCCAGCTCG ACCAGGATGG GCACCACCCC GGTGAACAGC TCCTCGCCCT
4801 TGCTCACCAT GGTGGCGGGA TCTGACGGTT CACTAAACCA GCTCTGCTTA TATAGACCTC
4861 CCACCGTACA CGCCTACCGC CCATTTGCGT CAATGGGGCG GAGTTGTTAC GACATTTTGG
4921 AAAGTCCCGT TGATTTTGGT GCCAAAACAA ACTCCCATTG ACGTCAATGG GGTGGAGACT
4981 TGGAAATCCC CGTGAGTCAA ACCGCTATCC ACGCCCATTG ATGTACTGCC AAAACCGCAT
5041 CACCATGGTA ATAGCGATGA CTAATACGTA GATGTACTGC CAAGTAGGAA AGTCCCATAA
5101 GGTCATGTAC TGGGCATAAT GCCAGGCGGG CCATTTACCG TCATTGACGT CAATAGGGGG
5161 CGTACTTGGC ATATGATACA CTTGATGTAC TGCCAAGTGG GCAGTTTACC GTAAATACTC
5221 CACCCATTGA CGTCAATGGA AAGTCCCTAT TGGCGTTACT ATGGGAACAT ACGTCATTAT
5281 TGACGTCAAT GGGCGGGGGT CGTTGGGCGG TCAGCCAGGC GGGCCATTTA CCGTAAGTTA
5341 TGTAACGACG TCTCAGCTGA CAATGAGATC ACATGGACAC AGGAAGGGGA ATATCACACT
5401 CTGGGGACTG TGGTGGGGTC GGGGGAGGGG GGAGGGATAG CATTGGGAGA TATACCTAAT
5461 GCTAGATGAC ACATTAGTGG GTGCAGCGCA CCAGCATGGC ACATGTATAC ATATGTAACT
5521 AACCTGCACA ATGTGCACAT GTACCCTAAA ACTTAGAGTA TAATGGATCC GCAGGCCTCT
5581 GCTAGCTTGA CTGACTGAGA TACAGCGTAC CTTCAGCTCA CAGACATGAT AAGATACATT
5641 GATGAGTTTG GACAAACCAC AACTAGAATG CAGTGAAAAA AATGCTTTAT TTGTGAAATT
5701 TGTGATGCTA TTGCTTTATT TGTAACCATT ATAAGCTGCA ATAAACAAGT T
(SEQ ID NO: 36)

LINE-1 plasmid GFP (SEQ ID NO: 37)
1 CGGCCGCGGG GGGAGGAGCC AAGATGGCCG AATAGGAACA GCTCCGGTCT ACAGCTCCCA
61 GCGTGAGCGA CGCAGAAGAC GGTGATTTCT GCATTTCCAT CTGAGGTACC GGGTTCATCT
121 CACTAGGGAG TGCCAGACAG TGGGCGCAGG CCAGTGTGTG TGCGCACCGT GCGCGAGCCG
181 AAGCAGGGCG AGGCATTGCC TCACCTGGGA AGCGCAAGGG GTCAGGGAGT TCCCTTTCCG
241 AGTCAAAGAA AGGGGTGACG GACGCACCTG GAAAATCGGG TCACTCCCAC CCGAATATTG
301 CGCTTTTCAG ACCGGCTTAA GAAACGGCGC ACCACGAGAC TATATCCCAC ACCTGGCTCG
361 GAGGGTCCTA CGCCCACGGA ATCTCGCTGA TTGCTAGCAC AGCAGTCTGA GATCAAACTG
421 CAAGGCGGCA ACGAGGCTGG GGGAGGGGCG CCCGCCATTG CCCAGGCTTG CTTAGGTAAA
481 CAAAGCAGCA GGGAAGCTCG AACTGGGTGG AGCCCACCAC AGCTCAAGGA GGCCTGCCTG
541 CCTCTGTAGG CTCCACCTCT GGGGGCAGGG CACAGACAAA CAAAAAGACA GCAGTAACCT
601 CTGCAGACTT AAGTGTCCCT GTCTGACAGC TTTGAAGAGA GCAGTGGTTC TCCCAGCACG
661 CAGCTGGAGA TCTGAGAACG GGCAGACTGC CTCCTCAAGT GGGTCCCTGA CCCCTGACCC
721 CCGAGCAGCC TAACTGGGAG GCACCCCCCA GCAGGGGCAC ACTGACACCT CACACGGCAG
781 GGTATTCCAA CAGACCTGCA GCTGAGGGTC CTGTCTGTTA GAAGGAAAAC TAACAACCAG
841 AAAGGACATC TACACCGAAA ACCCATCTGT ACATCACCAT CATCAAAGAC CAAAAGTAGA
901 TAAAACCACA AAGATGGGGA AAAAACAGAA CAGAAAAACT GGAAACTCTA AAACGCAGAG
961 CGCCTCTCCT CCTCCAAAGG AACGCAGTTC CTCACCAGCA ACAGAACAAA GCTGGATGGA
1021 GAATGATTTT GATGAGCTGA GAGAAGAAGG CTTCAGACGA TCAAATTACT CTGAGCTACG
1081 GGAGGACATT CAAACCAAAG GCAAAGAAGT TGAAAACTTT GAAAAAAATT TAGAAGAATG
1141 TATAACTAGA ATAACCAATA CAGAGAAGTG CTTAAAGGAG CTGATGGAGC TGAAAACCAA
1201 GGCTCGAGAA CTACGTGAAG AATGCAGAAG CCTCAGGAGC CGATGCGATC AACTGGAAGA
1261 AAGGGTATCA GCAATGGAAG ATGAAATGAA TGAAATGAAG CGAGAAGGGA AGTTTAGAGA
1321 AAAAAGAATA AAAAGAAATG AGCAAAGCCT CCAAGAAATA TGGGACTATG TGAAAAGACC
1381 AAATCTACGT CTGATTGGTG TACCTGAAAG TGATGTGGAG AATGGAACCA AGTTGGAAAA
1441 CACTCTGCAG GATATTATCC AGGAGAACTT CCCCAATCTA GCAAGGCAGG CCAACGTTCA
1501 GATTCAGGAA ATACAGAGAA CGCCACAAAG ATACTCCTCG AGAAGAGCAA CTCCAAGACA
1561 CATAATTGTC AGATTCACCA AAGTTGAAAT GAAGGAAAAA ATGTTAAGGG CAGCCAGAGA
1621 GAAAGGTCGG GTTACCCTCA AAGGAAAGCC CATCAGACTA ACAGCGGATC TCTCGGCAGA TABLE 8-continued

| Plasmid and mRNA construct sequences |
|---|
| 1681 AACCCTACAA GCCAGAAGAG AGTGGGGGCC AATATTCAAC ATTCTTAAAG AAAAGAATTT |
| 1741 TCAACCCAGA ATTTCATATC CAGCCAAACT AAGCTTCATA AGTGAAGGAG AAATAAAATA |
| 1801 CTTTATAGAC AAGCAAATGT TGAGAGATTT TGTCACCACC AGGCCTGCCC TAAAAGAGCT |
| 1861 CCTGAAGGAA GCGCTAAACA TGGAAAGGAA CAACCGGTAC CAGCCGCTGC AAAATCATGC |
| 1921 CAAAATGTAA AGACCATCAA GACTAGGAAG AAACTGCATC AACTAATGAG CAAAATCACC |
| 1981 AGCTAACATC ATAATGACAG GATCAACTTC ACACATAACA ATATTAACTT TAAATATAAA |
| 2041 TGGACTAAAT TCTGCAATTA AAAGACACAG ACTGGCAAGT TGGATAAAGA GTCAAGACCC |
| 2101 ATCAGTGTGC TGTATTCAGG AAACCCATCT CACGTGCAGA GACACACATA GGCTCAAAAT |
| 2161 AAAAGGATGG AGGAAGATCT ACCAAGCCAA TGGAAAACAA AAAAAGGCAG GGGTTGCAAT |
| 2221 CCTAGTCTCT GATAAAACAG ACTTTAAACC AACAAAGATC AAAAGAGACA AAGAAGGCCA |
| 2281 TTACATAATG GTAAAGGGAT CAATTCAACA AGAGGAGCTA ACTATCCTAA ATATTTATGC |
| 2341 ACCCAATACA GGAGCACCCA GATTCATAAA GCAAGTCCTC AGTGACCTAC AAAGAGACTT |
| 2401 AGACTCCCAC ACATTAATAA TGGGAGACTT TAACACCCCA CTGTCAACAT TAGACAGATC |
| 2461 AACGAGACAG AAAGTCAACA AGGATACCCA GGAATTGAAC TCAGCTCTGC ACCAAGCAGA |
| 2521 CCTAATAGAC ATCTACAGAA CTCTCCACCC CAAATCAACA GAATATACAT TTTTTTCAGC |
| 2581 ACCACACCAC ACCTATTCCA AAATTGACCA CATAGTTGGA AGTAAAGCTC TCCTCAGCAA |
| 2641 ATGTAAAAGA ACAGAAATTA TAACAAACTA TCTCTCAGAC CACAGTGCAA TCAAACTAGA |
| 2701 ACTCAGGATT AAGAATCTCA CTCAAAGCCG CTCAACTACA TGGAAACTGA ACAACCTGCT |
| 2761 CCTGAATGAC TACTGGGTAC ATAACGAAAT GAAGGCAGAA ATAAAGATGT TCTTTGAAAC |
| 2821 CAACGAGAAC AAAGACACCA CATACCAGAA TCTCTGGGAC GCATTCAAAG CAGTGTGTAG |
| 2881 AGGGAAATTT ATAGCACTAA ATGCCTACAA GAGAAAGCAG GAAAGATCCA AAATTGACAC |
| 2941 CCTAACATCA CAATTAAAAG AACTAGAAAA GCAAGAGCAA ACACATTCAA AAGCTAGCAG |
| 3001 AAGGCAAGAA ATAACTAAAA TCAGAGCAGA ACTGAAGGAA ATAGAGACAC AAAAAACCCT |
| 3061 TCAAAAAATC AATGAATCCA GGAGCTGGTT TTTTGAAAGG ATCAACAAAA TTGATAGACC |
| 3121 GCTAGCAAGA CTAATAAAGA AAAAAAGAGA GAAGAATCAA ATAGACACAA TAAAAAATGA |
| 3181 TAAAGGGGAT ATCACCACCG ATCCCACAGA AATACAAACT ACCATCAGAG AATACTACAA |
| 3241 ACACCTCTAC GCAAATAAAC TAGAAAATCT AGAAGAAATG GATACATTCC TCGACACATA |
| 3301 CACTCTCCCA AGACTAAACC AGGAAGAAGT TGAATCTCTG AATCGACCAA TAACAGGCTC |
| 3361 TGAAATTGTG GCAATAATCA ATAGTTTACC AACCAAAAAG AGTCCAGGAC CAGATGGATT |
| 3421 CACAGCCGAA TTCTACCAGA GGTACAAGGA GGAACTGGTA CCATTCCTTC TGAAACTATT |
| 3481 CCAATCAATA GAAAAAGAGG GAATCCTCCC TAACTCATTT TATGAGGCCA GCATCATTCT |
| 3541 GATACCAAAG CCGGGCAGAG ACACAACCAA AAAAGAGAAT TTTAGACCAA TATCCTTGAT |
| 3601 GAACATTGAT GCAAAAATCC TCAATAAAAT ACTGGCAAAC CGAATCCAGC AGCACATCAA |
| 3661 AAAGCTTATC CACCATGATC AAGTGGGCTT CATCCCTGGG ATGCAAGGCT GGTTCAATAT |
| 3721 ACGCAAATCA ATAAATGTAA TCCAGCATAT AAACAGAGCC AAAGACAAAA ACCACATGAT |
| 3781 TATCTCAATA GATGCAGAAA AAGCCTTTGA CAAAATTCAA CAACCCTTCA TGCTAAAAAC |
| 3841 TCTCAATAAA TTAGGTATTG ATGGGACGTA TTTCAAAATA ATAAGAGCTA TCTATGACAA |
| 3901 ACCCACAGCC AATATCATAC TGAATGGGCA AAAACTGGAA GCATTCCCTT TGAAAACCGG |
| 3961 CACAAGACAG GGATGCCCTC TCTCACCGCT CCTATTCAAC ATAGTGTTGG AAGTTCTGGC |
| 4021 CAGGGCAATC AGGCAGGAGA AGGAAATAAA GGGTATTCAA TTAGGAAAAG AGGAAGTCAA |
| 4081 ATTGTCCCTG TTTGCAGACG ACATGATTGT TTATCTAGAA AACCCCATCG TCTCAGCCCA |
| 4141 AAATCTCCTT AAGCTGATAA GCAACTTCAG CAAAGTCTCA GGATACAAAA TCAATGTACA |
| 4201 AAAATCACAA GCATTCTTAT ACACCAACAA CAGACAAACA GAGAGCCAAA TCATGGGTGA |
| 4261 ACTCCCATTC ACAATTGCTT CAAAGAGAAT AAAATACCTA GGAATCCAAC TTACAAGGGA |
| 4321 TGTGAAGGAC CTCTTCAAGG AGAACTACAA ACCACTGCTC AAGGAAATAA AAGAGGAGAC |
| 4381 AAACAAATGG AAGAACATTC CATGCTCATG GGTAGGAAGA ATCAATATCG TGAAAATGGC |
| 4441 CATACTGCCC AAGGTAATTT ACAGATTCAA TGCCATCCCC ATCAAGCTAC CAATGACTTT |
| 4501 CTTCACAGAA TTGGAAAAAA CTACTTTAAA GTTCATATGG AACCAAAAAA GAGCCCGCAT |
| 4561 TGCCAAGTCA ATCCTAAGCC AAAAGAACAA AGCTGGAGGC ATCACACTAC CTGACTTCAA |
| 4621 ACTATACTAC AAGGCTACAG TAACCAAAAC AGCATGGTAC TGGTACCAAA ACAGAGATAT |
| 4681 AGATCAATGG AACAGAACAG AGCCCTCAGA AATAATGCCG CATATCTACA ACTATCTGAT |
| 4741 CTTTGACAAA CCTGAGAAAA ACAAGCAATG GGGAAAGGAT TCCCTATTTA ATAAATGGTG |
| 4801 CTGGGAAAAC TGGCTAGCCA TATGTAGAAA GCTGAAACTG GATCCCTTCC TTACACCTTA |
| 4861 TACAAAAATC AATTCAAGAT GGATTAAAGA TTTAAACGTT AAACCTAAAA CCATAAAAAC |
| 4921 CCTAGAAGAA AACCTAGGCA TTACCATTCA GGACATAGGC GTGGGCAAGG ACTTCATGTC |
| 4981 CAAAACACCA AAAGCAATGG CAACAAAAGA CAAAATTGAC AAATGGGATC TAATTAAACT |
| 5041 AAAGAGCTTC TGCACAGCAA AAGAAACTAC CATCAGAGTG AACAGGCAAC CTACAACATG |
| 5101 GGAGAAAATT TTTGCAACCT ACTCATCTGA CAAAGGGCTA ATATCCAGAA TCTACAATGA |
| 5161 ACTCAAACAA ATTTACAAGA AAAAAACAAA CAACCCCATC AAAAAGTGGG CGAAGGACAT |
| 5221 GAACAGACAC TTCTCAAAAG AAGACATTTA TGCAGCCAAA AAACACATGA AGAAATGCTC |
| 5281 ATCATCACTG GCCATCAGAG AAATGCAAAT CAAAACCACT ATGAGATATC ATCTCACACC |
| 5341 AGTTAGAATG GCAATCATTA AAAAGTCAGG AAACAACAGG TGCTGGAGAG GATGCGGAGA |
| 5401 AATAGGAACA CTTTTACACT GTTGGTGGGA CTGTAAACTA GTTCAACCAT TGTGGAAGTC |
| 5461 AGTGTGGCGA TTCCTCAGGG ATCTAGAACT AGAAATACCA TTTGACCCAG CCATCCCATT |
| 5521 ACTGGGTATA TACCCAAATG AGTATAAATC ATGCTGCTAT AAAGACACAT GCACACGTAT |
| 5581 GTTTATTGCG GCACTATTCA CAATAGCAAA GACTTGGAAC CAACCCAAAT GTCCAACAAT |
| 5641 GATAGACTGG ATTAAGAAAA TGTGGCACAT ATACACCATG GAATACTATG CAGCCATAAA |
| 5701 AAATGATGAG TTCATATCCT TTGTAGGGAC ATGGATGAAA TTGGAAACCA TCATTCTCAG |
| 5761 TAAACTATCG CAAGAACAAA AAACCAAACA CCGCATATTC TCACTCATAG GTGGGAATTG |
| 5821 AACAATGAGA TCACATGGAC ACAGGAAGGG GAATATCACA CTCTGGGGAC TGTGGTGGGG |
| 5881 TCGGGGGAGG GGGGAGGGAT AGCATTGGGA GATATACCTA ATGCTAGATG ACACATTAGT |
| 5941 GGGTGCAGCG CACCAGCATG GCACATGTAT ACGGATCCGA ATTCTCGACG GATCGATCCG |
| 6001 AACAAACGAC CCAACACCCG TGCGTTTTAT TCTGTCTTTT TATTGCCGAT CCCCTCAGAA |
| 6061 GAACTCGTCA AGAAGGCGAT AGAAGGCGAT GCGCTGCGAA TCGGGAGCGG CGATACCGTA |
| 6121 AAGCACGAGG AAGCGGTCAG CCCATTCGCC GCCAAGCTCT TCAGCAATAT CACGGGTAGC |
| 6181 CAACGCTATG TCCTGATAGC GGTCGGCCGC TTTACTTGTA CAGCTCGTCC ATGCCGAGAG |
| 6241 TGATCCCGGC GGCGGTCACG AACTCCAGCA GGACCATGTG ATCGCGCTTC TCGTTGGGGT |
| 6301 CTTTGCTCAG GGCGGACTGG GTGCTCAGGT AGTGGTTGTC GGGCAGCAGC ACGGGGCCGT |

TABLE 8-continued

| Plasmid and mRNA construct sequences |
|---|
| 6361 CGCCGATGGG GGTGTTCTGC TGGTAGTGGT CGGCCAGGTG AGTCCAGGAG ATGTTTCAGC |
| 6421 ACTGTTGCCT TTAGTCTCGA GGCAACTTAG ACAACTGAGT ATTGATCTGA GCACAGCAGG |
| 6481 GTGTGAGCTG TTTGAAGATA CTGGGGTTGG GGGTGAAGAA ACTGCAGAGG ACTAACTGGG |
| 6541 CTGAGACCCA GTGGCAATGT TTTAGGGCCT AAGGAATGCC TCTGAAAATC TAGATGGACA |
| 6601 ACTTTGACTT TGAGAAAAGA GAGGTGGAAA TGAGGAAAAT GACTTTTCTT TATTAGATTT |
| 6661 CGGTAGAAAG AACTTTCATC TTTCCCCTAT TTTTGTTATT CGTTTTAAAA CATCTATCTG |
| 6721 GAGGCAGGAC AAGTATGGTC ATTAAAAAGA TGCAGGCAGA AGGCATATAT TGGCTCAGTC |
| 6781 AAAGTGGGGA ACTTTGGTGG CCAAACATAC ATTGCTAAGG CTATTCCTAT ATCAGCTGGA |
| 6841 CACATATAAA ATGCTGCTAA TGCTTCATTA CAAACTTATA TCCTTTAATT CCAGATGGGG |
| 6901 GCAAAGTATG TCCAGGGGTG AGGAACAATT GAAACATTTG GGCTGGAGTA GATTTTGAAA |
| 6961 GTCAGCTCTG TGTGTGTGTG TGTGTGTGTG TGTGTGAGAG CGTGTGTTTC TTTTAACGTT |
| 7021 TTCAGCCTAC AGCATACAGG GTTCATGGTG GCAAGAAGAT AACAAGATTT AAATTATGGC |
| 7081 CAGTGACTAG TGCTGCAAGA AGAACAACTA CCTGCATTTA ATGGGAAAGC AAAATCTCAG |
| 7141 GCTTTGAGGG AAGTTAACAT AGGCTTGATT CTGGGTGGAA GCTGGGTGTG TAGTTATCTG |
| 7201 GAGGCCAGGC TGGAGCTCTC AGCTCACTAT GGGTTCATCT TTATTGTCTC CTTTCATCTC |
| 7261 AACAGCTGCA CGCTGCCGTC CTCGATGTTG TGGCGGATCT TGAAGTTCAC CTTGATGCCG |
| 7321 TTCTTCTGCT TGTCGGCCAT GATATAGACG TTGTGGCTGT TGTAGTTGTA CTCCAGCTTG |
| 7381 TGCCCCAGGA TGTTGCCGTC CTCCTTGAAG TCGATGCCCT TCAGCTCGAT GCGGTTCACC |
| 7441 AGGGTGTCGC CCTCGAACTT CACCTCGGCG CGGGTCTTGT AGTTGCCGTC GTCCTTGAAG |
| 7501 AAGATGGTGC GCTCCTGGAC GTAGCCTTCG GGCATGGCGG ACTTGAAGAA GTCGTGCTGC |
| 7561 TTCATGTGGT CGGGGTAGCG GCTGAAGCAC TGCACGCCGT AGGTCAGGGT GGTCACGAGG |
| 7621 GTGGGCCAGG GCACGGGCAG CTTGCCGGTG GTGCAGATGA ACTTCAGGGT CAGCTTGCCG |
| 7681 TAGGTGGCAT CGCCCTCGCC CTCGCCGGAC ACGCTGAACT TGTGGCCGTT TACGTCGCCG |
| 7741 TCCAGCTCGA CCAGGATGGG CACCACCCCG GTGAACAGCT CCTCGCCCTT GCTCACCATG |
| 7801 GTGGCGAATT CGAAGCTTGA GCTCGAGATC TGAGTCCGGT AGCGCTAGCG GATCTGACGG |
| 7861 TTCACTAAAC CAGCTCTGCT TATATAGACC TCCCACCGTA CACGCCTACC GCCCATTTGC |
| 7921 GTCAATGGGG CGGAGTTGTT ACGACATTTT GGAAAGTCCC GTTGATTTTG GTGCCAAAAC |
| 7981 AAACTCCCAT TGACGTCAAT GGGGTGGAGA CTTGGAAATC CCCGTGAGTC AAACCGCTAT |
| 8041 CCACGCCCAT TGATGTACTG CCAAAACCGC ATCACCATGG TAATAGCGAT GACTAATACG |
| 8101 TAGATGTACT GCCAAGTAGG AAAGTCCCAT AAGGTCATGT ACTGGGCATA ATGCCAGGCG |
| 8161 GGCCATTTAC CGTCATTGAC GTCAATAGGG GGCGTACTTG GCATATGATA CACTTGATGT |
| 8221 ACTGCCAAGT GGGCAGTTTA CCGTAAATAC TCCACCCATT GACGTCAATG GAAAGTCCCT |
| 8281 ATTGGCGTTA CTATGGGAAC ATACGTCATT ATTGACGTCA ATGGGCGGGG GTCGTTGGGC |
| 8341 GGTCAGCCAG GCGGGCCATT TACCGTAAGT TATGTAACGC GGAACTCCAT ATATGGGCTA |
| 8401 TGAACTAATG ACCCCGTAAT TGATTACTAT TAGCCCGGGG GATCCAGACA TGATAAGATA |
| 8461 CATTGATGAG TTTGGACAAA CCACAACTAG AATGCAGTGA AAAAAATGCT TTATTTGTGA |
| 8521 AATTTGTGAT GCTATTGCTT TATTTGTAAC CATTATAAGC TGCAATAAAC AAGTTAACAA |
| 8581 CAACAATTGC ATTCATTTTA TGTTTCAGGT TCAGGGGGAG GTGTGGGAGG TTTTTTAAAG |
| 8641 CAAGTAAAAC CTCTACAAAT GTGGTATGGC TGATTATGAT CCGGCTGCCT CGCGCGTTTC |
| 8701 GGTGATGACG GTGAAAACCT CTGACACATG CAGCTCCCGG AGACGGTCAC AGCTTGTCTG |
| 8761 TAAGCGGATG CCGGGAGCAG ACAAGCCCGT CAGGGCGCGT CAGCGGGTGT TGGCGGGTGT |
| 8821 CGGGGCGCAG CCATGAGGTC GATCGACTCT AGAGGATCGA TCCCCGCCCC GGACGAACTA |
| 8881 AACCTGACTA CGACATCTCT GCCCCTTCTT CGCGGGGCAG TGCATGTAAT CCCTTCAGTT |
| 8941 GGTTGGTACA ACTTGCCAAC TGGGCCCTGT TCCACATGTG ACACGGGGGG GGACCAAACA |
| 9001 CAAAGGGGTT CTCTGACTGT AGTTGACATC CTTATAAATG GATGTGCACA TTTGCCAACA |
| 9061 CTGAGTGGCT TTCATCCTGG AGCAGACTTT GCAGTCTGTG GACTGCAACA CAACATTGCC |
| 9121 TTTATGTGTA ACTCTTGGCT GAAGCTCTTA CACCAATGCT GGGGGACATG TACCTCCCAG |
| 9181 GGGCCCAGGA AGACTACGGG AGGCTACACC AACGTCAATC AGAGGGGCCT GTGTAGCTAC |
| 9241 CGATAAGCGG ACCCTCAAGA GGGCATTAGC AATAGTGTTT ATAAGGCCCC CTTGTTAACC |
| 9301 CTAAACGGGT AGCATATGCT TCCCGGGTAG TAGTATATAC TATCCAGACT AACCCTAATT |
| 9361 CAATAGCATA TGTTACCCAA CGGGAAGCAT ATGCTATCGA ATTAGGGTTA GTAAAAGGGT |
| 9421 CCTAAGGAAC AGCGATATCT CCCACCCCAT GAGCTGTCAC GGTTTTATTT ACATGGGGTC |
| 9481 AGGATTCCAC GAGGGTAGTG AACCATTTTA GTCACAAGGG CAGTGGCTGA AGATCAAGGA |
| 9541 GCGGGCAGTG AACTCTCCTG AATCTTCGCC TGCTTCTTCA TTCTCCTTCG TTTAGCTAAT |
| 9601 AGAATAACTG CTGAGTTGTG AACAGTAAGG TGTATGTGAG GTGCTCGAAA ACAAGGTTTC |
| 9661 AGGTGACGCC CCCAGAATAA AATTTGGACG GGGGGTTCAG TGGTGGCATT GTGCTATGAC |
| 9721 ACCAATATAA CCCTCACAAA CCCCTTGGGC AATAAATACT AGTGTAGGAA TGAAACATTC |
| 9781 TGAATATCTT TAACAATAGA AATCCATGGG GTGGGGACAA GCCGTAAAGA CTGGATGTCC |
| 9841 ATCTCACACG AATTTATGGC TATGGGCAAC ACATAATCCT AGTGCAATAT GATACTGGGG |
| 9901 TTATTAAGAT GTGTCCCAGG CAGGGACCAA GACAGGTGAA CCATGTTGTT ACACTCTATT |
| 9961 TGTAACAAGG GGAAAGAGAG TGGACGCCGA CAGCAGCGGA CTCCACTGGT TGTCTCTAAC |
| 10021 ACCCCCGAAA ATTAAACGGG GCTCCACGCC AATGGGGCCC ATAAACAAAG ACAAGTGGCC |
| 10081 ACTCTTTTTT TTGAAATTGT GGAGTGGGGG CACGCGTCAG CCCCCACACG CCGCCCTGCG |
| 10141 GTTTTGGACT GTAAAATAAG GGTGTAATAA CTTGGCTGAT TGTAACCCCG CTAACCACTG |
| 10201 CGGTCAAACC ACTTGCCCAC AAAACCACTA ATGGCACCCC GGGGAATACC TGCATAAGTA |
| 10261 GGTGGGCGGG CCAAGATAGG GGCGCGATTG CTGCGATCTG GAGGACAAAT TACACACACT |
| 10321 TGCGCCTGAG CGCCAAGCAC AGGGTTGTTG GTCCTCATAT TCACGAGGTC GCTGAGAGCA |
| 10381 CGGTGGGCTA ATGTTGCCAT GGGTAGCATA TACTACCCAA ATATCTGGAT AGCATATGCT |
| 10441 ATCCTAATCT ATATCTGGGT AGCATAGGCT ATCCTAATCT ATATCTGGGT AGCATATGCT |
| 10501 ATCCTAATCT ATATCTGGGT AGTATATGCT ATCCTAATTT ATATCTGGGT AGCATAGGCT |
| 10561 ATCCTAATCT ATATCTGGGT AGCATATGCT ATCCTAATCT ATATCTGGGT AGTATATGCT |
| 10621 ATCCTAATCT GTATCCGGGT AGCATATGCT ATCCTAATAG AGATTAGGGT AGTATATGCT |
| 10681 ATCCTAATTT ATATCTGGGT AGCATATACT ACCCAAATAT CTGGATAGCA TATGCTATCC |
| 10741 TAATCTATAT CTGGGTAGCA TATGCTATCC TAATCTATAT CTGGGTAGCA TAGGCTATCC |
| 10801 TAATCTATAT CTGGGTAGCA TATGCTATCC TAATCTATAT CTGGGTAGTA TATGCTATCC |
| 10861 TAATTTATAT CTGGGTAGCA TAGGCTATCC TAATCTATAT CTGGGTAGCA TATGCTATCC |
| 10921 TAATCTATAT CTGGGTAGTA TATGCTATCC TAATCTGTAT CCGGGTAGCA TATGCTATCC |
| 10981 TCATGCATAT ACAGTCAGCA TATGATACCC AGTAGTAGAG TGGGAGTGCT ATCCTTTGCA |

TABLE 8-continued

| Plasmid and mRNA construct sequences |
|---|
| 11041 TATGCCGCCA CCTCCCAAGG GGGCGTGAAT TTTCGCTGCT TGTCCTTTTC CTGCATGCTG |
| 11101 GTTGCTCCCA TTCTTAGGTG AATTTAAGGA GGCCAGGCTA AAGCCGTCGC ATGTCTGATT |
| 11161 GCTCACCAGG TAAATGTCGC TAATGTTTTC CAACGCGAGA AGGTGTTGAG CGCGGAGCTG |
| 11221 AGTGACGTGA CAACATGGGT ATGCCCAATT GCCCCATGTT GGGAGGACGA AAATGGTGAC |
| 11281 AAGACAGATG GCCAGAAATA CACCAACAGC ACGCATGATG TCTACTGGGG ATTTATTCTT |
| 11341 TAGTGCGGGG GAATACACGG CTTTTAATAC GATTGAGGGC GTCTCCTAAC AAGTTACATC |
| 11401 ACTCCTGCCC TTCCTCACCC TCATCTCCAT CACCTCCTTC ATCTCCGTCA TCTCCGTCAT |
| 11461 CACCCTCCGC GGCAGCCCCT TCCACCATAG GTGGAAACCA GGGAGGCAAA TCTACTCCAT |
| 11521 CGTCAAAGCT GCACACAGTC ACCCTGATAT TGCAGGTAGG AGCGGGCTTT GTCATAACAA |
| 11581 GGTCCTTAAT CGCATCCTTC AAAACCTCAG CAAATATATG AGTTTGTAAA AAGACCATGA |
| 11641 AATAACAGAC AATGGACTCC CTTAGCGGGC CAGGTTGTGG GCCGGGTCCA GGGGCCATTC |
| 11701 CAAAGGGGAG ACGACTCAAT GGTGTAAGAC GACATTGTGG AATAGCAAGG GCAGTTCCTC |
| 11761 GCCTTAGGTT GTAAAGGGAG GTCTTACTAC CTCCATATAC GAACACACCG GCGACCCAAG |
| 11821 TTCCTTCGTC GGTAGTCCTT TCTACGTGAC TCCTAGCCAG GAGAGCTCTT AAACCTTCTG |
| 11881 CAATGTTCTC AAATTTCGGG TTGGAACCTC CTTGACCACG ATGCTTTCCA AACCACCCTC |
| 11941 CTTTTTTGCG CCTGCCTCCA TCACCCTGAC CCCGGGGTCC AGTGCTTGGG CCTTCTCCTG |
| 12001 GGTCATCTGC GGGGCCCTGC TCTATCGCTC CCGGGGGCAC GTCAGGCTCA CCATCTGGGC |
| 12061 CACCTTCTTG GTGGTATTCA AAATAATCGG CTTCCCCTAC AGGGTGGAAA AATGGCCTTC |
| 12121 TACCTGGAGG GGGCCTGCGC GGTGGAGACC CGGATGATGA TGACTGACTA CTGGGACTCC |
| 12181 TGGGCCTCTT TTCTCCACGT CCACGACCTC TCCCCCTGGC TCTTTCACGA CTTCCCCCCC |
| 12241 TGGCTCTTTC ACGTCCTCTA CCCCGGCGGC CTCCACTACC TCCTCGACCC CGGCCTCCAC |
| 12301 TACCTCCTCG ACCCCGGCCT CCACTGCCTC CTCGACCCCG GCCTCCACCT CCTGCTCCTG |
| 12361 CCCCTCCTGC TCCTGCCCCT CCTCCTGCTC CTGCCCCTCC TGCCCCTCCT GCTCCTGCCC |
| 12421 CTCCTGCCCC TCCTGCTCCT GCCCCTCCTG CCCCTCCTGC TCCTGCCCCT CCTGCCCCTC |
| 12481 CTCCTGCTCC TGCCCCTCCT GCCCCTCCTC CTGCTCCTGC CCCTCCTGCC CCTCCTGCTC |
| 12541 CTGCCCCTCC TGCCCCTCCT GCTCCTGCCC CTCCTGCCCC TCCTGCTCCT GCCCCTCCTG |
| 12601 CTCCTGCCCC TCCTGCTCCT GCCCCTCCTG CTCCTGCCCC TCCTGCCCCT CCTGCCCCTC |
| 12661 CTCCTGCTCC TGCCCCTCCT GCTCCTGCCC CTCCTGCCCC TCCTGCCCCT CCTGCTCCTG |
| 12721 CCCCTCCTCC TGCTCCTGCC CCTCCTGCCC CTCCTGCCCC TCCTCCTGCT CCTGCCCCTC |
| 12781 CTGCCCCTCC TCCTGCTCCT GCCCCTCCTC CTGCTCCTGC CCCTCCTGCC CCTCCTGCCC |
| 12841 CTCCTCCTGC TCCTGCCCCT CCTGCCCCTC CTCCTGCTCC TGCCCCTCCT CCTGCTCCTG |
| 12901 CCCCTCCTGC CCCTCCTGCC CCTCCTCCTG CTCCTGCCCC TCCTCCTGCT CCTGCCCCTC |
| 12961 CTGCCCCTCC TGCCCCTCCT GCCCCTCCTC CTGCTCCTGC CCCTCCTCCT GCTCCTGCCC |
| 13021 CTCCTGCTCC TGCCCCTCCC GCTCCTGCTC CTGCTCCTGT TCCACCGTGG GTCCCTTTGC |
| 13081 AGCCAATGCA ACTTGGACGT TTTTGGGGTC TCCGGACACC ATCTCTATGT CTTGGCCCTG |
| 13141 ATCCTGAGCC GCCCGGGGCT CCTGGTCTTC CGCCTCCTCG TCCTCGTCCT CTTCCCCGTC |
| 13201 CTCGTCCATG GTTATCACCC CCTCTTCTTT GAGGTCCACT GCCGCCGGAG CCTTCTGGTC |
| 13261 CAGATGTGTC TCCCTTCTCT CCTAGGCCAT TTCCAGGTCC TGTACCTGGC CCCTCGTCAG |
| 13321 ACATGATTCA CACTAAAAGA GATCAATAGA CATCTTTATT AGACGACGCT CAGTGAATAC |
| 13381 AGGGAGTGCA GACTCCTGCC CCCTCCAACA GCCCCCCCAC CCTCATCCCC TTCATGGTCG |
| 13441 CTGTCAGACA GATCCAGGTC TGAAAATTCC CCATCCTCCG AACCATCCTC GTCCTCATCA |
| 13501 CCAATTACTC GCAGCCCGGA AAACTCCCGC TGAACATCCT CAAGATTTGC GTCCTGAGCC |
| 13561 TCAAGCCAGG CCTCAAATTC CTCGTCCCCC TTTTTGCTGG ACGGTAGGGA TGGGGATTCT |
| 13621 CGGGACCCCT CCTCTTCCTC TTCAAGGTCA CCAGACAGAG ATGCTACTGG GGCAACGGAA |
| 13681 GAAAAGCTGG GTGCGGCCTG TGAGGATCAG CTTATCGATG ATAAGCTGTC AAACATGAGA |
| 13741 ATTCTTGAAG ACGAAAGGGC CTCGTGATAC GCCTATTTTT ATAGGTTAAT GTCATGATAA |
| 13801 TAATGGTTTC TTAGACGTCA GGTGGCACTT TTCGGGGAAA TGTGCGCGGA ACCCCTATTT |
| 13861 GTTTATTTTT CTAAATACAT TCAAATATGT ATCCGCTCAT GAGACAATAA CCCTGATAAA |
| 13921 TGCTTCAATA ATATTGAAAA AGGAAGAGTA TGAGTATTCA ACATTTCCGT GTCGCCCTTA |
| 13981 TTCCCTTTTT TGCGGCATTT TGCCTTCCTG TTTTTGCTCA CCCAGAAACG CTGGTGAAAG |
| 14041 TAAAAGATGC TGAAGATCAG TTGGGTGCAC GAGTGGGTTA CATCGAACTG GATCTCAACA |
| 14101 GCGGTAAGAT CCTTGAGAGT TTTCGCCCCG AAGAACGTTT TCCAATGATG AGCACTTTTA |
| 14161 AAGTTCTGCT ATGTGGCGCG GTATTATCCC GTGTTGACGC CGGGCAAGAG CAACTCGGTC |
| 14221 GCCGCATACA CTATTCTCAG AATGACTTGG TTGAGTACTC ACCAGTCACA GAAAAGCATC |
| 14281 TTACGGATGG CATGACAGTA AGAGAATTAT GCAGTGCTGC CATAACCATG AGTGATAACA |
| 14341 CTGCGGCCAA CTTACTTCTG ACAACGATCG GAGGACCGAA GGAGCTAACC GCTTTTTTGC |
| 14401 ACAACATGGG GGATCATGTA ACTCGCCTTG ATCGTTGGGA ACCGGAGCTG AATGAAGCCA |
| 14461 TACCAAACGA CGAGCGTGAC ACCACGATGC CTGCAGCAAT GGCAACAACG TTGCGCAAAC |
| 14521 TATTAACTGG CGAACTACTT ACTCTAGCTT CCCGGCAACA ATTAATAGAC TGGATGGAGG |
| 14581 CGGATAAAGT TGCAGGACCA CTTCTGCGCT CGGCCCTTCC GGCTGGCTGG TTTATTGCTG |
| 14641 ATAAATCTGG AGCCGGTGAG CGTGGGTCTC GCGGTATCAT TGCAGCACTG GGGCCAGATG |
| 14701 GTAAGCCCTC CCGTATCGTA GTTATCTACA CGACGGGGAG TCAGGCAACT ATGGATGAAC |
| 14761 GAAATAGACA GATCGCTGAG ATAGGTGCCT CACTGATTAA GCATTGGTAA CTGTCAGACC |
| 14821 AAGTTTACTC ATATATACTT TAGATTGATT TAAAACTTCA TTTTTAATTT AAAAGGATCT |
| 14881 AGGTGAAGAT CCTTTTTGAT AATCTCATGA CCAAAATCCC TTAACGTGAG TTTTCGTTCC |
| 14941 ACTGAGCGTC AGACCCCGTA GAAAAGATCA AAGGATCTTC TTGAGATCCT TTTTTTCTGC |
| 15001 GCGTAATCTG CTGCTTGCAA ACAAAAAAAC CACCGCTACC AGCGGTGGTT TGTTTGCCGG |
| 15061 ATCAAGAGCT ACCAACTCTT TTTCCGAAGG TAACTGGCTT CAGCAGAGCG CAGATACCAA |
| 15121 ATACTGTCCT TCTAGTGTAG CCGTAGTTAG GCCACCACTT CAAGAACTCT GTAGCACCGC |
| 15181 CTACATACCT CGCTCTGCTA ATCCTGTTAC CAGTGGCTGC TGCCAGTGGC GATAAGTCGT |
| 15241 GTCTTACCGG GTTGGACTCA AGACGATAGT TACCGGATAA GGCGCAGCGG TCGGGCTGAA |
| 15301 CGGGGGGTTC GTGCACACAG CCCAGCTTGG AGCGAACGAC CTACACCGAA CTGAGATACC |
| 15361 TACAGCGTGA GCTATGAGAA AGCGCCACGC TTCCCGAAGG GAGAAAGGCG GACAGGTATC |
| 15421 CGGTAAGCGG CAGGGTCGGA ACAGGAGAGC GCACGAGGGA GCTTCCAGGG GGAAACGCCT |
| 15481 GGTATCTTTA TAGTCCTGTC GGGTTTCGCC ACCTCTGACT TGAGCGTCGA TTTTTGTGAT |
| 15541 GCTCGTCAGG GGGGCGGAGC CTATGGAAAA ACGCCAGCAA CGCGGCCTTT TTACGGTTCC |
| 15601 TGGCCTTTTG CTGGCCTTTT GCTCACATGT TCTTTCCTGC GTTATCCCCT GATTCTGTGG |
| 15661 ATAACCGTAT TACCGCCTTT GAGTGAGCTG ATACCGCTCG CCGCAGCCGA ACGACCGAGC |

TABLE 8-continued

| Plasmid and mRNA construct sequences |
|---|
| 15721 GCAGCGAGTC AGTGAGCGAG GAAGCGGAAG AGCGCCTGAT GCGGTATTTT CTCCTTACGC |
| 15781 ATCTGTGCGG TATTTCACAC CGCATATGGT GCACTCTCAG TACAATCTGC TCTGATGCCG |
| 15841 CATAGTTAAG CCAGCTGTGG AATGTGTGTC AGTTAGGGTG TGGAAAGTCC CCAGGCTCCC |
| 15901 CAGCAGGCAG AAGTATGCAA AGCATGCATC TCAATTAGTC AGCAACCAGG TGTGGAAAGT |
| 15961 CCCCAGGCTC CCCAGCAGGC AGAAGTATGC AAAGCATGCA TCTCAATTAG TCAGCAACCA |
| 16021 TAGTCCCGCC CCTAACTCCG CCCATCCCGC CCCTAACTCC GCCCAGTTCC GCCCATTCTC |
| 16081 CGCCCCATGG CTGACTAATT TTTTTTATTT ATGCAGAGGC CGAGGCCGCC TCGGCCTCTG |
| 16141 AGCTATTCCA GAAGTAGTGA GGAGGCTTTT TTGGAGGCCT AGGCTTTTGC AAAAAGCTTG |
| 16201 CATGCCTGCA GGTCGGCCGC CACGACCGGT GCCGCCACCA TCCCCTGACC CACGCCCCTG |
| 16261 ACCCCTCACA AGGAGACGAC CTTCCATGAC CGAGTACAAG CCCACGGTGC GCCTCGCCAC |
| 16321 CCGCGACGAC GTCCCCCGGG CCGTACGCAC CCTCGCCGCC GCGTTCGCCG ACTACCCCGC |
| 16381 CACGCGCCAC ACCGTCGACC CGGACCGCCA CATCGAGCGG GTCACCGAGC TGCAAGAACT |
| 16441 CTTCCTCACG CGCGTCGGGC TCGACATCGG CAAGGTGTGG GTCGCGGACG ACGGCGCCGC |
| 16501 GGTGGCGGTC TGGACCACGC CGGAGAGCGT CGAAGCGGGG GCGGTGTTCG CCGAGATCGG |
| 16561 CCCGCGCATG GCCGAGTTGA GCGGTTCCCG GCTGGCCGCG CAGCAACAGA TGGAAGGCCT |
| 16621 CCTGGCGCCG CACCGGCCCA AGGAGCCCGC GTGGTTCCTG GCCACCGTCG GCGTCTCGCC |
| 16681 CGACCACCAG GGCAAGGGTC TGGGCAGCGC CGTCGTGCTC CCCGGAGTGG AGGCGGCCGA |
| 16741 GCGCGCCGGG GTGCCCGCCT TCCTGGAGAC CTCCGCGCCC CGCAACCTCC CCTTCTACGA |
| 16801 GCGGCTCGGC TTCACCGTCA CCGCCGACGT CGAGGTGCCC GAAGGACCGC GCACCTGGTG |
| 16861 CATGACCCGC AAGCCCGGTG CCTGACGCCC GCCCCACGAC CCGCAGCGCC CGACCGAAAG |
| 16921 GAGCGCACGA CCCCATGGCT CCGACCGAAG CCGACCCGGG CGGCCCCGCC GACCCCGCAC |
| 16981 CCGCCCCCGA GGCCCACCGA CTCTAGAGGA TCATAATCAG CCATACCACA TTTGTAGAGG |
| 17041 TTTTACTTGC TTTAAAAAAC CTCCCACACC TCCCCCTGAA CCTGAAACAT AAAATGAATG |
| 17101 CAATTGTTGT TGTTAACTTG TTTATTGCAG CTTATAATGG TTACAAATAA AGCAATAGCA |
| 17161 TCACAAATTT CACAAATAAA GCATTTTTTT CACTGCATTC TAGTTGTGGT TTGTCCAAAC |
| 17221 TCATCAATGT ATCTTATCAT GTCTGGATCA CTCGCCGATA GTGGAAACCG ACGCCCCAGC |
| 17281 ACTCGTCCGA GGGCAAAGGA ATAGGGGAGA TGGGGGAGGC TAACTGAAAC ACGGAAGGAG |
| 17341 ACAATACCGG AAGGAACCCG CGCTATGACG GCAATAAAAA GACAGAATAA AACGCACGGG |
| 17401 TGTTGGGTCG TTTGTTCATA AACGCGGGGT TCGGTCCCAG GGCTGGCACT CTGTCGATAC |
| 17461 CCCACCGAGA CCCCATTGGG GCCAATACGC CCGCGTTTCT TCCTTTTCCC CACCCCACCC |
| 17521 CCCAAGTTCG GGTGAAGGCC CAGGGCTCGC AGCCAACGTC GGGGCGGCAG GCCCTGCCAT |
| 17581 AGCCACTGGC CCCGTGGGTT AGGGACGGGG TCCCCCATGG GGAATGGTTT ATGGTTCGTG |
| 17641 GGGGTTATTA TTTTGGGCGT TGCGTGGGGT CTGGTCCACG ACTGGACTGA GCAGACAGAC |
| 17701 CCATGGTTTT TGGATGGCCT GGGCATGGAC CGCATGTACT GGCGCGACAC GAACACCGGG |
| 17761 CGTCTGTGGC TGCCAAACAC CCCCGACCCC CAAAAACCAC CGCGCGGATT TCTGGCGTGC |
| 17821 CAAGCTAGTC GACCAATTCT CATGTTTGAC AGCTTATCAT CGCAGATCCG GGCAACGTTG |
| 17881 TTGCATTGCT GCAGGCGCAG AACTGGTAGG TATGGAAGAT CTCTAGAAGC TGGGTACCAG |
| 17941 CTGCTAGCAA GCTTGCTAGC GGCCGGCTCG AGTTTACTCC CTATCAGTGA TAGAGAACGT |
| 18001 ATGTCGAGTT TACTCCCTAT CAGTGATAGA GAACGATGTC GAGTTTACTC CCTATCAGTG |
| 18061 ATAGAGAACG TATGTCGAGT TTACTCCCTA TCAGTGATAG AGAACGTATG TCGAGTTTAC |
| 18121 TCCCTATCAG TGATAGAGAA CGTATGTCGA GTTTATCCCT ATCAGTGATA GAGAACGTAT |
| 18181 GTCGAGTTTA CTCCCTATCA GTGATAGAGA ACGTATGTCG AGGTAGGCGT GTACGGTGGG |
| 18241 AGGCCTATAT AAGCAGAGCT CGTTTAGTGA ACCGTCAGAT CGCCG |
| (SEQ ID NO: 37) |
| |
| LINE 1- GFP mRNA (SEQ ID NO: 38) |
| 1 TAATACGACT CACTATAGGG AGAAGTACTG CCACCATGGG CAAGAAGCAA AATCGCAAGA |
| 61 CGGGGAATTC CAAGACACAA TCCGCTAGCC CACCACCTAA AGAGCGTTCT AGCTCCCCTG |
| 121 CTACTGAGCA GTCCTGGATG GAAAACGACT TCGATGAACT CCGGGAAGAG GGATTTAGGC |
| 181 GATCCAACTA TTCAGAACTC CGCGAAGATA TCCAGACAAA GGGGAAGGAA GTCGAGAATT |
| 241 TCGAGAAGAA CCTCGAGGAG TGCATCACCC GTATCACAAA CACTGAGAAA TGTCTCAAAG |
| 301 AACTCATGGA ACTTAAGACA AAAGCCAGGG AGCTTCGAGA GGAGTGTCGG AGTCTGAGAT |
| 361 CCAGGTGTGA CCAGCTCGAG GAGCGCGTGA GCGCGATGGA AGACGAGATG AACGAGATGA |
| 421 AAAGAGAGGG CAAATTCAGG GAGAAGCGCA TTAAGAGGAA CGAACAGAGT CTGCAGGAGA |
| 481 TTTGGGATTA CGTCAAGAGG CCTAACCTGC GGTTGATCGG CGTCCCCGAG AGCGACGTAG |
| 541 AAAACGGGAC TAAACTGGAG AATACACTTC AAGACATCAT TCAAGAAAAT TTTCCAAACC |
| 601 TGGCTCGGCA AGCTAATGTG CAAATCCAAG AGATCCAACG CACACCCCAG CGGTATAGCT |
| 661 CTCGGCGTGC CACCCCTAGG CATATTATCG TGCGCTTTAC TAAGGTGGAG ATGAAAGAGA |
| 721 AGATGCTGCG AGCCGCTCGG GAAAAGGGAA GGGTGACTTT GAAGGGCAAA CCTATTCGGC |
| 781 TGACGGTTGA CCTTAGCGCC GAGACACTCC AGGCACGCCG GGAATGGGGC CCCATCTTTA |
| 841 ATATCCTGAA GGAGAAGAAC TTCCAGCCAC GAATCTCTTA CCCTGCAAAG TTGAGTTTTA |
| 901 TCTCCGAGGG TGAGATTAAG TATTTCATCG ATAAACAGAT GCTGCGAGAC TTCGTGACAA |
| 961 CTCGCCCAGC TCTCAAGGAA CTGCTCAAAG AGGCTCTTAA TATGGAGCGC AATAATAGAT |
| 1021 ATCAACCCTT GCAGAACCAC GCAAAGATGT GAGACAGCCG TCAGACCATC AAGACTAGGA |
| 1081 AGAAACTGCA TCAACTAATG AGCAAAATCA CCAGCTAACA TCATAGTATA CATGACCGGC |
| 1141 TCTAACTCAC ATATCACCAT CCTTACACTT AACATTAACG GCCTCAACTC AGCTATCAAG |
| 1201 CGCCATCGGC TGGCCAGCTG GATCAAATCA CAGGATCCAA GCGTTTGTTG CATCCAAGAG |
| 1261 ACCCACCTGA CCTGTAGAGA TACTCACCGC CTCAAGATCA AGGGATGGCG AAAGATTTAT |
| 1321 CAGGCGAACG GTAAGCAGAA GAAAGCCGGA GTCGCAATTC TGGTCTCAGA CAAGACGGAT |
| 1381 TTCAAGCCCA CCAAAATTAA GCGTGATAAG GAAGGTCACT ATATTATGGT GAAAGGCAGC |
| 1441 ATACAGCAGG AAGAACTTAC CATATTGAAC ATCTACGCGC CAAACACCGG CGCACCTCGC |
| 1501 TTTATCAAAC AGGTCCTGTC CGATCTGCAG CGAGATCTGG ATTCTCATAC GTTGATTATG |
| 1561 GGTGATTTCA ATACACCATT GAGCACCCTG GATCGCAGCA CCAGGCAAAA GGTAAATAAA |
| 1621 GACACGCAAG AGCTCAATAG CGCACTGCAT CAGGCAGATC TCATTGATAT TTATCGCACT |
| 1681 CTTCATCCTA AGAGTACCGA GTACACATTC TTCAGCGCCC CACATCATAC ATACTCAAAG |
| 1741 ATCGATCATA TCGTCGGCTC AAAGGCTCTG CTGTCAAAGT GCAAGCGCAC AGAGATAATT |
| 1801 ACAAATTACC TGTCAGATCA TAGCGCGATC AAGCTCGAGC TGAGAATCAA GAACCTGACC |
| 1861 CAGAGCCGGA GTACCACTTG GAAGCTTAAT AACCTGCTGC TCAACGATTA TTGGGTCCAC |

TABLE 8-continued

| Plasmid and mRNA construct sequences | | | | | | |
|---|---|---|---|---|---|---|
| 1921 | AATGAGATGA | AGGCAGAGAT | TAAAATGTTC | TTCGAAACAA | ATGAGAATAA | GGATACTACC |
| 1981 | TATCAAAACC | TTTGGGATGC | CTTTAAGGCC | GTCTGCAGAG | GCAAGTTCAT | CGCCCTCAAC |
| 2041 | GCCTATAAAA | GAAAACAAGA | GAGATCTAAG | ATCGATACTC | TCACCTCTCA | GCTGAAGGAG |
| 2101 | TTGGAGAAAC | AGGAACAGAC | CCACTCCAAG | GCGTCAAGAC | GGCAGGAGAT | CACAAAGATT |
| 2161 | CGCGCCGAGT | TGAAAGAGAT | CGAAACCCAA | AAGACTCTTC | AGAAAATTAA | CGAGTCTCGT |
| 2221 | AGTTGGTTCT | TCGAGCGGAT | TAATAAGATA | GACAGACCTC | TGGCACGACT | GATTAAGAAG |
| 2281 | AAGCGCGAAA | AGAACCAGAT | TGATACCATC | AAGAACGACA | AGGGCGACAT | CACTACTGAC |
| 2341 | CCGACCGAGA | TCCAGACCAC | TATTCGGGAG | TATTATAAGC | ATTTGTATGC | TAACAAGCTT |
| 2401 | GAGAACCTGG | AAGAGATGGA | CACTTTTCTG | GATACCTATA | CTCTGCCACG | GCTTAATCAA |
| 2461 | GAGGAAGTCG | AGTCCCTCAA | CCGCCCAATT | ACAGGAAGCG | AGATTGTGGC | CATAATTAAC |
| 2521 | TCCCTGCCGA | CAAAGAAATC | TCCTGGTCCG | GACGGGTTTA | CAGCTGAGTT | TTATCAACGG |
| 2581 | TATATGGAAG | AGCTTGTACC | GTTTCTGCTC | AAGCTCTTTC | AGTCTATAGA | AAAGGAAGGC |
| 2641 | ATCTTGCCCA | ATTCCTTCTA | CGAAGCTTCT | ATAATACTTA | TTCCCAAACC | AGGACGCGAT |
| 2701 | ACCACAAAGA | AGGAAAACTT | CCGGCCCATT | AGTCTCATGA | ATATCGACGC | TAAAATATTG |
| 2761 | AACAAGATTC | TCGCCAACAG | AATCCAACAA | CATATTAAGA | AATTGATACA | TCACGACCAG |
| 2821 | GTGGGGTTTA | TACCTGGCAT | GCAGGGCTGG | TTTAACATCC | GGAAGAGTAT | TAACGTCATT |
| 2881 | CAACACATTA | ATAGAGCTAA | GGATAAGAAT | CATATGATCA | TCTCTATAGA | CGCGGAAAAG |
| 2941 | GCATTCGATA | AGATTCAGCA | GCCATTTATG | CTCAAGACTC | TGAACAAACT | CGGCATCGAC |
| 3001 | GGAACATATT | TTAAGATTAT | TCGCGCAATT | TACGATAAGC | CGACTGCTAA | CATTATCCTT |
| 3061 | AACGGCCAAA | AGCTCGAGGC | CTTTCCGCTC | AAGACTGGAA | CCCGCCAAGG | CTGTCCCCTC |
| 3121 | TCCCCGCTTT | TGTTTAATAT | TGTACTCGAG | GTGCTGGCTA | GGGCTATTCG | TCAAGAGAAA |
| 3181 | GAGATTAAAG | GGATACAGCT | CGGGAAGGAA | GAGGTCAAGC | TTTCCTTGTT | CGCCGATGAT |
| 3241 | ATGATTGTGT | ACCTGGAGAA | TCCTATTGTG | TCTGCTCAGA | ACCTTCTTAA | ACTTATTTCT |
| 3301 | AACTTTAGCA | AGGTCAGCGG | CTATAAGATT | AACGTCCAGA | AATCTCAGGC | CTTTCTGTAC |
| 3361 | ACAAATAATC | GACAGACCGA | ATCCCAGATA | ATGGGTGAGC | TTCCGTTTGT | CATAGCCAGC |
| 3421 | AAAAGGATAA | AGTATCTCGG | AATCCAGCTG | ACACGAGACG | TTAAAGATTT | GTTTAAGGAA |
| 3481 | AATTACAAGC | CTCTCCTGAA | AGAGATTAAG | GAAGATACTA | ATAAGTGGAA | GAATATCCCC |
| 3541 | TGTTCATGGG | TTGGCAGAAT | CAACATAGTG | AAGATGGCAA | TACTTCCTAA | AGTGATATAT |
| 3601 | CGCTTTAACG | CCATCCCAAT | TAAACTGCCT | ATGACCTTCT | TTACGGAGCT | CGAGAAAACA |
| 3661 | ACCCTTAAAT | TTATATGGAA | TCAAAAGAGA | GCAAGAATAG | CGAAGTCCAT | CTTGAGCCAG |
| 3721 | AAGAATAAGG | CCGGTGGGAT | TACTTTGCCT | GATTTTAAGT | TGTATTATAA | AGCCACAGTA |
| 3781 | ACTAAGACAG | CCTGGTATTG | GTATCAGAAT | AGAGACATCG | ACCAGTGGAA | TCGGACCGAA |
| 3841 | CCATCAGAGA | TAATGCCCCA | CATCTATAAT | TACCTTATAT | TCGATAAGCC | AGAAAAGAAT |
| 3901 | AAACAGTGGG | GCAAAGACAG | CCTCTTCAAC | AAGTGGTGTT | GGGAGAATTG | GCTGGCCATA |
| 3961 | TGCCGGAAAC | TCAAGCTCGA | CCCCTTTCTT | ACACCCTACA | CTAAAATCAA | CAGTAGGTGG |
| 4021 | ATCAAGGACT | TGAATGTCAA | GCCAAAGACT | ATAAAGACAC | TGGAAGAGAA | TCTTGGGATC |
| 4081 | ACAATACAAG | ATATAGGCGT | CGGCAAAGAT | TTTATGTCAA | AGACGCCCAA | GGCCATGGCC |
| 4141 | ACTAAGGATA | AGATTGATAA | GTGGGACCTT | ATTAAGCTCA | AAGCTTCTG | TACTGCCAAG |
| 4201 | GAGACCACGA | TCAGAGTTAA | TAGGCAGCCC | ACTACATGGG | AAAAGATTTT | CGCCACTTAT |
| 4261 | TCATCAGATA | AGGGGTTGAT | AAGCAGAATA | TATAACGAGC | TGAAGCAGAT | CTACAAGAAG |
| 4321 | AAAACGAATA | ATCCCATCAA | GAAGTGGGCA | AAAGATATGA | ACAGGCATTT | TAGCAAAGAG |
| 4381 | GATATCTACG | CCGCGAAGAA | GCATATGAAG | AAGTGTAGTT | CAAGCTTGGC | CATTCGTGAG |
| 4441 | ATGCAGATTA | AGACGACCAT | GCGATACCAC | CTTACCCCAG | TGAGGATGGC | AATTATCAAG |
| 4501 | AAATCTGGCA | ATAATAGATG | TTGGCGGGGC | TGTGGCGAGA | TTGGCACCCT | GCTCCATTGC |
| 4561 | TGGTGGGATT | GCAAGCTGGT | GCAGCCGCTT | TGGAAATCAG | TCTGGCGCTT | TCTGAGGGAC |
| 4621 | CTCGAGCTTG | AGATTCCCTT | CGATCCCGCA | ATTCCCTTGC | TCGGAATCTA | TCCTAACGAA |
| 4681 | TACAAGAGCT | GTTGTTACAA | GGATACGTGT | ACCCGGATGT | TCATCGCGGC | CTTGTTTACG |
| 4741 | ATAGCTAAGA | CGTGGAATCA | GCCTAAGTGC | CCCACAATGA | TCGATTGGAT | CAAGAAAATG |
| 4801 | TGGCATATTT | ATACCATGGA | GTATTACGCA | GCAATTAAGA | ATGACGAATT | TATTTCCTTC |
| 4861 | GTTGGGACCT | GGATGAAGCT | GGAGACTATT | ATTCTGAGCA | AGCTGTCTCA | GGAGCAAAAG |
| 4921 | ACAAAGCATA | GAATCTTCTC | TCTCATTGGT | GGTAACGACT | ACAAAGACGA | TGACGACAAG |
| 4981 | TAAAGCGCTT | CTAGAAGTTG | TCTCCTCCTG | CACTGACTGA | CTGATACAAT | CGATTTCTGG |
| 5041 | ATCCGCAGGC | CTAATCAACC | TCTGGATTAC | AAAATTTGTG | AAAGATTGAC | TGGTATTCTT |
| 5101 | AACTATGTTG | CTCCTTTTAC | GCTATGTGGA | TACGCTGCTT | TAATGCCTTT | GTATCATGCT |
| 5161 | ATTGCTTCCC | GTATGGCTTT | CATTTTCTCC | TCCTTGTATA | AATCCTGGTT | GCTGTCTCTT |
| 5221 | TATGAGGAGT | TGTGGCCCGT | TGTCAGGCAA | CGTGGCGTGG | TGTGCACTGT | GTTTGCTGAC |
| 5281 | GCAACCCCCA | CTGGTTGGGG | CATTGCCACC | ACCTGTCAGC | TCCTTTCCGG | GACTTTCGCT |
| 5341 | TTCCCCCTCC | CTATTGCCAC | GGCGGAACTC | ATCGCCGCCT | GCCTTGCCCG | CTGCTGGACA |
| 5401 | GGGGCTCGGC | TGTTGGGCAC | TGACAATTCC | GTGGTGTTGT | CGGGGAAGCT | GACGTCCTTT |
| 5461 | CCATGGCTGC | TCGCCTGTGT | TGCCACCTGG | ATTCTGCGCG | GGACGTCCTT | CTGCTACGTC |
| 5521 | CCTTCGGCCC | TCAATCCAGC | GGACCTTCCT | TCCCGCTGAG | AGACACAAAA | AATTCCAACA |
| 5581 | CACTATTGCA | ATGAAAATAA | ATTTCCTTTA | TTAGCCAGAA | GTCAGATGCT | CAAGGGGCTT |
| 5641 | CATGATGTCC | CCATAATTTT | TGGCAGAGGG | AAAAAGATCT | CAGTGGTATT | TGTGAGCCAG |
| 5701 | GGCATTGGCC | TTCTGATAGG | CAGCCTGCAC | CTGAGGAGTG | CGGCCGCTTT | ACTTGTACAG |
| 5761 | CTCGTCCATG | CCGAGAGTGA | TCCCGGCGGC | GGTCACGAAC | TCCAGCAGGA | CCATGTGATC |
| 5821 | GCGCTTCTCG | TTGGGGTCTT | TGCTCAGGGC | GGACTGGGTG | CTCAGGTAGT | GGTTGTCGGG |
| 5881 | CAGCAGCACG | GGGCCGTCGC | CGATGGGGGT | GTTCTGCTGG | TAGTGGTCGG | CGAGCTGCAC |
| 5941 | GCTGCCGTCC | TCGATGTTGT | GGCGGATCTT | GAAGTTCACC | TTGATGCCGT | TCTTCTGCTT |
| 6001 | GTCGGCCATG | ATATAGACGT | TGTGGCTGTT | GTAGTTGTAC | TCCAGCTTGT | GCCCCAGGAT |
| 6061 | GTTGCCGTCC | TCCTTGAAGT | CGATGCCCTT | CAGCTCGATG | CGGTTCACCA | GGGTGTCGCC |
| 6121 | CTCGAACTTC | ACCTCGGCGC | GGGTCTTGTA | GTTGCCGTCG | TCCTTGAAGA | AGATGGTGCG |
| 6181 | CTCCTGGACG | TAGCCTTCGG | GCATGGCGGA | CTTGAAGAAG | TCGTGCTGCT | TCATGTGGTC |
| 6241 | GGGGTAGCGG | CTGAAGCACT | GCACGCCGTA | GGTCAGGGTG | GTCACGAGGG | TGGGCCAGGG |
| 6301 | CACGGGCAGC | TTGCCGGTGG | TGCAGATGAA | CTTCAGGGTC | AGCTTGCCGT | AGGTGGCATC |
| 6361 | GCCCTCGCCC | TCGCCGGACA | CGCTGAACTT | GTGGCCGTTT | ACGTCGCCGT | CCAGCTCGAC |
| 6421 | CAGGATGGGC | ACCACCCCGG | TGAACAGCTC | CTCGCCCTTG | CTCACCATGG | TGGCGGGATC |
| 6481 | TGACGGTTCA | CTAAACCAGC | TCTGCTTATA | TAGACCTCCC | ACCGTACACG | CCTACCGCCC |
| 6541 | ATTTGCGTCA | ATGGGGCGGA | GTTGTTACGA | CATTTTGGAA | AGTCCCGTTG | ATTTTGGTGC |

TABLE 8-continued

| Plasmid and mRNA construct sequences |
|---|
| 6601 CAAAACAAAC TCCCATTGAC GTCAATGGGG TGGAGACTTG GAAATCCCCG TGAGTCAAAC |
| 6661 CGCTATCCAC GCCCATTGAT GTACTGCCAA AACCGCATCA CCATGGTAAT AGCGATGACT |
| 6721 AATACGTAGA TGTACTGCCA AGTAGGAAAG TCCCATAAGG TCATGTACTG GGCATAATGC |
| 6781 CAGGCGGGCC ATTTACCGTC ATTGACGTCA ATAGGGGGCG TACTTGGCAT ATGATACACT |
| 6841 TGATGTACTG CCAAGTGGGC AGTTTACCGT AAATACTCCA CCCATTGACG TCAATGGAAA |
| 6901 GTCCCTATTG GCGTTACTAT GGGAACATAC GTCATTATTG ACGTCAATGG GCGGGGGTCG |
| 6961 TTGGGCGGTC AGCCAGGCGG GCCATTTACC GTAAGTTATG TAACGGGCCT GCTGCCGGCT |
| 7021 CTGCGGCCTC TTCCGCGTCT TCGCCTTCGC CCTCAGACGA GTCGGATCTC CCTTTGGGCC |
| 7081 GCCTCCCCGC CTGTCTAGCT TGACTGACTG AGATACAGCG TACCTTCAGC TCACAGACAT |
| 7141 GATAAGATAC ATTGATGAGT TTGGACAAAC CACAACTAGA ATGCAGTGAA AAAAATGCTT |
| 7201 TATTTGTGAA ATTTGTGATG CTATTGCTTT ATTTGTAACC ATTATAAGCT GCAATAAACA |
| 7261 AGTT (SEQ ID NO: 38) |
| |
| LINE-1-plasmid_CD5-intron-FCR-PI3K (SEQ ID NO: 39) |
| 1 CGGCCGCGGG GGGAGGAGCC AAGATGGCCG AATAGGAACA GCTCCGGTCT ACAGCTCCCA |
| 61 GCGTGAGCGA CGCAGAAGAC GGTGATTTCT GCATTTCCAT CTGAGGTACC GGGTTCATCT |
| 121 CACTAGGGAG TGCCAGACAG TGGGCGCAGG CCAGTGTGTG TGCGCACCGT GCGCGAGCCG |
| 181 AAGCAGGGCG AGGCATTGCC TCACCTGGGA AGCGCAAGGG GTCAGGGAGT TCCCTTTCCG |
| 241 AGTCAAAGAA AGGGGTGACG GACGCACCTG GAAAATCGGG TCACTCCCAC CCGAATATTG |
| 301 CGCTTTTCAG ACCGGCTTAA GAAACGGCGC ACCACGAGAC TATATCCCAC ACCTGGCTCG |
| 361 GAGGGTCCTA CGCCCACGGA ATCTCGCTGA TTGCTAGCAC AGCAGTCTGA GATCAAACTG |
| 421 CAAGGCGGCA ACGAGGCTGG GGGAGGGGCG CCCGCCATTG CCCAGGCTTG CTTAGGTAAA |
| 481 CAAAGCAGCA GGGAAGCTCG AACTGGGTGG AGCCCACCAC AGCTCAAGGA GGCCTGCCTG |
| 541 CCTCTGTAGG CTCCACCTCT GGGGGCAGGG CACAGACAAA CAAAAAGACA GCAGTAACCT |
| 601 CTGCAGACTT AAGTGTCCCT GTCTGACAGC TTTGAAGAGA GCAGTGGTTC TCCCAGCACG |
| 661 CAGCTGGAGA TCTGAGAACG GGCAGACTGC CTCCTCAAGT GGGTCCCTGA CCCCTGACCC |
| 721 CCGAGCAGCC TAACTGGGAG GCACCCCCCA GCAGGGGCAC ACTGACACCT CACACGGCAG |
| 781 GGTATTCCAA CAGACCTGCA GCTGAGGGTC CTGTCTGTTA GAAGGAAAAC TAACAACCAG |
| 841 AAAGGACATC TACACCGAAA ACCCATCTGT ACATCACCAT CATCAAAGAC CAAAAGTAGA |
| 901 TAAAACCACA AAGATGGGGA AAAAACAGAA CAGAAAAACT GGAAACTCTA AAACGCAGAG |
| 961 CGCCTCTCCT CCTCCAAAGG AACGCAGTTC CTCACCAGCA ACAGAACAAA GCTGGATGGA |
| 1021 GAATGATTTT GATGAGCTGA GAGAAGAAGG CTTCAGACGA TCAAATTACT CTGAGCTACG |
| 1081 GGAGGACATT CAAACCAAAG GCAAAGAAGT TGAAAACTTT GAAAAAAATT TAGAAGAATG |
| 1141 TATAACTAGA ATAACCAATA CAGAGAAGTG CTTAAAGGAG CTGATGGAGC TGAAAACCAA |
| 1201 GGCTCGAGAA CTACGTGAAG AATGCAGAAG CCTCAGGAGC CGATGCGATC AACTGGAAGA |
| 1261 AAGGGTATCA GCAATGGAAG ATGAAATGAA TGAAATGAAG CGAGAAGGGA AGTTTAGAGA |
| 1321 AAAAAGAATA AAAAGAAATG AGCAAAGCCT CCAAGAAATA TGGGACTATG TGAAAAGACC |
| 1381 AAATCTACGT CTGATTGGTG TACCTGAAAG TGATGTGGAG AATGGAACCA AGTTGGAAAA |
| 1441 CACTCTGCAG GATATTATCC AGGAGAACTT CCCCAATCTA GCAAGGCAGG CCAACGTTCA |
| 1501 GATTCAGGAA ATACAGAGAA CGCCACAAAG ATACTCCTCG AGAAGAGCAA CTCCAAGACA |
| 1561 CATAATTGTC AGATTCACCA AAGTTGAAAT GAAGGAAAAA ATGTTAAGGG CAGCCAGAGA |
| 1621 GAAAGGTCGG GTTACCCTCA AAGGAAAGCC CATCAGACTA ACAGCGGATC TCTCGGCAGA |
| 1681 AACCCTACAA GCCAGAAGAG AGTGGGGGCC AATATTCAAC ATTCTTAAAG AAAAGAATTT |
| 1741 TCAACCCAGA ATTTCATATC CAGCCAAACT AAGCTTCATA AGTGAAGGAG AAATAAAATA |
| 1801 CTTTATAGAC AAGCAAATGT TGAGAGATTT TGTCACCACC AGGCCTGCCC TAAAAGAGCT |
| 1861 CCTGAAGGAA GCGCTAAACA TGGAAAGGAA CAACCGGTAC CAGCCGCTGC AAAATCATGC |
| 1921 CAAAATGTAA AGACCATCAA GACTAGGAAG AAACTGCATC AACTAATGAG CAAAATCACC |
| 1981 AGCTAACATC ATAATGACAG GATCAACTTC ACACATAACA ATATTAACTT TAAATATAAA |
| 2041 TGGACTAAAT TCTGCAATTA AAAGACACAG ACTGGCAAGT TGGATAAAGA GTCAAGACCC |
| 2101 ATCAGTGTGC TGTATTCAGG AAACCCATCT CACGTGCAGA GACACACATA GGCTCAAAAT |
| 2161 AAAAGGATGG AGGAAGATCT ACCAAGCCAA TGGAAAACAA AAAAAGGCAG GGGTTGCAAT |
| 2221 CCTAGTCTCT GATAAAACAG ACTTTAAACC AACAAAGATC AAAAGAGACA AAGAAGGCCA |
| 2281 TTACATAATG GTAAAGGGAT CAATTCAACA AGAGGAGCTA ACTATCCTAA ATATTTATGC |
| 2341 ACCCAATACA GGAGCACCCA GATTCATAAA GCAAGTCCTC AGTGACCTAC AAAGAGACTT |
| 2401 AGACTCCCAC ACATTAATAA TGGGAGACTT TAACACCCCA CTGTCAACAT TAGACAGATC |
| 2461 AACGAGACAG AAAGTCAACA AGGATACCCA GGAATTGAAC TCAGCTCTGC ACCAAGCAGA |
| 2521 CCTAATAGAC ATCTACAGAA CTCTCCACCC CAAATCAACA GAATATACAT TTTTTTCAGC |
| 2581 ACCACACCAC ACCTATTCCA AAATTGACCA CATAGTTGGA AGTAAAGCTC TCCTCAGCAA |
| 2641 ATGTAAAAGA ACAGAAATTA TAACAAACTA TCTCTCAGAC CACAGTGCAA TCAAACTAGA |
| 2701 ACTCAGGATT AAGAATCTCA CTCAAAGCCG CTCAACTACA TGGAAACTGA ACAACCTGCT |
| 2761 CCTGAATGAC TACTGGGTAC ATAACGAAAT GAAGGCAGAA ATAAAGATGT TCTTTGAAAC |
| 2821 CAACGAGAAC AAAGACACCA CATACCAGAA TCTCTGGGAC GCATTCAAAG CAGTGTGTAG |
| 2881 AGGGAAATTT ATAGCACTAA ATGCCTACAA GAGAAAGCAG GAAAGATCCA AAATTGACAC |
| 2941 CCTAACATCA CAATTAAAAG AACTAGAAAA GCAAGAGCAA ACACATTCAA AAGCTAGCAG |
| 3001 AAGGCAAGAA ATAACTAAAA TCAGAGCAGA ACTGAAGGAA ATAGAGACAC AAAAAACCCT |
| 3061 TCAAAAAATC AATGAATCCA GGAGCTGGTT TTTTGAAAGG ATCAACAAAA TTGATAGACC |
| 3121 GCTAGCAAGA CTAATAAAGA AAAAAGAGA GAAGAATCAA ATAGACACAA TAAAAAATGA |
| 3181 TAAAGGGGAT ATCACCACCG ATCCCACAGA AATACAAACT ACCATCAGAG AATACTACAA |
| 3241 ACACCTCTAC GCAAATAAAC TAGAAAATCT AGAAGAAATG GATACATTCC TCGACACATA |
| 3301 CACTCTCCCA AGACTAAACC AGGAAGAAGT TGAATCTCTG AATCGACCAA TAACAGGCTC |
| 3361 TGAAATTGTG GCAATAATCA ATAGTTTACC AACCAAAAAG AGTCCAGGAC CAGATGGATT |
| 3421 CACAGCCGAA TTCTACCAGA GGTACAAGGA GGAACTGGTA CCATTCCTTC TGAAACTATT |
| 3481 CCAATCAATA GAAAAAGAGG GAATCCTCCC TAACTCATTT TATGAGGCCA GCATCATTCT |
| 3541 GATACCAAAG CCGGGCAGAG ACACAACCAA AAAAGAGAAT TTTAGACCAA TATCCTTGAT |
| 3601 GAACATTGAT GCAAAAATCC TCAATAAAAT ACTGGCAAAC CGAATCCAGC AGCACATCAA |
| 3661 AAAGCTTATC CACCATGATC AAGTGGGCTT CATCCCTGGG ATGCAAGGCT GGTTCAATAT |
| 3721 ACGCAAATCA ATAAATGTAA TCCAGCATAT AAACAGAGCC AAAGACAAAA ACCACATGAT |
| 3781 TATCTCAATA GATGCAGAAA AAGCCTTTGA CAAAATTCAA CAACCCTTCA TGCTAAAAAC |

TABLE 8-continued

Plasmid and mRNA construct sequences

```
3841 TCTCAATAAA TTAGGTATTG ATGGGACGTA TTTCAAAATA ATAAGAGCTA TCTATGACAA
3901 ACCCACAGCC AATATCATAC TGAATGGGCA AAAACTGGAA GCATTCCCTT TGAAAACCGG
3961 CACAAGACAG GGATGCCCTC TCTCACCGCT CCTATTCAAC ATAGTGTTGG AAGTTCTGGC
4021 CAGGGCAATC AGGCAGGAGA AGGAAATAAA GGGTATTCAA TTAGGAAAAG AGGAAGTCAA
4081 ATTGTCCCTG TTTGCAGACG ACATGATTGT TTATCTAGAA AACCCCATCG TCTCAGCCCA
4141 AAATCTCCTT AAGCTGATAA GCAACTTCAG CAAAGTCTCA GGATACAAAA TCAATGTACA
4201 AAAATCACAA GCATTCTTAT ACACCAACAA CAGACAAACA GAGAGCCAAA TCATGGGTGA
4261 ACTCCCATTC ACAATTGCTT CAAAGAGAAT AAAATACCTA GGAATCCAAC TTACAAGGGA
4321 TGTGAAGGAC CTCTTCAAGG AGAACTACAA ACCACTGCTC AAGGAAATAA AAGAGGAGAC
4381 AAACAAATGG AAGAACATTC CATGCTCATG GGTAGGAAGA ATCAATATCG TGAAAATGGC
4441 CATACTGCCC AAGGTAATTT ACAGATTCAA TGCCATCCCC ATCAAGCTAC CAATGACTTT
4501 CTTCACAGAA TTGGAAAAAA CTACTTTAAA GTTCATATGG AACCAAAAAA GAGCCCGCAT
4561 TGCCAAGTCA ATCCTAAGCC AAAAGAACAA AGCTGGAGGC ATCACACTAC CTGACTTCAA
4621 ACTATACTAC AAGGCTACAG TAACCAAAAC AGCATGGTAC TGGTACCAAA ACAGAGATAT
4681 AGATCAATGG AACAGAACAG AGCCCTCAGA AATAATGCCG CATATCTACA ACTATCTGAT
4741 CTTTGACAAA CCTGAGAAAA ACAAGCAATG GGGAAAGGAT TCCCTATTTA ATAAATGGTG
4801 CTGGGAAAAC TGGCTAGCCA TATGTAGAAA GCTGAAACTG GATCCCTTCC TTACACCTTA
4861 TACAAAAATC AATTCAAGAT GGATTAAAGA TTTAAACGTT AAACCTAAAA CCATAAAAAC
4921 CCTAGAAGAA AACCTAGGCA TTACCATTCA GGACATAGGC GTGGGCAAGG ACTTCATGTC
4981 CAAAACACCA AAAGCAATGG CAACAAAAGA CAAAATTGAC AAATGGGATC TAATTAAACT
5041 AAAGAGCTTC TGCACAGCAA AAGAAACTAC CATCAGAGTG AACAGGCAAC CTACAACATG
5101 GGAGAAAATT TTTGCAACCT ACTCATCTGA CAAAGGGCTA ATATCCAGAA TCTACAATGA
5161 ACTCAAACAA ATTTACAAGA AAAAAACAAA CAACCCCATC AAAAAGTGGG CGAAGGACAT
5221 GAACAGACAC TTCTCAAAAG AAGACATTTA TGCAGCCAAA AAACACATGA AGAAATGCTC
5281 ATCATCACTG GCCATCAGAG AAATGCAAAT CAAAACCACT ATGAGATATC ATCTCACACC
5341 AGTTAGAATG GCAATCATTA AAAAGTCAGG AAACAACAGG TGCTGGAGAG GATGCGGAGA
5401 AATAGGAACA CTTTTACACT GTTGGTGGGA CTGTAAACTA GTTCAACCAT TGTGGAAGTC
5461 AGTGTGGCGA TTCCTCAGGG ATCTAGAACT AGAAATACCA TTTGACCCAG CCATCCCATT
5521 ACTGGGTATA TACCCAAATG AGTATAAATC ATGCTGCTAT AAAGACACAT GCACACGTAT
5581 GTTTATTGCG GCACTATTCA CAATAGCAAA GACTTGGAAC CAACCCAAAT GTCCAACAAT
5641 GATAGACTGG ATTAAGAAAA TGTGGCACAT ATACACCATG GAATACTATG CAGCCATAAA
5701 AAATGATGAG TTCATATCCT TTGTAGGGAC ATGGATGAAA TTGGAAACCA TCATTCTCAG
5761 TAAACTATCG CAAGAACAAA AAACCAAACA CCGCATATTC TCACTCATAG GTGGGAATTG
5821 AACAATGAGA TCACATGGAC ACAGGAAGGG GAATATCACA CTCTGGGGAC TGTGGTGGGG
5881 TCGGGGGAGG GGGGAGGGAT AGCATTGGGA GATATACCTA ATGCTAGATG ACACATTAGT
5941 GGGTGCAGCG CACCAGCATG GCACATGTAT ACGGATCCGA ATTCTCGACG GATCGATCCG
6001 AACAAACGAC CCAACACCCG TGCGTTTTAT TCTGTCTTTT TATTGCCGAT CCCCTCAGAA
6061 GAACTCGTCA AGAAGGCGAT AGAAGGCGAT GCGCTGCGAA TCGGGAGCGG CGATACCGTA
6121 AAGCACGAGG AAGCGGTCAG CCCATTCGCC GCCAAGCTCT TCAGCAATAT CACGGGTAGC
6181 CAACGCTATG TCCTGATAGC GGTCGGCCGC TCATGTTCTC GTAGGAGTCG GCGTCCTCTT
6241 CGTGGTTAGG TCCAGGTTGG CCTCTGATAG ACCGCAGCTG AGGAGCGGCG TACAGAATGC
6301 CTCTCATGTC CTCATAGCTG CCGCTGCCTT GTGGAGGCTT CTCGTGCTTC AGTGTCTCGT
6361 ATGTCTCTTG ATTCCGGGTG CTCAGGCCGG TGTACACGCC ATCAGATTTC TCGTAGCTGG
6421 TGATGGCGGC CTTCCGCACT TGGATCTTCA GCCGTCTGCA GTACAGGGTG ATGACCAGAG
6481 ACAGCAGCAG GACACCACAT GTGCCAGCCA GAGGGGCCCA AATGTAGATA TCCAGGCCTC
6541 TGGTATGCAC AGCTCCGCCT GCAGCAGGTC TACAGGCTTC AGGTCTGAGA GACAGAGGCT
6601 GGCTGGCGAT TGTAGGAGCT GGTGTAGGTG GTCTAGGAGC GGGTGTTGTT GTAGGCTTGG
6661 CGGGCAGAAA CACGGGCACG AAGTGGCTGA AGTACATGAT GCTATTGCTC AGGGCTCCGC
6721 TTCCTCCGCC GCCTGATTTG ATTTCCAGCT TGGTGCCTCC GCCAAATGTC CAAGGGCTCT
6781 CGTCGTACTG CTGGCAGTAG TAGATGCCGA AGTCCTCGTA CTGCAGGCTG CTGATTGTCA
6841 GGGTGTAGTC GGTGCCAGAG CCGCTGCCAG AAAATCTGCT TGGCACGCCG CTTTCCAGTC
6901 TGTTGGCCCG GTAGATCAGT GTCTTAGGGG CCTTGCCAGG CTTCTGCTGG AACCAGCTCA
6961 GGTAGCTGTT GATGTCCTGG CTGGCTCTAC AGGTGATGGT CACTCTATCG CCCACAGAGG
7021 CAGACAGGCT GCTAGGGCTC TGTGTCATCT GGATATCAGA GCCACCACCG CCAGATCCAC
7081 CGCCACCTGA TCCTCCGCCT CCGCTAGAAA CTGTCACTGT GGTGCCCTGG CCCCACACAT
7141 CGAAGTACCA GTCGTAGCCT CTTCTGGTGC AGAAGTACAC GGCGGTATCC TCGGCTCTCA
7201 GGCTGTTGAT CTGCAGGTAG GCGGTGTTCT TGCTGTCGTC CAGGCTGAAG GTGAATCTGC
7261 CCTTAAAGCT ATCGGCGTAG GTTGGCTCGC CGGTGTGGGT ATTGATCCAG CCCATCCACT
7321 CAAGGCCAGG TGAGTCCAGG AGATGTTTCA GCACTGTTGC CTTTAGTCTC GAGGCAACTT
7381 AGACAACTGA GTATTGATCT GAGCACAGCA GGGTGTGAGC TGTTTGAAGA TACTGGGGTT
7441 GGGGGTGAAG AAACTGCAGA GGACTAACTG GGCTGAGACC CAGTGGCAAT GTTTTAGGGC
7501 CTAAGGAATG CCTCTGAAAA TCTAGATGGA CAACTTTGAC TTTGAGAAAA GAGAGGTGGA
7561 AATGAGGAAA ATGACTTTTC TTTATTAGAT TTCGGTAGAA AGAACTTTCA TCTTTCCCCT
7621 ATTTTTGTTA TTCGTTTTAA AACATCTATC TGGAGGCAGG ACAAGTATGG TCATTAAAAA
7681 GATGCAGGCA GAAGGCATAT ATTGGCTCAG TCAAAGTGGG GAACTTTGGT GGCCAAACAT
7741 ACATTGCTAA GGCTATTCCT ATATCAGCTG GACACATATA AAATGCTGCT AATGCTTCAT
7801 TACAAACTTA TATCCTTTAA TTCCAGATGG GGGCAAAGTA TGTCCAGGGG TGAGGAACAA
7861 TTGAAACATT TGGGCTGGAG TAGATTTTGA AAGTCAGCTC TGTGTGTGTG TGTGTGTGTG
7921 TGTGTGTGAG AGCGTGTGTT TCTTTTAACG TTTTCAGCCT ACAGCATACA GGGTTCATGG
7981 TGGCAAGAAG ATAACAAGAT TTAAATTATG GCCAGTGACT AGTGCTGCAA GAAGAACAAC
8041 TACCTGCATT TAATGGGAAA GCAAAATCTC AGGCTTTGAG GGAAGTTAAC ATAGGCTTGA
8101 TTCTGGGTGG AAGCTGGGTG TGTAGTTATC TGGAGGCCAG GCTGGAGCTC TCAGCTCACT
8161 ATGGGTTCAT CTTTATTGTC TCCTTTTTCC AGGGGCCTGT CGGACCCAGT TCATGCCGTA
8221 GTTGGTGAAG GTGTAGCCGC TGGCGGCACA GCTGATTCTG ACAGATCCGC CAGGTTTCAC
8281 AAGTCCGCCG CCAGACTGAA CCAGCTGGAT CTCAGAGATG CTACAGGCCA CTGTTCCCAG
8341 CAGCAGCAGA GACTGCAGCC ACATCTGGTG GCGAATTCGA AGCTTGAGCT CGAGATCTGA
8401 GTCCGGTAGC GCTAGCGGAT CTGACGGTTC ACTAAACCAG CTCTGCTTAT ATAGACCTCC
8461 CACCGTACAC GCCTACCGCC CATTTGCGTC AATGGGGCGG AGTTGTTACG ACATTTTGGA
```

TABLE 8-continued

Plasmid and mRNA construct sequences

```
 8521 AAGTCCCGTT GATTTTGGTG CCAAAACAAA CTCCCATTGA CGTCAATGGG GTGGAGACTT
 8581 GGAAATCCCC GTGAGTCAAA CCGCTATCCA CGCCCATTGA TGTACTGCCA AAACCGCATC
 8641 ACCATGGTAA TAGCGATGAC TAATACGTAG ATGTACTGCC AAGTAGGAAA GTCCCATAAG
 8701 GTCATGTACT GGGCATAATG CCAGGCGGGC CATTTACCGT CATTGACGTC AATAGGGGGC
 8761 GTACTTGGCA TATGATACAC TTGATGTACT GCCAAGTGGG CAGTTTACCG TAAATACTCC
 8821 ACCCATTGAC GTCAATGGAA AGTCCCTATT GGCGTTACTA TGGGAACATA CGTCATTATT
 8881 GACGTCAATG GGCGGGGGTC GTTGGGCGGT CAGCCAGGCG GGCCATTTAC CGTAAGTTAT
 8941 GTAACGCGGA ACTCCATATA TGGGCTATGA ACTAATGACC CCGTAATTGA TTACTATTAG
 9001 CCCGGGGGAT CCAGACATGA TAAGATACAT TGATGAGTTT GGACAAACCA CAACTAGAAT
 9061 GCAGTGAAAA AAATGCTTTA TTTGTGAAAT TTGTGATGCT ATTGCTTTAT TTGTAACCAT
 9121 TATAAGCTGC AATAAACAAG TTAACAACAA CAATTGCATT CATTTTATGT TTCAGGTTCA
 9181 GGGGGAGGTG TGGGAGGTTT TTTAAAGCAA GTAAAACCTC TACAAATGTG GTATGGCTGA
 9241 TTATGATCCG GCTGCCTCGC GCGTTTCGGT GATGACGGTG AAAACCTCTG ACACATGCAG
 9301 CTCCCGGAGA CGGTCACAGC TTGTCTGTAA GCGGATGCCG GGAGCAGACA AGCCCGTCAG
 9361 GGCGCGTCAG CGGGTGTTGG CGGGTGTCGG GGCGCAGCCA TGAGGTCGAT CGACTCTAGA
 9421 GGATCGATCC CCGCCCCGGA CGAACTAAAC CTGACTACGA CATCTCTGCC CCTTCTTCGC
 9481 GGGGCAGTGC ATGTAATCCC TTCAGTTGGT TGGTACAACT TGCCAACTGG GCCCTGTTCC
 9541 ACATGTGACA CGGGGGGGGA CCAAACACAA AGGGGTTCTC TGACTGTAGT TGACATCCTT
 9601 ATAAATGGAT GTGCACATTT GCCAACACTG AGTGGCTTTC ATCCTGGAGC AGACTTTGCA
 9661 GTCTGTGGAC TGCAACACAA CATTGCCTTT ATGTGTAACT CTTGGCTGAA GCTCTTACAC
 9721 CAATGCTGGG GGACATGTAC CTCCCAGGGG CCCAGGAAGA CTACGGGAGG CTACACCAAC
 9781 GTCAATCAGA GGGGCCTGTG TAGCTACCGA TAAGCGGACC CTCAAGAGGG CATTAGCAAT
 9841 AGTGTTTATA AGGCCCCCTT GTTAACCCTA AACGGGTAGC ATATGCTTCC CGGGTAGTAG
 9901 TATATACTAT CCAGACTAAC CCTAATTCAA TAGCATATGT TACCCAACGG GAAGCATATG
 9961 CTATCGAATT AGGGTTAGTA AAAGGGTCCT AAGGAACAGC GATATCTCCC ACCCCATGAG
10021 CTGTCACGGT TTTATTTACA TGGGGTCAGG ATTCCACGAG GGTAGTGAAC CATTTTAGTC
10081 ACAAGGGCAG TGGCTGAAGA TCAAGGAGCG GGCAGTGAAC TCTCCTGAAT CTTCGCCTGC
10141 TTCTTCATTC TCCTTCGTTT AGCTAATAGA ATAACTGCTG AGTTGTGAAC AGTAAGGTGT
10201 ATGTGAGGTG CTCGAAAACA AGGTTTCAGG TGACGCCCCC AGAATAAAAT TTGGACGGGG
10261 GGTTCAGTGG TGGCATTGTG CTATGACACC AATATAACCC TCACAAACCC CTTGGGCAAT
10321 AAATACTAGT GTAGGAATGA AACATTCTGA ATATCTTTAA CAATAGAAAT CCATGGGGTG
10381 GGGACAAGCC GTAAAGACTG GATGTCCATC TCACACGAAT TTATGGCTAT GGGCAACACA
10441 TAATCCTAGT GCAATATGAT ACTGGGGTTA TTAAGATGTG TCCCAGGCAG GGACCAAGAC
10501 AGGTGAACCA TGTTGTTACA CTCTATTTGT AACAAGGGGA AAGAGAGTGG ACGCCGACAG
10561 CAGCGGACTC CACTGGTTGT CTCTAACACC CCCGAAAATT AAACGGGGCT CCACGCCAAT
10621 GGGGCCCATA AACAAAGACA AGTGGCCACT CTTTTTTTTG AAATTGTGGA GTGGGGGCAC
10681 GCGTCAGCCC CCACACGCCG CCCTGCGGTT TTGGACTGTA AAATAAGGGT GTAATAACTT
10741 GGCTGATTGT AACCCCGCTA ACCACTGCGG TCAAACCACT TGCCCACAAA ACCACTAATG
10801 GCACCCCGGG GAATACCTGC ATAAGTAGGT GGGCGGGCCA AGATAGGGGC GCGATTGCTG
10861 CGATCTGGAG GACAAATTAC ACACACTTGC GCCTGAGCGC CAAGCACAGG GTTGTTGGTC
10921 CTCATATTCA CGAGGTCGCT GAGAGCACGG TGGGCTAATG TTGCCATGGG TAGCATATAC
10981 TACCCAAATA TCTGGATAGC ATATGCTATC CTAATCTATA TCTGGGTAGC ATAGGCTATC
11041 CTAATCTATA TCTGGGTAGC ATATGCTATC CTAATCTATA TCTGGGTAGT ATATGCTATC
11101 CTAATTTATA TCTGGGTAGC ATAGGCTATC CTAATCTATA TCTGGGTAGC ATATGCTATC
11161 CTAATCTATA TCTGGGTAGT ATATGCTATC CTAATCTGTA TCCGGGTAGC ATATGCTATC
11221 CTAATAGAGA TTAGGGTAGT ATATGCTATC CTAATTTATA TCTGGGTAGC ATATACTACC
11281 CAAATATCTG GATAGCATAT GCTATCCTAA TCTATATCTG GGTAGCATAT GCTATCCTAA
11341 TCTATATCTG GGTAGCATAG GCTATCCTAA TCTATATCTG GGTAGCATAT GCTATCCTAA
11401 TCTATATCTG GGTAGTATAT GCTATCCTAA TTTATATCTG GGTAGCATAG GCTATCCTAA
11461 TCTATATCTG GGTAGCATAT GCTATCCTAA TCTATATCTG GGTAGTATAT GCTATCCTAA
11521 TCTGTATCCG GGTAGCATAT GCTATCCTCA TGCATATACA GTCAGCATAT GATACCCAGT
11581 AGTAGAGTGG GAGTGCTATC CTTTGCATAT GCCGCCACCT CCCAAGGGGG CGTGAATTTT
11641 CGCTGCTTGT CCTTTTCCTG CATGCTGGTT GCTCCCATTC TTAGGTGAAT TTAAGGAGGC
11701 CAGGCTAAAG CCGTCGCATG TCTGATTGCT CACCAGGTAA ATGTCGCTAA TGTTTTCCAA
11761 CGCGAGAAGG TGTTGAGCGC GGAGCTGAGT GACGTGACAA CATGGGTATG CCCAATTGCC
11821 CCATGTTGGG AGGACGAAAA TGGTGACAAG ACAGATGGCC AGAAATACAC CAACAGCACG
11881 CATGATGTCT ACTGGGGATT TATTCTTTAG TGCGGGGGAA TACACGGCTT TTAATACGAT
11941 TGAGGGCGTC TCCTAACAAG TTACATCACT CCTGCCCTTC CTCACCCTCA TCTCCATCAC
12001 CTCCTTCATC TCCGTCATCT CCGTCATCAC CCTCCGCGGC AGCCCCTTCC ACCATAGGTG
12061 GAAACCAGGG AGGCAAATCT ACTCCATCGT CAAAGCTGCA CACAGTCACC CTGATATTGC
12121 AGGTAGGAGC GGGCTTTGTC ATAACAAGGT CCTTAATCGC ATCCTTCAAA ACCTCAGCAA
12181 ATATATGAGT TTGTAAAAAG ACCATGAAAT AACAGACAAT GGACTCCCTT AGCGGGCCAG
12241 GTTGTGGGCC GGGTCCAGGG GCCATTCCAA AGGGGAGACG ACTCAATGGT GTAAGACGAC
12301 ATTGTGGAAT AGCAAGGGCA GTTCCTCGCC TTAGGTTGTA AAGGGAGGTC TTACTACCTC
12361 CATATACGAA CACACCGGCG ACCCAAGTTC CTTCGTCGGT AGTCCTTTCT ACGTGACTCC
12421 TAGCCAGGAG AGCTCTTAAA CCTTCTGCAA TGTTCTCAAA TTTCGGGTTG GAACCTCCTT
12481 GACCACGATG CTTTCCAAAC CACCCTCCTT TTTTGCGCCT GCCTCCATCA CCCTGACCCC
12541 GGGGTCCAGT GCTTGGGCCT TCTCCTGGGT CATCTGCGGG GCCCTGCTCT ATCGCTCCCG
12601 GGGGCACGTC AGGCTCACCA TCTGGGCCAC CTTCTTGGTG GTATTCAAAA TAATCGGCTT
12661 CCCCTACAGG GTGGAAAAAT GGCCTTCTAC CTGGAGGGGG CCTGCGCGGT GGAGACCCGG
12721 ATGATGATGA CTGACTACTG GGACTCCTGG GCCTCTTTTC TCCACGTCCA CGACCTCTCC
12781 CCCTGGCTCT TTCACGACTT CCCCCCCTGG CTCTTTCACG TCCTCTACCC CGGCGGCCTC
12841 CACTACCTCC TCGACCCCGG CCTCCACTAC CTCCTCGACC CCGGCCTCCA CTGCCTCCTC
12901 GACCCCGGCC TCCACCTCCT GCTCCTGCCC CTCCTGCTCC TGCCCCTCCT CCTGCTCCTG
12961 CCCCTCCTGC CCCTCCTGCT CCTGCCCCTC CTGCCCCTCC TGCTCCTGCC CCTCCTGCCC
13021 CTCCTGCTCC TGCCCCTCCT GCCCCTCCTC CTGCTCCTGC CCCTCCTGCC CCTCCTCCTG
13081 CTCCTGCCCC TCCTGCCCCT CCTGCTCCTG CCCCTCCTGC CCCTCCTGCT CCTGCCCCTC
13141 CTGCCCCTCC TGCTCCTGCC CCTCCTGCTC CTGCCCCTCC TGCTCCTGCC CCTCCTGCTC
```

TABLE 8-continued

| Plasmid and mRNA construct sequences |
|---|
| 13201 CTGCCCCTCC TGCCCCTCCT GCCCCTCCTC CTGCTCCTGC CCCTCCTGCT CCTGCCCCTC |
| 13261 CTGCCCCTCC TGCCCCTCCT GCTCCTGCCC CTCCTCCTGC TCCTGCCCCT CCTGCCCCTC |
| 13321 CTGCCCCTCC TCCTGCTCCT GCCCCTCCTG CCCCTCCTCC TGCTCCTGCC CCTCCTCCTG |
| 13381 CTCCTGCCCC TCCTGCCCCT CCTGCCCCTC CTCCTGCTCC TGCCCCTCCT GCCCCTCCTC |
| 13441 CTGCTCCTGC CCCTCCTCCT GCTCCTGCCC CTCCTGCCCC TCCTGCCCCT CCTCCTGCTC |
| 13501 CTGCCCCTCC TCCTGCTCCT GCCCCTCCTG CCCCTCCTGC CCCTCCTGCC CCTCCTCCTG |
| 13561 CTCCTGCCCC TCCTCCTGCT CCTGCCCCTC CTGCTCCTGC CCCTCCCGCT CCTGCTCCTG |
| 13621 CTCCTGTTCC ACCGTGGGTC CCTTTGCAGC CAATGCAACT TGGACGTTTT TGGGGTCTCC |
| 13681 GGACACCATC TCTATGTCTT GGCCCTGATC CTGAGCCGCC CGGGGCTCCT GGTCTTCCGC |
| 13741 CTCCTCGTCC TCGTCCTCTT CCCCGTCCTC GTCCATGGTT ATCACCCCCT CTTCTTTGAG |
| 13801 GTCCACTGCC GCCGGAGCCT TCTGGTCCAG ATGTGTCTCC CTTCTCTCCT AGGCCATTTC |
| 13861 CAGGTCCTGT ACCTGGCCCC TCGTCAGACA TGATTCACAC TAAAAGAGAT CAATAGACAT |
| 13921 CTTTATTAGA CGACGCTCAG TGAATACAGG GAGTGCAGAC TCCTGCCCCC TCCAACAGCC |
| 13981 CCCCCACCCT CATCCCCTTC ATGGTCGCTG TCAGACAGAT CCAGGTCTGA AAATTCCCCA |
| 14041 TCCTCCGAAC CATCCTCGTC CTCATCACCA ATTACTCGCA GCCCGGAAAA CTCCCGCTGA |
| 14101 ACATCCTCAA GATTTGCGTC CTGAGCCTCA AGCCAGGCCT CAAATTCCTC GTCCCCCTTT |
| 14161 TTGCTGGACG GTAGGGATGG GGATTCTCGG GACCCCTCCT CTTCCTCTTC AAGGTCACCA |
| 14221 GACAGAGATG CTACTGGGGC AACGGAAGAA AAGCTGGGTG CGGCCTGTGA GGATCAGCTT |
| 14281 ATCGATGATA AGCTGTCAAA CATGAGAATT CTTGAAGACG AAAGGGCCTC GTGATACGCC |
| 14341 TATTTTTATA GGTTAATGTC ATGATAATAA TGGTTTCTTA GACGTCAGGT GGCACTTTTC |
| 14401 GGGGAAATGT GCGCGGAACC CCTATTTGTT TATTTTTCTA AATACATTCA AATATGTATC |
| 14461 CGCTCATGAG ACAATAACCC TGATAAATGC TTCAATAATA TTGAAAAAGG AAGAGTATGA |
| 14521 GTATTCAACA TTTCCGTGTC GCCCTTATTC CCTTTTTTGC GGCATTTTGC CTTCCTGTTT |
| 14581 TTGCTCACCC AGAAACGCTG GTGAAAGTAA AAGATGCTGA AGATCAGTTG GGTGCACGAG |
| 14641 TGGGTTACAT CGAACTGGAT CTCAACAGCG GTAAGATCCT TGAGAGTTTT CGCCCCGAAG |
| 14701 AACGTTTTCC AATGATGAGC ACTTTTAAAG TTCTGCTATG TGGCGCGGTA TTATCCCGTG |
| 14761 TTGACGCCGG GCAAGAGCAA CTCGGTCGCC GCATACACTA TTCTCAGAAT GACTTGGTTG |
| 14821 AGTACTCACC AGTCACAGAA AAGCATCTTA CGGATGGCAT GACAGTAAGA GAATTATGCA |
| 14881 GTGCTGCCAT AACCATGAGT GATAACACTG CGGCCAACTT ACTTCTGACA ACGATCGGAG |
| 14941 GACCGAAGGA GCTAACCGCT TTTTTGCACA ACATGGGGGA TCATGTAACT CGCCTTGATC |
| 15001 GTTGGGAACC GGAGCTGAAT GAAGCCATAC CAAACGACGA GCGTGACACC ACGATGCCTG |
| 15061 CAGCAATGGC AACAACGTTG CGCAAACTAT TAACTGGCGA ACTACTTACT CTAGCTTCCC |
| 15121 GGCAACAATT AATAGACTGG ATGGAGGCGG ATAAAGTTGC AGGACCACTT CTGCGCTCGG |
| 15181 CCCTTCCGGC TGGCTGGTTT ATTGCTGATA AATCTGGAGC CGGTGAGCGT GGGTCTCGCG |
| 15241 GTATCATTGC AGCACTGGGG CCAGATGGTA AGCCCTCCCG TATCGTAGTT ATCTACACGA |
| 15301 CGGGGAGTCA GGCAACTATG GATGAACGAA ATAGACAGAT CGCTGAGATA GGTGCCTCAC |
| 15361 TGATTAAGCA TTGGTAACTG TCAGACCAAG TTTACTCATA TATACTTTAG ATTGATTTAA |
| 15421 AACTTCATTT TTAATTTAAA AGGATCTAGG TGAAGATCCT TTTTGATAAT CTCATGACCA |
| 15481 AAATCCCTTA ACGTGAGTTT TCGTTCCACT GAGCGTCAGA CCCCGTAGAA AAGATCAAAG |
| 15541 GATCTTCTTG AGATCCTTTT TTTCTGCGCG TAATCTGCTG CTTGCAAACA AAAAAACCAC |
| 15601 CGCTACCAGC GGTGGTTTGT TTGCCGGATC AAGAGCTACC AACTCTTTTT CCGAAGGTAA |
| 15661 CTGGCTTCAG CAGAGCGCAG ATACCAAATA CTGTCCTTCT AGTGTAGCCG TAGTTAGGCC |
| 15721 ACCACTTCAA GAACTCTGTA GCACCGCCTA CATACCTCGC TCTGCTAATC CTGTTACCAG |
| 15781 TGGCTGCTGC CAGTGGCGAT AAGTCGTGTC TTACCGGGTT GGACTCAAGA CGATAGTTAC |
| 15841 CGGATAAGGC GCAGCGGTCG GGCTGAACGG GGGGTTCGTG CACACAGCCC AGCTTGGAGC |
| 15901 GAACGACCTA CACCGAACTG AGATACCTAC AGCGTGAGCT ATGAGAAAGC GCCACGCTTC |
| 15961 CCGAAGGGAG AAAGGCGGAC AGGTATCCGG TAAGCGGCAG GGTCGGAACAGGAGAGCGCA |
| 16021 CGAGGGAGCT TCCAGGGGGA AACGCCTGGT ATCTTTATAG TCCTGTCGGG TTTCGCCACC |
| 16081 TCTGACTTGA GCGTCGATTT TTGTGATGCT CGTCAGGGGG GCGGAGCCTA TGGAAAAACG |
| 16141 CCAGCAACGC GGCCTTTTTA CGGTTCCTGG CCTTTTGCTG GCCTTTTGCT CACATGTTCT |
| 16201 TTCCTGCGTT ATCCCCTGAT TCTGTGGATA ACCGTATTAC CGCCTTTGAG TGAGCTGATA |
| 16261 CCGCTCGCCG CAGCCGAACG ACCGAGCGCA GCGAGTCAGT GAGCGAGGAA GCGGAAGAGC |
| 16321 GCCTGATGCG GTATTTTCTC CTTACGCATC TGTGCGGTAT TTCACACCGC ATATGGTGCA |
| 16381 CTCTCAGTAC AATCTGCTCT GATGCCGCAT AGTTAAGCCA GCTGTGGAAT GTGTGTCAGT |
| 16441 TAGGGTGTGG AAAGTCCCCA GGCTCCCCAG CAGGCAGAAG TATGCAAAGC ATGCATCTCA |
| 16501 ATTAGTCAGC AACCAGGTGT GGAAAGTCCC CAGGCTCCCC AGCAGGCAGA AGTATGCAAA |
| 16561 GCATGCATCT CAATTAGTCA GCAACCATAG TCCCGCCCCT AACTCCGCCC ATCCCGCCCC |
| 16621 TAACTCCGCC CAGTTCCGCC CATTCTCCGC CCCATGGCTG ACTAATTTTT TTTATTTATG |
| 16681 CAGAGGCCGA GGCCGCCTCG GCCTCTGAGC TATTCCAGAA GTAGTGAGGA GGCTTTTTTG |
| 16741 GAGGCCTAGG CTTTTGCAAA AAGCTTGCAT GCCTGCAGGT CGGCCGCCAC GACCGGTGCC |
| 16801 GCCACCATCC CCTGACCCAC GCCCCTGACC CCTCACAAGG AGACGACCTT CCATGACCGA |
| 16861 GTACAAGCCC ACGGTGCGCC TCGCCACCCG CGACGACGTC CCCCGGGCCG TACGCACCCT |
| 16921 CGCCGCCGCG TTCGCCGACT ACCCCGCCAC GCGCCACACC GTCGACCCGG ACCGCCACAT |
| 16981 CGAGCGGGTC ACCGAGCTGC AAGAACTCTT CCTCACGCGC GTCGGGCTCG ACATCGGCAA |
| 17041 GGTGTGGGTC GCGGACGACG GCGCCGCGGT GGCGGTCTGG ACCACGCCGG AGAGCGTCGA |
| 17101 AGCGGGGGCG GTGTTCGCCG AGATCGGCCC GCGCATGGCC GAGTTGAGCG GTTCCCGGCT |
| 17161 GGCCGCGCAG CAACAGATGG AAGGCCTCCT GGCGCCGCAC CGGCCCAAGG AGCCCGCGTG |
| 17221 GTTCCTGGCC ACCGTCGGCG TCTCGCCCGA CCACCAGGGC AAGGGTCTGG GCAGCGCCGT |
| 17281 CGTGCTCCCC GGAGTGGAGG CGGCCGAGCG CGCCGGGGTG CCCGCCTTCC TGGAGACCTC |
| 17341 CGCGCCCCGC AACCTCCCCT TCTACGAGCG GCTCGGCTTC ACCGTCACCG CCGACGTCGA |
| 17401 GGTGCCCGAA GGACCGCGCA CCTGGTGCAT GACCCGCAAG CCCGGTGCCT GACGCCCGCC |
| 17461 CCACGACCCG CAGCGCCCGA CCGAAAGGAG CGCACGACCC CATGGCTCCG ACCGAAGCCG |
| 17521 ACCCGGGCGG CCCCGCCGAC CCCGCACCCG CCCCCGAGGC CCACCGACTC TAGAGGATCA |
| 17581 TAATCAGCCA TACCACATTT GTAGAGGTTT TACTTGCTTT AAAAAACCTC CCACACCTCC |
| 17641 CCCTGAACCT GAAACATAAA ATGAATGCAA TTGTTGTTGT TAACTTGTTT ATTGCAGCTT |
| 17701 ATAATGGTTA CAAATAAAGC AATAGCATCA CAAATTTCAC AAATAAAGCA TTTTTTTCAC |
| 17761 TGCATTCTAG TTGTGGTTTG TCCAAACTCA TCAATGTATC TTATCATGTC TGGATCACTC |
| 17821 GCCGATAGTG GAAACCGACG CCCCAGCACT CGTCCGAGGG CAAAGGAATA GGGGAGATGG |

TABLE 8-continued

| Plasmid and mRNA construct sequences |
|---|
| 17881 GGGAGGCTAA CTGAAACACG GAAGGAGACA ATACCGGAAG GAACCCGCGC TATGACGGCA |
| 17941 ATAAAAAGAC AGAATAAAAC GCACGGGTGT TGGGTCGTTT GTTCATAAAC GCGGGGTTCG |
| 18001 GTCCCAGGGC TGGCACTCTG TCGATACCCC ACCGAGACCC CATTGGGGCC AATACGCCCG |
| 18061 CGTTTCTTCC TTTTCCCCAC CCCACCCCCC AAGTTCGGGT GAAGGCCCAG GGCTCGCAGC |
| 18121 CAACGTCGGG GCGGCAGGCC CTGCCATAGC CACTGGCCCC GTGGGTTAGG GACGGGGTCC |
| 18181 CCCATGGGGA ATGGTTTATG GTTCGTGGGG GTTATTATTT TGGGCGTTGC GTGGGGTCTG |
| 18241 GTCCACGACT GGACTGAGCA GACAGACCCA TGGTTTTTGG ATGGCCTGGG CATGGACCGC |
| 18301 ATGTACTGGC GCGACACGAA CACCGGGCGT CTGTGGCTGC CAAACACCCC CGACCCCCAA |
| 18361 AAACCACCGC GCGGATTTCT GGCGTGCCAA GCTAGTCGAC CAATTCTCAT GTTTGACAGC |
| 18421 TTATCATCGC AGATCCGGGC AACGTTGTTG CATTGCTGCA GGCGCAGAAC TGGTAGGTAT |
| 18481 GGAAGATCTC TAGAAGCTGG GTACCAGCTG CTAGCAAGCT TGCTAGCGGC CGGCTCGAGT |
| 18541 TTACTCCCTA TCAGTGATAG AGAACGTATG TCGAGTTTAC TCCCTATCAG TGATAGAGAA |
| 18601 CGATGTCGAG TTTACTCCCT ATCAGTGATA GAGAACGTAT GTCGAGTTTA CTCCCTATCA |
| 18661 GTGATAGAGA ACGTATGTCG AGTTTACTCC CTATCAGTGA TAGAGAACGT ATGTCGAGTT |
| 18721 TATCCCTATC AGTGATAGAG AACGTATGTC GAGTTTACTC CCTATCAGTG ATAGAGAACG |
| 18781 TATGTCGAGG TAGGCGTGTA CGGTGGGAGG CCTATATAAG CAGAGCTCGT TTAGTGAACC |
| 18841 GTCAGATCGC CG |
| (SEQ ID NO: 39) |
| |
| LINE-1plasmid-CD5_FCR-PI3K_T2A-GFPintron (SEQ ID NO: 40) |
| 1 CGGCCGCGGG GGGAGGAGCC AAGATGGCCG AATAGGAACA GCTCCGGTCT ACAGCTCCCA |
| 61 GCGTGAGCGA CGCAGAAGAC GGTGATTTCT GCATTTCCAT CTGAGGTACC GGGTTCATCT |
| 121 CACTAGGGAG TGCCAGACAG TGGGCGCAGG CCAGTGTGTG TGCGCACCGT GCGCGAGCCG |
| 181 AAGCAGGGCG AGGCATTGCC TCACCTGGGA AGCGCAAGGG GTCAGGGAGT TCCCTTTCCG |
| 241 AGTCAAAGAA AGGGGTGACG GACGCACCTG GAAAATCGGG TCACTCCCAC CCGAATATTG |
| 301 CGCTTTTCAG ACCGGCTTAA GAAACGGCGC ACCACGAGAC TATATCCCAC ACCTGGCTCG |
| 361 GAGGGTCCTA CGCCCACGGA ATCTCGCTGA TTGCTAGCAC AGCAGTCTGA GATCAAACTG |
| 421 CAAGGCGGCA ACGAGGCTGG GGGAGGGGCG CCCGCCATTG CCCAGGCTTG CTTAGGTAAA |
| 481 CAAAGCAGCA GGGAAGCTCG AACTGGGTGG AGCCCACCAC AGCTCAAGGA GGCCTGCCTG |
| 541 CCTCTGTAGG CTCCACCTCT GGGGGCAGGG CACAGACAAA CAAAAAGACA GCAGTAACCT |
| 601 CTGCAGACTT AAGTGTCCCT GTCTGACAGC TTTGAAGAGA GCAGTGGTTC TCCCAGCACG |
| 661 CAGCTGGAGA TCTGAGAACG GGCAGACTGC CTCCTCAAGT GGGTCCCTGA CCCCTGACCC |
| 721 CCGAGCAGCC TAACTGGGAG GCACCCCCCA GCAGGGGCAC ACTGACACCT CACACGGCAG |
| 781 GGTATTCCAA CAGACCTGCA GCTGAGGGTC CTGTCTGTTA GAAGGAAAAC TAACAACCAG |
| 841 AAAGGACATC TACACCGAAA ACCCATCTGT ACATCACCAT CATCAAAGAC CAAAAGTAGA |
| 901 TAAAACCACA AAGATGGGGA AAAAACAGAA CAGAAAAACT GGAAACTCTA AAACGCAGAG |
| 961 CGCCTCTCCT CCTCCAAAGG AACGCAGTTC CTCACCAGCA ACAGAACAAA GCTGGATGGA |
| 1021 GAATGATTTT GATGAGCTGA GAGAAGAAGG CTTCAGACGA TCAAATTACT CTGAGCTACG |
| 1081 GGAGGACATT CAAACCAAAG GCAAAGAAGT TGAAAACTTT GAAAAAAATT TAGAAGAATG |
| 1141 TATAACTAGA ATAACCAATA CAGAGAAGTG CTTAAAGGAG CTGATGGAGC TGAAAACCAA |
| 1201 GGCTCGAGAA CTACGTGAAG AATGCAGAAG CCTCAGGAGC CGATGCGATC AACTGGAAGA |
| 1261 AAGGGTATCA GCAATGGAAG ATGAAATGAA TGAAATGAAG CGAGAAGGGA AGTTTAGAGA |
| 1321 AAAAAGAATA AAAAGAAATG AGCAAAGCCT CCAAGAAATA TGGGACTATG TGAAAAGACC |
| 1381 AAATCTACGT CTGATTGGTG TACCTGAAAG TGATGTGGAG AATGGAACCA AGTTGGAAAA |
| 1441 CACTCTGCAG GATATTATCC AGGAGAACTT CCCCAATCTA GCAAGGCAGG CCAACGTTCA |
| 1501 GATTCAGGAA ATACAGAGAA CGCCACAAAG ATACTCCTCG AGAAGAGCAA CTCCAAGACA |
| 1561 CATAATTGTC AGATTCACCA AAGTTGAAAT GAAGGAAAAA ATGTTAAGGG CAGCCAGAGA |
| 1621 GAAAGGTCGG GTTACCCTCA AAGGAAAGCC CATCAGACTA ACAGCGGATC TCTCGGCAGA |
| 1681 AACCCTACAA GCCAGAAGAG AGTGGGGGCC AATATTCAAC ATTCTTAAAG AAAAGAATTT |
| 1741 TCAACCCAGA ATTTCATATC CAGCCAAACT AAGCTTCATA AGTGAAGGAG AAATAAAATA |
| 1801 CTTTATAGAC AAGCAAATGT TGAGAGATTT TGTCACCACC AGGCCTGCCC TAAAAGAGCT |
| 1861 CCTGAAGGAA GCGCTAAACA TGGAAAGGAA CAACCGGTAC CAGCCGCTGC AAAATCATGC |
| 1921 CAAAATGTAA AGACCATCAA GACTAGGAAG AAACTGCATC AACTAATGAG CAAAATCACC |
| 1981 AGCTAACATC ATAATGACAG GATCAACTTC ACACATAACA ATATTAACTT TAAATATAAA |
| 2041 TGGACTAAAT TCTGCAATTA AAAGACACAG ACTGGCAAGT TGGATAAAGA GTCAAGACCC |
| 2101 ATCAGTGTGC TGTATTCAGG AAACCCATCT CACGTGCAGA GACACACATA GGCTCAAAAT |
| 2161 AAAAGGATGG AGGAAGATCT ACCAAGCCAA TGGAAAACAA AAAAAGGCAG GGGTTGCAAT |
| 2221 CCTAGTCTCT GATAAAACAG ACTTTAAACC AACAAAGATC AAAAGAGACA AAGAAGGCCA |
| 2281 TTACATAATG GTAAAGGGAT CAATTCAACA AGAGGAGCTA ACTATCCTAA ATATTTATGC |
| 2341 ACCCAATACA GGAGCACCCA GATTCATAAA GCAAGTCCTC AGTGACCTAC AAAGAGACTT |
| 2401 AGACTCCCAC ACATTAATAA TGGGAGACTT TAACACCCCA CTGTCAACAT TAGACAGATC |
| 2461 AACGAGACAG AAAGTCAACA AGGATACCCA GGAATTGAAC TCAGCTCTGC ACCAAGCAGA |
| 2521 CCTAATAGAC ATCTACAGAA CTCTCCACCC CAAATCAACA GAATATACAT TTTTTTCAGC |
| 2581 ACCACACCAC ACCTATTCCA AAATTGACCA CATAGTTGGA AGTAAAGCTC TCCTCAGCAA |
| 2641 ATGTAAAAGA ACAGAAATTA TAACAAACTA TCTCTCAGAC CACAGTGCAA TCAAACTAGA |
| 2701 ACTCAGGATT AAGAATCTCA CTCAAAGCCG CTCAACTACA TGGAAACTGA ACAACCTGCT |
| 2761 CCTGAATGAC TACTGGGTAC ATAACGAAAT GAAGGCAGAA ATAAAGATGT TCTTTGAAAC |
| 2821 CAACGAGAAC AAAGACACCA CATACCAGAA TCTCTGGGAC GCATTCAAAG CAGTGTGTAG |
| 2881 AGGGAAATTT ATAGCACTAA ATGCCTACAA GAGAAAGCAG GAAAGATCCA AAATTGACAC |
| 2941 CCTAACATCA CAATTAAAAG AACTAGAAAA GCAAGAGCAA ACACATTCAA AAGCTAGCAG |
| 3001 AAGGCAAGAA ATAACTAAAA TCAGAGCAGA ACTGAAGGAA ATAGAGACAC AAAAAACCCT |
| 3061 TCAAAAAATC AATGAATCCA GGAGCTGGTT TTTTGAAAGG ATCAACAAAA TTGATAGACC |
| 3121 GCTAGCAAGA CTAATAAAGA AAAAAGAGA GAAGAATCAA ATAGACACAA TAAAAAATGA |
| 3181 TAAAGGGGAT ATCACCACCG ATCCCACAGA AATACAAACT ACCATCAGAG AATACTACAA |
| 3241 ACACCTCTAC GCAAATAAAC TAGAAAATCT AGAAGAAATG GATACATTCC TCGACACATA |
| 3301 CACTCTCCCA AGACTAAACC AGGAAGAAGT TGAATCTCTG AATCGACCAA TAACAGGCTC |
| 3361 TGAAATTGTG GCAATAATCA ATAGTTTACC AACCAAAAAG AGTCCAGGAC CAGATGGATT |
| 3421 CACAGCCGAA TTCTACCAGA GGTACAAGGA GGAACTGGTA CCATTCCTTC TGAAACTATT |

TABLE 8-continued

| Plasmid and mRNA construct sequences |
|---|
| 3481 CCAATCAATA GAAAAAGAGG GAATCCTCCC TAACTCATTT TATGAGGCCA GCATCATTCT |
| 3541 GATACCAAAG CCGGGCAGAG ACACAACCAA AAAAGAGAAT TTTAGACCAA TATCCTTGAT |
| 3601 GAACATTGAT GCAAAAATCC TCAATAAAAT ACTGGCAAAC CGAATCCAGC AGCACATCAA |
| 3661 AAAGCTTATC CACCATGATC AAGTGGGCTT CATCCCTGGG ATGCAAGGCT GGTTCAATAT |
| 3721 ACGCAAATCA ATAAATGTAA TCCAGCATAT AAACAGAGCC AAAGACAAAA ACCACATGAT |
| 3781 TATCTCAATA GATGCAGAAA AAGCCTTTGA CAAAATTCAA CAACCCTTCA TGCTAAAAAC |
| 3841 TCTCAATAAA TTAGGTATTG ATGGGACGTA TTTCAAAATA ATAAGAGCTA TCTATGACAA |
| 3901 ACCCACAGCC AATATCATAC TGAATGGGCA AAAACTGGAA GCATTCCCTT TGAAAACCGG |
| 3961 CACAAGACAG GGATGCCCTC TCTCACCGCT CCTATTCAAC ATAGTGTTGG AAGTTCTGGC |
| 4021 CAGGGCAATC AGGCAGGAGA AGGAAATAAA GGGTATTCAA TTAGGAAAAG AGGAAGTCAA |
| 4081 ATTGTCCCTG TTTGCAGACG ACATGATTGT TTATCTAGAA AACCCCATCG TCTCAGCCCA |
| 4141 AAATCTCCTT AAGCTGATAA GCAACTTCAG CAAAGTCTCA GGATACAAAA TCAATGTACA |
| 4201 AAAATCACAA GCATTCTTAT ACACCAACAA CAGACAAACA GAGAGCCAAA TCATGGGTGA |
| 4261 ACTCCCATTC ACAATTGCTT CAAAGAGAAT AAAATACCTA GGAATCCAAC TTACAAGGGA |
| 4321 TGTGAAGGAC CTCTTCAAGG AGAACTACAA ACCACTGCTC AAGGAAATAA AAGAGGAGAC |
| 4381 AAACAAATGG AAGAACATTC CATGCTCATG GGTAGGAAGA ATCAATATCG TGAAAATGGC |
| 4441 CATACTGCCC AAGGTAATTT ACAGATTCAA TGCCATCCCC ATCAAGCTAC CAATGACTTT |
| 4501 CTTCACAGAA TTGGAAAAAA CTACTTTAAA GTTCATATGG AACCAAAAAA GAGCCCGCAT |
| 4561 TGCCAAGTCA ATCCTAAGCC AAAAGAACAA AGCTGGAGGC ATCACACTAC CTGACTTCAA |
| 4621 ACTATACTAC AAGGCTACAG TAACCAAAAC AGCATGGTAC TGGTACCAAA ACAGAGATAT |
| 4681 AGATCAATGG AACAGAACAG AGCCCTCAGA AATAATGCCG CATATCTACA ACTATCTGAT |
| 4741 CTTTGACAAA CCTGAGAAAA ACAAGCAATG GGGAAAGGAT TCCCTATTTA ATAAATGGTG |
| 4801 CTGGGAAAAC TGGCTAGCCA TATGTAGAAA GCTGAAACTG GATCCCTTCC TTACACCTTA |
| 4861 TACAAAAATC AATTCAAGAT GGATTAAAGA TTTAAACGTT AAACCTAAAA CCATAAAAAC |
| 4921 CCTAGAAGAA AACCTAGGCA TTACCATTCA GGACATAGGC GTGGGCAAGG ACTTCATGTC |
| 4981 CAAAACACCA AAAGCAATGG CAACAAAAGA CAAAATTGAC AAATGGGATC TAATTAAACT |
| 5041 AAAGAGCTTC TGCACAGCAA AAGAAACTAC CATCAGAGTG AACAGGCAAC CTACAACATG |
| 5101 GGAGAAAATT TTTGCAACCT ACTCATCTGA CAAAGGGCTA ATATCCAGAA TCTACAATGA |
| 5161 ACTCAAACAA ATTTACAAGA AAAAAACAAA CAACCCCATC AAAAAGTGGG CGAAGGACAT |
| 5221 GAACAGACAC TTCTCAAAAG AAGACATTTA TGCAGCCAAA AAACACATGA AGAAATGCTC |
| 5281 ATCATCACTG GCCATCAGAG AAATGCAAAT CAAAACCACT ATGAGATATC ATCTCACACC |
| 5341 AGTTAGAATG GCAATCATTA AAAAGTCAGG AAACAACAGG TGCTGGAGAG GATGCGGAGA |
| 5401 AATAGGAACA CTTTTACACT GTTGGTGGGA CTGTAAACTA GTTCAACCAT TGTGGAAGTC |
| 5461 AGTGTGGCGA TTCCTCAGGG ATCTAGAACT AGAAATACCA TTTGACCCAG CCATCCCATT |
| 5521 ACTGGGTATA TACCCAAATG AGTATAAATC ATGCTGCTAT AAAGACACAT GCACACGTAT |
| 5581 GTTTATTGCG GCACTATTCA CAATAGCAAA GACTTGGAAC CAACCCAAAT GTCCAACAAT |
| 5641 GATAGACTGG ATTAAGAAAA TGTGGCACAT ATACACCATG GAATACTATG CAGCCATAAA |
| 5701 AAATGATGAG TTCATATCCT TTGTAGGGAC ATGGATGAAA TTGGAAACCA TCATTCTCAG |
| 5761 TAAACTATCG CAAGAACAAA AAACCAAACA CCGCATATTC TCACTCATAG GTGGGAATTG |
| 5821 AACAATGAGA TCACATGGAC ACAGGAAGGG GAATATCACA CTCTGGGGAC TGTGGTGGGG |
| 5881 TCGGGGGAGG GGGGAGGGAT AGCATTGGGA GATATACCTA ATGCTAGATG ACACATTAGT |
| 5941 GGGTGCAGCG CACCAGCATG GCACATGTAT ACGGATCCGA ATTCTCGACG GATCGATCCG |
| 6001 AACAAACGAC CCAACACCCG TGCGTTTTAT TCTGTCTTTT TATTGCCGAT CCCCTCAGAA |
| 6061 GAACTCGTCA AGAAGGCGAT AGAAGGCGAT GCGCTGCGAA TCGGGAGCGG CGATACCGTA |
| 6121 AAGCACGAGG AAGCGGTCAG CCCATTCGCC GCCAAGCTCT TCAGCAATAT CACGGGTAGC |
| 6181 CAACGCTATG TCCTGATAGC GGTCGGCCGC TTTACTTGTA CAGCTCGTCC ATGCCGAGAG |
| 6241 TGATCCCGGC GGCGGTCACG AACTCCAGCA GGACCATGTG ATCGCGCTTC TCGTTGGGGT |
| 6301 CTTTGCTCAG GGCGGACTGG GTGCTCAGGT AGTGGTTGTC GGGCAGCAGC ACGGGGCCGT |
| 6361 CGCCGATGGG GGTGTTCTGC TGGTAGTGGT CGGCCAGGTG AGTCCAGGAG ATGTTTCAGC |
| 6421 ACTGTTGCCT TTAGTCTCGA GGCAACTTAG ACAACTGAGT ATTGATCTGA GCACAGCAGG |
| 6481 GTGTGAGCTG TTTGAAGATA CTGGGGTTGG GGGTGAAGAA ACTGCAGAGG ACTAACTGGG |
| 6541 CTGAGACCCA GTGGCAATGT TTTAGGGCCT AAGGAATGCC TCTGAAAATC TAGATGGACA |
| 6601 ACTTTGACTT TGAGAAAAGA GAGGTGGAAA TGAGGAAAAT GACTTTTCTT TATTAGATTT |
| 6661 CGGTAGAAAG AACTTTCATC TTTCCCCTAT TTTTGTTATT CGTTTTAAAA CATCTATCTG |
| 6721 GAGGCAGGAC AAGTATGGTC ATTAAAAAGA TGCAGGCAGA AGGCATATAT TGGCTCAGTC |
| 6781 AAAGTGGGGA ACTTTGGTGG CCAAACATAC ATTGCTAAGG CTATTCCTAT ATCAGCTGGA |
| 6841 CACATATAAA ATGCTGCTAA TGCTTCATTA CAAACTTATA TCCTTTAATT CCAGATGGGG |
| 6901 GCAAAGTATG TCCAGGGGTG AGGAACAATT GAAACATTTG GGCTGGAGTA GATTTTGAAA |
| 6961 GTCAGCTCTG TGTGTGTGTG TGTGTGTGTG TGTGTGAGAG CGTGTGTTTC TTTTAACGTT |
| 7021 TTCAGCCTAC AGCATACAGG GTTCATGGTG GCAAGAAGAT AACAAGATTT AAATTATGGC |
| 7081 CAGTGACTAG TGCTGCAAGA AGAACAACTA CCTGCATTTA ATGGGAAAGC AAAATCTCAG |
| 7141 GCTTTGAGGG AAGTTAACAT AGGCTTGATT CTGGGTGGAA GCTGGGTGTG TAGTTATCTG |
| 7201 GAGGCCAGGC TGGAGCTCTC AGCTCACTAT GGGTTCATCT TTATTGTCTC CTTTCATCTC |
| 7261 AACAGCTGCA CGCTGCCGTC CTCGATGTTG TGGCGGATCT TGAAGTTCAC CTTGATGCCG |
| 7321 TTCTTCTGCT TGTCGGCCAT GATATAGACG TTGTGGCTGT TGTAGTTGTA CTCCAGCTTG |
| 7381 TGCCCCAGGA TGTTGCCGTC CTCCTTGAAG TCGATGCCCT TCAGCTCGAT GCGGTTCACC |
| 7441 AGGGTGTCGC CCTCGAACTT CACCTCGGCG CGGGTCTTGT AGTTGCCGTC GTCCTTGAAG |
| 7501 AAGATGGTGC GCTCCTGGAC GTAGCCTTCG GGCATGGCGG ACTTGAAGAA GTCGTGCTGC |
| 7561 TTCATGTGGT CGGGGTAGCG GCTGAAGCAC TGCACGCCGT AGGTCAGGGT GGTCACGAGG |
| 7621 GTGGGCCAGG GCACGGGCAG CTTGCCGGTG GTGCAGATGA ACTTCAGGGT CAGCTTGCCG |
| 7681 TAGGTGGCAT CGCCCTCGCC CTCGCCGGAC ACGCTGAACT TGTGGCCGTT TACGTCGCCG |
| 7741 TCCAGCTCGA CCAGGATGGG CACCACCCCG GTGAACAGCT CCTCGCCCTT GCTCACCATA |
| 7801 GGGCCGGGAT TCTCCTCCAC GTCACCGCAT GTTAGAAGAC TTCCTCTGCC CTCCATGTTC |
| 7861 TCGTAGGAGT CGGCGTCCTC TTCGTGGTTA GGTCCAGGTT GGCCTCTGAT AGACCGCAGC |
| 7921 TGAGGAGCGG CGTACAGAAT GCCTCTCATG TCCTCATAGC TGCCGCTGCC TTGTGGAGGC |
| 7981 TTCTCGTGCT TCAGTGTCTC GTATGTCTCT TGATTCCGGG TGCTCAGGCC GGTGTACACG |
| 8041 CCATCAGATT TCTCGTAGCT GGTGATGGCG GCCTTCCGCA CTTGGATCTT CAGCCGTCTG |
| 8101 CAGTACAGGG TGATGACCAG AGACAGCAGC AGGACACCAC ATGTGCCAGC CAGAGGGGCC |

TABLE 8-continued

| Plasmid and mRNA construct sequences |
|---|
| 8161 CAAATGTAGA TATCCAGGCC TCTGGTATGC ACAGCTCCGC CTGCAGCAGG TCTACAGGCT |
| 8221 TCAGGTCTGA GAGACAGAGG CTGGCTGGCG ATTGTAGGAG CTGGTGTAGG TGGTCTAGGA |
| 8281 GCGGGTGTTG TTGTAGGCTT GGCGGGCAGA AACACGGGCA CGAAGTGGCT GAAGTACATG |
| 8341 ATGCTATTGC TCAGGGCTCC GCTTCCTCCG CCGCCTGATT TGATTTCCAG CTTGGTGCCT |
| 8401 CCGCCAAATG TCCAAGGGCT CTCGTCGTAC TGCTGGCAGT AGTAGATGCC GAAGTCCTCG |
| 8461 TACTGCAGGC TGCTGATTGT CAGGGTGTAG TCGGTGCCAG AGCCGCTGCC AGAAAATCTG |
| 8521 CTTGGCACGC CGCTTTCCAG TCTGTTGGCC CGGTAGATCA GTGTCTTAGG GGCCTTGCCA |
| 8581 GGCTTCTGCT GGAACCAGCT CAGGTAGCTG TTGATGTCCT GGCTGGCTCT ACAGGTGATG |
| 8641 GTCACTCTAT CGCCCACAGA GGCAGACAGG CTGCTAGGGC TCTGTGTCAT CTGGATATCA |
| 8701 GAGCCACCAC CGCCAGATCC ACCGCCACCT GATCCTCCGC CTCCGCTAGA AACTGTCACT |
| 8761 GTGGTGCCCT GGCCCCACAC ATCGAAGTAC CAGTCGTAGC CTCTTCTGGT GCAGAAGTAC |
| 8821 ACGGCGGTAT CCTCGGCTCT CAGGCTGTTG ATCTGCAGGT AGGCGGTGTT CTTGCTGTCG |
| 8881 TCCAGGCTGA AGGTGAATCT GCCCTTAAAG CTATCGGCGT AGGTTGGCTC GCCGGTGTGG |
| 8941 GTATTGATCC AGCCCATCCA CTCAAGGCCT TTTCCAGGGG CCTGTCGGAC CCAGTTCATG |
| 9001 CCGTAGTTGG TGAAGGTGTA GCCGCTGGCG GCACAGCTGA TTCTGACAGA TCCGCCAGGT |
| 9061 TTCACAAGTC CGCCGCCAGA CTGAACCAGC TGGATCTCAG AGATGCTACA GGCCACTGTT |
| 9121 CCCAGCAGCA GCAGAGACTG CAGCCACATT CGAAGCTTGA GCTCGAGATC TGAGTCCGGT |
| 9181 AGCGCTAGCG GATCTGACGG TTCACTAAAC CAGCTCTGCT TATATAGACC TCCCACCGTA |
| 9241 CACGCCTACC GCCCATTTGC GTCAATGGGG CGGAGTTGTT ACGACATTTT GGAAAGTCCC |
| 9301 GTTGATTTTG GTGCCAAAAC AAACTCCCAT TGACGTCAAT GGGGTGGAGA CTTGGAAATC |
| 9361 CCCGTGAGTC AAACCGCTAT CCACGCCCAT TGATGTACTG CCAAAACCGC ATCACCATGG |
| 9421 TAATAGCGAT GACTAATACG TAGATGTACT GCCAAGTAGG AAAGTCCCAT AAGGTCATGT |
| 9481 ACTGGGCATA ATGCCAGGCG GGCCATTTAC CGTCATTGAC GTCAATAGGG GGCGTACTTG |
| 9541 GCATATGATA CACTTGATGT ACTGCCAAGT GGGCAGTTTA CCGTAAATAC TCCACCCATT |
| 9601 GACGTCAATG GAAAGTCCCT ATTGGCGTTA CTATGGGAAC ATACGTCATT ATTGACGTCA |
| 9661 ATGGGCGGGG GTCGTTGGGC GGTCAGCCAG GCGGGCCATT TACCGTAAGT TATGTAACGC |
| 9721 GGAACTCCAT ATATGGGCTA TGAACTAATG ACCCCGTAAT TGATTACTAT TAGCCCGGGG |
| 9781 GATCCAGACA TGATAAGATA CATTGATGAG TTTGGACAAA CCACAACTAG AATGCAGTGA |
| 9841 AAAAAATGCT TTATTTGTGA AATTTGTGAT GCTATTGCTT TATTTGTAAC CATTATAAGC |
| 9901 TGCAATAAAC AAGTTAACAA CAACAATTGC ATTCATTTTA TGTTTCAGGT TCAGGGGGAG |
| 9961 GTGTGGGAGG TTTTTTAAAG CAAGTAAAAC CTCTACAAAT GTGGTATGGC TGATTATGAT |
| 10021 CCGGCTGCCT CGCGCGTTTC GGTGATGACG GTGAAAACCT CTGACACATG CAGCTCCCGG |
| 10081 AGACGGTCAC AGCTTGTCTG TAAGCGGATG CCGGGAGCAG ACAAGCCCGT CAGGGCGCGT |
| 10141 CAGCGGGTGT TGGCGGGTGT CGGGGCGCAG CCATGAGGTC GATCGACTCT AGAGGATCGA |
| 10201 TCCCCGCCCC GGACGAACTA AACCTGACTA CGACATCTCT GCCCCTTCTT CGCGGGGCAG |
| 10261 TGCATGTAAT CCCTTCAGTT GGTTGGTACA ACTTGCCAAC TGGGCCCTGT TCCACATGTG |
| 10321 ACACGGGGGG GGACCAAACA CAAAGGGGTT CTCTGACTGT AGTTGACATC CTTATAAATG |
| 10381 GATGTGCACA TTTGCCAACA CTGAGTGGCT TTCATCCTGG AGCAGACTTT GCAGTCTGTG |
| 10441 GACTGCAACA CAACATTGCC TTTATGTGTA ACTCTTGGCT GAAGCTCTTA CACCAATGCT |
| 10501 GGGGGACATG TACCTCCCAG GGGCCCAGGA AGACTACGGG AGGCTACACC AACGTCAATC |
| 10561 AGAGGGGCCT GTGTAGCTAC CGATAAGCGG ACCCTCAAGA GGGCATTAGC AATAGTGTTT |
| 10621 ATAAGGCCCC CTTGTTAACC CTAAACGGGT AGCATATGCT TCCCGGGTAG TAGTATATAC |
| 10681 TATCCAGACT AACCCTAATT CAATAGCATA TGTTACCCAA CGGGAAGCAT ATGCTATCGA |
| 10741 ATTAGGGTTA GTAAAAGGGT CCTAAGGAAC AGCGATATCT CCCACCCCAT GAGCTGTCAC |
| 10801 GGTTTTATTT ACATGGGGTC AGGATTCCAC GAGGGTAGTG AACCATTTTA GTCACAAGGG |
| 10861 CAGTGGCTGA AGATCAAGGA GCGGGCAGTG AACTCTCCTG AATCTTCGCC TGCTTCTTCA |
| 10921 TTCTCCTTCG TTTAGCTAAT AGAATAACTG CTGAGTTGTG AACAGTAAGG TGTATGTGAG |
| 10981 GTGCTCGAAA ACAAGGTTTC AGGTGACGCC CCCAGAATAA AATTTGGACG GGGGGTTCAG |
| 11041 TGGTGGCATT GTGCTATGAC ACCAATATAA CCCTCACAAA CCCCTTGGGC AATAAATACT |
| 11101 AGTGTAGGAA TGAAACATTC TGAATATCTT TAACAATAGA AATCCATGGG GTGGGGACAA |
| 11161 GCCGTAAAGA CTGGATGTCC ATCTCACACG AATTTATGGC TATGGGCAAC ACATAATCCT |
| 11221 AGTGCAATAT GATACTGGGG TTATTAAGAT GTGTCCCAGG CAGGGACCAA GACAGGTGAA |
| 11281 CCATGTTGTT ACACTCTATT TGTAACAAGG GGAAAGAGAG TGGACGCCGA CAGCAGCGGA |
| 11341 CTCCACTGGT TGTCTCTAAC ACCCCCGAAA ATTAAACGGG GCTCCACGCC AATGGGGCCC |
| 11401 ATAAACAAAG ACAAGTGGCC ACTCTTTTTT TTGAAATTGT GGAGTGGGGG CACGCGTCAG |
| 11461 CCCCCACACG CCGCCCTGCG GTTTTGGACT GTAAAATAAG GGTGTAATAA CTTGGCTGAT |
| 11521 TGTAACCCCG CTAACCACTG CGGTCAAACC ACTTGCCCAC AAAACCACTA ATGGCACCCC |
| 11581 GGGGAATACC TGCATAAGTA GGTGGGCGGG CCAAGATAGG GGCGCGATTG CTGCGATCTG |
| 11641 GAGGACAAAT TACACACACT TGCGCCTGAG CGCCAAGCAC AGGGTTGTTG GTCCTCATAT |
| 11701 TCACGAGGTC GCTGAGAGCA CGGTGGGCTA ATGTTGCCAT GGGTAGCATA TACTACCCAA |
| 11761 ATATCTGGAT AGCATATGCT ATCCTAATCT ATATCTGGGT AGCATAGGCT ATCCTAATCT |
| 11821 ATATCTGGGT AGCATATGCT ATCCTAATCT ATATCTGGGT AGTATATGCT ATCCTAATTT |
| 11881 ATATCTGGGT AGCATAGGCT ATCCTAATCT ATATCTGGGT AGCATATGCT ATCCTAATCT |
| 11941 ATATCTGGGT AGTATATGCT ATCCTAATCT GTATCCGGGT AGCATATGCT ATCCTAATAG |
| 12001 AGATTAGGGT AGTATATGCT ATCCTAATTT ATATCTGGGT AGCATATACT ACCCAAATAT |
| 12061 CTGGATAGCA TATGCTATCC TAATCTATAT CTGGGTAGCA TATGCTATCC TAATCTATAT |
| 12121 CTGGGTAGCA TAGGCTATCC TAATCTATAT CTGGGTAGCA TATGCTATCC TAATCTATAT |
| 12181 CTGGGTAGTA TATGCTATCC TAATTTATAT CTGGGTAGCA TAGGCTATCC TAATCTATAT |
| 12241 CTGGGTAGCA TATGCTATCC TAATCTATAT CTGGGTAGTA TATGCTATCC TAATCTGTAT |
| 12301 CCGGGTAGCA TATGCTATCC TCATGCATAT ACAGTCAGCA TATGATACCC AGTAGTAGAG |
| 12361 TGGGAGTGCT ATCCTTTGCA TATGCCGCCA CCTCCCAAGG GGGCGTGAAT TTTCGCTGCT |
| 12421 TGTCCTTTTC CTGCATGCTG GTTGCTCCCA TTCTTAGGTG AATTTAAGGA GGCCAGGCTA |
| 12481 AAGCCGTCGC ATGTCTGATT GCTCACCAGG TAAATGTCGC TAATGTTTTC CAACGCGAGA |
| 12541 AGGTGTTGAG CGCGGAGCTG AGTGACGTGA CAACATGGGT ATGCCCAATT GCCCCATGTT |
| 12601 GGGAGGACGA AAATGGTGAC AAGACAGATG GCCAGAAATA CACCAACAGC ACGCATGATG |
| 12661 TCTACTGGGG ATTTATTCTT TAGTGCGGGG GAATACACGG CTTTTAATAC GATTGAGGGC |
| 12721 GTCTCCTAAC AAGTTACATC ACTCCTGCCC TTCCTCACCC TCATCTCCAT CACCTCCTTC |
| 12781 ATCTCCGTCA TCTCCGTCAT CACCCTCCGC GGCAGCCCCT TCCACCATAG GTGGAAACCA |

TABLE 8-continued

Plasmid and mRNA construct sequences

12841 GGGAGGCAAA TCTACTCCAT CGTCAAAGCT GCACACAGTC ACCCTGATAT TGCAGGTAGG
12901 AGCGGGCTTT GTCATAACAA GGTCCTTAAT CGCATCCTTC AAAACCTCAG CAAATATATG
12961 AGTTTGTAAA AAGACCATGA AATAACAGAC AATGGACTCC CTTAGCGGGC CAGGTTGTGG
13021 GCCGGGTCCA GGGGCCATTC CAAAGGGGAG ACGACTCAAT GGTGTAAGAC GACATTGTGG
13081 AATAGCAAGG GCAGTTCCTC GCCTTAGGTT GTAAAGGGAG GTCTTACTAC CTCCATATAC
13141 GAACACACCG GCGACCCAAG TTCCTTCGTC GGTAGTCCTT TCTACGTGAC TCCTAGCCAG
13201 GAGAGCTCTT AAACCTTCTG CAATGTTCTC AAATTTCGGG TTGGAACCTC CTTGACCACG
13261 ATGCTTTCCA AACCACCCTC CTTTTTTGCG CCTGCCTCCA TCACCCTGAC CCCGGGGTCC
13321 AGTGCTTGGG CCTTCTCCTG GGTCATCTGC GGGGCCCTGC TCTATCGCTC CCGGGGGCAC
13381 GTCAGGCTCA CCATCTGGGC CACCTTCTTG GTGGTATTCA AAATAATCGG CTTCCCCTAC
13441 AGGGTGGAAA AATGGCCTTC TACCTGGAGG GGGCCTGCGC GGTGGAGACC CGGATGATGA
13501 TGACTGACTA CTGGGACTCC TGGGCCTCTT TTCTCCACGT CCACGACCTC TCCCCCTGGC
13561 TCTTTCACGA CTTCCCCCCC TGGCTCTTTC ACGTCCTCTA CCCCGGCGGC CTCCACTACC
13621 TCCTCGACCC CGGCCTCCAC TACCTCCTCG ACCCCGGCCT CCACTGCCTC CTCGACCCCG
13681 GCCTCCACCT CCTGCTCCTG CCCCTCCTGC TCCTGCCCCT CCTCCTGCTC CTGCCCCTCC
13741 TGCCCCTCCT GCTCCTGCCC CTCCTGCCCC TCCTGCTCCT GCCCCTCCTG CCCCTCCTGC
13801 TCCTGCCCCT CCTGCCCCTC CTCCTGCTCC TGCCCCTCCT GCCCCTCCTC CTGCTCCTGC
13861 CCCTCCTGCC CCTCCTGCTC CTGCCCCTCC TGCCCCTCCT GCTCCTGCCC CTCCTGCCCC
13921 TCCTGCTCCT GCCCCTCCTG CTCCTGCCCC TCCTGCTCCT GCCCCTCCTG CTCCTGCCCC
13981 TCCTGCCCCT CCTGCCCCTC CTCCTGCTCC TGCCCCTCCT GCTCCTGCCC CTCCTGCCCC
14041 TCCTGCCCCT CCTGCTCCTG CCCCTCCTCC TGCTCCTGCC CCTCCTGCCC CTCCTGCCCC
14101 TCCTCCTGCT CCTGCCCCTC CTGCCCCTCC TCCTGCTCCT GCCCCTCCTC CTGCTCCTGC
14161 CCCTCCTGCC CCTCCTGCCC CTCCTCCTGC TCCTGCCCCT CCTGCCCCTC CTCCTGCTCC
14221 TGCCCCTCCT CCTGCTCCTG CCCCTCCTGC CCCTCCTGCC CCTCCTCCTG CTCCTGCCCC
14281 TCCTCCTGCT CCTGCCCCTC CTGCCCCTCC TGCCCCTCCT GCCCCTCCTC CTGCTCCTGC
14341 CCCTCCTCCT GCTCCTGCCC CTCCTGCTCC TGCCCCTCCC GCTCCTGCTC CTGCTCCTGT
14401 TCCACCGTGG GTCCCTTTGC AGCCAATGCA ACTTGGACGT TTTTGGGGTC TCCGGACACC
14461 ATCTCTATGT CTTGGCCCTG ATCCTGAGCC GCCCGGGGCT CCTGGTCTTC CGCCTCCTCG
14521 TCCTCGTCCT CTTCCCCGTC CTCGTCCATG GTTATCACCC CCTCTTCTTT GAGGTCCACT
14581 GCCGCCGGAG CCTTCTGGTC CAGATGTGTC TCCCTTCTCT CCTAGGCCAT TTCCAGGTCC
14641 TGTACCTGGC CCCTCGTCAG ACATGATTCA CACTAAAAGA GATCAATAGA CATCTTTATT
14701 AGACGACGCT CAGTGAATAC AGGGAGTGCA GACTCCTGCC CCCTCCAACA GCCCCCCCAC
14761 CCTCATCCCC TTCATGGTCG CTGTCAGACA GATCCAGGTC TGAAAATTCC CCATCCTCCG
14821 AACCATCCTC GTCCTCATCA CCAATTACTC GCAGCCCGGA AAACTCCCGC TGAACATCCT
14881 CAAGATTTGC GTCCTGAGCC TCAAGCCAGG CCTCAAATTC CTCGTCCCCC TTTTTGCTGG
14941 ACGGTAGGGA TGGGGATTCT CGGGACCCCT CCTCTTCCTC TTCAAGGTCA CCAGACAGAG
15001 ATGCTACTGG GGCAACGGAA GAAAAGCTGG GTGCGGCCTG TGAGGATCAG CTTATCGATG
15061 ATAAGCTGTC AAACATGAGA ATTCTTGAAG ACGAAAGGGC CTCGTGATAC GCCTATTTTT
15121 ATAGGTTAAT GTCATGATAA TAATGGTTTC TTAGACGTCA GGTGGCACTT TTCGGGGAAA
15181 TGTGCGCGGA ACCCCTATTT GTTTATTTTT CTAAATACAT TCAAATATGT ATCCGCTCAT
15241 GAGACAATAA CCCTGATAAA TGCTTCAATA ATATTGAAAA AGGAAGAGTA TGAGTATTCA
15301 ACATTTCCGT GTCGCCCTTA TTCCCTTTTT TGCGGCATTT TGCCTTCCTG TTTTTGCTCA
15361 CCCAGAAACG CTGGTGAAAG TAAAAGATGC TGAAGATCAG TTGGGTGCAC GAGTGGGTTA
15421 CATCGAACTG GATCTCAACA GCGGTAAGAT CCTTGAGAGT TTTCGCCCCG AAGAACGTTT
15481 TCCAATGATG AGCACTTTTA AAGTTCTGCT ATGTGGCGCG GTATTATCCC GTGTTGACGC
15541 CGGGCAAGAG CAACTCGGTC GCCGCATACA CTATTCTCAG AATGACTTGG TTGAGTACTC
15601 ACCAGTCACA GAAAAGCATC TTACGGATGG CATGACAGTA AGAGAATTAT GCAGTGCTGC
15661 CATAACCATG AGTGATAACA CTGCGGCCAA CTTACTTCTG ACAACGATCG GAGGACCGAA
15721 GGAGCTAACC GCTTTTTTGC ACAACATGGG GGATCATGTA ACTCGCCTTG ATCGTTGGGA
15781 ACCGGAGCTG AATGAAGCCA TACCAAACGA CGAGCGTGAC ACCACGATGC CTGCAGCAAT
15841 GGCAACAACG TTGCGCAAAC TATTAACTGG CGAACTACTT ACTCTAGCTT CCCGGCAACA
15901 ATTAATAGAC TGGATGGAGG CGGATAAAGT TGCAGGACCA CTTCTGCGCT CGGCCCTTCC
15961 GGCTGGCTGG TTTATTGCTG ATAAATCTGG AGCCGGTGAG CGTGGGTCTC GCGGTATCAT
16021 TGCAGCACTG GGGCCAGATG GTAAGCCCTC CCGTATCGTA GTTATCTACA CGACGGGGAG
16081 TCAGGCAACT ATGGATGAAC GAAATAGACA GATCGCTGAG ATAGGTGCCT CACTGATTAA
16141 GCATTGGTAA CTGTCAGACC AAGTTTACTC ATATATACTT TAGATTGATT TAAAACTTCA
16201 TTTTTAATTT AAAAGGATCT AGGTGAAGAT CCTTTTTGAT AATCTCATGA CCAAAATCCC
16261 TTAACGTGAG TTTTCGTTCC ACTGAGCGTC AGACCCCGTA GAAAAGATCA AAGGATCTTC
16321 TTGAGATCCT TTTTTTCTGC GCGTAATCTG CTGCTTGCAA ACAAAAAAAC CACCGCTACC
16381 AGCGGTGGTT TGTTTGCCGG ATCAAGAGCT ACCAACTCTT TTTCCGAAGG TAACTGGCTT
16441 CAGCAGAGCG CAGATACCAA ATACTGTCCT TCTAGTGTAG CCGTAGTTAG GCCACCACTT
16501 CAAGAACTCT GTAGCACCGC CTACATACCT CGCTCTGCTA ATCCTGTTAC CAGTGGCTGC
16561 TGCCAGTGGC GATAAGTCGT GTCTTACCGG GTTGGACTCA AGACGATAGT TACCGGATAA
16621 GGCGCAGCGG TCGGGCTGAA CGGGGGGTTC GTGCACACAG CCCAGCTTGG AGCGAACGAC
16681 CTACACCGAA CTGAGATACC TACAGCGTGA GCTATGAGAA AGCGCCACGC TTCCCGAAGG
16741 GAGAAAGGCG GACAGGTATC CGGTAAGCGG CAGGGTCGGA ACAGGAGAGC GCACGAGGGA
16801 GCTTCCAGGG GGAAACGCCT GGTATCTTTA TAGTCCTGTC GGGTTTCGCC ACCTCTGACT
16861 TGAGCGTCGA TTTTTGTGAT GCTCGTCAGG GGGGCGGAGC CTATGGAAAA ACGCCAGCAA
16921 CGCGGCCTTT TTACGGTTCC TGGCCTTTTG CTGGCCTTTT GCTCACATGT TCTTTCCTGC
16981 GTTATCCCCT GATTCTGTGG ATAACCGTAT TACCGCCTTT GAGTGAGCTG ATACCGCTCG
17041 CCGCAGCCGA ACGACCGAGC GCAGCGAGTC AGTGAGCGAG GAAGCGGAAG AGCGCCTGAT
17101 GCGGTATTTT CTCCTTACGC ATCTGTGCGG TATTTCACAC CGCATATGGT GCACTCTCAG
17161 TACAATCTGC TCTGATGCCG CATAGTTAAG CCAGCTGTGG AATGTGTGTC AGTTAGGGTG
17221 TGGAAAGTCC CCAGGCTCCC CAGCAGGCAG AAGTATGCAA AGCATGCATC TCAATTAGTC
17281 AGCAACCAGG TGTGGAAAGT CCCCAGGCTC CCCAGCAGGC AGAAGTATGC AAAGCATGCA
17341 TCTCAATTAG TCAGCAACCA TAGTCCCGCC CCTAACTCCG CCCATCCCGC CCCTAACTCC
17401 GCCCAGTTCC GCCCATTCTC CGCCCCATGG CTGACTAATT TTTTTTATTT ATGCAGAGGC
17461 CGAGGCCGCC TCGGCCTCTG AGCTATTCCA GAAGTAGTGA GGAGGCTTTT TTGGAGGCCT

TABLE 8-continued

| Plasmid and mRNA construct sequences |
|---|
| 17521 AGGCTTTTGC AAAAAGCTTG CATGCCTGCA GGTCGGCCGC CACGACCGGT GCCGCCACCA |
| 17581 TCCCCTGACC CACGCCCCTG ACCCCTCACA AGGAGACGAC CTTCCATGAC CGAGTACAAG |
| 17641 CCCACGGTGC GCCTCGCCAC CCGCGACGAC GTCCCCCGGG CCGTACGCAC CCTCGCCGCC |
| 17701 GCGTTCGCCG ACTACCCCGC CACGCGCCAC ACCGTCGACC CGGACCGCCA CATCGAGCGG |
| 17761 GTCACCGAGC TGCAAGAACT CTTCCTCACG CGCGTCGGGC TCGACATCGG CAAGGTGTGG |
| 17821 GTCGCGGACG ACGGCGCCGC GGTGGCGGTC TGGACCACGC CGGAGAGCGT CGAAGCGGGG |
| 17881 GCGGTGTTCG CCGAGATCGG CCCGCGCATG GCCGAGTTGA GCGGTTCCCG GCTGGCCGCG |
| 17941 CAGCAACAGA TGGAAGGCCT CCTGGCGCCG CACCGGCCCA AGGAGCCCGC GTGGTTCCTG |
| 18001 GCCACCGTCG GCGTCTCGCC CGACCACCAG GGCAAGGGTC TGGGCAGCGC CGTCGTGCTC |
| 18061 CCCGGAGTGG AGGCGGCCGA GCGCGCCGGG GTGCCCGCCT TCCTGGAGAC CTCCGCGCCC |
| 18121 CGCAACCTCC CCTTCTACGA GCGGCTCGGC TTCACCGTCA CCGCCGACGT CGAGGTGCCC |
| 18181 GAAGGACCGC GCACCTGGTG CATGACCCGC AAGCCCGGTG CCTGACGCCC GCCCCACGAC |
| 18241 CCGCAGCGCC CGACCGAAAG GAGCGCACGA CCCCATGGCT CCGACCGAAG CCGACCCGGG |
| 18301 CGGCCCCGCC GACCCCGCAC CCGCCCCCGA GGCCCACCGA CTCTAGAGGA TCATAATCAG |
| 18361 CCATACCACA TTTGTAGAGG TTTTACTTGC TTTAAAAAAC CTCCCACACC TCCCCCTGAA |
| 18421 CCTGAAACAT AAAATGAATG CAATTGTTGT TGTTAACTTG TTTATTGCAG CTTATAATGG |
| 18481 TTACAAATAA AGCAATAGCA TCACAAATTT CACAAATAAA GCATTTTTTT CACTGCATTC |
| 18541 TAGTTGTGGT TTGTCCAAAC TCATCAATGT ATCTTATCAT GTCTGGATCA CTCGCCGATA |
| 18601 GTGGAAACCG ACGCCCCAGC ACTCGTCCGA GGGCAAAGGA ATAGGGGAGA TGGGGGAGGC |
| 18661 TAACTGAAAC ACGGAAGGAG ACAATACCGG AAGGAACCCG CGCTATGACG GCAATAAAAA |
| 18721 GACAGAATAA AACGCACGGG TGTTGGGTCG TTTGTTCATA AACGCGGGGT TCGGTCCCAG |
| 18781 GGCTGGCACT CTGTCGATAC CCCACCGAGA CCCCATTGGG GCCAATACGC CCGCGTTTCT |
| 18841 TCCTTTTCCC CACCCCACCC CCCAAGTTCG GGTGAAGGCC CAGGGCTCGC AGCCAACGTC |
| 18901 GGGGCGGCAG GCCCTGCCAT AGCCACTGGC CCCGTGGGTT AGGGACGGGG TCCCCCATGG |
| 18961 GGAATGGTTT ATGGTTCGTG GGGGTTATTA TTTTGGGCGT TGCGTGGGGT CTGGTCCACG |
| 19021 ACTGGACTGA GCAGACAGAC CCATGGTTTT TGGATGGCCT GGGCATGGAC CGCATGTACT |
| 19081 GGCGCGACAC GAACACCGGG CGTCTGTGGC TGCCAAACAC CCCCGACCCC CAAAAACCAC |
| 19141 CGCGCGGATT TCTGGCGTGC CAAGCTAGTC GACCAATTCT CATGTTTGAC AGCTTATCAT |
| 19201 CGCAGATCCG GGCAACGTTG TTGCATTGCT GCAGGCGCAG AACTGGTAGG TATGGAAGAT |
| 19261 CTCTAGAAGC TGGGTACCAG CTGCTAGCAA GCTTGCTAGC GGCCGGCTCG AGTTTACTCC |
| 19321 CTATCAGTGA TAGAGAACGT ATGTCGAGTT TACTCCCTAT CAGTGATAGA GAACGATGTC |
| 19381 GAGTTTACTC CCTATCAGTG ATAGAGAACG TATGTCGAGT TTACTCCCTA TCAGTGATAG |
| 19441 AGAACGTATG TCGAGTTTAC TCCCTATCAG TGATAGAGAA CGTATGTCGA GTTTATCCCT |
| 19501 ATCAGTGATA GAGAACGTAT GTCGAGTTTA CTCCCTATCA GTGATAGAGA ACGTATGTCG |
| 19561 AGGTAGGCGT GTACGGTGGG AGGCCTATAT AAGCAGAGCT CGTTTAGTGA ACCGTCAGAT |
| 19621 CGCCG (SEQ ID NO: 40) |
| |
| LINE-1 plasmid Her2-Cd3z-T2A GFPintron (SEQ ID NO: 41) |
| 1 CGGCCGCGGG GGGAGGAGCC AAGATGGCCG AATAGGAACA GCTCCGGTCT ACAGCTCCCA |
| 61 GCGTGAGCGA CGCAGAAGAC GGTGATTTCT GCATTTCCAT CTGAGGTACC GGGTTCATCT |
| 121 CACTAGGGAG TGCCAGACAG TGGGCGCAGG CCAGTGTGTG TGCGCACCGT GCGCGAGCCG |
| 181 AAGCAGGGCG AGGCATTGCC TCACCTGGGA AGCGCAAGGG GTCAGGGAGT TCCCTTTCCG |
| 241 AGTCAAAGAA AGGGGTGACG GACGCACCTG GAAAATCGGG TCACTCCCAC CCGAATATTG |
| 301 CGCTTTTCAG ACCGGCTTAA GAAACGGCGC ACCACGAGAC TATATCCCAC ACCTGGCTCG |
| 361 GAGGGTCCTA CGCCCACGGA ATCTCGCTGA TTGCTAGCAC AGCAGTCTGA GATCAAACTG |
| 421 CAAGGCGGCA ACGAGGCTGG GGGAGGGGCG CCCGCCATTG CCCAGGCTTG CTTAGGTAAA |
| 481 CAAAGCAGCA GGGAAGCTCG AACTGGGTGG AGCCCACCAC AGCTCAAGGA GGCCTGCCTG |
| 541 CCTCTGTAGG CTCCACCTCT GGGGGCAGGG CACAGACAAA CAAAAAGACA GCAGTAACCT |
| 601 CTGCAGACTT AAGTGTCCCT GTCTGACAGC TTTGAAGAGA GCAGTGGTTC TCCCAGCACG |
| 661 CAGCTGGAGA TCTGAGAACG GGCAGACTGC CTCCTCAAGT GGGTCCCTGA CCCCTGACCC |
| 721 CCGAGCAGCC TAACTGGGAG GCACCCCCCA GCAGGGGCAC ACTGACACCT CACACGGCAG |
| 781 GGTATTCCAA CAGACCTGCA GCTGAGGGTC CTGTCTGTTA GAAGGAAAAC TAACAACCAG |
| 841 AAAGGACATC TACACCGAAA ACCCATCTGT ACATCACCAT CATCAAAGAC CAAAAGTAGA |
| 901 TAAAACCACA AAGATGGGGA AAAAACAGAA CAGAAAAACT GGAAACTCTA AAACGCAGAG |
| 961 CGCCTCTCCT CCTCCAAAGG AACGCAGTTC CTCACCAGCA ACAGAACAAA GCTGGATGGA |
| 1021 GAATGATTTT GATGAGCTGA GAGAAGAAGG CTTCAGACGA TCAAATTACT CTGAGCTACG |
| 1081 GGAGGACATT CAAACCAAAG GCAAAGAAGT TGAAAACTTT GAAAAAAATT TAGAAGAATG |
| 1141 TATAACTAGA ATAACCAATA CAGAGAAGTG CTTAAAGGAG CTGATGGAGC TGAAAACCAA |
| 1201 GGCTCGAGAA CTACGTGAAG AATGCAGAAG CCTCAGGAGC CGATGCGATC AACTGGAAGA |
| 1261 AAGGGTATCA GCAATGGAAG ATGAAATGAA TGAAATGAAG CGAGAAGGGA AGTTTAGAGA |
| 1321 AAAAAGAATA AAAAGAAATG AGCAAAGCCT CCAAGAAATA TGGGACTATG TGAAAAGACC |
| 1381 AAATCTACGT CTGATTGGTG TACCTGAAAG TGATGTGGAG AATGGAACCA AGTTGGAAAA |
| 1441 CACTCTGCAG GATATTATCC AGGAGAACTT CCCCAATCTA GCAAGGCAGG CCAACGTTCA |
| 1501 GATTCAGGAA ATACAGAGAA CGCCACAAAG ATACTCCTCG AGAAGAGCAA CTCCAAGACA |
| 1561 CATAATTGTC AGATTCACCA AAGTTGAAAT GAAGGAAAAA ATGTTAAGGG CAGCCAGAGA |
| 1621 GAAAGGTCGG GTTACCCTCA AAGGAAAGCC CATCAGACTA ACAGCGGATC TCTCGGCAGA |
| 1681 AACCCTACAA GCCAGAAGAG AGTGGGGGCC AATATTCAAC ATTCTTAAAG AAAAGAATTT |
| 1741 TCAACCCAGA ATTTCATATC CAGCCAAACT AAGCTTCATA AGTGAAGGAG AAATAAAATA |
| 1801 CTTTATAGAC AAGCAAATGT TGAGAGATTT TGTCACCACC AGGCCTGCCC TAAAAGAGCT |
| 1861 CCTGAAGGAA GCGCTAAACA TGGAAAGGAA CAACCGGTAC CAGCCGCTGC AAAATCATGC |
| 1921 CAAAATGTAA AGACCATCAA GACTAGGAAG AAACTGCATC AACTAATGAG CAAAATCACC |
| 1981 AGCTAACATC ATAATGACAG GATCAACTTC ACACATAACA ATATTAACTT TAAATATAAA |
| 2041 TGGACTAAAT TCTGCAATTA AAAGACACAG ACTGGCAAGT TGGATAAAGA GTCAAGACCC |
| 2101 ATCAGTGTGC TGTATTCAGG AAACCCATCT CACGTGCAGA GACACACATA GGCTCAAAAT |
| 2161 AAAAGGATGG AGGAAGATCT ACCAAGCCAA TGGAAAACAA AAAAAGGCAG GGGTTGCAAT |
| 2221 CCTAGTCTCT GATAAAACAG ACTTTAAACC AACAAAGATC AAAAGAGACA AAGAAGGCCA |
| 2281 TTACATAATG GTAAAGGGAT CAATTCAACA AGAGGAGCTA ACTATCCTAA ATATTTATGC |
| 2341 ACCCAATACA GGAGCACCCA GATTCATAAA GCAAGTCCTC AGTGACCTAC AAAGAGACTT |

TABLE 8-continued

Plasmid and mRNA construct sequences

```
2401 AGACTCCCAC ACATTAATAA TGGGAGACTT TAACACCCCA CTGTCAACAT TAGACAGATC
2461 AACGAGACAG AAAGTCAACA AGGATACCCA GGAATTGAAC TCAGCTCTGC ACCAAGCAGA
2521 CCTAATAGAC ATCTACAGAA CTCTCCACCC CAAATCAACA GAATATACAT TTTTTTCAGC
2581 ACCACACCAC ACCTATTCCA AAATTGACCA CATAGTTGGA AGTAAAGCTC TCCTCAGCAA
2641 ATGTAAAAGA ACAGAAATTA TAACAAACTA TCTCTCAGAC CACAGTGCAA TCAAACTAGA
2701 ACTCAGGATT AAGAATCTCA CTCAAAGCCG CTCAACTACA TGGAAACTGA ACAACCTGCT
2761 CCTGAATGAC TACTGGGTAC ATAACGAAAT GAAGGCAGAA ATAAAGATGT TCTTTGAAAC
2821 CAACGAGAAC AAAGACACCA CATACCAGAA TCTCTGGGAC GCATTCAAAG CAGTGTGTAG
2881 AGGGAAATTT ATAGCACTAA ATGCCTACAA GAGAAAGCAG GAAAGATCCA AAATTGACAC
2941 CCTAACATCA CAATTAAAAG AACTAGAAAA GCAAGAGCAA ACACATTCAA AAGCTAGCAG
3001 AAGGCAAGAA ATAACTAAAA TCAGAGCAGA ACTGAAGGAA ATAGAGACAC AAAAAACCCT
3061 TCAAAAAATC AATGAATCCA GGAGCTGGTT TTTTGAAAGG ATCAACAAAA TTGATAGACC
3121 GCTAGCAAGA CTAATAAAGA AAAAAAGAGA GAAGAATCAA ATAGACACAA TAAAAAATGA
3181 TAAAGGGGAT ATCACCACCG ATCCCACAGA AATACAAACT ACCATCAGAG AATACTACAA
3241 ACACCTCTAC GCAAATAAAC TAGAAAATCT AGAAGAAATG GATACATTCC TCGACACATA
3301 CACTCTCCCA AGACTAAACC AGGAAGAAGT TGAATCTCTG AATCGACCAA TAACAGGCTC
3361 TGAAATTGTG GCAATAATCA ATAGTTTACC AACCAAAAAG AGTCCAGGAC CAGATGGATT
3421 CACAGCCGAA TTCTACCAGA GGTACAAGGA GGAACTGGTA CCATTCCTTC TGAAACTATT
3481 CCAATCAATA GAAAAAGAGG GAATCCTCCC TAACTCATTT TATGAGGCCA GCATCATTCT
3541 GATACCAAAG CCGGGCAGAG ACACAACCAA AAAAGAGAAT TTTAGACCAA TATCCTTGAT
3601 GAACATTGAT GCAAAAATCC TCAATAAAAT ACTGGCAAAC CGAATCCAGC AGCACATCAA
3661 AAAGCTTATC CACCATGATC AAGTGGGCTT CATCCCTGGG ATGCAAGGCT GGTTCAATAT
3721 ACGCAAATCA ATAAATGTAA TCCAGCATAT AAACAGAGCC AAAGACAAAA ACCACATGAT
3781 TATCTCAATA GATGCAGAAA AAGCCTTTGA CAAAATTCAA CAACCCTTCA TGCTAAAAAC
3841 TCTCAATAAA TTAGGTATTG ATGGGACGTA TTTCAAAATA ATAAGAGCTA TCTATGACAA
3901 ACCCACAGCC AATATCATAC TGAATGGGCA AAAACTGGAA GCATTCCCTT TGAAAACCGG
3961 CACAAGACAG GGATGCCCTC TCTCACCGCT CCTATTCAAC ATAGTGTTGG AAGTTCTGGC
4021 CAGGGCAATC AGGCAGGAGA AGGAAATAAA GGGTATTCAA TTAGGAAAAG AGGAAGTCAA
4081 ATTGTCCCTG TTTGCAGACG ACATGATTGT TTATCTAGAA AACCCCATCG TCTCAGCCCA
4141 AAATCTCCTT AAGCTGATAA GCAACTTCAG CAAAGTCTCA GGATACAAAA TCAATGTACA
4201 AAAATCACAA GCATTCTTAT ACACCAACAA CAGACAAACA GAGAGCCAAA TCATGGGTGA
4261 ACTCCCATTC ACAATTGCTT CAAAGAGAAT AAAATACCTA GGAATCCAAC TTACAAGGGA
4321 TGTGAAGGAC CTCTTCAAGG AGAACTACAA ACCACTGCTC AAGGAAATAA AAGAGGAGAC
4381 AAACAAATGG AAGAACATTC CATGCTCATG GGTAGGAAGA ATCAATATCG TGAAAATGGC
4441 CATACTGCCC AAGGTAATTT ACAGATTCAA TGCCATCCCC ATCAAGCTAC CAATGACTTT
4501 CTTCACAGAA TTGGAAAAAA CTACTTTAAA GTTCATATGG AACCAAAAAA GAGCCCGCAT
4561 TGCCAAGTCA ATCCTAAGCC AAAAGAACAA AGCTGGAGGC ATCACACTAC CTGACTTCAA
4621 ACTATACTAC AAGGCTACAG TAACCAAAAC AGCATGGTAC TGGTACCAAA ACAGAGATAT
4681 AGATCAATGG AACAGAACAG AGCCCTCAGA AATAATGCCG CATATCTACA ACTATCTGAT
4741 CTTTGACAAA CCTGAGAAAA ACAAGCAATG GGGAAAGGAT TCCCTATTTA ATAAATGGTG
4801 CTGGGAAAAC TGGCTAGCCA TATGTAGAAA GCTGAAACTG GATCCCTTCC TTACACCTTA
4861 TACAAAAATC AATTCAAGAT GGATTAAAGA TTTAAACGTT AAACCTAAAA CCATAAAAAC
4921 CCTAGAAGAA AACCTAGGCA TTACCATTCA GGACATAGGC GTGGGCAAGG ACTTCATGTC
4981 CAAAACACCA AAAGCAATGG CAACAAAAGA CAAAATTGAC AAATGGGATC TAATTAAACT
5041 AAAGAGCTTC TGCACAGCAA AAGAAACTAC CATCAGAGTG AACAGGCAAC CTACAACATG
5101 GGAGAAAATT TTTGCAACCT ACTCATCTGA CAAAGGGCTA ATATCCAGAA TCTACAATGA
5161 ACTCAAACAA ATTTACAAGA AAAAAACAAA CAACCCCATC AAAAAGTGGG CGAAGGACAT
5221 GAACAGACAC TTCTCAAAAG AAGACATTTA TGCAGCCAAA AAACACATGA AGAAATGCTC
5281 ATCATCACTG GCCATCAGAG AAATGCAAAT CAAAACCACT ATGAGATATC ATCTCACACC
5341 AGTTAGAATG GCAATCATTA AAAAGTCAGG AAACAACAGG TGCTGGAGAG GATGCGGAGA
5401 AATAGGAACA CTTTTACACT GTTGGTGGGA CTGTAAACTA GTTCAACCAT TGTGGAAGTC
5461 AGTGTGGCGA TTCCTCAGGG ATCTAGAACT AGAAATACCA TTTGACCCAG CCATCCCATT
5521 ACTGGGTATA TACCCAAATG AGTATAAATC ATGCTGCTAT AAAGACACAT GCACACGTAT
5581 GTTTATTGCG GCACTATTCA CAATAGCAAA GACTTGGAAC CAACCCAAAT GTCCAACAAT
5641 GATAGACTGG ATTAAGAAAA TGTGGCACAT ATACACCATG GAATACTATG CAGCCATAAA
5701 AAATGATGAG TTCATATCCT TTGTAGGGAC ATGGATGAAA TTGGAAACCA TCATTCTCAG
5761 TAAACTATCG CAAGAACAAA AAACCAAACA CCGCATATTC TCACTCATAG GTGGGAATTG
5821 AACAATGAGA TCACATGGAC ACAGGAAGGG GAATATCACA CTCTGGGGAC TGTGGTGGGG
5881 TCGGGGGAGG GGGGAGGGAT AGCATTGGGA GATATACCTA ATGCTAGATG ACACATTAGT
5941 GGGTGCAGCG CACCAGCATG GCACATGTAT ACGGATCCGA ATTCTCGACG GATCGATCCG
6001 AACAAACGAC CCAACACCCG TGCGTTTTAT TCTGTCTTTT TATTGCCGAT CCCCTCAGAA
6061 GAACTCGTCA AGAAGGCGAT AGAAGGCGAT GCGCTGCGAA TCGGGAGCGG CGATACCGTA
6121 AAGCACGAGG AAGCGGTCAG CCCATTCGCC GCCAAGCTCT TCAGCAATAT CACGGGTAGC
6181 CAACGCTATG TCCTGATAGC GGTCGGCCGC TTTACTTGTA CAGCTCGTCC ATGCCGAGAG
6241 TGATCCCGGC GGCGGTCACG AACTCCAGCA GGACCATGTG ATCGCGCTTC TCGTTGGGGT
6301 CTTTGCTCAG GGCGGACTGG GTGCTCAGGT AGTGGTTGTC GGGCAGCAGC ACGGGGCCGT
6361 CGCCGATGGG GGTGTTCTGC TGGTAGTGGT CGGCCAGGTG AGTCCAGGAG ATGTTTCAGC
6421 ACTGTTGCCT TTAGTCTCGA GGCAACTTAG ACAACTGAGT ATTGATCTGA GCACAGCAGG
6481 GTGTGAGCTG TTTGAAGATA CTGGGGTTGG GGGTGAAGAA ACTGCAGAGG ACTAACTGGG
6541 CTGAGACCCA GTGGCAATGT TTTAGGGCCT AAGGAATGCC TCTGAAAATC TAGATGGACA
6601 ACTTTGACTT TGAGAAAAGA GAGGTGGAAA TGAGGAAAAT GACTTTTCTT TATTAGATTT
6661 CGGTAGAAAG AACTTTCATC TTTCCCCTAT TTTTGTTATT CGTTTTAAAA CATCTATCTG
6721 GAGGCAGGAC AAGTATGGTC ATTAAAAAGA TGCAGGCAGA AGGCATATAT TGGCTCAGTC
6781 AAAGTGGGGA ACTTTGGTGG CCAAACATAC ATTGCTAAGG CTATTCCTAT ATCAGCTGGA
6841 CACATATAAA ATGCTGCTAA TGCTTCATTA CAAACTTATA TCCTTTAATT CCAGATGGGG
6901 GCAAAGTATG TCCAGGGGTG AGGAACAATT GAAACATTTG GGCTGGAGTA GATTTTGAAA
6961 GTCAGCTCTG TGTGTGTGTG TGTGTGTGTG TGTGTGAGAG CGTGTGTTTC TTTTAACGTT
7021 TTCAGCCTAC AGCATACAGG GTTCATGGTG GCAAGAAGAT AACAAGATTT AAATTATGGC
```

TABLE 8-continued

| Plasmid and mRNA construct sequences |
|---|
| 7081 CAGTGACTAG TGCTGCAAGA AGAACAACTA CCTGCATTTA ATGGGAAAGC AAAATCTCAG |
| 7141 GCTTTGAGGG AAGTTAACAT AGGCTTGATT CTGGGTGGAA GCTGGGTGTG TAGTTATCTG |
| 7201 GAGGCCAGGC TGGAGCTCTC AGCTCACTAT GGGTTCATCT TTATTGTCTC CTTTCATCTC |
| 7261 AACAGCTGCA CGCTGCCGTC CTCGATGTTG TGGCGGATCT TGAAGTTCAC CTTGATGCCG |
| 7321 TTCTTCTGCT TGTCGGCCAT GATATAGACG TTGTGGCTGT TGTAGTTGTA CTCCAGCTTG |
| 7381 TGCCCCAGGA TGTTGCCGTC CTCCTTGAAG TCGATGCCCT TCAGCTCGAT GCGGTTCACC |
| 7441 AGGGTGTCGC CCTCGAACTT CACCTCGGCG CGGGTCTTGT AGTTGCCGTC GTCCTTGAAG |
| 7501 AAGATGGTGC GCTCCTGGAC GTAGCCTTCG GGCATGGCGG ACTTGAAGAA GTCGTGCTGC |
| 7561 TTCATGTGGT CGGGGTAGCG GCTGAAGCAC TGCACGCCGT AGGTCAGGGT GGTCACGAGG |
| 7621 GTGGGCCAGG GCACGGGCAG CTTGCCGGTG GTGCAGATGA ACTTCAGGGT CAGCTTGCCG |
| 7681 TAGGTGGCAT CGCCCTCGCC CTCGCCGGAC ACGCTGAACT TGTGGCCGTT TACGTCGCCG |
| 7741 TCCAGCTCGA CCAGGATGGG CACCACCCCG GTGAACAGCT CCTCGCCCTT GCTCACCATA |
| 7801 GGGCCGGGAT TCTCCTCCAC GTCACCGCAT GTTAGAAGAC TTCCTCTGCC CTCTCTTGGA |
| 7861 GGCAGGGCCT GCATGTGCAG GGCATCGTAG GTATCCTTGG TGGCTGTGCT CAGTCCCTGG |
| 7921 TACAGTCCAT CGTGGCCCTT GCCTCTTCTT CTCTCGCCCT TCATGCCGAT CTCGCTGTAG |
| 7981 GCCTCGGCCA TCTTGTCTTT CTGCAGCTCA TTATACAGGC CCTCTTGAGG ATTCTTTCTC |
| 8041 CGCTGGGGCT TGCCGCCCAT CTCAGGATCT CTGCCTCTCC GCTTATCCAG CACGTCGTAC |
| 8101 TCTTCTCTTC TCCCCAGGTT CAGCTCGTTG TACAGCTGAT TCTGGCCCTG CTGGTAAGCA |
| 8161 GGAGCGTCGG CGGATCTGCT GAACTTCACT CTGCAGTACA GGGTGATGAC CAGAGAGAGC |
| 8221 AGCAGAACGC CACATGTGCC AGCCAGAGGG GCCCAAATGT AGATATCCAG GCCTCTGGTA |
| 8281 TGCACAGCTC CGCCAGCTGC AGGTCTACAG GCTTCAGGTC TGAGAGACAG AGGCTGGCTG |
| 8341 GCGATTGTAG GAGCTGGTGT AGGTGGTCTA GGAGCGGGTG TTGTTGTAGG CTTGGCGGGC |
| 8401 AGAAACACGG GCACGAAGTG GCTGAAGTAC ATGATGCTAT TGCTCAGGGC TCCGCTTCCT |
| 8461 CCGCCTCCGC TAGAAGAAAC TGTGACCAGG GTGCCCTGTC CCCAAACATC CATGGCGTAG |
| 8521 AAGCCGTCGC CTCCCCATCT AGAACAGTAG TACACGGCGG TGTCCTCGGC TCTCAGGCTG |
| 8581 TTCATCTGCA GGTAGGCGGT GTTCTTGCTG GTGTCGGCGC TGATGGTGAA TCTGCCCTTC |
| 8641 ACGCTATCGG CGTATCTGGT GTAGCCGTTG GTGGGGTAGA TTCTGGCGAC CCATTCAAGT |
| 8701 CCCTTTCCAG GGGCCTGTCG GACCCAGTGG ATGTAGGTGT CCTTGATGTT GAAGCCGCTG |
| 8761 GCGGCACAAG ACAGTCTCAG AGAGCCGCCA GGCTGAACAA GTCCTCCGCC AGATTCAACC |
| 8821 AGCTGCACCT CAGATCCTTC GCCAGATCCA GGCTTTCCAG AGCCGCTGGT GCTGCCTGTT |
| 8881 CTCTTGATTT CCACCTTGGT GCCCTGGCCA AAGGTTGGAG GTGTGGTGTA GTGCTGCTGG |
| 8941 CAGTAGTAGG TGGCGAAGTC CTCAGGCTGC AGGCTAGAGA TGGTCAGGGT GAAGTCGGTG |
| 9001 CCAGATCTGC TGCCGCTGAA TCTGCTTGGC ACGCCGCTGT ACAGAAAGCT GGCGCTGTAG |
| 9061 ATCAGCAGCT TAGGGGCTTT TCCAGGCTTC TGCTGATACC AGGCCACGGC GGTATTCACA |
| 9121 TCCTGGCTGG CTCTACAGGT GATGGTCACT CTATCGCCCA CAGAGGCAGA CAGGCTGCTA |
| 9181 GGGCTCTGTG TCATCTGGAT GTCGCTGATG CTGCAGGCCA CTGTTCCCAG CAGCAGCAGA |
| 9241 GACTGCAGCC ACATTCGAAG CTTGAGCTCG AGATCTGAGT CCGGTAGCGC TAGCGGATCT |
| 9301 GACGGTTCAC TAAACCAGCT CTGCTTATAT AGACCTCCCA CCGTACACGC CTACCGCCCA |
| 9361 TTTGCGTCAA TGGGGCGGAG TTGTTACGAC ATTTTGGAAA GTCCCGTTGA TTTTGGTGCC |
| 9421 AAAACAAACT CCCATTGACG TCAATGGGGT GGAGACTTGG AAATCCCCGT GAGTCAAACC |
| 9481 GCTATCCACG CCCATTGATG TACTGCCAAA ACCGCATCAC CATGGTAATA GCGATGACTA |
| 9541 ATACGTAGAT GTACTGCCAA GTAGGAAAGT CCCATAAGGT CATGTACTGG GCATAATGCC |
| 9601 AGGCGGGCCA TTTACCGTCA TTGACGTCAA TAGGGGGCGT ACTTGGCATA TGATACACTT |
| 9661 GATGTACTGC CAAGTGGGCA GTTTACCGTA AATACTCCAC CCATTGACGT CAATGGAAAG |
| 9721 TCCCTATTGG CGTTACTATG GGAACATACG TCATTATTGA CGTCAATGGG CGGGGGTCGT |
| 9781 TGGGCGGTCA GCCAGGCGGG CCATTTACCG TAAGTTATGT AACGCGGAAC TCCATATATG |
| 9841 GGCTATGAAC TAATGACCCC GTAATTGATT ACTATTAGCC CGGGGGATCC AGACATGATA |
| 9901 AGATACATTG ATGAGTTTGG ACAAACCACA ACTAGAATGC AGTGAAAAAA ATGCTTTATT |
| 9961 TGTGAAATTT GTGATGCTAT TGCTTTATTT GTAACCATTA TAAGCTGCAA TAAACAAGTT |
| 10021 AACAACAACA ATTGCATTCA TTTTATGTTT CAGGTTCAGG GGGAGGTGTG GGAGGTTTTT |
| 10081 TAAAGCAAGT AAAACCTCTA CAAATGTGGT ATGGCTGATT ATGATCCGGC TGCCTCGCGC |
| 10141 GTTTCGGTGA TGACGGTGAA AACCTCTGAC ACATGCAGCT CCCGGAGACG GTCACAGCTT |
| 10201 GTCTGTAAGC GGATGCCGGG AGCAGACAAG CCCGTCAGGG CGCGTCAGCG GGTGTTGGCG |
| 10261 GGTGTCGGGG CGCAGCCATG AGGTCGATCG ACTCTAGAGG ATCGATCCCC GCCCCGGACG |
| 10321 AACTAAACCT GACTACGACA TCTCTGCCCC TTCTTCGCGG GGCAGTGCAT GTAATCCCTT |
| 10381 CAGTTGGTTG GTACAACTTG CCAACTGGGC CCTGTTCCAC ATGTGACACG GGGGGGGACC |
| 10441 AAACACAAAG GGGTTCTCTG ACTGTAGTTG ACATCCTTAT AAATGGATGT GCACATTTGC |
| 10501 CAACACTGAG TGGCTTTCAT CCTGGAGCAG ACTTTGCAGT CTGTGGACTG CAACACAACA |
| 10561 TTGCCTTTAT GTGTAACTCT TGGCTGAAGC TCTTACACCA ATGCTGGGGG ACATGTACCT |
| 10621 CCCAGGGGCC CAGGAAGACT ACGGGAGGCT ACACCAACGT CAATCAGAGG GGCCTGTGTA |
| 10681 GCTACCGATA AGCGGACCCT CAAGAGGGCA TTAGCAATAG TGTTTATAAG GCCCCCTTGT |
| 10741 TAACCCTAAA CGGGTAGCAT ATGCTTCCCG GGTAGTAGTA TATACTATCC AGACTAACCC |
| 10801 TAATTCAATA GCATATGTTA CCCAACGGGA AGCATATGCT ATCGAATTAG GGTTAGTAAA |
| 10861 AGGGTCCTAA GGAACAGCGA TATCTCCCAC CCCATGAGCT GTCACGGTTT TATTTACATG |
| 10921 GGGTCAGGAT TCCACGAGGG TAGTGAACCA TTTTAGTCAC AAGGGCAGTG GCTGAAGATC |
| 10981 AAGGAGCGGG CAGTGAACTC TCCTGAATCT TCGCCTGCTT CTTCATTCTC CTTCGTTTAG |
| 11041 CTAATAGAAT AACTGCTGAG TTGTGAACAG TAAGGTGTAT GTGAGGTGCT CGAAAACAAG |
| 11101 GTTTCAGGTG ACGCCCCCAG AATAAAATTT GGACGGGGGG TTCAGTGGTG GCATTGTGCT |
| 11161 ATGACACCAA TATAACCCTC ACAAACCCCT TGGGCAATAA ATACTAGTGT AGGAATGAAA |
| 11221 CATTCTGAAT ATCTTTAACA ATAGAAATCC ATGGGGTGGG GACAAGCCGT AAAGACTGGA |
| 11281 TGTCCATCTC ACACGAATTT ATGGCTATGG GCAACACATA ATCCTAGTGC AATATGATAC |
| 11341 TGGGGTTATT AAGATGTGTC CCAGGCAGGG ACCAAGACAG GTGAACCATG TTGTTACACT |
| 11401 CTATTTGTAA CAAGGGGAAA GAGAGTGGAC GCCGACAGCA GCGGACTCCA CTGGTTGTCT |
| 11461 CTAACACCCC CGAAAATTAA ACGGGGCTCC ACGCCAATGG GGCCCATAAA CAAAGACAAG |
| 11521 TGGCCACTCT TTTTTTTGAA ATTGTGGAGT GGGGGCACGC GTCAGCCCCC ACACGCCGCC |
| 11581 CTGCGGTTTT GGACTGTAAA ATAAGGGTGT AATAACTTGG CTGATTGTAA CCCCGCTAAC |
| 11641 CACTGCGGTC AAACCACTTG CCCACAAAAC CACTAATGGC ACCCCGGGGA ATACCTGCAT |
| 11701 AAGTAGGTGG GCGGGCCAAG ATAGGGGCGC GATTGCTGCG ATCTGGAGGA CAAATTACAC |

TABLE 8-continued

| Plasmid and mRNA construct sequences |
|---|
| 11761 ACACTTGCGC CTGAGCGCCA AGCACAGGGT TGTTGGTCCT CATATTCACG AGGTCGCTGA |
| 11821 GAGCACGGTG GGCTAATGTT GCCATGGGTA GCATATACTA CCCAAATATC TGGATAGCAT |
| 11881 ATGCTATCCT AATCTATATC TGGGTAGCAT AGGCTATCCT AATCTATATC TGGGTAGCAT |
| 11941 ATGCTATCCT AATCTATATC TGGGTAGTAT ATGCTATCCT AATTTATATC TGGGTAGCAT |
| 12001 AGGCTATCCT AATCTATATC TGGGTAGCAT ATGCTATCCT AATCTATATC TGGGTAGTAT |
| 12061 ATGCTATCCT AATCTGTATC CGGGTAGCAT ATGCTATCCT AATAGAGATT AGGGTAGTAT |
| 12121 ATGCTATCCT AATTTATATC TGGGTAGCAT ATACTACCCA AATATCTGGA TAGCATATGC |
| 12181 TATCCTAATC TATATCTGGG TAGCATATGC TATCCTAATC TATATCTGGG TAGCATAGGC |
| 12241 TATCCTAATC TATATCTGGG TAGCATATGC TATCCTAATC TATATCTGGG TAGTATATGC |
| 12301 TATCCTAATT TATATCTGGG TAGCATAGGC TATCCTAATC TATATCTGGG TAGCATATGC |
| 12361 TATCCTAATC TATATCTGGG TAGTATATGC TATCCTAATC TGTATCCGGG TAGCATATGC |
| 12421 TATCCTCATG CATATACAGT CAGCATATGA TACCCAGTAG TAGAGTGGGA GTGCTATCCT |
| 12481 TTGCATATGC CGCCACCTCC CAAGGGGGCG TGAATTTTCG CTGCTTGTCC TTTTCCTGCA |
| 12541 TGCTGGTTGC TCCCATTCTT AGGTGAATTT AAGGAGGCCA GGCTAAAGCC GTCGCATGTC |
| 12601 TGATTGCTCA CCAGGTAAAT GTCGCTAATG TTTTCCAACG CGAGAAGGTG TTGAGCGCGG |
| 12661 AGCTGAGTGA CGTGACAACA TGGGTATGCC CAATTGCCCC ATGTTGGGAG GACGAAAATG |
| 12721 GTGACAAGAC AGATGGCCAG AAATACACCA ACAGCACGCA TGATGTCTAC TGGGGATTTA |
| 12781 TTCTTTAGTG CGGGGGAATA CACGGCTTTT AATACGATTG AGGGCGTCTC CTAACAAGTT |
| 12841 ACATCACTCC TGCCCTTCCT CACCCTCATC TCCATCACCT CCTTCATCTC CGTCATCTCC |
| 12901 GTCATCACCC TCCGCGGCAG CCCCTTCCAC CATAGGTGGA AACCAGGGAG GCAAATCTAC |
| 12961 TCCATCGTCA AAGCTGCACA CAGTCACCCT GATATTGCAG GTAGGAGCGG GCTTTGTCAT |
| 13021 AACAAGGTCC TTAATCGCAT CCTTCAAAAC CTCAGCAAAT ATATGAGTTT GTAAAAAGAC |
| 13081 CATGAAATAA CAGACAATGG ACTCCCTTAG CGGGCCAGGT TGTGGGCCGG GTCCAGGGGC |
| 13141 CATTCCAAAG GGGAGACGAC TCAATGGTGT AAGACGACAT TGTGGAATAG CAAGGGCAGT |
| 13201 TCCTCGCCTT AGGTTGTAAA GGGAGGTCTT ACTACCTCCA TATACGAACA CACCGGCGAC |
| 13261 CCAAGTTCCT TCGTCGGTAG TCCTTTCTAC GTGACTCCTA GCCAGGAGAG CTCTTAAACC |
| 13321 TTCTGCAATG TTCTCAAATT TCGGGTTGGA ACCTCCTTGA CCACGATGCT TTCCAAACCA |
| 13381 CCCTCCTTTT TTGCGCCTGC CTCCATCACC CTGACCCCGG GGTCCAGTGC TTGGGCCTTC |
| 13441 TCCTGGGTCA TCTGCGGGGC CCTGCTCTAT CGCTCCCGGG GGCACGTCAG GCTCACCATC |
| 13501 TGGGCCACCT TCTTGGTGGT ATTCAAAATA ATCGGCTTCC CCTACAGGGT GGAAAAATGG |
| 13561 CCTTCTACCT GGAGGGGGCC TGCGCGGTGG AGACCCGGAT GATGATGACT GACTACTGGG |
| 13621 ACTCCTGGGC CTCTTTTCTC CACGTCCACG ACCTCTCCCC CTGGCTCTTT CACGACTTCC |
| 13681 CCCCCTGGCT CTTTCACGTC CTCTACCCCG GCGGCCTCCA CTACCTCCTC GACCCCGGCC |
| 13741 TCCACTACCT CCTCGACCCC GGCCTCCACT GCCTCCTCGA CCCCGGCCTC CACCTCCTGC |
| 13801 TCCTGCCCCT CCTGCTCCTG CCCCTCCTCC TGCTCCTGCC CCTCCTGCCC CTCCTGCTCC |
| 13861 TGCCCCTCCT GCCCCTCCTG CTCCTGCCCC TCCTGCCCCT CCTGCTCCTG CCCCTCCTGC |
| 13921 CCCTCCTCCT GCTCCTGCCC CTCCTGCCCC TCCTCCTGCT CCTGCCCCTC CTGCCCCTCC |
| 13981 TGCTCCTGCC CCTCCTGCCC CTCCTGCTCC TGCCCCTCCT GCCCCTCCTG CTCCTGCCCC |
| 14041 TCCTGCTCCT GCCCCTCCTG CTCCTGCCCC TCCTGCTCCT GCCCCTCCTG CCCCTCCTGC |
| 14101 CCCTCCTCCT GCTCCTGCCC CTCCTGCTCC TGCCCCTCCT GCCCCTCCTG CCCCTCCTGC |
| 14161 TCCTGCCCCT CCTCCTGCTC CTGCCCCTCC TGCCCCTCCT GCCCCTCCTC CTGCTCCTGC |
| 14221 CCCTCCTGCC CCTCCTCCTG CTCCTGCCCC TCCTCCTGCT CCTGCCCCTC CTGCCCCTCC |
| 14281 TGCCCCTCCT CCTGCTCCTG CCCCTCCTGC CCCTCCTCCT GCTCCTGCCC CTCCTCCTGC |
| 14341 TCCTGCCCCT CCTGCCCCTC CTGCCCCTCC TCCTGCTCCT GCCCCTCCTC CTGCTCCTGC |
| 14401 CCCTCCTGCC CCTCCTGCCC CTCCTGCCCC TCCTCCTGCT CCTGCCCCTC CTCCTGCTCC |
| 14461 TGCCCCTCCT GCTCCTGCCC CTCCCGCTCC TGCTCCTGCT CCTGTTCCAC CGTGGGTCCC |
| 14521 TTTGCAGCCA ATGCAACTTG GACGTTTTTG GGGTCTCCGG ACACCATCTC TATGTCTTGG |
| 14581 CCCTGATCCT GAGCCGCCCG GGGCTCCTGG TCTTCCGCCT CCTCGTCCTC GTCCTCTTCC |
| 14641 CCGTCCTCGT CCATGGTTAT CACCCCCTCT TCTTTGAGGT CCACTGCCGC CGGAGCCTTC |
| 14701 TGGTCCAGAT GTGTCTCCCT TCTCTCCTAG GCCATTTCCA GGTCCTGTAC CTGGCCCCTC |
| 14761 GTCAGACATG ATTCACACTA AAAGAGATCA ATAGACATCT TTATTAGACG ACGCTCAGTG |
| 14821 AATACAGGGA GTGCAGACTC CTGCCCCCTC CAACAGCCCC CCCACCCTCA TCCCCTTCAT |
| 14881 GGTCGCTGTC AGACAGATCC AGGTCTGAAA ATTCCCCATC CTCCGAACCA TCCTCGTCCT |
| 14941 CATCACCAAT TACTCGCAGC CCGGAAAACT CCCGCTGAAC ATCCTCAAGA TTTGCGTCCT |
| 15001 GAGCCTCAAG CCAGGCCTCA AATTCCTCGT CCCCCTTTTT GCTGGACGGT AGGGATGGGG |
| 15061 ATTCTCGGGA CCCCTCCTCT TCCTCTTCAA GGTCACCAGA CAGAGATGCT ACTGGGGCAA |
| 15121 CGGAAGAAAA GCTGGGTGCG GCCTGTGAGG ATCAGCTTAT CGATGATAAG CTGTCAAACA |
| 15181 TGAGAATTCT TGAAGACGAA AGGGCCTCGT GATACGCCTA TTTTTATAGG TTAATGTCAT |
| 15241 GATAATAATG GTTTCTTAGA CGTCAGGTGG CACTTTTCGG GGAAATGTGC GCGGAACCCC |
| 15301 TATTTGTTTA TTTTTCTAAA TACATTCAAA TATGTATCCG CTCATGAGAC AATAACCCTG |
| 15361 ATAAATGCTT CAATAATATT GAAAAAGGAA GAGTATGAGT ATTCAACATT TCCGTGTCGC |
| 15421 CCTTATTCCC TTTTTTGCGG CATTTTGCCT TCCTGTTTTT GCTCACCCAG AAACGCTGGT |
| 15481 GAAAGTAAAA GATGCTGAAG ATCAGTTGGG TGCACGAGTG GGTTACATCG AACTGGATCT |
| 15541 CAACAGCGGT AAGATCCTTG AGAGTTTTCG CCCCGAAGAA CGTTTTCCAA TGATGAGCAC |
| 15601 TTTTAAAGTT CTGCTATGTG GCGCGGTATT ATCCCGTGTT GACGCCGGGC AAGAGCAACT |
| 15661 CGGTCGCCGC ATACACTATT CTCAGAATGA CTTGGTTGAG TACTCACCAG TCACAGAAAA |
| 15721 GCATCTTACG GATGGCATGA CAGTAAGAGA ATTATGCAGT GCTGCCATAA CCATGAGTGA |
| 15781 TAACACTGCG GCCAACTTAC TTCTGACAAC GATCGGAGGA CCGAAGGAGC TAACCGCTTT |
| 15841 TTTGCACAAC ATGGGGGATC ATGTAACTCG CCTTGATCGT TGGGAACCGG AGCTGAATGA |
| 15901 AGCCATACCA AACGACGAGC GTGACACCAC GATGCCTGCA GCAATGGCAA CAACGTTGCG |
| 15961 CAAACTATTA ACTGGCGAAC TACTTACTCT AGCTTCCCGG CAACAATTAA TAGACTGGAT |
| 16021 GGAGGCGGAT AAAGTTGCAG GACCACTTCT GCGCTCGGCC CTTCCGGCTG GCTGGTTTAT |
| 16081 TGCTGATAAA TCTGGAGCCG GTGAGCGTGG GTCTCGCGGT ATCATTGCAG CACTGGGGCC |
| 16141 AGATGGTAAG CCCTCCCGTA TCGTAGTTAT CTACACGACG GGGAGTCAGG CAACTATGGA |
| 16201 TGAACGAAAT AGACAGATCG CTGAGATAGG TGCCTCACTG ATTAAGCATT GGTAACTGTC |
| 16261 AGACCAAGTT TACTCATATA TACTTTAGAT TGATTTAAAA CTTCATTTTT AATTTAAAAG |
| 16321 GATCTAGGTG AAGATCCTTT TTGATAATCT CATGACCAAA ATCCCTTAAC GTGAGTTTTC |
| 16381 GTTCCACTGA GCGTCAGACC CCGTAGAAAA GATCAAAGGA TCTTCTTGAG ATCCTTTTTT |

TABLE 8-continued

Plasmid and mRNA construct sequences

```
16441 TCTGCGCGTA ATCTGCTGCT TGCAAACAAA AAAACCACCG CTACCAGCGG TGGTTTGTTT
16501 GCCGGATCAA GAGCTACCAA CTCTTTTTCC GAAGGTAACT GGCTTCAGCA GAGCGCAGAT
16561 ACCAAATACT GTCCTTCTAG TGTAGCCGTA GTTAGGCCAC CACTTCAAGA ACTCTGTAGC
16621 ACCGCCTACA TACCTCGCTC TGCTAATCCT GTTACCAGTG GCTGCTGCCA GTGGCGATAA
16681 GTCGTGTCTT ACCGGGTTGG ACTCAAGACG ATAGTTACCG GATAAGGCGC AGCGGTCGGG
16741 CTGAACGGGG GGTTCGTGCA CACAGCCCAG CTTGGAGCGA ACGACCTACA CCGAACTGAG
16801 ATACCTACAG CGTGAGCTAT GAGAAAGCGC CACGCTTCCC GAAGGGAGAA AGGCGGACAG
16861 GTATCCGGTA AGCGGCAGGG TCGGAACAGG AGAGCGCACG AGGGAGCTTC CAGGGGGAAA
16921 CGCCTGGTAT CTTTATAGTC CTGTCGGGTT TCGCCACCTC TGACTTGAGC GTCGATTTTT
16981 GTGATGCTCG TCAGGGGGGC GGAGCCTATG GAAAAACGCC AGCAACGCGG CCTTTTTACG
17041 GTTCCTGGCC TTTTGCTGGC CTTTTGCTCA CATGTTCTTT CCTGCGTTAT CCCCTGATTC
17101 TGTGGATAAC CGTATTACCG CCTTTGAGTG AGCTGATACC GCTCGCCGCA GCCGAACGAC
17161 CGAGCGCAGC GAGTCAGTGA GCGAGGAAGC GGAAGAGCGC CTGATGCGGT ATTTTCTCCT
17221 TACGCATCTG TGCGGTATTT CACACCGCAT ATGGTGCACT CTCAGTACAA TCTGCTCTGA
17281 TGCCGCATAG TTAAGCCAGC TGTGGAATGT GTGTCAGTTA GGGTGTGGAA AGTCCCCAGG
17341 CTCCCCAGCA GGCAGAAGTA TGCAAAGCAT GCATCTCAAT TAGTCAGCAA CCAGGTGTGG
17401 AAAGTCCCCA GGCTCCCCAG CAGGCAGAAG TATGCAAAGC ATGCATCTCA ATTAGTCAGC
17461 AACCATAGTC CCGCCCCTAA CTCCGCCCAT CCCGCCCCTA ACTCCGCCCA GTTCCGCCCA
17521 TTCTCCGCCC CATGGCTGAC TAATTTTTTT TATTTATGCA GAGGCCGAGG CCGCCTCGGC
17581 CTCTGAGCTA TTCCAGAAGT AGTGAGGAGG CTTTTTTGGA GGCCTAGGCT TTTGCAAAAA
17641 GCTTGCATGC CTGCAGGTCG GCCGCCACGA CCGGTGCCGC CACCATCCCC TGACCCACGC
17701 CCCTGACCCC TCACAAGGAG ACGACCTTCC ATGACCGAGT ACAAGCCCAC GGTGCGCCTC
17761 GCCACCCGCG ACGACGTCCC CCGGGCCGTA CGCACCCTCG CCGCCGCGTT CGCCGACTAC
17821 CCCGCCACGC GCCACACCGT CGACCCGGAC CGCCACATCG AGCGGGTCAC CGAGCTGCAA
17881 GAACTCTTCC TCACGCGCGT CGGGCTCGAC ATCGGCAAGG TGTGGGTCGC GGACGACGGC
17941 GCCGCGGTGG CGGTCTGGAC CACGCCGGAG AGCGTCGAAG CGGGGGCGGT GTTCGCCGAG
18001 ATCGGCCCGC GCATGGCCGA GTTGAGCGGT TCCCGGCTGG CCGCGCAGCA ACAGATGGAA
18061 GGCCTCCTGG CGCCGCACCG GCCCAAGGAG CCCGCGTGGT TCCTGGCCAC CGTCGGCGTC
18121 TCGCCCGACC ACCAGGGCAA GGGTCTGGGC AGCGCCGTCG TGCTCCCCGG AGTGGAGGCG
18181 GCCGAGCGCG CCGGGGTGCC CGCCTTCCTG GAGACCTCCG CGCCCCGCAA CCTCCCCTTC
18241 TACGAGCGGC TCGGCTTCAC CGTCACCGCC GACGTCGAGG TGCCCGAAGG ACCGCGCACC
18301 TGGTGCATGA CCCGCAAGCC CGGTGCCTGA CGCCCGCCCC ACGACCCGCA GCGCCCGACC
18361 GAAAGGAGCG CACGACCCCA TGGCTCCGAC CGAAGCCGAC CCGGGCGGCC CCGCCGACCC
18421 CGCACCCGCC CCCGAGGCCC ACCGACTCTA GAGGATCATA ATCAGCCATA CCACATTTGT
18481 AGAGGTTTTA CTTGCTTTAA AAAACCTCCC ACACCTCCCC CTGAACCTGA AACATAAAAT
18541 GAATGCAATT GTTGTTGTTA ACTTGTTTAT TGCAGCTTAT AATGGTTACA AATAAAGCAA
18601 TAGCATCACA AATTTCACAA ATAAAGCATT TTTTTCACTG CATTCTAGTT GTGGTTTGTC
18661 CAAACTCATC AATGTATCTT ATCATGTCTG GATCACTCGC CGATAGTGGA AACCGACGCC
18721 CCAGCACTCG TCCGAGGGCA AAGGAATAGG GGAGATGGGG GAGGCTAACT GAAACACGGA
18781 AGGAGACAAT ACCGGAAGGA ACCCGCGCTA TGACGGCAAT AAAAAGACAG AATAAAACGC
18841 ACGGGTGTTG GGTCGTTTGT TCATAAACGC GGGGTTCGGT CCCAGGGCTG GCACTCTGTC
18901 GATACCCCAC CGAGACCCCA TTGGGGCCAA TACGCCCGCG TTTCTTCCTT TTCCCCACCC
18961 CACCCCCCAA GTTCGGGTGA AGGCCCAGGG CTCGCAGCCA ACGTCGGGGC GGCAGGCCCT
19021 GCCATAGCCA CTGGCCCCGT GGGTTAGGGA CGGGGTCCCC CATGGGGAAT GGTTTATGGT
19081 TCGTGGGGGT TATTATTTTG GGCGTTGCGT GGGGTCTGGT CCACGACTGG ACTGAGCAGA
19141 CAGACCCATG GTTTTTGGAT GGCCTGGGCA TGGACCGCAT GTACTGGCGC GACACGAACA
19201 CCGGGCGTCT GTGGCTGCCA AACACCCCCG ACCCCCAAAA ACCACCGCGC GGATTTCTGG
19261 CGTGCCAAGC TAGTCGACCA ATTCTCATGT TTGACAGCTT ATCATCGCAG ATCCGGGCAA
19321 CGTTGTTGCA TTGCTGCAGG CGCAGAACTG GTAGGTATGG AAGATCTCTA GAAGCTGGGT
19381 ACCAGCTGCT AGCAAGCTTG CTAGCGGCCG GCTCGAGTTT ACTCCCTATC AGTGATAGAG
19441 AACGTATGTC GAGTTTACTC CCTATCAGTG ATAGAGAACG ATGTCGAGTT TACTCCCTAT
19501 CAGTGATAGA GAACGTATGT CGAGTTTACT CCCTATCAGT GATAGAGAAC GTATGTCGAG
19561 TTTACTCCCT ATCAGTGATA GAGAACGTAT GTCGAGTTTA TCCCTATCAG TGATAGAGAA
19621 CGTATGTCGA GTTTACTCCC TATCAGTGAT AGAGAACGTA TGTCGAGGTA GGCGTGTACG
19681 GTGGGAGGCC TATATAAGCA GAGCTCGTTT AGTGAACCGT CAGATCGCCG
      (SEQ ID NO: 41)
```

LINE-1 ORF2-NLS mRNA (SEQ ID NO: 42)

```
   1 TAATACGACT CACTATAGGG AGAAGTACTG CCACCATGGG CAAGAAGCAA AATCGCAAGA
  61 CGGGGAATTC CAAGACACAA TCCGCTAGCC CACCACCTAA AGAGCGTTCT AGCTCCCCTG
 121 CTACTGAGCA GTCCTGGATG GAAAACGACT TCGATGAACT CCGGGAAGAG GGATTTAGGC
 181 GATCCAACTA TTCAGAACTC CGCGAAGATA TCCAGACAAA GGGGAAGGAA GTCGAGAATT
 241 TCGAGAAGAA CCTCGAGGAG TGCATCACCC GTATCACAAA CACTGAGAAA TGTCTCAAAG
 301 AACTCATGGA ACTTAAGACA AAAGCCAGGG AGCTTCGAGA GGAGTGTCGG AGTCTGAGAT
 361 CCAGGTGTGA CCAGCTCGAG GAGCGCGTGA GCGCGATGGA AGACGAGATG AACGAGATGA
 421 AAAGAGAGGG CAAATTCAGG GAGAAGCGCA TTAAGAGGAA CGAACAGAGT CTGCAGGAGA
 481 TTTGGGATTA CGTCAAGAGG CCTAACCTGC GGTTGATCGG CGTCCCCGAG AGCGACGTAG
 541 AAAACGGGAC TAAACTGGAG AATACACTTC AAGACATCAT TCAAGAAAAT TTTCCAAACC
 601 TGGCTCGGCA AGCTAATGTG CAAATCCAAG AGATCCAACG CACACCCCAG CGGTATAGCT
 661 CTCGGCGTGC CACCCCTAGG CATATTATCG TGCGCTTTAC TAAGGTGGAG ATGAAAGAGA
 721 AGATGCTGCG AGCCGCTCGG GAAAAGGGAA GGGTGACTTT GAAGGGCAAA CCTATTCGGC
 781 TGACGGTTGA CCTTAGCGCC GAGACACTCC AGGCACGCCG GGAATGGGGC CCCATCTTTA
 841 ATATCCTGAA GGAGAAGAAC TTCCAGCCAC GAATCTCTTA CCCTGCAAAG TTGAGTTTTA
 901 TCTCCGAGGG TGAGATTAAG TATTTCATCG ATAAACAGAT GCTGCGAGAC TTCGTGACAA
 961 CTCGCCCAGC TCTCAAGGAA CTGCTCAAAG AGGCTCTTAA TATGGAGCGC AATAATAGAT
1021 ATCAACCCTT GCAGAACCAC GCAAAGATGT GAGACAGCCG TCAGACCATC AAGACTAGGA
1081 AGAAACTGCA TCAACTAATG AGCAAAATCA CCAGCTAACA TCATAGTATA CATGACCGGC
1141 TCTAACTCAC ATATCACCAT CCTTACACTT AACATTAACG GCCTCAACTC AGCTATCAAG
```

TABLE 8-continued

| Plasmid and mRNA construct sequences |
| --- |
| 1201 CGCCATCGGC TGGCCAGCTG GATCAAATCA CAGGATCCAA GCGTTTGTTG CATCCAAGAG |
| 1261 ACCCACCTGA CCTGTAGAGA TACTCACCGC CTCAAGATCA AGGGATGGCG AAAGATTTAT |
| 1321 CAGGCGAACG GTAAGCAGAA GAAAGCCGGA GTCGCAATTC TGGTCTCAGA CAAGACGGAT |
| 1381 TTCAAGCCCA CCAAAATTAA GCGTGATAAG GAAGGTCACT ATATTATGGT GAAAGGCAGC |
| 1441 ATACAGCAGG AAGAACTTAC CATATTGAAC ATCTACGCGC CAAACACCGG CGCACCTCGC |
| 1501 TTTATCAAAC AGGTCCTGTC CGATCTGCAG CGAGATCTGG ATTCTCATAC GTTGATTATG |
| 1561 GGTGATTTCA ATACACCATT GAGCACCCTG GATCGCAGCA CCAGGCAAAA GGTAAATAAA |
| 1621 GACACGCAAG AGCTCAATAG CGCACTGCAT CAGGCAGATC TCATTGATAT TTATCGCACT |
| 1681 CTTCATCCTA AGAGTACCGA GTACACATTC TTCAGCGCCC CACATCATAC ATACTCAAAG |
| 1741 ATCGATCATA TCGTCGGCTC AAAGGCTCTG CTGTCAAAGT GCAAGCGCAC AGAGATAATT |
| 1801 ACAAATTACC TGTCAGATCA TAGCGCGATC AAGCTCGAGC TGAGAATCAA GAACCTGACC |
| 1861 CAGAGCCGGA GTACCACTTG GAAGCTTAAT AACCTGCTGC TCAACGATTA TTGGGTCCAC |
| 1921 AATGAGATGA AGGCAGAGAT TAAAATGTTC TTCGAAACAA ATGAGAATAA GGATACTACC |
| 1981 TATCAAAACC TTTGGGATGC CTTTAAGGCC GTCTGCAGAG GCAAGTTCAT CGCCCTCAAC |
| 2041 GCCTATAAAA GAAAACAAGA GAGATCTAAG ATCGATACTC TCACCTCTCA GCTGAAGGAG |
| 2101 TTGGAGAAAC AGGAACAGAC CCACTCCAAG GCGTCAAGAC GGCAGGAGAT CACAAAGATT |
| 2161 CGCGCCGAGT TGAAAGAGAT CGAAACCCAA AAGACTCTTC AGAAAATTAA CGAGTCTCGT |
| 2221 AGTTGGTTCT TCGAGCGGAT TAATAAGATA GACAGACCTC TGGCACGACT GATTAAGAAG |
| 2281 AAGCGCGAAA AGAACCAGAT TGATACCATC AAGAACGACA AGGGCGACAT CACTACTGAC |
| 2341 CCGACCGAGA TCCAGACCAC TATTCGGGAG TATTATAAGC ATTTGTATGC TAACAAGCTT |
| 2401 GAGAACCTGG AAGAGATGGA CACTTTTCTG GATACCTATA CTCTGCCACG GCTTAATCAA |
| 2461 GAGGAAGTCG AGTCCCTCAA CCGCCCAATT ACAGGAAGCG AGATTGTGGC CATAATTAAC |
| 2521 TCCCTGCCGA CAAAGAAATC TCCTGGTCCG GACGGGTTTA CAGCTGAGTT TTATCAACGG |
| 2581 TATATGGAAG AGCTTGTACC GTTTCTGCTC AAGCTCTTTC AGTCTATAGA AAAGGAAGGC |
| 2641 ATCTTGCCCA ATTCCTTCTA CGAAGCTTCT ATAATACTTA TTCCCAAACC AGGACGCGAT |
| 2701 ACCACAAAGA AGGAAAACTT CCGGCCCATT AGTCTCATGA ATATCGACGC TAAAATATTG |
| 2761 AACAAGATTC TCGCCAACAG AATCCAACAA CATATTAAGA AATTGATACA TCACGACCAG |
| 2821 GTGGGGTTTA TACCTGGCAT GCAGGGCTGG TTTAACATCC GGAAGAGTAT TAACGTCATT |
| 2881 CAACACATTA ATAGAGCTAA GGATAAGAAT CATATGATCA TCTCTATAGA CGCGGAAAAG |
| 2941 GCATTCGATA AGATTCAGCA GCCATTTATG CTCAAGACTC TGAACAAACT CGGCATCGAC |
| 3001 GGAACATATT TTAAGATTAT TCGCGCAATT TACGATAAGC CGACTGCTAA CATTATCCTT |
| 3061 AACGGCCAAA AGCTCGAGGC CTTTCCGCTC AAGACTGGAA CCCGCCAAGG CTGTCCCCTC |
| 3121 TCCCCGCTTT TGTTTAATAT TGTACTCGAG GTGCTGGCTA GGGCTATTCG TCAAGAGAAA |
| 3181 GAGATTAAAG GGATACAGCT CGGGAAGGAA GAGGTCAAGC TTTCCTTGTT CGCCGATGAT |
| 3241 ATGATTGTGT ACCTGGAGAA TCCTATTGTG TCTGCTCAGA ACCTTCTTAA ACTTATTTCT |
| 3301 AACTTTAGCA AGGTCAGCGG CTATAAGATT AACGTCCAGA AATCTCAGGC CTTTCTGTAC |
| 3361 ACAAATAATC GACAGACCGA ATCCCAGATA ATGGGTGAGC TTCCGTTTGT CATAGCCAGC |
| 3421 AAAAGGATAA AGTATCTCGG AATCCAGCTG ACACGAGACG TTAAAGATTT GTTTAAGGAA |
| 3481 AATTACAAGC CTCTCCTGAA AGAGATTAAG GAAGATACTA ATAAGTGGAA GAATATCCCC |
| 3541 TGTTCATGGG TTGGCAGAAT CAACATAGTG AAGATGGCAA TACTTCCTAA AGTGATATAT |
| 3601 CGCTTTAACG CCATCCCAAT TAAACTGCCT ATGACCTTCT TTACGGAGCT CGAGAAAACA |
| 3661 ACCCTTAAAT TTATATGGAA TCAAAAGAGA GCAAGAATAG CGAAGTCCAT CTTGAGCCAG |
| 3721 AAGAATAAGG CCGGTGGGAT TACTTTGCCT GATTTTAAGT TGTATTATAA AGCCACAGTA |
| 3781 ACTAAGACAG CCTGGTATTG GTATCAGAAT AGAGACATCG ACCAGTGGAA TCGGACCGAA |
| 3841 CCATCAGAGA TAATGCCCCA CATCTATAAT TACCTTATAT TCGATAAGCC AGAAAAGAAT |
| 3901 AAACAGTGGG GCAAAGACAG CCTCTTCAAC AAGTGGTGTT GGGAGAATTG GCTGGCCATA |
| 3961 TGCCGGAAAC TCAAGCTCGA CCCCTTTCTT ACACCCTACA CTAAAATCAA CAGTAGGTGG |
| 4021 ATCAAGGACT TGAATGTCAA GCCAAAGACT ATAAAGACAC TGGAAGAGAA TCTTGGGATC |
| 4081 ACAATACAAG ATATAGGCGT CGGCAAAGAT TTTATGTCAA AGACGCCCAA GGCCATGGCC |
| 4141 ACTAAGGATA AGATTGATAA GTGGGACCTT ATTAAGCTCA AAAGCTTCTG TACTGCCAAG |
| 4201 GAGACCACGA TCAGAGTTAA TAGGCAGCCC ACTACATGGG AAAAGATTTT CGCCACTTAT |
| 4261 TCATCAGATA AGGGGTTGAT AAGCAGAATA TATAACGAGC TGAAGCAGAT CTACAAGAAG |
| 4321 AAAACGAATA ATCCCATCAA GAAGTGGGCA AAAGATATGA ACAGGCATTT TAGCAAAGAG |
| 4381 GATATCTACG CCGCGAAGAA GCATATGAAG AAGTGTAGTT CAAGCTTGGC CATTCGTGAG |
| 4441 ATGCAGATTA AGACGACCAT GCGATACCAC CTTACCCCAG TGAGGATGGC AATTATCAAG |
| 4501 AAATCTGGCA ATAATAGATG TTGGCGGGGC TGTGGCGAGA TTGGCACCCT GCTCCATTGC |
| 4561 TGGTGGGATT GCAAGCTGGT GCAGCCGCTT TGGAAATCAG TCTGGCGCTT TCTGAGGGAC |
| 4621 CTCGAGCTTG AGATTCCCTT CGATCCCGCA ATTCCCTTGC TCGGAATCTA TCCTAACGAA |
| 4681 TACAAGAGCT GTTGTTACAA GGATACGTGT ACCCGGATGT TCATCGCGGC CTTGTTTACG |
| 4741 ATAGCTAAGA CGTGGAATCA GCCTAAGTGC CCCACAATGA TCGATTGGAT CAAGAAAATG |
| 4801 TGGCATATTT ATACCATGGA GTATTACGCA GCAATTAAGA ATGACGAATT TATTTCCTTC |
| 4861 GTTGGGACCT GGATGAAGCT GGAGACTATT ATTCTGAGCA AGCTGTCTCA GGAGCAAAAG |
| 4921 ACAAAGCATA GAATCTTCTC TCTCATTGGT GGTAACGACT ACAAAGACGA TGACGACAAG |
| 4981 CCCGCCGCCA AGAGGGTGAA GCTGGACTAA AGCGCTTCTA GAAGTTGTCT CCTCCTGCAC |
| 5041 TGACTGACTG ATACAATCGA TTTCTGGATC CGCAGGCCTA ATCAACCTCT GGATTACAAA |
| 5101 ATTTGTGAAA GATTGACTGG TATTCTTAAC TATGTTGCTC CTTTTACGCT ATGTGGATAC |
| 5161 GCTGCTTTAA TGCCTTTGTA TCATGCTATT GCTTCCCGTA TGGCTTTCAT TTTCTCCTCC |
| 5221 TTGTATAAAT CCTGGTTGCT GTCTCTTTAT GAGGAGTTGT GGCCCGTTGT CAGGCAACGT |
| 5281 GGCGTGGTGT GCACTGTGTT TGCTGACGCA ACCCCCACTG GTTGGGGCAT TGCCACCACC |
| 5341 TGTCAGCTCC TTTCCGGGAC TTTCGCTTTC CCCCTCCCTA TTGCCACGGC GGAACTCATC |
| 5401 GCCGCCTGCC TTGCCCGCTG CTGGACAGGG GCTCGGCTGT TGGGCACTGA CAATTCCGTG |
| 5461 GTGTTGTCGG GGAAGCTGAC GTCCTTTCCA TGGCTGCTCG CCTGTGTTGC CACCTGGATT |
| 5521 CTGCGCGGGA CGTCCTTCTG CTACGTCCCT TCGGCCCTCA ATCCAGCGGA CCTTCCTTCC |
| 5581 CGCTGAGAGA CACAAAAAAT TCCAACACAC TATTGCAATG AAAATAAATT TCCTTTATTA |
| 5641 GCCAGAAGTC AGATGCTCAA GGGGCTTCAT GATGTCCCCA TAATTTTTGG CAGAGGGAAA |
| 5701 AAGATCTCAG TGGTATTTGT GAGCCAGGGC ATTGGCCTTC TGATAGGCAG CCTGCACCTG |
| 5761 AGGAGTGCGG CCGCTTTACT TGTACAGCTC GTCCATGCCG AGAGTGATCC CGGCGGCGGT |
| 5821 CACGAACTCC AGCAGGACCA TGTGATCGCG CTTCTCGTTG GGTCTTTGC TCAGGGCGGA |

TABLE 8-continued

Plasmid and mRNA construct sequences

```
5881 CTGGGTGCTC AGGTAGTGGT TGTCGGGCAG CAGCACGGGG CCGTCGCCGA TGGGGGTGTT
5941 CTGCTGGTAG TGGTCGGCGA GCTGCACGCT GCCGTCCTCG ATGTTGTGGC GGATCTTGAA
6001 GTTCACCTTG ATGCCGTTCT TCTGCTTGTC GGCCATGATA TAGACGTTGT GGCTGTTGTA
6061 GTTGTACTCC AGCTTGTGCC CCAGGATGTT GCCGTCCTCC TTGAAGTCGA TGCCCTTCAG
6121 CTCGATGCGG TTCACCAGGG TGTCGCCCTC GAACTTCACC TCGGCGCGGG TCTTGTAGTT
6181 GCCGTCGTCC TTGAAGAAGA TGGTGCGCTC CTGGACGTAG CCTTCGGGCA TGGCGGACTT
6241 GAAGAAGTCG TGCTGCTTCA TGTGGTCGGG GTAGCGGCTG AAGCACTGCA CGCCGTAGGT
6301 CAGGGTGGTC ACGAGGGTGG GCCAGGGCAC GGGCAGCTTG CCGGTGGTGC AGATGAACTT
6361 CAGGGTCAGC TTGCCGTAGG TGGCATCGCC CTCGCCCTCG CCGGACACGC TGAACTTGTG
6421 GCCGTTTACG TCGCCGTCCA GCTCGACCAG GATGGGCACC ACCCCGGTGA ACAGCTCCTC
6481 GCCCTTGCTC ACCATGGTGG CGGGATCTGA CGGTTCACTA AACCAGCTCT GCTTATATAG
6541 ACCTCCCACC GTACACGCCT ACCGCCCATT TGCGTCAATG GGGCGGAGTT GTTACGACAT
6601 TTTGGAAAGT CCCGTTGATT TTGGTGCCAA AACAAACTCC CATTGACGTC AATGGGGTGG
6661 AGACTTGGAA ATCCCCGTGA GTCAAACCGC TATCCACGCC CATTGATGTA CTGCCAAAAC
6721 CGCATCACCA TGGTAATAGC GATGACTAAT ACGTAGATGT ACTGCCAAGT AGGAAAGTCC
6781 CATAAGGTCA TGTACTGGGC ATAATGCCAG GCGGGCCATT TACCGTCATT GACGTCAATA
6841 GGGGGCGTAC TTGGCATATG ATACACTTGA TGTACTGCCA AGTGGGCAGT TTACCGTAAA
6901 TACTCCACCC ATTGACGTCA ATGGAAAGTC CCTATTGGCG TTACTATGGG AACATACGTC
6961 ATTATTGACG TCAATGGGCG GGGGTCGTTG GGCGGTCAGC CAGGCGGGCC ATTTACCGTA
7021 AGTTATGTAA CGGGCCTGCT GCCGGCTCTG CGGCCTCTTC CGCGTCTTCG CCTTCGCCCT
7081 CAGACGAGTC GGATCTCCCT TTGGGCCGCC TCCCCGCCTG TCTAGCTTGA CTGACTGAGA
7141 TACAGCGTAC CTTCAGCTCA CAGACATGAT AAGATACATT GATGAGTTTG GACAAACCAC
7201 AACTAGAATG CAGTGAAAAA AATGCTTTAT TTGTGAAATT TGTGATGCTA TTGCTTTATT
7261 TGTAACCATT ATAAGCTGCA ATAAACAAGT T (SEQ ID NO: 42)
```

LINE-1 alu mRNA GFP (SEQ ID NO: 43)

```
   1 TAATACGACT CACTATAGGG AGAAGTACTG CCACCATGGG CAAGAAGCAA AATCGCAAGA
  61 CGGGGAATTC CAAGACACAA TCCGCTAGCC CACCACCTAA AGAGCGTTCT AGCTCCCCTG
 121 CTACTGAGCA GTCCTGGATG GAAAACGACT TCGATGAACT CCGGGAAGAG GGATTTAGGC
 181 GATCCAACTA TTCAGAACTC CGCGAAGATA TCCAGACAAA GGGGAAGGAA GTCGAGAATT
 241 TCGAGAAGAA CCTCGAGGAG TGCATCACCC GTATCACAAA CACTGAGAAA TGTCTCAAAG
 301 AACTCATGGA ACTTAAGACA AAAGCCAGGG AGCTTCGAGA GGAGTGTCGG AGTCTGAGAT
 361 CCAGGTGTGA CCAGCTCGAG GAGCGCGTGA GCGCGATGGA AGACGAGATG AACGAGATGA
 421 AAAGAGAGGG CAAATTCAGG GAGAAGCGCA TTAAGAGGAA CGAACAGAGT CTGCAGGAGA
 481 TTTGGGATTA CGTCAAGAGG CCTAACCTGC GGTTGATCGG CGTCCCCGAG AGCGACGTAG
 541 AAAACGGGAC TAAACTGGAG AATACACTTC AAGACATCAT TCAAGAAAAT TTTCCAAACC
 601 TGGCTCGGCA AGCTAATGTG CAAATCCAAG AGATCCAACG CACACCCCAG CGGTATAGCT
 661 CTCGGCGTGC CACCCCTAGG CATATTATCG TGCGCTTTAC TAAGGTGGAG ATGAAAGAGA
 721 AGATGCTGCG AGCCGCTCGG GAAAAGGGAA GGGTGACTTT GAAGGGCAAA CCTATTCGGC
 781 TGACGGTTGA CCTTAGCGCC GAGACACTCC AGGCACGCCG GGAATGGGGC CCCATCTTTA
 841 ATATCCTGAA GGAGAAGAAC TTCCAGCCAC GAATCTCTTA CCCTGCAAAG TTGAGTTTTA
 901 TCTCCGAGGG TGAGATTAAG TATTTCATCG ATAAACAGAT GCTGCGAGAC TTCGTGACAA
 961 CTCGCCCAGC TCTCAAGGAA CTGCTCAAAG AGGCTCTTAA TATGGAGCGC AATAATAGAT
1021 ATCAACCCTT GCAGAACCAC GCAAAGATGT GAGACAGCCG TCAGACCATC AAGACTAGGA
1081 AGAAACTGCA TCAACTAATG AGCAAAATCA CCAGCTAACA TCATAGTATA CATGACCGGC
1141 TCTAACTCAC ATATCACCAT CCTTACACTT AACATTAACG GCCTCAACTC AGCTATCAAG
1201 CGCCATCGGC TGGCCAGCTG GATCAAATCA CAGGATCCAA GCGTTTGTTG CATCCAAGAG
1261 ACCCACCTGA CCTGTAGAGA TACTCACCGC CTCAAGATCA AGGGATGGCG AAAGATTTAT
1321 CAGGCGAACG GTAAGCAGAA GAAAGCCGGA GTCGCAATTC TGGTCTCAGA CAAGACGGAT
1381 TTCAAGCCCA CCAAAATTAA GCGTGATAAG GAAGGTCACT ATATTATGGT GAAAGGCAGC
1441 ATACAGCAGG AAGAACTTAC CATATTGAAC ATCTACGCGC CAAACACCGG CGCACCTCGC
1501 TTTATCAAAC AGGTCCTGTC CGATCTGCAG CGAGATCTGG ATTCTCATAC GTTGATTATG
1561 GGTGATTTCA ATACACCATT GAGCACCCTG GATCGCAGCA CCAGGCAAAA GGTAAATAAA
1621 GACACGCAAG AGCTCAATAG CGCACTGCAT CAGGCAGATC TCATTGATAT TTATCGCACT
1681 CTTCATCCTA AGAGTACCGA GTACACATTC TTCAGCGCCC CACATCATAC ATACTCAAAG
1741 ATCGATCATA TCGTCGGCTC AAAGGCTCTG CTGTCAAAGT GCAAGCGCAC AGAGATAATT
1801 ACAAATTACC TGTCAGATCA TAGCGCGATC AAGCTCGAGC TGAGAATCAA GAACCTGACC
1861 CAGAGCCGGA GTACCACTTG GAAGCTTAAT AACCTGCTGC TCAACGATTA TTGGGTCCAC
1921 AATGAGATGA AGGCAGAGAT TAAAATGTTC TTCGAAACAA ATGAGAATAA GGATACTACC
1981 TATCAAAACC TTTGGGATGC CTTTAAGGCC GTCTGCAGAG GCAAGTTCAT CGCCCTCAAC
2041 GCCTATAAAA GAAAACAAGA GAGATCTAAG ATCGATACTC TCACCTCTCA GCTGAAGGAG
2101 TTGGAGAAAC AGGAACAGAC CCACTCCAAG GCGTCAAGAC GGCAGGAGAT CACAAAGATT
2161 CGCGCCGAGT TGAAAGAGAT CGAAACCCAA AAGACTCTTC AGAAAATTAA CGAGTCTCGT
2221 AGTTGGTTCT TCGAGCGGAT TAATAAGATA GACAGACCTC TGGCACGACT GATTAAGAAG
2281 AAGCGCGAAA AGAACCAGAT TGATACCATC AAGAACGACA AGGGCGACAT CACTACTGAC
2341 CCGACCGAGA TCCAGACCAC TATTCGGGAG TATTATAAGC ATTTGTATGC TAACAAGCTT
2401 GAGAACCTGG AAGAGATGGA CACTTTTCTG GATACCTATA CTCTGCCACG GCTTAATCAA
2461 GAGGAAGTCG AGTCCCTCAA CCGCCCAATT ACAGGAAGCG AGATTGTGGC CATAATTAAC
2521 TCCCTGCCGA CAAAGAAATC TCCTGGTCCG GACGGGTTTA CAGCTGAGTT TTATCAACGG
2581 TATATGGAAG AGCTTGTACC GTTTCTGCTC AAGCTCTTTC AGTCTATAGA AAAGGAAGGC
2641 ATCTTGCCCA ATTCCTTCTA CGAAGCTTCT ATAATACTTA TTCCCAAACC AGGACGCGAT
2701 ACCACAAAGA AGGAAAACTT CCGGCCCATT AGTCTCATGA ATATCGACGC TAAAATATTG
2761 AACAAGATTC TCGCCAACAG AATCCAACAA CATATTAAGA AATTGATACA TCACGACCAG
2821 GTGGGGTTTA TACCTGGCAT GCAGGGCTGG TTTAACATCC GGAAGAGTAT TAACGTCATT
2881 CAACACATTA ATAGAGCTAA GGATAAGAAT CATATGATCA TCTCTATAGA CGCGGAAAAG
2941 GCATTCGATA AGATTCAGCA GCCATTTATG CTCAAGACTC TGAACAAACT CGGCATCGAC
3001 GGAACATATT TTAAGATTAT TCGCGCAATT TACGATAAGC CGACTGCTAA CATTATCCTT
3061 AACGGCCAAA AGCTCGAGGC CTTTCCGCTC AAGACTGGAA CCCGCCAAGG CTGTCCCCTC
```

TABLE 8-continued

Plasmid and mRNA construct sequences

```
3121 TCCCCGCTTT TGTTTAATAT TGTACTCGAG GTGCTGGCTA GGGCTATTCG TCAAGAGAAA
3181 GAGATTAAAG GGATACAGCT CGGGAAGGAA GAGGTCAAGC TTTCCTTGTT CGCCGATGAT
3241 ATGATTGTGT ACCTGGAGAA TCCTATTGTG TCTGCTCAGA ACCTTCTTAA ACTTATTTCT
3301 AACTTTAGCA AGGTCAGCGG CTATAAGATT AACGTCCAGA AATCTCAGGC CTTTCTGTAC
3361 ACAAATAATC GACAGACCGA ATCCCAGATA ATGGGTGAGC TTCCGTTTGT CATAGCCAGC
3421 AAAAGGATAA AGTATCTCGG AATCCAGCTG ACACGAGACG TTAAAGATTT GTTTAAGGAA
3481 AATTACAAGC CTCTCCTGAA AGAGATTAAG GAAGATACTA ATAAGTGGAA GAATATCCCC
3541 TGTTCATGGG TTGGCAGAAT CAACATAGTG AAGATGGCAA TACTTCCTAA AGTGATATAT
3601 CGCTTTAACG CCATCCCAAT TAAACTGCCT ATGACCTTCT TTACGGAGCT CGAGAAAACA
3661 ACCCTTAAAT TTATATGGAA TCAAAAGAGA GCAAGAATAG CGAAGTCCAT CTTGAGCCAG
3721 AAGAATAAGG CCGGTGGGAT TACTTTGCCT GATTTTAAGT TGTATTATAA AGCCACAGTA
3781 ACTAAGACAG CCTGGTATTG GTATCAGAAT AGAGACATCG ACCAGTGGAA TCGGACCGAA
3841 CCATCAGAGA TAATGCCCCA CATCTATAAT TACCTTATAT TCGATAAGCC AGAAAAGAAT
3901 AAACAGTGGG GCAAAGACAG CCTCTTCAAC AAGTGGTGTT GGGAGAATTG GCTGGCCATA
3961 TGCCGGAAAC TCAAGCTCGA CCCCTTTCTT ACACCCTACA CTAAAATCAA CAGTAGGTGG
4021 ATCAAGGACT TGAATGTCAA GCCAAAGACT ATAAAGACAC TGGAAGAGAA TCTTGGGATC
4081 ACAATACAAG ATATAGGCGT CGGCAAAGAT TTTATGTCAA AGACGCCCAA GGCCATGGCC
4141 ACTAAGGATA AGATTGATAA GTGGGACCTT ATTAAGCTCA AAAGCTTCTG TACTGCCAAG
4201 GAGACCACGA TCAGAGTTAA TAGGCAGCCC ACTACATGGG AAAAGATTTT CGCCACTTAT
4261 TCATCAGATA AGGGGTTGAT AAGCAGAATA TATAACGAGC TGAAGCAGAT CTACAAGAAG
4321 AAAACGAATA ATCCCATCAA GAAGTGGGCA AAAGATATGA ACAGGCATTT TAGCAAAGAG
4381 GATATCTACG CCGCGAAGAA GCATATGAAG AAGTGTAGTT CAAGCTTGGC CATTCGTGAG
4441 ATGCAGATTA AGACGACCAT GCGATACCAC CTTACCCCAG TGAGGATGGC AATTATCAAG
4501 AAATCTGGCA ATAATAGATG TTGGCGGGGC TGTGGCGAGA TTGGCACCCT GCTCCATTGC
4561 TGGTGGGATT GCAAGCTGGT GCAGCCGCTT TGGAAATCAG TCTGGCGCTT TCTGAGGGAC
4621 CTCGAGCTTG AGATTCCCTT CGATCCCGCA ATTCCCTTGC TCGGAATCTA TCCTAACGAA
4681 TACAAGAGCT GTTGTTACAA GGATACGTGT ACCCGGATGT TCATCGCGGC CTTGTTTACG
4741 ATAGCTAAGA CGTGGAATCA GCCTAAGTGC CCCACAATGA TCGATTGGAT CAAGAAAATG
4801 TGGCATATTT ATACCATGGA GTATTACGCA GCAATTAAGA ATGACGAATT TATTTCCTTC
4861 GTTGGGACCT GGATGAAGCT GGAGACTATT ATTCTGAGCA AGCTGTCTCA GGAGCAAAAG
4921 ACAAAGCATA GAATCTTCTC TCTCATTGGT GGTAACGACT ACAAAGACGA TGACGACAAG
4981 TAAAGCGGCC GGGCGCGGTG GCTCACGCCT GTAATCCCAG CACTTTGGGA GGCCGAGGCG
5041 GGAGGATCGC AGTTCGAGAC CAGCGCGAGA CCCCGTCTCT ACAAAAATAC AAAAATTAGC
5101 TTCTAGAAGT TGTCTCCTCC TGCACTGACT GACTGATACA ATCGATTTCT GGATCCGCAG
5161 GCCTAATCAA CCTCTGGATT ACAAAATTTG TGAAAGATTG ACTGGTATTC TTAACTATGT
5221 TGCTCCTTTT ACGCTATGTG GATACGCTGC TTTAATGCCT TTGTATCATG CTATTGCTTC
5281 CCGTATGGCT TTCATTTTCT CCTCCTTGTA TAAATCCTGG TTGCTGTCTC TTTATGAGGA
5341 GTTGTGGCCC GTTGTCAGGC AACGTGGCGT GGTGTGCACT GTGTTTGCTG ACGCAACCCC
5401 CACTGGTTGG GGCATTGCCA CCACCTGTCA GCTCCTTTCC GGGACTTTCG CTTTCCCCCT
5461 CCCTATTGCC ACGGCGGAAC TCATCGCCGC CTGCCTTGCC CGCTGCTGGA CAGGGGCTCG
5521 GCTGTTGGGC ACTGACAATT CCGTGGTGTT GTCGGGGAAG CTGACGTCCT TTCCATGGCT
5581 GCTCGCCTGT GTTGCCACCT GGATTCTGCG CGGGACGTCC TTCTGCTACG TCCCTTCGGC
5641 CCTCAATCCA GCGGACCTTC CTTCCCGCTG AGAGACACAA AAAATTCCAA CACACTATTG
5701 CAATGAAAAT AAATTTCCTT TATTAGCCAG AAGTCAGATG CTCAAGGGGC TTCATGATGT
5761 CCCCATAATT TTTGGCAGAG GGAAAAAGAT CTCAGTGGTA TTTGTGAGCC AGGGCATTGG
5821 CCTTCTGATA GGCAGCCTGC ACCTGAGGAG TGCGGCCGCT TTACTTGTAC AGCTCGTCCA
5881 TGCCGAGAGT GATCCCGGCG GCGGTCACGA ACTCCAGCAG GACCATGTGA TCGCGCTTCT
5941 CGTTGGGGTC TTTGCTCAGG GCGGACTGGG TGCTCAGGTA GTGGTTGTCG GGCAGCAGCA
6001 CGGGGCCGTC GCCGATGGGG GTGTTCTGCT GGTAGTGGTC GGCGAGCTGC ACGCTGCCGT
6061 CCTCGATGTT GTGGCGGATC TTGAAGTTCA CCTTGATGCC GTTCTTCTGC TTGTCGGCCA
6121 TGATATAGAC GTTGTGGCTG TTGTAGTTGT ACTCCAGCTT GTGCCCCAGG ATGTTGCCGT
6181 CCTCCTTGAA GTCGATGCCC TTCAGCTCGA TGCGGTTCAC CAGGGTGTCG CCCTCGAACT
6241 TCACCTCGGC GCGGGTCTTG TAGTTGCCGT CGTCCTTGAA GAAGATGGTG CGCTCCTGGA
6301 CGTAGCCTTC GGGCATGGCG GACTTGAAGA AGTCGTGCTG CTTCATGTGG TCGGGGTAGC
6361 GGCTGAAGCA CTGCACGCCG TAGGTCAGGG TGGTCACGAG GGTGGGCCAG GGCACGGGCA
6421 GCTTGCCGGT GGTGCAGATG AACTTCAGGG TCAGCTTGCC GTAGGTGGCA TCGCCCTCGC
6481 CCTCGCCGGA CACGCTGAAC TTGTGGCCGT TTACGTCGCC GTCCAGCTCG ACCAGGATGG
6541 GCACCACCCC GGTGAACAGC TCCTCGCCCT TGCTCACCAT GGTGGCGGGA TCTGACGGTT
6601 CACTAAACCA GCTCTGCTTA TATAGACCTC CCACCGTACA CGCCTACCGC CCATTTGCGT
6661 CAATGGGGCG GAGTTGTTAC GACATTTTGG AAAGTCCCGT TGATTTTGGT GCCAAAACAA
6721 ACTCCCATTG ACGTCAATGG GGTGGAGACT TGGAAATCCC CGTGAGTCAA ACCGCTATCC
6781 ACGCCCATTG ATGTACTGCC AAAACCGCAT CACCATGGTA ATAGCGATGA CTAATACGTA
6841 GATGTACTGC CAAGTAGGAA AGTCCCATAA GGTCATGTAC TGGGCATAAT GCCAGGCGGG
6901 CCATTTACCG TCATTGACGT CAATAGGGGG CGTACTTGGC ATATGATACA CTTGATGTAC
6961 TGCCAAGTGG GCAGTTTACC GTAAATACTC CACCCATTGA CGTCAATGGA AAGTCCCTAT
7021 TGGCGTTACT ATGGGAACAT ACGTCATTAT TGACGTCAAT GGGCGGGGGT CGTTGGGCGG
7081 TCAGCCAGGC GGGCCATTTA CCGTAAGTTA TGTAACGGGC CTGCTGCCGG CTCTGCGGCC
7141 TCTTCCGCGT CTTCGCCTTC GCCCTCAGAC GAGTCGGATC TCCCTTTGGG CCGCCTCCCC
7201 GCCTGTCTAG CTTGACTGAC TGAGATACAG CGTACCTTCA GCTCACAGAC ATGATAAGAT
7261 ACATTGATGA GTTTGGACAA ACCACAACTA GAATGCAGTG AAAAAAATGC TTTATTTGTG
7321 AAATTTGTGA TGCTATTGCT TTATTTGTAA CCATTATAAG CTGCAATAAA CAAGTT
     (SEQ ID NO: 43)
```

LINE-1 plasmid CVBE IRES GFP (SEQ ID NO: 44)

```
  1 TAATACGACT CACTATAGGG AGAAGTACTG CCACCATGGG CAAGAAGCAA AATCGCAAGA
 61 CGGGGAATTC CAAGACACAA TCCGCTAGCC CACCACCTAA AGAGCGTTCT AGCTCCCCTG
121 CTACTGAGCA GTCCTGGATG GAAAACGACT TCGATGAACT CCGGGAAGAG GGATTTAGGC
181 GATCCAACTA TTCAGAACTC CGCGAAGATA TCCAGACAAA GGGGAAGGAA GTCGAGAATT
```

TABLE 8-continued

| Plasmid and mRNA construct sequences |
|---|
| 241 TCGAGAAGAA CCTCGAGGAG TGCATCACCC GTATCACAAA CACTGAGAAA TGTCTCAAAG |
| 301 AACTCATGGA ACTTAAGACA AAAGCCAGGG AGCTTCGAGA GGAGTGTCGG AGTCTGAGAT |
| 361 CCAGGTGTGA CCAGCTCGAG GAGCGCGTGA GCGCGATGGA AGACGAGATG AACGAGATGA |
| 421 AAAGAGAGGG CAAATTCAGG GAGAAGCGCA TTAAGAGGAA CGAACAGAGT CTGCAGGAGA |
| 481 TTTGGGATTA CGTCAAGAGG CCTAACCTGC GGTTGATCGG CGTCCCCGAG AGCGACGTAG |
| 541 AAAACGGGAC TAAACTGGAG AATACACTTC AAGACATCAT TCAAGAAAAT TTTCCAAACC |
| 601 TGGCTCGGCA AGCTAATGTG CAAATCCAAG AGATCCAACG CACACCCCAG CGGTATAGCT |
| 661 CTCGGCGTGC CACCCCTAGG CATATTATCG TGCGCTTTAC TAAGGTGGAG ATGAAAGAGA |
| 721 AGATGCTGCG AGCCGCTCGG GAAAAGGGAA GGGTGACTTT GAAGGGCAAA CCTATTCGGC |
| 781 TGACGGTTGA CCTTAGCGCC GAGACACTCC AGGCACGCCG GGAATGGGGC CCCATCTTTA |
| 841 ATATCCTGAA GGAGAAGAAC TTCCAGCCAC GAATCTCTTA CCCTGCAAAG TTGAGTTTTA |
| 901 TCTCCGAGGG TGAGATTAAG TATTTCATCG ATAAACAGAT GCTGCGAGAC TTCGTGACAA |
| 961 CTCGCCCAGC TCTCAAGGAA CTGCTCAAAG AGGCTCTTAA TATGGAGCGC AATAATAGAT |
| 1021 ATCAACCCTT GCAGAACCAC GCAAAGATGT GAGACAGTTA AAACAGCCTG TGGGTTGATC |
| 1081 CCACCCACAG GCCCATTGGG CGCTAGCACT CTGGTATCAC GGTACCTTTG TGCGCCTGTT |
| 1141 TTATACCCCC TCCCCCAACT GTAACTTAGA AGTAACACAC ACCGATCAAC AGTCAGCGTG |
| 1201 GCACACCAGC CACGTTTTGA TCAAGCACTT CTGTTACCCC GGACTGAGTA TCAATAGACT |
| 1261 GCTCACGCGG TTGAAGGAGA AAGCGTTCGT TATCCGGCCA ACTACTTCGA AAAACCTAGT |
| 1321 AACACCGTGG AAGTTGCAGA GTGTTTCGCT CAGCACTACC CCAGTGTAGA TCAGGTCGAT |
| 1381 GAGTCACCGC ATTCCCCACG GGCGACCGTG GCGGTGGCTG CGTTGGCGGC CTGCCCATGG |
| 1441 GGAAACCCAT GGGACGCTCT AATACAGACA TGGTGCGAAG AGTCTATTGA GCTAGTTGGT |
| 1501 AGTCCTCCGG CCCCTGAATG CGGCTAATCC TAACTGCGGA GCACACACCC TCAAGCCAGA |
| 1561 GGGCAGTGTG TCGTAACGGG CAACTCTGCA GCGGAACCGA CTACTTTGGG TGTCCGTGTT |
| 1621 TCATTTTATT CCTATACTGG CTGCTTATGG TGACAATTGA GAGATCGTTA CCATATAGCT |
| 1681 ATTGGATTGG CCATCCGGTG ACTAATAGAG CTATTATATA TCCCTTTGTT GGGTTTATAC |
| 1741 CACTTAGCTT GAAAGAGGTT AAAACATTAC AATTCATTGT TAAGTTGAAT ACAGCAAATA |
| 1801 CATGACCGGC TCTAACTCAC ATATCACCAT CCTTACACTT AACATTAACG GCCTCAACTC |
| 1861 AGCTATCAAG CGCCATCGGC TGGCCAGCTG GATCAAATCA CAGGATCCAA GCGTTTGTTG |
| 1921 CATCCAAGAG ACCCACCTGA CCTGTAGAGA TACTCACCGC CTCAAGATCA AGGGATGGCG |
| 1981 AAAGATTTAT CAGGCGAACG GTAAGCAGAA GAAAGCCGGA GTCGCAATTC TGGTCTCAGA |
| 2041 CAAGACGGAT TTCAAGCCCA CCAAAATTAA GCGTGATAAG GAAGGTCACT ATATTATGGT |
| 2101 GAAAGGCAGC ATACAGCAGG AAGAACTTAC CATATTGAAC ATCTACGCGC CAAACACCGG |
| 2161 CGCACCTCGC TTTATCAAAC AGGTCCTGTC CGATCTGCAG CGAGATCTGG ATTCTCATAC |
| 2221 GTTGATTATG GGTGATTTCA ATACACCATT GAGCACCCTG GATCGCAGCA CCAGGCAAAA |
| 2281 GGTAAATAAA GACACGCAAG AGCTCAATAG CGCACTGCAT CAGGCAGATC TCATTGATAT |
| 2341 TTATCGCACT CTTCATCCTA AGAGTACCGA GTACACATTC TTCAGCGCCC CACATCATAC |
| 2401 ATACTCAAAG ATCGATCATA TCGTCGGCTC AAAGGCTCTG CTGTCAAAGT GCAAGCGCAC |
| 2461 AGAGATAATT ACAAATTACC TGTCAGATCA TAGCGCGATC AAGCTCGAGC TGAGAATCAA |
| 2521 GAACCTGACC CAGAGCCGGA GTACCACTTG GAAGCTTAAT AACCTGCTGC TCAACGATTA |
| 2581 TTGGGTCCAC AATGAGATGA AGGCAGAGAT TAAAATGTTC TTCGAAACAA ATGAGAATAA |
| 2641 GGATACTACC TATCAAAACC TTTGGGATGC CTTTAAGGCC GTCTGCAGAG GCAAGTTCAT |
| 2701 CGCCCTCAAC GCCTATAAAA GAAAACAAGA GAGATCTAAG ATCGATACTC TCACCTCTCA |
| 2761 GCTGAAGGAG TTGGAGAAAC AGGAACAGAC CCACTCCAAG GCGTCAAGAC GGCAGGAGAT |
| 2821 CACAAAGATT CGCGCCGAGT TGAAAGAGAT CGAAACCCAA AAGACTCTTC AGAAAATTAA |
| 2881 CGAGTCTCGT AGTTGGTTCT TCGAGCGGAT TAATAAGATA GACAGACCTC TGGCACGACT |
| 2941 GATTAAGAAG AAGCGCGAAA AGAACCAGAT TGATACCATC AAGAACGACA AGGGCGACAT |
| 3001 CACTACTGAC CCGACCGAGA TCCAGACCAC TATTCGGGAG TATTATAAGC ATTTGTATGC |
| 3061 TAACAAGCTT GAGAACCTGG AAGAGATGGA CACTTTTCTG GATACCTATA CTCTGCCACG |
| 3121 GCTTAATCAA GAGGAAGTCG AGTCCCTCAA CCGCCCAATT ACAGGAAGCG AGATTGTGGC |
| 3181 CATAATTAAC TCCCTGCCGA CAAAGAAATC TCCTGGTCCG GACGGGTTTA CAGCTGAGTT |
| 3241 TTATCAACGG TATATGGAAG AGCTTGTACC GTTTCTGCTC AAGCTCTTTC AGTCTATAGA |
| 3301 AAAGGAAGGC ATCTTGCCCA ATTCCTTCTA CGAAGCTTCT ATAATACTTA TTCCCAAACC |
| 3361 AGGACGCGAT ACCACAAAGA AGGAAAACTT CCGGCCCATT AGTCTCATGA ATATCGACGC |
| 3421 TAAAATATTG AACAAGATTC TCGCCAACAG AATCCAACAA CATATTAAGA AATTGATACA |
| 3481 TCACGACCAG GTGGGGTTTA TACCTGGCAT GCAGGGCTGG TTTAACATCC GGAAGAGTAT |
| 3541 TAACGTCATT CAACACATTA ATAGAGCTAA GGATAAGAAT CATATGATCA TCTCTATAGA |
| 3601 CGCGGAAAAG GCATTCGATA AGATTCAGCA GCCATTTATG CTCAAGACTC TGAACAAACT |
| 3661 CGGCATCGAC GGAACATATT TTAAGATTAT TCGCGCAATT TACGATAAGC CGACTGCTAA |
| 3721 CATTATCCTT AACGGCCAAA AGCTCGAGGC CTTTCCGCTC AAGACTGGAA CCCGCCAAGG |
| 3781 CTGTCCCCTC TCCCCGCTTT TGTTTAATAT TGTACTCGAG GTGCTGGCTA GGGCTATTCG |
| 3841 TCAAGAGAAA GAGATTAAAG GGATACAGCT CGGGAAGGAA GAGGTCAAGC TTTCCTTGTT |
| 3901 CGCCGATGAT ATGATTGTGT ACCTGGAGAA TCCTATTGTG TCTGCTCAGA ACCTTCTTAA |
| 3961 ACTTATTTCT AACTTTAGCA AGGTCAGCGG CTATAAGATT AACGTCCAGA AATCTCAGGC |
| 4021 CTTTCTGTAC ACAAATAATC GACAGACCGA ATCCCAGATA ATGGGTGAGC TTCCGTTTGT |
| 4081 CATAGCCAGC AAAAGGATAA AGTATCTCGG AATCCAGCTG ACACGAGACG TTAAAGATTT |
| 4141 GTTTAAGGAA AATTACAAGC CTCTCCTGAA AGAGATTAAG GAAGATACTA ATAAGTGGAA |
| 4201 GAATATCCCC TGTTCATGGG TTGGCAGAAT CAACATAGTG AAGATGGCAA TACTTCCTAA |
| 4261 AGTGATATAT CGCTTTAACG CCATCCCAAT TAAACTGCCT ATGACCTTCT TTACGGAGCT |
| 4321 CGAGAAAACA ACCCTTAAAT TTATATGGAA TCAAAAGAGA GCAAGAATAG CGAAGTCCAT |
| 4381 CTTGAGCCAG AAGAATAAGG CCGGTGGGAT TACTTTGCCT GATTTTAAGT TGTATTATAA |
| 4441 AGCCACAGTA ACTAAGACAG CCTGGTATTG GTATCAGAAT AGAGACATCG ACCAGTGGAA |
| 4501 TCGGACCGAA CCATCAGAGA TAATGCCCCA CATCTATAAT TACCTTATAT TCGATAAGCC |
| 4561 AGAAAAGAAT AAACAGTGGG GCAAAGACAG CCTCTTCAAC AAGTGGTGTT GGGAGAATTG |
| 4621 GCTGGCCATA TGCCGGAAAC TCAAGCTCGA CCCCTTTCTT ACACCCTACA CTAAAATCAA |
| 4681 CAGTAGGTGG ATCAAGGACT TGAATGTCAA GCCAAAGACT ATAAAGACAC TGGAAGAGAA |
| 4741 TCTTGGGATC ACAATACAAG ATATAGGCGT CGGCAAAGAT TTTATGTCAA AGACGCCCAA |
| 4801 GGCCATGGCC ACTAAGGATA AGATTGATAA GTGGGACCTT ATTAAGCTCA AAAGCTTCTG |
| 4861 TACTGCCAAG GAGACCACGA TCAGAGTTAA TAGGCAGCCC ACTACATGGG AAAAGATTTT |

TABLE 8-continued

| Plasmid and mRNA construct sequences |
|---|
| 4921 CGCCACTTAT TCATCAGATA AGGGGTTGAT AAGCAGAATA TATAACGAGC TGAAGCAGAT |
| 4981 CTACAAGAAG AAAACGAATA ATCCCATCAA GAAGTGGGCA AAAGATATGA ACAGGCATTT |
| 5041 TAGCAAAGAG GATATCTACG CCGCGAAGAA GCATATGAAG AAGTGTAGTT CAAGCTTGGC |
| 5101 CATTCGTGAG ATGCAGATTA AGACGACCAT GCGATACCAC CTTACCCCAG TGAGGATGGC |
| 5161 AATTATCAAG AAATCTGGCA ATAATAGATG TTGGCGGGGC TGTGGCGAGA TTGGCACCCT |
| 5221 GCTCCATTGC TGGTGGGATT GCAAGCTGGT GCAGCCGCTT TGGAAATCAG TCTGGCGCTT |
| 5281 TCTGAGGGAC CTCGAGCTTG AGATTCCCTT CGATCCCGCA ATTCCCTTGC TCGGAATCTA |
| 5341 TCCTAACGAA TACAAGAGCT GTTGTTACAA GGATACGTGT ACCCGGATGT TCATCGCGGC |
| 5401 CTTGTTTACG ATAGCTAAGA CGTGGAATCA GCCTAAGTGC CCCACAATGA TCGATTGGAT |
| 5461 CAAGAAAATG TGGCATATTT ATACCATGGA GTATTACGCA GCAATTAAGA ATGACGAATT |
| 5521 TATTTCCTTC GTTGGGACCT GGATGAAGCT GGAGACTATT ATTCTGAGCA AGCTGTCTCA |
| 5581 GGAGCAAAAG ACAAAGCATA GAATCTTCTC TCTCATTGGT GGTAACGACT ACAAAGACGA |
| 5641 TGACGACAAG TAAAGCGCTT CTAGAAGTTG TCTCCTCCTG CACTGACTGA CTGATACAAT |
| 5701 CGATTTCTGG ATCCGCAGGC CTAATCAACC TCTGGATTAC AAAATTTGTG AAAGATTGAC |
| 5761 TGGTATTCTT AACTATGTTG CTCCTTTTAC GCTATGTGGA TACGCTGCTT TAATGCCTTT |
| 5821 GTATCATGCT ATTGCTTCCC GTATGGCTTT CATTTTCTCC TCCTTGTATA AATCCTGGTT |
| 5881 GCTGTCTCTT TATGAGGAGT TGTGGCCCGT TGTCAGGCAA CGTGGCGTGG TGTGCACTGT |
| 5941 GTTTGCTGAC GCAACCCCCA CTGGTTGGGG CATTGCCACC ACCTGTCAGC TCCTTTCCGG |
| 6001 GACTTTCGCT TTCCCCCTCC CTATTGCCAC GGCGGAACTC ATCGCCGCCT GCCTTGCCCG |
| 6061 CTGCTGGACA GGGGCTCGGC TGTTGGGCAC TGACAATTCC GTGGTGTTGT CGGGGAAGCT |
| 6121 GACGTCCTTT CCATGGCTGC TCGCCTGTGT TGCCACCTGG ATTCTGCGCG GGACGTCCTT |
| 6181 CTGCTACGTC CCTTCGGCCC TCAATCCAGC GGACCTTCCT TCCCGCGAAC AAACGACCCA |
| 6241 ACACCCGTGC GTTTTATTCT GTCTTTTTAT TGCCGATCCC CTCAGAAGAA CTCGTCAAGA |
| 6301 AGGCGATAGA AGGCGATGCG CTGCGAATCG GGAGCGGCGA TACCGTAAAG CACGAGGAAG |
| 6361 CGGTCAGCCC ATTCGCCGCC AAGCTCTTCA GCAATATCAC GGGTAGCCAA CGCTATGTCC |
| 6421 TGATAGCGGT CGGCCGCTTT ACTTGTACAG CTCGTCCATG CCGAGAGTGA TCCCGGCGGC |
| 6481 GGTCACGAAC TCCAGCAGGA CCATGTGATC GCGCTTCTCG TTGGGGTCTT TGCTCAGGGC |
| 6541 GGACTGGGTG CTCAGGTAGT GGTTGTCGGG CAGCAGCACG GGGCCGTCGC CGATGGGGGT |
| 6601 GTTCTGCTGG TAGTGGTCGG CCAGGTGAGT CCAGGAGATG TTTCAGCACT GTTGCCTTTA |
| 6661 GTCTCGAGGC AACTTAGACA ACTGAGTATT GATCTGAGCA CAGCAGGGTG TGAGCTGTTT |
| 6721 GAAGATACTG GGGTTGGGGG TGAAGAAACT GCAGAGGACT AACTGGGCTG AGACCCAGTG |
| 6781 GCAATGTTTT AGGGCCTAAG GAATGCCTCT GAAAATCTAG ATGGACAACT TTGACTTTGA |
| 6841 GAAAAGAGAG GTGGAAATGA GGAAAATGAC TTTTCTTTAT TAGATTTCGG TAGAAAGAAC |
| 6901 TTTCATCTTT CCCCTATTTT TGTTATTCGT TTTAAAACAT CTATCTGGAG GCAGGACAAG |
| 6961 TATGGTCATT AAAAAGATGC AGGCAGAAGG CATATATTGG CTCAGTCAAA GTGGGGAACT |
| 7021 TTGGTGGCCA AACATACATT GCTAAGGCTA TTCCTATATC AGCTGGACAC ATATAAAATG |
| 7081 CTGCTAATGC TTCATTACAA ACTTATATCC TTTAATTCCA GATGGGGGCA AAGTATGTCC |
| 7141 AGGGGTGAGG AACAATTGAA ACATTTGGGC TGGAGTAGAT TTTGAAAGTC AGCTCTGTGT |
| 7201 GTGTGTGTGT GTGTGTGTGT GTGAGAGCGT GTGTTTCTTT TAACGTTTTC AGCCTACAGC |
| 7261 ATACAGGGTT CATGGTGGCA AGAAGATAAC AAGATTTAAA TTATGGCCAG TGACTAGTGC |
| 7321 TGCAAGAAGA ACAACTACCT GCATTTAATG GGAAAGCAAA ATCTCAGGCT TTGAGGGAAG |
| 7381 TTAACATAGG CTTGATTCTG GGTGGAAGCT GGGTGTGTAG TTATCTGGAG GCCAGGCTGG |
| 7441 AGCTCTCAGC TCACTATGGG TTCATCTTTA TTGTCTCCTT TCATCTCAAC AGCTGCACGC |
| 7501 TGCCGTCCTC GATGTTGTGG CGGATCTTGA AGTTCACCTT GATGCCGTTC TTCTGCTTGT |
| 7561 CGGCCATGAT ATAGACGTTG TGGCTGTTGT AGTTGTACTC CAGCTTGTGC CCCAGGATGT |
| 7621 TGCCGTCCTC CTTGAAGTCG ATGCCCTTCA GCTCGATGCG GTTCACCAGG GTGTCGCCCT |
| 7681 CGAACTTCAC CTCGGCGCGG GTCTTGTAGT TGCCGTCGTC CTTGAAGAAG ATGGTGCGCT |
| 7741 CCTGGACGTA GCCTTCGGGC ATGGCGGACT TGAAGAAGTC GTGCTGCTTC ATGTGGTCGG |
| 7801 GGTAGCGGCT GAAGCACTGC ACGCCGTAGG TCAGGGTGGT CACGAGGGTG GGCCAGGGCA |
| 7861 CGGGCAGCTT GCCGGTGGTG CAGATGAACT TCAGGGTCAG CTTGCCGTAG GTGGCATCGC |
| 7921 CCTCGCCCTC GCCGGACACG CTGAACTTGT GGCCGTTTAC GTCGCCGTCC AGCTCGACCA |
| 7981 GGATGGGCAC CACCCCGGTG AACAGCTCCT CGCCCTTGCT CACCATGGTG GCGAATTCGA |
| 8041 AGCTTGAGCA CGAGATCTGA GTCCGGTAGG CCTAGCGGAT CTGACGGTTC ACTAAACCAG |
| 8101 CTCTGCTTAT ATAGACCTCC CACCGTACAC GCCTACCGCC CATTTGCGTC AATGGGGCGG |
| 8161 AGTTGTTACG ACATTTTGGA AAGTCCCGTT GATTTTGGTG CCAAAACAAA CTCCCATTGA |
| 8221 CGTCAATGGG GTGGAGACTT GGAAATCCCC GTGAGTCAAA CCGCTATCCA CGCCCATTGA |
| 8281 TGTACTGCCA AAACCGCATC ACCATGGTAA TAGCGATGAC TAATACGTAG ATGTACTGCC |
| 8341 AAGTAGGAAA GTCCCATAAG GTCATGTACT GGGCATAATG CCAGGCGGGC CATTTACCGT |
| 8401 CATTGACGTC AATAGGGGGC GTACTTGGCA TATGATACAC TTGATGTACT GCCAAGTGGG |
| 8461 CAGTTTACCG TAAATACTCC ACCCATTGAC GTCAATGGAA AGTCCCTATT GGCGTTACTA |
| 8521 TGGGAACATA CGTCATTATT GACGTCAATG GGCGGGGGTC GTTGGGCGGT CAGCCAGGCG |
| 8581 GGCCATTTAC CGTAAGTTAT GTAACGGGCC TGCTGCCGGC TCTGCGGCCT CTTCCGCGTC |
| 8641 TTCGCCTTCG CCCTCAGACG AGTCGGATCT CCCTTTGGGC CGCCTCCCCG CCTGTCTAGC |
| 8701 TTGACTGACT GAGATACAGC GTACCTTCAG CTCACAGACA TGATAAGATA CATTGATGAG |
| 8761 TTTGGACAAA CCACAACTAG AATGCAGTGA AAAAAATGCT TTATTTGTGA AATTTGTGAT |
| 8821 GCTATTGCTT TATTTGTAAC CATTATAAGC TGCAATAAAC AAGTTAACAA CAACAATTGC |
| 8881 ATTCATTTTA TGTTTCAGGT TCAGGGGGAG GTGTGGGAGG TTTTTTAAAG CAAGTAAAAC |
| 8941 CTCTACAAAT GTGGTATTGG CCCATCTCTA TCGGTATCGT AGCATAACCC CTTGGGGCCT |
| 9001 CTAAACGGGT CTTGAGGGGT TTTTTGTGCC CCTCGGGCCG GATTGCTATC TACCGGCATT |
| 9061 GGCGCAGAAA AAAATGCCTG ATGCGACGCT GCGCGTCTTA TACTCCCACA TATGCCAGAT |
| 9121 TCAGCAACGG ATACGGCTTC CCCAACTTGC CCACTTCCAT ACGTGTCCTC CTTACCAGAA |
| 9181 ATTTATCCTT AAGGTCGTCA GCTATCCTGC AGGCGATCTC TCGATTTCGA TCAAGACATT |
| 9241 CCTTTAATGG TCTTTTCTGG ACACCACTAG GGGTCAGAAG TAGTTCATCA AACTTTCTTC |
| 9301 CCTCCCTAAT CTCATTGGTT ACCTTGGGCT ATCGAAACTT AATTAAGCGA TCTGCATCTC |
| 9361 AATTAGTCAG CAACCATAGT CCCGCCCCTA ACTCCGCCCA TCCCGCCCCT AACTCCGCCC |
| 9421 AGTTCCGCCC ATTCTCCGCC CCATCGCTGA CTAATTTTTT TTATTTATGC AGAGGCCGAG |
| 9481 GCCGCCTCGG CCTCTGAGCT ATTCCAGAAG TAGTGAGGAG GCTTTTTTGG AGGCCTAGGC |
| 9541 TTTTGCAAAG GAGGTAGCCA ACATGATTGA ACAAGATGGA TTGCACGCAG GTTCTCCCGC |

TABLE 8-continued

| Plasmid and mRNA construct sequences |
|---|
| 9601 CGCTTGGGTG GAGAGGCTAT TCGGCTATGA CTGGGCACAA CAGACAATCG GCTGCTCTGA |
| 9661 TGCCGCCGTG TTCCGGCTGT CAGCGCAGGG GCGCCCGGTT CTTTTTGTCA AGACCGACCT |
| 9721 GTCCGGTGCC CTGAATGAAC TCCAGGACGA GGCAGCGCGG CTATCGTGGC TGGCCACGAC |
| 9781 GGGCGTTCCT TGCGCAGCTG TGCTCGACGT TGTCACTGAA GCGGGAAGGG ACTGGCTGCT |
| 9841 ATTGGGCGAA GTGCCGGGGC AGGATCTCCT GTCATCTCAC CTTGCTCCTG CCGAGAAAGT |
| 9901 ATCCATCATG GCTGATGCAA TGCGGCGGCT GCATACGCTT GATCCGGCTA CCTGCCCATT |
| 9961 CGACCACCAA GCGAAACATC GCATCGAGCG AGCACGTACT CGGATGGAAG CCGGTCTTGT |
| 10021 CGATCAGGAT GATCTGGACG AAGAGCATCA GGGGCTCGCG CCAGCCGAAC TGTTCGCCAG |
| 10081 GCTCAAGGCG CGGATGCCCG ACGGCGAGGA TCTCGTCGTG ACCCACGGCG ATGCCTGCTT |
| 10141 GCCGAATATC ATGGTGGAAA ATGGCCGCTT TTCTGGATTC ATCGACTGTG GCCGGCTGGG |
| 10201 TGTGGCGGAC CGCTATCAGG ACATAGCGTT GGCTACCCGT GATATTGCTG AAGAGCTTGG |
| 10261 CGGCGAATGG GCTGACCGCT TCCTCGTGCT TTACGGTATC GCCGCTCCCG ATTCGCAGCG |
| 10321 CATCGCCTTC TATCGCCTTC TTGACGAGTT CTTCTAGTAT GTAAGCCCTG TGCCTTCTAG |
| 10381 TTGCCAGCCA TCTGTTGTTT GCCCCTCCCC CGTGCCTTCC TTGACCCTGG AAGGTGCCAC |
| 10441 TCCCACTGTC CTTTCCTAAT AAAATGAGGA AATTGCATCG CATTGTCTGA GTAGGTGTCA |
| 10501 TTCTATTCTG GGGGGTGGGG TGGGGCAGGA CAGCAAGGGG GAGGATTGGG AAGACAATAG |
| 10561 CAGGCATGCT GGGGATGCGG TGGGCTCTAT GGTTAATTAA CCAGTCAAGT CAGCTACTTG |
| 10621 GCGAGATCGA CTTGTCTGGG TTTCGACTAC GCTCAGAATT GCGTCAGTCA AGTTCGATCT |
| 10681 GGTCCTTGCT ATTGCACCCG TTCTCCGATT ACGAGTTTCA TTTAAATCAT GTGAGCAAAA |
| 10741 GGCCAGCAAA AGGCCAGGAA CCGTAAAAAG GCCGCGTTGC TGGCGTTTTT CCATAGGCTC |
| 10801 CGCCCCCCTG ACGAGCATCA CAAAAATCGA CGCTCAAGTC AGAGGTGGCG AAACCCGACA |
| 10861 GGACTATAAA GATACCAGGC GTTTCCCCCT GGAAGCTCCC TCGTGCGCTC TCCTGTTCCG |
| 10921 ACCCTGCCGC TTACCGGATA CCTGTCCGCC TTTCTCCCTT CGGGAAGCGT GGCGCTTTCT |
| 10981 CATAGCTCAC GCTGTAGGTA TCTCAGTTCG GTGTAGGTCG TTCGCTCCAA GCTGGGCTGT |
| 11041 GTGCACGAAC CCCCCGTTCA GCCCGACCGC TGCGCCTTAT CCGGTAACTA TCGTCTTGAG |
| 11101 TCCAACCCGG TAAGACACGA CTTATCGCCA CTGGCAGCAG CCACTGGTAA CAGGATTAGC |
| 11161 AGAGCGAGGT ATGTAGGCGG TGCTACAGAG TTCTTGAAGT GGTGGCCTAA CTACGGCTAC |
| 11221 ACTAGAAGAA CAGTATTTGG TATCTGCGCT CTGCTGAAGC CAGTTACCTT CGGAAAAAGA |
| 11281 GTTGGTAGCT CTTGATCCGG CAAACAAACC ACCGCTGGTA GCGGTGGTTT TTTTGTTTGC |
| 11341 AAGCAGCAGA TTACGCGCAG AAAAAAAGGA TCTCAAGAAG ATCCTTTGAT CTTTTCTACG |
| 11401 GGGTCTGACG CTCAGTGGAA CGAAAACTCA CGTTAAGGGA TTTTGGTCAT GAGATTATCA |
| 11461 AAAAGGATCT TCACCTAGAT CCTTTTAAAT TAAAAATGAA GTTTTAAATC AATCTAAAGT |
| 11521 ATATATGAGT AAACTTGGTC TGACAGTTAC CAATGCTTAA TCAGTGAGGC ACCTATCTCA |
| 11581 GCGATCTGTC TATTTCGTTC ATCCATAGTT GCATTTAAAT TTCCGAACTC TCCAAGGCCC |
| 11641 TCGTCGGAAA ATCTTCAAAC CTTTCGTCCG ATCCATCTTG CAGGCTACCT CTCGAACGAA |
| 11701 CTATCGCAAG TCTCTTGGCC GGCCTTGCGC CTTGGCTATT GCTTGGCAGC GCCTATCGCC |
| 11761 AGGTATTACT CCAATCCCGA ATATCCGAGA TCGGGATCAC CCGAGAGAAG TTCAACCTAC |
| 11821 ATCCTCAATC CCGATCTATC CGAGATCCGA GGAATATCGA AATCGGGGCG CGCCTGGTGT |
| 11881 ACCGAGAACG ATCCTCTCAG TGCGAGTCTC GACGATCCAT ATCGTTGCTT GGCAGTCAGC |
| 11941 CAGTCGGAAT CCAGCTTGGG ACCCAGGAAG TCCAATCGTC AGATATTGTA CTCAAGCCTG |
| 12001 GTCACGGCAG CGTACCGATC TGTTTAAACC TAGATATTGA TAGTCTGATC GGTCAACGTA |
| 12061 TAATCGAGTC CTAGCTTTTG CAAACATCTA TCAAGAGACA GGATCAGCAG GAGGCTTTCG |
| 12121 CATGAGTATT CAACATTTCC GTGTCGCCCT TATTCCCTTT TTTGCGGCAT TTTGCCTTCC |
| 12181 TGTTTTTGCT CACCCAGAAA CGCTGGTGAA AGTAAAAGAT GCTGAAGATC AGTTGGGTGC |
| 12241 GCGAGTGGGT TACATCGAAC TGGATCTCAA CAGCGGTAAG ATCCTTGAGA GTTTTCGCCC |
| 12301 CGAAGAACGC TTTCCAATGA TGAGCACTTT TAAAGTTCTG CTATGTGGCG CGGTATTATC |
| 12361 CCGTATTGAC GCCGGGCAAG AGCAACTCGG TCGCCGCATA CACTATTCTC AGAATGACTT |
| 12421 GGTTGAGTAT TCACCAGTCA CAGAAAAGCA TCTTACGGAT GGCATGACAG TAAGAGAATT |
| 12481 ATGCAGTGCT GCCATAACCA TGAGTGATAA CACTGCGGCC AACTTACTTC TGACAACGAT |
| 12541 TGGAGGACCG AAGGAGCTAA CCGCTTTTTT GCACAACATG GGGGATCATG TAACTCGCCT |
| 12601 TGATCGTTGG GAACCGGAGC TGAATGAAGC CATACCAAAC GACGAGCGTG ACACCACGAT |
| 12661 GCCTGTAGCA ATGGCAACAA CCTTGCGTAA ACTATTAACT GGCGAACTAC TTACTCTAGC |
| 12721 TTCCCGGCAA CAGTTGATAG ACTGGATGGA GGCGGATAAA GTTGCAGGAC CACTTCTGCG |
| 12781 CTCGGCCCTT CCGGCTGGCT GGTTTATTGC TGATAAATCT GGAGCCGGTG AGCGTGGGTC |
| 12841 TCGCGGTATC ATTGCAGCAC TGGGGCCAGA TGGTAAGCCC TCCCGTATCG TAGTTATCTA |
| 12901 CACGACGGGG AGTCAGGCAA CTATGGATGA ACGAAATAGA CAGATCGCTG AGATAGGTGC |
| 12961 CTCACTGATT AAGCATTGGT AACCGATTCT AGGTGCATTG GCGCAGAAAA AAATGCCTGA |
| 13021 TGCGACGCTG CGCGTCTTAT ACTCCCACAT ATGCCAGATT CAGCAACGGA TACGGCTTCC |
| 13081 CCAACTTGCC CACTTCCATA CGTGTCCTCC TTACCAGAAA TTTATCCTTA AGATCGTTTA |
| 13141 AACTCGACTC TGGCTCTATC GAATCTCCGT CGTTTCGAGC TTACGCGAAC AGCCGTGGCG |
| 13201 CTCATTTGCT CGTCGGGCAT CGAATCTCGT CAGCTATCGT CAGCTTACCT TTTTGGCAGC |
| 13261 GATCGCGGCT CCCGACATCT TGGACCATTA GCTCCACAGG TATCTTCTTC CCTCTAGTGG |
| 13321 TCATAACAGC AGCTTCAGCT ACCTCTCAAT TCAAAAAACC CCTCAAGACC CGTTTAGAGG |
| 13381 CCCCAAGGGG TTATGCTATC AATCGTTGCG TTACACACAC AAAAAACCAA CACACATCCA |
| 13441 TCTTCGATGG ATAGCGATTT TATTATCTAA CTGCTGATCG AGTGTAGCCA GATCTAGTAA |
| 13501 TCAATTACGG GGTCATTAGT TCATAGCCCA TATATGGAGT TCCGCGTTAC ATAACTTACG |
| 13561 GTAAATGGCC CGCCTGGCTG ACCGCCCAAC GACCCCCGCC CATTGACGTC AATAATGACG |
| 13621 TATGTTCCCA TAGTAACGCC AATAGGGACT TTCCATTGAC GTCAATGGGT GGAGTATTTA |
| 13681 CGGTAAACTG CCCACTTGGC AGTACATCAA GTGTATCATA TGCCAAGTAC GCCCCCTATT |
| 13741 GACGTCAATG ACGGTAAATG GCCCGCCTGG CATTATGCCC AGTACATGAC CTTATGGGAC |
| 13801 TTTCCTACTT GGCAGTACAT CTACGTATTA GTCATCGCTA TTACCATGCT GATGCGGTTT |
| 13861 TGGCAGTACA TCAATGGGCG TGGATAGCGG TTTGACTCAC GGGGATTTCC AAGTCTCCAC |

TABLE 8-continued

Plasmid and mRNA construct sequences

13921 CCCATTGACG TCAATGGGAG TTTGTTTTGG CACCAAAATC AACGGGACTT TCCAAAATGT
13981 CGTAACAACT CCGCCCCATT GACGCAAATG GGCGGTAGGC GTGTACGGTG GGAGGTCTAT
14041 ATAAGCAGAG CTGGTTTAGT GAACCGTCAG ATCAGATCTT TGTCGATCCT ACCATCCACT
14101 CGACACACCC GCCAGCGGCC GC
(SEQ ID NO: 44)

LINE-1 Plasmid EV71 IRES (SEQ ID NO: 45)
1 TAATACGACT CACTATAGGG AGAAGTACTG CCACCATGGG CAAGAAGCAA AATCGCAAGA
61 CGGGGAATTC CAAGACACAA TCCGCTAGCC CACCACCTAA AGAGCGTTCT AGCTCCCCTG
121 CTACTGAGCA GTCCTGGATG GAAAACGACT TCGATGAACT CCGGGAAGAG GGATTTAGGC
181 GATCCAACTA TTCAGAACTC CGCGAAGATA TCCAGACAAA GGGGAAGGAA GTCGAGAATT
241 TCGAGAAGAA CCTCGAGGAG TGCATCACCC GTATCACAAA CACTGAGAAA TGTCTCAAAG
301 AACTCATGGA ACTTAAGACA AAAGCCAGGG AGCTTCGAGA GGAGTGTCGG AGTCTGAGAT
361 CCAGGTGTGA CCAGCTCGAG GAGCGCGTGA GCGCGATGGA AGACGAGATG AACGAGATGA
421 AAAGAGAGGG CAAATTCAGG GAGAAGCGCA TTAAGAGGAA CGAACAGAGT CTGCAGGAGA
481 TTTGGGATTA CGTCAAGAGG CCTAACCTGC GGTTGATCGG CGTCCCCGAG AGCGACGTAG
541 AAAACGGGAC TAAACTGGAG AATACACTTC AAGACATCAT TCAAGAAAAT TTTCCAAACC
601 TGGCTCGGCA AGCTAATGTG CAAATCCAAG AGATCCAACG CACACCCCAG CGGTATAGCT
661 CTCGGCGTGC CACCCCTAGG CATATTATCG TGCGCTTTAC TAAGGTGGAG ATGAAAGAGA
721 AGATGCTGCG AGCCGCTCGG GAAAAGGGAA GGGTGACTTT GAAGGGCAAA CCTATTCGGC
781 TGACGGTTGA CCTTAGCGCC GAGACACTCC AGGCACGCCG GGAATGGGGC CCCATCTTTA
841 ATATCCTGAA GGAGAAGAAC TTCCAGCCAC GAATCTCTTA CCCTGCAAAG TTGAGTTTTA
901 TCTCCGAGGG TGAGATTAAG TATTTCATCG ATAAACAGAT GCTGCGAGAC TTCGTGACAA
961 CTCGCCCAGC TCTCAAGGAA CTGCTCAAAG AGGCTCTTAA TATGGAGCGC AATAATAGAT
1021 ATCAACCCTT GCAGAACCAC GCAAAGATGT GAGACAGTTA AAACAGCTGT GGGTTGTCAC
1081 CCACCCACAG GGTCCACTGG GCGCTAGTAC ACTGGTATCT CGGTACCTTT GTACGCCTGT
1141 TTTATACCCC CTCCCTGATT TGCAACTTAG AAGCAACGCA AACCAGATCA ATAGTAGGTG
1201 TGACATACCA GTCGCATCTT GATCAAGCAC TTCTGTATCC CCGGACCGAG TATCAATAGA
1261 CTGTGCACAC GGTTGAAGGA GAAAACGTCC GTTACCCGGC TAACTACTTC GAGAAGCCTA
1321 GTAACGCCAT TGAAGTTGCA GAGTGTTTCG CTCAGCACTC CCCCCGTGTA GATCAGGTCG
1381 ATGAGTCACC GCATTCCCCA CGGGCGACCG TGGCGGTGGC TGCGTTGGCG GCCTGCCTAT
1441 GGGGTAACCC ATAGGACGCT CTAATACGGA CATGGCGTGA AGAGTCTATT GAGCTAGTTA
1501 GTAGTCCTCC GGCCCCTGAA TGCGGCTAAT CCTAACTGCG GAGCACATAC CCTTAATCCA
1561 AAGGGCAGTG TGTCGTAACG GGCAACTCTG CAGCGGAACC GACTACTTTG GGTGTCCGTG
1621 TTTCTTTTTA TTCTTGTATT GGCTGCTTAT GGTGACAATT AAAGAATTGT TACCATATAG
1681 CTATTGGATT GGCCATCCAG TGTCAAACAG AGCTATTGTA TATCTCTTTG TTGGATTCAC
1741 ACCTCTCACT CTTGAAACGT TACACACCCT CAATTACATT ATACTGCTGA ACACGAAGCG
1801 TACATGACCG GCTCTAACTC ACATATCACC ATCCTTACAC TTAACATTAA CGGCCTCAAC
1861 TCAGCTATCA AGCGCCATCG GCTGGCCAGC TGGATCAAAT CACAGGATCC AAGCGTTTGT
1921 TGCATCCAAG AGACCCACCT GACCTGTAGA GATACTCACC GCCTCAAGAT CAAGGGATGG
1981 CGAAAGATTT ATCAGGCGAA CGGTAAGCAG AAGAAAGCCG GAGTCGCAAT TCTGGTCTCA
2041 GACAAGACGG ATTTCAAGCC CACCAAAATT AAGCGTGATA AGGAAGGTCA CTATATTATG
2101 GTGAAAGGCA GCATACAGCA GGAAGAACTT ACCATATTGA ACATCTACGC GCCAAACACC
2161 GGCGCACCTC GCTTTATCAA ACAGGTCCTG TCCGATCTGC AGCGAGATCT GGATTCTCAT
2221 ACGTTGATTA TGGGTGATTT CAATACACCA TTGAGCACCC TGGATCGCAG CACCAGGCAA
2281 AAGGTAAATA AAGACACGCA AGAGCTCAAT AGCGCACTGC ATCAGGCAGA TCTCATTGAT
2341 ATTTATCGCA CTCTTCATCC TAAGAGTACC GAGTACACAT TCTTCAGCGC CCCACATCAT
2401 ACATACTCAA AGATCGATCA TATCGTCGGC TCAAAGGCTC TGCTGTCAAA GTGCAAGCGC
2461 ACAGAGATAA TTACAAATTA CCTGTCAGAT CATAGCGCGA TCAAGCTCGA GCTGAGAATC
2521 AAGAACCTGA CCCAGAGCCG GAGTACCACT TGGAAGCTTA ATAACCTGCT GCTCAACGAT
2581 TATTGGGTCC ACAATGAGAT GAAGGCAGAG ATTAAAATGT TCTTCGAAAC AAATGAGAAT
2641 AAGGATACTA CCTATCAAAA CCTTTGGGAT GCCTTTAAGG CCGTCTGCAG AGGCAAGTTC
2701 ATCGCCCTCA ACGCCTATAA AAGAAAACAA GAGAGATCTA AGATCGATAC TCTCACCTCT
2761 CAGCTGAAGG AGTTGGAGAA ACAGGAACAG ACCCACTCCA AGGCGTCAAG ACGGCAGGAG
2821 ATCACAAAGA TTCGCGCCGA GTTGAAAGAG ATCGAAACCC AAAAGACTCT TCAGAAAATT
2881 AACGAGTCTC GTAGTTGGTT CTTCGAGCGG ATTAATAAGA TAGACAGACC TCTGGCACGA
2941 CTGATTAAGA AGAAGCGCGA AAAGAACCAG ATTGATACCA TCAAGAACGA CAAGGGCGAC
3001 ATCACTACTG ACCCGACCGA GATCCAGACC ACTATTCGGG AGTATTATAA GCATTTGTAT
3061 GCTAACAAGC TTGAGAACCT GGAAGAGATG GACACTTTTC TGGATACCTA TACTCTGCCA
3121 CGGCTTAATC AAGAGGAAGT CGAGTCCCTC AACCGCCCAA TTACAGGAAG CGAGATTGTG
3181 GCCATAATTA ACTCCCTGCC GACAAAGAAA TCTCCTGGTC CGGACGGGTT TACAGCTGAG
3241 TTTTATCAAC GGTATATGGA AGAGCTTGTA CCGTTTCTGC TCAAGCTCTT TCAGTCTATA
3301 GAAAAGGAAG GCATCTTGCC CAATTCCTTC TACGAAGCTT CTATAATACT TATTCCCAAA
3361 CCAGGACGCG ATACCACAAA GAAGGAAAAC TTCCGGCCCA TTAGTCTCAT GAATATCGAC
3421 GCTAAAATAT TGAACAAGAT TCTCGCCAAC AGAATCCAAC AACATATTAA GAAATTGATA
3481 CATCACGACC AGGTGGGGTT TATACCTGGC ATGCAGGGCT GGTTTAACAT CCGGAAGAGT
3541 ATTAACGTCA TTCAACACAT TAATAGAGCT AAGGATAAGA ATCATATGAT CATCTCTATA
3601 GACGCGGAAA AGGCATTCGA TAAGATTCAG CAGCCATTTA TGCTCAAGAC TCTGAACAAA
3661 CTCGGCATCG ACGGAACATA TTTTAAGATT ATTCGCGCAA TTTACGATAA GCCGACTGCT
3721 AACATTATCC TTAACGGCCA AAAGCTCGAG GCCTTTCCGC TCAAGACTGG AACCCGCCAA
3781 GGCTGTCCCC TCTCCCCGCT TTTGTTTAAT ATTGTACTCG AGGTGCTGGC TAGGGCTATT
3841 CGTCAAGAGA AAGAGATTAA AGGGATACAG CTCGGGAAGG AAGAGGTCAA GCTTTCCTTG
3901 TTCGCCGATG ATATGATTGT GTACCTGGAG AATCCTATTG TGTCTGCTCA GAACCTTCTT
3961 AAACTTATTT CTAACTTTAG CAAGGTCAGC GGCTATAAGA TTAACGTCCA GAAATCTCAG
4021 GCCTTTCTGT ACACAAATAA TCGACAGACC GAATCCCAGA TAATGGGTGA GCTTCCGTTT
4081 GTCATAGCCA GCAAAAGGAT AAAGTATCTC GGAATCCAGC TGACACGAGA CGTTAAAGAT
4141 TTGTTTAAGG AAAATTACAA GCCTCTCCTG AAAGAGATTA AGGAAGATAC TAATAAGTGG
4201 AAGAATATCC CCTGTTCATG GGTTGGCAGA ATCAACATAG TGAAGATGGC AATACTTCCT TABLE 8-continued

| Plasmid and mRNA construct sequences |
| --- |
| 4261 AAAGTGATAT ATCGCTTTAA CGCCATCCCA ATTAAACTGC CTATGACCTT CTTTACGGAG |
| 4321 CTCGAGAAAA CAACCCTTAA ATTTATATGG AATCAAAAGA GAGCAAGAAT AGCGAAGTCC |
| 4381 ATCTTGAGCC AGAAGAATAA GGCCGGTGGG ATTACTTTGC CTGATTTTAA GTTGTATTAT |
| 4441 AAAGCCACAG TAACTAAGAC AGCCTGGTAT TGGTATCAGA ATAGAGACAT CGACCAGTGG |
| 4501 AATCGGACCG AACCATCAGA GATAATGCCC CACATCTATA ATTACCTTAT ATTCGATAAG |
| 4561 CCAGAAAAGA ATAAACAGTG GGGCAAAGAC AGCCTCTTCA ACAAGTGGTG TTGGGAGAAT |
| 4621 TGGCTGGCCA TATGCCGGAA ACTCAAGCTC GACCCCTTTC TTACACCCTA CACTAAAATC |
| 4681 AACAGTAGGT GGATCAAGGA CTTGAATGTC AAGCCAAAGA CTATAAAGAC ACTGGAAGAG |
| 4741 AATCTTGGGA TCACAATACA AGATATAGGC GTCGGCAAAG ATTTTATGTC AAAGACGCCC |
| 4801 AAGGCCATGG CCACTAAGGA TAAGATTGAT AAGTGGGACC TTATTAAGCT CAAAAGCTTC |
| 4861 TGTACTGCCA AGGAGACCAC GATCAGAGTT AATAGGCAGC CCACTACATG GGAAAAGATT |
| 4921 TTCGCCACTT ATTCATCAGA TAAGGGGTTG ATAAGCAGAA TATATAACGA GCTGAAGCAG |
| 4981 ATCTACAAGA AGAAAACGAA TAATCCCATC AAGAAGTGGG CAAAAGATAT GAACAGGCAT |
| 5041 TTTAGCAAAG AGGATATCTA CGCCGCGAAG AAGCATATGA AGAAGTGTAG TTCAAGCTTG |
| 5101 GCCATTCGTG AGATGCAGAT TAAGACGACC ATGCGATACC ACCTTACCCC AGTGAGGATG |
| 5161 GCAATTATCA AGAAATCTGG CAATAATAGA TGTTGGCGGG GCTGTGGCGA GATTGGCACC |
| 5221 CTGCTCCATT GCTGGTGGGA TTGCAAGCTG GTGCAGCCGC TTTGGAAATC AGTCTGGCGC |
| 5281 TTTCTGAGGG ACCTCGAGCT TGAGATTCCC TTCGATCCCG CAATTCCCTT GCTCGGAATC |
| 5341 TATCCTAACG AATACAAGAG CTGTTGTTAC AAGGATACGT GTACCCGGAT GTTCATCGCG |
| 5401 GCCTTGTTTA CGATAGCTAA GACGTGGAAT CAGCCTAAGT GCCCCACAAT GATCGATTGG |
| 5461 ATCAAGAAAA TGTGGCATAT TTATACCATG GAGTATTACG CAGCAATTAA GAATGACGAA |
| 5521 TTTATTTCCT TCGTTGGGAC CTGGATGAAG CTGGAGACTA TTATTCTGAG CAAGCTGTCT |
| 5581 CAGGAGCAAA AGACAAAGCA TAGAATCTTC TCTCTCATTG GTGGTAACGA CTACAAAGAC |
| 5641 GATGACGACA AGTAAAGCGC TTCTAGAAGT TGTCTCCTCC TGCACTGACT GACTGATACA |
| 5701 ATCGATTTCT GGATCCGCAG GCCTAATCAA CCTCTGGATT ACAAAATTTG TGAAAGATTG |
| 5761 ACTGGTATTC TTAACTATGT TGCTCCTTTT ACGCTATGTG GATACGCTGC TTTAATGCCT |
| 5821 TTGTATCATG CTATTGCTTC CCGTATGGCT TTCATTTTCT CCTCCTTGTA TAAATCCTGG |
| 5881 TTGCTGTCTC TTTATGAGGA GTTGTGGCCC GTTGTCAGGC AACGTGGCGT GGTGTGCACT |
| 5941 GTGTTTGCTG ACGCAACCCC CACTGGTTGG GGCATTGCCA CCACCTGTCA GCTCCTTTCC |
| 6001 GGGACTTTCG CTTTCCCCCT CCCTATTGCC ACGGCGGAAC TCATCGCCGC CTGCCTTGCC |
| 6061 CGCTGCTGGA CAGGGGCTCG GCTGTTGGGC ACTGACAATT CCGTGGTGTT GTCGGGGAAG |
| 6121 CTGACGTCCT TTCCATGGCT GCTCGCCTGT GTTGCCACCT GGATTCTGCG CGGGACGTCC |
| 6181 TTCTGCTACG TCCCTTCGGC CCTCAATCCA GCGGACCTTC CTTCCCGCGA ACAAACGACC |
| 6241 CAACACCCGT GCGTTTTATT CTGTCTTTTT ATTGCCGATC CCCTCAGAAG AACTCGTCAA |
| 6301 GAAGGCGATA GAAGGCGATG CGCTGCGAAT CGGGAGCGGC GATACCGTAA AGCACGAGGA |
| 6361 AGCGGTCAGC CCATTCGCCG CCAAGCTCTT CAGCAATATC ACGGGTAGCC AACGCTATGT |
| 6421 CCTGATAGCG GTCGGCCGCT TTACTTGTAC AGCTCGTCCA TGCCGAGAGT GATCCCGGCG |
| 6481 GCGGTCACGA ACTCCAGCAG GACCATGTGA TCGCGCTTCT CGTTGGGGTC TTTGCTCAGG |
| 6541 GCGGACTGGG TGCTCAGGTA GTGGTTGTCG GGCAGCAGCA CGGGGCCGTC GCCGATGGGG |
| 6601 GTGTTCTGCT GGTAGTGGTC GGCCAGGTGA GTCCAGGAGA TGTTTCAGCA CTGTTGCCTT |
| 6661 TAGTCTCGAG GCAACTTAGA CAACTGAGTA TTGATCTGAG CACAGCAGGG TGTGAGCTGT |
| 6721 TTGAAGATAC TGGGGTTGGG GGTGAAGAAA CTGCAGAGGA CTAACTGGGC TGAGACCCAG |
| 6781 TGGCAATGTT TTAGGGCCTA AGGAATGCCT CTGAAAATCT AGATGGACAA CTTTGACTTT |
| 6841 GAGAAAAGAG AGGTGGAAAT GAGGAAAATG ACTTTTCTTT ATTAGATTTC GGTAGAAAGA |
| 6901 ACTTTCATCT TTCCCCTATT TTTGTTATTC GTTTTAAAAC ATCTATCTGG AGGCAGGACA |
| 6961 AGTATGGTCA TTAAAAAGAT GCAGGCAGAA GGCATATATT GGCTCAGTCA AAGTGGGGAA |
| 7021 CTTTGGTGGC CAAACATACA TTGCTAAGGC TATTCCTATA TCAGCTGGAC ACATATAAAA |
| 7081 TGCTGCTAAT GCTTCATTAC AAACTTATAT CCTTTAATTC CAGATGGGGG CAAAGTATGT |
| 7141 CCAGGGGTGA GGAACAATTG AAACATTTGG GCTGGAGTAG ATTTTGAAAG TCAGCTCTGT |
| 7201 GTGTGTGTGT GTGTGTGTGT GTGTGAGAGC GTGTGTTTCT TTTAACGTTT TCAGCCTACA |
| 7261 GCATACAGGG TTCATGGTGG CAAGAAGATA ACAAGATTTA AATTATGGCC AGTGACTAGT |
| 7321 GCTGCAAGAA GAACAACTAC CTGCATTTAA TGGGAAAGCA AAATCTCAGG CTTTGAGGGA |
| 7381 AGTTAACATA GGCTTGATTC TGGGTGGAAG CTGGGTGTGT AGTTATCTGG AGGCCAGGCT |
| 7441 GGAGCTCTCA GCTCACTATG GGTTCATCTT TATTGTCTCC TTTCATCTCA ACAGCTGCAC |
| 7501 GCTGCCGTCC TCGATGTTGT GGCGGATCTT GAAGTTCACC TTGATGCCGT TCTTCTGCTT |
| 7561 GTCGGCCATG ATATAGACGT TGTGGCTGTT GTAGTTGTAC TCCAGCTTGT GCCCCAGGAT |
| 7621 GTTGCCGTCC TCCTTGAAGT CGATGCCCTT CAGCTCGATG CGGTTCACCA GGGTGTCGCC |
| 7681 CTCGAACTTC ACCTCGGCGC GGGTCTTGTA GTTGCCGTCG TCCTTGAAGA AGATGGTGCG |
| 7741 CTCCTGGACG TAGCCTTCGG GCATGGCGGA CTTGAAGAAG TCGTGCTGCT TCATGTGGTC |
| 7801 GGGGTAGCGG CTGAAGCACT GCACGCCGTA GGTCAGGGTG GTCACGAGGG TGGGCCAGGG |
| 7861 CACGGGCAGC TTGCCGGTGG TGCAGATGAA CTTCAGGGTC AGCTTGCCGT AGGTGGCATC |
| 7921 GCCCTCGCCC TCGCCGGACA CGCTGAACTT GTGGCCGTTT ACGTCGCCGT CCAGCTCGAC |
| 7981 CAGGATGGGC ACCACCCCGG TGAACAGCTC CTCGCCCTTG CTCACCATGG TGGCGAATTC |
| 8041 GAAGCTTGAG CACGAGATCT GAGTCCGGTA GGCCTAGCGG ATCTGACGGT TCACTAAACC |
| 8101 AGCTCTGCTT ATATAGACCT CCCACCGTAC ACGCCTACCG CCCATTTGCG TCAATGGGGC |
| 8161 GGAGTTGTTA CGACATTTTG GAAAGTCCCG TTGATTTTGG TGCCAAAACA AACTCCCATT |
| 8221 GACGTCAATG GGGTGGAGAC TTGGAAATCC CCGTGAGTCA AACCGCTATC CACGCCCATT |
| 8281 GATGTACTGC CAAAACCGCA TCACCATGGT AATAGCGATG ACTAATACGT AGATGTACTG |
| 8341 CCAAGTAGGA AAGTCCCATA AGGTCATGTA CTGGGCATAA TGCCAGGCGG GCCATTTACC |
| 8401 GTCATTGACG TCAATAGGGG GCGTACTTGG CATATGATAC ACTTGATGTA CTGCCAAGTG |
| 8461 GGCAGTTTAC CGTAAATACT CCACCCATTG ACGTCAATGG AAAGTCCCTA TTGGCGTTAC |
| 8521 TATGGGAACA TACGTCATTA TTGACGTCAA TGGGCGGGGG TCGTTGGGCG GTCAGCCAGG |
| 8581 CGGGCCATTT ACCGTAAGTT ATGTAACGGG CCTGCTGCCG GCTCTGCGGC CTCTTCCGCG |
| 8641 TCTTCGCCTT CGCCCTCAGA CGAGTCGGAT CTCCCTTTGG GCCGCCTCCC CGCCTGTCTA |
| 8701 GCTTGACTGA CTGAGATACA GCGTACCTTC AGCTCACAGA CATGATAAGA TACATTGATG |
| 8761 AGTTTGGACA AACCACAACT AGAATGCAGT GAAAAAAATG CTTTATTTGT GAAATTTGTG |
| 8821 ATGCTATTGC TTTATTTGTA ACCATTATAA GCTGCAATAA ACAAGTTAAC AACAACAATT |
| 8881 GCATTCATTT TATGTTTCAG GTTCAGGGGG AGGTGTGGGA GGTTTTTTAA AGCAAGTAAA |

TABLE 8-continued

Plasmid and mRNA construct sequences

| | |
|---|---|
| 8941 | ACCTCTACAA ATGTGGTATT GGCCCATCTC TATCGGTATC GTAGCATAAC CCCTTGGGGC |
| 9001 | CTCTAAACGG GTCTTGAGGG GTTTTTTGTG CCCCTCGGGC CGGATTGCTA TCTACCGGCA |
| 9061 | TTGGCGCAGA AAAAAATGCC TGATGCGACG CTGCGCGTCT TATACTCCCA CATATGCCAG |
| 9121 | ATTCAGCAAC GGATACGGCT TCCCCAACTT GCCCACTTCC ATACGTGTCC TCCTTACCAG |
| 9181 | AAATTTATCC TTAAGGTCGT CAGCTATCCT GCAGGCGATC TCTCGATTTC GATCAAGACA |
| 9241 | TTCCTTTAAT GGTCTTTTCT GGACACCACT AGGGGTCAGA AGTAGTTCAT CAAACTTTCT |
| 9301 | TCCCTCCCTA ATCTCATTGG TTACCTTGGG CTATCGAAAC TTAATTAAGC GATCTGCATC |
| 9361 | TCAATTAGTC AGCAACCATA GTCCCGCCCC TAACTCCGCC CATCCCGCCC CTAACTCCGC |
| 9421 | CCAGTTCCGC CCATTCTCCG CCCCATCGCT GACTAATTTT TTTTATTTAT GCAGAGGCCG |
| 9481 | AGGCCGCCTC GGCCTCTGAG CTATTCCAGA AGTAGTGAGG AGGCTTTTTT GGAGGCCTAG |
| 9541 | GCTTTTGCAA AGGAGGTAGC CAACATGATT GAACAAGATG GATTGCACGC AGGTTCTCCC |
| 9601 | GCCGCTTGGG TGGAGAGGCT ATTCGGCTAT GACTGGGCAC AACAGACAAT CGGCTGCTCT |
| 9661 | GATGCCGCCG TGTTCCGGCT GTCAGCGCAG GGGCGCCCGG TTCTTTTTGT CAAGACCGAC |
| 9721 | CTGTCCGGTG CCCTGAATGA ACTCCAGGAC GAGGCAGCGC GGCTATCGTG GCTGGCCACG |
| 9781 | ACGGGCGTTC CTTGCGCAGC TGTGCTCGAC GTTGTCACTG AAGCGGGAAG GGACTGGCTG |
| 9841 | CTATTGGGCG AAGTGCCGGG GCAGGATCTC CTGTCATCTC ACCTTGCTCC TGCCGAGAAA |
| 9901 | GTATCCATCA TGGCTGATGC AATGCGGCGG CTGCATACGC TTGATCCGGC TACCTGCCCA |
| 9961 | TTCGACCACC AAGCGAAACA TCGCATCGAG CGAGCACGTA CTCGGATGGA AGCCGGTCTT |
| 10021 | GTCGATCAGG ATGATCTGGA CGAAGAGCAT CAGGGGCTCG CGCCAGCCGA ACTGTTCGCC |
| 10081 | AGGCTCAAGG CGCGGATGCC CGACGGCGAG GATCTCGTCG TGACCCACGG CGATGCCTGC |
| 10141 | TTGCCGAATA TCATGGTGGA AAATGGCCGC TTTTCTGGAT TCATCGACTG TGGCCGGCTG |
| 10201 | GGTGTGGCGG ACCGCTATCA GGACATAGCG TTGGCTACCC GTGATATTGC TGAAGAGCTT |
| 10261 | GGCGGCGAAT GGGCTGACCG CTTCCTCGTG CTTTACGGTA TCGCCGCTCC CGATTCGCAG |
| 10321 | CGCATCGCCT TCTATCGCCT TCTTGACGAG TTCTTCTAGT ATGTAAGCCC TGTGCCTTCT |
| 10381 | AGTTGCCAGC CATCTGTTGT TTGCCCCTCC CCCGTGCCTT CCTTGACCCT GGAAGGTGCC |
| 10441 | ACTCCCACTG TCCTTTCCTA ATAAAATGAG GAAATTGCAT CGCATTGTCT GAGTAGGTGT |
| 10501 | CATTCTATTC TGGGGGGTGG GGTGGGGCAG GACAGCAAGG GGGAGGATTG GGAAGACAAT |
| 10561 | AGCAGGCATG CTGGGGATGC GGTGGGCTCT ATGGTTAATT AACCAGTCAA GTCAGCTACT |
| 10621 | TGGCGAGATC GACTTGTCTG GGTTTCGACT ACGCTCAGAA TTGCGTCAGT CAAGTTCGAT |
| 10681 | CTGGTCCTTG CTATTGCACC CGTTCTCCGA TTACGAGTTT CATTTAAATC ATGTGAGCAA |
| 10741 | AAGGCCAGCA AAAGGCCAGG AACCGTAAAA AGGCCGCGTT GCTGGCGTTT TTCCATAGGC |
| 10801 | TCCGCCCCCC TGACGAGCAT CACAAAAATC GACGCTCAAG TCAGAGGTGG CGAAACCCGA |
| 10861 | CAGGACTATA AAGATACCAG GCGTTTCCCC CTGGAAGCTC CCTCGTGCGC TCTCCTGTTC |
| 10921 | CGACCCTGCC GCTTACCGGA TACCTGTCCG CCTTTCTCCC TTCGGGAAGC GTGGCGCTTT |
| 10981 | CTCATAGCTC ACGCTGTAGG TATCTCAGTT CGGTGTAGGT CGTTCGCTCC AAGCTGGGCT |
| 11041 | GTGTGCACGA ACCCCCCGTT CAGCCCGACC GCTGCGCCTT ATCCGGTAAC TATCGTCTTG |
| 11101 | AGTCCAACCC GGTAAGACAC GACTTATCGC CACTGGCAGC AGCCACTGGT AACAGGATTA |
| 11161 | GCAGAGCGAG GTATGTAGGC GGTGCTACAG AGTTCTTGAA GTGGTGGCCT AACTACGGCT |
| 11221 | ACACTAGAAG AACAGTATTT GGTATCTGCG CTCTGCTGAA GCCAGTTACC TTCGGAAAAA |
| 11281 | GAGTTGGTAG CTCTTGATCC GGCAAACAAA CCACCGCTGG TAGCGGTGGT TTTTTTGTTT |
| 11341 | GCAAGCAGCA GATTACGCGC AGAAAAAAAG GATCTCAAGA AGATCCTTTG ATCTTTTCTA |
| 11401 | CGGGGTCTGA CGCTCAGTGG AACGAAAACT CACGTTAAGG GATTTTGGTC ATGAGATTAT |
| 11461 | CAAAAAGGAT CTTCACCTAG ATCCTTTTAA ATTAAAAATG AAGTTTTAAA TCAATCTAAA |
| 11521 | GTATATATGA GTAAACTTGG TCTGACAGTT ACCAATGCTT AATCAGTGAG GCACCTATCT |
| 11581 | CAGCGATCTG TCTATTTCGT TCATCCATAG TTGCATTTAA ATTTCCGAAC TCTCCAAGGC |
| 11641 | CCTCGTCGGA AAATCTTCAA ACCTTTCGTC CGATCCATCT TGCAGGCTAC CTCTCGAACG |
| 11701 | AACTATCGCA AGTCTCTTGG CCGGCCTTGC GCCTTGGCTA TTGCTTGGCA GCGCCTATCG |
| 11761 | CCAGGTATTA CTCCAATCCC GAATATCCGA GATCGGGATC ACCCGAGAGA AGTTCAACCT |
| 11821 | ACATCCTCAA TCCCGATCTA TCCGAGATCC GAGGAATATC GAAATCGGGG CGCGCCTGGT |
| 11881 | GTACCGAGAA CGATCCTCTC AGTGCGAGTC TCGACGATCC ATATCGTTGC TTGGCAGTCA |
| 11941 | GCCAGTCGGA ATCCAGCTTG GGACCCAGGA AGTCCAATCG TCAGATATTG TACTCAAGCC |
| 12001 | TGGTCACGGC AGCGTACCGA TCTGTTTAAA CCTAGATATT GATAGTCTGA TCGGTCAACG |
| 12061 | TATAATCGAG TCCTAGCTTT TGCAAACATC TATCAAGAGA CAGGATCAGC AGGAGGCTTT |
| 12121 | CGCATGAGTA TTCAACATTT CCGTGTCGCC CTTATTCCCT TTTTTGCGGC ATTTTGCCTT |
| 12181 | CCTGTTTTTG CTCACCCAGA AACGCTGGTG AAAGTAAAAG ATGCTGAAGA TCAGTTGGGT |
| 12241 | GCGCGAGTGG GTTACATCGA ACTGGATCTC AACAGCGGTA AGATCCTTGA GAGTTTTCGC |
| 12301 | CCCGAAGAAC GCTTTCCAAT GATGAGCACT TTTAAAGTTC TGCTATGTGG CGCGGTATTA |
| 12361 | TCCCGTATTG ACGCCGGGCA AGAGCAACTC GGTCGCCGCA TACACTATTC TCAGAATGAC |
| 12421 | TTGGTTGAGT ATTCACCAGT CACAGAAAAG CATCTTACGG ATGGCATGAC AGTAAGAGAA |
| 12481 | TTATGCAGTG CTGCCATAAC CATGAGTGAT AACACTGCGG CCAACTTACT TCTGACAACG |
| 12541 | ATTGGAGGAC CGAAGGAGCT AACCGCTTTT TTGCACAACA TGGGGGATCA TGTAACTCGC |
| 12601 | CTTGATCGTT GGGAACCGGA GCTGAATGAA GCCATACCAA ACGACGAGCG TGACACCACG |
| 12661 | ATGCCTGTAG CAATGGCAAC AACCTTGCGT AAACTATTAA CTGGCGAACT ACTTACTCTA |
| 12721 | GCTTCCCGGC AACAGTTGAT AGACTGGATG GAGGCGGATA AAGTTGCAGG ACCACTTCTG |
| 12781 | CGCTCGGCCC TTCCGGCTGG CTGGTTTATT GCTGATAAAT CTGGAGCCGG TGAGCGTGGG |
| 12841 | TCTCGCGGTA TCATTGCAGC ACTGGGGCCA GATGGTAAGC CCTCCCGTAT CGTAGTTATC |
| 12901 | TACACGACGG GGAGTCAGGC AACTATGGAT GAACGAAATA GACAGATCGC TGAGATAGGT |
| 12961 | GCCTCACTGA TTAAGCATTG GTAACCGATT CTAGGTGCAT TGGCGCAGAA AAAAATGCCT |
| 13021 | GATGCGACGC TGCGCGTCTT ATACTCCCAC ATATGCCAGA TTCAGCAACG GATACGGCTT |
| 13081 | CCCCAACTTG CCCACTTCCA TACGTGTCCT CCTTACCAGA AATTTATCCT TAAGATCGTT |
| 13141 | TAAACTCGAC TCTGGCTCTA TCGAATCTCC GTCGTTTCGA GCTTACGCGA ACAGCCGTGG |
| 13201 | CGCTCATTTG CTCGTCGGGC ATCGAATCTC GTCAGCTATC GTCAGCTTAC CTTTTTGGCA |
| 13261 | GCGATCGCGG CTCCCGACAT CTTGGACCAT TAGCTCCACA GGTATCTTCT TCCCTCTAGT |
| 13321 | GGTCATAACA GCAGCTTCAG CTACCTCTCA ATTCAAAAAA CCCCTCAAGA CCCGTTTAGA |
| 13381 | GGCCCCAAGG GGTTATGCTA TCAATCGTTG CGTTACACAC ACAAAAAACC AACACACATC |
| 13441 | CATCTTCGAT GGATAGCGAT TTTATTATCT AACTGCTGAT CGAGTGTAGC CAGATCTAGT |
| 13501 | AATCAATTAC GGGGTCATTA GTTCATAGCC CATATATGGA GTTCCGCGTT ACATAACTTA |
| 13561 | CGGTAAATGG CCCGCCTGGC TGACCGCCCA ACGACCCCCG CCCATTGACG TCAATAATGA |

TABLE 8-continued

Plasmid and mRNA construct sequences

```
13621 CGTATGTTCC CATAGTAACG CCAATAGGGA CTTTCCATTG ACGTCAATGG GTGGAGTATT
13681 TACGGTAAAC TGCCCACTTG GCAGTACATC AAGTGTATCA TATGCCAAGT ACGCCCCCTA
13741 TTGACGTCAA TGACGGTAAA TGGCCCGCCT GGCATTATGC CCAGTACATG ACCTTATGGG
13801 ACTTTCCTAC TTGGCAGTAC ATCTACGTAT TAGTCATCGC TATTACCATG CTGATGCGGT
13861 TTTGGCAGTA CATCAATGGG CGTGGATAGC GGTTTGACTC ACGGGGATTT CCAAGTCTCC
13921 ACCCCATTGA CGTCAATGGG AGTTTGTTTT GGCACCAAAA TCAACGGGAC TTTCCAAAAT
13981 GTCGTAACAA CTCCGCCCCA TTGACGCAAA TGGGCGGTAG GCGTGTACGG TGGGAGGTCT
14041 ATATAAGCAG AGCTGGTTTA GTGAACCGTC AGATCAGATC TTTGTCGATC CTACCATCCA
14101 CTCGACACAC CCGCCAGCGG CCGC
      (SEQ ID NO: 45)

LINE-1 plasmid ORF 1- E2A-ORF2 GFP (SEQ ID NO: 46)
    1 TAATACGACT CACTATAGGG AGAAGTACTG CCACCATGGG CAAGAAGCAA AATCGCAAGA
   61 CGGGGAATTC CAAGACACAA TCCGCTAGCC CACCACCTAA AGAGCGTTCT AGCTCCCCTG
  121 CTACTGAGCA GTCCTGGATG GAAAACGACT TCGATGAACT CCGGGAAGAG GGATTTAGGC
  181 GATCCAACTA TTCAGAACTC CGCGAAGATA TCCAGACAAA GGGGAAGGAA GTCGAGAATT
  241 TCGAGAAGAA CCTCGAGGAG TGCATCACCC GTATCACAAA CACTGAGAAA TGTCTCAAAG
  301 AACTCATGGA ACTTAAGACA AAAGCCAGGG AGCTTCGAGA GGAGTGTCGG AGTCTGAGAT
  361 CCAGGTGTGA CCAGCTCGAG GAGCGCGTGA GCGCGATGGA AGACGAGATG AACGAGATGA
  421 AAAGAGAGGG CAAATTCAGG GAGAAGCGCA TTAAGAGGAA CGAACAGAGT CTGCAGGAGA
  481 TTTGGGATTA CGTCAAGAGG CCTAACCTGC GGTTGATCGG CGTCCCCGAG AGCGACGTAG
  541 AAAACGGGAC TAAACTGGAG AATACACTTC AAGACATCAT TCAAGAAAAT TTTCCAAACC
  601 TGGCTCGGCA AGCTAATGTG CAAATCCAAG AGATCCAACG CACACCCCAG CGGTATAGCT
  661 CTCGGCGTGC CACCCCTAGG CATATTATCG TGCGCTTTAC TAAGGTGGAG ATGAAAGAGA
  721 AGATGCTGCG AGCCGCTCGG GAAAAGGGAA GGGTGACTTT GAAGGGCAAA CCTATTCGGC
  781 TGACGGTTGA CCTTAGCGCC GAGACACTCC AGGCACGCCG GGAATGGGGC CCCATCTTTA
  841 ATATCCTGAA GGAGAAGAAC TTCCAGCCAC GAATCTCTTA CCCTGCAAAG TTGAGTTTTA
  901 TCTCCGAGGG TGAGATTAAG TATTTCATCG ATAAACAGAT GCTGCGAGAC TTCGTGACAA
  961 CTCGCCCAGC TCTCAAGGAA CTGCTCAAAG AGGCTCTTAA TATGGAGCGC AATAATAGAT
 1021 ATCAACCCTT GCAGAACCAC GCAAAGATGG GAAGCGGACA GTGTACTAAT TATGCTCTCT
 1081 TGAAATTGGC TGGAGATGTT GAGAGCAACC CTGGACCTAT GACCGGCTCT AACTCACATA
 1141 TCACCATCCT TACACTTAAC ATTAACGGCC TCAACTCAGC TATCAAGCGC CATCGGCTGG
 1201 CCAGCTGGAT CAAATCACAG GATCCAAGCG TTTGTTGCAT CCAAGAGACC CACCTGACCT
 1261 GTAGAGATAC TCACCGCCTC AAGATCAAGG GATGGCGAAA GATTTATCAG GCGAACGGTA
 1321 AGCAGAAGAA AGCCGGAGTC GCAATTCTGG TCTCAGACAA GACGGATTTC AAGCCCACCA
 1381 AAATTAAGCG TGATAAGGAA GGTCACTATA TTATGGTGAA AGGCAGCATA CAGCAGGAAG
 1441 AACTTACCAT ATTGAACATC TACGCGCCAA ACACCGGCGC ACCTCGCTTT ATCAAACAGG
 1501 TCCTGTCCGA TCTGCAGCGA GATCTGGATT CTCATACGTT GATTATGGGT GATTTCAATA
 1561 CACCATTGAG CACCCTGGAT CGCAGCACCA GGCAAAAGGT AAATAAAGAC ACGCAAGAGC
 1621 TCAATAGCGC ACTGCATCAG GCAGATCTCA TTGATATTTA TCGCACTCTT CATCCTAAGA
 1681 GTACCGAGTA CACATTCTTC AGCGCCCCAC ATCATACATA CTCAAAGATC GATCATATCG
 1741 TCGGCTCAAA GGCTCTGCTG TCAAAGTGCA AGCGCACAGA GATAATTACA AATTACCTGT
 1801 CAGATCATAG CGCGATCAAG CTCGAGCTGA GAATCAAGAA CCTGACCCAG AGCCGGAGTA
 1861 CCACTTGGAA GCTTAATAAC CTGCTGCTCA ACGATTATTG GGTCCACAAT GAGATGAAGG
 1921 CAGAGATTAA AATGTTCTTC GAAACAAATG AGAATAAGGA TACTACCTAT CAAAACCTTT
 1981 GGGATGCCTT TAAGGCCGTC TGCAGAGGCA AGTTCATCGC CCTCAACGCC TATAAAAGAA
 2041 AACAAGAGAG ATCTAAGATC GATACTCTCA CCTCTCAGCT GAAGGAGTTG GAGAAACAGG
 2101 AACAGACCCA CTCCAAGGCG TCAAGACGGC AGGAGATCAC AAAGATTCGC GCCGAGTTGA
 2161 AAGAGATCGA AACCCAAAAG ACTCTTCAGA AAATTAACGA GTCTCGTAGT TGGTTCTTCG
 2221 AGCGGATTAA TAAGATAGAC AGACCTCTGG CACGACTGAT TAAGAAGAAG CGCGAAAAGA
 2281 ACCAGATTGA TACCATCAAG AACGACAAGG GCGACATCAC TACTGACCCG ACCGAGATCC
 2341 AGACCACTAT TCGGGAGTAT TATAAGCATT TGTATGCTAA CAAGCTTGAG AACCTGGAAG
 2401 AGATGGACAC TTTTCTGGAT ACCTATACTC TGCCACGGCT TAATCAAGAG GAAGTCGAGT
 2461 CCCTCAACCG CCCAATTACA GGAAGCGAGA TTGTGGCCAT AATTAACTCC CTGCCGACAA
 2521 AGAAATCTCC TGGTCCGGAC GGGTTTACAG CTGAGTTTTA TCAACGGTAT ATGGAAGAGC
 2581 TTGTACCGTT TCTGCTCAAG CTCTTTCAGT CTATAGAAAA GGAAGGCATC TTGCCCAATT
 2641 CCTTCTACGA AGCTTCTATA ATACTTATTC CCAAACCAGG ACGCGATACC ACAAAGAAGG
 2701 AAAACTTCCG GCCCATTAGT CTCATGAATA TCGACGCTAA AATATTGAAC AAGATTCTCG
 2761 CCAACAGAAT CCAACAACAT ATTAAGAAAT TGATACATCA CGACCAGGTG GGGTTTATAC
 2821 CTGGCATGCA GGGCTGGTTT AACATCCGGA AGAGTATTAA CGTCATTCAA CACATTAATA
 2881 GAGCTAAGGA TAAGAATCAT ATGATCATCT CTATAGACGC GGAAAAGGCA TTCGATAAGA
 2941 TTCAGCAGCC ATTTATGCTC AAGACTCTGA ACAAACTCGG CATCGACGGA ACATATTTTA
 3001 AGATTATTCG CGCAATTTAC GATAAGCCGA CTGCTAACAT TATCCTTAAC GGCCAAAAGC
 3061 TCGAGGCCTT TCCGCTCAAG ACTGGAACCC GCCAAGGCTG TCCCCTCTCC CCGCTTTTGT
 3121 TTAATATTGT ACTCGAGGTG CTGGCTAGGG CTATTCGTCA AGAGAAAGAG ATTAAAGGGA
 3181 TACAGCTCGG GAAGGAAGAG GTCAAGCTTT CCTTGTTCGC CGATGATATG ATTGTGTACC
 3241 TGGAGAATCC TATTGTGTCT GCTCAGAACC TTCTTAAACT TATTTCTAAC TTTAGCAAGG
 3301 TCAGCGGCTA TAAGATTAAC GTCCAGAAAT CTCAGGCCTT TCTGTACACA AATAATCGAC
 3361 AGACCGAATC CCAGATAATG GGTGAGCTTC CGTTTGTCAT AGCCAGCAAA AGGATAAAGT
 3421 ATCTCGGAAT CCAGCTGACA CGAGACGTTA AAGATTTGTT TAAGGAAAAT TACAAGCCTC
 3481 TCCTGAAAGA GATTAAGGAA GATACTAATA AGTGGAAGAA TATCCCCTGT TCATGGGTTG
 3541 GCAGAATCAA CATAGTGAAG ATGGCAATAC TTCCTAAAGT GATATATCGC TTTAACGCCA
 3601 TCCCAATTAA ACTGCCTATG ACCTTCTTTA CGGAGCTCGA GAAAACAACC CTTAAATTTA
 3661 TATGGAATCA AAAGAGAGCA AGAATAGCGA AGTCCATCTT GAGCCAGAAG AATAAGGCCG
 3721 GTGGGATTAC TTTGCCTGAT TTTAAGTTGT ATTATAAAGC CACAGTAACT AAGACAGCCT
 3781 GGTATTGGTA TCAGAATAGA GACATCGACC AGTGGAATCG GACCGAACCA TCAGAGATAA
 3841 TGCCCCACAT CTATAATTAC CTTATATTCG ATAAGCCAGA AAAGAATAAA CAGTGGGGCA
 3901 AAGACAGCCT CTTCAACAAG TGGTGTTGGG AGAATTGGCT GGCCATATGC CGGAAACTCA
```

TABLE 8-continued

Plasmid and mRNA construct sequences

3961 AGCTCGACCC CTTTCTTACA CCCTACACTA AAATCAACAG TAGGTGGATC AAGGACTTGA
4021 ATGTCAAGCC AAAGACTATA AAGACACTGG AAGAGAATCT TGGGATCACA ATACAAGATA
4081 TAGGCGTCGG CAAAGATTTT ATGTCAAAGA CGCCCAAGGC CATGGCCACT AAGGATAAGA
4141 TTGATAAGTG GGACCTTATT AAGCTCAAAA GCTTCTGTAC TGCCAAGGAG ACCACGATCA
4201 GAGTTAATAG GCAGCCCACT ACATGGGAAA AGATTTTCGC CACTTATTCA TCAGATAAGG
4261 GGTTGATAAG CAGAATATAT AACGAGCTGA AGCAGATCTA CAAGAAGAAA ACGAATAATC
4321 CCATCAAGAA GTGGGCAAAA GATATGAACA GGCATTTTAG CAAAGAGGAT ATCTACGCCG
4381 CGAAGAAGCA TATGAAGAAG TGTAGTTCAA GCTTGGCCAT TCGTGAGATG CAGATTAAGA
4441 CGACCATGCG ATACCACCTT ACCCCAGTGA GGATGGCAAT TATCAAGAAA TCTGGCAATA
4501 ATAGATGTTG GCGGGGCTGT GGCGAGATTG GCACCCTGCT CCATTGCTGG TGGGATTGCA
4561 AGCTGGTGCA GCCGCTTTGG AAATCAGTCT GGCGCTTTCT GAGGGACCTC GAGCTTGAGA
4621 TTCCCTTCGA TCCCGCAATT CCCTTGCTCG GAATCTATCC TAACGAATAC AAGAGCTGTT
4681 GTTACAAGGA TACGTGTACC CGGATGTTCA TCGCGGCCTT GTTTACGATA GCTAAGACGT
4741 GGAATCAGCC TAAGTGCCCC ACAATGATCG ATTGGATCAA GAAAATGTGG CATATTTATA
4801 CCATGGAGTA TTACGCAGCA ATTAAGAATG ACGAATTTAT TTCCTTCGTT GGGACCTGGA
4861 TGAAGCTGGA GACTATTATT CTGAGCAAGC TGTCTCAGGA GCAAAAGACA AAGCATAGAA
4921 TCTTCTCTCT CATTGGTGGT AACGACTACA AAGACGATGA CGACAAGTAA AGCGCTTCTA
4981 GAAGTTGTCT CCTCCTGCAC TGACTGACTG ATACAATCGA TTTCTGGATC CGCAGGCCTA
5041 ATCAACCTCT GGATTACAAA ATTTGTGAAA GATTGACTGG TATTCTTAAC TATGTTGCTC
5101 CTTTTACGCT ATGTGGATAC GCTGCTTTAA TGCCTTTGTA TCATGCTATT GCTTCCCGTA
5161 TGGCTTTCAT TTTCTCCTCC TTGTATAAAT CCTGGTTGCT GTCTCTTTAT GAGGAGTTGT
5221 GGCCCGTTGT CAGGCAACGT GGCGTGGTGT GCACTGTGTT TGCTGACGCA ACCCCCACTG
5281 GTTGGGGCAT TGCCACCACC TGTCAGCTCC TTTCCGGGAC TTTCGCTTTC CCCCTCCCTA
5341 TTGCCACGGC GGAACTCATC GCCGCCTGCC TTGCCCGCTG CTGGACAGGG GCTCGGCTGT
5401 TGGGCACTGA CAATTCCGTG GTGTTGTCGG GGAAGCTGAC GTCCTTTCCA TGGCTGCTCG
5461 CCTGTGTTGC CACCTGGATT CTGCGCGGGA CGTCCTTCTG CTACGTCCCT TCGGCCCTCA
5521 ATCCAGCGGA CCTTCCTTCC CGCGAACAAA CGACCCAACA CCCGTGCGTT TTATTCTGTC
5581 TTTTTATTGC CGATCCCCTC AGAAGAACTC GTCAAGAAGG CGATAGAAGG CGATGCGCTG
5641 CGAATCGGGA GCGGCGATAC CGTAAAGCAC GAGGAAGCGG TCAGCCCATT CGCCGCCAAG
5701 CTCTTCAGCA ATATCACGGG TAGCCAACGC TATGTCCTGA TAGCGGTCGG CCGCTTTACT
5761 TGTACAGCTC GTCCATGCCG AGAGTGATCC CGGCGGCGGT CACGAACTCC AGCAGGACCA
5821 TGTGATCGCG CTTCTCGTTG GGGTCTTTGC TCAGGGCGGA CTGGGTGCTC AGGTAGTGGT
5881 TGTCGGGCAG CAGCACGGGG CCGTCGCCGA TGGGGGTGTT CTGCTGGTAG TGGTCGGCCA
5941 GGTGAGTCCA GGAGATGTTT CAGCACTGTT GCCTTTAGTC TCGAGGCAAC TTAGACAACT
6001 GAGTATTGAT CTGAGCACAG CAGGGTGTGA GCTGTTTGAA GATACTGGGG TTGGGGGTGA
6061 AGAAACTGCA GAGGACTAAC TGGGCTGAGA CCCAGTGGCA ATGTTTTAGG GCCTAAGGAA
6121 TGCCTCTGAA AATCTAGATG GACAACTTTG ACTTTGAGAA AAGAGAGGTG GAAATGAGGA
6181 AAATGACTTT TCTTTATTAG ATTTCGGTAG AAAGAACTTT CATCTTTCCC CTATTTTTGT
6241 TATTCGTTTT AAAACATCTA TCTGGAGGCA GGACAAGTAT GGTCATTAAA AAGATGCAGG
6301 CAGAAGGCAT ATATTGGCTC AGTCAAAGTG GGGAACTTTG GTGGCCAAAC ATACATTGCT
6361 AAGGCTATTC CTATATCAGC TGGACACATA TAAAATGCTG CTAATGCTTC ATTACAAACT
6421 TATATCCTTT AATTCCAGAT GGGGGCAAAG TATGTCCAGG GGTGAGGAAC AATTGAAACA
6481 TTTGGGCTGG AGTAGATTTT GAAAGTCAGC TCTGTGTGTG TGTGTGTGTG TGTGTGTGTG
6541 AGAGCGTGTG TTTCTTTTAA CGTTTTCAGC CTACAGCATA CAGGGTTCAT GGTGGCAAGA
6601 AGATAACAAG ATTTAAATTA TGGCCAGTGA CTAGTGCTGC AAGAAGAACA ACTACCTGCA
6661 TTTAATGGGA AAGCAAAATC TCAGGCTTTG AGGGAAGTTA ACATAGGCTT GATTCTGGGT
6721 GGAAGCTGGG TGTGTAGTTA TCTGGAGGCC AGGCTGGAGC TCTCAGCTCA CTATGGGTTC
6781 ATCTTTATTG TCTCCTTTCA TCTCAACAGC TGCACGCTGC CGTCCTCGAT GTTGTGGCGG
6841 ATCTTGAAGT TCACCTTGAT GCCGTTCTTC TGCTTGTCGG CCATGATATA GACGTTGTGG
6901 CTGTTGTAGT TGTACTCCAG CTTGTGCCCC AGGATGTTGC CGTCCTCCTT GAAGTCGATG
6961 CCCTTCAGCT CGATGCGGTT CACCAGGGTG TCGCCCTCGA ACTTCACCTC GGCGCGGGTC
7021 TTGTAGTTGC CGTCGTCCTT GAAGAAGATG GTGCGCTCCT GGACGTAGCC TTCGGGCATG
7081 GCGGACTTGA AGAAGTCGTG CTGCTTCATG TGGTCGGGGT AGCGGCTGAA GCACTGCACG
7141 CCGTAGGTCA GGGTGGTCAC GAGGGTGGGC CAGGGCACGG GCAGCTTGCC GGTGGTGCAG
7201 ATGAACTTCA GGGTCAGCTT GCCGTAGGTG GCATCGCCCT CGCCCTCGCC GGACACGCTG
7261 AACTTGTGGC CGTTTACGTC GCCGTCCAGC TCGACCAGGA TGGGCACCAC CCCGGTGAAC
7321 AGCTCCTCGC CCTTGCTCAC CATGGTGGCG AATTCGAAGC TTGAGCACGA GATCTGAGTC
7381 CGGTAGGCCT AGCGGATCTG ACGGTTCACT AAACCAGCTC TGCTTATATA GACCTCCCAC
7441 CGTACACGCC TACCGCCCAT TTGCGTCAAT GGGGCGGAGT TGTTACGACA TTTTGGAAAG
7501 TCCCGTTGAT TTTGGTGCCA AAACAAACTC CCATTGACGT CAATGGGGTG GAGACTTGGA
7561 AATCCCCGTG AGTCAAACCG CTATCCACGC CCATTGATGT ACTGCCAAAA CCGCATCACC
7621 ATGGTAATAG CGATGACTAA TACGTAGATG TACTGCCAAG TAGGAAAGTC CCATAAGGTC
7681 ATGTACTGGG CATAATGCCA GGCGGGCCAT TTACCGTCAT TGACGTCAAT AGGGGGCGTA
7741 CTTGGCATAT GATACACTTG ATGTACTGCC AAGTGGGCAG TTTACCGTAA ATACTCCACC
7801 CATTGACGTC AATGGAAAGT CCCTATTGGC GTTACTATGG GAACATACGT CATTATTGAC
7861 GTCAATGGGC GGGGGTCGTT GGGCGGTCAG CCAGGCGGGC CATTTACCGT AAGTTATGTA
7921 ACGGGCCTGC TGCCGGCTCT GCGGCCTCTT CCGCGTCTTC GCCTTCGCCC TCAGACGAGT
7981 CGGATCTCCC TTTGGGCCGC CTCCCCGCCT GTCTAGCTTG ACTGACTGAG ATACAGCGTA
8041 CCTTCAGCTC ACAGACATGA TAAGATACAT TGATGAGTTT GGACAAACCA CAACTAGAAT
8101 GCAGTGAAAA AAATGCTTTA TTTGTGAAAT TTGTGATGCT ATTGCTTTAT TTGTAACCAT
8161 TATAAGCTGC AATAAACAAG TTAACAACAA CAATTGCATT CATTTTATGT TTCAGGTTCA
8221 GGGGGAGGTG TGGGAGGTTT TTTAAAGCAA GTAAAACCTC TACAAATGTG GTATTGGCCC
8281 ATCTCTATCG GTATCGTAGC ATAACCCCTT GGGGCCTCTA AACGGGTCTT GAGGGGTTTT
8341 TTGTGCCCCT CGGGCCGGAT TGCTATCTAC CGGCATTGGC GCAGAAAAAA ATGCCTGATG
8401 CGACGCTGCG CGTCTTATAC TCCCACATAT GCCAGATTCA GCAACGGATA CGGCTTCCCC
8461 AACTTGCCCA CTTCCATACG TGTCCTCCTT ACCAGAAATT TATCCTTAAG GTCGTCAGCT
8521 ATCCTGCAGG CGATCTCTCG ATTTCGATCA AGACATTCCT TTAATGGTCT TTTCTGGACA
8581 CCACTAGGGG TCAGAAGTAG TTCATCAAAC TTTCTTCCCT CCCTAATCTC ATTGGTTACC

TABLE 8-continued

Plasmid and mRNA construct sequences

8641 TTGGGCTATC GAAACTTAAT TAAGCGATCT GCATCTCAAT TAGTCAGCAA CCATAGTCCC
8701 GCCCCTAACT CCGCCCATCC CGCCCCTAAC TCCGCCCAGT TCCGCCCATT CTCCGCCCCA
8761 TCGCTGACTA ATTTTTTTTA TTTATGCAGA GGCCGAGGCC GCCTCGGCCT CTGAGCTATT
8821 CCAGAAGTAG TGAGGAGGCT TTTTTGGAGG CCTAGGCTTT TGCAAAGGAG GTAGCCAACA
8881 TGATTGAACA AGATGGATTG CACGCAGGTT CTCCCGCCGC TTGGGTGGAG AGGCTATTCG
8941 GCTATGACTG GGCACAACAG ACAATCGGCT GCTCTGATGC CGCCGTGTTC CGGCTGTCAG
9001 CGCAGGGGCG CCCGGTTCTT TTTGTCAAGA CCGACCTGTC CGGTGCCCTG AATGAACTCC
9061 AGGACGAGGC AGCGCGGCTA TCGTGGCTGG CCACGACGGG CGTTCCTTGC GCAGCTGTGC
9121 TCGACGTTGT CACTGAAGCG GGAAGGGACT GGCTGCTATT GGGCGAAGTG CCGGGGCAGG
9181 ATCTCCTGTC ATCTCACCTT GCTCCTGCCG AGAAAGTATC CATCATGGCT GATGCAATGC
9241 GGCGGCTGCA TACGCTTGAT CCGGCTACCT GCCCATTCGA CCACCAAGCG AAACATCGCA
9301 TCGAGCGAGC ACGTACTCGG ATGGAAGCCG GTCTTGTCGA TCAGGATGAT CTGGACGAAG
9361 AGCATCAGGG GCTCGCGCCA GCCGAACTGT TCGCCAGGCT CAAGGCGCGG ATGCCCGACG
9421 GCGAGGATCT CGTCGTGACC CACGGCGATG CCTGCTTGCC GAATATCATG GTGGAAAATG
9481 GCCGCTTTTC TGGATTCATC GACTGTGGCC GGCTGGGTGT GGCGGACCGC TATCAGGACA
9541 TAGCGTTGGC TACCCGTGAT ATTGCTGAAG AGCTTGGCGG CGAATGGGCT GACCGCTTCC
9601 TCGTGCTTTA CGGTATCGCC GCTCCCGATT CGCAGCGCAT CGCCTTCTAT CGCCTTCTTG
9661 ACGAGTTCTT CTAGTATGTA AGCCCTGTGC CTTCTAGTTG CCAGCCATCT GTTGTTTGCC
9721 CCTCCCCCGT GCCTTCCTTG ACCCTGGAAG GTGCCACTCC CACTGTCCTT TCCTAATAAA
9781 ATGAGGAAAT TGCATCGCAT TGTCTGAGTA GGTGTCATTC TATTCTGGGG GGTGGGGTGG
9841 GGCAGGACAG CAAGGGGGAG GATTGGGAAG ACAATAGCAG GCATGCTGGG GATGCGGTGG
9901 GCTCTATGGT TAATTAACCA GTCAAGTCAG CTACTTGGCG AGATCGACTT GTCTGGGTTT
9961 CGACTACGCT CAGAATTGCG TCAGTCAAGT TCGATCTGGT CCTTGCTATT GCACCCGTTC
10021 TCCGATTACG AGTTTCATTT AAATCATGTG AGCAAAAGGC CAGCAAAAGG CCAGGAACCG
10081 TAAAAAGGCC GCGTTGCTGG CGTTTTTCCA TAGGCTCCGC CCCCCTGACG AGCATCACAA
10141 AAATCGACGC TCAAGTCAGA GGTGGCGAAA CCCGACAGGA CTATAAAGAT ACCAGGCGTT
10201 TCCCCCTGGA AGCTCCCTCG TGCGCTCTCC TGTTCCGACC CTGCCGCTTA CCGGATACCT
10261 GTCCGCCTTT CTCCCTTCGG GAAGCGTGGC GCTTTCTCAT AGCTCACGCT GTAGGTATCT
10321 CAGTTCGGTG TAGGTCGTTC GCTCCAAGCT GGGCTGTGTG CACGAACCCC CCGTTCAGCC
10381 CGACCGCTGC GCCTTATCCG GTAACTATCG TCTTGAGTCC AACCCGGTAA GACACGACTT
10441 ATCGCCACTG GCAGCAGCCA CTGGTAACAG GATTAGCAGA GCGAGGTATG TAGGCGGTGC
10501 TACAGAGTTC TTGAAGTGGT GGCCTAACTA CGGCTACACT AGAAGAACAG TATTTGGTAT
10561 CTGCGCTCTG CTGAAGCCAG TTACCTTCGG AAAAAGAGTT GGTAGCTCTT GATCCGGCAA
10621 ACAAACCACC GCTGGTAGCG GTGGTTTTTT TGTTTGCAAG CAGCAGATTA CGCGCAGAAA
10681 AAAGGATCTC AAGAAGATCC TTTGATCTTT TCTACGGGGT CTGACGCTCA GTGGAACGAA
10741 AACTCACGTT AAGGGATTTT GGTCATGAGA TTATCAAAAA GGATCTTCAC CTAGATCCTT
10801 TTAAATTAAA AATGAAGTTT TAAATCAATC TAAAGTATAT ATGAGTAAAC TTGGTCTGAC
10861 AGTTACCAAT GCTTAATCAG TGAGGCACCT ATCTCAGCGA TCTGTCTATT TCGTTCATCC
10921 ATAGTTGCAT TTAAATTTCC GAACTCTCCA AGGCCCTCGT CGGAAAATCT TCAAACCTTT
10981 CGTCCGATCC ATCTTGCAGG CTACCTCTCG AACGAACTAT CGCAAGTCTC TTGGCCGGCC
11041 TTGCGCCTTG GCTATTGCTT GGCAGCGCCT ATCGCCAGGT ATTACTCCAA TCCCGAATAT
11101 CCGAGATCGG GATCACCCGA GAGAAGTTCA ACCTACATCC TCAATCCCGA TCTATCCGAT
11161 GATCCGAGGA ATATCGAAAT CGGGGCGCGC CTGGTGTACC GAGAACGATC CTCTCAGTGC
11221 GAGTCTCGAC GATCCATATC GTTGCTTGGC AGTCAGCCAG TCGGAATCCA GCTTGGGACC
11281 CAGGAAGTCC AATCGTCAGA TATTGTACTC AAGCCTGGTC ACGGCAGCGT ACCGATCTGT
11341 TTAAACCTAG ATATTGATAG TCTGATCGGT CAACGTATAA TCGAGTCCTA GCTTTTGCAA
11401 ACATCTATCA AGAGACAGGA TCAGCAGGAG GCTTTCGCAT GAGTATTCAA CATTTCCGTG
11461 TCGCCCTTAT TCCCTTTTTT GCGGCATTTT GCCTTCCTGT TTTTGCTCAC CCAGAAACGC
11521 TGGTGAAAGT AAAAGATGCT GAAGATCAGT TGGGTGCGCG AGTGGGTTAC ATCGAACTGG
11581 ATCTCAACAG CGGTAAGATC CTTGAGAGTT TTCGCCCCGA AGAACGCTTT CCAATGATGA
11641 GCACTTTTAA AGTTCTGCTA TGTGGCGCGG TATTATCCCG TATTGACGCC GGGCAAGAGC
11701 AACTCGGTCG CCGCATACAC TATTCTCAGA ATGACTTGGT TGAGTATTCA CCAGTCACAG
11761 AAAAGCATCT TACGGATGGC ATGACAGTAA GAGAATTATG CAGTGCTGCC ATAACCATGA
11821 GTGATAACAC TGCGGCCAAC TTACTTCTGA CAACGATTGG AGGACCGAAG GAGCTAACCG
11881 CTTTTTTGCA CAACATGGGG GATCATGTAA CTCGCCTTGA TCGTTGGGAA CCGGAGCTGA
11941 ATGAAGCCAT ACCAAACGAC GAGCGTGACA CCACGATGCC TGTAGCAATG GCAACAACCT
12001 TGCGTAAACT ATTAACTGGC GAACTACTTA CTCTAGCTTC CCGGCAACAG TTGATAGACT
12061 GGATGGAGGC GGATAAAGTT GCAGGACCAC TTCTGCGCTC GGCCCTTCCG GCTGGCTGGT
12121 TTATTGCTGA TAAATCTGGA GCCGGTGAGC GTGGGTCTCG CGGTATCATT GCAGCACTGG
12181 GGCCAGATGG TAAGCCCTCC CGTATCGTAG TTATCTACAC GACGGGGAGT CAGGCAACTA
12241 TGGATGAACG AAATAGACAG ATCGCTGAGA TAGGTGCCTC ACTGATTAAG CATTGGTAAC
12301 CGATTCTAGG TGCATTGGCG CAGAAAAAAA TGCCTGATGC GACGCTGCGC GTCTTATACT
12361 CCCACATATG CCAGATTCAG CAACGGATAC GGCTTCCCCA ACTTGCCCAC TTCCATACGT
12421 GTCCTCCTTA CCAGAAATTT ATCCTTAAGA TCGTTTAAAC TCGACTCTGG CTCTATCGAA
12481 TCTCCGTCGT TTCGAGCTTA CGCGAACAGC CGTGGCGCTC ATTTGCTCGT CGGGCATCGA
12541 ATCTCGTCAG CTATCGTCAG CTTACCTTTT TGGCAGCGAT CGCGGCTCCC GACATCTTGG
12601 ACCATTAGCT CCACAGGTAT CTTCTTCCCT CTAGTGGTCA TAACAGCAGC TTCAGCTACC
12661 TCTCAATTCA AAAAACCCCT CAAGACCCGT TTAGAGGCCC CAAGGGGTTA TGCTATCAAT
12721 CGTTGCGTTA CACACACAAA AAACCAACAC ACATCCATCT TCGATGGATA GCGATTTTAT
12781 TATCTAACTG CTGATCGAGT GTAGCCAGAT CTAGTAATCA ATTACGGGGT CATTAGTTCA
12841 TAGCCCATAT ATGGAGTTCC GCGTTACATA ACTTACGGTA AATGGCCCGC CTGGCTGACC
12901 GCCCAACGAC CCCCGCCCAT TGACGTCAAT AATGACGTAT GTTCCCATAG TAACGCCAAT
12961 AGGGACTTTC CATTGACGTC AATGGGTGGA GTATTTACGG TAAACTGCCC ACTTGGCAGT
13021 ACATCAAGTG TATCATATGC CAAGTACGCC CCCTATTGAC GTCAATGACG GTAAATGGCC
13081 CGCCTGGCAT TATGCCCAGT ACATGACCTT ATGGGACTTT CCTACTTGGC AGTACATCTA
13141 CGTATTAGTC ATCGCTATTA CCATGCTGAT GCGGTTTTGG CAGTACATCA ATGGGCGTGG
13201 ATAGCGGTTT GACTCACGGG GATTTCCAAG TCTCCACCCC ATTGACGTCA ATGGGAGTTT
13261 GTTTTGGCAC CAAAATCAAC GGGACTTTCC AAAATGTCGT AACAACTCCG CCCCATTGAC

TABLE 8-continued

Plasmid and mRNA construct sequences

13321 GCAAATGGGC GGTAGGCGTG TACGGTGGGA GGTCTATATA AGCAGAGCTG GTTTAGTGAA
13381 CCGTCAGATC AGATCTTTGT CGATCCTACC ATCCACTCGA CACACCCGCC AGCGGCCGC
(SEQ ID NO: 46)

LINE-1 plasmid ORF 1- P2A-ORF2 GFP (SEQ ID NO: 47)
1 TAATACGACT CACTATAGGG AGAAGTACTG CCACCATGGG CAAGAAGCAA AATCGCAAGA
61 CGGGGAATTC CAAGACACAA TCCGCTAGCC CACCACCTAA AGAGCGTTCT AGCTCCCCTG
121 CTACTGAGCA GTCCTGGATG GAAAACGACT TCGATGAACT CCGGGAAGAG GGATTTAGGC
181 GATCCAACTA TTCAGAACTC CGCGAAGATA TCCAGACAAA GGGGAAGGAA GTCGAGAATT
241 TCGAGAAGAA CCTCGAGGAG TGCATCACCC GTATCACAAA CACTGAGAAA TGTCTCAAAG
301 AACTCATGGA ACTTAAGACA AAAGCCAGGG AGCTTCGAGA GGAGTGTCGG AGTCTGAGAT
361 CCAGGTGTGA CCAGCTCGAG GAGCGCGTGA GCGCGATGGA AGACGAGATG AACGAGATGA
421 AAAGAGAGGG CAAATTCAGG GAGAAGCGCA TTAAGAGGAA CGAACAGAGT CTGCAGGAGA
481 TTTGGGATTA CGTCAAGAGG CCTAACCTGC GGTTGATCGG CGTCCCCGAG AGCGACGTAG
541 AAAACGGGAC TAAACTGGAG AATACACTTC AAGACATCAT TCAAGAAAAT TTTCCAAACC
601 TGGCTCGGCA AGCTAATGTG CAAATCCAAG AGATCCAACG CACACCCCAG CGGTATAGCT
661 CTCGGCGTGC CACCCCTAGG CATATTATCG TGCGCTTTAC TAAGGTGGAG ATGAAAGAGA
721 AGATGCTGCG AGCCGCTCGG GAAAAGGGAA GGGTGACTTT GAAGGGCAAA CCTATTCGGC
781 TGACGGTTGA CCTTAGCGCC GAGACACTCC AGGCACGCCG GGAATGGGGC CCCATCTTTA
841 ATATCCTGAA GGAGAAGAAC TTCCAGCCAC GAATCTCTTA CCCTGCAAAG TTGAGTTTTA
901 TCTCCGAGGG TGAGATTAAG TATTTCATCG ATAAACAGAT GCTGCGAGAC TTCGTGACAA
961 CTCGCCCAGC TCTCAAGGAA CTGCTCAAAG AGGCTCTTAA TATGGAGCGC AATAATAGAT
1021 ATCAACCCTT GCAGAACCAC GCAAAGATGG GAAGCGGAGC TACTAACTTC AGCCTGCTGA
1081 AGCAGGCTGG AGACGTGGAG GAGAACCCTG GACCTATGAC CGGCTCTAAC TCACATATCA
1141 CCATCCTTAC ACTTAACATT AACGGCCTCA ACTCAGCTAT CAAGCGCCAT CGGCTGGCCA
1201 GCTGGATCAA ATCACAGGAT CCAAGCGTTT GTTGCATCCA AGAGACCCAC CTGACCTGTA
1261 GAGATACTCA CCGCCTCAAG ATCAAGGGAT GGCGAAAGAT TTATCAGGCG AACGGTAAGC
1321 AGAAGAAAGC CGGAGTCGCA ATTCTGGTCT CAGACAAGAC GGATTTCAAG CCCACCAAAA
1381 TTAAGCGTGA TAAGGAAGGT CACTATATTA TGGTGAAAGG CAGCATACAG CAGGAAGAAC
1441 TTACCATATT GAACATCTAC GCGCCAAACA CCGGCGCACC TCGCTTTATC AAACAGGTCC
1501 TGTCCGATCT GCAGCGAGAT CTGGATTCTC ATACGTTGAT TATGGGTGAT TTCAATACAC
1561 CATTGAGCAC CCTGGATCGC AGCACCAGGC AAAAGGTAAA TAAAGACACG CAAGAGCTCA
1621 ATAGCGCACT GCATCAGGCA GATCTCATTG ATATTTATCG CACTCTTCAT CCTAAGAGTA
1681 CCGAGTACAC ATTCTTCAGC GCCCCACATC ATACATACTC AAAGATCGAT CATATCGTCG
1741 GCTCAAAGGC TCTGCTGTCA AAGTGCAAGC GCACAGAGAT AATTACAAAT TACCTGTCAG
1801 ATCATAGCGC GATCAAGCTC GAGCTGAGAA TCAAGAACCT GACCCAGAGC CGGAGTACCA
1861 CTTGGAAGCT TAATAACCTG CTGCTCAACG ATTATTGGGT CCACAATGAG ATGAAGGCAG
1921 AGATTAAAAT GTTCTTCGAA ACAAATGAGA ATAAGGATAC TACCTATCAA AACCTTTGGG
1981 ATGCCTTTAA GGCCGTCTGC AGAGGCAAGT TCATCGCCCT CAACGCCTAT AAAAGAAAAC
2041 AAGAGAGATC TAAGATCGAT ACTCTCACCT CTCAGCTGAA GGAGTTGGAG AAACAGGAAC
2101 AGACCCACTC CAAGGCGTCA AGACGGCAGG AGATCACAAA GATTCGCGCC GAGTTGAAAG
2161 AGATCGAAAC CCAAAAGACT CTTCAGAAAA TTAACGAGTC TCGTAGTTGG TTCTTCGAGC
2221 GGATTAATAA GATAGACAGA CCTCTGGCAC GACTGATTAA GAAGAAGCGC GAAAAGAACC
2281 AGATTGATAC CATCAAGAAC GACAAGGGCG ACATCACTAC TGACCCGACC GAGATCCAGA
2341 CCACTATTCG GGAGTATTAT AAGCATTTGT ATGCTAACAA GCTTGAGAAC CTGGAAGAGA
2401 TGGACACTTT TCTGGATACC TATACTCTGC CACGGCTTAA TCAAGAGGAA GTCGAGTCCC
2461 TCAACCGCCC AATTACAGGA AGCGAGATTG TGGCCATAAT TAACTCCCTG CCGACAAAGA
2521 AATCTCCTGG TCCGGACGGG TTTACAGCTG AGTTTTATCA ACGGTATATG GAAGAGCTTG
2581 TACCGTTTCT GCTCAAGCTC TTTCAGTCTA TAGAAAAGGA AGGCATCTTG CCCAATTCCT
2641 TCTACGAAGC TTCTATAATA CTTATTCCCA AACCAGGACG CGATACCACA AAGAAGGAAA
2701 ACTTCCGGCC CATTAGTCTC ATGAATATCG ACGCTAAAAT ATTGAACAAG ATTCTCGCCA
2761 ACAGAATCCA ACAACATATT AAGAAATTGA TACATCACGA CCAGGTGGGG TTTATACCTG
2821 GCATGCAGGG CTGGTTTAAC ATCCGGAAGA GTATTAACGT CATTCAACAC ATTAATAGAG
2881 CTAAGGATAA GAATCATATG ATCATCTCTA TAGACGCGGA AAAGGCATTC GATAAGATTC
2941 AGCAGCCATT TATGCTCAAG ACTCTGAACA AACTCGGCAT CGACGGAACA TATTTTAAGA
3001 TTATTCGCGC AATTTACGAT AAGCCGACTG CTAACATTAT CCTTAACGGC CAAAAGCTCG
3061 AGGCCTTTCC GCTCAAGACT GGAACCCGCC AAGGCTGTCC CCTCTCCCCG CTTTTGTTTA
3121 ATATTGTACT CGAGGTGCTG GCTAGGGCTA TTCGTCAAGA GAAAGAGATT AAAGGGATAC
3181 AGCTCGGGAA GGAAGAGGTC AAGCTTTCCT TGTTCGCCGA TGATATGATT GTGTACCTGG
3241 AGAATCCTAT TGTGTCTGCT CAGAACCTTC TTAAACTTAT TTCTAACTTT AGCAAGGTCA
3301 GCGGCTATAA GATTAACGTC CAGAAATCTC AGGCCTTTCT GTACACAAAT AATCGACAGA
3361 CCGAATCCCA GATAATGGGT GAGCTTCCGT TTGTCATAGC CAGCAAAAGG ATAAAGTATC
3421 TCGGAATCCA GCTGACACGA GACGTTAAAG ATTTGTTTAA GGAAAATTAC AAGCCTCTCC
3481 TGAAAGAGAT TAAGGAAGAT ACTAATAAGT GGAAGAATAT CCCCTGTTCA TGGGTTGGCA
3541 GAATCAACAT AGTGAAGATG GCAATACTTC CTAAAGTGAT ATATCGCTTT AACGCCATCC
3601 CAATTAAACT GCCTATGACC TTCTTTACGG AGCTCGAGAA AACAACCCTT AAATTTATAT
3661 GGAATCAAAA GAGAGCAAGA ATAGCGAAGT CCATCTTGAG CCAGAAGAAT AAGGCCGGTG
3721 GGATTACTTT GCCTGATTTT AAGTTGTATT ATAAAGCCAC AGTAACTAAG ACAGCCTGGT
3781 ATTGGTATCA GAATAGAGAC ATCGACCAGT GGAATCGGAC CGAACCATCA GAGATAATGC
3841 CCCACATCTA TAATTACCTT ATATTCGATA AGCCAGAAAA GAATAAACAG TGGGGCAAAG
3901 ACAGCCTCTT CAACAAGTGG TGTTGGGAGA ATTGGCTGGC CATATGCCGG AAACTCAAGC
3961 TCGACCCCTT TCTTACACCC TACACTAAAA TCAACAGTAG GTGGATCAAG GACTTGAATG
4021 TCAAGCCAAA GACTATAAAG ACACTGGAAG AGAATCTTGG GATCACAATA CAAGATATAG
4081 GCGTCGGCAA AGATTTTATG TCAAAGACGC CCAAGGCCAT GGCCACTAAG GATAAGATTG
4141 ATAAGTGGGA CCTTATTAAG CTCAAAAGCT TCTGTACTGC CAAGGAGACC ACGATCAGAG
4201 TTAATAGGCA GCCCACTACA TGGGAAAAGA TTTTCGCCAC TTATTCATCA GATAAGGGGT
4261 TGATAAGCAG AATATATAAC GAGCTGAAGC AGATCTACAA GAAGAAAACG AATAATCCCA
4321 TCAAGAAGTG GGCAAAAGAT ATGAACAGGC ATTTTAGCAA AGAGGATATC TACGCCGCGA TABLE 8-continued

| Plasmid and mRNA construct sequences |
|---|
| 4381 AGAAGCATAT GAAGAAGTGT AGTTCAAGCT TGGCCATTCG TGAGATGCAG ATTAAGACGA |
| 4441 CCATGCGATA CCACCTTACC CCAGTGAGGA TGGCAATTAT CAAGAAATCT GGCAATAATA |
| 4501 GATGTTGGCG GGGCTGTGGC GAGATTGGCA CCCTGCTCCA TTGCTGGTGG GATTGCAAGC |
| 4561 TGGTGCAGCC GCTTTGGAAA TCAGTCTGGC GCTTTCTGAG GGACCTCGAG CTTGAGATTC |
| 4621 CCTTCGATCC CGCAATTCCC TTGCTCGGAA TCTATCCTAA CGAATACAAG AGCTGTTGTT |
| 4681 ACAAGGATAC GTGTACCCGG ATGTTCATCG CGGCCTTGTT TACGATAGCT AAGACGTGGA |
| 4741 ATCAGCCTAA GTGCCCCACA ATGATCGATT GGATCAAGAA AATGTGGCAT ATTTATACCA |
| 4801 TGGAGTATTA CGCAGCAATT AAGAATGACG AATTTATTTC CTTCGTTGGG ACCTGGATGA |
| 4861 AGCTGGAGAC TATTATTCTG AGCAAGCTGT CTCAGGAGCA AAAGACAAAG CATAGAATCT |
| 4921 TCTCTCTCAT TGGTGGTAAC GACTACAAAG ACGATGACGA CAAGTAAAGC GCTTCTAGAA |
| 4981 GTTGTCTCCT CCTGCACTGA CTGACTGATA CAATCGATTT CTGGATCCGC AGGCCTAATC |
| 5041 AACCTCTGGA TTACAAAATT TGTGAAAGAT TGACTGGTAT TCTTAACTAT GTTGCTCCTT |
| 5101 TTACGCTATG TGGATACGCT GCTTTAATGC CTTTGTATCA TGCTATTGCT TCCCGTATGG |
| 5161 CTTTCATTTT CTCCTCCTTG TATAAATCCT GGTTGCTGTC TCTTTATGAG GAGTTGTGGC |
| 5221 CCGTTGTCAG GCAACGTGGC GTGGTGTGCA CTGTGTTTGC TGACGCAACC CCCACTGGTT |
| 5281 GGGGCATTGC CACCACCTGT CAGCTCCTTT CCGGGACTTT CGCTTTCCCC CTCCCTATTG |
| 5341 CCACGGCGGA ACTCATCGCC GCCTGCCTTG CCCGCTGCTG GACAGGGGCT CGGCTGTTGG |
| 5401 GCACTGACAA TTCCGTGGTG TTGTCGGGGA AGCTGACGTC CTTTCCATGG CTGCTCGCCT |
| 5461 GTGTTGCCAC CTGGATTCTG CGCGGGACGT CCTTCTGCTA CGTCCCTTCG GCCCTCAATC |
| 5521 CAGCGGACCT TCCTTCCCGC GAACAAACGA CCCAACACCC GTGCGTTTTA TTCTGTCTTT |
| 5581 TTATTGCCGA TCCCCTCAGA AGAACTCGTC AAGAAGGCGA TAGAAGGCGA TGCGCTGCGA |
| 5641 ATCGGGAGCG GCGATACCGT AAAGCACGAG GAAGCGGTCA GCCCATTCGC CGCCAAGCTC |
| 5701 TTCAGCAATA TCACGGGTAG CCAACGCTAT GTCCTGATAG CGGTCGGCCG CTTTACTTGT |
| 5761 ACAGCTCGTC CATGCCGAGA GTGATCCCGG CGGCGGTCAC GAACTCCAGC AGGACCATGT |
| 5821 GATCGCGCTT CTCGTTGGGG TCTTTGCTCA GGGCGGACTG GGTGCTCAGG TAGTGGTTGT |
| 5881 CGGGCAGCAG CACGGGGCCG TCGCCGATGG GGGTGTTCTG CTGGTAGTGG TCGGCCAGGT |
| 5941 GAGTCCAGGA GATGTTTCAG CACTGTTGCC TTTAGTCTCG AGGCAACTTA GACAACTGAG |
| 6001 TATTGATCTG AGCACAGCAG GGTGTGAGCT GTTTGAAGAT ACTGGGGTTG GGGGTGAAGA |
| 6061 AACTGCAGAG GACTAACTGG GCTGAGACCC AGTGGCAATG TTTTAGGGCC TAAGGAATGC |
| 6121 CTCTGAAAAT CTAGATGGAC AACTTTGACT TTGAGAAAAG AGAGGTGGAA ATGAGGAAAA |
| 6181 TGACTTTTCT TTATTAGATT TCGGTAGAAA GAACTTTCAT CTTTCCCCTA TTTTTGTTAT |
| 6241 TCGTTTTAAA ACATCTATCT GGAGGCAGGA CAAGTATGGT CATTAAAAAG ATGCAGGCAG |
| 6301 AAGGCATATA TTGGCTCAGT CAAAGTGGGG AACTTTGGTG GCCAAACATA CATTGCTAAG |
| 6361 GCTATTCCTA TATCAGCTGG ACACATATAA AATGCTGCTA ATGCTTCATT ACAAACTTAT |
| 6421 ATCCTTTAAT TCCAGATGGG GGCAAAGTAT GTCCAGGGGT GAGGAACAAT TGAAACATTT |
| 6481 GGGCTGGAGT AGATTTTGAA AGTCAGCTCT GTGTGTGTGT GTGTGTGTGT GTGTGTGAGA |
| 6541 GCGTGTGTTT CTTTTAACGT TTTCAGCCTA CAGCATACAG GGTTCATGGT GGCAAGAAGA |
| 6601 TAACAAGATT TAAATTATGG CCAGTGACTA GTGCTGCAAG AAGAACAACT ACCTGCATTT |
| 6661 AATGGGAAAG CAAAATCTCA GGCTTTGAGG GAAGTTAACA TAGGCTTGAT TCTGGGTGGA |
| 6721 AGCTGGGTGT GTAGTTATCT GGAGGCCAGG CTGGAGCTCT CAGCTCACTA TGGGTTCATC |
| 6781 TTTATTGTCT CCTTTCATCT CAACAGCTGC ACGCTGCCGT CCTCGATGTT GTGGCGGATC |
| 6841 TTGAAGTTCA CCTTGATGCC GTTCTTCTGC TTGTCGGCCA TGATATAGAC GTTGTGGCTG |
| 6901 TTGTAGTTGT ACTCCAGCTT GTGCCCCAGG ATGTTGCCGT CCTCCTTGAA GTCGATGCCC |
| 6961 TTCAGCTCGA TGCGGTTCAC CAGGGTGTCG CCCTCGAACT TCACCTCGGC GCGGGTCTTG |
| 7021 TAGTTGCCGT CGTCCTTGAA GAAGATGGTG CGCTCCTGGA CGTAGCCTTC GGGCATGGCG |
| 7081 GACTTGAAGA AGTCGTGCTG CTTCATGTGG TCGGGGTAGC GGCTGAAGCA CTGCACGCCG |
| 7141 TAGGTCAGGG TGGTCACGAG GGTGGGCCAG GGCACGGGCA GCTTGCCGGT GGTGCAGATG |
| 7201 AACTTCAGGG TCAGCTTGCC GTAGGTGGCA TCGCCCTCGC CCTCGCCGGA CACGCTGAAC |
| 7261 TTGTGGCCGT TTACGTCGCC GTCCAGCTCG ACCAGGATGG GCACCACCCC GGTGAACAGC |
| 7321 TCCTCGCCCT TGCTCACCAT GGTGGCGAAT TCGAAGCTTG AGCACGAGAT CTGAGTCCGG |
| 7381 TAGGCCTAGC GGATCTGACG GTTCACTAAA CCAGCTCTGC TTATATAGAC CTCCCACCGT |
| 7441 ACACGCCTAC CGCCCATTTG CGTCAATGGG GCGGAGTTGT TACGACATTT TGGAAAGTCC |
| 7501 CGTTGATTTT GGTGCCAAAA CAAACTCCCA TTGACGTCAA TGGGGTGGAG ACTTGGAAAT |
| 7561 CCCCGTGAGT CAAACCGCTA TCCACGCCCA TTGATGTACT GCCAAAACCG CATCACCATG |
| 7621 GTAATAGCGA TGACTAATAC GTAGATGTAC TGCCAAGTAG GAAAGTCCCA TAAGGTCATG |
| 7681 TACTGGGCAT AATGCCAGGC GGGCCATTTA CCGTCATTGA CGTCAATAGG GGGCGTACTT |
| 7741 GGCATATGAT ACACTTGATG TACTGCCAAG TGGGCAGTTT ACCGTAAATA CTCCACCCAT |
| 7801 TGACGTCAAT GGAAAGTCCC TATTGGCGTT ACTATGGGAA CATACGTCAT TATTGACGTC |
| 7861 AATGGGCGGG GGTCGTTGGG CGGTCAGCCA GGCGGGCCAT TTACCGTAAG TTATGTAACG |
| 7921 GGCCTGCTGC CGGCTCTGCG GCCTCTTCCG CGTCTTCGCC TTCGCCCTCA GACGAGTCGG |
| 7981 ATCTCCCTTT GGGCCGCCTC CCCGCCTGTC TAGCTTGACT GACTGAGATA CAGCGTACCT |
| 8041 TCAGCTCACA GACATGATAA GATACATTGA TGAGTTTGGA CAAACCACAA CTAGAATGCA |
| 8101 GTGAAAAAAA TGCTTTATTT GTGAAATTTG TGATGCTATT GCTTTATTTG TAACCATTAT |
| 8161 AAGCTGCAAT AAACAAGTTA ACAACAACAA TTGCATTCAT TTTATGTTTC AGGTTCAGGG |
| 8221 GGAGGTGTGG GAGGTTTTTT AAAGCAAGTA AAACCTCTAC AAATGTGGTA TTGGCCCATC |
| 8281 TCTATCGGTA TCGTAGCATA ACCCCTTGGG GCCTCTAAAC GGGTCTTGAG GGGTTTTTTG |
| 8341 TGCCCCTCGG GCCGGATTGC TATCTACCGG CATTGGCGCA GAAAAAAATG CCTGATGCGA |
| 8401 CGCTGCGCGT CTTATACTCC CACATATGCC AGATTCAGCA ACGGATACGG CTTCCCCAAC |
| 8461 TTGCCCACTT CCATACGTGT CCTCCTTACC AGAAATTTAT CCTTAAGGTC GTCAGCTATC |
| 8521 CTGCAGGCGA TCTCTCGATT TCGATCAAGA CATTCCTTTA ATGGTCTTTT CTGGACACCA |
| 8581 CTAGGGGTCA GAAGTAGTTC ATCAAACTTT CTTCCCTCCC TAATCTCATT GGTTACCTTG |
| 8641 GGCTATCGAA ACTTAATTAA GCGATCTGCA TCTCAATTAG TCAGCAACCA TAGTCCCGCC |
| 8701 CCTAACTCCG CCCATCCCGC CCCTAACTCC GCCCAGTTCC GCCCATTCTC CGCCCCATCG |
| 8761 CTGACTAATT TTTTTTATTT ATGCAGAGGC CGAGGCCGCC TCGGCCTCTG AGCTATTCCA |
| 8821 GAAGTAGTGA GGAGGCTTTT TTGGAGGCCT AGGCTTTTGC AAAAGGAGGTA GCCAACATGA |
| 8881 TTGAACAAGA TGGATTGCAC GCAGGTTCTC CCGCCGCTTG GGTGGAGAGG CTATTCGGCT |
| 8941 ATGACTGGGC ACAACAGACA ATCGGCTGCT CTGATGCCGC CGTGTTCCGG CTGTCAGCGC |
| 9001 AGGGGCGCCC GGTTCTTTTT GTCAAGACCG ACCTGTCCGG TGCCCTGAAT GAACTCCAGG |

TABLE 8-continued

| Plasmid and mRNA construct sequences |
|---|
| 9061 ACGAGGCAGC GCGGCTATCG TGGCTGGCCA CGACGGGCGT TCCTTGCGCA GCTGTGCTCG |
| 9121 ACGTTGTCAC TGAAGCGGGA AGGGACTGGC TGCTATTGGG CGAAGTGCCG GGGCAGGATC |
| 9181 TCCTGTCATC TCACCTTGCT CCTGCCGAGA AAGTATCCAT CATGGCTGAT GCAATGCGGC |
| 9241 GGCTGCATAC GCTTGATCCG GCTACCTGCC CATTCGACCA CCAAGCGAAA CATCGCATCG |
| 9301 AGCGAGCACG TACTCGGATG GAAGCCGGTC TTGTCGATCA GGATGATCTG GACGAAGAGC |
| 9361 ATCAGGGGCT CGCGCCAGCC GAACTGTTCG CCAGGCTCAA GGCGCGGATG CCCGACGGCG |
| 9421 AGGATCTCGT CGTGACCCAC GGCGATGCCT GCTTGCCGAA TATCATGGTG GAAAATGGCC |
| 9481 GCTTTTCTGG ATTCATCGAC TGTGGCCGGC TGGGTGTGGC GGACCGCTAT CAGGACATAG |
| 9541 CGTTGGCTAC CCGTGATATT GCTGAAGAGC TTGGCGGCGA ATGGGCTGAC CGCTTCCTCG |
| 9601 TGCTTTACGG TATCGCCGCT CCCGATTCGC AGCGCATCGC CTTCTATCGC CTTCTTGACG |
| 9661 AGTTCTTCTA GTATGTAAGC CCTGTGCCTT CTAGTTGCCA GCCATCTGTT GTTTGCCCCT |
| 9721 CCCCCGTGCC TTCCTTGACC CTGGAAGGTG CCACTCCCAC TGTCCTTTCC TAATAAAATG |
| 9781 AGGAAATTGC ATCGCATTGT CTGAGTAGGT GTCATTCTAT TCTGGGGGGT GGGGTGGGGC |
| 9841 AGGACAGCAA GGGGGAGGAT TGGGAAGACA ATAGCAGGCA TGCTGGGGAT GCGGTGGGCT |
| 9901 CTATGGTTAA TTAACCAGTC AAGTCAGCTA CTTGGCGAGA TCGACTTGTC TGGGTTTCGA |
| 9961 CTACGCTCAG AATTGCGTCA GTCAAGTTCG ATCTGGTCCT TGCTATTGCA CCCGTTCTCC |
| 10021 GATTACGAGT TTCATTTAAA TCATGTGAGC AAAAGGCCAG CAAAAGGCCA GGAACCGTAA |
| 10081 AAAGGCCGCG TTGCTGGCGT TTTTCCATAG GCTCCGCCCC CCTGACGAGC ATCACAAAAA |
| 10141 TCGACGCTCA AGTCAGAGGT GGCGAAACCC GACAGGACTA TAAAGATACC AGGCGTTTCC |
| 10201 CCCTGGAAGC TCCCTCGTGC GCTCTCCTGT TCCGACCCTG CCGCTTACCG GATACCTGTC |
| 10261 CGCCTTTCTC CCTTCGGGAA GCGTGGCGCT TTCTCATAGC TCACGCTGTA GGTATCTCAG |
| 10321 TTCGGTGTAG GTCGTTCGCT CCAAGCTGGG CTGTGTGCAC GAACCCCCCG TTCAGCCCGA |
| 10381 CCGCTGCGCC TTATCCGGTA ACTATCGTCT TGAGTCCAAC CCGGTAAGAC ACGACTTATC |
| 10441 GCCACTGGCA GCAGCCACTG GTAACAGGAT TAGCAGAGCG AGGTATGTAG GCGGTGCTAC |
| 10501 AGAGTTCTTG AAGTGGTGGC CTAACTACGG CTACACTAGA AGAACAGTAT TTGGTATCTG |
| 10561 CGCTCTGCTG AAGCCAGTTA CCTTCGGAAA AAGAGTTGGT AGCTCTTGAT CCGGCAAACA |
| 10621 AACCACCGCT GGTAGCGGTG GTTTTTTTGT TTGCAAGCAG CAGATTACGC GCAGAAAAAA |
| 10681 AGGATCTCAA GAAGATCCTT TGATCTTTTC TACGGGGTCT GACGCTCAGT GGAACGAAAA |
| 10741 CTCACGTTAA GGGATTTTGG TCATGAGATT ATCAAAAAGG ATCTTCACCT AGATCCTTTT |
| 10801 AAATTAAAAA TGAAGTTTTA AATCAATCTA AAGTATATAT GAGTAAACTT GGTCTGACAG |
| 10861 TTACCAATGC TTAATCAGTG AGGCACCTAT CTCAGCGATC TGTCTATTTC GTTCATCCAT |
| 10921 AGTTGCATTT AAATTTCCGA ACTCTCCAAG GCCCTCGTCG GAAAATCTTC AAACCTTTCG |
| 10981 TCCGATCCAT CTTGCAGGCT ACCTCTCGAA CGAACTATCG CAAGTCTCTT GGCCGGCCTT |
| 11041 GCGCCTTGGC TATTGCTTGG CAGCGCCTAT CGCCAGGTAT TACTCCAATC CCGAATATCC |
| 11101 GAGATCGGGA TCACCCGAGA GAAGTTCAAC CTACATCCTC AATCCCGATC TATCCGAGAT |
| 11161 CCGAGGAATA TCGAAATCGG GGCGCGCCTG GTGTACCGAG AACGATCCTC TCAGTGCGAG |
| 11221 TCTCGACGAT CCATATCGTT GCTTGGCAGT CAGCCAGTCG GAATCCAGCT TGGGACCCAG |
| 11281 GAAGTCCAAT CGTCAGATAT TGTACTCAAG CCTGGTCACG GCAGCGTACC GATCTGTTTA |
| 11341 AACCTAGATA TTGATAGTCT GATCGGTCAA CGTATAATCG AGTCCTAGCT TTTGCAAACA |
| 11401 TCTATCAAGA GACAGGATCA GCAGGAGGCT TTCGCATGAG TATTCAACAT TTCCGTGTCG |
| 11461 CCCTTATTCC CTTTTTTGCG GCATTTTGCC TTCCTGTTTT TGCTCACCCA GAAACGCTGG |
| 11521 TGAAAGTAAA AGATGCTGAA GATCAGTTGG GTGCGCGAGT GGGTTACATC GAACTGGATC |
| 11581 TCAACAGCGG TAAGATCCTT GAGAGTTTTC GCCCCGAAGA ACGCTTTCCA ATGATGAGCA |
| 11641 CTTTTAAAGT TCTGCTATGT GGCGCGGTAT TATCCCGTAT TGACGCCGGG CAAGAGCAAC |
| 11701 TCGGTCGCCG CATACACTAT TCTCAGAATG ACTTGGTTGA GTATTCACCA GTCACAGAAA |
| 11761 AGCATCTTAC GGATGGCATG ACAGTAAGAG AATTATGCAG TGCTGCCATA ACCATGAGTG |
| 11821 ATAACACTGC GGCCAACTTA CTTCTGACAA CGATTGGAGG ACCGAAGGAG CTAACCGCTT |
| 11881 TTTTGCACAA CATGGGGGAT CATGTAACTC GCCTTGATCG TTGGGAACCG GAGCTGAATG |
| 11941 AAGCCATACC AAACGACGAG CGTGACACCA CGATGCCTGT AGCAATGGCA ACAACCTTGC |
| 12001 GTAAACTATT AACTGGCGAA CTACTTACTC TAGCTTCCCG GCAACAGTTG ATAGACTGGA |
| 12061 TGGAGGCGGA TAAAGTTGCA GGACCACTTC TGCGCTCGGC CCTTCCGGCT GGCTGGTTTA |
| 12121 TTGCTGATAA ATCTGGAGCC GGTGAGCGTG GGTCTCGCGG TATCATTGCA GCACTGGGGC |
| 12181 CAGATGGTAA GCCCTCCCGT ATCGTAGTTA TCTACACGAC GGGGAGTCAG GCAACTATGG |
| 12241 ATGAACGAAA TAGACAGATC GCTGAGATAG GTGCCTCACT GATTAAGCAT TGGTAACCGA |
| 12301 TTCTAGGTGC ATTGGCGCAG AAAAAAATGC CTGATGCGAC GCTGCGCGTC TTATACTCCC |
| 12361 ACATATGCCA GATTCAGCAA CGGATACGGC TTCCCCAACT TGCCCACTTC CATACGTGTC |
| 12421 CTCCTTACCA GAAATTTATC CTTAAGATCG TTTAAACTCG ACTCTGGCTC TATCGAATCT |
| 12481 CCGTCGTTTC GAGCTTACGC GAACAGCCGT GGCGCTCATT TGCTCGTCGG GCATCGAATC |
| 12541 TCGTCAGCTA TCGTCAGCTT ACCTTTTTGG CAGCGATCGC GGCTCCCGAC ATCTTGGACC |
| 12601 ATTAGCTCCA CAGGTATCTT CTTCCCTCTA GTGGTCATAA CAGCAGCTTC AGCTACCTCT |
| 12661 CAATTCAAAA AACCCCTCAA GACCCGTTTA GAGGCCCCAA GGGGTTATGC TATCAATCGT |
| 12721 TGCGTTACAC ACACAAAAAA CCAACACACA TCCATCTTCG ATGGATAGCG ATTTTATTAT |
| 12781 CTAACTGCTG ATCGAGTGTA GCCAGATCTA GTAATCAATT ACGGGGTCAT TAGTTCATAG |
| 12841 CCCATATATG GAGTTCCGCG TTACATAACT TACGGTAAAT GGCCCGCCTG GCTGACCGCC |
| 12901 CAACGACCCC CGCCCATTGA CGTCAATAAT GACGTATGTT CCCATAGTAA CGCCAATAGG |
| 12961 GACTTTCCAT TGACGTCAAT GGGTGGAGTA TTTACGGTAA ACTGCCCACT TGGCAGTACA |
| 13021 TCAAGTGTAT CATATGCCAA GTACGCCCCC TATTGACGTC AATGACGGTA AATGGCCCGC |
| 13081 CTGGCATTAT GCCCAGTACA TGACCTTATG GGACTTTCCT ACTTGGCAGT ACATCTACGT |
| 13141 ATTAGTCATC GCTATTACCA TGCTGATGCG GTTTTGGCAG TACATCAATG GGCGTGGATA |
| 13201 GCGGTTTGAC TCACGGGGAT TTCCAAGTCT CCACCCCATT GACGTCAATG GGAGTTTGTT |
| 13261 TTGGCACCAA AATCAACGGG ACTTTCCAAA ATGTCGTAAC AACTCCGCCC CATTGACGCA |
| 13321 AATGGGCGGT AGGCGTGTAC GGTGGGAGGT CTATATAAGC AGAGCTGGTT TAGTGAACCG |
| 13381 TCAGATCAGA TCTTTGTCGA TCCTACCATC CACTCGACAC ACCCGCCAGC GGCCGC (SEQ ID NO: 47) |
| |
| LINE-1 plasmid ORF1- T2A ORF2 GFP (SEQ ID NO: 48) |
| 1 TAATACGACT CACTATAGGG AGAAGTACTG CCACCATGGG CAAGAAGCAA AATCGCAAGA |
| 61 CGGGGAATTC CAAGACACAA TCCGCTAGCC CACCACCTAA AGAGCGTTCT AGCTCCCCTG |

TABLE 8-continued

Plasmid and mRNA construct sequences

| | | | | | | |
|---|---|---|---|---|---|---|
| 121 | CTACTGAGCA | GTCCTGGATG | GAAAACGACT | TCGATGAACT | CCGGGAAGAG | GGATTTAGGC |
| 181 | GATCCAACTA | TTCAGAACTC | CGCGAAGATA | TCCAGACAAA | GGGGAAGGAA | GTCGAGAATT |
| 241 | TCGAGAAGAA | CCTCGAGGAG | TGCATCACCC | GTATCACAAA | CACTGAGAAA | TGTCTCAAAG |
| 301 | AACTCATGGA | ACTTAAGACA | AAAGCCAGGG | AGCTTCGAGA | GGAGTGTCGG | AGTCTGAGAT |
| 361 | CCAGGTGTGA | CCAGCTCGAG | GAGCGCGTGA | GCGCGATGGA | AGACGAGATG | AACGAGATGA |
| 421 | AAAGAGAGGG | CAAATTCAGG | GAGAAGCGCA | TTAAGAGGAA | CGAACAGAGT | CTGCAGGAGA |
| 481 | TTTGGGATTA | CGTCAAGAGG | CCTAACCTGC | GGTTGATCGG | CGTCCCCGAG | AGCGACGTAG |
| 541 | AAAACGGGAC | TAAACTGGAG | AATACACTTC | AAGACATCAT | TCAAGAAAAT | TTTCCAAACC |
| 601 | TGGCTCGGCA | AGCTAATGTG | CAAATCCAAG | AGATCCAACG | CACACCCCAG | CGGTATAGCT |
| 661 | CTCGGCGTGC | CACCCCTAGG | CATATTATCG | TGCGCTTTAC | TAAGGTGGAG | ATGAAAGAGA |
| 721 | AGATGCTGCG | AGCCGCTCGG | GAAAAGGGAA | GGGTGACTTT | GAAGGGCAAA | CCTATTCGGC |
| 781 | TGACGGTTGA | CCTTAGCGCC | GAGACACTCC | AGGCACGCCG | GGAATGGGGC | CCCATCTTTA |
| 841 | ATATCCTGAA | GGAGAAGAAC | TTCCAGCCAC | GAATCTCTTA | CCCTGCAAAG | TTGAGTTTTA |
| 901 | TCTCCGAGGG | TGAGATTAAG | TATTTCATCG | ATAAACAGAT | GCTGCGAGAC | TTCGTGACAA |
| 961 | CTCGCCCAGC | TCTCAAGGAA | CTGCTCAAAG | AGGCTCTTAA | TATGGAGCGC | AATAATAGAT |
| 1021 | ATCAACCCTT | GCAGAACCAC | GCAAAGATGG | GAAGCGGAGA | GGGCAGAGGA | AGTCTGCTAA |
| 1081 | CATGCGGTGA | CGTCGAGGAG | AATCCTGGAC | CTATGACCGG | CTCTAACTCA | CATATCACCA |
| 1141 | TCCTTACACT | TAACATTAAC | GGCCTCAACT | CAGCTATCAA | GCGCCATCGG | CTGGCCAGCT |
| 1201 | GGATCAAATC | ACAGGATCCA | AGCGTTTGTT | GCATCCAAGA | GACCCACCTG | ACCTGTAGAG |
| 1261 | ATACTCACCG | CCTCAAGATC | AAGGGATGGC | GAAAGATTTA | TCAGGCGAAC | GGTAAGCAGA |
| 1321 | AGAAAGCCGG | AGTCGCAATT | CTGGTCTCAG | ACAAGACGGA | TTTCAAGCCC | ACCAAAATTA |
| 1381 | AGCGTGATAA | GGAAGGTCAC | TATATTATGG | TGAAAGGCAG | CATACAGCAG | GAAGAACTTA |
| 1441 | CCATATTGAA | CATCTACGCG | CCAAACACCG | GCGCACCTCG | CTTTATCAAA | CAGGTCCTGT |
| 1501 | CCGATCTGCA | GCGAGATCTG | GATTCTCATA | CGTTGATTAT | GGGTGATTTC | AATACACCAT |
| 1561 | TGAGCACCCT | GGATCGCAGC | ACCAGGCAAA | AGGTAAATAA | AGACACGCAA | GAGCTCAATA |
| 1621 | GCGCACTGCA | TCAGGCAGAT | CTCATTGATA | TTTATCGCAC | TCTTCATCCT | AAGAGTACCG |
| 1681 | AGTACACATT | CTTCAGCGCC | CCACATCATA | CATACTCAAA | GATCGATCAT | ATCGTCGGCT |
| 1741 | CAAAGGCTCT | GCTGTCAAAG | TGCAAGCGCA | CAGAGATAAT | TACAAATTAC | CTGTCAGATC |
| 1801 | ATAGCGCGAT | CAAGCTCGAG | CTGAGAATCA | AGAACCTGAC | CCAGAGCCGG | AGTACCACTT |
| 1861 | GGAAGCTTAA | TAACCTGCTG | CTCAACGATT | ATTGGGTCCA | CAATGAGATG | AAGGCAGAGA |
| 1921 | TTAAAATGTT | CTTCGAAACA | AATGAGAATA | AGGATACTAC | CTATCAAAAC | CTTTGGGATG |
| 1981 | CCTTTAAGGC | CGTCTGCAGA | GGCAAGTTCA | TCGCCCTCAA | CGCCTATAAA | AGAAAACAAG |
| 2041 | AGAGATCTAA | GATCGATACT | CTCACCTCTC | AGCTGAAGGA | GTTGGAGAAA | CAGGAACAGA |
| 2101 | CCCACTCCAA | GGCGTCAAGA | CGGCAGGAGA | TCACAAAGAT | TCGCGCCGAG | TTGAAAGAGA |
| 2161 | TCGAAACCCA | AAAGACTCTT | CAGAAAATTA | ACGAGTCTCG | TAGTTGGTTC | TTCGAGCGGA |
| 2221 | TTAATAAGAT | AGACAGACCT | CTGGCACGAC | TGATTAAGAA | GAAGCGCGAA | AAGAACCAGA |
| 2281 | TTGATACCAT | CAAGAACGAC | AAGGGCGACA | TCACTACTGA | CCCGACCGAG | ATCCAGACCA |
| 2341 | CTATTCGGGA | GTATTATAAG | CATTTGTATG | CTAACAAGCT | TGAGAACCTG | GAAGAGATGG |
| 2401 | ACACTTTTCT | GGATACCTAT | ACTCTGCCAC | GGCTTAATCA | AGAGGAAGTC | GAGTCCCTCA |
| 2461 | ACCGCCCAAT | TACAGGAAGC | GAGATTGTGG | CCATAATTAA | CTCCCTGCCG | ACAAAGAAAT |
| 2521 | CTCCTGGTCC | GGACGGGTTT | ACAGCTGAGT | TTTATCAACG | GTATATGGAA | GAGCTTGTAC |
| 2581 | CGTTTCTGCT | CAAGCTCTTT | CAGTCTATAG | AAAAGGAAGG | CATCTTGCCC | AATTCCTTCT |
| 2641 | ACGAAGCTTC | TATAATACTT | ATTCCCAAAC | CAGGACGCGA | TACCACAAAG | AAGGAAAACT |
| 2701 | TCCGGCCCAT | TAGTCTCATG | AATATCGACG | CTAAAATATT | GAACAAGATT | CTCGCCAACA |
| 2761 | GAATCCAACA | ACATATTAAG | AAATTGATAC | ATCACGACCA | GGTGGGGTTT | ATACCTGGCA |
| 2821 | TGCAGGGCTG | GTTTAACATC | CGGAAGAGTA | TTAACGTCAT | TCAACACATT | AATAGAGCTA |
| 2881 | AGGATAAGAA | TCATATGATC | ATCTCTATAG | ACGCGGAAAA | GGCATTCGAT | AAGATTCAGC |
| 2941 | AGCCATTTAT | GCTCAAGACT | CTGAACAAAC | TCGGCATCGA | CGGAACATAT | TTTAAGATTA |
| 3001 | TTCGCGCAAT | TTACGATAAG | CCGACTGCTA | ACATTATCCT | TAACGGCCAA | AAGCTCGAGG |
| 3061 | CCTTTCCGCT | CAAGACTGGA | ACCCGCCAAG | GCTGTCCCCT | CTCCCCGCTT | TTGTTTAATA |
| 3121 | TTGTACTCGA | GGTGCTGGCT | AGGGCTATTC | GTCAAGAGAA | AGAGATTAAA | GGGATACAGC |
| 3181 | TCGGGAAGGA | AGAGGTCAAG | CTTTCCTTGT | TCGCCGATGA | TATGATTGTG | TACCTGGAGA |
| 3241 | ATCCTATTGT | GTCTGCTCAG | AACCTTCTTA | AACTTATTTC | TAACTTTAGC | AAGGTCAGCG |
| 3301 | GCTATAAGAT | TAACGTCCAG | AAATCTCAGG | CCTTTCTGTA | CACAAATAAT | CGACAGACCG |
| 3361 | AATCCCAGAT | AATGGGTGAG | CTTCCGTTTG | TCATAGCCAG | CAAAAGGATA | AAGTATCTCG |
| 3421 | GAATCCAGCT | GACACGAGAC | GTTAAAGATT | TGTTTAAGGA | AAATTACAAG | CCTCTCCTGA |
| 3481 | AAGAGATTAA | GGAAGATACT | AATAAGTGGA | AGAATATCCC | CTGTTCATGG | GTTGGCAGAA |
| 3541 | TCAACATAGT | GAAGATGGCA | ATACTTCCTA | AAGTGATATA | TCGCTTTAAC | GCCATCCCAA |
| 3601 | TTAAACTGCC | TATGACCTTC | TTTACGGAGC | TCGAGAAAAC | AACCCTTAAA | TTTATATGGA |
| 3661 | ATCAAAAGAG | AGCAAGAATA | GCGAAGTCCA | TCTTGAGCCA | GAAGAATAAG | GCCGGTGGGA |
| 3721 | TTACTTTGCC | TGATTTTAAG | TTGTATTATA | AAGCCACAGT | AACTAAGACA | GCCTGGTATT |
| 3781 | GGTATCAGAA | TAGAGACATC | GACCAGTGGA | ATCGGACCGA | ACCATCAGAG | ATAATGCCCC |
| 3841 | ACATCTATAA | TTACCTTATA | TTCGATAAGC | CAGAAAAGAA | TAAACAGTGG | GGCAAAGACA |
| 3901 | GCCTCTTCAA | CAAGTGGTGT | TGGGAGAATT | GGCTGGCCAT | ATGCCGGAAA | CTCAAGCTCG |
| 3961 | ACCCCTTTCT | TACACCCTAC | ACTAAAATCA | ACAGTAGGTG | GATCAAGGAC | TTGAATGTCA |
| 4021 | AGCCAAAGAC | TATAAAGACA | CTGGAAGAGA | ATCTTGGGAT | CACAATACAA | GATATAGGCG |
| 4081 | TCGGCAAAGA | TTTTATGTCA | AAGACGCCCA | AGGCCATGGC | CACTAAGGAT | AAGATTGATA |
| 4141 | AGTGGGACCT | TATTAAGCTC | AAAAGCTTCT | GTACTGCCAA | GGAGACCACG | ATCAGAGTTA |
| 4201 | ATAGGCAGCC | CACTACATGG | GAAAAGATTT | TCGCCACTTA | TTCATCAGAT | AAGGGGTTGA |
| 4261 | TAAGCAGAAT | ATATAACGAG | CTGAAGCAGA | TCTACAAGAA | GAAAACGAAT | AATCCCATCA |
| 4321 | AGAAGTGGGC | AAAAGATATG | AACAGGCATT | TTAGCAAAGA | GGATATCTAC | GCCGCGAAGA |
| 4381 | AGCATATGAA | GAAGTGTAGT | TCAAGCTTGG | CCATTCGTGA | GATGCAGATT | AAGACGACCA |
| 4441 | TGCGATACCA | CCTTACCCCA | GTGAGGATGG | CAATTATCAA | GAAATCTGGC | AATAATAGAT |
| 4501 | GTTGGCGGGG | CTGTGGCGAG | ATTGGCACCC | TGCTCCATTG | CTGGTGGGAT | TGCAAGCTGG |
| 4561 | TGCAGCCGCT | TTGGAAATCA | GTCTGGCGCT | TTCTGAGGGA | CCTCGAGCTT | GAGATTCCCT |
| 4621 | TCGATCCCGC | AATTCCCTTG | CTCGGAATCT | ATCCTAACGA | ATACAAGAGC | TGTTGTTACA |
| 4681 | AGGATACGTG | TACCCGGATG | TTCATCGCGG | CCTTGTTTAC | GATAGCTAAG | ACGTGGAATC |
| 4741 | AGCCTAAGTG | CCCCACAATG | ATCGATTGGA | TCAAGAAAAT | GTGGCATATT | TATACCATGG |

TABLE 8-continued

| Plasmid and mRNA construct sequences |
|---|
| 4801 AGTATTACGC AGCAATTAAG AATGACGAAT TTATTTCCTT CGTTGGGACC TGGATGAAGC |
| 4861 TGGAGACTAT TATTCTGAGC AAGCTGTCTC AGGAGCAAAA GACAAAGCAT AGAATCTTCT |
| 4921 CTCTCATTGG TGGTAACGAC TACAAAGACG ATGACGACAA GTAAAGCGCT TCTAGAAGTT |
| 4981 GTCTCCTCCT GCACTGACTG ACTGATACAA TCGATTTCTG GATCCGCAGG CCTAATCAAC |
| 5041 CTCTGGATTA CAAAATTTGT GAAAGATTGA CTGGTATTCT TAACTATGTT GCTCCTTTTA |
| 5101 CGCTATGTGG ATACGCTGCT TTAATGCCTT TGTATCATGC TATTGCTTCC CGTATGGCTT |
| 5161 TCATTTTCTC CTCCTTGTAT AAATCCTGGT TGCTGTCTCT TTATGAGGAG TTGTGGCCCG |
| 5221 TTGTCAGGCA ACGTGGCGTG GTGTGCACTG TGTTTGCTGA CGCAACCCCC ACTGGTTGGG |
| 5281 GCATTGCCAC CACCTGTCAG CTCCTTTCCG GGACTTTCGC TTTCCCCCTC CCTATTGCCA |
| 5341 CGGCGGAACT CATCGCCGCC TGCCTTGCCC GCTGCTGGAC AGGGGCTCGG CTGTTGGGCA |
| 5401 CTGACAATTC CGTGGTGTTG TCGGGGAAGC TGACGTCCTT TCCATGGCTG CTCGCCTGTG |
| 5461 TTGCCACCTG GATTCTGCGC GGGACGTCCT TCTGCTACGT CCCTTCGGCC CTCAATCCAG |
| 5521 CGGACCTTCC TTCCCGCGAA CAAACGACCC AACACCCGTG CGTTTTATTC TGTCTTTTTA |
| 5581 TTGCCGATCC CCTCAGAAGA ACTCGTCAAG AAGGCGATAG AAGGCGATGC GCTGCGAATC |
| 5641 GGGAGCGGCG ATACCGTAAA GCACGAGGAA GCGGTCAGCC CATTCGCCGC CAAGCTCTTC |
| 5701 AGCAATATCA CGGGTAGCCA ACGCTATGTC CTGATAGCGG TCGGCCGCTT TACTTGTACA |
| 5761 GCTCGTCCAT GCCGAGAGTG ATCCCGGCGG CGGTCACGAA CTCCAGCAGG ACCATGTGAT |
| 5821 CGCGCTTCTC GTTGGGGTCT TTGCTCAGGG CGGACTGGGT GCTCAGGTAG TGGTTGTCGG |
| 5881 GCAGCAGCAC GGGGCCGTCG CCGATGGGGG TGTTCTGCTG GTAGTGGTCG GCCAGGTGAG |
| 5941 TCCAGGAGAT GTTTCAGCAC TGTTGCCTTT AGTCTCGAGG CAACTTAGAC AACTGAGTAT |
| 6001 TGATCTGAGC ACAGCAGGGT GTGAGCTGTT TGAAGATACT GGGGTTGGGG GTGAAGAAAC |
| 6061 TGCAGAGGAC TAACTGGGCT GAGACCCAGT GGCAATGTTT TAGGGCCTAA GGAATGCCTC |
| 6121 TGAAAATCTA GATGGACAAC TTTGACTTTG AGAAAAGAGA GGTGGAAATG AGGAAAATGA |
| 6181 CTTTTCTTTA TTAGATTTCG GTAGAAAGAA CTTTCATCTT TCCCCTATTT TTGTTATTCG |
| 6241 TTTTAAAACA TCTATCTGGA GGCAGGACAA GTATGGTCAT TAAAAAGATG CAGGCAGAAG |
| 6301 GCATATATTG GCTCAGTCAA AGTGGGGAAC TTTGGTGGCC AAACATACAT TGCTAAGGCT |
| 6361 ATTCCTATAT CAGCTGGACA CATATAAAAT GCTGCTAATG CTTCATTACA AACTTATATC |
| 6421 CTTTAATTCC AGATGGGGGC AAAGTATGTC CAGGGGTGAG GAACAATTGA AACATTTGGG |
| 6481 CTGGAGTAGA TTTTGAAAGT CAGCTCTGTG TGTGTGTGTG TGTGTGTGTG TGTGAGAGCG |
| 6541 TGTGTTTCTT TTAACGTTTT CAGCCTACAG CATACAGGGT TCATGGTGGC AAGAAGATAA |
| 6601 CAAGATTTAA ATTATGGCCA GTGACTAGTG CTGCAAGAAG AACAACTACC TGCATTTAAT |
| 6661 GGGAAAGCAA AATCTCAGGC TTTGAGGGAA GTTAACATAG GCTTGATTCT GGGTGGAAGC |
| 6721 TGGGTGTGTA GTTATCTGGA GGCCAGGCTG GAGCTCTCAG CTCACTATGG GTTCATCTTT |
| 6781 ATTGTCTCCT TTCATCTCAA CAGCTGCACG CTGCCGTCCT CGATGTTGTG GCGGATCTTG |
| 6841 AAGTTCACCT TGATGCCGTT CTTCTGCTTG TCGGCCATGA TATAGACGTT GTGGCTGTTG |
| 6901 TAGTTGTACT CCAGCTTGTG CCCCAGGATG TTGCCGTCCT CCTTGAAGTC GATGCCCTTC |
| 6961 AGCTCGATGC GGTTCACCAG GGTGTCGCCC TCGAACTTCA CCTCGGCGCG GGTCTTGTAG |
| 7021 TTGCCGTCGT CCTTGAAGAA GATGGTGCGC TCCTGGACGT AGCCTTCGGG CATGGCGGAC |
| 7081 TTGAAGAAGT CGTGCTGCTT CATGTGGTCG GGGTAGCGGC TGAAGCACTG CACGCCGTAG |
| 7141 GTCAGGGTGG TCACGAGGGT GGGCCAGGGC ACGGGCAGCT TGCCGGTGGT GCAGATGAAC |
| 7201 TTCAGGGTCA GCTTGCCGTA GGTGGCATCG CCCTCGCCCT CGCCGGACAC GCTGAACTTG |
| 7261 TGGCCGTTTA CGTCGCCGTC CAGCTCGACC AGGATGGGCA CCACCCCGGT GAACAGCTCC |
| 7321 TCGCCCTTGC TCACCATGGT GGCGAATTCG AAGCTTGAGC ACGAGATCTG AGTCCGGTAG |
| 7381 GCCTAGCGGA TCTGACGGTT CACTAAACCA GCTCTGCTTA TATAGACCTC CCACCGTACA |
| 7441 CGCCTACCGC CCATTTGCGT CAATGGGGCG GAGTTGTTAC GACATTTTGG AAAGTCCCGT |
| 7501 TGATTTTGGT GCCAAAACAA ACTCCCATTG ACGTCAATGG GGTGGAGACT TGGAAATCCC |
| 7561 CGTGAGTCAA ACCGCTATCC ACGCCCATTG ATGTACTGCC AAAACCGCAT CACCATGGTA |
| 7621 ATAGCGATGA CTAATACGTA GATGTACTGC CAAGTAGGAA AGTCCCATAA GGTCATGTAC |
| 7681 TGGGCATAAT GCCAGGCGGG CCATTTACCG TCATTGACGT CAATAGGGGG CGTACTTGGC |
| 7741 ATATGATACA CTTGATGTAC TGCCAAGTGG GCAGTTTACC GTAAATACTC CACCCATTGA |
| 7801 CGTCAATGGA AAGTCCCTAT TGGCGTTACT ATGGGAACAT ACGTCATTAT TGACGTCAAT |
| 7861 GGGCGGGGGT CGTTGGGCGG TCAGCCAGGC GGGCCATTTA CCGTAAGTTA TGTAACGGGC |
| 7921 CTGCTGCCGG CTCTGCGGCC TCTTCCGCGT CTTCGCCTTC GCCCTCAGAC GAGTCGGATC |
| 7981 TCCCTTTGGG CCGCCTCCCC GCCTGTCTAG CTTGACTGAC TGAGATACAG CGTACCTTCA |
| 8041 GCTCACAGAC ATGATAAGAT ACATTGATGA GTTTGGACAA ACCACAACTA GAATGCAGTG |
| 8101 AAAAAAATGC TTTATTTGTG AAATTTGTGA TGCTATTGCT TTATTTGTAA CCATTATAAG |
| 8161 CTGCAATAAA CAAGTTAACA ACAACAATTG CATTCATTTT ATGTTTCAGG TTCAGGGGGA |
| 8221 GGTGTGGGAG GTTTTTTAAA GCAAGTAAAA CCTCTACAAA TGTGGTATTG GCCCATCTCT |
| 8281 ATCGGTATCG TAGCATAACC CCTTGGGGCC TCTAAACGGG TCTTGAGGGG TTTTTTGTGC |
| 8341 CCCTCGGGCC GGATTGCTAT CTACCGGCAT TGGCGCAGAA AAAAATGCCT GATGCGACGC |
| 8401 TGCGCGTCTT ATACTCCCAC ATATGCCAGA TTCAGCAACG GATACGGCTT CCCCAACTTG |
| 8461 CCCACTTCCA TACGTGTCCT CCTTACCAGA AATTTATCCT TAAGGTCGTC AGCTATCCTG |
| 8521 CAGGCGATCT CTCGATTTCG ATCAAGACAT TCCTTTAATG GTCTTTTCTG GACACCACTA |
| 8581 GGGGTCAGAA GTAGTTCATC AAACTTTCTT CCCTCCCTAA TCTCATTGGT TACCTTGGGC |
| 8641 TATCGAAACT TAATTAAGCG ATCTGCATCT CAATTAGTCA GCAACCATAG TCCCGCCCCT |
| 8701 AACTCCGCCC ATCCCGCCCC TAACTCCGCC CAGTTCCGCC CATTCTCCGC CCCATCGCTG |
| 8761 ACTAATTTTT TTTATTTATG CAGAGGCCGA GGCCGCCTCG GCCTCTGAGC TATTCCAGAA |
| 8821 GTAGTGAGGA GGCTTTTTTG GAGGCCTAGG CTTTTGCAAA GGAGGTAGCC AACATGATTG |
| 8881 AACAAGATGG ATTGCACGCA GGTTCTCCCG CCGCTTGGGT GGAGAGGCTA TTCGGCTATG |
| 8941 ACTGGGCACA ACAGACAATC GGCTGCTCTG ATGCCGCCGT GTTCCGGCTG TCAGCGCAGG |
| 9001 GGCGCCCGGT TCTTTTTGTC AAGACCGACC TGTCCGGTGC CCTGAATGAA CTCCAGGACG |
| 9061 AGGCAGCGCG GCTATCGTGG CTGGCCACGA CGGGCGTTCC TTGCGCAGCT GTGCTCGACG |
| 9121 TTGTCACTGA AGCGGGAAGG GACTGGCTGC TATTGGGCGA AGTGCCGGGG CAGGATCTCC |
| 9181 TGTCATCTCA CCTTGCTCCT GCCGAGAAAG TATCCATCAT GGCTGATGCA ATGCGGCGGC |
| 9241 TGCATACGCT TGATCCGGCT ACCTGCCCAT TCGACCACCA AGCGAAACAT CGCATCGAGC |
| 9301 GAGCACGTAC TCGGATGGAA GCCGGTCTTG TCGATCAGGA TGATCTGGAC GAAGAGCATC |
| 9361 AGGGGCTCGC GCCAGCCGAA CTGTTCGCCA GGCTCAAGGC GCGGATGCCC GACGGCGAGG |
| 9421 ATCTCGTCGT GACCCACGGC GATGCCTGCT TGCCGAATAT CATGGTGGAA AATGGCCGCT |

TABLE 8-continued

Plasmid and mRNA construct sequences

```
 9481 TTTCTGGATT CATCGACTGT GGCCGGCTGG GTGTGGCGGA CCGCTATCAG GACATAGCGT
 9541 TGGCTACCCG TGATATTGCT GAAGAGCTTG GCGGCGAATG GGCTGACCGC TTCCTCGTGC
 9601 TTTACGGTAT CGCCGCTCCC GATTCGCAGC GCATCGCCTT CTATCGCCTT CTTGACGAGT
 9661 TCTTCTAGTA TGTAAGCCCT GTGCCTTCTA GTTGCCAGCC ATCTGTTGTT TGCCCCTCCC
 9721 CCGTGCCTTC CTTGACCCTG GAAGGTGCCA CTCCCACTGT CCTTTCCTAA TAAAATGAGG
 9781 AAATTGCATC GCATTGTCTG AGTAGGTGTC ATTCTATTCT GGGGGGTGGG GTGGGGCAGG
 9841 ACAGCAAGGG GGAGGATTGG GAAGACAATA GCAGGCATGC TGGGGATGCG GTGGGCTCTA
 9901 TGGTTAATTA ACCAGTCAAG TCAGCTACTT GGCGAGATCG ACTTGTCTGG GTTTCGACTA
 9961 CGCTCAGAAT TGCGTCAGTC AAGTTCGATC TGGTCCTTGC TATTGCACCC GTTCTCCGAT
10021 TACGAGTTTC ATTTAAATCA TGTGAGCAAA AGGCCAGCAA AAGGCCAGGA ACCGTAAAAA
10081 GGCCGCGTTG CTGGCGTTTT TCCATAGGCT CCGCCCCCCT GACGAGCATC ACAAAAATCG
10141 ACGCTCAAGT CAGAGGTGGC GAAACCCGAC AGGACTATAA AGATACCAGG CGTTTCCCCC
10201 TGGAAGCTCC CTCGTGCGCT CTCCTGTTCC GACCCTGCCG CTTACCGGAT ACCTGTCCGC
10261 CTTTCTCCCT TCGGGAAGCG TGGCGCTTTC TCATAGCTCA CGCTGTAGGT ATCTCAGTTC
10321 GGTGTAGGTC GTTCGCTCCA AGCTGGGCTG TGTGCACGAA CCCCCCGTTC AGCCCGACCG
10381 CTGCGCCTTA TCCGGTAACT ATCGTCTTGA GTCCAACCCG GTAAGACACG ACTTATCGCC
10441 ACTGGCAGCA GCCACTGGTA ACAGGATTAG CAGAGCGAGG TATGTAGGCG GTGCTACAGA
10501 GTTCTTGAAG TGGTGGCCTA ACTACGGCTA CACTAGAAGA ACAGTATTTG GTATCTGCGC
10561 TCTGCTGAAG CCAGTTACCT TCGGAAAAAG AGTTGGTAGC TCTTGATCCG GCAAACAAAC
10621 CACCGCTGGT AGCGGTGGTT TTTTTGTTTG CAAGCAGCAG ATTACGCGCA GAAAAAAAGG
10681 ATCTCAAGAA GATCCTTTGA TCTTTTCTAC GGGGTCTGAC GCTCAGTGGA ACGAAAACTC
10741 ACGTTAAGGG ATTTTGGTCA TGAGATTATC AAAAAGGATC TTCACCTAGA TCCTTTTAAA
10801 TTAAAAATGA AGTTTTAAAT CAATCTAAAG TATATATGAG TAAACTTGGT CTGACAGTTA
10861 CCAATGCTTA ATCAGTGAGG CACCTATCTC AGCGATCTGT CTATTTCGTT CATCCATAGT
10921 TGCATTTAAA TTTCCGAACT CTCCAAGGCC CTCGTCGGAA AATCTTCAAA CCTTTCGTCC
10981 GATCCATCTT GCAGGCTACC TCTCGAACGA ACTATCGCAA GTCTCTTGGC CGGCCTTGCG
11041 CCTTGGCTAT TGCTTGGCAG CGCCTATCGC CAGGTATTAC TCCAATCCCG AATATCCGAG
11101 ATCGGGATCA CCCGAGAGAA GTTCAACCTA CATCCTCAAT CCCGATCTAT CCGAGATCCG
11161 AGGAATATCG AAATCGGGGC GCGCCTGGTG TACCGAGAAC GATCCTCTCA GTGCGAGTCT
11221 CGACGATCCA TATCGTTGCT TGGCAGTCAG CCAGTCGGAA TCCAGCTTGG GACCCAGGAA
11281 GTCCAATCGT CAGATATTGT ACTCAAGCCT GGTCACGGCA GCGTACCGAT CTGTTTAAAC
11341 CTAGATATTG ATAGTCTGAT CGGTCAACGT ATAATCGAGT CCTAGCTTTT GCAAACATCT
11401 ATCAAGAGAC AGGATCAGCA GGAGGCTTTC GCATGAGTAT TCAACATTTC CGTGTCGCCC
11461 TTATTCCCTT TTTTGCGGCA TTTTGCCTTC CTGTTTTTGC TCACCCAGAA ACGCTGGTGA
11521 AAGTAAAAGA TGCTGAAGAT CAGTTGGGTG CGCGAGTGGG TTACATCGAA CTGGATCTCA
11581 ACAGCGGTAA GATCCTTGAG AGTTTTCGCC CCGAAGAACG CTTTCCAATG ATGAGCACTT
11641 TTAAAGTTCT GCTATGTGGC GCGGTATTAT CCCGTATTGA CGCCGGGCAA GAGCAACTCG
11701 GTCGCCGCAT ACACTATTCT CAGAATGACT TGGTTGAGTA TTCACCAGTC ACAGAAAAGC
11761 ATCTTACGGA TGGCATGACA GTAAGAGAAT TATGCAGTGC TGCCATAACC ATGAGTGATA
11821 ACACTGCGGC CAACTTACTT CTGACAACGA TTGGAGGACC GAAGGAGCTA ACCGCTTTTT
11881 TGCACAACAT GGGGGATCAT GTAACTCGCC TTGATCGTTG GGAACCGGAG CTGAATGAAG
11941 CCATACCAAA CGACGAGCGT GACACCACGA TGCCTGTAGC AATGGCAACA ACCTTGCGTA
12001 AACTATTAAC TGGCGAACTA CTTACTCTAG CTTCCCGGCA ACAGTTGATA GACTGGATGG
12061 AGGCGGATAA AGTTGCAGGA CCACTTCTGC GCTCGGCCCT TCCGGCTGGC TGGTTTATTG
12121 CTGATAAATC TGGAGCCGGT GAGCGTGGGT CTCGCGGTAT CATTGCAGCA CTGGGGCCAG
12181 ATGGTAAGCC CTCCCGTATC GTAGTTATCT ACACGACGGG GAGTCAGGCA ACTATGGATG
12241 AACGAAATAG ACAGATCGCT GAGATAGGTG CCTCACTGAT TAAGCATTGG TAACCGATTC
12301 TAGGTGCATT GGCGCAGAAA AAAATGCCTG ATGCGACGCT GCGCGTCTTA TACTCCCACA
12361 TATGCCAGAT TCAGCAACGG ATACGGCTTC CCCAACTTGC CCACTTCCAT ACGTGTCCTC
12421 CTTACCAGAA ATTTATCCTT AAGATCGTTT AAACTCGACT CTGGCTCTAT CGAATCTCCG
12481 TCGTTTCGAG CTTACGCGAA CAGCCGTGGC GCTCATTTGC TCGTCGGGCA TCGAATCTCG
12541 TCAGCTATCG TCAGCTTACC TTTTTGGCAG CGATCGCGGC TCCCGACATC TTGGACCATT
12601 AGCTCCACAG GTATCTTCTT CCCTCTAGTG GTCATAACAG CAGCTTCAGC TACCTCTCAA
12661 TTCAAAAAAC CCCTCAAGAC CCGTTTAGAG GCCCCAAGGG GTTATGCTAT CAATCGTTGC
12721 GTTACACACA CAAAAAACCA ACACACATCC ATCTTCGATG GATAGCGATT TTATTATCTA
12781 ACTGCTGATC GAGTGTAGCC AGATCTAGTA ATCAATTACG GGGTCATTAG TTCATAGCCC
12841 ATATATGGAG TTCCGCGTTA CATAACTTAC GGTAAATGGC CCGCCTGGCT GACCGCCCAA
12901 CGACCCCCGC CCATTGACGT CAATAATGAC GTATGTTCCC ATAGTAACGC CAATAGGGAC
12961 TTTCCATTGA CGTCAATGGG TGGAGTATTT ACGGTAAACT GCCCACTTGG CAGTACATCA
13021 AGTGTATCAT ATGCCAAGTA CGCCCCCTAT TGACGTCAAT GACGGTAAAT GGCCCGCCTG
13081 GCATTATGCC CAGTACATGA CCTTATGGGA CTTTCCTACT TGGCAGTACA TCTACGTATT
13141 AGTCATCGCT ATTACCATGC TGATGCGGTT TTGGCAGTAC ATCAATGGGC GTGGATAGCG
13201 GTTTGACTCA CGGGGATTTC CAAGTCTCCA CCCCATTGAC GTCAATGGGA GTTTGTTTTG
13261 GCACCAAAAT CAACGGGACT TTCCAAAATG TCGTAACAAC TCCGCCCCAT TGACGCAAAT
13321 GGGCGGTAGG CGTGTACGGT GGGAGGTCTA TATAAGCAGA GCTGGTTTAG TGAACCGTCA
13381 GATCAGATCT TTGTCGATCC TACCATCCAC TCGACACACC CGCCAGCGGC CGC
      (SEQ ID NO: 48)
```

LINE-1_ORF2-MCP_MS2_mRNA (SEQ ID NO: 49)

```
    1 TAATACGACT CACTATAGGG AGAAGTACTG CCACCATGGG CAAGAAGCAA AATCGCAAGA
   61 CGGGGAATTC CAAGACACAA TCCGCTAGCC CACCACCTAA AGAGCGTTCT AGCTCCCCTG
  121 CTACTGAGCA GTCCTGGATG GAAAACGACT TCGATGAACT CCGGGAAGAG GGATTTAGGC
  181 GATCCAACTA TTCAGAACTC CGCGAAGATA TCCAGACAAA GGGGAAGGAA GTCGAGAATT
  241 TCGAGAAGAA CCTCGAGGAG TGCATCACCC GTATCACAAA CACTGAGAAA TGTCTCAAAG
  301 AACTCATGGA ACTTAAGACA AAAGCCAGGG AGCTTCGAGA GGAGTGTCGG AGTCTGAGAT
  361 CCAGGTGTGA CCAGCTCGAG GAGCGCGTGA GCGCGATGGA AGACGAGATG AACGAGATGA
  421 AAAGAGAGGG CAAATTCAGG GAGAAGCGCA TTAAGAGGAA CGAACAGAGT CTGCAGGAGA
  481 TTTGGGATTA CGTCAAGAGG CCTAACCTGC GGTTGATCGG CGTCCCCGAG AGCGACGTAG
```

TABLE 8-continued

| Plasmid and mRNA construct sequences |
| --- |
| 541 AAAACGGGAC TAAACTGGAG AATACACTTC AAGACATCAT TCAAGAAAAT TTTCCAAACC |
| 601 TGGCTCGGCA AGCTAATGTG CAAATCCAAG AGATCCAACG CACACCCCAG CGGTATAGCT |
| 661 CTCGGCGTGC CACCCCTAGG CATATTATCG TGCGCTTTAC TAAGGTGGAG ATGAAAGAGA |
| 721 AGATGCTGCG AGCCGCTCGG GAAAAGGGAA GGGTGACTTT GAAGGGCAAA CCTATTCGGC |
| 781 TGACGGTTGA CCTTAGCGCC GAGACACTCC AGGCACGCCG GGAATGGGGC CCCATCTTTA |
| 841 ATATCCTGAA GGAGAAGAAC TTCCAGCCAC GAATCTCTTA CCCTGCAAAG TTGAGTTTTA |
| 901 TCTCCGAGGG TGAGATTAAG TATTTCATCG ATAAACAGAT GCTGCGAGAC TTCGTGACAA |
| 961 CTCGCCCAGC TCTCAAGGAA CTGCTCAAAG AGGCTCTTAA TATGGAGCGC AATAATAGAT |
| 1021 ATCAACCCTT GCAGAACCAC GCAAAGATGT GAGACAGCCG TCAGACCATC AAGACTAGGA |
| 1081 AGAAACTGCA TCAACTAATG AGCAAAATCA CCAGCTAACA TCATAGTATA CATGACCGGC |
| 1141 TCTAACTCAC ATATCACCAT CCTTACACTT AACATTAACG GCCTCAACTC AGCTATCAAG |
| 1201 CGCCATCGGC TGGCCAGCTG GATCAAATCA CAGGATCCAA GCGTTTGTTG CATCCAAGAG |
| 1261 ACCCACCTGA CCTGTAGAGA TACTCACCGC CTCAAGATCA AGGGATGGCG AAAGATTTAT |
| 1321 CAGGCGAACG GTAAGCAGAA GAAAGCCGGA GTCGCAATTC TGGTCTCAGA CAAGACGGAT |
| 1381 TTCAAGCCCA CCAAAATTAA GCGTGATAAG GAAGGTCACT ATATTATGGT GAAAGGCAGC |
| 1441 ATACAGCAGG AAGAACTTAC CATATTGAAC ATCTACGCGC CAAACACCGG CGCACCTCGC |
| 1501 TTTATCAAAC AGGTCCTGTC CGATCTGCAG CGAGATCTGG ATTCTCATAC GTTGATTATG |
| 1561 GGTGATTTCA ATACACCATT GAGCACCCTG GATCGCAGCA CCAGGCAAAA GGTAAATAAA |
| 1621 GACACGCAAG AGCTCAATAG CGCACTGCAT CAGGCAGATC TCATTGATAT TTATCGCACT |
| 1681 CTTCATCCTA AGAGTACCGA GTACACATTC TTCAGCGCCC CACATCATAC ATACTCAAAG |
| 1741 ATCGATCATA TCGTCGGCTC AAAGGCTCTG CTGTCAAAGT GCAAGCGCAC AGAGATAATT |
| 1801 ACAAATTACC TGTCAGATCA TAGCGCGATC AAGCTCGAGC TGAGAATCAA GAACCTGACC |
| 1861 CAGAGCCGGA GTACCACTTG GAAGCTTAAT AACCTGCTGC TCAACGATTA TTGGGTCCAC |
| 1921 AATGAGATGA AGGCAGAGAT TAAAATGTTC TTCGAAACAA ATGAGAATAA GGATACTACC |
| 1981 TATCAAAACC TTTGGGATGC CTTTAAGGCC GTCTGCAGAG GCAAGTTCAT CGCCCTCAAC |
| 2041 GCCTATAAAA GAAAACAAGA GAGATCTAAG ATCGATACTC TCACCTCTCA GCTGAAGGAG |
| 2101 TTGGAGAAAC AGGAACAGAC CCACTCCAAG GCGTCAAGAC GGCAGGAGAT CACAAAGATT |
| 2161 CGCGCCGAGT TGAAAGAGAT CGAAACCCAA AAGACTCTTC AGAAAATTAA CGAGTCTCGT |
| 2221 AGTTGGTTCT TCGAGCGGAT TAATAAGATA GACAGACCTC TGGCACGACT GATTAAGAAG |
| 2281 AAGCGCGAAA AGAACCAGAT TGATACCATC AAGAACGACA AGGGCGACAT CACTACTGAC |
| 2341 CCGACCGAGA TCCAGACCAC TATTCGGGAG TATTATAAGC ATTTGTATGC TAACAAGCTT |
| 2401 GAGAACCTGG AAGAGATGGA CACTTTTCTG GATACCTATA CTCTGCCACG GCTTAATCAA |
| 2461 GAGGAAGTCG AGTCCCTCAA CCGCCCAATT ACAGGAAGCG AGATTGTGGC CATAATTAAC |
| 2521 TCCCTGCCGA CAAAGAAATC TCCTGGTCCG GACGGGTTTA CAGCTGAGTT TTATCAACGG |
| 2581 TATATGGAAG AGCTTGTACC GTTTCTGCTC AAGCTCTTTC AGTCTATAGA AAAGGAAGGC |
| 2641 ATCTTGCCCA ATTCCTTCTA CGAAGCTTCT ATAATACTTA TTCCCAAACC AGGACGCGAT |
| 2701 ACCACAAAGA AGGAAAACTT CCGGCCCATT AGTCTCATGA ATATCGACGC TAAAATATTG |
| 2761 AACAAGATTC TCGCCAACAG AATCCAACAA CATATTAAGA AATTGATACA TCACGACCAG |
| 2821 GTGGGGTTTA TACCTGGCAT GCAGGGCTGG TTTAACATCC GGAAGAGTAT TAACGTCATT |
| 2881 CAACACATTA ATAGAGCTAA GGATAAGAAT CATATGATCA TCTCTATAGA CGCGGAAAAG |
| 2941 GCATTCGATA AGATTCAGCA GCCATTTATG CTCAAGACTC TGAACAAACT CGGCATCGAC |
| 3001 GGAACATATT TTAAGATTAT TCGCGCAATT TACGATAAGC CGACTGCTAA CATTATCCTT |
| 3061 AACGGCCAAA AGCTCGAGGC CTTTCCGCTC AAGACTGGAA CCCGCCAAGG CTGTCCCCTC |
| 3121 TCCCCGCTTT TGTTTAATAT TGTACTCGAG GTGCTGGCTA GGGCTATTCG TCAAGAGAAA |
| 3181 GAGATTAAAG GGATACAGCT CGGGAAGGAA GAGGTCAAGC TTTCCTTGTT CGCCGATGAT |
| 3241 ATGATTGTGT ACCTGGAGAA TCCTATTGTG TCTGCTCAGA ACCTTCTTAA ACTTATTTCT |
| 3301 AACTTTAGCA AGGTCAGCGG CTATAAGATT AACGTCCAGA AATCTCAGGC CTTTCTGTAC |
| 3361 ACAAATAATC GACAGACCGA ATCCCAGATA ATGGGTGAGC TTCCGTTTGT CATAGCCAGC |
| 3421 AAAAGGATAA AGTATCTCGG AATCCAGCTG ACACGAGACG TTAAAGATTT GTTTAAGGAA |
| 3481 AATTACAAGC CTCTCCTGAA AGAGATTAAG GAAGATACTA ATAAGTGGAA GAATATCCCC |
| 3541 TGTTCATGGG TTGGCAGAAT CAACATAGTG AAGATGGCAA TACTTCCTAA AGTGATATAT |
| 3601 CGCTTTAACG CCATCCCAAT TAAACTGCCT ATGACCTTCT TTACGGAGCT CGAGAAAACA |
| 3661 ACCCTTAAAT TTATATGGAA TCAAAAGAGA GCAAGAATAG CGAAGTCCAT CTTGAGCCAG |
| 3721 AAGAATAAGG CCGGTGGGAT TACTTTGCCT GATTTTAAGT TGTATTATAA AGCCACAGTA |
| 3781 ACTAAGACAG CCTGGTATTG GTATCAGAAT AGAGACATCG ACCAGTGGAA TCGGACCGAA |
| 3841 CCATCAGAGA TAATGCCCCA CATCTATAAT TACCTTATAT TCGATAAGCC AGAAAAGAAT |
| 3901 AAACAGTGGG GCAAAGACAG CCTCTTCAAC AAGTGGTGTT GGGAGAATTG GCTGGCCATA |
| 3961 TGCCGGAAAC TCAAGCTCGA CCCCTTTCTT ACACCCTACA CTAAAATCAA CAGTAGGTGG |
| 4021 ATCAAGGACT TGAATGTCAA GCCAAAGACT ATAAAGACAC TGGAAGAGAA TCTTGGGATC |
| 4081 ACAATACAAG ATATAGGCGT CGGCAAAGAT TTTATGTCAA AGACGCCCAA GGCCATGGCC |
| 4141 ACTAAGGATA AGATTGATAA GTGGGACCTT ATTAAGCTCA AAAGCTTCTG TACTGCCAAG |
| 4201 GAGACCACGA TCAGAGTTAA TAGGCAGCCC ACTACATGGG AAAAGATTTT CGCCACTTAT |
| 4261 TCATCAGATA AGGGGTTGAT AAGCAGAATA TATAACGAGC TGAAGCAGAT CTACAAGAAG |
| 4321 AAAACGAATA ATCCCATCAA GAAGTGGGCA AAAGATATGA ACAGGCATTT TAGCAAAGAG |
| 4381 GATATCTACG CCGCGAAGAA GCATATGAAG AAGTGTAGTT CAAGCTTGGC CATTCGTGAG |
| 4441 ATGCAGATTA AGACGACCAT GCGATACCAC CTTACCCCAG TGAGGATGGC AATTATCAAG |
| 4501 AAATCTGGCA ATAATAGATG TTGGCGGGGC TGTGGCGAGA TTGGCACCCT GCTCCATTGC |
| 4561 TGGTGGGATT GCAAGCTGGT GCAGCCGCTT TGGAAATCAG TCTGGCGCTT TCTGAGGGAC |
| 4621 CTCGAGCTTG AGATTCCCTT CGATCCCGCA ATTCCCTTGC TCGGAATCTA TCCTAACGAA |
| 4681 TACAAGAGCT GTTGTTACAA GGATACGTGT ACCCGGATGT TCATCGCGGC CTTGTTTACG |
| 4741 ATAGCTAAGA CGTGGAATCA GCCTAAGTGC CCCACAATGA TCGATTGGAT CAAGAAAATG |
| 4801 TGGCATATTT ATACCATGGA GTATTACGCA GCAATTAAGA ATGACGAATT TATTTCCTTC |
| 4861 GTTGGGACCT GGATGAAGCT GGAGACTATT ATTCTGAGCA AGCTGTCTCA GGAGCAAAAG |
| 4921 ACAAAGCATA GAATCTTCTC TCTCATTGGT GGTAACGCTT CTAACTTTAC TCAGTTCGTT |
| 4981 CTCGTCGACA ATGGCGGAAC TGGCGACGTG ACTGTCGCCC CAAGCAACTT CGCTAACGGG |
| 5041 ATCGCTGAAT GGATCAGCTC TAACTCGCGT TCACAGGCTT ACAAAGTAAC CTGTAGCGTT |
| 5101 CGTCAGAGCT CTGCGCAGAA TCGCAAATAC ACCATCAAAG TCGAGGTGCC TAAAGGCGCC |
| 5161 TGGCGTTCGT ACTTAAATAT GGAACTAACC ATTCCAATTT TCGCCACGAA TTCCGACTGC |

TABLE 8-continued

| Plasmid and mRNA construct sequences |
|---|
| 5221 GAGCTTATTG TTAAGGCAAT GCAAGGTCTC CTAAAAGATG GAAACCCGAT TCCCTCAGCA<br>5281 ATCGCAGCAA ACTCCGGCAT CTACGCCATG GCCAGCAACT TCACCCAGTT CGTGCTGGTG<br>5341 GACAACGGCG GCACCGGCGA CGTGACCGTG GCCCCCAGCA ACTTCGCCAA CGGCATCGCC<br>5401 GAGTGGATCA GCAGCAACAG CAGAAGCCAG GCCTACAAGG TGACCTGCAG CGTGAGACAG<br>5461 AGCAGCGCCC AGAACAGAAA GTACACCATC AAGGTGGAGG TGCCCAAGGG CGCCTGGAGA<br>5521 AGCTACCTGA ACATGGAGCT GACCATCCCC ATCTTCGCCA CCAACAGCGA CTGCGAGCTG<br>5581 ATCGTGAAGG CCATGCAGGG CCTGCTGAAG GACGGCAACC CCATCCCCAG CGCCATCGCC<br>5641 GCCAACAGCG GCATCTACGA CTACAAAGAC GATGACGACA AGTAAAGCAA CCTACAAACG<br>5701 GGTGGAGGAT CACCCCACCC GACACTTCAC AATCAAGGGG TACAATACAC AAGGGTGGAG<br>5761 GAACACCCCA CCCTCCAGAC ACATTACACA GAAATCCAAT CAAACAGAAG CACCATCAGG<br>5821 GCTTCTGCTA CCAAATTTAT CTCAAAAAAC TACAACAAGG AATCACCATC AGGGATTCCC<br>5881 TGTGCAATAT ACGTCAAACG AGGGCCACGA CGGGAGGACG ATCACGCCTC CCGAATATCG<br>5941 GCATGTCTGG CTTTCGAATT CAGTGCGTGG AGCATCAGCC CACGCAGCCA ATCAGAGTCG<br>6001 AATACAAGTC GACTTTCGCG AAGAGCATCA GCCTTCGCGC CATTCTTACA CAAACCACAC<br>6061 TCTCCCCTAC AGGAACAGCA TCAGCGTTCC TGCCCAGTAC CCAACTCAAG AAAATTTATG<br>6121 TCCCCATGCA GCATCAGCGC ATGGGCCCCA AGAATACATC CCCAACAAAA TCACATCCGA<br>6181 GCACCAACAG GGCTCGGAGT GTTGTTTCTT GTCCAACTGG ACAAACCCTC CATGGACCAT<br>6241 CAGGCCATGG ACTCTCACCA ACAAGACAAA AACTACTCTT CTCGAAGCAG CATCAGCGCT<br>6301 TCGAAACACT CGAGCATACA TTGTGCCTAT TTCTTGGGTG GACGATCACG CCACCCATGC<br>6361 TCTCACGAAT TTCAAAACAC GGACAAGGAC GAGCACCACC AGGGCTCGTC GTTCCACGTC<br>6421 CAATACGATT ACTTACCTTT CGGGATCACG ATCACGGATC CCGCAGCTAC ATCACTTCCA<br>6481 CTCAGGACAT TCAAGCATGC ACGATCACGG CATGCTCCAC AAGTCTCAAC CACAGAAACT<br>6541 ACCAAATGGG TTCAGCACCA GCGAACCCAC TCCTACCTCA AACCTCTTCC CACAAAACTG<br>6601 GCAAGCAGGA TCACCGCTTG CCCATTCCAA CATACCAAAT CAAAAACAAT TACTGGTACA<br>6661 GCATCAGCGT ACCAGCCCAC ATCTCTCACT ACTATCAAAA ACCAAACCGT TCAGCAACAG<br>6721 CGAACGGTAC ACACGGAAAA ATCAACTGGT TTACAAATAC GAAAGACGAT CACGCTTTCG<br>6781 TCCAGCGCAA ACTATTACGA AAAACATCCG ACGGGAAGAG CAACAGCCTT CCCGCGGCGG<br>6841 AAAACCTCAC AAAAACACGA CAAACGGATG CACGAACACG GCATCCGCCG ACAACCCACA<br>6901 AACTTACAAC CAGGCAAACG GTGCAGGATC ACCGCACCGT ACATCAAACA CCTCAGATCT<br>6961 CATGCTTCTA GAAGTTGTCT CCTCCTGCAC TGACTGACTG ATACAATCGA TTTCTGGATC<br>7021 CGCAGGCCTA ATCAACCTCT GGATTACAAA ATTTGTGAAA GATTGACTGG TATTCTTAAC<br>7081 TATGTTGCTC CTTTTACGCT ATGTGGATAC GCTGCTTTAA TGCCTTTGTA TCATGCTATT<br>7141 GCTTCCCGTA TGGCTTTCAT TTTCTCCTCC TTGTATAAAT CCTGGTTGCT GTCTCTTTAT<br>7201 GAGGAGTTGT GGCCCGTTGT CAGGCAACGT GGCGTGGTGT GCACTGTGTT TGCTGACGCA<br>7261 ACCCCCACTG GTTGGGGCAT TGCCACCACC TGTCAGCTCC TTTCCGGGAC TTTCGCTTTC<br>7321 CCCCTCCCTA TTGCCACGGC GGAACTCATC GCCGCCTGCC TTGCCCGCTG CTGGACAGGG<br>7381 GCTCGGCTGT TGGGCACTGA CAATTCCGTG GTGTTGTCGG GGAAGCTGAC GTCCTTTCCA<br>7441 TGGCTGCTCG CCTGTGTTGC CACCTGGATT CTGCGCGGGA CGTCCTTCTG CTACGTCCCT<br>7501 TCGGCCCTCA ATCCAGCGGA CCTTCCTTCC CGCTGAGAGA CACAAAAAAT TCCAACACAC<br>7561 TATTGCAATG AAAATAAATT TCCTTTATTA GCCAGAAGTC AGATGCTCAA GGGGCTTCAT<br>7621 GATGTCCCCA TAATTTTTGG CAGAGGGAAA AAGATCTCAG TGGTATTTGT GAGCCAGGGC<br>7681 ATTGGCCTTC TGATAGGCAG CCTGCACCTG AGGAGTGCGG CCGCTTTACT TGTACAGCTC<br>7741 GTCCATGCCG AGAGTGATCC CGGCGGCGGT CACGAACTCC AGCAGGACCA TGTGATCGCG<br>7801 CTTCTCGTTG GGGTCTTTGC TCAGGGCGGA CTGGGTGCTC AGGTAGTGGT TGTCGGGCAG<br>7861 CAGCACGGGG CCGTCGCCGA TGGGGGTGTT CTGCTGGTAG TGGTCGGCGA GCTGCACGCT<br>7921 GCCGTCCTCG ATGTTGTGGC GGATCTTGAA GTTCACCTTG ATGCCGTTCT TCTGCTTGTC<br>7981 GGCCATGATA TAGACGTTGT GGCTGTTGTA GTTGTACTCC AGCTTGTGCC CCAGGATGTT<br>8041 GCCGTCCTCC TTGAAGTCGA TGCCCTTCAG CTCGATGCGG TTCACCAGGG TGTCGCCCTC<br>8101 GAACTTCACC TCGGCGCGGG TCTTGTAGTT GCCGTCGTCC TTGAAGAAGA TGGTGCGCTC<br>8161 CTGGACGTAG CCTTCGGGCA TGGCGGACTT GAAGAAGTCG TGCTGCTTCA TGTGGTCGGG<br>8221 GTAGCGGCTG AAGCACTGCA CGCCGTAGGT CAGGGTGGTC ACGAGGGTGG GCCAGGGCAC<br>8281 GGGCAGCTTG CCGGTGGTGC AGATGAACTT CAGGGTCAGC TTGCCGTAGG TGGCATCGCC<br>8341 CTCGCCCTCG CCGGACACGC TGAACTTGTG GCCGTTTACG TCGCCGTCCA GCTCGACCAG<br>8401 GATGGGCACC ACCCCGGTGA ACAGCTCCTC GCCCTTGCTC ACCATGGTGG CGGGATCTGA<br>8461 CGGTTCACTA AACCAGCTCT GCTTATATAG ACCTCCCACC GTACACGCCT ACCGCCCATT<br>8521 TGCGTCAATG GGGCGGAGTT GTTACGACAT TTTGGAAAGT CCCGTTGATT TTGGTGCCAA<br>8581 AACAAACTCC CATTGACGTC AATGGGGTGG AGACTTGGAA ATCCCCGTGA GTCAAACCGC<br>8641 TATCCACGCC CATTGATGTA CTGCCAAAAC CGCATCACCA TGGTAATAGC GATGACTAAT<br>8701 ACGTAGATGT ACTGCCAAGT AGGAAAGTCC CATAAGGTCA TGTACTGGGC ATAATGCCAG<br>8761 GCGGGCCATT TACCGTCATT GACGTCAATA GGGGGCGTAC TTGGCATATG ATACACTTGA<br>8821 TGTACTGCCA AGTGGGCAGT TTACCGTAAA TACTCCACCC ATTGACGTCA ATGGAAAGTC<br>8881 CCTATTGGCG TTACTATGGG AACATACGTC ATTATTGACG TCAATGGGCG GGGGTCGTTG<br>8941 GGCGGTCAGC CAGGCGGGCC ATTTACCGTA AGTTATGTAA CGGGCCTGCT GCCGGCTCTG<br>9001 CGGCCTCTTC CGCGTCTTCG CCTTCGCCCT CAGACGAGTC GGATCTCCCT TTGGGCCGCC<br>9061 TCCCCGCCTG TCTAGCTTGA CTGACTGAGA TACAGCGTAC CTTCAGCTCA CAGACATGAT<br>9121 AAGATACATT GATGAGTTTG GACAAACCAC AACTAGAATG CAGTGAAAAA AATGCTTTAT<br>9181 TTGTGAAATT TGTGATGCTA TTGCTTTATT TGTAACCATT ATAAGCTGCA ATAAACAAGT<br>9241 T<br>(SEQ ID NO: 49)<br><br>LINE 1 ORF2-minke mRNA GFP (SEQ ID NO: 50)<br>1 TAATACGACT CACTATAGGG AGAAGTACTG CCACCATGGG CAAGAAGCAA AATCGCAAGA<br>61 CGGGGAATTC CAAGACACAA TCCGCTAGCC CACCACCTAA AGAGCGTTCT AGCTCCCCTG<br>121 CTACTGAGCA GTCCTGGATG GAAAACGACT TCGATGAACT CCGGGAAGAG GGATTTAGGC<br>181 GATCCAACTA TTCAGAACTC CGCGAAGATA TCCAGACAAA GGGGAAGGAA GTCGAGAATT<br>241 TCGAGAAGAA CCTCGAGGAG TGCATCACCC GTATCACAAA CACTGAGAAA TGTCTCAAAG<br>301 AACTCATGGA ACTTAAGACA AAAGCCAGGG AGCTTCGAGA GGAGTGTCGG AGTCTGAGAT<br>361 CCAGGTGTGA CCAGCTCGAG GAGCGCGTGA GCGCGATGGA AGACGAGATG AACGAGATGA |

TABLE 8-continued

| Plasmid and mRNA construct sequences |
|---|
| 421 AAAGAGAGGG CAAATTCAGG GAGAAGCGCA TTAAGAGGAA CGAACAGAGT CTGCAGGAGA |
| 481 TTTGGGATTA CGTCAAGAGG CCTAACCTGC GGTTGATCGG CGTCCCCGAG AGCGACGTAG |
| 541 AAAACGGGAC TAAACTGGAG AATACACTTC AAGACATCAT TCAAGAAAAT TTTCCAAACC |
| 601 TGGCTCGGCA AGCTAATGTG CAAATCCAAG AGATCCAACG CACACCCCAG CGGTATAGCT |
| 661 CTCGGCGTGC CACCCCTAGG CATATTATCG TGCGCTTTAC TAAGGTGGAG ATGAAAGAGA |
| 721 AGATGCTGCG AGCCGCTCGG GAAAAGGGAA GGGTGACTTT GAAGGGCAAA CCTATTCGGC |
| 781 TGACGGTTGA CCTTAGCGCC GAGACACTCC AGGCACGCCG GGAATGGGGC CCCATCTTTA |
| 841 ATATCCTGAA GGAGAAGAAC TTCCAGCCAC GAATCTCTTA CCCTGCAAAG TTGAGTTTTA |
| 901 TCTCCGAGGG TGAGATTAAG TATTTCATCG ATAAACAGAT GCTGCGAGAC TTCGTGACAA |
| 961 CTCGCCCAGC TCTCAAGGAA CTGCTCAAAG AGGCTCTTAA TATGGAGCGC AATAATAGAT |
| 1021 ATCAACCCTT GCAGAACCAC GCAAAGATGT GAGACAGCCG TCAGACCATC AAGACTAGGA |
| 1081 AGAAACTGCA TCAACTAATG AGCAAAATCA CCAGCTAACA TCATAGTATA CATGGTCATA |
| 1141 GGAACTTACA TTTCGATTAT TACCTTAAAC GTGAATGGGT TAAATGCCCC AACCAAGAGA |
| 1201 CATCGGCTGG CTGAATGGAT TCAGAAACAG GACCCCTATA TTTGCTGTCT GCAGGAGACC |
| 1261 CACTTCCGTC CTCGCGACAC ATACAGACTG AAAGTGAGGG GCTGGAAAAA GATCTTCCAT |
| 1321 GCCAATGGAA ATCAAAAGAA AGCTGGAGTG GCTATTCTCA TCTCAGATAA AATTGACTTC |
| 1381 AAAATAAAGA ATGTTACTCG AGATAAGGAG GGACACTACA TAATGATCCA GGGGTCCATC |
| 1441 CAAGAAGAGG ATATAACTAT TATTAATATT TATGCACCCA ACATTGGCGC CCCTCAGTAC |
| 1501 ATCAGGCAGC TGCTTACAGC TATCAAGGAG GAAATCGACA GTAACACGAT TATCGTGGGG |
| 1561 GACTTTAACA CCAGCCTTAC TCCGATGGAT AGATCATCCA AAATGAAAAT AAATAAGGAA |
| 1621 ACAGAGGCTC TTAATGACAC CATTGACCAG ATAGATCTGA TTGATATATA TAGGACATTC |
| 1681 CATCCAAAAA CTGCCGATTA CACTTTCTTC AGCAGTGCGC ATGGAACCTT CTCCAGGATA |
| 1741 GATCACATCT TGGGTCACAA AAGTAGCCTC AGTAAGTTTA AGAAAATTGA AATCATTAGC |
| 1801 AGCATCTTTT CTGACCATAA CGCTATGCGC CTGGAGATGA ATCACAGGGA GAAGAACGTA |
| 1861 AAGAAGACAA ACACCTGGAG GCTGAACAAT ACGCTGCTAA ATAACCAAGA GATCACTGAG |
| 1921 GAAATCAAAC AGGAAATAAA AAAATACTTG GAGACAAATG ACAATGAAAA CACGACCACC |
| 1981 CAGAACTTGT GGGATGCAGC TAAAGCGGTT CTGAGAGGGA AGTTTATAGC TATTCAAGCC |
| 2041 TACCTTAAGA AACAGGAAAA ATCTCAAGTG AACAATTTGA CCTTACACCT AAAGAAACTG |
| 2101 GAGAAGGAGG AGCAGACCAA ACCCAAAGTG AGCAGGAGGA AAGAAATCAT CAAGATCAGA |
| 2161 GCCGAAATCA ATGAAATAGA AACTAAGAAG ACAATTGCCA AGATCAATAA AACTAAATCC |
| 2221 TGGTTCTTTG AGAAGATCAA CAAAATTGAT AAGCCATTAG CCAGACTCAT CAAGAAAAAG |
| 2281 AGGGAGAGGA CTCAGATCAA TAAGATCAGA AATGAGAAAG GGGAAGTTAC AACCGACACC |
| 2341 GCGGAGATTC AGAACATCCT GAGAGACTAC TACAAGCAAC TTTATGCCAA TAAAATGGAC |
| 2401 AACCTGGAAG AAATGGACAA ATTCCTGGAA AGGTATAACC TTCCCCGGCT GAACCAGGAG |
| 2461 GAGACTGAAA ATATCAACCG CCCAATCACA AGTAATGAGA TTGAGACTGT GATTAAGAAT |
| 2521 CTTCCAACTA ACAAAAGTCC CGGCCCCGAT GGCTTCACAG GTGAATTCTA TCAGACCTTT |
| 2581 CGGGAGGAGT TGACACCCAT CCTTCTCAAG CTCTTCCAAA AAATTGCAGA GGAGGGCACA |
| 2641 CTCCCGAACT CATTCTATGA GGCCACCATC ACCCTGATCC CAAAGCCCGA CAAGGACACT |
| 2701 ACAAAGAAAG AAAATTACCG ACCAATTTCC CTGATGAATA TCGATGCCAA GATCCTCAAC |
| 2761 AAAATCTTGG CAAACAGAAT CCAGCAGCAC ATTAAGAGGA TCATACACCA CGATCAGGTG |
| 2821 GGCTTTATCC CGGGGATGCA AGGATTCTTC AATATCCGCA AATCAATCAA TGTGATCCAC |
| 2881 CATATTAACA AGTTGAAGAA GAAGAACCAT ATGATCATCT CCATCGATGC AGAGAAAGCT |
| 2941 TTTGACAAAA TTCAACACCC ATTTATGATC AAAACTCTCC AGAAGGTGGG CATCGAGGGG |
| 3001 ACCTACCTCA ACATAATTAA GGCCATCTAT GATAAGCCCA CAGCCAACAT CATTCTCAAT |
| 3061 GGTGAAAAGC TGAAGGCATT TCCTCTGCGG TCCGGAACGA GACAGGGATG TCCTCTCTCT |
| 3121 CCTCTTCTGT TCAACATCGT TCTGGAAGTC CTAGCCACCG CTATCCGCGA GGAAAAGGAA |
| 3181 ATTAAAGGCA TACAGATTGG AAAGGAAGAG GTAAAACTGT CTCTGTTTGC GGATGATATG |
| 3241 ATACTGTACA TAGAGAATCC TAAAACTGCC ACCCGGAAGC TGTTGGAGCT AATTAATGAG |
| 3301 TATGGTAAGG TCGCCGGTTA CAAGATTAAT GCTCAGAAGT CTCTTGCTTT CCTGTACACT |
| 3361 AATGATGAAA AGTCTGAACG GGAAATTATG GAGACACTCC CCTTTACCAT TGCAACCAAA |
| 3421 CGTATTAAAT ACCTTGGCAT TAACCTGCCT AAGGAGACAA AAGACCTGTA TGCTGAAAAC |
| 3481 TATAAGACAC TGATGAAAGA GATTAAAGAT GATACCAACC GGTGGCGGGA TATCCCATGT |
| 3541 TCTTGGATTG GCAGAATCAA CATTGTGAAG ATGAGCATCC TGCCCAAGGC CATCTACAGA |
| 3601 TTCAATGCCA TCCCTATCAA ATTACCTATG GCATTTTTTA CGGAGCTGGA ACAGATCATC |
| 3661 TTAAAATTTG TGTGGCGCCA CAAGCGGCCC CGAATCGCCA AAGCGGTCTT GAGGCAGAAG |
| 3721 AATGGCGCTG GGGGAATCCG ACTCCCTGAC TTCAGATTGT ACTACAAAGC TACCGTCATC |
| 3781 AAGACAATCT GGTACTGGCA CAAGAACAGA AACATCGATC AGTGGAACAA GATCGAAAGC |
| 3841 CCTGAGATTA ACCCCCGCAC CTATGGTCAA CTGATCTATG ACAAAGGGGG CAAGGATATA |
| 3901 CAATGGCGCA AGGACAGCCT CTTCAATAAG TGGTGCTGGG AAAACTGGAC AGCCACCTGC |
| 3961 AAGCGTATGA AGCTGGAGTA CTCCCTGACA CCATACACAA AAATAAACTC AAAGTGGATT |
| 4021 CGAGACCTCA ATATTCGGCT GGACACTATA AAACTCCTGG AGGAGAACAT TGGGCGTACA |
| 4081 CTCTTTGACA TTAATCATAG CAAGATCTTT TTCGATCCCC CTCCTCGTGT AATGGAAATA |
| 4141 AAAACAAAAA TAAACAAGTG GGATCTGATG AAACTTCAGA GCTTTTGCAC CGCAAAGGAG |
| 4201 ACCATAAACA AGACGAAGCG CCAACCCTCA GAATGGGAGA AAATATTTGC GAATGAGTCT |
| 4261 ACGGACAAAG GCTTAATCTC CAAAATATAT AAGCAGCTCA TTCAGCTCAA TATCAAGGAA |
| 4321 ACAAACACCC CGATCCAAAA GTGGGCAGAG GACCTAAATC GGCATTTCTC CAAGGAAGAC |
| 4381 ATCCAGACGG CCACGAAGCA CATGAAGCGA TGCTCAACTT CCCTGATTAT TCGCGAAATG |
| 4441 CAGATCAAGA CTACTATGCG CTATCACCTC ACTCCTGTTC GGATGGGCAT CATCCGGAAA |
| 4501 TCTACAAACA ACAAGTGCTG GAGAGGGTGT GGCGAAAAGG GAACCCTCTT GCATTGTTGG |
| 4561 TGGGAGTGTA AGTTGATCCA GCCACTATGG CGGACCATAT GGAGGTTCCT TAAAAAACTG |
| 4621 AAGATTGAGC TGCCATATGA CCCAGCAATC CCACTGCTGG GCATATACCC GGAGAAAACC |
| 4681 GTGATTCAGA AAGACACTTG CACCCGAATG TTCATTGCAG CATTGTTTAC AATAGCCAGG |
| 4741 TCATGGAAGC AGCCTAAGTG CCCCTCGACA GACGAGTGGA TCAAGAAGAT GTGGTACATT |
| 4801 TATACTATGG AATATTACAG CGCCATCAAA CGCAACGAAA TTGGGTCTTT TCTGGAGACG |
| 4861 TGGATGGATC TAGAGACTGT CATCCAGAGT GAGGTAAGTC AGAAAGAGAA GAACAAATAT |
| 4921 CGTATTTTAA CGCATATTTG TGGAACCTGG AAGAATGGTA CAGATGAGCC GGTCTGCCGA |
| 4981 ACCGAGATTG AGACCCAGAT GGACTACAAA GACGATGACG ACAAGTGAAG CGCTTCTAGA |
| 5041 AGTTGTCTCC TCCTGCACTG ACTGACTGAT ACAATCGATT TCTGGATCCG CAGGCCTAAT |

TABLE 8-continued

| Plasmid and mRNA construct sequences |
| --- |
| 5101 CAACCTCTGG ATTACAAAAT TTGTGAAAGA TTGACTGGTA TTCTTAACTA TGTTGCTCCT |
| 5161 TTTACGCTAT GTGGATACGC TGCTTTAATG CCTTTGTATC ATGCTATTGC TTCCCGTATG |
| 5221 GCTTTCATTT TCTCCTCCTT GTATAAATCC TGGTTGCTGT CTCTTTATGA GGAGTTGTGG |
| 5281 CCCGTTGTCA GGCAACGTGG CGTGGTGTGC ACTGTGTTTG CTGACGCAAC CCCCACTGGT |
| 5341 TGGGGCATTG CCACCACCTG TCAGCTCCTT TCCGGGACTT TCGCTTTCCC CCTCCCTATT |
| 5401 GCCACGGCGG AACTCATCGC CGCCTGCCTT GCCCGCTGCT GGACAGGGGC TCGGCTGTTG |
| 5461 GGCACTGACA ATTCCGTGGT GTTGTCGGGG AAGCTGACGT CCTTTCCATG GCTGCTCGCC |
| 5521 TGTGTTGCCA CCTGGATTCT GCGCGGGACG TCCTTCTGCT ACGTCCCTTC GGCCCTCAAT |
| 5581 CCAGCGGACC TTCCTTCCCG CTGAGAGACA CAAAAAATTC CAACACACTA TTGCAATGAA |
| 5641 AATAAATTTC CTTTATTAGC CAGAAGTCAG ATGCTCAAGG GGCTTCATGA TGTCCCCATA |
| 5701 ATTTTTGGCA GAGGGAAAAA GATCTCAGTG GTATTTGTGA GCCAGGGCAT TGGCCTTCTG |
| 5761 ATAGGCAGCC TGCACCTGAG GAGTGCGGCC GCTTTACTTG TACAGCTCGT CCATGCCGAG |
| 5821 AGTGATCCCG GCGGCGGTCA CGAACTCCAG CAGGACCATG TGATCGCGCT TCTCGTTGGG |
| 5881 GTCTTTGCTC AGGGCGGACT GGGTGCTCAG GTAGTGGTTG TCGGGCAGCA GCACGGGGCC |
| 5941 GTCGCCGATG GGGGTGTTCT GCTGGTAGTG GTCGGCGAGC TGCACGCTGC CGTCCTCGAT |
| 6001 GTTGTGGCGG ATCTTGAAGT TCACCTTGAT GCCGTTCTTC TGCTTGTCGG CCATGATATA |
| 6061 GACGTTGTGG CTGTTGTAGT TGTACTCCAG CTTGTGCCCC AGGATGTTGC CGTCCTCCTT |
| 6121 GAAGTCGATG CCCTTCAGCT CGATGCGGTT CACCAGGGTG TCGCCCTCGA ACTTCACCTC |
| 6181 GGCGCGGGTC TTGTAGTTGC CGTCGTCCTT GAAGAAGATG GTGCGCTCCT GGACGTAGCC |
| 6241 TTCGGGCATG GCGGACTTGA AGAAGTCGTG CTGCTTCATG TGGTCGGGGT AGCGGCTGAA |
| 6301 GCACTGCACG CCGTAGGTCA GGGTGGTCAC GAGGGTGGGC CAGGGCACGG GCAGCTTGCC |
| 6361 GGTGGTGCAG ATGAACTTCA GGGTCAGCTT GCCGTAGGTG GCATCGCCCT CGCCCTCGCC |
| 6421 GGACACGCTG AACTTGTGGC CGTTTACGTC GCCGTCCAGC TCGACCAGGA TGGGCACCAC |
| 6481 CCCGGTGAAC AGCTCCTCGC CCTTGCTCAC CATGGTGGCG GGATCTGACG GTTCACTAAA |
| 6541 CCAGCTCTGC TTATATAGAC CTCCCACCGT ACACGCCTAC CGCCCATTTG CGTCAATGGG |
| 6601 GCGGAGTTGT TACGACATTT TGGAAAGTCC CGTTGATTTT GGTGCCAAAA CAAACTCCCA |
| 6661 TTGACGTCAA TGGGGTGGAG ACTTGGAAAT CCCCGTGAGT CAAACCGCTA TCCACGCCCA |
| 6721 TTGATGTACT GCCAAAACCG CATCACCATG GTAATAGCGA TGACTAATAC GTAGATGTAC |
| 6781 TGCCAAGTAG GAAAGTCCCA TAAGGTCATG TACTGGGCAT AATGCCAGGC GGGCCATTTA |
| 6841 CCGTCATTGA CGTCAATAGG GGGCGTACTT GGCATATGAT ACACTTGATG TACTGCCAAG |
| 6901 TGGGCAGTTT ACCGTAAATA CTCCACCCAT TGACGTCAAT GGAAAGTCCC TATTGGCGTT |
| 6961 ACTATGGGAA CATACGTCAT TATTGACGTC AATGGGCGGG GGTCGTTGGG CGGTCAGCCA |
| 7021 GGCGGGCCAT TTACCGTAAG TTATGTAACG GGCCTGCTGC CGGCTCTGCG GCCTCTTCCG |
| 7081 CGTCTTCGCC TTCGCCCTCA GACGAGTCGG ATCTCCCTTT GGGCCGCCTC CCCGCCTGTC |
| 7141 TAGCTTGACT GACTGAGATA CAGCGTACCT TCAGCTCACA GACATGATAA GATACATTGA |
| 7201 TGAGTTTGGA CAAACCACAA CTAGAATGCA GTGAAAAAAA TGCTTTATTT GTGAAATTTG |
| 7261 TGATGCTATT GCTTTATTTG TAACCATTAT AAGCTGCAAT AAACAAGTT (SEQ ID NO: 50) |

What is claimed is:

1. A composition comprising a genome editing system comprising (i) one or more synthetic or recombinant RNA molecules comprising:

(I)(a) a sequence encoding a Cas endonuclease, wherein the Cas endonuclease is Cas9 nickase capable of cleavage of a strand of genomic DNA at a target site; and (b) a guide RNA, wherein the guide RNA comprises a sequence capable of guiding the Cas endonuclease to the target site of the genomic DNA to create a 5'-P terminus and a 3'-OH terminus at the target site, (II) (a) a cassette comprising (i) a sequence encoding human LINE1 ORF2p, wherein the human LINE1 ORF2p comprises a reverse transcriptase (RT) domain capable of target-primed reverse transcription (TPRT) at the 3'-OH terminus at the target site and an endonuclease (EN) domain:

wherein the sequence encoding human LINE1 ORF2p is fused to a first sequence encoding a nuclear localization sequence (NLS) that is N-terminal to the sequence encoding the human LINE1 ORF2p and a second sequence encoding an NLS sequence that is C-terminal to the sequence encoding the human LINE1 ORF2p to facilitate nuclear import, wherein the human LINE1 ORF2p comprises a sequence with at least 95% sequence identity to SEQ ID NO: 55; and wherein the LINE1 ORF2p comprises a D205 mutation that abrogates endonuclease activity; and (ii) a sequence encoding human LINE1 ORF1p;

(b) an insert sequence, wherein the insert sequence comprises a sequence encoding an exogenous therapeutic polypeptide;

(c) a 5' nucleic acid sequence flanking the insert sequence and upstream of the insert sequence, wherein the 5' nucleic acid sequence is an untranslated region (UTR), and (d) a 3' nucleic acid sequence flanking the insert sequence and downstream of the insert sequence, wherein the 3' nucleic acid sequence is an untranslated region (UTR) and comprises:

(i) a genomic DNA priming sequence capable of binding to and priming the genomic DNA at the target site cleaved by the Cas endonuclease, and (ii) binding site for the human LINE1 ORF2p, wherein the genomic DNA priming sequence and the binding site for the human LINE1 ORF2p are capable of starting TPRT at the 3'-OH terminus at the target site by the human LINE1 ORF2p for incorporating the insert sequence.

2. The composition of claim 1, wherein the human LINE1 ORF2p comprises the sequence according to SEQ ID NO: 55 with a D205 mutation that abrogates endonuclease activity.

3. The composition of claim 1, wherein the sequence encoding the Cas9 nickase is on a different synthetic or recombinant RNA molecule than the cassette and the insert sequence.

4. The composition of claim 1, wherein the genomic DNA priming sequence of the 3' nucleic acid sequence flanking the insert sequence is 2-15 nucleotides in length.

5. The composition of claim 1, wherein the first NLS sequence and the second NLS sequence are derived from the same protein.

6. The composition of claim 1, wherein the first NLS sequence and the second NLS sequence are derived from different proteins.

7. The composition of claim 1, wherein the human LINE1 ORF1p sequence is fused with one or more NLS sequences.

8. The composition of claim 1, wherein the cassette comprises one, two, three or more stop codons designed to be both in multiple reading frames and in tandem.

9. A pharmaceutical composition comprising the composition of claim 1, and a pharmaceutically acceptable excipient, wherein the composition is formulated for systemic administration to a subject.

10. The pharmaceutical composition of claim 9, further comprising a lipid nanoparticle.

11. The composition of claim 1, wherein the sequence encoding the exogenous therapeutic polypeptide is at least 3 kb in length.

12. The composition of claim 1, wherein the 5' nucleic acid sequence flanking the insert sequence is downstream of the cassette.

13. The composition of claim 1, wherein the 5' nucleic acid sequence flanking the insert sequence comprises a binding site for the human LINE1 ORF2p.

14. The composition of claim 1, wherein the 5' nucleic acid sequence flanking the insert sequence comprises a sequence that is complementary to the sequence of a target region within the genome.

15. The composition of claim 2, wherein the first NLS sequence and the second NLS sequence are derived from the same protein.

16. The composition of claim 2, wherein the first NLS sequence and the second NLS sequence are derived from different proteins.

* * * * *

SEQUENCE LISTING

<160> NUMBER OF SEQ ID NOS: 85

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 1

Glu Ile Gln Leu Val Gln Ser Gly Gly Gly Leu Val Lys Pro Gly Gly
1 5 10 15

Ser Val Arg Ile Ser Cys Ala Ala Ser Gly Tyr Thr Phe Thr Asn Tyr
20 25 30

Gly Met Asn Trp Val Arg Gln Ala Pro Gly Lys Gly Leu Glu Trp Met
35 40 45

Gly Trp Ile Asn Thr His Thr Gly Glu Pro Thr Tyr Ala Asp Ser Phe
50 55 60

Lys Gly Arg Phe Thr Phe Ser Leu Asp Asp Ser Lys Asn Thr Ala Tyr
65 70 75 80

Leu Gln Ile Asn Ser Leu Arg Ala Glu Asp Thr Ala Val Tyr Phe Cys
85 90 95

Thr Arg Arg Gly Tyr Asp Trp Tyr Phe Asp Val Trp Gly Gln Gly Thr
100 105 110

```
Thr Val Thr Val
        115


<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95

Thr Phe Gly Gly Gly Thr Lys Leu Glu Ile Lys
            100                 105


<210> SEQ ID NO 3
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Tyr Cys Arg Arg Leu Lys Ile Gln Val Arg Lys Ala Ala Ile Thr
1               5                   10                  15

Ser Tyr Glu Lys Ser Asp Gly Val Tyr Thr Gly Leu Ser Thr Arg Asn
            20                  25                  30

Gln Glu Thr Tyr Glu Thr Leu Lys His Glu Lys Pro Pro Gln
        35                  40                  45


<210> SEQ ID NO 4
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Tyr Glu Asp Met Arg Gly Ile Leu Tyr Ala Ala Pro Gln Leu Arg Ser
1               5                   10                  15

Ile Arg Gly Gln Pro Gly Pro Asn His Glu Glu Asp Ala Asp Ser Tyr
            20                  25                  30

Glu Asn Met
        35


<210> SEQ ID NO 5
<211> LENGTH: 62
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 5

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60


<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Tyr Ile Trp Ala Pro Leu Ala Gly Thr Cys Gly Val Leu Leu Leu
1               5                   10                  15

Ser Leu Val Ile Thr
            20


<210> SEQ ID NO 7
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp
    50                  55                  60


<210> SEQ ID NO 8
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Gly Ser Thr
            100                 105                 110

Ser Gly Ser Gly Lys Pro Gly Ser Gly Glu Gly Ser Glu Val Gln Leu
        115                 120                 125

Val Glu
    130


<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Leu Val Gln Pro Gly Gly Ser Leu Arg Leu Ser Cys Ala Ala Ser Gly
1               5                   10                  15

Phe Asn Ile Lys Asp Thr Tyr Ile His Trp Val Arg Gln Ala Pro Gly
            20                  25                  30

Lys Gly Leu Glu Trp Val Ala Arg Ile Tyr Pro Thr Asn Gly Tyr Thr
        35                  40                  45

Arg Tyr Ala Asp Ser Val Lys Gly Arg Phe Thr Ile Ser Ala Asp Thr
    50                  55                  60

Ser Lys Asn Thr Ala Tyr Leu Gln Met Asn Ser Leu Arg Ala Glu Asp
65                  70                  75                  80

Thr Ala Val Tyr Tyr Cys Ser Arg Trp Gly Gly Asp Gly Phe Tyr Ala
                85                  90                  95

Met Asp Val Trp Gly Gln Gly Thr Leu Val Thr Val
            100                 105


<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ser Gly Gly Gly Gly Ser Gly Gly Gly Gly Ser Gly Gly Gly Gly
1               5                   10                  15

Ser


<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gly Gly Gly Gly Ser Gly
1               5
```

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Ser Gly Gly Gly
1
```

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Gly Ser Gly Ser
1
```

<210> SEQ ID NO 14
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205
```

```
Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Leu Lys Ile Gln Val Arg Lys Ala Ala Ile Thr Ser Tyr Glu Lys Ser
        355                 360                 365

Asp Gly Val Tyr Thr Gly Leu Ser Thr Arg Asn Gln Glu Thr Tyr Glu
    370                 375                 380

Thr Leu Lys His Glu Lys Pro Pro Gln Gly Ser Gly Ser Tyr Glu Asp
385                 390                 395                 400

Met Arg Gly Ile Leu Tyr Ala Ala Pro Gln Leu Arg Ser Ile Arg Gly
                405                 410                 415

Gln Pro Gly Pro Asn His Glu Glu Asp Ala Asp Ser Tyr Glu Asn Met
            420                 425                 430
```

<210> SEQ ID NO 15
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Met Trp Leu Gln Ser Leu Leu Leu Leu Gly Thr Val Ala Cys Ser Ile
1               5                   10                  15

Ser Asp Ile Gln Met Thr Gln Ser Pro Ser Ser Leu Ser Ala Ser Val
            20                  25                  30

Gly Asp Arg Val Thr Ile Thr Cys Arg Ala Ser Gln Asp Val Asn Thr
        35                  40                  45

Ala Val Ala Trp Tyr Gln Gln Lys Pro Gly Lys Ala Pro Lys Leu Leu
    50                  55                  60

Ile Tyr Ser Ala Ser Phe Leu Tyr Ser Gly Val Pro Ser Arg Phe Ser
65                  70                  75                  80

Gly Ser Arg Ser Gly Thr Asp Phe Thr Leu Thr Ile Ser Ser Leu Gln
                85                  90                  95

Pro Glu Asp Phe Ala Thr Tyr Tyr Cys Gln Gln His Tyr Thr Thr Pro
            100                 105                 110

Pro Thr Phe Gly Gln Gly Thr Lys Val Glu Ile Lys Arg Thr Gly Ser
        115                 120                 125

Thr Ser Gly Ser Gly Lys Pro Gly Ser Gly Glu Gly Ser Glu Val Gln
    130                 135                 140
```

Leu Val Glu Ser Gly Gly Gly Leu Val Gln Pro Gly Gly Ser Leu Arg
145 150 155 160

Leu Ser Cys Ala Ala Ser Gly Phe Asn Ile Lys Asp Thr Tyr Ile His
165 170 175

Trp Val Arg Gln Ala Pro Gly Lys Gly Leu Glu Trp Val Ala Arg Ile
180 185 190

Tyr Pro Thr Asn Gly Tyr Thr Arg Tyr Ala Asp Ser Val Lys Gly Arg
195 200 205

Phe Thr Ile Ser Ala Asp Thr Ser Lys Asn Thr Ala Tyr Leu Gln Met
210 215 220

Asn Ser Leu Arg Ala Glu Asp Thr Ala Val Tyr Tyr Cys Ser Arg Trp
225 230 235 240

Gly Gly Asp Gly Phe Tyr Ala Met Asp Val Trp Gly Gln Gly Thr Leu
245 250 255

Val Thr Val Ser Ser Ser Gly Gly Gly Gly Ser Gly Ala Leu Ser Asn
260 265 270

Ser Ile Met Tyr Phe Ser His Phe Val Pro Val Phe Leu Pro Ala Lys
275 280 285

Pro Thr Thr Thr Pro Ala Pro Arg Pro Pro Thr Pro Ala Pro Thr Ile
290 295 300

Ala Ser Gln Pro Leu Ser Leu Arg Pro Glu Ala Cys Arg Pro Ala Ala
305 310 315 320

Gly Gly Ala Val His Thr Arg Gly Leu Asp Ile Tyr Ile Trp Ala Pro
325 330 335

Leu Ala Gly Thr Cys Gly Val Leu Leu Leu Ser Leu Val Ile Thr Leu
340 345 350

Tyr Cys Arg Arg Leu Lys Ile Gln Val Arg Lys Ala Ala Ile Thr Ser
355 360 365

Tyr Glu Lys Ser Asp Gly Val Tyr Thr Gly Leu Ser Thr Arg Asn Gln
370 375 380

Glu Thr Tyr Glu Thr Leu Lys His Glu Lys Pro Pro Gln Gly Ser Gly
385 390 395 400

Ser Tyr Glu Asp Met Arg Gly Ile Leu Tyr Ala Ala Pro Gln Leu Arg
405 410 415

Ser Ile Arg Gly Gln Pro Gly Pro Asn His Glu Glu Asp Ala Asp Ser
420 425 430

Tyr Glu Asn Met
435

<210> SEQ ID NO 16
<211> LENGTH: 454
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Met Trp Leu Gln Ser Leu Leu Leu Leu Gly Thr Val Ala Cys Ser Ile
1 5 10 15

Ser Glu Ile Gln Leu Val Gln Ser Gly Gly Gly Leu Val Lys Pro Gly
20 25 30

Gly Ser Val Arg Ile Ser Cys Ala Ala Ser Gly Tyr Thr Phe Thr Asn
35 40 45

Tyr Gly Met Asn Trp Val Arg Gln Ala Pro Gly Lys Gly Leu Glu Trp

```
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
        355                 360                 365

Gly Val Tyr Thr Gly Leu Ser Thr Arg Asn Gln Glu Thr Tyr Glu Thr
    370                 375                 380

Leu Lys His Glu Lys Pro Pro Gln Lys Lys Val Ala Lys Lys Pro Thr
385                 390                 395                 400

Asn Lys Ala Pro His Pro Lys Gln Glu Pro Gln Glu Ile Asn Phe Pro
                405                 410                 415

Asp Asp Leu Pro Gly Ser Asn Thr Ala Ala Pro Val Gln Glu Thr Leu
            420                 425                 430

His Gly Cys Gln Pro Val Thr Gln Glu Asp Gly Lys Glu Ser Arg Ile
        435                 440                 445

Ser Val Gln Glu Arg Gln
    450
```

<210> SEQ ID NO 17

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Trp Leu Gln Ser Leu Leu Leu Leu Gly Thr Val Ala Cys Ser Ile
1               5                   10                  15

Ser


<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Leu Leu Pro Leu Ile Ile Gly Leu Ile Leu Leu Gly Leu Leu Ala
1               5                   10                  15

Leu Val Leu Ile Ala Phe Cys Ile Ile
            20                  25


<210> SEQ ID NO 20
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Tyr Cys Arg Leu Lys Ile Gln Val Arg Lys Ala Ala Ile Thr Ser
1               5                   10                  15

Tyr Glu Lys Ser Asp Gly Val Tyr Thr Gly Leu Ser Thr Arg Asn Gln
            20                  25                  30

Glu Thr Tyr Glu Thr Leu Lys His Glu Lys Pro Pro Gln
        35                  40                  45


<210> SEQ ID NO 21
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

```
Gln Arg Trp Lys Ser Lys Leu Tyr Ser Ile Val Cys Gly Lys Ser Thr
1               5                   10                  15

Pro Glu Lys Glu Gly Glu Leu Glu Gly Thr Thr Thr Lys Pro Leu Ala
            20                  25                  30

Pro Asn Pro Ser Phe Ser Pro Thr Pro Gly Phe Thr Pro Thr Leu Gly
        35                  40                  45

Phe Ser Pro Val Pro Ser Ser Thr Phe Thr Ser Ser Ser Thr Tyr Thr
    50                  55                  60

Pro Gly Asp Cys Pro Asn Phe Ala Ala Pro Arg Arg Glu Val Ala Pro
65                  70                  75                  80

Pro Tyr Gln Gly Ala Asp Pro Ile Leu Ala Thr Ala Leu Ala Ser Asp
                85                  90                  95

Pro Ile Pro Asn Pro Leu Gln Lys Trp Glu Asp Ser Ala His Lys Pro
            100                 105                 110

Gln Ser Leu Asp Thr Asp Asp Pro Ala Thr Leu Tyr Ala Val Val Glu
        115                 120                 125

Asn Val Pro Pro Leu Arg Trp Lys Glu Phe Val Arg Arg Leu Gly Leu
    130                 135                 140

Ser Asp His Glu Ile Asp Arg Leu Glu Leu Gln Asn Gly Arg Cys Leu
145                 150                 155                 160

Arg Glu Ala Gln Tyr Ser Met Leu Ala Thr Trp Arg Arg Arg Thr Pro
                165                 170                 175

Arg Arg Glu Ala Thr Leu Glu Leu Leu Gly Arg Val Leu Arg Asp Met
            180                 185                 190

Asp Leu Leu Gly Cys Leu Glu Asp Ile Glu Glu Ala Leu Cys Gly Pro
        195                 200                 205

Ala Ala Leu Pro Pro Ala Pro Ser Leu Leu Arg
    210                 215


<210> SEQ ID NO 22
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Pro Leu Cys Leu Gln Arg Glu Ala Lys Val Pro His Leu Pro Ala Asp
1               5                   10                  15

Lys Ala Arg Gly Thr Gln Gly Pro Glu Gln Gln His Leu Leu Ile Thr
            20                  25                  30

Ala Pro Ser Ser Ser Ser Ser Ser Leu Glu Ser Ser Ala Ser Ala Leu
        35                  40                  45

Asp Arg Arg Ala Pro Thr Arg Asn Gln Pro Gln Ala Pro Gly Val Glu
    50                  55                  60

Ala Ser Gly Ala Gly Glu Ala Arg Ala Ser Thr Gly Ser Ser Asp Ser
65                  70                  75                  80

Ser Pro Gly Gly His Gly Thr Gln Val Asn Val Thr Cys Ile Val Asn
                85                  90                  95

Val Cys Ser Ser Ser Asp His Ser Ser Gln Cys Ser Ser Gln Ala Ser
            100                 105                 110

Ser Thr Met Gly Asp Thr Asp Ser Ser Pro Ser Glu Ser Pro Lys Asp
        115                 120                 125

Glu Gln Val Pro Phe Ser Lys Glu Glu Cys Ala Phe Arg Ser Gln Leu
    130                 135                 140
```

```
Glu Thr Pro Glu Thr Leu Leu Gly Ser Thr Glu Glu Lys Pro Leu Pro
145                 150                 155                 160

Leu Gly Val Pro Asp Ala Gly Met Lys Pro Ser
                165                 170


<210> SEQ ID NO 23
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ser Asn Gly Tyr Ser Thr Asp Glu Asn Phe Arg Tyr Leu Ile Ser
1               5                   10                  15

Cys Phe Arg Ala Arg Val Lys Met Tyr Ile Gln Val Glu Pro Val Leu
            20                  25                  30

Asp Tyr Leu Thr Phe Leu Pro Ala Glu Val Lys Glu Gln Ile Gln Arg
        35                  40                  45

Thr Val Ala Thr Ser Gly Asn Met Gln Ala Val Glu Leu Leu Leu Ser
    50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Ala Arg Tyr Met Asn
                85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
        115                 120                 125

Leu Leu Val Arg Asp Val Leu Asp Lys Cys Met Glu Glu Glu Leu Leu
    130                 135                 140

Thr Ile Glu Asp Arg Asn Arg Ile Ala Ala Ala Glu Asn Asn Gly Asn
145                 150                 155                 160

Glu Ser Gly Val Arg Glu Leu Leu Lys Arg Ile Val Gln Lys Glu Asn
                165                 170                 175

Trp Phe Ser Ala Phe Leu Asn Val Leu Arg Gln Thr Gly Asn Asn Glu
            180                 185                 190

Leu Val Gln Glu Leu Thr Gly Ser Asp Cys Ser Glu Ser Asn Ala Glu
        195                 200                 205

Ile Glu Asn
    210


<210> SEQ ID NO 24
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45
```

```
Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
        355                 360                 365

Gly Val Tyr Thr Gly Leu Ser Thr Arg Asn Gln Glu Thr Tyr Glu Thr
    370                 375                 380

Leu Lys His Glu Lys Pro Pro Gln Gly Ser Gly Ser Met Ser Asn Gly
385                 390                 395                 400

Tyr Ser Thr Asp Glu Asn Phe Arg Tyr Leu Ile Ser Cys Phe Arg Ala
                405                 410                 415

Arg Val Lys Met Tyr Ile Gln Val Glu Pro Val Leu Asp Tyr Leu Thr
            420                 425                 430

Phe Leu Pro Ala Glu Val Lys Glu Gln Ile Gln Arg Thr Val Ala Thr
        435                 440                 445

Ser Gly Asn Met Gln Ala Val Glu Leu Leu Leu Ser Thr Leu Glu Lys
    450                 455                 460
```

```
Gly Val Trp His Leu Gly Trp Thr Arg Glu Phe Val Glu Ala Leu Arg
465                 470                 475                 480

Arg Thr Gly Ser Pro Leu Ala Ala Arg Tyr Met Asn Pro Glu Leu Thr
                485                 490                 495

Asp Leu Pro Ser Pro Ser Phe Glu Asn Ala His Asp Glu Tyr Leu Gln
            500                 505                 510

Leu Leu Asn Leu Leu Gln Pro Thr Leu Val Asp Lys Leu Leu Val Arg
        515                 520                 525

Asp Val Leu Asp Lys Cys Met Glu Glu Glu Leu Leu Thr Ile Glu Asp
    530                 535                 540

Arg Asn Arg Ile Ala Ala Ala Glu Asn Asn Gly Asn Glu Ser Gly Val
545                 550                 555                 560

Arg Glu Leu Leu Lys Arg Ile Val Gln Lys Glu Asn Trp Phe Ser Ala
                565                 570                 575

Phe Leu Asn Val Leu Arg Gln Thr Gly Asn Asn Glu Leu Val Gln Glu
            580                 585                 590

Leu Thr Gly Ser Asp Cys Ser Glu Ser Asn Ala Glu Ile Glu Asn
        595                 600                 605


<210> SEQ ID NO 25
<211> LENGTH: 615
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220
```

```
Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
        355                 360                 365

Gly Val Tyr Thr Gly Leu Ser Thr Arg Asn Gln Glu Thr Tyr Glu Thr
    370                 375                 380

Leu Lys His Glu Lys Pro Pro Gln Gly Ser Gly Ser Gln Arg Trp Lys
385                 390                 395                 400

Ser Lys Leu Tyr Ser Ile Val Cys Gly Lys Ser Thr Pro Glu Lys Glu
                405                 410                 415

Gly Glu Leu Glu Gly Thr Thr Thr Lys Pro Leu Ala Pro Asn Pro Ser
            420                 425                 430

Phe Ser Pro Thr Pro Gly Phe Thr Pro Thr Leu Gly Phe Ser Pro Val
        435                 440                 445

Pro Ser Ser Thr Phe Thr Ser Ser Ser Thr Tyr Thr Pro Gly Asp Cys
    450                 455                 460

Pro Asn Phe Ala Ala Pro Arg Arg Glu Val Ala Pro Pro Tyr Gln Gly
465                 470                 475                 480

Ala Asp Pro Ile Leu Ala Thr Ala Leu Ala Ser Asp Pro Ile Pro Asn
                485                 490                 495

Pro Leu Gln Lys Trp Glu Asp Ser Ala His Lys Pro Gln Ser Leu Asp
            500                 505                 510

Thr Asp Asp Pro Ala Thr Leu Tyr Ala Val Val Glu Asn Val Pro Pro
        515                 520                 525

Leu Arg Trp Lys Glu Phe Val Arg Arg Leu Gly Leu Ser Asp His Glu
    530                 535                 540

Ile Asp Arg Leu Glu Leu Gln Asn Gly Arg Cys Leu Arg Glu Ala Gln
545                 550                 555                 560

Tyr Ser Met Leu Ala Thr Trp Arg Arg Arg Thr Pro Arg Arg Glu Ala
                565                 570                 575

Thr Leu Glu Leu Leu Gly Arg Val Leu Arg Asp Met Asp Leu Leu Gly
            580                 585                 590

Cys Leu Glu Asp Ile Glu Glu Ala Leu Cys Gly Pro Ala Ala Leu Pro
        595                 600                 605

Pro Ala Pro Ser Leu Leu Arg
    610                 615
```

<210> SEQ ID NO 26
<211> LENGTH: 567

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
        355                 360                 365

Gly Val Tyr Thr Gly Leu Ser Thr Arg Asn Gln Glu Thr Tyr Glu Thr
    370                 375                 380
```

```
Leu Lys His Glu Lys Pro Pro Gln Gly Ser Gly Ser Pro Leu Cys Leu
385                 390                 395                 400

Gln Arg Glu Ala Lys Val Pro His Leu Pro Ala Asp Lys Ala Arg Gly
                405                 410                 415

Thr Gln Gly Pro Glu Gln Gln His Leu Leu Ile Thr Ala Pro Ser Ser
            420                 425                 430

Ser Ser Ser Ser Leu Glu Ser Ser Ala Ser Ala Leu Asp Arg Arg Ala
        435                 440                 445

Pro Thr Arg Asn Gln Pro Gln Ala Pro Gly Val Glu Ala Ser Gly Ala
    450                 455                 460

Gly Glu Ala Arg Ala Ser Thr Gly Ser Ser Asp Ser Ser Pro Gly Gly
465                 470                 475                 480

His Gly Thr Gln Val Asn Val Thr Cys Ile Val Asn Val Cys Ser Ser
                485                 490                 495

Ser Asp His Ser Ser Gln Cys Ser Ser Gln Ala Ser Ser Thr Met Gly
            500                 505                 510

Asp Thr Asp Ser Ser Pro Ser Glu Ser Pro Lys Asp Glu Gln Val Pro
        515                 520                 525

Phe Ser Lys Glu Glu Cys Ala Phe Arg Ser Gln Leu Glu Thr Pro Glu
    530                 535                 540

Thr Leu Leu Gly Ser Thr Glu Glu Lys Pro Leu Pro Leu Gly Val Pro
545                 550                 555                 560

Asp Ala Gly Met Lys Pro Ser
                565
```

<210> SEQ ID NO 27
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
            20                  25                  30

Glu Thr Leu Lys His Glu Lys Pro Pro Gln
        35                  40
```

<210> SEQ ID NO 28
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
            20                  25                  30

Glu Thr Leu Lys His Glu Lys Pro Pro Gln
        35                  40
```

<210> SEQ ID NO 29

<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 30
<211> LENGTH: 86
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 30

```
Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Ile Tyr
    50                  55                  60

Ile Trp Ala Pro Leu Ala Gly Thr Cys Gly Val Leu Leu Leu Ser Leu
65                  70                  75                  80

Val Ile Thr Leu Tyr Cys
                85
```

<210> SEQ ID NO 31
<211> LENGTH: 83
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

```
Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Ile Tyr
    50                  55                  60

Ile Trp Ala Pro Leu Ala Gly Thr Cys Gly Val Leu Leu Leu Ser Leu
65                  70                  75                  80

Val Ile Thr
```

<210> SEQ ID NO 32
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg Thr Gly Ser Thr
100 105 110

Ser Gly Ser Gly Lys Pro Gly Ser Gly Glu Gly Ser Glu Val Gln Leu
115 120 125

Val Glu Ser Ser Gly Gly Gly Gly Ser Gly Gly Gly Gly Ser Gly Gly
130 135 140

Gly Gly Ser Leu Val Gln Pro Gly Gly Ser Leu Arg Leu Ser Cys Ala
145 150 155 160

Ala Ser Gly Phe Asn Ile Lys Asp Thr Tyr Ile His Trp Val Arg Gln
165 170 175

Ala Pro Gly Lys Gly Leu Glu Trp Val Ala Arg Ile Tyr Pro Thr Asn
180 185 190

Gly Tyr Thr Arg Tyr Ala Asp Ser Val Lys Gly Arg Phe Thr Ile Ser
195 200 205

Ala Asp Thr Ser Lys Asn Thr Ala Tyr Leu Gln Met Asn Ser Leu Arg
210 215 220

Ala Glu Asp Thr Ala Val Tyr Tyr Cys Ser Arg Trp Gly Gly Asp Gly
225 230 235 240

Phe Tyr Ala Met Asp Val Trp Gly Gln Gly Thr Leu Val Thr Val
245 250 255

<210> SEQ ID NO 33
<211> LENGTH: 240
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

Glu Ile Gln Leu Val Gln Ser Gly Gly Gly Leu Val Lys Pro Gly Gly
1 5 10 15

Ser Val Arg Ile Ser Cys Ala Ala Ser Gly Tyr Thr Phe Thr Asn Tyr
20 25 30

Gly Met Asn Trp Val Arg Gln Ala Pro Gly Lys Gly Leu Glu Trp Met
35 40 45

Gly Trp Ile Asn Thr His Thr Gly Glu Pro Thr Tyr Ala Asp Ser Phe
50 55 60

Lys Gly Arg Phe Thr Phe Ser Leu Asp Asp Ser Lys Asn Thr Ala Tyr
65 70 75 80

Leu Gln Ile Asn Ser Leu Arg Ala Glu Asp Thr Ala Val Tyr Phe Cys

```
                85                  90                  95

Thr Arg Arg Gly Tyr Asp Trp Tyr Phe Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Asp Ile Asn Ser Tyr Leu Ser Trp Phe Gln Gln Lys Pro Gly Lys Ala
                165                 170                 175

Pro Lys Thr Leu Ile Tyr Arg Ala Asn Arg Leu Glu Ser Gly Val Pro
            180                 185                 190

Ser Arg Phe Ser Gly Ser Gly Ser Gly Thr Asp Tyr Thr Leu Thr Ile
        195                 200                 205

Ser Ser Leu Gln Tyr Glu Asp Phe Gly Ile Tyr Tyr Cys Gln Gln Tyr
    210                 215                 220

Asp Glu Ser Pro Trp Thr Phe Gly Gly Gly Thr Lys Leu Glu Ile Lys
225                 230                 235                 240


<210> SEQ ID NO 34
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Tyr Leu Ile Ile Gly Ile Cys Gly Gly Gly Ser Leu Leu Met Val
1               5                   10                  15

Phe Val Ala Leu Leu Val Phe Tyr Ile Thr
            20                  25


<210> SEQ ID NO 35
<211> LENGTH: 1075
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

taatacgact cactataggg agaaagacgc caccatgggc aagaagcaaa atcgcaagac      60

ggggaattcc aagacacaat ccgctagccc accacctaaa gagcgttcta gctcccctgc     120

tactgagcag tcctggatgg aaaacgactt cgatgaactc cgggaagagg gatttaggcg     180

atccaactat tcagaactcc gcgaagatat ccagacaaag ggaaggaag tcgagaattt     240

cgagaagaac ctcgaggagt gcatcacccg tatcacaaac actgagaaat gtctcaaaga     300

actcatggaa cttaagacaa aagccaggga gcttcgagag gagtgtcgga gtctgagatc     360

caggtgtgac cagctcgagg agcgcgtgag cgcgatggaa gacgagatga acgagatgaa     420

aagagagggc aaattcaggg agaagcgcat taagaggaac gaacagagtc tgcaggagat     480

ttgggattac gtcaagaggc ctaacctgcg gttgatcggc gtccccgaga gcgacgtaga     540

aaacgggact aaactggaga atacacttca agacatcatt caagaaaatt ttccaaacct     600

ggctcggcaa gctaatgtgc aaatccaaga gatccaacgc acaccccagc ggtatagctc     660
```

tcggcgtgcc acccctaggc atattatcgt gcgctttact aaggtggaga tgaaagagaa 720
gatgctgcga gccgctcggg aaaagggaag ggtgactttg aagggcaaac ctattcggct 780
gacggttgac cttagcgccg agacactcca ggcacgccgg gaatggggcc ccatctttaa 840
tatcctgaag gagaagaact tccagccacg aatctcttac cctgcaaagt tgagttttat 900
ctccgagggt gagattaagt atttcatcga taaacagatg ctgcgagact tcgtgacaac 960
tcgcccagct ctcaaggaac tgctcaaaga ggctcttaat atggagcgca ataatagata 1020
tcaacccttg cagaaccacg caaagatgga ttataaggat gacgatgata aatga 1075

<210> SEQ ID NO 36
<211> LENGTH: 5751
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36
taatacgact cactataggg agaaagacgc caccatgaca ggttcaaata gtcacattac 60
gattctcact ctgaatataa atgggctgaa ttctgcaatt aaacggcaca ggcttgcttc 120
ctggataaag tctcaagacc cctcagtgtg ctgtattcag gaaacgcatc tcacgtgcag 180
ggacacccat cggctgaaaa taaaaggctg gcggaagatc taccaagcca atggaaaaca 240
aaagaaggct ggggtggcga tacttgtaag cgataaaaca gactttaaac caactaagat 300
caaacgggac aaagagggcc attacatcat ggtaaagggt agtattcaac aagaggagct 360
gactatcctg aatatttatg cacctaatac tggagccccc agattcataa agcaagtgtt 420
gagtgacctt caacgcgacc tcgactccca cactctgatc atgggagact ttaacacccc 480
gctgtccact ctcgacagat ctactagaca gaaagtcaac aaggatacac aggaactgaa 540
cagtgctctc caccaagcgg accttatcga catctacaga acactccacc ccaaaagcac 600
agaatatacc ttcttttcag cccctcacca cacctattcc aaaattgacc acattgtggg 660
gagtaaagcc cttctctcca aatgtaaacg gaccgaaatt atcactaact atctctccga 720
ccacagtgca ataaaacttg aattgcgaat taagaatctc actcaaagta gatccacgac 780
atggaaactg aacaatctcc tcttgaatga ctactgggtg cataacgaaa tgaaggctga 840
aataaagatg ttctttgaga ccaacgaaaa caaagacacc acgtaccaga atctctggga 900
cgctttcaaa gcagtgtgtc gaggaaaatt tattgcactg aatgcttaca agcggaagca 960
ggaaagatcc aaaatagaca ccctgactag ccaacttaaa gaactggaaa agcaagagca 1020
aactcatagc aaagctagcc gtcgccaaga aattacgaaa atcagagctg aactgaagga 1080
aattgagaca cagaaaaccc tgcaaaagat aaatgaaagc cgcagctggt tctttgaacg 1140
catcaacaaa atcgataggc cacttgctcg ccttatcaag aagaaaaggg agaagaatca 1200
aatcgacact ataaagaatg ataaaggcga tataaccacc gatcccacag aaattcaaac 1260
aaccatacgc gaatactaca aacacctcta cgccaataaa ctcgaaaatc tcgaggaaat 1320
ggatacattc ctcgacacgt acacccttcc caggctgaac caggaagaag ttgaatcact 1380
gaatcggcct atcacgggga gtgaaatagt agctatcatc aattcactcc ctaccaagaa 1440
gtcacccgga cctgatggat tcaccgccga attctaccag agatacatgg aagaactggt 1500
gcccttcttg ctgaaacttt tccaaagtat tgagaaagag ggaatacttc caaactcatt 1560
ttatgaggca tccatcattc tgatcccgaa gcccggcagg gacacgacca agaaagagaa 1620
ttttcgacca atctcattga tgaacattga tgcaaagatc ctcaataaaa tactggcaaa 1680
tcggattcag cagcacataa agaagctgat ccaccatgat caagtaggct tcatccccgg 1740
tatgcaaggt tggttcaata tacgaaaatc aatcaatgtt atccagcata taaaccgggc 1800
caaagacaag aaccacatga ttattagtat cgatgctgag aaagcctttg acaaaataca 1860
acaacccttc atgctgaaaa cattgaataa gctgggaatt gatggcacct acttcaaaat 1920
catcagagcc atatatgaca aaccaacagc aaatatcatt ctgaatggtc agaaattgga 1980
agcattcccc ttgaaaaccg gcacacggca gggttgccct ctgtcaccac tcctcttcaa 2040
catcgtgttg gaagttcttg cccgcgcaat ccggcaggaa aaggaaatca agggcattca 2100
actgggcaaa gaggaagtta aattgagcct gtttgcagac gacatgatcg tctatttgga 2160
aaaccccata gttagtgcac aaaatctgct gaagttgatc agtaatttct ccaaagtgag 2220
tgggtacaaa atcaatgtgc aaaagagcca agctttcttg tacaccaaca acaggcaaac 2280
tgagtctcaa atcatgggcg aactcccctt cgtgattgca tccaagcgga tcaaatacct 2340
ggggattcaa ttgactcgtg atgtgaagga cctcttcaag gagaactaca aacccctgct 2400
caaggaaatc aaagaggaca caaacaaatg gaagaacatt ccatgctctt gggtgggaag 2460
gatcaatatc gtcaaaatgg ccatcctgcc caaggtaatt tacaggttca atgctatacc 2520
catcaagctc cccatgacat tcttcacaga acttgaaaag acgacgctga agttcatttg 2580
gaaccagaaa cgtgccagga ttgctaaatc tattctctcc caaaagaaca aagctggcgg 2640
aatcacactc ccagacttca aactttacta caaggcgacc gtgacgaaaa cggcttggta 2700
ctggtaccaa aacagggata tagatcaatg gaaccgaacg gagcccagcg aaattatgcc 2760
tcatatatac aactatctga tctttgacaa accggagaag aacaagcaat ggggaaagga 2820
tagtctgttt aataaatggt gctgggaaaa ctggctcgca atctgtagga agctgaaact 2880
ggatccattc ttgacgcctt atacaaagat aaattcccga tggattaaag atctcaacgt 2940
gaaacccaaa acaattaaaa ccctcgagga aaacctgggt attacgattc aggacattgg 3000
ggtgggaaag gacttcatgt ccaaaacccc aaaagcgatg gcaaccaaag acaaaatcga 3060
caaatgggat ctcataaaac ttaagtcatt ttgcacagct aaagaaacga caattagggt 3120
gaaccgacaa ccgaccactt gggagaaaat cttcgcaaca tacagttctg acaaaggcct 3180
gatttccagg atctacaatg aattgaaaca aatttacaag aagaagacga acaaccctat 3240
aaagaaatgg gccaaggaca tgaacagaca cttctctaag gaagacattt atgcagccaa 3300
gaaacacatg aagaaatgca gctcttcact ggcaatcagg gaaatgcaaa tcaaaacaac 3360
aatgagatat catctcacac ccgtcagaat ggccatcatt aagaagagcg gaaacaaccg 3420
gtgctggcgt ggttgcggag aaatcggtac tctccttcac tgttggtggg actgtaaact 3480
cgttcaacca ctgtggaagt ctgtgtggcg gttcctcaga gatctggaac tcgaaatccc 3540
atttgaccca gccatccctc tcctgggtat atacccgaat gagtataaat cctgctgcta 3600
taaagacacc tgcacaagga tgtttattgc agctctcttc acaatcgcga agacgtggaa 3660
ccaacccaaa tgtccgacta tgattgactg gattaagaag atgtggcaca tatacactat 3720
ggaatactat gctgcgatca agaacgatga gttcatatca tttgtgggca catggatgaa 3780
actcgaaacc atcatactct ctaaattgag tcaagaacag aaaactaaac accgtatatt 3840
ttccctgatc ggtgggaatt agctacaaag acgatgacga caaggaccat ggagacggtg 3900
agagacacaa aaaattccaa cacactattg caatgaaaat aaatttcctt tattagccag 3960
aagtcagatg ctcaaggggc ttcatgatgt ccccataatt tttggcagag ggaaaaagat 4020
ctcagtggta tttgtgagcc agggcattgg ccttctgata ggcagcctgc acctgaggag 4080
tgcggccgct ttacttgtac agctcgtcca tgccgagagt gatcccggcg gcggtcacga 4140
actccagcag gaccatgtga tcgcgcttct cgttggggtc tttgctcagg gcggactggg 4200
tgctcaggta gtggttgtcg ggcagcagca cggggccgtc gccgatgggg gtgttctgct 4260
ggtagtggtc ggcgagctgc acgctgccgt cctcgatgtt gtggcggatc ttgaagttca 4320
ccttgatgcc gttcttctgc ttgtcggcca tgatatagac gttgtggctg ttgtagttgt 4380
actccagctt gtgccccagg atgttgccgt cctccttgaa gtcgatgccc ttcagctcga 4440
tgcggttcac cagggtgtcg ccctcgaact tcacctcggc gcgggtcttg tagttgccgt 4500
cgtccttgaa gaagatggtg cgctcctgga cgtagccttc gggcatggcg gacttgaaga 4560
agtcgtgctg cttcatgtgg tcggggtagc ggctgaagca ctgcacgccg taggtcaggg 4620
tggtcacgag ggtgggccag ggcacgggca gcttgccggt ggtgcagatg aacttcaggg 4680
tcagcttgcc gtaggtggca tcgccctcgc cctcgccgga cacgctgaac ttgtggccgt 4740
ttacgtcgcc gtccagctcg accaggatgg gcaccacccc ggtgaacagc tcctcgccct 4800
tgctcaccat ggtggcggga tctgacggtt cactaaacca gctctgctta tatagacctc 4860
ccaccgtaca cgcctaccgc ccatttgcgt caatggggcg gagttgttac gacattttgg 4920
aaagtcccgt tgattttggt gccaaaacaa actcccattg acgtcaatgg ggtggagact 4980
tggaaatccc cgtgagtcaa accgctatcc acgcccattg atgtactgcc aaaaccgcat 5040
caccatggta atagcgatga ctaatacgta gatgtactgc caagtaggaa agtcccataa 5100
ggtcatgtac tgggcataat gccaggcggg ccatttaccg tcattgacgt caataggggg 5160
cgtacttggc atatgataca cttgatgtac tgccaagtgg gcagtttacc gtaaatactc 5220
cacccattga cgtcaatgga aagtccctat tggcgttact atgggaacat acgtcattat 5280
tgacgtcaat gggcgggggt cgttgggcgg tcagccaggc gggccattta ccgtaagtta 5340
tgtaacgacg tctcagctga caatgagatc acatggacac aggaagggga atatcacact 5400
ctggggactg tggtggggtc gggggagggg ggagggatag cattgggaga tatacctaat 5460
gctagatgac acattagtgg gtgcagcgca ccagcatggc acatgtatac atatgtaact 5520
aacctgcaca atgtgcacat gtaccctaaa acttagagta taatggatcc gcaggcctct 5580
gctagcttga ctgactgaga tacagcgtac cttcagctca cagacatgat aagatacatt 5640
gatgagtttg gacaaaccac aactagaatg cagtgaaaaa aatgctttat ttgtgaaatt 5700
tgtgatgcta ttgctttatt tgtaaccatt ataagctgca ataaacaagt t 5751

<210> SEQ ID NO 37
<211> LENGTH: 18285
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
cggccgcggg gggaggagcc aagatggccg aataggaaca gctccggtct acagctccca 60
gcgtgagcga cgcagaagac ggtgatttct gcatttccat ctgaggtacc gggttcatct 120
cactagggag tgccagacag tgggcgcagg ccagtgtgtg tgcgcaccgt gcgcgagccg 180
aagcagggcg aggcattgcc tcacctggga agcgcaaggg gtcagggagt tccctttccg 240
agtcaaagaa aggggtgacg gacgcacctg gaaaatcggg tcactcccac ccgaatattg 300

```
cgcttttcag accggcttaa gaaacggcgc accacgagac tatatcccac acctggctcg    360
gagggtccta cgcccacgga atctcgctga ttgctagcac agcagtctga gatcaaactg    420
caaggcggca acgaggctgg gggaggggcg cccgccattg cccaggcttg cttaggtaaa    480
caaagcagca gggaagctcg aactgggtgg agcccaccac agctcaagga ggcctgcctg    540
cctctgtagg ctccacctct gggggcaggg cacagacaaa caaaaagaca gcagtaacct    600
ctgcagactt aagtgtccct gtctgacagc tttgaagaga gcagtggttc tcccagcacg    660
cagctggaga tctgagaacg ggcagactgc ctcctcaagt gggtccctga cccctgaccc    720
ccgagcagcc taactgggag gcaccccca gcaggggcac actgacacct cacacggcag     780
ggtattccaa cagacctgca gctgagggtc ctgtctgtta gaaggaaaac taacaaccag    840
aaaggacatc tacaccgaaa acccatctgt acatcaccat catcaaagac caaaagtaga    900
taaaaccaca aagatgggga aaaaacagaa cagaaaaact ggaaactcta aaacgcagag    960
cgcctctcct cctccaaagg aacgcagttc ctcaccagca acagaacaaa gctggatgga   1020
gaatgatttt gatgagctga gagaagaagg cttcagacga tcaaattact ctgagctacg   1080
ggaggacatt caaaccaaag gcaaagaagt tgaaaacttt gaaaaaaatt tagaagaatg   1140
tataactaga ataaccaata cagagaagtg cttaaaggag ctgatggagc tgaaaaccaa   1200
ggctcgagaa ctacgtgaag aatgcagaag cctcaggagc cgatgcgatc aactggaaga   1260
aagggtatca gcaatggaag atgaaatgaa tgaaatgaag cgagaaggga agtttagaga   1320
aaaaagaata aaaagaaatg agcaaagcct ccaagaaata tgggactatg tgaaaagacc   1380
aaatctacgt ctgattggtg tacctgaaag tgatgtggag aatggaacca agttggaaaa   1440
cactctgcag gatattatcc aggagaactt ccccaatcta gcaaggcagg ccaacgttca   1500
gattcaggaa atacagagaa cgccacaaag atactcctcg agaagagcaa ctccaagaca   1560
cataattgtc agattcacca aagttgaaat gaaggaaaaa atgttaaggg cagccagaga   1620
gaaaggtcgg gttaccctca aaggaaagcc catcagacta acagcggatc tctcggcaga   1680
aaccctacaa gccagaagag agtgggggcc aatattcaac attcttaaag aaaagaattt   1740
tcaacccaga atttcatatc cagccaaact aagcttcata agtgaaggag aaataaaata   1800
ctttatagac aagcaaatgt tgagagattt tgtcaccacc aggcctgccc taaaagagct   1860
cctgaaggaa gcgctaaaca tggaaaggaa caaccggtac cagccgctgc aaaatcatgc   1920
caaaatgtaa agaccatcaa gactaggaag aaactgcatc aactaatgag caaaatcacc   1980
agctaacatc ataatgacag gatcaacttc acacataaca atattaactt taaatataaa   2040
tggactaaat tctgcaatta aaagacacag actggcaagt tggataaaga gtcaagaccc   2100
atcagtgtgc tgtattcagg aaacccatct cacgtgcaga gacacacata ggctcaaaat   2160
aaaaggatgg aggaagatct accaagccaa tggaaaacaa aaaaaggcag gggttgcaat   2220
cctagtctct gataaaacag actttaaacc aacaaagatc aaaagagaca aagaaggcca   2280
ttacataatg gtaaagggat caattcaaca agaggagcta actatcctaa atatttatgc   2340
acccaataca ggagcaccca gattcataaa gcaagtcctc agtgacctac aaagagactt   2400
agactcccac acattaataa tgggagactt taacacccca ctgtcaacat tagacagatc   2460
aacgagacag aaagtcaaca aggataccca ggaattgaac tcagctctgc accaagcaga   2520
cctaatagac atctacagaa ctctccaccc caaatcaaca gaatatacat ttttttcagc   2580
accacaccac acctattcca aaattgacca catagttgga agtaaagctc tcctcagcaa   2640
```

```
atgtaaaaga acagaaatta taacaaacta tctctcagac cacagtgcaa tcaaactaga   2700
actcaggatt aagaatctca ctcaaagccg ctcaactaca tggaaactga acaacctgct   2760
cctgaatgac tactgggtac ataacgaaat gaaggcagaa ataaagatgt tctttgaaac   2820
caacgagaac aaagacacca cataccagaa tctctgggac gcattcaaag cagtgtgtag   2880
agggaaattt atagcactaa atgcctacaa gagaaagcag gaaagatcca aaattgacac   2940
cctaacatca caattaaaag aactagaaaa gcaagagcaa acacattcaa aagctagcag   3000
aaggcaagaa ataactaaaa tcagagcaga actgaaggaa atagagacac aaaaaaccct   3060
tcaaaaaatc aatgaatcca ggagctggtt ttttgaaagg atcaacaaaa ttgatagacc   3120
gctagcaaga ctaataaaga aaaaaagaga gaagaatcaa atagacacaa taaaaaatga   3180
taaaggggat atcaccaccg atcccacaga aatacaaact accatcagag aatactacaa   3240
acacctctac gcaaataaac tagaaaatct agaagaaatg gatacattcc tcgacacata   3300
cactctccca agactaaacc aggaagaagt tgaatctctg aatcgaccaa taacaggctc   3360
tgaaattgtg gcaataatca atagtttacc aaccaaaaag agtccaggac cagatggatt   3420
cacagccgaa ttctaccaga ggtacaagga ggaactggta ccattccttc tgaaactatt   3480
ccaatcaata gaaaaagagg gaatcctccc taactcattt tatgaggcca gcatcattct   3540
gataccaaag ccgggcagag acacaaccaa aaaagagaat tttagaccaa tatccttgat   3600
gaacattgat gcaaaaatcc tcaataaaat actggcaaac cgaatccagc agcacatcaa   3660
aaagcttatc caccatgatc aagtgggctt catccctggg atgcaaggct ggttcaatat   3720
acgcaaatca ataaatgtaa tccagcatat aaacagagcc aaagacaaaa accacatgat   3780
tatctcaata gatgcagaaa aagcctttga caaaattcaa caacccttca tgctaaaaac   3840
tctcaataaa ttaggtattg atgggacgta tttcaaaata ataagagcta tctatgacaa   3900
acccacagcc aatatcatac tgaatgggca aaaactggaa gcattccctt tgaaaaccgg   3960
cacaagacag ggatgccctc tctcaccgct cctattcaac atagtgttgg aagttctggc   4020
cagggcaatc aggcaggaga aggaaataaa gggtattcaa ttaggaaaag aggaagtcaa   4080
attgtccctg tttgcagacg acatgattgt ttatctagaa aaccccatcg tctcagccca   4140
aaatctcctt aagctgataa gcaacttcag caaagtctca ggatacaaaa tcaatgtaca   4200
aaaatcacaa gcattcttat acaccaacaa cagacaaaca gagagccaaa tcatgggtga   4260
actcccattc acaattgctt caaagagaat aaaataccta ggaatccaac ttacaaggga   4320
tgtgaaggac ctcttcaagg agaactacaa accactgctc aaggaaataa aagaggagac   4380
aaacaaatgg aagaacattc catgctcatg ggtaggaaga atcaatatcg tgaaaatggc   4440
catactgccc aaggtaattt acagattcaa tgccatcccc atcaagctac caatgacttt   4500
cttcacagaa ttggaaaaaa ctactttaaa gttcatatgg aaccaaaaaa gagcccgcat   4560
tgccaagtca atcctaagcc aaaagaacaa agctggaggc atcacactac ctgacttcaa   4620
actatactac aaggctacag taaccaaaac agcatggtac tggtaccaaa acagagatat   4680
agatcaatgg aacagaacag agccctcaga aataatgccg catatctaca actatctgat   4740
ctttgacaaa cctgagaaaa acaagcaatg gggaaaggat tccctattta ataaatggtg   4800
ctgggaaaac tggctagcca tatgtagaaa gctgaaactg gatcccttcc ttacacctta   4860
tacaaaaatc aattcaagat ggattaaaga tttaaacgtt aaacctaaaa ccataaaaac   4920
cctagaagaa aacctaggca ttaccattca ggacataggc gtgggcaagg acttcatgtc   4980
caaaacacca aaagcaatgg caacaaaaga caaaattgac aaatgggatc taattaaact   5040
```

aaagagcttc tgcacagcaa aagaaactac catcagagtg aacaggcaac ctacaacatg 5100
ggagaaaatt tttgcaacct actcatctga caaagggcta atatccagaa tctacaatga 5160
actcaaacaa atttacaaga aaaaaacaaa caaccccatc aaaaagtggg cgaaggacat 5220
gaacagacac ttctcaaaag aagacattta tgcagccaaa aaacacatga agaaatgctc 5280
atcatcactg gccatcagag aaatgcaaat caaaaccact atgagatatc atctcacacc 5340
agttagaatg gcaatcatta aaaagtcagg aaacaacagg tgctggagag gatgcggaga 5400
aataggaaca cttttacact gttggtggga ctgtaaacta gttcaaccat tgtggaagtc 5460
agtgtggcga ttcctcaggg atctagaact agaaatacca tttgacccag ccatcccatt 5520
actgggtata tacccaaatg agtataaatc atgctgctat aaagacacat gcacacgtat 5580
gtttattgcg gcactattca caatagcaaa gacttggaac caacccaaat gtccaacaat 5640
gatagactgg attaagaaaa tgtggcacat atacaccatg gaatactatg cagccataaa 5700
aaatgatgag ttcatatcct ttgtagggac atggatgaaa ttggaaacca tcattctcag 5760
taaactatcg caagaacaaa aaaccaaaca ccgcatattc tcactcatag gtgggaattg 5820
aacaatgaga tcacatggac acaggaaggg gaatatcaca ctctggggac tgtggtgggg 5880
tcgggggagg ggggagggat agcattggga gatataccta atgctagatg acacattagt 5940
gggtgcagcg caccagcatg gcacatgtat acggatccga attctcgacg gatcgatccg 6000
aacaaacgac ccaacacccg tgcgttttat tctgtctttt tattgccgat cccctcagaa 6060
gaactcgtca agaaggcgat agaaggcgat gcgctgcgaa tcgggagcgg cgataccgta 6120
aagcacgagg aagcggtcag cccattcgcc gccaagctct tcagcaatat cacgggtagc 6180
caacgctatg tcctgatagc ggtcggccgc tttacttgta cagctcgtcc atgccgagag 6240
tgatcccggc ggcggtcacg aactccagca ggaccatgtg atcgcgcttc tcgttggggt 6300
ctttgctcag ggcggactgg gtgctcaggt agtggttgtc gggcagcagc acggggccgt 6360
cgccgatggg ggtgttctgc tggtagtggt cggccaggtg agtccaggag atgtttcagc 6420
actgttgcct ttagtctcga ggcaacttag acaactgagt attgatctga gcacagcagg 6480
gtgtgagctg tttgaagata ctggggttgg gggtgaagaa actgcagagg actaactggg 6540
ctgagaccca gtggcaatgt tttagggcct aaggaatgcc tctgaaaatc tagatggaca 6600
actttgactt tgagaaaaga gaggtggaaa tgaggaaaat gacttttctt tattagattt 6660
cggtagaaag aactttcatc tttcccctat ttttgttatt cgttttaaaa catctatctg 6720
gaggcaggac aagtatggtc attaaaaaga tgcaggcaga aggcatatat tggctcagtc 6780
aaagtgggga actttggtgg ccaaacatac attgctaagg ctattcctat atcagctgga 6840
cacatataaa atgctgctaa tgcttcatta caaacttata tcctttaatt ccagatgggg 6900
gcaaagtatg tccaggggtg aggaacaatt gaaacatttg ggctggagta gattttgaaa 6960
gtcagctctg tgtgtgtgtg tgtgtgtgtg tgtgtgagag cgtgtgtttc ttttaacgtt 7020
ttcagcctac agcatacagg gttcatggtg gcaagaagat aacaagattt aaattatggc 7080
cagtgactag tgctgcaaga agaacaacta cctgcattta atgggaaagc aaaatctcag 7140
gctttgaggg aagttaacat aggcttgatt ctgggtggaa gctgggtgtg tagttatctg 7200
gaggccaggc tggagctctc agctcactat gggttcatct ttattgtctc ctttcatctc 7260
aacagctgca cgctgccgtc ctcgatgttg tggcggatct tgaagttcac cttgatgccg 7320
ttcttctgct tgtcggccat gatatagacg ttgtggctgt tgtagttgta ctccagcttg 7380

```
tgccccagga tgttgccgtc ctccttgaag tcgatgccct tcagctcgat gcggttcacc   7440
agggtgtcgc cctcgaactt cacctcggcg cgggtcttgt agttgccgtc gtccttgaag   7500
aagatggtgc gctcctggac gtagccttcg ggcatggcgg acttgaagaa gtcgtgctgc   7560
ttcatgtggt cggggtagcg gctgaagcac tgcacgccgt aggtcagggt ggtcacgagg   7620
gtgggccagg gcacgggcag cttgccggtg gtgcagatga acttcagggt cagcttgccg   7680
taggtggcat cgccctcgcc ctcgccggac acgctgaact tgtggccgtt tacgtcgccg   7740
tccagctcga ccaggatggg caccaccccg gtgaacagct cctcgccctt gctcaccatg   7800
gtggcgaatt cgaagcttga gctcgagatc tgagtccggt agcgctagcg gatctgacgg   7860
ttcactaaac cagctctgct tatatagacc tcccaccgta cacgcctacc gcccatttgc   7920
gtcaatgggg cggagttgtt acgacatttt ggaaagtccc gttgattttg gtgccaaaac   7980
aaactcccat tgacgtcaat ggggtggaga cttggaaatc cccgtgagtc aaaccgctat   8040
ccacgcccat tgatgtactg ccaaaaccgc atcaccatgg taatagcgat gactaatacg   8100
tagatgtact gccaagtagg aaagtcccat aaggtcatgt actgggcata atgccaggcg   8160
ggccatttac cgtcattgac gtcaataggg ggcgtacttg gcatatgata cacttgatgt   8220
actgccaagt gggcagttta ccgtaaatac tccacccatt gacgtcaatg gaaagtccct   8280
attggcgtta ctatgggaac atacgtcatt attgacgtca atgggcgggg gtcgttgggc   8340
ggtcagccag gcgggccatt taccgtaagt tatgtaacgc ggaactccat atatgggcta   8400
tgaactaatg accccgtaat tgattactat tagcccgggg gatccagaca tgataagata   8460
cattgatgag tttggacaaa ccacaactag aatgcagtga aaaaaatgct ttatttgtga   8520
aatttgtgat gctattgctt tatttgtaac cattataagc tgcaataaac aagttaacaa   8580
caacaattgc attcatttta tgtttcaggt tcagggggag gtgtgggagg ttttttaaag   8640
caagtaaaac ctctacaaat gtggtatggc tgattatgat ccggctgcct cgcgcgtttc   8700
ggtgatgacg gtgaaaacct ctgacacatg cagctcccgg agacggtcac agcttgtctg   8760
taagcggatg ccgggagcag acaagcccgt cagggcgcgt cagcgggtgt tggcgggtgt   8820
cggggcgcag ccatgaggtc gatcgactct agaggatcga tccccgcccc ggacgaacta   8880
aacctgacta cgacatctct gccccttctt cgcggggcag tgcatgtaat cccttcagtt   8940
ggttggtaca acttgccaac tgggccctgt tccacatgtg acacgggggg ggaccaaaca   9000
caaaggggtt ctctgactgt agttgacatc cttataaatg gatgtgcaca tttgccaaca   9060
ctgagtggct ttcatcctgg agcagacttt gcagtctgtg gactgcaaca caacattgcc   9120
tttatgtgta actcttggct gaagctctta caccaatgct gggggacatg tacctcccag   9180
gggcccagga agactacggg aggctacacc aacgtcaatc agaggggcct gtgtagctac   9240
cgataagcgg accctcaaga gggcattagc aatagtgttt ataaggcccc cttgttaacc   9300
ctaaacgggt agcatatgct tcccgggtag tagtatatac tatccagact aaccctaatt   9360
caatagcata tgttacccaa cgggaagcat atgctatcga attagggtta gtaaaagggt   9420
cctaaggaac agcgatatct cccaccccat gagctgtcac ggttttattt acatggggtc   9480
aggattccac gagggtagtg aaccatttta gtcacaaggg cagtggctga agatcaagga   9540
gcgggcagtg aactctcctg aatcttcgcc tgcttcttca ttctccttcg tttagctaat   9600
agaataactg ctgagttgtg aacagtaagg tgtatgtgag gtgctcgaaa acaaggtttc   9660
aggtgacgcc cccagaataa aatttggacg gggggttcag tggtggcatt gtgctatgac   9720
accaatataa ccctcacaaa ccccttgggc aataaatact agtgtaggaa tgaaacattc   9780
```

```
tgaatatctt taacaataga aatccatggg gtggggacaa gccgtaaaga ctggatgtcc   9840
atctcacacg aatttatggc tatgggcaac acataatcct agtgcaatat gatactgggg   9900
ttattaagat gtgtcccagg cagggaccaa gacaggtgaa ccatgttgtt acactctatt   9960
tgtaacaagg ggaaagagag tggacgccga cagcagcgga ctccactggt tgtctctaac  10020
acccccgaaa attaaacggg gctccacgcc aatggggccc ataaacaaag acaagtggcc  10080
actctttttt ttgaaattgt ggagtggggg cacgcgtcag cccccacacg ccgccctgcg  10140
gttttggact gtaaaataag ggtgtaataa cttggctgat tgtaaccccg ctaaccactg  10200
cggtcaaacc acttgcccac aaaaccacta atggcacccc ggggaatacc tgcataagta  10260
ggtgggcggg ccaagatagg ggcgcgattg ctgcgatctg gaggacaaat tacacacact  10320
tgcgcctgag cgccaagcac agggttgttg gtcctcatat tcacgaggtc gctgagagca  10380
cggtgggcta atgttgccat gggtagcata tactacccaa atatctggat agcatatgct  10440
atcctaatct atatctgggt agcataggct atcctaatct atatctgggt agcatatgct  10500
atcctaatct atatctgggt agtatatgct atcctaattt atatctgggt agcataggct  10560
atcctaatct atatctgggt agcatatgct atcctaatct atatctgggt agtatatgct  10620
atcctaatct gtatccgggt agcatatgct atcctaatag agattagggt agtatatgct  10680
atcctaattt atatctgggt agcatatact acccaaatat ctggatagca tatgctatcc  10740
taatctatat ctgggtagca tatgctatcc taatctatat ctgggtagca taggctatcc  10800
taatctatat ctgggtagca tatgctatcc taatctatat ctgggtagta tatgctatcc  10860
taatttatat ctgggtagca taggctatcc taatctatat ctgggtagca tatgctatcc  10920
taatctatat ctgggtagta tatgctatcc taatctgtat ccgggtagca tatgctatcc  10980
tcatgcatat acagtcagca tatgataccc agtagtagag tgggagtgct atcctttgca  11040
tatgccgcca cctcccaagg gggcgtgaat tttcgctgct tgtccttttc ctgcatgctg  11100
gttgctccca ttcttaggtg aatttaagga ggccaggcta aagccgtcgc atgtctgatt  11160
gctcaccagg taaatgtcgc taatgttttc caacgcgaga aggtgttgag cgcggagctg  11220
agtgacgtga caacatgggt atgcccaatt gccccatgtt gggaggacga aaatggtgac  11280
aagacagatg gccagaaata caccaacagc acgcatgatg tctactgggg atttattctt  11340
tagtgcgggg gaatacacgg cttttaatac gattgagggc gtctcctaac aagttacatc  11400
actcctgccc ttcctcaccc tcatctccat cacctccttc atctccgtca tctccgtcat  11460
caccctccgc ggcagcccct tccaccatag gtggaaacca gggaggcaaa tctactccat  11520
cgtcaaagct gcacacagtc accctgatat tgcaggtagg agcgggcttt gtcataacaa  11580
ggtccttaat cgcatccttc aaaacctcag caaatatatg agtttgtaaa aagaccatga  11640
aataacagac aatggactcc cttagcgggc caggttgtgg gccgggtcca ggggccattc  11700
caaaggggag acgactcaat ggtgtaagac gacattgtgg aatagcaagg gcagttcctc  11760
gccttaggtt gtaaagggag gtcttactac ctccatatac gaacacaccg gcgacccaag  11820
ttccttcgtc ggtagtcctt tctacgtgac tcctagccag gagagctctt aaaccttctg  11880
caatgttctc aaatttcggg ttggaacctc cttgaccacg atgctttcca aaccaccctc  11940
ctttttgcg cctgcctcca tcaccctgac cccggggtcc agtgcttggg ccttctcctg  12000
ggtcatctgc ggggccctgc tctatcgctc ccgggggcac gtcaggctca ccatctgggc  12060
caccttcttg gtggtattca aaataatcgg cttcccctac agggtggaaa aatggccttc  12120
```

```
tacctggagg gggcctgcgc ggtggagacc cggatgatga tgactgacta ctgggactcc  12180
tgggcctctt ttctccacgt ccacgacctc tccccctggc tctttcacga cttccccccc  12240
tggctctttc acgtcctcta ccccggcggc ctccactacc tcctcgaccc cggcctccac  12300
tacctcctcg accccggcct ccactgcctc ctcgaccccg gcctccacct cctgctcctg  12360
cccctcctgc tcctgcccct cctcctgctc ctgcccctcc tgcccctcct gctcctgccc  12420
ctcctgcccc tcctgctcct gcccctcctg cccctcctgc tcctgcccct cctgcccctc  12480
ctcctgctcc tgcccctcct gcccctcctc ctgctcctgc ccctcctgcc cctcctgctc  12540
ctgcccctcc tgcccctcct gctcctgccc ctcctgcccc tcctgctcct gcccctcctg  12600
ctcctgcccc tcctgctcct gcccctcctg ctcctgcccc tcctgcccct cctgcccctc  12660
ctcctgctcc tgcccctcct gctcctgccc ctcctgcccc tcctgcccct cctgctcctg  12720
cccctcctcc tgctcctgcc cctcctgccc ctcctgcccc tcctcctgct cctgcccctc  12780
ctgcccctcc tcctgctcct gcccctcctc ctgctcctgc ccctcctgcc cctcctgccc  12840
ctcctcctgc tcctgcccct cctgcccctc ctcctgctcc tgcccctcct cctgctcctg  12900
cccctcctgc ccctcctgcc cctcctcctg ctcctgcccc tcctcctgct cctgcccctc  12960
ctgcccctcc tgcccctcct gcccctcctc ctgctcctgc ccctcctcct gctcctgccc  13020
ctcctgctcc tgcccctccc gctcctgctc ctgctcctgt tccaccgtgg gtccctttgc  13080
agccaatgca acttggacgt ttttggggtc tccggacacc atctctatgt cttggccctg  13140
atcctgagcc gcccggggct cctggtcttc cgcctcctcg tcctcgtcct cttccccgtc  13200
ctcgtccatg gttatcaccc cctcttcttt gaggtccact gccgccggag ccttctggtc  13260
cagatgtgtc tcccttctct cctaggccat ttccaggtcc tgtacctggc ccctcgtcag  13320
acatgattca cactaaaaga gatcaataga catctttatt agacgacgct cagtgaatac  13380
agggagtgca gactcctgcc ccctccaaca gcccccccac cctcatcccc ttcatggtcg  13440
ctgtcagaca gatccaggtc tgaaaattcc ccatcctccg aaccatcctc gtcctcatca  13500
ccaattactc gcagcccgga aaactcccgc tgaacatcct caagatttgc gtcctgagcc  13560
tcaagccagg cctcaaattc ctcgtccccc tttttgctgg acggtaggga tggggattct  13620
cgggacccct cctcttcctc ttcaaggtca ccagacagag atgctactgg ggcaacggaa  13680
gaaaagctgg gtgcggcctg tgaggatcag cttatcgatg ataagctgtc aaacatgaga  13740
attcttgaag acgaaagggc ctcgtgatac gcctattttt ataggttaat gtcatgataa  13800
taatggtttc ttagacgtca ggtggcactt ttcggggaaa tgtgcgcgga acccctattt  13860
gtttattttt ctaaatacat tcaaatatgt atccgctcat gagacaataa ccctgataaa  13920
tgcttcaata atattgaaaa aggaagagta tgagtattca acatttccgt gtcgccctta  13980
ttcccttttt tgcggcattt tgccttcctg tttttgctca cccagaaacg ctggtgaaag  14040
taaaagatgc tgaagatcag ttgggtgcac gagtgggtta catcgaactg gatctcaaca  14100
gcggtaagat ccttgagagt tttcgccccg aagaacgttt tccaatgatg agcactttta  14160
aagttctgct atgtggcgcg gtattatccc gtgttgacgc cgggcaagag caactcggtc  14220
gccgcataca ctattctcag aatgacttgg ttgagtactc accagtcaca gaaaagcatc  14280
ttacggatgg catgacagta agagaattat gcagtgctgc cataaccatg agtgataaca  14340
ctgcggccaa cttacttctg acaacgatcg gaggaccgaa ggagctaacc gcttttttgc  14400
acaacatggg ggatcatgta actcgccttg atcgttggga accggagctg aatgaagcca  14460
taccaaacga cgagcgtgac accacgatgc ctgcagcaat ggcaacaacg ttgcgcaaac  14520
```

tattaactgg cgaactactt actctagctt cccggcaaca attaatagac tggatggagg 14580
cggataaagt tgcaggacca cttctgcgct cggcccttcc ggctggctgg tttattgctg 14640
ataaatctgg agccggtgag cgtgggtctc gcggtatcat tgcagcactg gggccagatg 14700
gtaagccctc ccgtatcgta gttatctaca cgacggggag tcaggcaact atggatgaac 14760
gaaatagaca gatcgctgag ataggtgcct cactgattaa gcattggtaa ctgtcagacc 14820
aagtttactc atatatactt tagattgatt taaaacttca tttttaattt aaaaggatct 14880
aggtgaagat cctttttgat aatctcatga ccaaaatccc ttaacgtgag ttttcgttcc 14940
actgagcgtc agaccccgta gaaaagatca aaggatcttc ttgagatcct ttttttctgc 15000
gcgtaatctg ctgcttgcaa acaaaaaaac caccgctacc agcggtggtt tgtttgccgg 15060
atcaagagct accaactctt tttccgaagg taactggctt cagcagagcg cagataccaa 15120
atactgtcct tctagtgtag ccgtagttag gccaccactt caagaactct gtagcaccgc 15180
ctacatacct cgctctgcta atcctgttac cagtggctgc tgccagtggc gataagtcgt 15240
gtcttaccgg gttggactca agacgatagt taccggataa ggcgcagcgg tcgggctgaa 15300
cggggggttc gtgcacacag cccagcttgg agcgaacgac ctacaccgaa ctgagatacc 15360
tacagcgtga gctatgagaa agcgccacgc ttcccgaagg gagaaaggcg gacaggtatc 15420
cggtaagcgg cagggtcgga acaggagagc gcacgaggga gcttccaggg ggaaacgcct 15480
ggtatcttta tagtcctgtc gggtttcgcc acctctgact tgagcgtcga tttttgtgat 15540
gctcgtcagg ggggcggagc ctatggaaaa acgccagcaa cgcggccttt ttacggttcc 15600
tggccttttg ctggcctttt gctcacatgt tctttcctgc gttatcccct gattctgtgg 15660
ataaccgtat taccgccttt gagtgagctg ataccgctcg ccgcagccga acgaccgagc 15720
gcagcgagtc agtgagcgag gaagcggaag agcgcctgat gcggtatttt ctccttacgc 15780
atctgtgcgg tatttcacac cgcatatggt gcactctcag tacaatctgc tctgatgccg 15840
catagttaag ccagctgtgg aatgtgtgtc agttagggtg tggaaagtcc ccaggctccc 15900
cagcaggcag aagtatgcaa agcatgcatc tcaattagtc agcaaccagg tgtggaaagt 15960
ccccaggctc cccagcaggc agaagtatgc aaagcatgca tctcaattag tcagcaacca 16020
tagtcccgcc cctaactccg cccatcccgc ccctaactcc gcccagttcc gcccattctc 16080
cgccccatgg ctgactaatt ttttttattt atgcagaggc cgaggccgcc tcggcctctg 16140
agctattcca gaagtagtga ggaggctttt ttggaggcct aggcttttgc aaaaagcttg 16200
catgcctgca ggtcggccgc cacgaccggt gccgccacca tcccctgacc cacgcccctg 16260
acccctcaca aggagacgac cttccatgac cgagtacaag cccacggtgc gcctcgccac 16320
ccgcgacgac gtcccccggg ccgtacgcac cctcgccgcc gcgttcgccg actaccccgc 16380
cacgcgccac accgtcgacc cggaccgcca catcgagcgg gtcaccgagc tgcaagaact 16440
cttcctcacg cgcgtcgggc tcgacatcgg caaggtgtgg gtcgcggacg acggcgccgc 16500
ggtggcggtc tggaccacgc cggagagcgt cgaagcgggg gcggtgttcg ccgagatcgg 16560
cccgcgcatg gccgagttga gcggttcccg gctggccgcg cagcaacaga tggaaggcct 16620
cctggcgccg caccggccca aggagcccgc gtggttcctg gccaccgtcg gcgtctcgcc 16680
cgaccaccag ggcaagggtc tgggcagcgc cgtcgtgctc cccggagtgg aggcggccga 16740
gcgcgccggg gtgcccgcct tcctggagac ctccgcgccc cgcaacctcc ccttctacga 16800
gcggctcggc ttcaccgtca ccgccgacgt cgaggtgccc gaaggaccgc gcacctggtg 16860

```
catgacccgc aagcccggtg cctgacgccc gccccacgac ccgcagcgcc cgaccgaaag  16920
gagcgcacga ccccatggct ccgaccgaag ccgacccggg cggccccgcc gaccccgcac  16980
ccgcccccga ggcccaccga ctctagagga tcataatcag ccataccaca tttgtagagg  17040
ttttacttgc tttaaaaaac ctcccacacc tccccctgaa cctgaaacat aaaatgaatg  17100
caattgttgt tgttaacttg tttattgcag cttataatgg ttacaaataa agcaatagca  17160
tcacaaattt cacaaataaa gcattttttt cactgcattc tagttgtggt ttgtccaaac  17220
tcatcaatgt atcttatcat gtctggatca ctcgccgata gtggaaaccg acgccccagc  17280
actcgtccga gggcaaagga ataggggaga tgggggaggc taactgaaac acggaaggag  17340
acaataccgg aaggaacccg cgctatgacg gcaataaaaa gacagaataa aacgcacggg  17400
tgttgggtcg tttgttcata aacgcggggt tcggtcccag ggctggcact ctgtcgatac  17460
cccaccgaga ccccattggg gccaatacgc ccgcgtttct tccttttccc caccccaccc  17520
cccaagttcg ggtgaaggcc cagggctcgc agccaacgtc ggggcggcag gccctgccat  17580
agccactggc cccgtgggtt agggacgggg tcccccatgg ggaatggttt atggttcgtg  17640
ggggttatta ttttgggcgt tgcgtggggt ctggtccacg actggactga gcagacagac  17700
ccatggtttt tggatggcct gggcatggac cgcatgtact ggcgcgacac gaacaccggg  17760
cgtctgtggc tgccaaacac cccccgaccc caaaaaccac cgcgcggatt tctggcgtgc  17820
caagctagtc gaccaattct catgtttgac agcttatcat cgcagatccg ggcaacgttg  17880
ttgcattgct gcaggcgcag aactggtagg tatggaagat ctctagaagc tgggtaccag  17940
ctgctagcaa gcttgctagc ggccggctcg agtttactcc ctatcagtga tagagaacgt  18000
atgtcgagtt tactccctat cagtgataga gaacgatgtc gagtttactc cctatcagtg  18060
atagagaacg tatgtcgagt ttactcccta tcagtgatag agaacgtatg tcgagtttac  18120
tccctatcag tgatagagaa cgtatgtcga gtttatccct atcagtgata gagaacgtat  18180
gtcgagttta ctccctatca gtgatagaga acgtatgtcg aggtaggcgt gtacggtggg  18240
aggcctatat aagcagagct cgtttagtga accgtcagat cgccg                  18285
```

```
<210> SEQ ID NO 38
<211> LENGTH: 7264
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
```

```
taatacgact cactataggg agaagtactg ccaccatggg caagaagcaa aatcgcaaga     60
cggggaattc caagacacaa tccgctagcc caccacctaa agagcgttct agctcccctg    120
ctactgagca gtcctggatg gaaaacgact tcgatgaact ccgggaagag ggatttaggc    180
gatccaacta ttcagaactc cgcgaagata tccagacaaa ggggaaggaa gtcgagaatt    240
tcgagaagaa cctcgaggag tgcatcaccc gtatcacaaa cactgagaaa tgtctcaaag    300
aactcatgga acttaagaca aaagccaggg agcttcgaga ggagtgtcgg agtctgagat    360
ccaggtgtga ccagctcgag gagcgcgtga gcgcgatgga agacgagatg aacgagatga    420
aaagagaggg caaattcagg gagaagcgca ttaagaggaa cgaacagagt ctgcaggaga    480
tttgggatta cgtcaagagg cctaacctgc ggttgatcgg cgtccccgag agcgacgtag    540
aaaacgggac taaactggag aatacacttc aagacatcat tcaagaaaat tttccaaacc    600
```

tggctcggca agctaatgtg caaatccaag agatccaacg cacaccccag cggtatagct 660
ctcggcgtgc cacccctagg catattatcg tgcgctttac taaggtggag atgaaagaga 720
agatgctgcg agccgctcgg gaaaagggaa gggtgacttt gaagggcaaa cctattcggc 780
tgacggttga ccttagcgcc gagacactcc aggcacgccg ggaatggggc cccatcttta 840
atatcctgaa ggagaagaac ttccagccac gaatctctta ccctgcaaag ttgagtttta 900
tctccgaggg tgagattaag tatttcatcg ataaacagat gctgcgagac ttcgtgacaa 960
ctcgcccagc tctcaaggaa ctgctcaaag aggctcttaa tatggagcgc aataatagat 1020
atcaaccctt gcagaaccac gcaaagatgt gagacagccg tcagaccatc aagactagga 1080
agaaactgca tcaactaatg agcaaaatca ccagctaaca tcatagtata catgaccggc 1140
tctaactcac atatcaccat ccttacactt aacattaacg gcctcaactc agctatcaag 1200
cgccatcggc tggccagctg gatcaaatca caggatccaa gcgtttgttg catccaagag 1260
acccacctga cctgtagaga tactcaccgc ctcaagatca agggatggcg aaagatttat 1320
caggcgaacg gtaagcagaa gaaagccgga gtcgcaattc tggtctcaga caagacggat 1380
ttcaagccca ccaaaattaa gcgtgataag gaaggtcact atattatggt gaaaggcagc 1440
atacagcagg aagaacttac catattgaac atctacgcgc caaacaccgg cgcacctcgc 1500
tttatcaaac aggtcctgtc cgatctgcag cgagatctgg attctcatac gttgattatg 1560
ggtgatttca atacaccatt gagcaccctg gatcgcagca ccaggcaaaa ggtaaataaa 1620
gacacgcaag agctcaatag cgcactgcat caggcagatc tcattgatat ttatcgcact 1680
cttcatccta agagtaccga gtacacattc ttcagcgccc cacatcatac atactcaaag 1740
atcgatcata tcgtcggctc aaaggctctg ctgtcaaagt gcaagcgcac agagataatt 1800
acaaattacc tgtcagatca tagcgcgatc aagctcgagc tgagaatcaa gaacctgacc 1860
cagagccgga gtaccacttg gaagcttaat aacctgctgc tcaacgatta ttgggtccac 1920
aatgagatga aggcagagat taaaatgttc ttcgaaacaa atgagaataa ggatactacc 1980
tatcaaaacc tttgggatgc ctttaaggcc gtctgcagag gcaagttcat cgccctcaac 2040
gcctataaaa gaaaacaaga gagatctaag atcgatactc tcacctctca gctgaaggag 2100
ttggagaaac aggaacagac ccactccaag gcgtcaagac ggcaggagat cacaaagatt 2160
cgcgccgagt tgaaagagat cgaaacccaa aagactcttc agaaaattaa cgagtctcgt 2220
agttggttct tcgagcggat taataagata gacagacctc tggcacgact gattaagaag 2280
aagcgcgaaa agaaccagat tgataccatc aagaacgaca agggcgacat cactactgac 2340
ccgaccgaga tccagaccac tattcgggag tattataagc atttgtatgc taacaagctt 2400
gagaacctgg aagagatgga cacttttctg gatacctata ctctgccacg gcttaatcaa 2460
gaggaagtcg agtccctcaa ccgcccaatt acaggaagcg agattgtggc cataattaac 2520
tccctgccga caaagaaatc tcctggtccg gacgggttta cagctgagtt ttatcaacgg 2580
tatatggaag agcttgtacc gtttctgctc aagctctttc agtctataga aaaggaaggc 2640
atcttgccca attccttcta cgaagcttct ataatactta ttcccaaacc aggacgcgat 2700
accacaaaga aggaaaactt ccggcccatt agtctcatga atatcgacgc taaaatattg 2760
aacaagattc tcgccaacag aatccaacaa catattaaga aattgataca tcacgaccag 2820
gtggggttta tacctggcat gcagggctgg tttaacatcc ggaagagtat taacgtcatt 2880
caacacatta atagagctaa ggataagaat catatgatca tctctataga cgcggaaaag 2940
gcattcgata agattcagca gccatttatg ctcaagactc tgaacaaact cggcatcgac 3000
ggaacatatt ttaagattat tcgcgcaatt tacgataagc cgactgctaa cattatcctt 3060
aacggccaaa agctcgaggc ctttccgctc aagactggaa cccgccaagg ctgtcccctc 3120
tccccgcttt tgtttaatat tgtactcgag gtgctggcta gggctattcg tcaagagaaa 3180
gagattaaag ggatacagct cgggaaggaa gaggtcaagc tttccttgtt cgccgatgat 3240
atgattgtgt acctggagaa tcctattgtg tctgctcaga accttcttaa acttatttct 3300
aactttagca aggtcagcgg ctataagatt aacgtccaga aatctcaggc ctttctgtac 3360
acaaataatc gacagaccga atcccagata atgggtgagc ttccgtttgt catagccagc 3420
aaaaggataa agtatctcgg aatccagctg acacgagacg ttaaagattt gtttaaggaa 3480
aattacaagc ctctcctgaa agagattaag gaagatacta ataagtggaa gaatatcccc 3540
tgttcatggg ttggcagaat caacatagtg aagatggcaa tacttcctaa agtgatatat 3600
cgctttaacg ccatcccaat taaactgcct atgaccttct ttacggagct cgagaaaaca 3660
acccttaaat ttatatggaa tcaaaagaga gcaagaatag cgaagtccat cttgagccag 3720
aagaataagg ccggtgggat tactttgcct gattttaagt tgtattataa agccacagta 3780
actaagacag cctggtattg gtatcagaat agagacatcg accagtggaa tcggaccgaa 3840
ccatcagaga taatgcccca catctataat taccttatat tcgataagcc agaaaagaat 3900
aaacagtggg gcaaagacag cctcttcaac aagtggtgtt gggagaattg gctggccata 3960
tgccggaaac tcaagctcga ccccttctt acaccctaca ctaaaatcaa cagtaggtgg 4020
atcaaggact tgaatgtcaa gccaaagact ataaagacac tggaagagaa tcttgggatc 4080
acaatacaag atataggcgt cggcaaagat tttatgtcaa agacgcccaa ggccatggcc 4140
actaaggata agattgataa gtgggacctt attaagctca aaagcttctg tactgccaag 4200
gagaccacga tcagagttaa taggcagccc actacatggg aaaagatttt cgccacttat 4260
tcatcagata aggggttgat aagcagaata tataacgagc tgaagcagat ctacaagaag 4320
aaaacgaata atcccatcaa gaagtgggca aaagatatga acaggcattt tagcaaagag 4380
gatatctacg ccgcgaagaa gcatatgaag aagtgtagtt caagcttggc cattcgtgag 4440
atgcagatta agacgaccat gcgataccac cttaccccag tgaggatggc aattatcaag 4500
aaatctggca ataatagatg ttggcggggc tgtggcgaga ttggcaccct gctccattgc 4560
tggtgggatt gcaagctggt gcagccgctt tggaaatcag tctggcgctt tctgagggac 4620
ctcgagcttg agattccctt cgatcccgca attcccttgc tcggaatcta tcctaacgaa 4680
tacaagagct gttgttacaa ggatacgtgt acccggatgt tcatcgcggc cttgtttacg 4740
atagctaaga cgtggaatca gcctaagtgc cccacaatga tcgattggat caagaaaatg 4800
tggcatattt ataccatgga gtattacgca gcaattaaga atgacgaatt tatttccttc 4860
gttgggacct ggatgaagct ggagactatt attctgagca agctgtctca ggagcaaaag 4920
acaaagcata gaatcttctc tctcattggt ggtaacgact acaaagacga tgacgacaag 4980
taaagcgctt ctagaagttg tctcctcctg cactgactga ctgatacaat cgatttctgg 5040
atccgcaggc ctaatcaacc tctggattac aaaatttgtg aaagattgac tggtattctt 5100
aactatgttg ctccttttac gctatgtgga tacgctgctt taatgccttt gtatcatgct 5160
attgcttccc gtatggcttt cattttctcc tccttgtata aatcctggtt gctgtctctt 5220
tatgaggagt tgtggcccgt tgtcaggcaa cgtggcgtgg tgtgcactgt gtttgctgac 5280 gcaacccccca ctggttgggg cattgccacc acctgtcagc tcctttccgg gactttcgct 5340

```
ttccccctcc ctattgccac ggcggaactc atcgccgcct gccttgcccg ctgctggaca   5400

ggggctcggc tgttgggcac tgacaattcc gtggtgttgt cggggaagct gacgtccttt   5460

ccatggctgc tcgcctgtgt tgccacctgg attctgcgcg ggacgtcctt ctgctacgtc   5520

ccttcggccc tcaatccagc ggaccttcct tcccgctgag agacacaaaa aattccaaca   5580

cactattgca atgaaaataa atttccttta ttagccagaa gtcagatgct caaggggctt   5640

catgatgtcc ccataatttt tggcagaggg aaaaagatct cagtggtatt tgtgagccag   5700

ggcattggcc ttctgatagg cagcctgcac ctgaggagtg cggccgcttt acttgtacag   5760

ctcgtccatg ccgagagtga tcccggcggc ggtcacgaac tccagcagga ccatgtgatc   5820

gcgcttctcg ttggggtctt tgctcagggc ggactgggtg ctcaggtagt ggttgtcggg   5880

cagcagcacg gggccgtcgc cgatgggggt gttctgctgg tagtggtcgg cgagctgcac   5940

gctgccgtcc tcgatgttgt ggcggatctt gaagttcacc ttgatgccgt tcttctgctt   6000

gtcggccatg atatagacgt tgtggctgtt gtagttgtac tccagcttgt gccccaggat   6060

gttgccgtcc tccttgaagt cgatgccctt cagctcgatg cggttcacca gggtgtcgcc   6120

ctcgaacttc acctcggcgc gggtcttgta gttgccgtcg tccttgaaga agatggtgcg   6180

ctcctggacg tagccttcgg gcatggcgga cttgaagaag tcgtgctgct tcatgtggtc   6240

ggggtagcgg ctgaagcact gcacgccgta ggtcagggtg gtcacgaggg tgggccaggg   6300

cacgggcagc ttgccggtgg tgcagatgaa cttcagggtc agcttgccgt aggtggcatc   6360

gccctcgccc tcgccggaca cgctgaactt gtggccgttt acgtcgccgt ccagctcgac   6420

caggatgggc accaccccgg tgaacagctc ctcgcccttg ctcaccatgg tggcgggatc   6480

tgacggttca ctaaaccagc tctgcttata tagacctccc accgtacacg cctaccgccc   6540

atttgcgtca atggggcgga gttgttacga cattttggaa agtcccgttg attttggtgc   6600

caaaacaaac tcccattgac gtcaatgggg tggagacttg gaaatccccg tgagtcaaac   6660

cgctatccac gcccattgat gtactgccaa aaccgcatca ccatggtaat agcgatgact   6720

aatacgtaga tgtactgcca agtaggaaag tcccataagg tcatgtactg ggcataatgc   6780

caggcgggcc atttaccgtc attgacgtca ataggggcg tacttggcat atgatacact    6840

tgatgtactg ccaagtgggc agtttaccgt aaatactcca cccattgacg tcaatggaaa   6900

gtccctattg gcgttactat gggaacatac gtcattattg acgtcaatgg gcgggggtcg   6960

ttgggcggtc agccaggcgg gccatttacc gtaagttatg taacgggcct gctgccggct   7020

ctgcggcctc ttccgcgtct tcgccttcgc cctcagacga gtcggatctc cctttgggcc   7080

gcctccccgc ctgtctagct tgactgactg agatacagcg taccttcagc tcacagacat   7140

gataagatac attgatgagt ttggacaaac cacaactaga atgcagtgaa aaaaatgctt   7200

tatttgtgaa atttgtgatg ctattgcttt atttgtaacc attataagct gcaataaaca   7260

agtt                                                              7264
```

<210> SEQ ID NO 39
<211> LENGTH: 18852
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
cggccgcggg gggaggagcc aagatggccg aataggaaca gctccggtct acagctccca     60
```

```
gcgtgagcga cgcagaagac ggtgatttct gcatttccat ctgaggtacc gggttcatct    120
cactagggag tgccagacag tgggcgcagg ccagtgtgtg tgcgcaccgt gcgcgagccg    180
aagcagggcg aggcattgcc tcacctggga agcgcaaggg gtcagggagt tccctttccg    240
agtcaaagaa aggggtgacg gacgcacctg gaaaatcggg tcactcccac ccgaatattg    300
cgcttttcag accggcttaa gaaacggcgc accacgagac tatatcccac acctggctcg    360
gagggtccta cgcccacgga atctcgctga ttgctagcac agcagtctga gatcaaactg    420
caaggcggca acgaggctgg gggaggggcg cccgccattg cccaggcttg cttaggtaaa    480
caaagcagca gggaagctcg aactgggtgg agcccaccac agctcaagga ggcctgcctg    540
cctctgtagg ctccacctct gggggcaggg cacagacaaa caaaaagaca gcagtaacct    600
ctgcagactt aagtgtccct gtctgacagc tttgaagaga gcagtggttc tcccagcacg    660
cagctggaga tctgagaacg ggcagactgc ctcctcaagt gggtccctga cccctgaccc    720
ccgagcagcc taactgggag gcaccccca gcaggggcac actgacacct cacacggcag     780
ggtattccaa cagacctgca gctgagggtc ctgtctgtta gaaggaaaac taacaaccag    840
aaaggacatc tacaccgaaa acccatctgt acatcaccat catcaaagac caaaagtaga    900
taaaaccaca aagatgggga aaaaacagaa cagaaaaact ggaaactcta aaacgcagag    960
cgcctctcct cctccaaagg aacgcagttc ctcaccagca acagaacaaa gctggatgga   1020
gaatgatttt gatgagctga gagaagaagg cttcagacga tcaaattact ctgagctacg   1080
ggaggacatt caaaccaaag gcaaagaagt tgaaaacttt gaaaaaaatt tagaagaatg   1140
tataactaga ataaccaata cagagaagtg cttaaaggag ctgatggagc tgaaaaccaa   1200
ggctcgagaa ctacgtgaag aatgcagaag cctcaggagc cgatgcgatc aactggaaga   1260
aagggtatca gcaatggaag atgaaatgaa tgaaatgaag cgagaaggga agtttagaga   1320
aaaaagaata aaaagaaatg agcaaagcct ccaagaaata tgggactatg tgaaaagacc   1380
aaatctacgt ctgattggtg tacctgaaag tgatgtggag aatggaacca agttggaaaa   1440
cactctgcag gatattatcc aggagaactt ccccaatcta gcaaggcagg ccaacgttca   1500
gattcaggaa atacagagaa cgccacaaag atactcctcg agaagagcaa ctccaagaca   1560
cataattgtc agattcacca aagttgaaat gaaggaaaaa atgttaaggg cagccagaga   1620
gaaaggtcgg gttaccctca aaggaaagcc catcagacta acagcggatc tctcggcaga   1680
aaccctacaa gccagaagag agtgggggcc aatattcaac attcttaaag aaaagaattt   1740
tcaacccaga atttcatatc cagccaaact aagcttcata agtgaaggag aaataaaata   1800
ctttatagac aagcaaatgt tgagagattt tgtcaccacc aggcctgccc taaaagagct   1860
cctgaaggaa gcgctaaaca tggaaaggaa caaccggtac cagccgctgc aaaatcatgc   1920
caaaatgtaa agaccatcaa gactaggaag aaactgcatc aactaatgag caaaatcacc   1980
agctaacatc ataatgacag gatcaacttc acacataaca atattaactt taaatataaa   2040
tggactaaat tctgcaatta aaagacacag actggcaagt tggataaaga gtcaagaccc   2100
atcagtgtgc tgtattcagg aaacccatct cacgtgcaga gacacacata ggctcaaaat   2160
aaaaggatgg aggaagatct accaagccaa tggaaaacaa aaaaaggcag gggttgcaat   2220
cctagtctct gataaaacag actttaaacc aacaaagatc aaaagagaca aagaaggcca   2280
ttacataatg gtaaagggat caattcaaca agaggagcta actatcctaa atatttatgc   2340
acccaataca ggagcaccca gattcataaa gcaagtcctc agtgacctac aaagagactt   2400
agactcccac acattaataa tgggagactt taacacccca ctgtcaacat tagacagatc   2460
```

aacgagacag aaagtcaaca aggataccca ggaattgaac tcagctctgc accaagcaga 2520
cctaatagac atctacagaa ctctccaccc caaatcaaca gaatatacat ttttttcagc 2580
accacaccac acctattcca aaattgacca catagttgga agtaaagctc tcctcagcaa 2640
atgtaaaaga acagaaatta taacaaacta tctctcagac cacagtgcaa tcaaactaga 2700
actcaggatt aagaatctca ctcaaagccg ctcaactaca tggaaactga acaacctgct 2760
cctgaatgac tactgggtac ataacgaaat gaaggcagaa ataaagatgt tctttgaaac 2820
caacgagaac aaagacacca cataccagaa tctctgggac gcattcaaag cagtgtgtag 2880
agggaaattt atagcactaa atgcctacaa gagaaagcag gaaagatcca aaattgacac 2940
cctaacatca caattaaaag aactagaaaa gcaagagcaa acacattcaa aagctagcag 3000
aaggcaagaa ataactaaaa tcagagcaga actgaaggaa atagagacac aaaaaaccct 3060
tcaaaaaatc aatgaatcca ggagctggtt ttttgaaagg atcaacaaaa ttgatagacc 3120
gctagcaaga ctaataaaga aaaaaagaga gaagaatcaa atagacacaa taaaaaatga 3180
taaaggggat atcaccaccg atcccacaga aatacaaact accatcagag aatactacaa 3240
acacctctac gcaaataaac tagaaaatct agaagaaatg gatacattcc tcgacacata 3300
cactctccca agactaaacc aggaagaagt tgaatctctg aatcgaccaa taacaggctc 3360
tgaaattgtg gcaataatca atagtttacc aaccaaaaag agtccaggac cagatggatt 3420
cacagccgaa ttctaccaga ggtacaagga ggaactggta ccattccttc tgaaactatt 3480
ccaatcaata gaaaaagagg gaatcctccc taactcattt tatgaggcca gcatcattct 3540
gataccaaag ccgggcagag acacaaccaa aaaagagaat tttagaccaa tatccttgat 3600
gaacattgat gcaaaaatcc tcaataaaat actggcaaac cgaatccagc agcacatcaa 3660
aaagcttatc caccatgatc aagtgggctt catccctggg atgcaaggct ggttcaatat 3720
acgcaaatca ataaatgtaa tccagcatat aaacagagcc aaagacaaaa accacatgat 3780
tatctcaata gatgcagaaa aagcctttga caaaattcaa caacccttca tgctaaaaac 3840
tctcaataaa ttaggtattg atgggacgta tttcaaaata ataagagcta tctatgacaa 3900
acccacagcc aatatcatac tgaatgggca aaaactggaa gcattccctt tgaaaaccgg 3960
cacaagacag ggatgccctc tctcaccgct cctattcaac atagtgttgg aagttctggc 4020
cagggcaatc aggcaggaga aggaaataaa gggtattcaa ttaggaaaag aggaagtcaa 4080
attgtccctg tttgcagacg acatgattgt ttatctagaa aaccccatcg tctcagccca 4140
aaatctcctt aagctgataa gcaacttcag caaagtctca ggatacaaaa tcaatgtaca 4200
aaaatcacaa gcattcttat acaccaacaa cagacaaaca gagagccaaa tcatgggtga 4260
actcccattc acaattgctt caaagagaat aaaataccta ggaatccaac ttacaaggga 4320
tgtgaaggac ctcttcaagg agaactacaa accactgctc aaggaaataa aagaggagac 4380
aaacaaatgg aagaacattc catgctcatg ggtaggaaga atcaatatcg tgaaaatggc 4440
catactgccc aaggtaattt acagattcaa tgccatcccc atcaagctac caatgacttt 4500
cttcacagaa ttggaaaaaa ctactttaaa gttcatatgg aaccaaaaaa gagcccgcat 4560
tgccaagtca atcctaagcc aaaagaacaa agctggaggc atcacactac ctgacttcaa 4620
actatactac aaggctacag taaccaaaac agcatggtac tggtaccaaa acagagatat 4680
agatcaatgg aacagaacag agccctcaga aataatgccg catatctaca actatctgat 4740
ctttgacaaa cctgagaaaa acaagcaatg ggaaaggat tccctattta ataaatggtg 4800

```
ctgggaaaac tggctagcca tatgtagaaa gctgaaactg gatcccttcc ttacacctta   4860
tacaaaaatc aattcaagat ggattaaaga tttaaacgtt aaacctaaaa ccataaaaac   4920
cctagaagaa aacctaggca ttaccattca ggacataggc gtgggcaagg acttcatgtc   4980
caaaacacca aaagcaatgg caacaaaaga caaaattgac aaatgggatc taattaaact   5040
aaagagcttc tgcacagcaa aagaaactac catcagagtg aacaggcaac ctacaacatg   5100
ggagaaaatt tttgcaacct actcatctga caaagggcta atatccagaa tctacaatga   5160
actcaaacaa atttacaaga aaaaaacaaa caaccccatc aaaaagtggg cgaaggacat   5220
gaacagacac ttctcaaaag aagacattta tgcagccaaa aaacacatga agaaatgctc   5280
atcatcactg gccatcagag aaatgcaaat caaaaccact atgagatatc atctcacacc   5340
agttagaatg gcaatcatta aaaagtcagg aaacaacagg tgctggagag gatgcggaga   5400
aataggaaca cttttacact gttggtggga ctgtaaacta gttcaaccat tgtggaagtc   5460
agtgtggcga ttcctcaggg atctagaact agaaatacca tttgacccag ccatcccatt   5520
actgggtata tacccaaatg agtataaatc atgctgctat aaagacacat gcacacgtat   5580
gtttattgcg gcactattca caatagcaaa gacttggaac caacccaaat gtccaacaat   5640
gatagactgg attaagaaaa tgtggcacat atacaccatg gaatactatg cagccataaa   5700
aaatgatgag ttcatatcct ttgtagggac atggatgaaa ttggaaacca tcattctcag   5760
taaactatcg caagaacaaa aaccaaacac ccgcatattc tcactcatag gtgggaattg   5820
aacaatgaga tcacatggac acaggaaggg gaatatcaca ctctggggac tgtggtgggg   5880
tcgggggagg ggggagggat agcattggga gatataccta atgctagatg acacattagt   5940
gggtgcagcg caccagcatg gcacatgtat acggatccga attctcgacg gatcgatccg   6000
aacaaacgac ccaacacccg tgcgttttat tctgtctttt tattgccgat cccctcagaa   6060
gaactcgtca agaaggcgat agaaggcgat gcgctgcgaa tcgggagcgg cgataccgta   6120
aagcacgagg aagcggtcag cccattcgcc gccaagctct tcagcaatat cacgggtagc   6180
caacgctatg tcctgatagc ggtcggccgc tcatgttctc gtaggagtcg gcgtcctctt   6240
cgtggttagg tccaggttgg cctctgatag accgcagctg aggagcggcg tacagaatgc   6300
ctctcatgtc ctcatagctg ccgctgcctt gtggaggctt ctcgtgcttc agtgtctcgt   6360
atgtctcttg attccgggtg ctcaggccgg tgtacacgcc atcagatttc tcgtagctgg   6420
tgatggcggc cttccgcact tggatcttca gccgtctgca gtacagggtg atgaccagag   6480
acagcagcag gacaccacat gtgccagcca gaggggccca aatgtagata tccaggcctc   6540
tggtatgcac agctccgcct gcagcaggtc tacaggcttc aggtctgaga gacagaggct   6600
ggctggcgat tgtaggagct ggtgtaggtg gtctaggagc gggtgttgtt gtaggcttgg   6660
cgggcagaaa cacgggcacg aagtggctga agtacatgat gctattgctc agggctccgc   6720
ttcctccgcc gcctgatttg atttccagct tggtgcctcc gccaaatgtc caagggctct   6780
cgtcgtactg ctggcagtag tagatgccga agtcctcgta ctgcaggctg ctgattgtca   6840
gggtgtagtc ggtgccagag ccgctgccag aaaatctgct tggcacgccg ctttccagtc   6900
tgttggcccg gtagatcagt gtcttagggg ccttgccagg cttctgctgg aaccagctca   6960
ggtagctgtt gatgtcctgg ctggctctac aggtgatggt cactctatcg cccacagagg   7020
cagacaggct gctagggctc tgtgtcatct ggatatcaga gccaccaccg ccagatccac   7080
cgccacctga tcctccgcct ccgctagaaa ctgtcactgt ggtgccctgg ccccacacat   7140
cgaagtacca gtcgtagcct cttctggtgc agaagtacac ggcggtatcc tcggctctca   7200
```

-continued

```
ggctgttgat ctgcaggtag gcggtgttct tgctgtcgtc caggctgaag gtgaatctgc   7260
ccttaaagct atcggcgtag gttggctcgc cggtgtgggt attgatccag cccatccact   7320
caaggccagg tgagtccagg agatgtttca gcactgttgc ctttagtctc gaggcaactt   7380
agacaactga gtattgatct gagcacagca gggtgtgagc tgtttgaaga tactggggtt   7440
gggggtgaag aaactgcaga ggactaactg ggctgagacc cagtggcaat gttttagggc   7500
ctaaggaatg cctctgaaaa tctagatgga caactttgac tttgagaaaa gagaggtgga   7560
aatgaggaaa atgacttttc tttattagat ttcggtagaa agaactttca tctttcccct   7620
atttttgtta ttcgttttaa aacatctatc tggaggcagg acaagtatgg tcattaaaaa   7680
gatgcaggca gaaggcatat attggctcag tcaaagtggg gaactttggt ggccaaacat   7740
acattgctaa ggctattcct atatcagctg gacacatata aaatgctgct aatgcttcat   7800
tacaaactta tatcctttaa ttccagatgg gggcaaagta tgtccagggg tgaggaacaa   7860
ttgaaacatt tgggctggag tagattttga aagtcagctc tgtgtgtgtg tgtgtgtgtg   7920
tgtgtgtgag agcgtgtgtt tcttttaacg ttttcagcct acagcataca gggttcatgg   7980
tggcaagaag ataacaagat ttaaattatg gccagtgact agtgctgcaa gaagaacaac   8040
tacctgcatt taatgggaaa gcaaaatctc aggctttgag ggaagttaac ataggcttga   8100
ttctgggtgg aagctgggtg tgtagttatc tggaggccag gctggagctc tcagctcact   8160
atgggttcat ctttattgtc tcctttttcc aggggcctgt cggacccagt tcatgccgta   8220
gttggtgaag gtgtagccgc tggcggcaca gctgattctg acagatccgc caggtttcac   8280
aagtccgccg ccagactgaa ccagctggat ctcagagatg ctacaggcca ctgttcccag   8340
cagcagcaga gactgcagcc acatctggtg gcgaattcga agcttgagct cgagatctga   8400
gtccggtagc gctagcggat ctgacggttc actaaaccag ctctgcttat atagacctcc   8460
caccgtacac gcctaccgcc catttgcgtc aatggggcgg agttgttacg acattttgga   8520
aagtcccgtt gattttggtg ccaaaacaaa ctcccattga cgtcaatggg gtggagactt   8580
ggaaatcccc gtgagtcaaa ccgctatcca cgcccattga tgtactgcca aaaccgcatc   8640
accatggtaa tagcgatgac taatacgtag atgtactgcc aagtaggaaa gtcccataag   8700
gtcatgtact gggcataatg ccaggcgggc catttaccgt cattgacgtc aatagggggc   8760
gtacttggca tatgatacac ttgatgtact gccaagtggg cagtttaccg taaatactcc   8820
acccattgac gtcaatggaa agtccctatt ggcgttacta tgggaacata cgtcattatt   8880
gacgtcaatg ggcgggggtc gttgggcggt cagccaggcg ggccatttac cgtaagttat   8940
gtaacgcgga actccatata tgggctatga actaatgacc ccgtaattga ttactattag   9000
cccgggggat ccagacatga taagatacat tgatgagttt ggacaaacca caactagaat   9060
gcagtgaaaa aaatgcttta tttgtgaaat ttgtgatgct attgctttat ttgtaaccat   9120
tataagctgc aataaacaag ttaacaacaa caattgcatt cattttatgt ttcaggttca   9180
gggggaggtg tgggaggttt tttaaagcaa gtaaaacctc tacaaatgtg gtatggctga   9240
ttatgatccg gctgcctcgc gcgtttcggt gatgacggtg aaaacctctg acacatgcag   9300
ctcccggaga cggtcacagc ttgtctgtaa gcggatgccg ggagcagaca agcccgtcag   9360
ggcgcgtcag cgggtgttgg cgggtgtcgg ggcgcagcca tgaggtcgat cgactctaga   9420
ggatcgatcc ccgccccgga cgaactaaac ctgactacga catctctgcc ccttcttcgc   9480
ggggcagtgc atgtaatccc ttcagttggt tggtacaact tgccaactgg gccctgttcc   9540
```

```
acatgtgaca cgggggggga ccaaacacaa aggggttctc tgactgtagt tgacatcctt   9600
ataaatggat gtgcacattt gccaacactg agtggctttc atcctggagc agactttgca   9660
gtctgtggac tgcaacacaa cattgccttt atgtgtaact cttggctgaa gctcttacac   9720
caatgctggg ggacatgtac ctcccagggg cccaggaaga ctacgggagg ctacaccaac   9780
gtcaatcaga ggggcctgtg tagctaccga taagcggacc ctcaagaggg cattagcaat   9840
agtgtttata aggccccctt gttaacccta aacgggtagc atatgcttcc cgggtagtag   9900
tatatactat ccagactaac cctaattcaa tagcatatgt tacccaacgg gaagcatatg   9960
ctatcgaatt agggttagta aaagggtcct aaggaacagc gatatctccc accccatgag  10020
ctgtcacggt tttatttaca tggggtcagg attccacgag ggtagtgaac cattttagtc  10080
acaagggcag tggctgaaga tcaaggagcg ggcagtgaac tctcctgaat cttcgcctgc  10140
ttcttcattc tccttcgttt agctaataga ataactgctg agttgtgaac agtaaggtgt  10200
atgtgaggtg ctcgaaaaca aggtttcagg tgacgccccc agaataaaat ttggacgggg  10260
ggttcagtgg tggcattgtg ctatgacacc aatataaccc tcacaaaccc cttgggcaat  10320
aaatactagt gtaggaatga aacattctga atatctttaa caatagaaat ccatggggtg  10380
gggacaagcc gtaaagactg gatgtccatc tcacacgaat ttatggctat gggcaacaca  10440
taatcctagt gcaatatgat actggggtta ttaagatgtg tcccaggcag ggaccaagac  10500
aggtgaacca tgttgttaca ctctatttgt aacaagggga aagagagtgg acgccgacag  10560
cagcggactc cactggttgt ctctaacacc cccgaaaatt aaacggggct ccacgccaat  10620
ggggcccata aacaaagaca agtggccact cttttttttg aaattgtgga gtgggggcac  10680
gcgtcagccc ccacacgccg ccctgcggtt ttggactgta aaataagggt gtaataactt  10740
ggctgattgt aaccccgcta accactgcgg tcaaaccact tgcccacaaa accactaatg  10800
gcaccccggg gaatacctgc ataagtaggt gggcgggcca agataggggc gcgattgctg  10860
cgatctggag gacaaattac acacacttgc gcctgagcgc caagcacagg gttgttggtc  10920
ctcatattca cgaggtcgct gagagcacgg tgggctaatg ttgccatggg tagcatatac  10980
tacccaaata tctggatagc atatgctatc ctaatctata tctgggtagc ataggctatc  11040
ctaatctata tctgggtagc atatgctatc ctaatctata tctgggtagt atatgctatc  11100
ctaatttata tctgggtagc ataggctatc ctaatctata tctgggtagc atatgctatc  11160
ctaatctata tctgggtagt atatgctatc ctaatctgta tccgggtagc atatgctatc  11220
ctaatagaga ttagggtagt atatgctatc ctaatttata tctgggtagc atatactacc  11280
caaatatctg gatagcatat gctatcctaa tctatatctg ggtagcatat gctatcctaa  11340
tctatatctg ggtagcatag gctatcctaa tctatatctg ggtagcatat gctatcctaa  11400
tctatatctg ggtagtatat gctatcctaa tttatatctg ggtagcatag gctatcctaa  11460
tctatatctg ggtagcatat gctatcctaa tctatatctg ggtagtatat gctatcctaa  11520
tctgtatccg ggtagcatat gctatcctca tgcatataca gtcagcatat gatacccagt  11580
agtagagtgg gagtgctatc ctttgcatat gccgccacct cccaaggggg cgtgaatttt  11640
cgctgcttgt ccttttcctg catgctggtt gctcccattc ttaggtgaat ttaaggaggc  11700
caggctaaag ccgtcgcatg tctgattgct caccaggtaa atgtcgctaa tgttttccaa  11760
cgcgagaagg tgttgagcgc ggagctgagt gacgtgacaa catgggtatg cccaattgcc  11820
ccatgttggg aggacgaaaa tggtgacaag acagatggcc agaaatacac caacagcacg  11880
catgatgtct actggggatt tattctttag tgcgggggaa tacacggctt ttaatacgat  11940
```

tgagggcgtc tcctaacaag ttacatcact cctgcccttc ctcaccctca tctccatcac 12000
ctccttcatc tccgtcatct ccgtcatcac cctccgcggc agccccttcc accataggtg 12060
gaaaccaggg aggcaaatct actccatcgt caaagctgca cacagtcacc ctgatattgc 12120
aggtaggagc gggctttgtc ataacaaggt ccttaatcgc atccttcaaa acctcagcaa 12180
atatatgagt ttgtaaaaag accatgaaat aacagacaat ggactccctt agcgggccag 12240
gttgtgggcc gggtccaggg gccattccaa aggggagacg actcaatggt gtaagacgac 12300
attgtggaat agcaagggca gttcctcgcc ttaggttgta aagggaggtc ttactacctc 12360
catatacgaa cacaccggcg acccaagttc cttcgtcggt agtcctttct acgtgactcc 12420
tagccaggag agctcttaaa ccttctgcaa tgttctcaaa tttcgggttg gaacctcctt 12480
gaccacgatg ctttccaaac caccctcctt ttttgcgcct gcctccatca ccctgacccc 12540
ggggtccagt gcttgggcct tctcctgggt catctgcggg gccctgctct atcgctcccg 12600
ggggcacgtc aggctcacca tctgggccac cttcttggtg gtattcaaaa taatcggctt 12660
cccctacagg gtggaaaaat ggccttctac ctggaggggg cctgcgcggt ggagacccgg 12720
atgatgatga ctgactactg ggactcctgg gcctcttttc tccacgtcca cgacctctcc 12780
ccctggctct ttcacgactt ccccccctgg ctctttcacg tcctctaccc cggcggcctc 12840
cactacctcc tcgaccccgg cctccactac ctcctcgacc ccggcctcca ctgcctcctc 12900
gaccccggcc tccacctcct gctcctgccc ctcctgctcc tgcccctcct cctgctcctg 12960
cccctcctgc ccctcctgct cctgcccctc ctgcccctcc tgctcctgcc cctcctgccc 13020
ctcctgctcc tgcccctcct gcccctcctc ctgctcctgc ccctcctgcc cctcctcctg 13080
ctcctgcccc tcctgcccct cctgctcctg cccctcctgc ccctcctgct cctgcccctc 13140
ctgcccctcc tgctcctgcc cctcctgctc ctgcccctcc tgctcctgcc cctcctgctc 13200
ctgcccctcc tgcccctcct gcccctcctc ctgctcctgc ccctcctgct cctgcccctc 13260
ctgcccctcc tgcccctcct gctcctgccc ctcctcctgc tcctgcccct cctgcccctc 13320
ctgcccctcc tcctgctcct gcccctcctg cccctcctcc tgctcctgcc cctcctcctg 13380
ctcctgcccc tcctgcccct cctgcccctc ctcctgctcc tgcccctcct gcccctcctc 13440
ctgctcctgc ccctcctcct gctcctgccc ctcctgcccc tcctgcccct cctcctgctc 13500
ctgcccctcc tcctgctcct gcccctcctg cccctcctgc ccctcctgcc cctcctcctg 13560
ctcctgcccc tcctcctgct cctgcccctc ctgctcctgc ccctcccgct cctgctcctg 13620
ctcctgttcc accgtgggtc cctttgcagc caatgcaact tggacgtttt tggggtctcc 13680
ggacaccatc tctatgtctt ggccctgatc ctgagccgcc cggggctcct ggtcttccgc 13740
ctcctcgtcc tcgtcctctt ccccgtcctc gtccatggtt atcacccccct cttctttgag 13800
gtccactgcc gccggagcct tctggtccag atgtgtctcc cttctctcct aggccatttc 13860
caggtcctgt acctggcccc tcgtcagaca tgattcacac taaaagagat caatagacat 13920
ctttattaga cgacgctcag tgaatacagg gagtgcagac tcctgccccc tccaacagcc 13980
cccccaccct catccccttc atggtcgctg tcagacagat ccaggtctga aaattcccca 14040
tcctccgaac catcctcgtc ctcatcacca attactcgca gcccggaaaa ctcccgctga 14100
acatcctcaa gatttgcgtc ctgagcctca agccaggcct caaattcctc gtccccccttt 14160
ttgctggacg gtagggatgg ggattctcgg gacccctcct cttcctcttc aaggtcacca 14220
gacagagatg ctactggggc aacggaagaa aagctgggtg cggcctgtga ggatcagctt 14280
atcgatgata agctgtcaaa catgagaatt cttgaagacg aaagggcctc gtgatacgcc 14340
tatttttata ggttaatgtc atgataataa tggtttctta gacgtcaggt ggcacttttc 14400
ggggaaatgt gcgcggaacc cctatttgtt tatttttcta aatacattca aatatgtatc 14460
cgctcatgag acaataaccc tgataaatgc ttcaataata ttgaaaaagg aagagtatga 14520
gtattcaaca tttccgtgtc gcccttattc ccttttttgc ggcattttgc cttcctgttt 14580
ttgctcaccc agaaacgctg gtgaaagtaa aagatgctga agatcagttg ggtgcacgag 14640
tgggttacat cgaactggat ctcaacagcg gtaagatcct tgagagtttt cgccccgaag 14700
aacgttttcc aatgatgagc acttttaaag ttctgctatg tggcgcggta ttatcccgtg 14760
ttgacgccgg gcaagagcaa ctcggtcgcc gcatacacta ttctcagaat gacttggttg 14820
agtactcacc agtcacagaa aagcatctta cggatggcat gacagtaaga gaattatgca 14880
gtgctgccat aaccatgagt gataacactg cggccaactt acttctgaca acgatcggag 14940
gaccgaagga gctaaccgct tttttgcaca acatggggga tcatgtaact cgccttgatc 15000
gttgggaacc ggagctgaat gaagccatac caaacgacga gcgtgacacc acgatgcctg 15060
cagcaatggc aacaacgttg cgcaaactat taactggcga actacttact ctagcttccc 15120
ggcaacaatt aatagactgg atggaggcgg ataaagttgc aggaccactt ctgcgctcgg 15180
cccttccggc tggctggttt attgctgata aatctggagc cggtgagcgt gggtctcgcg 15240
gtatcattgc agcactgggg ccagatggta agccctcccg tatcgtagtt atctacacga 15300
cggggagtca ggcaactatg gatgaacgaa atagacagat cgctgagata ggtgcctcac 15360
tgattaagca ttggtaactg tcagaccaag tttactcata tatactttag attgatttaa 15420
aacttcattt ttaatttaaa aggatctagg tgaagatcct ttttgataat ctcatgacca 15480
aaatccctta acgtgagttt tcgttccact gagcgtcaga ccccgtagaa aagatcaaag 15540
gatcttcttg agatcctttt tttctgcgcg taatctgctg cttgcaaaca aaaaaaccac 15600
cgctaccagc ggtggtttgt ttgccggatc aagagctacc aactcttttt ccgaaggtaa 15660
ctggcttcag cagagcgcag ataccaaata ctgtccttct agtgtagccg tagttaggcc 15720
accacttcaa gaactctgta gcaccgccta catacctcgc tctgctaatc ctgttaccag 15780
tggctgctgc cagtggcgat aagtcgtgtc ttaccgggtt ggactcaaga cgatagttac 15840
cggataaggc gcagcggtcg ggctgaacgg ggggttcgtg cacacagccc agcttggagc 15900
gaacgaccta caccgaactg agatacctac agcgtgagct atgagaaagc gccacgcttc 15960
ccgaagggag aaaggcggac aggtatccgg taagcggcag ggtcggaaca ggagagcgca 16020
cgagggagct tccaggggga aacgcctggt atctttatag tcctgtcggg tttcgccacc 16080
tctgacttga gcgtcgattt ttgtgatgct cgtcaggggg gcggagccta tggaaaaacg 16140
ccagcaacgc ggccttttta cggttcctgg ccttttgctg gccttttgct cacatgttct 16200
ttcctgcgtt atcccctgat tctgtggata accgtattac cgcctttgag tgagctgata 16260
ccgctcgccg cagccgaacg accgagcgca gcgagtcagt gagcgaggaa gcggaagagc 16320
gcctgatgcg gtattttctc cttacgcatc tgtgcggtat ttcacaccgc atatggtgca 16380
ctctcagtac aatctgctct gatgccgcat agttaagcca gctgtggaat gtgtgtcagt 16440
tagggtgtgg aaagtcccca ggctccccag caggcagaag tatgcaaagc atgcatctca 16500
attagtcagc aaccaggtgt ggaaagtccc caggctcccc agcaggcaga agtatgcaaa 16560
gcatgcatct caattagtca gcaaccatag tcccgcccct aactccgccc atcccgcccc 16620
taactccgcc cagttccgcc cattctccgc cccatggctg actaattttt tttatttatg 16680

```
cagaggccga ggccgcctcg gcctctgagc tattccagaa gtagtgagga ggcttttttg  16740
gaggcctagg cttttgcaaa aagcttgcat gcctgcaggt cggccgccac gaccggtgcc  16800
gccaccatcc cctgacccac gcccctgacc cctcacaagg agacgacctt ccatgaccga  16860
gtacaagccc acggtgcgcc tcgccacccg cgacgacgtc cccgggccg tacgcaccct  16920
cgccgccgcg ttcgccgact accccgccac gcgccacacc gtcgacccgg accgccacat  16980
cgagcgggtc accgagctgc aagaactctt cctcacgcgc gtcgggctcg acatcggcaa  17040
ggtgtgggtc gcggacgacg gcgccgcggt ggcggtctgg accacgccgg agagcgtcga  17100
agcgggggcg gtgttcgccg agatcggccc gcgcatggcc gagttgagcg gttcccggct  17160
ggccgcgcag caacagatgg aaggcctcct ggcgccgcac cggcccaagg agcccgcgtg  17220
gttcctggcc accgtcggcg tctcgcccga ccaccagggc aagggtctgg gcagcgccgt  17280
cgtgctcccc ggagtggagg cggccgagcg cgccggggtg cccgccttcc tggagacctc  17340
cgcgccccgc aacctcccct tctacgagcg gctcggcttc accgtcaccg ccgacgtcga  17400
ggtgcccgaa ggaccgcgca cctggtgcat gacccgcaag cccggtgcct gacgcccgcc  17460
ccacgacccg cagcgcccga ccgaaaggag cgcacgaccc catggctccg accgaagccg  17520
acccgggcgg ccccgccgac cccgcacccg cccccgaggc ccaccgactc tagaggatca  17580
taatcagcca taccacattt gtagaggttt tacttgcttt aaaaaacctc ccacacctcc  17640
ccctgaacct gaaacataaa atgaatgcaa ttgttgttgt taacttgttt attgcagctt  17700
ataatggtta caaataaagc aatagcatca caaatttcac aaataaagca tttttttcac  17760
tgcattctag ttgtggtttg tccaaactca tcaatgtatc ttatcatgtc tggatcactc  17820
gccgatagtg gaaaccgacg ccccagcact cgtccgaggg caaaggaata ggggagatgg  17880
gggaggctaa ctgaaacacg gaaggagaca ataccggaag gaacccgcgc tatgacggca  17940
ataaaaagac agaataaaac gcacgggtgt tgggtcgttt gttcataaac gcggggttcg  18000
gtcccagggc tggcactctg tcgatacccc accgagaccc cattggggcc aatacgcccg  18060
cgtttcttcc ttttccccac cccacccccc aagttcgggt gaaggcccag ggctcgcagc  18120
caacgtcggg gcggcaggcc ctgccatagc cactggcccc gtgggttagg gacggggtcc  18180
cccatgggga atggtttatg gttcgtgggg gttattattt tgggcgttgc gtggggtctg  18240
gtccacgact ggactgagca gacagaccca tggtttttgg atggcctggg catggaccgc  18300
atgtactggc gcgacacgaa caccgggcgt ctgtggctgc caaacacccc cgaccccaa  18360
aaaccaccgc gcggatttct ggcgtgccaa gctagtcgac caattctcat gtttgacagc  18420
ttatcatcgc agatccgggc aacgttgttg cattgctgca ggcgcagaac tggtaggtat  18480
ggaagatctc tagaagctgg gtaccagctg ctagcaagct tgctagcggc cggctcgagt  18540
ttactcccta tcagtgatag agaacgtatg tcgagtttac tccctatcag tgatagagaa  18600
cgatgtcgag tttactccct atcagtgata gagaacgtat gtcgagttta ctccctatca  18660
gtgatagaga acgtatgtcg agtttactcc ctatcagtga tagagaacgt atgtcgagtt  18720
tatccctatc agtgatagag aacgtatgtc gagtttactc cctatcagtg atagagaacg  18780
tatgtcgagg taggcgtgta cggtgggagg cctatataag cagagctcgt ttagtgaacc  18840
gtcagatcgc cg                                                    18852
```

<210> SEQ ID NO 40
<211> LENGTH: 19625
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 40
cggccgcggg gggaggagcc aagatggccg aataggaaca gctccggtct acagctccca 60
gcgtgagcga cgcagaagac ggtgatttct gcatttccat ctgaggtacc gggttcatct 120
cactagggag tgccagacag tgggcgcagg ccagtgtgtg tgcgcaccgt gcgcgagccg 180
aagcagggcg aggcattgcc tcacctggga agcgcaaggg gtcagggagt tccctttccg 240
agtcaaagaa aggggtgacg gacgcacctg gaaaatcggg tcactcccac ccgaatattg 300
cgcttttcag accggcttaa gaaacggcgc accacgagac tatatcccac acctggctcg 360
gagggtccta cgcccacgga atctcgctga ttgctagcac agcagtctga gatcaaactg 420
caaggcggca acgaggctgg gggaggggcg cccgccattg cccaggcttg cttaggtaaa 480
caaagcagca gggaagctcg aactgggtgg agcccaccac agctcaagga ggcctgcctg 540
cctctgtagg ctccacctct gggggcaggg cacagacaaa caaaaagaca gcagtaacct 600
ctgcagactt aagtgtccct gtctgacagc tttgaagaga gcagtggttc tcccagcacg 660
cagctggaga tctgagaacg ggcagactgc ctcctcaagt gggtccctga cccctgaccc 720
ccgagcagcc taactgggag gcaccccca gcaggggcac actgacacct cacacggcag 780
ggtattccaa cagacctgca gctgagggtc ctgtctgtta gaaggaaaac taacaaccag 840
aaaggacatc tacaccgaaa acccatctgt acatcaccat catcaaagac caaaagtaga 900
taaaaccaca aagatgggga aaaaacagaa cagaaaaact ggaaactcta aaacgcagag 960
cgcctctcct cctccaaagg aacgcagttc ctcaccagca acagaacaaa gctggatgga 1020
gaatgatttt gatgagctga gagaagaagg cttcagacga tcaaattact ctgagctacg 1080
ggaggacatt caaaccaaag gcaaagaagt tgaaaacttt gaaaaaaatt tagaagaatg 1140
tataactaga ataaccaata cagagaagtg cttaaaggag ctgatggagc tgaaaaccaa 1200
ggctcgagaa ctacgtgaag aatgcagaag cctcaggagc cgatgcgatc aactggaaga 1260
aagggtatca gcaatggaag atgaaatgaa tgaaatgaag cgagaaggga agtttagaga 1320
aaaaagaata aaaagaaatg agcaaagcct ccaagaaata tgggactatg tgaaaagacc 1380
aaatctacgt ctgattggtg tacctgaaag tgatgtggag aatggaacca agttggaaaa 1440
cactctgcag gatattatcc aggagaactt ccccaatcta gcaaggcagg ccaacgttca 1500
gattcaggaa atacagagaa cgccacaaag atactcctcg agaagagcaa ctccaagaca 1560
cataattgtc agattcacca aagttgaaat gaaggaaaaa atgttaaggg cagccagaga 1620
gaaaggtcgg gttaccctca aaggaaagcc catcagacta acagcggatc tctcggcaga 1680
aaccctacaa gccagaagag agtgggggcc aatattcaac attcttaaag aaaagaattt 1740
tcaacccaga atttcatatc cagccaaact aagcttcata agtgaaggag aaataaaata 1800
ctttatagac aagcaaatgt tgagagattt tgtcaccacc aggcctgccc taaaagagct 1860
cctgaaggaa gcgctaaaca tggaaaggaa caaccggtac cagccgctgc aaaatcatgc 1920
caaaatgtaa agaccatcaa gactaggaag aaactgcatc aactaatgag caaaatcacc 1980
agctaacatc ataatgacag gatcaacttc acacataaca atattaactt taaatataaa 2040
tggactaaat tctgcaatta aaagacacag actggcaagt tggataaaga gtcaagaccc 2100
atcagtgtgc tgtattcagg aaacccatct cacgtgcaga gacacacata ggctcaaaat 2160

```
aaaaggatgg aggaagatct accaagccaa tggaaaacaa aaaaaggcag gggttgcaat   2220
cctagtctct gataaaacag actttaaacc aacaaagatc aaaagagaca aagaaggcca   2280
ttacataatg gtaaagggat caattcaaca agaggagcta actatcctaa atatttatgc   2340
acccaataca ggagcaccca gattcataaa gcaagtcctc agtgacctac aaagagactt   2400
agactcccac acattaataa tgggagactt taacacccca ctgtcaacat tagacagatc   2460
aacgagacag aaagtcaaca aggataccca ggaattgaac tcagctctgc accaagcaga   2520
cctaatagac atctacagaa ctctccaccc caaatcaaca gaatatacat ttttttcagc   2580
accacaccac acctattcca aaattgacca catagttgga agtaaagctc tcctcagcaa   2640
atgtaaaaga acagaaatta taacaaacta tctctcagac cacagtgcaa tcaaactaga   2700
actcaggatt aagaatctca ctcaaagccg ctcaactaca tggaaactga acaacctgct   2760
cctgaatgac tactgggtac ataacgaaat gaaggcagaa ataaagatgt tctttgaaac   2820
caacgagaac aaagacacca cataccagaa tctctgggac gcattcaaag cagtgtgtag   2880
agggaaattt atagcactaa atgcctacaa gagaaagcag gaaagatcca aaattgacac   2940
cctaacatca caattaaaag aactagaaaa gcaagagcaa acacattcaa aagctagcag   3000
aaggcaagaa ataactaaaa tcagagcaga actgaaggaa atagagacac aaaaaaccct   3060
tcaaaaaatc aatgaatcca ggagctggtt ttttgaaagg atcaacaaaa ttgatagacc   3120
gctagcaaga ctaataaaga aaaaaagaga gaagaatcaa atagacacaa taaaaaatga   3180
taaaggggat atcaccaccg atcccacaga aatacaaact accatcagag aatactacaa   3240
acacctctac gcaaataaac tagaaaatct agaagaaatg gatacattcc tcgacacata   3300
cactctccca agactaaacc aggaagaagt tgaatctctg aatcgaccaa taacaggctc   3360
tgaaattgtg gcaataatca atagtttacc aaccaaaaag agtccaggac cagatggatt   3420
cacagccgaa ttctaccaga ggtacaagga ggaactggta ccattccttc tgaaactatt   3480
ccaatcaata gaaaaagagg gaatcctccc taactcattt tatgaggcca gcatcattct   3540
gataccaaag ccgggcagag acacaaccaa aaaagagaat tttagaccaa tatccttgat   3600
gaacattgat gcaaaaatcc tcaataaaat actggcaaac cgaatccagc agcacatcaa   3660
aaagcttatc caccatgatc aagtgggctt catccctggg atgcaaggct ggttcaatat   3720
acgcaaatca ataaatgtaa tccagcatat aaacagagcc aaagacaaaa accacatgat   3780
tatctcaata gatgcagaaa aagcctttga caaaattcaa caacccttca tgctaaaaac   3840
tctcaataaa ttaggtattg atgggacgta tttcaaaata ataagagcta tctatgacaa   3900
acccacagcc aatatcatac tgaatgggca aaaactggaa gcattccctt tgaaaaccgg   3960
cacaagacag ggatgccctc tctcaccgct cctattcaac atagtgttgg aagttctggc   4020
cagggcaatc aggcaggaga aggaaataaa gggtattcaa ttaggaaaag aggaagtcaa   4080
attgtccctg tttgcagacg acatgattgt ttatctagaa aaccccatcg tctcagccca   4140
aaatctcctt aagctgataa gcaacttcag caaagtctca ggatacaaaa tcaatgtaca   4200
aaaatcacaa gcattcttat acaccaacaa cagacaaaca gagagccaaa tcatgggtga   4260
actcccattc acaattgctt caaagagaat aaaataccta ggaatccaac ttacaaggga   4320
tgtgaaggac ctcttcaagg agaactacaa accactgctc aaggaaataa aagaggagac   4380
aaacaaatgg aagaacattc catgctcatg ggtaggaaga atcaatatcg tgaaaatggc   4440
catactgccc aaggtaattt acagattcaa tgccatcccc atcaagctac caatgacttt   4500
cttcacagaa ttggaaaaaa ctactttaaa gttcatatgg aaccaaaaaa gagcccgcat   4560
```

tgccaagtca atcctaagcc aaaagaacaa agctggaggc atcacactac ctgacttcaa 4620
actatactac aaggctacag taaccaaaac agcatggtac tggtaccaaa acagagatat 4680
agatcaatgg aacagaacag agccctcaga aataatgccg catatctaca actatctgat 4740
ctttgacaaa cctgagaaaa acaagcaatg ggaaaggat tccctattta ataaatggtg 4800
ctgggaaaac tggctagcca tatgtagaaa gctgaaactg gatcccttcc ttacacctta 4860
tacaaaaatc aattcaagat ggattaaaga tttaaacgtt aaacctaaaa ccataaaaac 4920
cctagaagaa aacctaggca ttaccattca ggacataggc gtgggcaagg acttcatgtc 4980
caaaacacca aaagcaatgg caacaaaaga caaaattgac aaatgggatc taattaaact 5040
aaagagcttc tgcacagcaa aagaaactac catcagagtg aacaggcaac ctacaacatg 5100
ggagaaaatt tttgcaacct actcatctga caaagggcta atatccagaa tctacaatga 5160
actcaaacaa atttacaaga aaaaaacaaa caaccccatc aaaaagtggg cgaaggacat 5220
gaacagacac ttctcaaaag aagacattta tgcagccaaa aaacacatga agaaatgctc 5280
atcatcactg gccatcagag aaatgcaaat caaaaccact atgagatatc atctcacacc 5340
agttagaatg gcaatcatta aaaagtcagg aaacaacagg tgctggagag gatgcggaga 5400
aataggaaca cttttacact gttggtggga ctgtaaacta gttcaaccat tgtggaagtc 5460
agtgtggcga ttcctcaggg atctagaact agaaatacca tttgacccag ccatcccatt 5520
actgggtata tacccaaatg agtataaatc atgctgctat aaagacacat gcacacgtat 5580
gtttattgcg gcactattca caatagcaaa gacttggaac caacccaaat gtccaacaat 5640
gatagactgg attaagaaaa tgtggcacat atacaccatg gaatactatg cagccataaa 5700
aaatgatgag ttcatatcct ttgtagggac atggatgaaa ttggaaacca tcattctcag 5760
taaactatcg caagaacaaa aaaccaaaca ccgcatattc tcactcatag gtgggaattg 5820
aacaatgaga tcacatggac acaggaaggg gaatatcaca ctctggggac tgtggtgggg 5880
tcgggggagg ggggagggat agcattggga gatataccta atgctagatg acacattagt 5940
gggtgcagcg caccagcatg gcacatgtat acggatccga attctcgacg gatcgatccg 6000
aacaaacgac ccaacacccg tgcgttttat tctgtctttt tattgccgat cccctcagaa 6060
gaactcgtca agaaggcgat agaaggcgat gcgctgcgaa tcgggagcgg cgataccgta 6120
aagcacgagg aagcggtcag cccattcgcc gccaagctct tcagcaatat cacgggtagc 6180
caacgctatg tcctgatagc ggtcggccgc tttacttgta cagctcgtcc atgccgagag 6240
tgatcccggc ggcggtcacg aactccagca ggaccatgtg atcgcgcttc tcgttggggt 6300
ctttgctcag ggcggactgg gtgctcaggt agtggttgtc gggcagcagc acggggccgt 6360
cgccgatggg ggtgttctgc tggtagtggt cggccaggtg agtccaggag atgtttcagc 6420
actgttgcct ttagtctcga ggcaacttag acaactgagt attgatctga gcacagcagg 6480
gtgtgagctg tttgaagata ctggggttgg gggtgaagaa actgcagagg actaactggg 6540
ctgagaccca gtggcaatgt tttagggcct aaggaatgcc tctgaaaatc tagatggaca 6600
actttgactt tgagaaaaga gaggtggaaa tgaggaaaat gacttttctt tattagattt 6660
cggtagaaag aactttcatc tttcccctat ttttgttatt cgttttaaaa catctatctg 6720
gaggcaggac aagtatggtc attaaaaaga tgcaggcaga aggcatatat tggctcagtc 6780
aaagtgggga actttggtgg ccaaacatac attgctaagg ctattcctat atcagctgga 6840
cacatataaa atgctgctaa tgcttcatta caaacttata tcctttaatt ccagatgggg 6900
gcaaagtatg tccaggggtg aggaacaatt gaaacatttg ggctggagta gattttgaaa 6960
gtcagctctg tgtgtgtgtg tgtgtgtgtg tgtgtgagag cgtgtgtttc ttttaacgtt 7020
ttcagcctac agcatacagg gttcatggtg gcaagaagat aacaagattt aaattatggc 7080
cagtgactag tgctgcaaga agaacaacta cctgcattta atgggaaagc aaaatctcag 7140
gctttgaggg aagttaacat aggcttgatt ctgggtggaa gctgggtgtg tagttatctg 7200
gaggccaggc tggagctctc agctcactat gggttcatct ttattgtctc ctttcatctc 7260
aacagctgca cgctgccgtc ctcgatgttg tggcggatct tgaagttcac cttgatgccg 7320
ttcttctgct tgtcggccat gatatagacg ttgtggctgt tgtagttgta ctccagcttg 7380
tgccccagga tgttgccgtc ctccttgaag tcgatgccct tcagctcgat gcggttcacc 7440
agggtgtcgc cctcgaactt cacctcggcg cgggtcttgt agttgccgtc gtccttgaag 7500
aagatggtgc gctcctggac gtagccttcg ggcatggcgg acttgaagaa gtcgtgctgc 7560
ttcatgtggt cggggtagcg gctgaagcac tgcacgccgt aggtcagggt ggtcacgagg 7620
gtgggccagg gcacgggcag cttgccggtg gtgcagatga acttcagggt cagcttgccg 7680
taggtggcat cgccctcgcc ctcgccggac acgctgaact tgtggccgtt tacgtcgccg 7740
tccagctcga ccaggatggg caccaccccg gtgaacagct cctcgccctt gctcaccata 7800
gggccgggat tctcctccac gtcaccgcat gttagaagac ttcctctgcc ctccatgttc 7860
tcgtaggagt cggcgtcctc ttcgtggtta ggtccaggtt ggcctctgat agaccgcagc 7920
tgaggagcgg cgtacagaat gcctctcatg tcctcatagc tgccgctgcc ttgtggaggc 7980
ttctcgtgct tcagtgtctc gtatgtctct tgattccggg tgctcaggcc ggtgtacacg 8040
ccatcagatt tctcgtagct ggtgatggcg gccttccgca cttggatctt cagccgtctg 8100
cagtacaggg tgatgaccag agacagcagc aggacaccac atgtgccagc cagaggggcc 8160
caaatgtaga tatccaggcc tctggtatgc acagctccgc ctgcagcagg tctacaggct 8220
tcaggtctga gagacagagg ctggctggcg attgtaggag ctggtgtagg tggtctagga 8280
gcgggtgttg ttgtaggctt ggcgggcaga aacacgggca cgaagtggct gaagtacatg 8340
atgctattgc tcagggctcc gcttcctccg ccgcctgatt tgatttccag cttggtgcct 8400
ccgccaaatg tccaagggct ctcgtcgtac tgctggcagt agtagatgcc gaagtcctcg 8460
tactgcaggc tgctgattgt cagggtgtag tcggtgccag agccgctgcc agaaaatctg 8520
cttggcacgc cgctttccag tctgttggcc cggtagatca gtgtcttagg ggccttgcca 8580
ggcttctgct ggaaccagct caggtagctg ttgatgtcct ggctggctct acaggtgatg 8640
gtcactctat cgcccacaga ggcagacagg ctgctagggc tctgtgtcat ctggatatca 8700
gagccaccac cgccagatcc accgccacct gatcctccgc ctccgctaga aactgtcact 8760
gtggtgccct ggccccacac atcgaagtac cagtcgtagc ctcttctggt gcagaagtac 8820
acggcggtat cctcggctct caggctgttg atctgcaggt aggcggtgtt cttgctgtcg 8880
tccaggctga aggtgaatct gcccttaaag ctatcggcgt aggttggctc gccggtgtgg 8940
gtattgatcc agcccatcca ctcaaggcct tttccagggg cctgtcggac ccagttcatg 9000
ccgtagttgg tgaaggtgta gccgctggcg gcacagctga ttctgacaga tccgccaggt 9060
ttcacaagtc cgccgccaga ctgaaccagc tggatctcag agatgctaca ggccactgtt 9120
cccagcagca gcagagactg cagccacatt cgaagcttga gctcgagatc tgagtccggt 9180
agcgctagcg gatctgacgg ttcactaaac cagctctgct tatatagacc tcccaccgta 9240
cacgcctacc gcccatttgc gtcaatgggg cggagttgtt acgacatttt ggaaagtccc 9300

```
gttgattttg gtgccaaaac aaactcccat tgacgtcaat ggggtggaga cttggaaatc   9360
cccgtgagtc aaaccgctat ccacgcccat tgatgtactg ccaaaaccgc atcaccatgg   9420
taatagcgat gactaatacg tagatgtact gccaagtagg aaagtcccat aaggtcatgt   9480
actgggcata atgccaggcg ggccatttac cgtcattgac gtcaataggg ggcgtacttg   9540
gcatatgata cacttgatgt actgccaagt gggcagttta ccgtaaatac tccacccatt   9600
gacgtcaatg gaaagtccct attggcgtta ctatgggaac atacgtcatt attgacgtca   9660
atgggcgggg gtcgttgggc ggtcagccag gcgggccatt taccgtaagt tatgtaacgc   9720
ggaactccat atatgggcta tgaactaatg accccgtaat tgattactat tagcccgggg   9780
gatccagaca tgataagata cattgatgag tttggacaaa ccacaactag aatgcagtga   9840
aaaaaatgct ttatttgtga aatttgtgat gctattgctt tatttgtaac cattataagc   9900
tgcaataaac aagttaacaa caacaattgc attcatttta tgtttcaggt tcagggggag   9960
gtgtgggagg tttttaaag caagtaaaac ctctacaaat gtggtatggc tgattatgat  10020
ccggctgcct cgcgcgtttc ggtgatgacg gtgaaaacct ctgacacatg cagctcccgg  10080
agacggtcac agcttgtctg taagcggatg ccgggagcag acaagcccgt cagggcgcgt  10140
cagcgggtgt tggcgggtgt cggggcgcag ccatgaggtc gatcgactct agaggatcga  10200
tccccgcccc ggacgaacta aacctgacta cgacatctct gccccttctt cgcggggcag  10260
tgcatgtaat cccttcagtt ggttggtaca acttgccaac tgggccctgt tccacatgtg  10320
acacgggggg ggaccaaaca caaaggggtt ctctgactgt agttgacatc cttataaatg  10380
gatgtgcaca tttgccaaca ctgagtggct ttcatcctgg agcagacttt gcagtctgtg  10440
gactgcaaca caacattgcc tttatgtgta actcttggct gaagctctta caccaatgct  10500
gggggacatg tacctcccag gggcccagga agactacggg aggctacacc aacgtcaatc  10560
agaggggcct gtgtagctac cgataagcgg accctcaaga gggcattagc aatagtgttt  10620
ataaggcccc cttgttaacc ctaaacgggt agcatatgct tcccgggtag tagtatatac  10680
tatccagact aaccctaatt caatagcata tgttacccaa cgggaagcat atgctatcga  10740
attagggtta gtaaaagggt cctaaggaac agcgatatct cccaccccat gagctgtcac  10800
ggttttattt acatggggtc aggattccac gagggtagtg aaccatttta gtcacaaggg  10860
cagtggctga agatcaagga gcgggcagtg aactctcctg aatcttcgcc tgcttcttca  10920
ttctccttcg tttagctaat agaataactg ctgagttgtg aacagtaagg tgtatgtgag  10980
gtgctcgaaa acaaggtttc aggtgacgcc cccagaataa aatttggacg gggggttcag  11040
tggtggcatt gtgctatgac accaatataa ccctcacaaa ccccttgggc aataaatact  11100
agtgtaggaa tgaaacattc tgaatatctt taacaataga aatccatggg gtggggacaa  11160
gccgtaaaga ctggatgtcc atctcacacg aatttatggc tatgggcaac acataatcct  11220
agtgcaatat gatactgggg ttattaagat gtgtcccagg cagggaccaa gacaggtgaa  11280
ccatgttgtt acactctatt tgtaacaagg ggaaagagag tggacgccga cagcagcgga  11340
ctccactggt tgtctctaac acccccgaaa attaaacggg gctccacgcc aatggggccc  11400
ataaacaaag acaagtggcc actctttttt ttgaaattgt ggagtggggg cacgcgtcag  11460
cccccacacg ccgccctgcg gttttggact gtaaaataag ggtgtaataa cttggctgat  11520
tgtaaccccg ctaaccactg cggtcaaacc acttgcccac aaaaccacta atggcacccc  11580
ggggaatacc tgcataagta ggtgggcggg ccaagatagg ggcgcgattg ctgcgatctg  11640
```

```
gaggacaaat tacacacact tgcgcctgag cgccaagcac agggttgttg gtcctcatat  11700
tcacgaggtc gctgagagca cggtgggcta atgttgccat gggtagcata tactacccaa  11760
atatctggat agcatatgct atcctaatct atatctgggt agcataggct atcctaatct  11820
atatctgggt agcatatgct atcctaatct atatctgggt agtatatgct atcctaattt  11880
atatctgggt agcataggct atcctaatct atatctgggt agcatatgct atcctaatct  11940
atatctgggt agtatatgct atcctaatct gtatccgggt agcatatgct atcctaatag  12000
agattagggt agtatatgct atcctaattt atatctgggt agcatatact acccaaatat  12060
ctggatagca tatgctatcc taatctatat ctgggtagca tatgctatcc taatctatat  12120
ctgggtagca taggctatcc taatctatat ctgggtagca tatgctatcc taatctatat  12180
ctgggtagta tatgctatcc taatttatat ctgggtagca taggctatcc taatctatat  12240
ctgggtagca tatgctatcc taatctatat ctgggtagta tatgctatcc taatctgtat  12300
ccgggtagca tatgctatcc tcatgcatat acagtcagca tatgataccc agtagtagag  12360
tgggagtgct atcctttgca tatgccgcca cctcccaagg gggcgtgaat tttcgctgct  12420
tgtccttttc ctgcatgctg gttgctccca ttcttaggtg aatttaagga ggccaggcta  12480
aagccgtcgc atgtctgatt gctcaccagg taaatgtcgc taatgttttc caacgcgaga  12540
aggtgttgag cgcggagctg agtgacgtga caacatgggt atgcccaatt gccccatgtt  12600
gggaggacga aaatggtgac aagacagatg gccagaaata caccaacagc acgcatgatg  12660
tctactgggg atttattctt tagtgcgggg gaatacacgg cttttaatac gattgagggc  12720
gtctcctaac aagttacatc actcctgccc ttcctcaccc tcatctccat cacctccttc  12780
atctccgtca tctccgtcat caccctccgc ggcagcccct tccaccatag gtggaaacca  12840
gggaggcaaa tctactccat cgtcaaagct gcacacagtc accctgatat tgcaggtagg  12900
agcgggcttt gtcataacaa ggtccttaat cgcatccttc aaaacctcag caaatatatg  12960
agtttgtaaa aagaccatga aataacagac aatggactcc cttagcgggc caggttgtgg  13020
gccgggtcca ggggccattc caaaggggag acgactcaat ggtgtaagac gacattgtgg  13080
aatagcaagg gcagttcctc gccttaggtt gtaaagggag gtcttactac ctccatatac  13140
gaacacaccg gcgacccaag ttccttcgtc ggtagtcctt tctacgtgac tcctagccag  13200
gagagctctt aaaccttctg caatgttctc aaatttcggg ttggaacctc cttgaccacg  13260
atgctttcca aaccaccctc ctttttgcg cctgcctcca tcaccctgac cccggggtcc  13320
agtgcttggg ccttctcctg ggtcatctgc ggggccctgc tctatcgctc ccgggggcac  13380
gtcaggctca ccatctgggc caccttcttg gtggtattca aaataatcgg cttcccctac  13440
agggtggaaa aatggccttc tacctggagg gggcctgcgc ggtggagacc cggatgatga  13500
tgactgacta ctgggactcc tgggcctctt ttctccacgt ccacgacctc tccccctggc  13560
tctttcacga cttccccccc tggctctttc acgtcctcta ccccggcggc ctccactacc  13620
tcctcgaccc cggcctccac tacctcctcg accccggcct ccactgcctc ctcgaccccg  13680
gcctccacct cctgctcctg cccctcctgc tcctgcccct cctcctgctc ctgcccctcc  13740
tgcccctcct gctcctgccc ctcctgcccc tcctgctcct gcccctcctg cccctcctgc  13800
tcctgcccct cctgcccctc ctcctgctcc tgcccctcct gcccctcctc ctgctcctgc  13860
ccctcctgcc cctcctgctc ctgcccctcc tgcccctcct gctcctgccc ctcctgcccc  13920
tcctgctcct gcccctcctg ctcctgcccc tcctgctcct gcccctcctg ctcctgcccc  13980
tcctgcccct cctgcccctc ctcctgctcc tgcccctcct gctcctgccc ctcctgcccc  14040
```

```
tcctgcccct cctgctcctg cccctcctcc tgctcctgcc cctcctgccc ctcctgcccc 14100
tcctcctgct cctgcccctc ctgcccctcc tcctgctcct gcccctcctc ctgctcctgc 14160
ccctcctgcc cctcctgccc ctcctcctgc tcctgcccct cctgcccctc ctcctgctcc 14220
tgcccctcct cctgctcctg cccctcctgc ccctcctgcc cctcctcctg ctcctgcccc 14280
tcctcctgct cctgcccctc ctgcccctcc tgcccctcct gcccctcctc ctgctcctgc 14340
ccctcctcct gctcctgccc ctcctgctcc tgcccctccc gctcctgctc ctgctcctgt 14400
tccaccgtgg gtccctttgc agccaatgca acttggacgt ttttggggtc tccggacacc 14460
atctctatgt cttggccctg atcctgagcc gcccggggct cctggtcttc cgcctcctcg 14520
tcctcgtcct cttccccgtc ctcgtccatg gttatcaccc cctcttcttt gaggtccact 14580
gccgccggag ccttctggtc cagatgtgtc tcccttctct cctaggccat ttccaggtcc 14640
tgtacctggc ccctcgtcag acatgattca cactaaaaga gatcaataga catctttatt 14700
agacgacgct cagtgaatac agggagtgca gactcctgcc ccctccaaca gcccccccac 14760
cctcatcccc ttcatggtcg ctgtcagaca gatccaggtc tgaaaattcc ccatcctccg 14820
aaccatcctc gtcctcatca ccaattactc gcagcccgga aaactcccgc tgaacatcct 14880
caagatttgc gtcctgagcc tcaagccagg cctcaaattc ctcgtccccc tttttgctgg 14940
acggtaggga tggggattct cgggacccct cctcttcctc ttcaaggtca ccagacagag 15000
atgctactgg ggcaacggaa gaaaagctgg gtgcggcctg tgaggatcag cttatcgatg 15060
ataagctgtc aaacatgaga attcttgaag acgaaagggc ctcgtgatac gcctattttt 15120
ataggttaat gtcatgataa taatggtttc ttagacgtca ggtggcactt ttcggggaaa 15180
tgtgcgcgga acccctattt gtttattttt ctaaatacat tcaaatatgt atccgctcat 15240
gagacaataa ccctgataaa tgcttcaata atattgaaaa aggaagagta tgagtattca 15300
acatttccgt gtcgccctta ttcccttttt tgcggcattt tgccttcctg tttttgctca 15360
cccagaaacg ctggtgaaag taaaagatgc tgaagatcag ttgggtgcac gagtgggtta 15420
catcgaactg gatctcaaca gcggtaagat ccttgagagt tttcgccccg aagaacgttt 15480
tccaatgatg agcactttta aagttctgct atgtggcgcg gtattatccc gtgttgacgc 15540
cgggcaagag caactcggtc gccgcataca ctattctcag aatgacttgg ttgagtactc 15600
accagtcaca gaaaagcatc ttacggatgg catgacagta agagaattat gcagtgctgc 15660
cataaccatg agtgataaca ctgcggccaa cttacttctg acaacgatcg gaggaccgaa 15720
ggagctaacc gcttttttgc acaacatggg ggatcatgta actcgccttg atcgttggga 15780
accggagctg aatgaagcca taccaaacga cgagcgtgac accacgatgc ctgcagcaat 15840
ggcaacaacg ttgcgcaaac tattaactgg cgaactactt actctagctt cccggcaaca 15900
attaatagac tggatggagg cggataaagt tgcaggacca cttctgcgct cggcccttcc 15960
ggctggctgg tttattgctg ataaatctgg agccggtgag cgtgggtctc gcggtatcat 16020
tgcagcactg gggccagatg gtaagccctc ccgtatcgta gttatctaca cgacggggag 16080
tcaggcaact atggatgaac gaaatagaca gatcgctgag ataggtgcct cactgattaa 16140
gcattggtaa ctgtcagacc aagtttactc atatatactt tagattgatt taaaacttca 16200
tttttaattt aaaaggatct aggtgaagat cctttttgat aatctcatga ccaaaatccc 16260
ttaacgtgag ttttcgttcc actgagcgtc agaccccgta gaaaagatca aaggatcttc 16320
ttgagatcct ttttttctgc gcgtaatctg ctgcttgcaa acaaaaaaac caccgctacc 16380
```

```
agcggtggtt tgtttgccgg atcaagagct accaactctt tttccgaagg taactggctt  16440
cagcagagcg cagataccaa atactgtcct tctagtgtag ccgtagttag gccaccactt  16500
caagaactct gtagcaccgc ctacatacct cgctctgcta atcctgttac cagtggctgc  16560
tgccagtggc gataagtcgt gtcttaccgg gttggactca agacgatagt taccggataa  16620
ggcgcagcgg tcgggctgaa cggggggttc gtgcacacag cccagcttgg agcgaacgac  16680
ctacaccgaa ctgagatacc tacagcgtga gctatgagaa agcgccacgc ttcccgaagg  16740
gagaaaggcg gacaggtatc cggtaagcgg cagggtcgga acaggagagc gcacgaggga  16800
gcttccaggg ggaaacgcct ggtatcttta tagtcctgtc gggtttcgcc acctctgact  16860
tgagcgtcga tttttgtgat gctcgtcagg ggggcggagc ctatggaaaa acgccagcaa  16920
cgcggccttt ttacggttcc tggccttttg ctggcctttt gctcacatgt tctttcctgc  16980
gttatcccct gattctgtgg ataaccgtat taccgccttt gagtgagctg ataccgctcg  17040
ccgcagccga acgaccgagc gcagcgagtc agtgagcgag gaagcggaag agcgcctgat  17100
gcggtatttt ctccttacgc atctgtgcgg tatttcacac cgcatatggt gcactctcag  17160
tacaatctgc tctgatgccg catagttaag ccagctgtgg aatgtgtgtc agttagggtg  17220
tggaaagtcc ccaggctccc cagcaggcag aagtatgcaa agcatgcatc tcaattagtc  17280
agcaaccagg tgtggaaagt ccccaggctc cccagcaggc agaagtatgc aaagcatgca  17340
tctcaattag tcagcaacca tagtcccgcc cctaactccg cccatcccgc ccctaactcc  17400
gcccagttcc gcccattctc cgccccatgg ctgactaatt ttttttattt atgcagaggc  17460
cgaggccgcc tcggcctctg agctattcca gaagtagtga ggaggctttt ttggaggcct  17520
aggcttttgc aaaaagcttg catgcctgca ggtcggccgc cacgaccggt gccgccacca  17580
tcccctgacc cacgcccctg acccctcaca aggagacgac cttccatgac cgagtacaag  17640
cccacggtgc gcctcgccac ccgcgacgac gtcccccggg ccgtacgcac cctcgccgcc  17700
gcgttcgccg actaccccgc cacgcgccac accgtcgacc cggaccgcca catcgagcgg  17760
gtcaccgagc tgcaagaact cttcctcacg cgcgtcgggc tcgacatcgg caaggtgtgg  17820
gtcgcggacg acggcgccgc ggtggcggtc tggaccacgc cggagagcgt cgaagcgggg  17880
gcggtgttcg ccgagatcgg cccgcgcatg gccgagttga gcggttcccg gctggccgcg  17940
cagcaacaga tggaaggcct cctggcgccg caccggccca aggagcccgc gtggttcctg  18000
gccaccgtcg gcgtctcgcc cgaccaccag ggcaagggtc tgggcagcgc cgtcgtgctc  18060
cccggagtgg aggcggccga gcgcgccggg gtgcccgcct tcctggagac ctccgcgccc  18120
cgcaacctcc ccttctacga gcggctcggc ttcaccgtca ccgccgacgt cgaggtgccc  18180
gaaggaccgc gcacctggtg catgacccgc aagcccggtg cctgacgccc gccccacgac  18240
ccgcagcgcc cgaccgaaag gagcgcacga ccccatggct ccgaccgaag ccgacccggg  18300
cggccccgcc gaccccgcac ccgcccccga ggcccaccga ctctagagga tcataatcag  18360
ccataccaca tttgtagagg ttttacttgc tttaaaaaac ctcccacacc tccccctgaa  18420
cctgaaacat aaaatgaatg caattgttgt tgttaacttg tttattgcag cttataatgg  18480
ttacaaataa agcaatagca tcacaaattt cacaaataaa gcattttttt cactgcattc  18540
tagttgtggt ttgtccaaac tcatcaatgt atcttatcat gtctggatca ctcgccgata  18600
gtggaaaccg acgccccagc actcgtccga gggcaaagga ataggggaga tgggggaggc  18660
taactgaaac acggaaggag acaataccgg aaggaacccg cgctatgacg gcaataaaaa  18720
gacagaataa aacgcacggg tgttgggtcg tttgttcata aacgcggggt tcggtcccag  18780
```

ggctggcact ctgtcgatac cccaccgaga ccccattggg gccaatacgc ccgcgtttct 18840
tccttttccc caccccaccc cccaagttcg ggtgaaggcc cagggctcgc agccaacgtc 18900
ggggcggcag gccctgccat agccactggc cccgtgggtt agggacgggg tcccccatgg 18960
ggaatggttt atggttcgtg gggttatta ttttgggcgt tgcgtggggt ctggtccacg 19020
actggactga gcagacagac ccatggtttt tggatggcct gggcatggac cgcatgtact 19080
ggcgcgacac gaacaccggg cgtctgtggc tgccaaacac ccccgacccc caaaaaccac 19140
cgcgcggatt tctggcgtgc caagctagtc gaccaattct catgtttgac agcttatcat 19200
cgcagatccg ggcaacgttg ttgcattgct gcaggcgcag aactggtagg tatggaagat 19260
ctctagaagc tgggtaccag ctgctagcaa gcttgctagc ggccggctcg agtttactcc 19320
ctatcagtga tagagaacgt atgtcgagtt tactccctat cagtgataga gaacgatgtc 19380
gagtttactc cctatcagtg atagagaacg tatgtcgagt ttactcccta tcagtgatag 19440
agaacgtatg tcgagtttac tccctatcag tgatagagaa cgtatgtcga gtttatccct 19500
atcagtgata gagaacgtat gtcgagttta ctccctatca gtgatagaga acgtatgtcg 19560
aggtaggcgt gtacggtggg aggcctatat aagcagagct cgtttagtga accgtcagat 19620
cgccg 19625

<210> SEQ ID NO 41
<211> LENGTH: 19730
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
cggccgcggg gggaggagcc aagatggccg aataggaaca gctccggtct acagctccca 60
gcgtgagcga cgcagaagac ggtgatttct gcatttccat ctgaggtacc gggttcatct 120
cactagggag tgccagacag tgggcgcagg ccagtgtgtg tgcgcaccgt gcgcgagccg 180
aagcagggcg aggcattgcc tcacctggga agcgcaaggg gtcagggagt tccctttccg 240
agtcaaagaa aggggtgacg gacgcacctg gaaaatcggg tcactcccac ccgaatattg 300
cgcttttcag accggcttaa gaaacggcgc accacgagac tatatcccac acctggctcg 360
gagggtccta cgcccacgga atctcgctga ttgctagcac agcagtctga gatcaaactg 420
caaggcggca acgaggctgg gggaggggcg cccgccattg cccaggcttg cttaggtaaa 480
caaagcagca gggaagctcg aactgggtgg agcccaccac agctcaagga ggcctgcctg 540
cctctgtagg ctccacctct gggggcaggg cacagacaaa caaaaagaca gcagtaacct 600
ctgcagactt aagtgtccct gtctgacagc tttgaagaga gcagtggttc tcccagcacg 660
cagctggaga tctgagaacg ggcagactgc ctcctcaagt gggtccctga cccctgaccc 720
ccgagcagcc taactgggag gcaccccca gcaggggcac actgacacct cacacggcag 780
ggtattccaa cagacctgca gctgagggtc ctgtctgtta gaaggaaaac taacaaccag 840
aaaggacatc tacaccgaaa acccatctgt acatcaccat catcaaagac caaaagtaga 900
taaaaccaca aagatgggga aaaaacagaa cagaaaaact ggaaactcta aaacgcagag 960
cgcctctcct cctccaaagg aacgcagttc ctcaccagca acagaacaaa gctggatgga 1020
gaatgatttt gatgagctga gagaagaagg cttcagacga tcaaattact ctgagctacg 1080
ggaggacatt caaaccaaag gcaaagaagt tgaaaacttt gaaaaaaatt tagaagaatg 1140

```
tataactaga ataaccaata cagagaagtg cttaaaggag ctgatggagc tgaaaaccaa   1200
ggctcgagaa ctacgtgaag aatgcagaag cctcaggagc cgatgcgatc aactggaaga   1260
aagggtatca gcaatggaag atgaaatgaa tgaaatgaag cgagaaggga agtttagaga   1320
aaaaagaata aaaagaaatg agcaaagcct ccaagaaata tgggactatg tgaaaagacc   1380
aaatctacgt ctgattggtg tacctgaaag tgatgtggag aatggaacca agttggaaaa   1440
cactctgcag gatattatcc aggagaactt ccccaatcta gcaaggcagg ccaacgttca   1500
gattcaggaa atacagagaa cgccacaaag atactcctcg agaagagcaa ctccaagaca   1560
cataattgtc agattcacca aagttgaaat gaaggaaaaa atgttaaggg cagccagaga   1620
gaaaggtcgg gttaccctca aaggaaagcc catcagacta acagcggatc tctcggcaga   1680
aaccctacaa gccagaagag agtgggggcc aatattcaac attcttaaag aaaagaattt   1740
tcaacccaga atttcatatc cagccaaact aagcttcata agtgaaggag aaataaaata   1800
ctttatagac aagcaaatgt tgagagattt tgtcaccacc aggcctgccc taaaagagct   1860
cctgaaggaa gcgctaaaca tggaaaggaa caaccggtac cagccgctgc aaaatcatgc   1920
caaaatgtaa agaccatcaa gactaggaag aaactgcatc aactaatgag caaaatcacc   1980
agctaacatc ataatgacag gatcaacttc acacataaca atattaactt taaatataaa   2040
tggactaaat tctgcaatta aaagacacag actggcaagt tggataaaga gtcaagaccc   2100
atcagtgtgc tgtattcagg aaacccatct cacgtgcaga gacacacata ggctcaaaat   2160
aaaaggatgg aggaagatct accaagccaa tggaaaacaa aaaaaggcag ggttgcaat    2220
cctagtctct gataaaacag actttaaacc aacaaagatc aaaagagaca aagaaggcca   2280
ttacataatg gtaaagggat caattcaaca agaggagcta actatcctaa atatttatgc   2340
acccaataca ggagcaccca gattcataaa gcaagtcctc agtgacctac aaagagactt   2400
agactcccac acattaataa tgggagactt taacacccca ctgtcaacat tagacagatc   2460
aacgagacag aaagtcaaca aggataccca ggaattgaac tcagctctgc accaagcaga   2520
cctaatagac atctacagaa ctctccaccc caaatcaaca gaatatacat ttttttcagc   2580
accacaccac acctattcca aaattgacca catagttgga agtaaagctc tcctcagcaa   2640
atgtaaaaga acagaaatta taacaaacta tctctcagac cacagtgcaa tcaaactaga   2700
actcaggatt aagaatctca ctcaaagccg ctcaactaca tggaaactga acaacctgct   2760
cctgaatgac tactgggtac ataacgaaat gaaggcagaa ataaagatgt tctttgaaac   2820
caacgagaac aaagacacca cataccagaa tctctgggac gcattcaaag cagtgtgtag   2880
agggaaattt atagcactaa atgcctacaa gagaaagcag gaaagatcca aaattgacac   2940
cctaacatca caattaaaag aactagaaaa gcaagagcaa acacattcaa aagctagcag   3000
aaggcaagaa ataactaaaa tcagagcaga actgaaggaa atagagacac aaaaaaccct   3060
tcaaaaaatc aatgaatcca ggagctggtt ttttgaaagg atcaacaaaa ttgatagacc   3120
gctagcaaga ctaataaaga aaaaaagaga gaagaatcaa atagacacaa taaaaaatga   3180
taaaggggat atcaccaccg atcccacaga aatacaaact accatcagag aatactacaa   3240
acacctctac gcaaataaac tagaaaatct agaagaaatg gatacattcc tcgacacata   3300
cactctccca agactaaacc aggaagaagt tgaatctctg aatcgaccaa taacaggctc   3360
tgaaattgtg gcaataatca atagtttacc aaccaaaaag agtccaggac cagatggatt   3420
cacagccgaa ttctaccaga ggtacaagga ggaactggta ccattccttc tgaaactatt   3480
```

```
ccaatcaata gaaaaagagg gaatcctccc taactcattt tatgaggcca gcatcattct   3540
gataccaaag ccgggcagag acacaaccaa aaaagagaat tttagaccaa tatccttgat   3600
gaacattgat gcaaaaatcc tcaataaaat actggcaaac cgaatccagc agcacatcaa   3660
aaagcttatc caccatgatc aagtgggctt catccctggg atgcaaggct ggttcaatat   3720
acgcaaatca ataaatgtaa tccagcatat aaacagagcc aaagacaaaa accacatgat   3780
tatctcaata gatgcagaaa aagcctttga caaaattcaa caacccttca tgctaaaaac   3840
tctcaataaa ttaggtattg atgggacgta tttcaaaata ataagagcta tctatgacaa   3900
acccacagcc aatatcatac tgaatgggca aaaactggaa gcattccctt tgaaaaccgg   3960
cacaagacag ggatgccctc tctcaccgct cctattcaac atagtgttgg aagttctggc   4020
cagggcaatc aggcaggaga aggaaataaa gggtattcaa ttaggaaaag aggaagtcaa   4080
attgtccctg tttgcagacg acatgattgt ttatctagaa aaccccatcg tctcagccca   4140
aaatctcctt aagctgataa gcaacttcag caaagtctca ggatacaaaa tcaatgtaca   4200
aaaatcacaa gcattcttat acaccaacaa cagacaaaca gagagccaaa tcatgggtga   4260
actcccattc acaattgctt caaagagaat aaaataccta ggaatccaac ttacaaggga   4320
tgtgaaggac ctcttcaagg agaactacaa accactgctc aaggaaataa aagaggagac   4380
aaacaaatgg aagaacattc catgctcatg ggtaggaaga atcaatatcg tgaaaatggc   4440
catactgccc aaggtaattt acagattcaa tgccatcccc atcaagctac caatgacttt   4500
cttcacagaa ttggaaaaaa ctactttaaa gttcatatgg aaccaaaaaa gagcccgcat   4560
tgccaagtca atcctaagcc aaaagaacaa agctggaggc atcacactac ctgacttcaa   4620
actatactac aaggctacag taaccaaaac agcatggtac tggtaccaaa acagagatat   4680
agatcaatgg aacagaacag agccctcaga aataatgccg catatctaca actatctgat   4740
ctttgacaaa cctgagaaaa acaagcaatg ggaaaggat tccctattta ataaatggtg   4800
ctgggaaaac tggctagcca tatgtagaaa gctgaaactg gatcccttcc ttacacctta   4860
tacaaaaatc aattcaagat ggattaaaga tttaaacgtt aaacctaaaa ccataaaaac   4920
cctagaagaa aacctaggca ttaccattca ggacataggc gtgggcaagg acttcatgtc   4980
caaaacacca aaagcaatgg caacaaaaga caaaattgac aaatgggatc taattaaact   5040
aaagagcttc tgcacagcaa aagaaactac catcagagtg aacaggcaac ctacaacatg   5100
ggagaaaatt tttgcaacct actcatctga caaagggcta atatccagaa tctacaatga   5160
actcaaacaa atttacaaga aaaaaacaaa caaccccatc aaaaagtggg cgaaggacat   5220
gaacagacac ttctcaaaag aagacattta tgcagccaaa aaacacatga agaaatgctc   5280
atcatcactg gccatcagag aaatgcaaat caaaaccact atgagatatc atctcacacc   5340
agttagaatg gcaatcatta aaaagtcagg aaacaacagg tgctggagag gatgcggaga   5400
aataggaaca cttttacact gttggtggga ctgtaaacta gttcaaccat tgtggaagtc   5460
agtgtggcga ttcctcaggg atctagaact agaaatacca tttgacccag ccatcccatt   5520
actgggtata tacccaaatg agtataaatc atgctgctat aaagacacat gcacacgtat   5580
gtttattgcg gcactattca caatagcaaa gacttggaac caacccaaat gtccaacaat   5640
gatagactgg attaagaaaa tgtggcacat atacaccatg gaatactatg cagccataaa   5700
aaatgatgag ttcatatcct ttgtagggac atggatgaaa ttggaaacca tcattctcag   5760
taaactatcg caagaacaaa aaaccaaaca ccgcatattc tcactcatag gtgggaattg   5820
aacaatgaga tcacatggac acaggaaggg gaatatcaca ctctggggac tgtggtgggg   5880
```

```
tcgggggagg ggggagggat agcattggga gatataccta atgctagatg acacattagt   5940
gggtgcagcg caccagcatg gcacatgtat acggatccga attctcgacg gatcgatccg   6000
aacaaacgac ccaacacccg tgcgttttat tctgtctttt tattgccgat cccctcagaa   6060
gaactcgtca agaaggcgat agaaggcgat gcgctgcgaa tcgggagcgg cgataccgta   6120
aagcacgagg aagcggtcag cccattcgcc gccaagctct tcagcaatat cacgggtagc   6180
caacgctatg tcctgatagc ggtcggccgc tttacttgta cagctcgtcc atgccgagag   6240
tgatcccggc ggcggtcacg aactccagca ggaccatgtg atcgcgcttc tcgttggggt   6300
ctttgctcag ggcggactgg gtgctcaggt agtggttgtc gggcagcagc acggggccgt   6360
cgccgatggg ggtgttctgc tggtagtggt cggccaggtg agtccaggag atgtttcagc   6420
actgttgcct ttagtctcga ggcaacttag acaactgagt attgatctga gcacagcagg   6480
gtgtgagctg tttgaagata ctggggttgg gggtgaagaa actgcagagg actaactggg   6540
ctgagaccca gtggcaatgt tttagggcct aaggaatgcc tctgaaaatc tagatggaca   6600
actttgactt tgagaaaaga gaggtggaaa tgaggaaaat gacttttctt tattagattt   6660
cggtagaaag aactttcatc tttcccctat ttttgttatt cgttttaaaa catctatctg   6720
gaggcaggac aagtatggtc attaaaaaga tgcaggcaga aggcatatat tggctcagtc   6780
aaagtgggga actttggtgg ccaaacatac attgctaagg ctattcctat atcagctgga   6840
cacatataaa atgctgctaa tgcttcatta caaacttata tcctttaatt ccagatgggg   6900
gcaaagtatg tccaggggtg aggaacaatt gaaacatttg ggctggagta gattttgaaa   6960
gtcagctctg tgtgtgtgtg tgtgtgtgtg tgtgtgagag cgtgtgtttc ttttaacgtt   7020
ttcagcctac agcatacagg gttcatggtg gcaagaagat aacaagattt aaattatggc   7080
cagtgactag tgctgcaaga agaacaacta cctgcattta atgggaaagc aaaatctcag   7140
gctttgaggg aagttaacat aggcttgatt ctgggtggaa gctgggtgtg tagttatctg   7200
gaggccaggc tggagctctc agctcactat gggttcatct ttattgtctc ctttcatctc   7260
aacagctgca cgctgccgtc ctcgatgttg tggcggatct tgaagttcac cttgatgccg   7320
ttcttctgct tgtcggccat gatatagacg ttgtggctgt tgtagttgta ctccagcttg   7380
tgccccagga tgttgccgtc ctccttgaag tcgatgccct tcagctcgat gcggttcacc   7440
agggtgtcgc cctcgaactt cacctcggcg cgggtcttgt agttgccgtc gtccttgaag   7500
aagatggtgc gctcctggac gtagccttcg ggcatggcgg acttgaagaa gtcgtgctgc   7560
ttcatgtggt cggggtagcg gctgaagcac tgcacgccgt aggtcagggt ggtcacgagg   7620
gtgggccagg gcacgggcag cttgccggtg gtgcagatga acttcagggt cagcttgccg   7680
taggtggcat cgccctcgcc ctcgccggac acgctgaact tgtggccgtt tacgtcgccg   7740
tccagctcga ccaggatggg caccaccccg gtgaacagct cctcgccctt gctcaccata   7800
gggccgggat tctcctccac gtcaccgcat gttagaagac ttcctctgcc ctctcttgga   7860
ggcagggcct gcatgtgcag ggcatcgtag gtatccttgg tggctgtgct cagtccctgg   7920
tacagtccat cgtggccctt gcctcttctt ctctcgccct tcatgccgat ctcgctgtag   7980
gcctcggcca tcttgtcttt ctgcagctca ttatacaggc cctcttgagg attctttctc   8040
cgctggggct tgccgcccat ctcaggatct ctgcctctcc gcttatccag cacgtcgtac   8100
tcttctcttc tccccaggtt cagctcgttg tacagctgat tctggccctg ctggtaagca   8160
ggagcgtcgg cggatctgct gaacttcact ctgcagtaca gggtgatgac cagagagagc   8220
```

```
agcagaacgc cacatgtgcc agccagaggg gcccaaatgt agatatccag gcctctggta   8280
tgcacagctc cgccagctgc aggtctacag gcttcaggtc tgagagacag aggctggctg   8340
gcgattgtag gagctggtgt aggtggtcta ggagcgggtg ttgttgtagg cttggcgggc   8400
agaaacacgg gcacgaagtg gctgaagtac atgatgctat tgctcagggc tccgcttcct   8460
ccgcctccgc tagaagaaac tgtgaccagg gtgccctgtc cccaaacatc catggcgtag   8520
aagccgtcgc ctccccatct agaacagtag tacacggcgg tgtcctcggc tctcaggctg   8580
ttcatctgca ggtaggcggt gttcttgctg gtgtcggcgc tgatggtgaa tctgcccttc   8640
acgctatcgg cgtatctggt gtagccgttg gtggggtaga ttctggcgac ccattcaagt   8700
ccctttccag ggcctgtcg gacccagtgg atgtaggtgt ccttgatgtt gaagccgctg    8760
gcggcacaag acagtctcag agagccgcca ggctgaacaa gtcctccgcc agattcaacc   8820
agctgcacct cagatccttc gccagatcca ggctttccag agccgctggt gctgcctgtt   8880
ctcttgattt ccaccttggt gccctggcca aaggttggag gtgtggtgta gtgctgctgg   8940
cagtagtagg tggcgaagtc ctcaggctgc aggctagaga tggtcagggt gaagtcggtg   9000
ccagatctgc tgccgctgaa tctgcttggc acgccgctgt acagaaagct ggcgctgtag   9060
atcagcagct taggggcttt tccaggcttc tgctgatacc aggccacggc ggtattcaca   9120
tcctggctgg ctctacaggt gatggtcact ctatcgccca cagaggcaga caggctgcta   9180
gggctctgtg tcatctggat gtcgctgatg ctgcaggcca ctgttcccag cagcagcaga   9240
gactgcagcc acattcgaag cttgagctcg agatctgagt ccggtagcgc tagcggatct   9300
gacggttcac taaaccagct ctgcttatat agacctccca ccgtacacgc ctaccgccca   9360
tttgcgtcaa tggggcggag ttgttacgac attttggaaa gtcccgttga ttttggtgcc   9420
aaaacaaact cccattgacg tcaatggggt ggagacttgg aaatccccgt gagtcaaacc   9480
gctatccacg cccattgatg tactgccaaa accgcatcac catggtaata gcgatgacta   9540
atacgtagat gtactgccaa gtaggaaagt cccataaggt catgtactgg gcataatgcc   9600
aggcgggcca tttaccgtca ttgacgtcaa tagggggcgt acttggcata tgatacactt   9660
gatgtactgc caagtgggca gtttaccgta aatactccac ccattgacgt caatggaaag   9720
tccctattgg cgttactatg ggaacatacg tcattattga cgtcaatggg cgggggtcgt   9780
tgggcggtca gccaggcggg ccatttaccg taagttatgt aacgcggaac tccatatatg   9840
ggctatgaac taatgacccc gtaattgatt actattagcc cgggggatcc agacatgata   9900
agatacattg atgagtttgg acaaaccaca actagaatgc agtgaaaaaa atgctttatt   9960
tgtgaaattt gtgatgctat tgctttattt gtaaccatta taagctgcaa taaacaagtt  10020
aacaacaaca attgcattca ttttatgttt caggttcagg gggaggtgtg ggaggttttt  10080
taaagcaagt aaaacctcta caaatgtggt atggctgatt atgatccggc tgcctcgcgc  10140
gtttcggtga tgacggtgaa aacctctgac acatgcagct cccggagacg gtcacagctt  10200
gtctgtaagc ggatgccggg agcagacaag cccgtcaggg cgcgtcagcg ggtgttggcg  10260
ggtgtcgggg cgcagccatg aggtcgatcg actctagagg atcgatcccc gccccggacg  10320
aactaaacct gactacgaca tctctgcccc ttcttcgcgg ggcagtgcat gtaatccctt  10380
cagttggttg gtacaacttg ccaactgggc cctgttccac atgtgacacg gggggggacc  10440
aaacacaaag ggttctctg actgtagttg acatccttat aaatggatgt gcacatttgc   10500
caacactgag tggctttcat cctggagcag actttgcagt ctgtggactg caacacaaca  10560
ttgcctttat gtgtaactct tggctgaagc tcttacacca atgctggggg acatgtacct  10620
```

```
cccaggggcc caggaagact acgggaggct acaccaacgt caatcagagg ggcctgtgta  10680
gctaccgata agcggaccct caagagggca ttagcaatag tgtttataag gccccccttgt  10740
taaccctaaa cgggtagcat atgcttcccg ggtagtagta tatactatcc agactaaccc  10800
taattcaata gcatatgtta cccaacggga agcatatgct atcgaattag ggttagtaaa  10860
agggtcctaa ggaacagcga tatctcccac cccatgagct gtcacggttt tatttacatg  10920
gggtcaggat tccacgaggg tagtgaacca ttttagtcac aagggcagtg gctgaagatc  10980
aaggagcggg cagtgaactc tcctgaatct tcgcctgctt cttcattctc cttcgtttag  11040
ctaatagaat aactgctgag ttgtgaacag taaggtgtat gtgaggtgct cgaaaacaag  11100
gtttcaggtg acgcccccag aataaaattt ggacgggggg ttcagtggtg gcattgtgct  11160
atgacaccaa tataaccctc acaaacccct tgggcaataa atactagtgt aggaatgaaa  11220
cattctgaat atctttaaca atagaaatcc atggggtggg gacaagccgt aaagactgga  11280
tgtccatctc acacgaattt atggctatgg gcaacacata atcctagtgc aatatgatac  11340
tggggttatt aagatgtgtc ccaggcaggg accaagacag gtgaaccatg ttgttacact  11400
ctatttgtaa caaggggaaa gagagtggac gccgacagca gcggactcca ctggttgtct  11460
ctaacacccc cgaaaattaa acggggctcc acgccaatgg ggcccataaa caaagacaag  11520
tggccactct ttttttgaa attgtggagt gggggcacgc gtcagccccc acacgccgcc  11580
ctgcggtttt ggactgtaaa ataagggtgt aataacttgg ctgattgtaa ccccgctaac  11640
cactgcggtc aaaccacttg cccacaaaac cactaatggc accccgggga atacctgcat  11700
aagtaggtgg gcgggccaag atagggcgc gattgctgcg atctggagga caaattacac  11760
acacttgcgc ctgagcgcca agcacagggt tgttggtcct catattcacg aggtcgctga  11820
gagcacggtg ggctaatgtt gccatgggta gcatatacta cccaaatatc tggatagcat  11880
atgctatcct aatctatatc tgggtagcat aggctatcct aatctatatc tgggtagcat  11940
atgctatcct aatctatatc tgggtagtat atgctatcct aatttatatc tgggtagcat  12000
aggctatcct aatctatatc tgggtagcat atgctatcct aatctatatc tgggtagtat  12060
atgctatcct aatctgtatc cgggtagcat atgctatcct aatagagatt agggtagtat  12120
atgctatcct aatttatatc tgggtagcat atactaccca aatatctgga tagcatatgc  12180
tatcctaatc tatatctggg tagcatatgc tatcctaatc tatatctggg tagcataggc  12240
tatcctaatc tatatctggg tagcatatgc tatcctaatc tatatctggg tagtatatgc  12300
tatcctaatt tatatctggg tagcataggc tatcctaatc tatatctggg tagcatatgc  12360
tatcctaatc tatatctggg tagtatatgc tatcctaatc tgtatccggg tagcatatgc  12420
tatcctcatg catatacagt cagcatatga tacccagtag tagagtggga gtgctatcct  12480
ttgcatatgc cgccacctcc caaggggcg tgaattttcg ctgcttgtcc ttttcctgca  12540
tgctggttgc tcccattctt aggtgaattt aaggaggcca ggctaaagcc gtcgcatgtc  12600
tgattgctca ccaggtaaat gtcgctaatg ttttccaacg cgagaaggtg ttgagcgcgg  12660
agctgagtga cgtgacaaca tgggtatgcc caattgcccc atgttgggag gacgaaaatg  12720
gtgacaagac agatggccag aaatacacca acagcacgca tgatgtctac tggggattta  12780
ttctttagtg cgggggaata cacggctttt aatacgattg agggcgtctc ctaacaagtt  12840
acatcactcc tgcccttcct caccctcatc tccatcacct ccttcatctc cgtcatctcc  12900
gtcatcaccc tccgcggcag ccccttccac cataggtgga aaccagggag gcaaatctac  12960
```

tccatcgtca aagctgcaca cagtcaccct gatattgcag gtaggagcgg gctttgtcat 13020
aacaaggtcc ttaatcgcat ccttcaaaac ctcagcaaat atatgagttt gtaaaaagac 13080
catgaaataa cagacaatgg actcccttag cgggccaggt tgtgggccgg gtccaggggc 13140
cattccaaag gggagacgac tcaatggtgt aagacgacat tgtggaatag caagggcagt 13200
tcctcgcctt aggttgtaaa gggaggtctt actacctcca tatacgaaca caccggcgac 13260
ccaagttcct tcgtcggtag tcctttctac gtgactccta gccaggagag ctcttaaacc 13320
ttctgcaatg ttctcaaatt tcgggttgga acctccttga ccacgatgct ttccaaacca 13380
ccctcctttt ttgcgcctgc ctccatcacc ctgaccccgg ggtccagtgc ttgggccttc 13440
tcctgggtca tctgcggggc cctgctctat cgctcccggg ggcacgtcag gctcaccatc 13500
tgggccacct tcttggtggt attcaaaata atcggcttcc cctacagggt ggaaaaatgg 13560
ccttctacct ggagggggcc tgcgcggtgg agacccggat gatgatgact gactactggg 13620
actcctgggc ctcttttctc cacgtccacg acctctcccc ctggctcttt cacgacttcc 13680
ccccctggct ctttcacgtc ctctaccccg gcggcctcca ctacctcctc gaccccggcc 13740
tccactacct cctcgacccc ggcctccact gcctcctcga ccccggcctc cacctcctgc 13800
tcctgcccct cctgctcctg cccctcctcc tgctcctgcc cctcctgccc ctcctgctcc 13860
tgcccctcct gcccctcctg ctcctgcccc tcctgcccct cctgctcctg cccctcctgc 13920
ccctcctcct gctcctgccc ctcctgcccc tcctcctgct cctgcccctc ctgcccctcc 13980
tgctcctgcc cctcctgccc ctcctgctcc tgcccctcct gcccctcctg ctcctgcccc 14040
tcctgctcct gcccctcctg ctcctgcccc tcctgctcct gcccctcctg cccctcctgc 14100
ccctcctcct gctcctgccc ctcctgctcc tgcccctcct gcccctcctg cccctcctgc 14160
tcctgcccct cctcctgctc ctgcccctcc tgcccctcct gcccctcctc ctgctcctgc 14220
ccctcctgcc cctcctcctg ctcctgcccc tcctcctgct cctgcccctc ctgcccctcc 14280
tgcccctcct cctgctcctg cccctcctgc ccctcctcct gctcctgccc ctcctcctgc 14340
tcctgcccct cctgcccctc ctgcccctcc tcctgctcct gcccctcctc ctgctcctgc 14400
ccctcctgcc cctcctgccc ctcctgcccc tcctcctgct cctgcccctc ctcctgctcc 14460
tgcccctcct gctcctgccc ctcccgctcc tgctcctgct cctgttccac cgtgggtccc 14520
tttgcagcca atgcaacttg gacgtttttg gggtctccgg acaccatctc tatgtcttgg 14580
ccctgatcct gagccgcccg gggctcctgg tcttccgcct cctcgtcctc gtcctcttcc 14640
ccgtcctcgt ccatggttat caccccctct tctttgaggt ccactgccgc cggagccttc 14700
tggtccagat gtgtctccct tctctcctag gccatttcca ggtcctgtac ctggcccctc 14760
gtcagacatg attcacacta aaagagatca atagacatct ttattagacg acgctcagtg 14820
aatacaggga gtgcagactc ctgccccctc caacagcccc cccaccctca tccccttcat 14880
ggtcgctgtc agacagatcc aggtctgaaa attccccatc ctccgaacca tcctcgtcct 14940
catcaccaat tactcgcagc ccggaaaact cccgctgaac atcctcaaga tttgcgtcct 15000
gagcctcaag ccaggcctca aattcctcgt ccccctttt gctggacggt agggatgggg 15060
attctcggga cccctcctct tcctcttcaa ggtcaccaga cagagatgct actggggcaa 15120
cggaagaaaa gctgggtgcg gcctgtgagg atcagcttat cgatgataag ctgtcaaaca 15180
tgagaattct tgaagacgaa agggcctcgt gatacgccta tttttatagg ttaatgtcat 15240
gataataatg gtttcttaga cgtcaggtgg cacttttcgg ggaaatgtgc gcggaacccc 15300
tatttgttta tttttctaaa tacattcaaa tatgtatccg ctcatgagac aataaccctg 15360

```
ataaatgctt caataatatt gaaaaaggaa gagtatgagt attcaacatt tccgtgtcgc  15420
ccttattccc ttttttgcgg cattttgcct tcctgttttt gctcacccag aaacgctggt  15480
gaaagtaaaa gatgctgaag atcagttggg tgcacgagtg ggttacatcg aactggatct  15540
caacagcggt aagatccttg agagttttcg ccccgaagaa cgttttccaa tgatgagcac  15600
ttttaaagtt ctgctatgtg gcgcggtatt atcccgtgtt gacgccgggc aagagcaact  15660
cggtcgccgc atacactatt ctcagaatga cttggttgag tactcaccag tcacagaaaa  15720
gcatcttacg gatggcatga cagtaagaga attatgcagt gctgccataa ccatgagtga  15780
taacactgcg gccaacttac ttctgacaac gatcggagga ccgaaggagc taaccgcttt  15840
tttgcacaac atgggggatc atgtaactcg ccttgatcgt tgggaaccgg agctgaatga  15900
agccatacca aacgacgagc gtgacaccac gatgcctgca gcaatggcaa caacgttgcg  15960
caaactatta actggcgaac tacttactct agcttcccgg caacaattaa tagactggat  16020
ggaggcggat aaagttgcag gaccacttct gcgctcggcc cttccggctg gctggtttat  16080
tgctgataaa tctggagccg gtgagcgtgg gtctcgcggt atcattgcag cactggggcc  16140
agatggtaag ccctcccgta tcgtagttat ctacacgacg gggagtcagg caactatgga  16200
tgaacgaaat agacagatcg ctgagatagg tgcctcactg attaagcatt ggtaactgtc  16260
agaccaagtt tactcatata tactttagat tgatttaaaa cttcattttt aatttaaaag  16320
gatctaggtg aagatccttt ttgataatct catgaccaaa atcccttaac gtgagttttc  16380
gttccactga gcgtcagacc ccgtagaaaa gatcaaagga tcttcttgag atcctttttt  16440
tctgcgcgta atctgctgct tgcaaacaaa aaaaccaccg ctaccagcgg tggtttgttt  16500
gccggatcaa gagctaccaa ctctttttcc gaaggtaact ggcttcagca gagcgcagat  16560
accaaatact gtccttctag tgtagccgta gttaggccac cacttcaaga actctgtagc  16620
accgcctaca tacctcgctc tgctaatcct gttaccagtg gctgctgcca gtggcgataa  16680
gtcgtgtctt accgggttgg actcaagacg atagttaccg gataaggcgc agcggtcggg  16740
ctgaacgggg ggttcgtgca cacagcccag cttggagcga acgacctaca ccgaactgag  16800
atacctacag cgtgagctat gagaaagcgc cacgcttccc gaagggagaa aggcggacag  16860
gtatccggta agcggcaggg tcggaacagg agagcgcacg agggagcttc caggggggaaa  16920
cgcctggtat ctttatagtc ctgtcgggtt tcgccacctc tgacttgagc gtcgattttt  16980
gtgatgctcg tcaggggggc ggagcctatg gaaaaacgcc agcaacgcgg cctttttacg  17040
gttcctggcc ttttgctggc cttttgctca catgttcttt cctgcgttat cccctgattc  17100
tgtggataac cgtattaccg cctttgagtg agctgatacc gctcgccgca gccgaacgac  17160
cgagcgcagc gagtcagtga gcgaggaagc ggaagagcgc ctgatgcggt attttctcct  17220
tacgcatctg tgcggtattt cacaccgcat atggtgcact ctcagtacaa tctgctctga  17280
tgccgcatag ttaagccagc tgtggaatgt gtgtcagtta gggtgtggaa agtccccagg  17340
ctccccagca ggcagaagta tgcaaagcat gcatctcaat tagtcagcaa ccaggtgtgg  17400
aaagtcccca ggctccccag caggcagaag tatgcaaagc atgcatctca attagtcagc  17460
aaccatagtc ccgcccctaa ctccgcccat cccgccccta actccgccca gttccgccca  17520
ttctccgccc catggctgac taattttttt tatttatgca gaggccgagg ccgcctcggc  17580
ctctgagcta ttccagaagt agtgaggagg cttttttgga ggcctaggct tttgcaaaaa  17640
gcttgcatgc ctgcaggtcg gccgccacga ccggtgccgc caccatcccc tgacccacgc  17700
```

```
ccctgacccc tcacaaggag acgaccttcc atgaccgagt acaagcccac ggtgcgcctc  17760
gccacccgcg acgacgtccc ccgggccgta cgcaccctcg ccgccgcgtt cgccgactac  17820
cccgccacgc gccacaccgt cgacccggac cgccacatcg agcgggtcac cgagctgcaa  17880
gaactcttcc tcacgcgcgt cgggctcgac atcggcaagg tgtgggtcgc ggacgacggc  17940
gccgcggtgg cggtctggac cacgccggag agcgtcgaag cgggggcggt gttcgccgag  18000
atcggcccgc gcatggccga gttgagcggt tcccggctgg ccgcgcagca acagatggaa  18060
ggcctcctgg cgccgcaccg gcccaaggag cccgcgtggt tcctggccac cgtcggcgtc  18120
tcgcccgacc accagggcaa gggtctgggc agcgccgtcg tgctccccgg agtggaggcg  18180
gccgagcgcg ccggggtgcc cgccttcctg gagacctccg cgccccgcaa cctccccttc  18240
tacgagcggc tcggcttcac cgtcaccgcc gacgtcgagg tgcccgaagg accgcgcacc  18300
tggtgcatga cccgcaagcc cggtgcctga cgcccgcccc acgacccgca gcgcccgacc  18360
gaaaggagcg cacgacccca tggctccgac cgaagccgac ccgggcggcc ccgccgaccc  18420
cgcacccgcc cccgaggccc accgactcta gaggatcata atcagccata ccacatttgt  18480
agaggtttta cttgctttaa aaaacctccc acacctcccc ctgaacctga aacataaaat  18540
gaatgcaatt gttgttgtta acttgtttat tgcagcttat aatggttaca aataaagcaa  18600
tagcatcaca aatttcacaa ataaagcatt tttttcactg cattctagtt gtggtttgtc  18660
caaactcatc aatgtatctt atcatgtctg gatcactcgc cgatagtgga aaccgacgcc  18720
ccagcactcg tccgagggca aaggaatagg ggagatgggg gaggctaact gaaacacgga  18780
aggagacaat accggaagga acccgcgcta tgacggcaat aaaaagacag aataaaacgc  18840
acgggtgttg ggtcgtttgt tcataaacgc ggggttcggt cccagggctg gcactctgtc  18900
gataccccac cgagacccca ttggggccaa tacgcccgcg tttcttcctt ttccccaccc  18960
caccccccaa gttcgggtga aggcccaggg ctcgcagcca acgtcggggc ggcaggccct  19020
gccatagcca ctggccccgt gggttaggga cggggtcccc catggggaat ggtttatggt  19080
tcgtgggggt tattattttg ggcgttgcgt ggggtctggt ccacgactgg actgagcaga  19140
cagacccatg gtttttggat ggcctgggca tggaccgcat gtactggcgc gacacgaaca  19200
ccgggcgtct gtggctgcca aacacccccg acccccaaaa accaccgcgc ggatttctgg  19260
cgtgccaagc tagtcgacca attctcatgt ttgacagctt atcatcgcag atccgggcaa  19320
cgttgttgca ttgctgcagg cgcagaactg gtaggtatgg aagatctcta gaagctgggt  19380
accagctgct agcaagcttg ctagcggccg gctcgagttt actccctatc agtgatagag  19440
aacgtatgtc gagtttactc cctatcagtg atagagaacg atgtcgagtt tactccctat  19500
cagtgataga gaacgtatgt cgagtttact ccctatcagt gatagagaac gtatgtcgag  19560
tttactccct atcagtgata gagaacgtat gtcgagttta tccctatcag tgatagagaa  19620
cgtatgtcga gtttactccc tatcagtgat agagaacgta tgtcgaggta ggcgtgtacg  19680
gtgggaggcc tatataagca gagctcgttt agtgaaccgt cagatcgccg             19730
```

<210> SEQ ID NO 42
<211> LENGTH: 7291
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 42

```
taatacgact cactataggg agaagtactg ccaccatggg caagaagcaa aatcgcaaga     60
cggggaattc caagacacaa tccgctagcc caccacctaa agagcgttct agctcccctg    120
ctactgagca gtcctggatg gaaaacgact tcgatgaact ccgggaagag ggatttaggc    180
gatccaacta ttcagaactc cgcgaagata tccagacaaa ggggaaggaa gtcgagaatt    240
tcgagaagaa cctcgaggag tgcatcaccc gtatcacaaa cactgagaaa tgtctcaaag    300
aactcatgga acttaagaca aaagccaggg agcttcgaga ggagtgtcgg agtctgagat    360
ccaggtgtga ccagctcgag gagcgcgtga gcgcgatgga agacgagatg aacgagatga    420
aaagagaggg caaattcagg gagaagcgca ttaagaggaa cgaacagagt ctgcaggaga    480
tttgggatta cgtcaagagg cctaacctgc ggttgatcgg cgtccccgag agcgacgtag    540
aaaacgggac taaactggag aatacacttc aagacatcat tcaagaaaat tttccaaacc    600
tggctcggca agctaatgtg caaatccaag agatccaacg cacaccccag cggtatagct    660
ctcggcgtgc caccccctagg catattatcg tgcgctttac taaggtggag atgaaagaga    720
agatgctgcg agccgctcgg gaaaagggaa gggtgacttt gaagggcaaa cctattcggc    780
tgacggttga ccttagcgcc gagacactcc aggcacgccg ggaatggggc cccatcttta    840
atatcctgaa ggagaagaac ttccagccac gaatctctta ccctgcaaag ttgagtttta    900
tctccgaggg tgagattaag tatttcatcg ataaacagat gctgcgagac ttcgtgacaa    960
ctcgcccagc tctcaaggaa ctgctcaaag aggctcttaa tatggagcgc aataatagat   1020
atcaaccctt gcagaaccac gcaaagatgt gagacagccg tcagaccatc aagactagga   1080
agaaactgca tcaactaatg agcaaaatca ccagctaaca tcatagtata catgaccggc   1140
tctaactcac atatcaccat ccttacactt aacattaacg gcctcaactc agctatcaag   1200
cgccatcggc tggccagctg gatcaaatca caggatccaa gcgtttgttg catccaagag   1260
acccacctga cctgtagaga tactcaccgc ctcaagatca agggatggcg aaagatttat   1320
caggcgaacg gtaagcagaa gaaagccgga gtcgcaattc tggtctcaga caagacggat   1380
ttcaagccca ccaaaattaa gcgtgataag gaaggtcact atattatggt gaaaggcagc   1440
atacagcagg aagaacttac catattgaac atctacgcgc caaacaccgg cgcacctcgc   1500
tttatcaaac aggtcctgtc cgatctgcag cgagatctgg attctcatac gttgattatg   1560
ggtgatttca atacaccatt gagcaccctg gatcgcagca ccaggcaaaa ggtaaataaa   1620
gacacgcaag agctcaatag cgcactgcat caggcagatc tcattgatat ttatcgcact   1680
cttcatccta agagtaccga gtacacattc ttcagcgccc cacatcatac atactcaaag   1740
atcgatcata tcgtcggctc aaaggctctg ctgtcaaagt gcaagcgcac agagataatt   1800
acaaattacc tgtcagatca tagcgcgatc aagctcgagc tgagaatcaa gaacctgacc   1860
cagagccgga gtaccacttg gaagcttaat aacctgctgc tcaacgatta ttgggtccac   1920
aatgagatga aggcagagat taaaatgttc ttcgaaacaa atgagaataa ggatactacc   1980
tatcaaaacc tttgggatgc ctttaaggcc gtctgcagag gcaagttcat cgccctcaac   2040
gcctataaaa gaaaacaaga gagatctaag atcgatactc tcacctctca gctgaaggag   2100
ttggagaaac aggaacagac ccactccaag gcgtcaagac ggcaggagat cacaaagatt   2160
cgcgccgagt tgaaagagat cgaaacccaa aagactcttc agaaaattaa cgagtctcgt   2220
agttggttct tcgagcggat taataagata gacagacctc tggcacgact gattaagaag   2280
aagcgcgaaa agaaccagat tgataccatc aagaacgaca agggcgacat cactactgac   2340
ccgaccgaga tccagaccac tattcgggag tattataagc atttgtatgc taacaagctt   2400
```

```
gagaacctgg aagagatgga cacttttctg gatacctata ctctgccacg gcttaatcaa   2460
gaggaagtcg agtccctcaa ccgcccaatt acaggaagcg agattgtggc cataattaac   2520
tccctgccga caaagaaatc tcctggtccg gacgggttta cagctgagtt ttatcaacgg   2580
tatatggaag agcttgtacc gtttctgctc aagctctttc agtctataga aaaggaaggc   2640
atcttgccca attccttcta cgaagcttct ataatactta ttcccaaacc aggacgcgat   2700
accacaaaga aggaaaactt ccggcccatt agtctcatga atatcgacgc taaaatattg   2760
aacaagattc tcgccaacag aatccaacaa catattaaga aattgataca tcacgaccag   2820
gtggggttta tacctggcat gcagggctgg tttaacatcc ggaagagtat taacgtcatt   2880
caacacatta atagagctaa ggataagaat catatgatca tctctataga cgcggaaaag   2940
gcattcgata agattcagca gccatttatg ctcaagactc tgaacaaact cggcatcgac   3000
ggaacatatt ttaagattat tcgcgcaatt tacgataagc cgactgctaa cattatcctt   3060
aacggccaaa agctcgaggc ctttccgctc aagactggaa cccgccaagg ctgtcccctc   3120
tccccgcttt tgtttaatat tgtactcgag gtgctggcta gggctattcg tcaagagaaa   3180
gagattaaag ggatacagct cgggaaggaa gaggtcaagc tttccttgtt cgccgatgat   3240
atgattgtgt acctggagaa tcctattgtg tctgctcaga accttcttaa acttatttct   3300
aactttagca aggtcagcgg ctataagatt aacgtccaga aatctcaggc ctttctgtac   3360
acaaataatc gacagaccga atcccagata atgggtgagc ttccgtttgt catagccagc   3420
aaaaggataa agtatctcgg aatccagctg acacgagacg ttaaagattt gtttaaggaa   3480
aattacaagc ctctcctgaa agagattaag gaagatacta ataagtggaa gaatatcccc   3540
tgttcatggg ttggcagaat caacatagtg aagatggcaa tacttcctaa agtgatatat   3600
cgctttaacg ccatcccaat taaactgcct atgaccttct ttacggagct cgagaaaaca   3660
acccttaaat ttatatggaa tcaaaagaga gcaagaatag cgaagtccat cttgagccag   3720
aagaataagg ccggtgggat tactttgcct gattttaagt tgtattataa agccacagta   3780
actaagacag cctggtattg gtatcagaat agagacatcg accagtggaa tcggaccgaa   3840
ccatcagaga taatgcccca catctataat taccttatat tcgataagcc agaaaagaat   3900
aaacagtggg gcaaagacag cctcttcaac aagtggtgtt gggagaattg gctggccata   3960
tgccggaaac tcaagctcga cccctttctt acaccctaca ctaaaatcaa cagtaggtgg   4020
atcaaggact tgaatgtcaa gccaaagact ataaagacac tggaagagaa tcttgggatc   4080
acaatacaag atataggcgt cggcaaagat tttatgtcaa agacgcccaa ggccatggcc   4140
actaaggata agattgataa gtgggacctt attaagctca aaagcttctg tactgccaag   4200
gagaccacga tcagagttaa taggcagccc actacatggg aaaagatttt cgccacttat   4260
tcatcagata aggggttgat aagcagaata tataacgagc tgaagcagat ctacaagaag   4320
aaaacgaata atcccatcaa gaagtgggca aaagatatga acaggcattt tagcaaagag   4380
gatatctacg ccgcgaagaa gcatatgaag aagtgtagtt caagcttggc cattcgtgag   4440
atgcagatta agacgaccat gcgataccac cttaccccag tgaggatggc aattatcaag   4500
aaatctggca ataatagatg ttggcggggc tgtggcgaga ttggcaccct gctccattgc   4560
tggtgggatt gcaagctggt gcagccgctt tggaaatcag tctggcgctt tctgagggac   4620
ctcgagcttg agattccctt cgatcccgca attcccttgc tcggaatcta tcctaacgaa   4680
tacaagagct gttgttacaa ggatacgtgt acccggatgt tcatcgcggc cttgtttacg   4740
```

```
atagctaaga cgtggaatca gcctaagtgc cccacaatga tcgattggat caagaaaatg   4800
tggcatattt ataccatgga gtattacgca gcaattaaga atgacgaatt tatttccttc   4860
gttgggacct ggatgaagct ggagactatt attctgagca agctgtctca ggagcaaaag   4920
acaaagcata gaatcttctc tctcattggt ggtaacgact acaaagacga tgacgacaag   4980
cccgccgcca agagggtgaa gctggactaa agcgcttcta gaagttgtct cctcctgcac   5040
tgactgactg atacaatcga tttctggatc cgcaggccta atcaacctct ggattacaaa   5100
atttgtgaaa gattgactgg tattcttaac tatgttgctc cttttacgct atgtggatac   5160
gctgctttaa tgcctttgta tcatgctatt gcttcccgta tggctttcat tttctcctcc   5220
ttgtataaat cctggttgct gtctctttat gaggagttgt ggcccgttgt caggcaacgt   5280
ggcgtggtgt gcactgtgtt tgctgacgca acccccactg gttggggcat tgccaccacc   5340
tgtcagctcc tttccgggac tttcgctttc cccctcccta ttgccacggc ggaactcatc   5400
gccgcctgcc ttgcccgctg ctggacaggg gctcggctgt tgggcactga caattccgtg   5460
gtgttgtcgg ggaagctgac gtcctttcca tggctgctcg cctgtgttgc cacctggatt   5520
ctgcgcggga cgtccttctg ctacgtccct tcggccctca atccagcgga ccttccttcc   5580
cgctgagaga cacaaaaaat tccaacacac tattgcaatg aaaataaatt tcctttatta   5640
gccagaagtc agatgctcaa ggggcttcat gatgtcccca taatttttgg cagagggaaa   5700
aagatctcag tggtatttgt gagccagggc attggccttc tgataggcag cctgcacctg   5760
aggagtgcgg ccgctttact tgtacagctc gtccatgccg agagtgatcc cggcggcggt   5820
cacgaactcc agcaggacca tgtgatcgcg cttctcgttg gggtctttgc tcagggcgga   5880
ctgggtgctc aggtagtggt tgtcgggcag cagcacgggg ccgtcgccga tgggggtgtt   5940
ctgctggtag tggtcggcga gctgcacgct gccgtcctcg atgttgtggc ggatcttgaa   6000
gttcaccttg atgccgttct tctgcttgtc ggccatgata tagacgttgt ggctgttgta   6060
gttgtactcc agcttgtgcc ccaggatgtt gccgtcctcc ttgaagtcga tgcccttcag   6120
ctcgatgcgg ttcaccaggg tgtcgccctc gaacttcacc tcggcgcggg tcttgtagtt   6180
gccgtcgtcc ttgaagaaga tggtgcgctc ctggacgtag ccttcgggca tggcggactt   6240
gaagaagtcg tgctgcttca tgtggtcggg gtagcggctg aagcactgca cgccgtaggt   6300
cagggtggtc acgagggtgg gccagggcac gggcagcttg ccggtggtgc agatgaactt   6360
cagggtcagc ttgccgtagg tggcatcgcc ctcgccctcg ccggacacgc tgaacttgtg   6420
gccgtttacg tcgccgtcca gctcgaccag gatgggcacc accccggtga acagctcctc   6480
gcccttgctc accatggtgg cgggatctga cggttcacta aaccagctct gcttatatag   6540
acctcccacc gtacacgcct accgcccatt tgcgtcaatg gggcggagtt gttacgacat   6600
tttggaaagt cccgttgatt ttggtgccaa aacaaactcc cattgacgtc aatggggtgg   6660
agacttggaa atccccgtga gtcaaaccgc tatccacgcc cattgatgta ctgccaaaac   6720
cgcatcacca tggtaatagc gatgactaat acgtagatgt actgccaagt aggaaagtcc   6780
cataaggtca tgtactgggc ataatgccag gcgggccatt taccgtcatt gacgtcaata   6840
gggggcgtac ttggcatatg atacacttga tgtactgcca agtgggcagt ttaccgtaaa   6900
tactccaccc attgacgtca atggaaagtc cctattggcg ttactatggg aacatacgtc   6960
attattgacg tcaatgggcg ggggtcgttg ggcggtcagc caggcgggcc atttaccgta   7020
agttatgtaa cgggcctgct gccggctctg cggcctcttc cgcgtcttcg ccttcgccct   7080
cagacgagtc ggatctccct ttgggccgcc tccccgcctg tctagcttga ctgactgaga   7140
```

tacagcgtac cttcagctca cagacatgat aagatacatt gatgagtttg gacaaaccac 7200
aactagaatg cagtgaaaaa aatgctttat ttgtgaaatt tgtgatgcta ttgctttatt 7260
tgtaaccatt ataagctgca ataaacaagt t 7291

<210> SEQ ID NO 43
<211> LENGTH: 7376
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43
taatacgact cactataggg agaagtactg ccaccatggg caagaagcaa aatcgcaaga 60
cggggaattc caagacacaa tccgctagcc caccacctaa agagcgttct agctcccctg 120
ctactgagca gtcctggatg gaaaacgact tcgatgaact ccgggaagag ggatttaggc 180
gatccaacta ttcagaactc cgcgaagata tccagacaaa ggggaaggaa gtcgagaatt 240
tcgagaagaa cctcgaggag tgcatcaccc gtatcacaaa cactgagaaa tgtctcaaag 300
aactcatgga acttaagaca aaagccaggg agcttcgaga ggagtgtcgg agtctgagat 360
ccaggtgtga ccagctcgag gagcgcgtga gcgcgatgga agacgagatg aacgagatga 420
aaagagaggg caaattcagg gagaagcgca ttaagaggaa cgaacagagt ctgcaggaga 480
tttgggatta cgtcaagagg cctaacctgc ggttgatcgg cgtccccgag agcgacgtag 540
aaaacgggac taaactggag aatacacttc aagacatcat tcaagaaaat tttccaaacc 600
tggctcggca agctaatgtg caaatccaag agatccaacg cacaccccag cggtatagct 660
ctcggcgtgc cacccctagg catattatcg tgcgctttac taaggtggag atgaaagaga 720
agatgctgcg agccgctcgg gaaaagggaa gggtgacttt gaagggcaaa cctattcggc 780
tgacggttga ccttagcgcc gagacactcc aggcacgccg ggaatggggc cccatcttta 840
atatcctgaa ggagaagaac ttccagccac gaatctctta ccctgcaaag ttgagtttta 900
tctccgaggg tgagattaag tatttcatcg ataaacagat gctgcgagac ttcgtgacaa 960
ctcgcccagc tctcaaggaa ctgctcaaag aggctcttaa tatggagcgc aataatagat 1020
atcaaccctt gcagaaccac gcaaagatgt gagacagccg tcagaccatc aagactagga 1080
agaaactgca tcaactaatg agcaaaatca ccagctaaca tcatagtata catgaccggc 1140
tctaactcac atatcaccat ccttacactt aacattaacg gcctcaactc agctatcaag 1200
cgccatcggc tggccagctg gatcaaatca caggatccaa gcgtttgttg catccaagag 1260
acccacctga cctgtagaga tactcaccgc ctcaagatca agggatggcg aaagatttat 1320
caggcgaacg gtaagcagaa gaaagccgga gtcgcaattc tggtctcaga caagacggat 1380
ttcaagccca ccaaaattaa gcgtgataag gaaggtcact atattatggt gaaaggcagc 1440
atacagcagg aagaacttac catattgaac atctacgcgc caaacaccgg cgcacctcgc 1500
tttatcaaac aggtcctgtc cgatctgcag cgagatctgg attctcatac gttgattatg 1560
ggtgatttca atacaccatt gagcaccctg gatcgcagca ccaggcaaaa ggtaaataaa 1620
gacacgcaag agctcaatag cgcactgcat caggcagatc tcattgatat ttatcgcact 1680
cttcatccta agagtaccga gtacacattc ttcagcgccc cacatcatac atactcaaag 1740
atcgatcata tcgtcggctc aaaggctctg ctgtcaaagt gcaagcgcac agagataatt 1800
acaaattacc tgtcagatca tagcgcgatc aagctcgagc tgagaatcaa gaacctgacc 1860

```
cagagccgga gtaccacttg gaagcttaat aacctgctgc tcaacgatta ttgggtccac   1920
aatgagatga aggcagagat taaaatgttc ttcgaaacaa atgagaataa ggatactacc   1980
tatcaaaacc tttgggatgc ctttaaggcc gtctgcagag gcaagttcat cgccctcaac   2040
gcctataaaa gaaaacaaga gagatctaag atcgatactc tcacctctca gctgaaggag   2100
ttggagaaac aggaacagac ccactccaag gcgtcaagac ggcaggagat cacaaagatt   2160
cgcgccgagt tgaaagagat cgaaacccaa aagactcttc agaaaattaa cgagtctcgt   2220
agttggttct tcgagcggat taataagata gacagacctc tggcacgact gattaagaag   2280
aagcgcgaaa agaaccagat tgataccatc aagaacgaca agggcgacat cactactgac   2340
ccgaccgaga tccagaccac tattcgggag tattataagc atttgtatgc taacaagctt   2400
gagaacctgg aagagatgga cacttttctg gatacctata ctctgccacg gcttaatcaa   2460
gaggaagtcg agtccctcaa ccgcccaatt acaggaagcg agattgtggc cataattaac   2520
tccctgccga caaagaaatc tcctggtccg gacgggttta cagctgagtt ttatcaacgg   2580
tatatggaag agcttgtacc gtttctgctc aagctctttc agtctataga aaaggaaggc   2640
atcttgccca attccttcta cgaagcttct ataatactta ttcccaaacc aggacgcgat   2700
accacaaaga aggaaaactt ccggcccatt agtctcatga atatcgacgc taaaatattg   2760
aacaagattc tcgccaacag aatccaacaa catattaaga aattgataca tcacgaccag   2820
gtggggttta tacctggcat gcagggctgg tttaacatcc ggaagagtat taacgtcatt   2880
caacacatta atagagctaa ggataagaat catatgatca tctctataga cgcggaaaag   2940
gcattcgata agattcagca gccatttatg ctcaagactc tgaacaaact cggcatcgac   3000
ggaacatatt ttaagattat tcgcgcaatt tacgataagc cgactgctaa cattatcctt   3060
aacggccaaa agctcgaggc ctttccgctc aagactggaa cccgccaagg ctgtcccctc   3120
tccccgcttt tgtttaatat tgtactcgag gtgctggcta gggctattcg tcaagagaaa   3180
gagattaaag ggatacagct cgggaaggaa gaggtcaagc tttccttgtt cgccgatgat   3240
atgattgtgt acctggagaa tcctattgtg tctgctcaga accttcttaa acttatttct   3300
aactttagca aggtcagcgg ctataagatt aacgtccaga aatctcaggc ctttctgtac   3360
acaaataatc gacagaccga atcccagata atgggtgagc ttccgtttgt catagccagc   3420
aaaaggataa agtatctcgg aatccagctg acacgagacg ttaaagattt gtttaaggaa   3480
aattacaagc ctctcctgaa agagattaag gaagatacta ataagtggaa gaatatcccc   3540
tgttcatggg ttggcagaat caacatagtg aagatggcaa tacttcctaa agtgatatat   3600
cgctttaacg ccatcccaat taaactgcct atgaccttct ttacggagct cgagaaaaca   3660
acccttaaat ttatatggaa tcaaaagaga gcaagaatag cgaagtccat cttgagccag   3720
aagaataagg ccggtgggat tactttgcct gattttaagt tgtattataa agccacagta   3780
actaagacag cctggtattg gtatcagaat agagacatcg accagtggaa tcggaccgaa   3840
ccatcagaga taatgcccca catctataat taccttatat tcgataagcc agaaaagaat   3900
aaacagtggg gcaaagacag cctcttcaac aagtggtgtt gggagaattg gctggccata   3960
tgccggaaac tcaagctcga cccctttctt acaccctaca ctaaaatcaa cagtaggtgg   4020
atcaaggact tgaatgtcaa gccaaagact ataaagacac tggaagagaa tcttgggatc   4080
acaatacaag atataggcgt cggcaaagat tttatgtcaa agacgcccaa ggccatggcc   4140
actaaggata agattgataa gtgggacctt attaagctca aaagcttctg tactgccaag   4200
```

gagaccacga tcagagttaa taggcagccc actacatggg aaaagatttt cgccacttat 4260
tcatcagata aggggttgat aagcagaata tataacgagc tgaagcagat ctacaagaag 4320
aaaacgaata atcccatcaa gaagtgggca aaagatatga acaggcattt tagcaaagag 4380
gatatctacg ccgcgaagaa gcatatgaag aagtgtagtt caagcttggc cattcgtgag 4440
atgcagatta agacgaccat gcgataccac cttaccccag tgaggatggc aattatcaag 4500
aaatctggca ataatagatg ttggcggggc tgtggcgaga ttggcaccct gctccattgc 4560
tggtgggatt gcaagctggt gcagccgctt tggaaatcag tctggcgctt tctgagggac 4620
ctcgagcttg agattccctt cgatcccgca attcccttgc tcggaatcta tcctaacgaa 4680
tacaagagct gttgttacaa ggatacgtgt acccggatgt tcatcgcggc cttgtttacg 4740
atagctaaga cgtggaatca gcctaagtgc cccacaatga tcgattggat caagaaaatg 4800
tggcatattt ataccatgga gtattacgca gcaattaaga atgacgaatt tatttccttc 4860
gttgggacct ggatgaagct ggagactatt attctgagca agctgtctca ggagcaaaag 4920
acaaagcata gaatcttctc tctcattggt ggtaacgact acaaagacga tgacgacaag 4980
taaagcggcc gggcgcggtg gctcacgcct gtaatcccag cactttggga ggccgaggcg 5040
ggaggatcgc agttcgagac cagcgcgaga ccccgtctct acaaaaatac aaaaaattagc 5100
ttctagaagt tgtctcctcc tgcactgact gactgataca atcgatttct ggatccgcag 5160
gcctaatcaa cctctggatt acaaaatttg tgaaagattg actggtattc ttaactatgt 5220
tgctcctttt acgctatgtg gatacgctgc tttaatgcct ttgtatcatg ctattgcttc 5280
ccgtatggct ttcattttct cctccttgta taaatcctgg ttgctgtctc tttatgagga 5340
gttgtggccc gttgtcaggc aacgtggcgt ggtgtgcact gtgtttgctg acgcaacccc 5400
cactggttgg ggcattgcca ccacctgtca gctcctttcc gggactttcg ctttccccct 5460
ccctattgcc acggcggaac tcatcgccgc ctgccttgcc cgctgctgga caggggctcg 5520
gctgttgggc actgacaatt ccgtggtgtt gtcggggaag ctgacgtcct ttccatggct 5580
gctcgcctgt gttgccacct ggattctgcg cgggacgtcc ttctgctacg tcccttcggc 5640
cctcaatcca gcggaccttc cttcccgctg agagacacaa aaaattccaa cacactattg 5700
caatgaaaat aaatttcctt tattagccag aagtcagatg ctcaaggggc ttcatgatgt 5760
ccccataatt tttggcagag ggaaaaagat ctcagtggta tttgtgagcc agggcattgg 5820
ccttctgata ggcagcctgc acctgaggag tgcggccgct ttacttgtac agctcgtcca 5880
tgccgagagt gatcccggcg gcggtcacga actccagcag gaccatgtga tcgcgcttct 5940
cgttggggtc tttgctcagg gcggactggg tgctcaggta gtggttgtcg ggcagcagca 6000
cggggccgtc gccgatgggg gtgttctgct ggtagtggtc ggcgagctgc acgctgccgt 6060
cctcgatgtt gtggcggatc ttgaagttca ccttgatgcc gttcttctgc ttgtcggcca 6120
tgatatagac gttgtggctg ttgtagttgt actccagctt gtgccccagg atgttgccgt 6180
cctccttgaa gtcgatgccc ttcagctcga tgcggttcac cagggtgtcg ccctcgaact 6240
tcacctcggc gcgggtcttg tagttgccgt cgtccttgaa gaagatggtg cgctcctgga 6300
cgtagccttc gggcatggcg gacttgaaga agtcgtgctg cttcatgtgg tcggggtagc 6360
ggctgaagca ctgcacgccg taggtcaggg tggtcacgag ggtgggccag ggcacgggca 6420
gcttgccggt ggtgcagatg aacttcaggg tcagcttgcc gtaggtggca tcgccctcgc 6480
cctcgccgga cacgctgaac ttgtggccgt ttacgtcgcc gtccagctcg accaggatgg 6540
gcaccacccc ggtgaacagc tcctcgccct tgctcaccat ggtggcggga tctgacggtt 6600
cactaaacca gctctgctta tatagacctc ccaccgtaca cgcctaccgc ccatttgcgt 6660
caatggggcg gagttgttac gacattttgg aaagtcccgt tgattttggt gccaaaacaa 6720
actcccattg acgtcaatgg ggtggagact tggaaatccc cgtgagtcaa accgctatcc 6780
acgcccattg atgtactgcc aaaaccgcat caccatggta atagcgatga ctaatacgta 6840
gatgtactgc caagtaggaa agtcccataa ggtcatgtac tgggcataat gccaggcggg 6900
ccatttaccg tcattgacgt caataggggg cgtacttggc atatgataca cttgatgtac 6960
tgccaagtgg gcagtttacc gtaaatactc cacccattga cgtcaatgga aagtccctat 7020
tggcgttact atgggaacat acgtcattat tgacgtcaat gggcgggggt cgttgggcgg 7080
tcagccaggc gggccattta ccgtaagtta tgtaacgggc ctgctgccgg ctctgcggcc 7140
tcttccgcgt cttcgccttc gccctcagac gagtcggatc tccctttggg ccgcctcccc 7200
gcctgtctag cttgactgac tgagatacag cgtaccttca gctcacagac atgataagat 7260
acattgatga gtttggacaa accacaacta gaatgcagtg aaaaaaatgc tttatttgtg 7320
aaatttgtga tgctattgct ttatttgtaa ccattataag ctgcaataaa caagtt 7376

<210> SEQ ID NO 44
<211> LENGTH: 14122
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 44
taatacgact cactataggg agaagtactg ccaccatggg caagaagcaa aatcgcaaga 60
cggggaattc caagacacaa tccgctagcc caccacctaa agagcgttct agctcccctg 120
ctactgagca gtcctggatg gaaaacgact tcgatgaact ccgggaagag ggatttaggc 180
gatccaacta ttcagaactc cgcgaagata tccagacaaa ggggaaggaa gtcgagaatt 240
tcgagaagaa cctcgaggag tgcatcaccc gtatcacaaa cactgagaaa tgtctcaaag 300
aactcatgga acttaagaca aaagccaggg agcttcgaga ggagtgtcgg agtctgagat 360
ccaggtgtga ccagctcgag gagcgcgtga gcgcgatgga agacgagatg aacgagatga 420
aaagagaggg caaattcagg gagaagcgca ttaagaggaa cgaacagagt ctgcaggaga 480
tttgggatta cgtcaagagg cctaacctgc ggttgatcgg cgtccccgag agcgacgtag 540
aaaacgggac taaactggag aatacacttc aagacatcat tcaagaaaat tttccaaacc 600
tggctcggca agctaatgtg caaatccaag agatccaacg cacaccccag cggtatagct 660
ctcggcgtgc cacccctagg catattatcg tgcgctttac taaggtggag atgaaagaga 720
agatgctgcg agccgctcgg gaaaagggaa gggtgacttt gaagggcaaa cctattcggc 780
tgacggttga ccttagcgcc gagacactcc aggcacgccg ggaatggggc cccatcttta 840
atatcctgaa ggagaagaac ttccagccac gaatctctta ccctgcaaag ttgagtttta 900
tctccgaggg tgagattaag tatttcatcg ataaacagat gctgcgagac ttcgtgacaa 960
ctcgcccagc tctcaaggaa ctgctcaaag aggctcttaa tatggagcgc aataatagat 1020
atcaaccctt gcagaaccac gcaaagatgt gagacagtta aaacagcctg tgggttgatc 1080
ccacccacag gcccattggg cgctagcact ctggtatcac ggtacctttg tgcgcctgtt 1140 ttatacccccc tcccccaact gtaacttaga agtaacacac accgatcaac agtcagcgtg 1200
gcacaccagc cacgttttga tcaagcactt ctgttacccc ggactgagta tcaatagact 1260

-continued

```
gctcacgcgg ttgaaggaga aagcgttcgt tatccggcca actacttcga aaaacctagt   1320
aacaccgtgg aagttgcaga gtgtttcgct cagcactacc ccagtgtaga tcaggtcgat   1380
gagtcaccgc attccccacg ggcgaccgtg gcggtggctg cgttggcggc ctgcccatgg   1440
ggaaacccat gggacgctct aatacagaca tggtgcgaag agtctattga gctagttggt   1500
agtcctccgg cccctgaatg cggctaatcc taactgcgga gcacacaccc tcaagccaga   1560
gggcagtgtg tcgtaacggg caactctgca gcggaaccga ctactttggg tgtccgtgtt   1620
tcattttatt cctatactgg ctgcttatgg tgacaattga gagatcgtta ccatatagct   1680
attggattgg ccatccggtg actaatagag ctattatata tccctttgtt gggtttatac   1740
cacttagctt gaaagaggtt aaaacattac aattcattgt taagttgaat acagcaaata   1800
catgaccggc tctaactcac atatcaccat ccttacactt aacattaacg gcctcaactc   1860
agctatcaag cgccatcggc tggccagctg gatcaaatca caggatccaa gcgtttgttg   1920
catccaagag acccacctga cctgtagaga tactcaccgc ctcaagatca agggatggcg   1980
aaagatttat caggcgaacg gtaagcagaa gaaagccgga gtcgcaattc tggtctcaga   2040
caagacggat ttcaagccca ccaaaattaa gcgtgataag gaaggtcact atattatggt   2100
gaaaggcagc atacagcagg aagaacttac catattgaac atctacgcgc caaacaccgg   2160
cgcacctcgc tttatcaaac aggtcctgtc cgatctgcag cgagatctgg attctcatac   2220
gttgattatg ggtgatttca atacaccatt gagcaccctg gatcgcagca ccaggcaaaa   2280
ggtaaataaa gacacgcaag agctcaatag cgcactgcat caggcagatc tcattgatat   2340
ttatcgcact cttcatccta agagtaccga gtacacattc ttcagcgccc cacatcatac   2400
atactcaaag atcgatcata tcgtcggctc aaaggctctg ctgtcaaagt gcaagcgcac   2460
agagataatt acaaattacc tgtcagatca tagcgcgatc aagctcgagc tgagaatcaa   2520
gaacctgacc cagagccgga gtaccacttg gaagcttaat aacctgctgc tcaacgatta   2580
ttgggtccac aatgagatga aggcagagat taaaatgttc ttcgaaacaa atgagaataa   2640
ggatactacc tatcaaaacc tttgggatgc ctttaaggcc gtctgcagag gcaagttcat   2700
cgccctcaac gcctataaaa gaaaacaaga gagatctaag atcgatactc tcacctctca   2760
gctgaaggag ttggagaaac aggaacagac ccactccaag gcgtcaagac ggcaggagat   2820
cacaaagatt cgcgccgagt tgaaagagat cgaaacccaa aagactcttc agaaaattaa   2880
cgagtctcgt agttggttct tcgagcggat taataagata gacagacctc tggcacgact   2940
gattaagaag aagcgcgaaa agaaccagat tgataccatc aagaacgaca agggcgacat   3000
cactactgac ccgaccgaga tccagaccac tattcgggag tattataagc atttgtatgc   3060
taacaagctt gagaacctgg aagagatgga cacttttctg gatacctata ctctgccacg   3120
gcttaatcaa gaggaagtcg agtccctcaa ccgcccaatt acaggaagcg agattgtggc   3180
cataattaac tccctgccga caaagaaatc tcctggtccg gacgggttta cagctgagtt   3240
ttatcaacgg tatatggaag agcttgtacc gtttctgctc aagctctttc agtctataga   3300
aaaggaaggc atcttgccca attccttcta cgaagcttct ataatactta ttcccaaacc   3360
aggacgcgat accacaaaga aggaaaactt ccggcccatt agtctcatga atatcgacgc   3420
taaaatattg aacaagattc tcgccaacag aatccaacaa catattaaga aattgataca   3480
tcacgaccag gtggggttta tacctggcat gcagggctgg tttaacatcc ggaagagtat   3540
taacgtcatt caacacatta atagagctaa ggataagaat catatgatca tctctataga   3600
```

```
cgcggaaaag gcattcgata agattcagca gccatttatg ctcaagactc tgaacaaact   3660
cggcatcgac ggaacatatt ttaagattat tcgcgcaatt tacgataagc cgactgctaa   3720
cattatcctt aacggccaaa agctcgaggc ctttccgctc aagactggaa cccgccaagg   3780
ctgtcccctc tccccgcttt tgtttaatat tgtactcgag gtgctggcta gggctattcg   3840
tcaagagaaa gagattaaag ggatacagct cgggaaggaa gaggtcaagc tttccttgtt   3900
cgccgatgat atgattgtgt acctggagaa tcctattgtg tctgctcaga accttcttaa   3960
acttatttct aactttagca aggtcagcgg ctataagatt aacgtccaga aatctcaggc   4020
ctttctgtac acaaataatc gacagaccga atcccagata atgggtgagc ttccgtttgt   4080
catagccagc aaaaggataa agtatctcgg aatccagctg acacgagacg ttaaagattt   4140
gtttaaggaa aattacaagc ctctcctgaa agagattaag gaagatacta ataagtggaa   4200
gaatatcccc tgttcatggg ttggcagaat caacatagtg aagatggcaa tacttcctaa   4260
agtgatatat cgctttaacg ccatcccaat taaactgcct atgaccttct ttacggagct   4320
cgagaaaaca acccttaaat ttatatggaa tcaaaagaga gcaagaatag cgaagtccat   4380
cttgagccag aagaataagg ccggtgggat tactttgcct gattttaagt tgtattataa   4440
agccacagta actaagacag cctggtattg gtatcagaat agagacatcg accagtggaa   4500
tcggaccgaa ccatcagaga taatgcccca catctataat taccttatat tcgataagcc   4560
agaaaagaat aaacagtggg gcaaagacag cctcttcaac aagtggtgtt gggagaattg   4620
gctggccata tgccggaaac tcaagctcga cccctttctt acaccctaca ctaaaatcaa   4680
cagtaggtgg atcaaggact tgaatgtcaa gccaaagact ataaagacac tggaagagaa   4740
tcttgggatc acaatacaag atataggcgt cggcaaagat tttatgtcaa agacgcccaa   4800
ggccatggcc actaaggata agattgataa gtgggacctt attaagctca aaagcttctg   4860
tactgccaag gagaccacga tcagagttaa taggcagccc actacatggg aaaagatttt   4920
cgccacttat tcatcagata aggggttgat aagcagaata tataacgagc tgaagcagat   4980
ctacaagaag aaaacgaata atcccatcaa gaagtgggca aaagatatga acaggcattt   5040
tagcaaagag gatatctacg ccgcgaagaa gcatatgaag aagtgtagtt caagcttggc   5100
cattcgtgag atgcagatta agacgaccat gcgataccac cttaccccag tgaggatggc   5160
aattatcaag aaatctggca ataatagatg ttggcggggc tgtggcgaga ttggcaccct   5220
gctccattgc tggtgggatt gcaagctggt gcagccgctt tggaaatcag tctggcgctt   5280
tctgagggac ctcgagcttg agattccctt cgatcccgca attcccttgc tcggaatcta   5340
tcctaacgaa tacaagagct gttgttacaa ggatacgtgt acccggatgt tcatcgcggc   5400
cttgtttacg atagctaaga cgtggaatca gcctaagtgc cccacaatga tcgattggat   5460
caagaaaatg tggcatattt ataccatgga gtattacgca gcaattaaga atgacgaatt   5520
tatttccttc gttgggacct ggatgaagct ggagactatt attctgagca agctgtctca   5580
ggagcaaaag acaaagcata gaatcttctc tctcattggt ggtaacgact acaaagacga   5640
tgacgacaag taaagcgctt ctagaagttg tctcctcctg cactgactga ctgatacaat   5700
cgatttctgg atccgcaggc ctaatcaacc tctggattac aaaatttgtg aaagattgac   5760
tggtattctt aactatgttg ctccttttac gctatgtgga tacgctgctt taatgccttt   5820
gtatcatgct attgcttccc gtatggcttt cattttctcc tccttgtata aatcctggtt   5880
gctgtctctt tatgaggagt tgtggcccgt tgtcaggcaa cgtggcgtgg tgtgcactgt   5940
gtttgctgac gcaaccccca ctggttgggg cattgccacc acctgtcagc tcctttccgg   6000
```

```
gactttcgct ttccccctcc ctattgccac ggcggaactc atcgccgcct gccttgcccg   6060
ctgctggaca ggggctcggc tgttgggcac tgacaattcc gtggtgttgt cggggaagct   6120
gacgtccttt ccatggctgc tcgcctgtgt tgccacctgg attctgcgcg ggacgtcctt   6180
ctgctacgtc ccttcggccc tcaatccagc ggaccttcct tcccgcgaac aaacgaccca   6240
acacccgtgc gttttattct gtctttttat tgccgatccc ctcagaagaa ctcgtcaaga   6300
aggcgataga aggcgatgcg ctgcgaatcg ggagcggcga taccgtaaag cacgaggaag   6360
cggtcagccc attcgccgcc aagctcttca gcaatatcac gggtagccaa cgctatgtcc   6420
tgatagcggt cggccgcttt acttgtacag ctcgtccatg ccgagagtga tcccggcggc   6480
ggtcacgaac tccagcagga ccatgtgatc gcgcttctcg ttggggtctt tgctcagggc   6540
ggactgggtg ctcaggtagt ggttgtcggg cagcagcacg gggccgtcgc cgatgggggt   6600
gttctgctgg tagtggtcgg ccaggtgagt ccaggagatg tttcagcact gttgccttta   6660
gtctcgaggc aacttagaca actgagtatt gatctgagca cagcagggtg tgagctgttt   6720
gaagatactg gggttggggg tgaagaaact gcagaggact aactgggctg agacccagtg   6780
gcaatgtttt agggcctaag gaatgcctct gaaaatctag atggacaact ttgactttga   6840
gaaaagagag gtggaaatga ggaaaatgac ttttctttat tagatttcgg tagaaagaac   6900
tttcatcttt cccctatttt tgttattcgt tttaaaacat ctatctggag gcaggacaag   6960
tatggtcatt aaaaagatgc aggcagaagg catatattgg ctcagtcaaa gtggggaact   7020
ttggtggcca aacatacatt gctaaggcta ttcctatatc agctggacac atataaaatg   7080
ctgctaatgc ttcattacaa acttatatcc tttaattcca gatgggggca aagtatgtcc   7140
aggggtgagg aacaattgaa acatttgggc tggagtagat tttgaaagtc agctctgtgt   7200
gtgtgtgtgt gtgtgtgtgt gtgagagcgt gtgtttcttt taacgttttc agcctacagc   7260
atacagggtt catggtggca agaagataac aagatttaaa ttatggccag tgactagtgc   7320
tgcaagaaga acaactacct gcatttaatg ggaaagcaaa atctcaggct ttgagggaag   7380
ttaacatagg cttgattctg ggtggaagct gggtgtgtag ttatctggag gccaggctgg   7440
agctctcagc tcactatggg ttcatcttta ttgtctcctt tcatctcaac agctgcacgc   7500
tgccgtcctc gatgttgtgg cggatcttga agttcacctt gatgccgttc ttctgcttgt   7560
cggccatgat atagacgttg tggctgttgt agttgtactc cagcttgtgc cccaggatgt   7620
tgccgtcctc cttgaagtcg atgcccttca gctcgatgcg gttcaccagg gtgtcgccct   7680
cgaacttcac ctcggcgcgg gtcttgtagt tgccgtcgtc cttgaagaag atggtgcgct   7740
cctggacgta gccttcgggc atggcggact tgaagaagtc gtgctgcttc atgtggtcgg   7800
ggtagcggct gaagcactgc acgccgtagg tcagggtggt cacgagggtg ggccagggca   7860
cgggcagctt gccggtggtg cagatgaact tcagggtcag cttgccgtag gtggcatcgc   7920
cctcgccctc gccggacacg ctgaacttgt ggccgtttac gtcgccgtcc agctcgacca   7980
ggatgggcac caccccggtg aacagctcct cgcccttgct caccatggtg gcgaattcga   8040
agcttgagca cgagatctga gtccggtagg cctagcggat ctgacggttc actaaaccag   8100
ctctgcttat atagacctcc caccgtacac gcctaccgcc catttgcgtc aatggggcgg   8160
agttgttacg acattttgga aagtcccgtt gattttggtg ccaaaacaaa ctcccattga   8220
cgtcaatggg gtggagactt ggaaatcccc gtgagtcaaa ccgctatcca cgcccattga   8280
tgtactgcca aaaccgcatc accatggtaa tagcgatgac taatacgtag atgtactgcc   8340
```

```
aagtaggaaa gtcccataag gtcatgtact gggcataatg ccaggcgggc catttaccgt   8400
cattgacgtc aatagggggc gtacttggca tatgatacac ttgatgtact gccaagtggg   8460
cagtttaccg taaatactcc acccattgac gtcaatggaa agtccctatt ggcgttacta   8520
tgggaacata cgtcattatt gacgtcaatg ggcgggggtc gttgggcggt cagccaggcg   8580
ggccatttac cgtaagttat gtaacgggcc tgctgccggc tctgcggcct cttccgcgtc   8640
ttcgccttcg ccctcagacg agtcggatct ccctttgggc cgcctccccg cctgtctagc   8700
ttgactgact gagatacagc gtaccttcag ctcacagaca tgataagata cattgatgag   8760
tttggacaaa ccacaactag aatgcagtga aaaaaatgct ttatttgtga aatttgtgat   8820
gctattgctt tatttgtaac cattataagc tgcaataaac aagttaacaa caacaattgc   8880
attcatttta tgtttcaggt tcagggggag gtgtgggagg ttttttaaag caagtaaaac   8940
ctctacaaat gtggtattgg cccatctcta tcggtatcgt agcataaccc cttggggcct   9000
ctaaacgggt cttgaggggt tttttgtgcc cctcgggccg gattgctatc taccggcatt   9060
ggcgcagaaa aaaatgcctg atgcgacgct gcgcgtctta tactcccaca tatgccagat   9120
tcagcaacgg atacggcttc cccaacttgc ccacttccat acgtgtcctc cttaccagaa   9180
atttatcctt aaggtcgtca gctatcctgc aggcgatctc tcgatttcga tcaagacatt   9240
cctttaatgg tcttttctgg acaccactag ggtcagaag tagttcatca aactttcttc    9300
cctccctaat ctcattggtt accttgggct atcgaaactt aattaagcga tctgcatctc   9360
aattagtcag caaccatagt cccgccccta actccgccca tcccgcccct aactccgccc   9420
agttccgccc attctccgcc ccatcgctga ctaatttttt ttatttatgc agaggccgag   9480
gccgcctcgg cctctgagct attccagaag tagtgaggag gcttttttgg aggcctaggc   9540
ttttgcaaag gaggtagcca acatgattga acaagatgga ttgcacgcag gttctcccgc   9600
cgcttgggtg gagaggctat tcggctatga ctgggcacaa cagacaatcg gctgctctga   9660
tgccgccgtg ttccggctgt cagcgcaggg gcgcccggtt ctttttgtca agaccgacct   9720
gtccggtgcc ctgaatgaac tccaggacga ggcagcgcgg ctatcgtggc tggccacgac   9780
gggcgttcct tgcgcagctg tgctcgacgt tgtcactgaa gcgggaaggg actggctgct   9840
attgggcgaa gtgccggggc aggatctcct gtcatctcac cttgctcctg ccgagaaagt   9900
atccatcatg gctgatgcaa tgcggcggct gcatacgctt gatccggcta cctgcccatt   9960
cgaccaccaa gcgaaacatc gcatcgagcg agcacgtact cggatggaag ccggtcttgt  10020
cgatcaggat gatctggacg aagagcatca ggggctcgcg ccagccgaac tgttcgccag  10080
gctcaaggcg cggatgcccg acggcgagga tctcgtcgtg acccacggcg atgcctgctt  10140
gccgaatatc atggtggaaa atggccgctt ttctggattc atcgactgtg gccggctggg  10200
tgtggcggac cgctatcagg acatagcgtt ggctacccgt gatattgctg aagagcttgg  10260
cggcgaatgg gctgaccgct tcctcgtgct ttacggtatc gccgctcccg attcgcagcg  10320
catcgccttc tatcgccttc ttgacgagtt cttctagtat gtaagccctg tgccttctag  10380
ttgccagcca tctgttgttt gcccctcccc cgtgccttcc ttgaccctgg aaggtgccac  10440
tcccactgtc ctttcctaat aaaatgagga aattgcatcg cattgtctga gtaggtgtca  10500
ttctattctg gggggtgggg tggggcagga cagcaagggg gaggattggg aagacaatag  10560
caggcatgct ggggatgcgg tgggctctat ggttaattaa ccagtcaagt cagctacttg  10620
gcgagatcga cttgtctggg tttcgactac gctcagaatt gcgtcagtca agttcgatct  10680
ggtccttgct attgcacccg ttctccgatt acgagtttca tttaaatcat gtgagcaaaa  10740
```

ggccagcaaa aggccaggaa ccgtaaaaag gccgcgttgc tggcgttttt ccataggctc 10800
cgcccccctg acgagcatca caaaaatcga cgctcaagtc agaggtggcg aaacccgaca 10860
ggactataaa gataccaggc gtttccccct ggaagctccc tcgtgcgctc tcctgttccg 10920
accctgccgc ttaccggata cctgtccgcc tttctccctt cgggaagcgt ggcgctttct 10980
catagctcac gctgtaggta tctcagttcg gtgtaggtcg ttcgctccaa gctgggctgt 11040
gtgcacgaac cccccgttca gcccgaccgc tgcgccttat ccggtaacta tcgtcttgag 11100
tccaacccgg taagacacga cttatcgcca ctggcagcag ccactggtaa caggattagc 11160
agagcgaggt atgtaggcgg tgctacagag ttcttgaagt ggtggcctaa ctacggctac 11220
actagaagaa cagtatttgg tatctgcgct ctgctgaagc cagttacctt cggaaaaaga 11280
gttggtagct cttgatccgg caaacaaacc accgctggta gcggtggttt ttttgtttgc 11340
aagcagcaga ttacgcgcag aaaaaaagga tctcaagaag atcctttgat cttttctacg 11400
gggtctgacg ctcagtggaa cgaaaactca cgttaaggga ttttggtcat gagattatca 11460
aaaaggatct tcacctagat ccttttaaat taaaaatgaa gttttaaatc aatctaaagt 11520
atatatgagt aaacttggtc tgacagttac caatgcttaa tcagtgaggc acctatctca 11580
gcgatctgtc tatttcgttc atccatagtt gcatttaaat ttccgaactc tccaaggccc 11640
tcgtcggaaa atcttcaaac ctttcgtccg atccatcttg caggctacct ctcgaacgaa 11700
ctatcgcaag tctcttggcc ggccttgcgc cttggctatt gcttggcagc gcctatcgcc 11760
aggtattact ccaatcccga atatccgaga tcgggatcac ccgagagaag ttcaacctac 11820
atcctcaatc ccgatctatc cgagatccga ggaatatcga aatcggggcg cgcctggtgt 11880
accgagaacg atcctctcag tgcgagtctc gacgatccat atcgttgctt ggcagtcagc 11940
cagtcggaat ccagcttggg acccaggaag tccaatcgtc agatattgta ctcaagcctg 12000
gtcacggcag cgtaccgatc tgtttaaacc tagatattga tagtctgatc ggtcaacgta 12060
taatcgagtc ctagcttttg caaacatcta tcaagagaca ggatcagcag gaggctttcg 12120
catgagtatt caacatttcc gtgtcgccct tattcccttt tttgcggcat tttgccttcc 12180
tgtttttgct cacccagaaa cgctggtgaa agtaaaagat gctgaagatc agttgggtgc 12240
gcgagtgggt tacatcgaac tggatctcaa cagcggtaag atccttgaga gttttcgccc 12300
cgaagaacgc tttccaatga tgagcacttt taaagttctg ctatgtggcg cggtattatc 12360
ccgtattgac gccgggcaag agcaactcgg tcgccgcata cactattctc agaatgactt 12420
ggttgagtat tcaccagtca cagaaaagca tcttacggat ggcatgacag taagagaatt 12480
atgcagtgct gccataacca tgagtgataa cactgcggcc aacttacttc tgacaacgat 12540
tggaggaccg aaggagctaa ccgctttttt gcacaacatg ggggatcatg taactcgcct 12600
tgatcgttgg gaaccggagc tgaatgaagc cataccaaac gacgagcgtg acaccacgat 12660
gcctgtagca atggcaacaa ccttgcgtaa actattaact ggcgaactac ttactctagc 12720
ttcccggcaa cagttgatag actggatgga ggcggataaa gttgcaggac cacttctgcg 12780
ctcggccctt ccggctggct ggtttattgc tgataaatct ggagccggtg agcgtgggtc 12840
tcgcggtatc attgcagcac tggggccaga tggtaagccc tcccgtatcg tagttatcta 12900
cacgacgggg agtcaggcaa ctatggatga acgaaataga cagatcgctg agataggtgc 12960
ctcactgatt aagcattggt aaccgattct aggtgcattg gcgcagaaaa aaatgcctga 13020
tgcgacgctg cgcgtcttat actcccacat atgccagatt cagcaacgga tacggcttcc 13080
ccaacttgcc cacttccata cgtgtcctcc ttaccagaaa tttatcctta agatcgttta 13140
aactcgactc tggctctatc gaatctccgt cgtttcgagc ttacgcgaac agccgtggcg 13200
ctcatttgct cgtcgggcat cgaatctcgt cagctatcgt cagcttacct ttttggcagc 13260
gatcgcggct cccgacatct tggaccatta gctccacagg tatcttcttc cctctagtgg 13320
tcataacagc agcttcagct acctctcaat tcaaaaaacc cctcaagacc cgtttagagg 13380
ccccaagggg ttatgctatc aatcgttgcg ttacacacac aaaaaaccaa cacacatcca 13440
tcttcgatgg atagcgattt tattatctaa ctgctgatcg agtgtagcca gatctagtaa 13500
tcaattacgg ggtcattagt tcatagccca tatatggagt tccgcgttac ataacttacg 13560
gtaaatggcc cgcctggctg accgcccaac gacccccgcc cattgacgtc aataatgacg 13620
tatgttccca tagtaacgcc aatagggact ttccattgac gtcaatgggt ggagtattta 13680
cggtaaactg cccacttggc agtacatcaa gtgtatcata tgccaagtac gccccctatt 13740
gacgtcaatg acggtaaatg gcccgcctgg cattatgccc agtacatgac cttatgggac 13800
tttcctactt ggcagtacat ctacgtatta gtcatcgcta ttaccatgct gatgcggttt 13860
tggcagtaca tcaatgggcg tggatagcgg tttgactcac ggggatttcc aagtctccac 13920
cccattgacg tcaatgggag tttgttttgg caccaaaatc aacgggactt tccaaaatgt 13980
cgtaacaact ccgccccatt gacgcaaatg ggcggtaggc gtgtacggtg ggaggtctat 14040
ataagcagag ctggtttagt gaaccgtcag atcagatctt tgtcgatcct accatccact 14100
cgacacaccc gccagcggcc gc 14122

<210> SEQ ID NO 45
<211> LENGTH: 14124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
taatacgact cactataggg agaagtactg ccaccatggg caagaagcaa aatcgcaaga 60
cggggaattc caagacacaa tccgctagcc caccacctaa agagcgttct agctcccctg 120
ctactgagca gtcctggatg gaaaacgact tcgatgaact ccgggaagag ggatttaggc 180
gatccaacta ttcagaactc cgcgaagata tccagacaaa ggggaaggaa gtcgagaatt 240
tcgagaagaa cctcgaggag tgcatcaccc gtatcacaaa cactgagaaa tgtctcaaag 300
aactcatgga acttaagaca aaagccaggg agcttcgaga ggagtgtcgg agtctgagat 360
ccaggtgtga ccagctcgag gagcgcgtga gcgcgatgga agacgagatg aacgagatga 420
aaagagaggg caaattcagg gagaagcgca ttaagaggaa cgaacagagt ctgcaggaga 480
tttgggatta cgtcaagagg cctaacctgc ggttgatcgg cgtccccgag agcgacgtag 540
aaaacgggac taaactggag aatacacttc aagacatcat tcaagaaaat tttccaaacc 600
tggctcggca agctaatgtg caaatccaag agatccaacg cacaccccag cggtatagct 660
ctcggcgtgc caccoctagg catattatcg tgcgctttac taaggtggag atgaaagaga 720
agatgctgcg agccgctcgg gaaaagggaa gggtgacttt gaagggcaaa cctattcggc 780
tgacggttga ccttagcgcc gagacactcc aggcacgccg ggaatggggc cccatcttta 840
atatcctgaa ggagaagaac ttccagccac gaatctctta ccctgcaaag ttgagtttta 900
tctccgaggg tgagattaag tatttcatcg ataaacagat gctgcgagac ttcgtgacaa 960

```
ctcgcccagc tctcaaggaa ctgctcaaag aggctcttaa tatggagcgc aataatagat   1020
atcaaccctt gcagaaccac gcaaagatgt gagacagtta aaacagctgt gggttgtcac   1080
ccacccacag ggtccactgg gcgctagtac actggtatct cggtaccttt gtacgcctgt   1140
tttatacccc ctccctgatt tgcaacttag aagcaacgca aaccagatca atagtaggtg   1200
tgacatacca gtcgcatctt gatcaagcac ttctgtatcc ccggaccgag tatcaataga   1260
ctgtgcacac ggttgaagga gaaaacgtcc gttacccggc taactacttc gagaagccta   1320
gtaacgccat tgaagttgca gagtgtttcg ctcagcactc cccccgtgta gatcaggtcg   1380
atgagtcacc gcattcccca cgggcgaccg tggcggtggc tgcgttggcg gcctgcctat   1440
ggggtaaccc ataggacgct ctaatacgga catggcgtga agagtctatt gagctagtta   1500
gtagtcctcc ggcccctgaa tgcggctaat cctaactgcg gagcacatac ccttaatcca   1560
aagggcagtg tgtcgtaacg ggcaactctg cagcggaacc gactactttg ggtgtccgtg   1620
tttcttttta ttcttgtatt ggctgcttat ggtgacaatt aaagaattgt taccatatag   1680
ctattggatt ggccatccag tgtcaaacag agctattgta tatctctttg ttggattcac   1740
acctctcact cttgaaacgt tacacaccct caattacatt atactgctga acacgaagcg   1800
tacatgaccg gctctaactc acatatcacc atccttacac ttaacattaa cggcctcaac   1860
tcagctatca agcgccatcg gctggccagc tggatcaaat cacaggatcc aagcgtttgt   1920
tgcatccaag agacccacct gacctgtaga gatactcacc gcctcaagat caagggatgg   1980
cgaaagattt atcaggcgaa cggtaagcag aagaaagccg gagtcgcaat tctggtctca   2040
gacaagacgg atttcaagcc caccaaaatt aagcgtgata aggaaggtca ctatattatg   2100
gtgaaaggca gcatacagca ggaagaactt accatattga acatctacgc gccaaacacc   2160
ggcgcacctc gctttatcaa acaggtcctg tccgatctgc agcgagatct ggattctcat   2220
acgttgatta tgggtgattt caatacacca ttgagcaccc tggatcgcag caccaggcaa   2280
aaggtaaata aagacacgca agagctcaat agcgcactgc atcaggcaga tctcattgat   2340
atttatcgca ctcttcatcc taagagtacc gagtacacat tcttcagcgc cccacatcat   2400
acatactcaa agatcgatca tatcgtcggc tcaaaggctc tgctgtcaaa gtgcaagcgc   2460
acagagataa ttacaaatta cctgtcagat catagcgcga tcaagctcga gctgagaatc   2520
aagaacctga cccagagccg gagtaccact tggaagctta ataacctgct gctcaacgat   2580
tattgggtcc acaatgagat gaaggcagag attaaaatgt tcttcgaaac aaatgagaat   2640
aaggatacta cctatcaaaa cctttgggat gcctttaagg ccgtctgcag aggcaagttc   2700
atcgccctca acgcctataa aagaaaacaa gagagatcta agatcgatac tctcacctct   2760
cagctgaagg agttggagaa acaggaacag acccactcca aggcgtcaag acggcaggag   2820
atcacaaaga ttcgcgccga gttgaaagag atcgaaaccc aaaagactct tcagaaaatt   2880
aacgagtctc gtagttggtt cttcgagcgg attaataaga tagacagacc tctggcacga   2940
ctgattaaga agaagcgcga aaagaaccag attgatacca tcaagaacga caagggcgac   3000
atcactactg acccgaccga gatccagacc actattcggg agtattataa gcatttgtat   3060
gctaacaagc ttgagaacct ggaagagatg gacacttttc tggataccta tactctgcca   3120
cggcttaatc aagaggaagt cgagtccctc aaccgcccaa ttacaggaag cgagattgtg   3180
gccataatta actccctgcc gacaaagaaa tctcctggtc cggacgggtt tacagctgag   3240
ttttatcaac ggtatatgga agagcttgta ccgtttctgc tcaagctctt tcagtctata   3300
gaaaaggaag gcatcttgcc caattccttc tacgaagctt ctataatact tattcccaaa   3360
```

ccaggacgcg ataccacaaa gaaggaaaac ttccggccca ttagtctcat gaatatcgac 3420
gctaaaatat tgaacaagat tctcgccaac agaatccaac aacatattaa gaaattgata 3480
catcacgacc aggtggggtt tatacctggc atgcagggct ggtttaacat ccggaagagt 3540
attaacgtca ttcaacacat taatagagct aaggataaga atcatatgat catctctata 3600
gacgcggaaa aggcattcga taagattcag cagccattta tgctcaagac tctgaacaaa 3660
ctcggcatcg acggaacata ttttaagatt attcgcgcaa tttacgataa gccgactgct 3720
aacattatcc ttaacggcca aaagctcgag gcctttccgc tcaagactgg aacccgccaa 3780
ggctgtcccc tctccccgct tttgtttaat attgtactcg aggtgctggc tagggctatt 3840
cgtcaagaga aagagattaa agggatacag ctcgggaagg aagaggtcaa gctttccttg 3900
ttcgccgatg atatgattgt gtacctggag aatcctattg tgtctgctca gaaccttctt 3960
aaacttattt ctaactttag caaggtcagc ggctataaga ttaacgtcca gaaatctcag 4020
gcctttctgt acacaaataa tcgacagacc gaatcccaga taatgggtga gcttccgttt 4080
gtcatagcca gcaaaaggat aaagtatctc ggaatccagc tgacacgaga cgttaaagat 4140
ttgtttaagg aaaattacaa gcctctcctg aaagagatta aggaagatac taataagtgg 4200
aagaatatcc cctgttcatg ggttggcaga atcaacatag tgaagatggc aatacttcct 4260
aaagtgatat atcgctttaa cgccatccca attaaactgc ctatgacctt ctttacggag 4320
ctcgagaaaa caacccttaa atttatatgg aatcaaaaga gagcaagaat agcgaagtcc 4380
atcttgagcc agaagaataa ggccggtggg attactttgc ctgattttaa gttgtattat 4440
aaagccacag taactaagac agcctggtat tggtatcaga atagagacat cgaccagtgg 4500
aatcggaccg aaccatcaga gataatgccc cacatctata attaccttat attcgataag 4560
ccagaaaaga ataaacagtg gggcaaagac agcctcttca acaagtggtg ttgggagaat 4620
tggctggcca tatgccggaa actcaagctc gacccctttc ttacacccta cactaaaatc 4680
aacagtaggt ggatcaagga cttgaatgtc aagccaaaga ctataaagac actggaagag 4740
aatcttggga tcacaataca agatataggc gtcggcaaag attttatgtc aaagacgccc 4800
aaggccatgg ccactaagga taagattgat aagtgggacc ttattaagct caaaagcttc 4860
tgtactgcca aggagaccac gatcagagtt aataggcagc ccactacatg ggaaaagatt 4920
ttcgccactt attcatcaga taaggggttg ataagcagaa tatataacga gctgaagcag 4980
atctacaaga agaaaacgaa taatcccatc aagaagtggg caaaagatat gaacaggcat 5040
tttagcaaag aggatatcta cgccgcgaag aagcatatga agaagtgtag ttcaagcttg 5100
gccattcgtg agatgcagat taagacgacc atgcgatacc accttacccc agtgaggatg 5160
gcaattatca agaaatctgg caataataga tgttggcggg gctgtggcga gattggcacc 5220
ctgctccatt gctggtggga ttgcaagctg gtgcagccgc tttggaaatc agtctggcgc 5280
tttctgaggg acctcgagct tgagattccc ttcgatcccg caattccctt gctcggaatc 5340
tatcctaacg aatacaagag ctgttgttac aaggatacgt gtacccggat gttcatcgcg 5400
gccttgttta cgatagctaa gacgtggaat cagcctaagt gccccacaat gatcgattgg 5460
atcaagaaaa tgtggcatat ttataccatg gagtattacg cagcaattaa gaatgacgaa 5520
tttatttcct tcgttgggac ctggatgaag ctggagacta ttattctgag caagctgtct 5580
caggagcaaa agacaaagca tagaatcttc tctctcattg gtggtaacga ctacaaagac 5640
gatgacgaca agtaaagcgc ttctagaagt tgtctcctcc tgcactgact gactgataca 5700

```
atcgatttct ggatccgcag gcctaatcaa cctctggatt acaaaatttg tgaaagattg   5760
actggtattc ttaactatgt tgctcctttt acgctatgtg gatacgctgc tttaatgcct   5820
ttgtatcatg ctattgcttc ccgtatggct ttcattttct cctccttgta taaatcctgg   5880
ttgctgtctc tttatgagga gttgtggccc gttgtcaggc aacgtggcgt ggtgtgcact   5940
gtgtttgctg acgcaacccc cactggttgg ggcattgcca ccacctgtca gctcctttcc   6000
gggactttcg ctttccccct ccctattgcc acggcggaac tcatcgccgc ctgccttgcc   6060
cgctgctgga caggggctcg gctgttgggc actgacaatt ccgtggtgtt gtcggggaag   6120
ctgacgtcct ttccatggct gctcgcctgt gttgccacct ggattctgcg cgggacgtcc   6180
ttctgctacg tcccttcggc cctcaatcca gcggaccttc cttcccgcga acaaacgacc   6240
caacacccgt gcgttttatt ctgtcttttt attgccgatc ccctcagaag aactcgtcaa   6300
gaaggcgata gaaggcgatg cgctgcgaat cgggagcggc gataccgtaa agcacgagga   6360
agcggtcagc ccattcgccg ccaagctctt cagcaatatc acgggtagcc aacgctatgt   6420
cctgatagcg gtcggccgct ttacttgtac agctcgtcca tgccgagagt gatcccggcg   6480
gcggtcacga actccagcag gaccatgtga tcgcgcttct cgttggggtc tttgctcagg   6540
gcggactggg tgctcaggta gtggttgtcg ggcagcagca cggggccgtc gccgatgggg   6600
gtgttctgct ggtagtggtc ggccaggtga gtccaggaga tgtttcagca ctgttgcctt   6660
tagtctcgag gcaacttaga caactgagta ttgatctgag cacagcaggg tgtgagctgt   6720
ttgaagatac tggggttggg ggtgaagaaa ctgcagagga ctaactgggc tgagacccag   6780
tggcaatgtt ttagggccta aggaatgcct ctgaaaatct agatggacaa ctttgacttt   6840
gagaaaagag aggtggaaat gaggaaaatg actttttcttt attagatttc ggtagaaaga   6900
actttcatct ttcccctatt tttgttattc gttttaaaac atctatctgg aggcaggaca   6960
agtatggtca ttaaaaagat gcaggcagaa ggcatatatt ggctcagtca aagtggggaa   7020
ctttggtggc caaacataca ttgctaaggc tattcctata tcagctggac acatataaaa   7080
tgctgctaat gcttcattac aaacttatat cctttaattc cagatggggg caaagtatgt   7140
ccaggggtga ggaacaattg aaacatttgg gctggagtag attttgaaag tcagctctgt   7200
gtgtgtgtgt gtgtgtgtgt gtgtgagagc gtgtgtttct tttaacgttt tcagcctaca   7260
gcatacaggg ttcatggtgg caagaagata acaagattta aattatggcc agtgactagt   7320
gctgcaagaa gaacaactac ctgcatttaa tgggaaagca aaatctcagg ctttgaggga   7380
agttaacata ggcttgattc tgggtggaag ctgggtgtgt agttatctgg aggccaggct   7440
ggagctctca gctcactatg ggttcatctt tattgtctcc tttcatctca acagctgcac   7500
gctgccgtcc tcgatgttgt ggcggatctt gaagttcacc ttgatgccgt tcttctgctt   7560
gtcggccatg atatagacgt tgtggctgtt gtagttgtac tccagcttgt gccccaggat   7620
gttgccgtcc tccttgaagt cgatgccctt cagctcgatg cggttcacca gggtgtcgcc   7680
ctcgaacttc acctcggcgc gggtcttgta gttgccgtcg tccttgaaga agatggtgcg   7740
ctcctggacg tagccttcgg gcatggcgga cttgaagaag tcgtgctgct tcatgtggtc   7800
ggggtagcgg ctgaagcact gcacgccgta ggtcagggtg gtcacgaggg tgggccaggg   7860
cacgggcagc ttgccggtgg tgcagatgaa cttcagggtc agcttgccgt aggtggcatc   7920
gccctcgccc tcgccggaca cgctgaactt gtggccgttt acgtcgccgt ccagctcgac   7980
caggatgggc accaccccgg tgaacagctc ctcgcccttg ctcaccatgg tggcgaattc   8040
gaagcttgag cacgagatct gagtccggta ggcctagcgg atctgacggt tcactaaacc   8100
```

```
agctctgctt atatagacct cccaccgtac acgcctaccg cccatttgcg tcaatggggc   8160
ggagttgtta cgacattttg gaaagtcccg ttgattttgg tgccaaaaca aactcccatt   8220
gacgtcaatg gggtggagac ttggaaatcc ccgtgagtca aaccgctatc cacgcccatt   8280
gatgtactgc caaaaccgca tcaccatggt aatagcgatg actaatacgt agatgtactg   8340
ccaagtagga aagtcccata aggtcatgta ctgggcataa tgccaggcgg gccatttacc   8400
gtcattgacg tcaatagggg gcgtacttgg catatgatac acttgatgta ctgccaagtg   8460
ggcagtttac cgtaaatact ccacccattg acgtcaatgg aaagtcccta ttggcgttac   8520
tatgggaaca tacgtcatta ttgacgtcaa tgggcggggg tcgttgggcg gtcagccagg   8580
cgggccattt accgtaagtt atgtaacggg cctgctgccg gctctgcggc ctcttccgcg   8640
tcttcgcctt cgccctcaga cgagtcggat ctccctttgg gccgcctccc cgcctgtcta   8700
gcttgactga ctgagataca gcgtaccttc agctcacaga catgataaga tacattgatg   8760
agtttggaca aaccacaact agaatgcagt gaaaaaaatg ctttatttgt gaaatttgtg   8820
atgctattgc tttatttgta accattataa gctgcaataa acaagttaac aacaacaatt   8880
gcattcattt tatgtttcag gttcaggggg aggtgtggga ggttttttaa agcaagtaaa   8940
acctctacaa atgtggtatt ggcccatctc tatcggtatc gtagcataac cccttggggc   9000
ctctaaacgg gtcttgaggg gttttttgtg cccctcgggc cggattgcta tctaccggca   9060
ttggcgcaga aaaaaatgcc tgatgcgacg ctgcgcgtct tatactccca catatgccag   9120
attcagcaac ggatacggct tccccaactt gcccacttcc atacgtgtcc tccttaccag   9180
aaatttatcc ttaaggtcgt cagctatcct gcaggcgatc tctcgatttc gatcaagaca   9240
ttcctttaat ggtcttttct ggacaccact aggggtcaga agtagttcat caaactttct   9300
tccctcccta atctcattgg ttaccttggg ctatcgaaac ttaattaagc gatctgcatc   9360
tcaattagtc agcaaccata gtcccgcccc taactccgcc catcccgccc ctaactccgc   9420
ccagttccgc ccattctccg ccccatcgct gactaatttt ttttatttat gcagaggccg   9480
aggccgcctc ggcctctgag ctattccaga agtagtgagg aggctttttt ggaggcctag   9540
gcttttgcaa aggaggtagc caacatgatt gaacaagatg gattgcacgc aggttctccc   9600
gccgcttggg tggagaggct attcggctat gactgggcac aacagacaat cggctgctct   9660
gatgccgccg tgttccggct gtcagcgcag gggcgcccgg ttctttttgt caagaccgac   9720
ctgtccggtg ccctgaatga actccaggac gaggcagcgc ggctatcgtg gctggccacg   9780
acgggcgttc cttgcgcagc tgtgctcgac gttgtcactg aagcgggaag ggactggctg   9840
ctattgggcg aagtgccggg gcaggatctc ctgtcatctc accttgctcc tgccgagaaa   9900
gtatccatca tggctgatgc aatgcggcgg ctgcatacgc ttgatccggc tacctgccca   9960
ttcgaccacc aagcgaaaca tcgcatcgag cgagcacgta ctcggatgga agccggtctt  10020
gtcgatcagg atgatctgga cgaagagcat caggggctcg cgccagccga actgttcgcc  10080
aggctcaagg cgcggatgcc cgacggcgag gatctcgtcg tgacccacgg cgatgcctgc  10140
ttgccgaata tcatggtgga aaatggccgc ttttctggat tcatcgactg tggccggctg  10200
ggtgtggcgg accgctatca ggacatagcg ttggctaccc gtgatattgc tgaagagctt  10260
ggcggcgaat gggctgaccg cttcctcgtg ctttacggta tcgccgctcc cgattcgcag  10320
cgcatcgcct tctatcgcct tcttgacgag ttcttctagt atgtaagccc tgtgccttct  10380
agttgccagc catctgttgt ttgcccctcc cccgtgcctt ccttgaccct ggaaggtgcc  10440
```

actcccactg tcctttccta ataaaatgag gaaattgcat cgcattgtct gagtaggtgt 10500
cattctattc tggggggtgg ggtggggcag gacagcaagg gggaggattg ggaagacaat 10560
agcaggcatg ctggggatgc ggtgggctct atggttaatt aaccagtcaa gtcagctact 10620
tggcgagatc gacttgtctg ggtttcgact acgctcagaa ttgcgtcagt caagttcgat 10680
ctggtccttg ctattgcacc cgttctccga ttacgagttt catttaaatc atgtgagcaa 10740
aaggccagca aaaggccagg aaccgtaaaa aggccgcgtt gctggcgttt ttccataggc 10800
tccgcccccc tgacgagcat cacaaaaatc gacgctcaag tcagaggtgg cgaaacccga 10860
caggactata aagataccag gcgtttcccc ctggaagctc cctcgtgcgc tctcctgttc 10920
cgaccctgcc gcttaccgga tacctgtccg cctttctccc ttcgggaagc gtggcgcttt 10980
ctcatagctc acgctgtagg tatctcagtt cggtgtaggt cgttcgctcc aagctgggct 11040
gtgtgcacga accccccgtt cagcccgacc gctgcgcctt atccggtaac tatcgtcttg 11100
agtccaaccc ggtaagacac gacttatcgc cactggcagc agccactggt aacaggatta 11160
gcagagcgag gtatgtaggc ggtgctacag agttcttgaa gtggtggcct aactacggct 11220
acactagaag aacagtattt ggtatctgcg ctctgctgaa gccagttacc ttcggaaaaa 11280
gagttggtag ctcttgatcc ggcaaacaaa ccaccgctgg tagcggtggt ttttttgttt 11340
gcaagcagca gattacgcgc agaaaaaaag gatctcaaga agatcctttg atcttttcta 11400
cggggtctga cgctcagtgg aacgaaaact cacgttaagg gattttggtc atgagattat 11460
caaaaaggat cttcacctag atccttttaa attaaaaatg aagttttaaa tcaatctaaa 11520
gtatatatga gtaaacttgg tctgacagtt accaatgctt aatcagtgag gcacctatct 11580
cagcgatctg tctatttcgt tcatccatag ttgcatttaa atttccgaac tctccaaggc 11640
cctcgtcgga aaatcttcaa acctttcgtc cgatccatct tgcaggctac ctctcgaacg 11700
aactatcgca agtctcttgg ccggccttgc gccttggcta ttgcttggca gcgcctatcg 11760
ccaggtatta ctccaatccc gaatatccga gatcgggatc acccgagaga agttcaacct 11820
acatcctcaa tcccgatcta tccgagatcc gaggaatatc gaaatcgggg cgcgcctggt 11880
gtaccgagaa cgatcctctc agtgcgagtc tcgacgatcc atatcgttgc ttggcagtca 11940
gccagtcgga atccagcttg ggacccagga agtccaatcg tcagatattg tactcaagcc 12000
tggtcacggc agcgtaccga tctgtttaaa cctagatatt gatagtctga tcggtcaacg 12060
tataatcgag tcctagcttt tgcaaacatc tatcaagaga caggatcagc aggaggcttt 12120
cgcatgagta ttcaacattt ccgtgtcgcc cttattccct tttttgcggc attttgcctt 12180
cctgtttttg ctcacccaga aacgctggtg aaagtaaaag atgctgaaga tcagttgggt 12240
gcgcgagtgg gttacatcga actggatctc aacagcggta agatccttga gagttttcgc 12300
cccgaagaac gctttccaat gatgagcact tttaaagttc tgctatgtgg cgcggtatta 12360
tcccgtattg acgccgggca agagcaactc ggtcgccgca tacactattc tcagaatgac 12420
ttggttgagt attcaccagt cacagaaaag catcttacgg atggcatgac agtaagagaa 12480
ttatgcagtg ctgccataac catgagtgat aacactgcgg ccaacttact tctgacaacg 12540
attggaggac cgaaggagct aaccgctttt ttgcacaaca tgggggatca tgtaactcgc 12600
cttgatcgtt gggaaccgga gctgaatgaa gccataccaa acgacgagcg tgacaccacg 12660
atgcctgtag caatggcaac aaccttgcgt aaactattaa ctggcgaact acttactcta 12720
gcttcccggc aacagttgat agactggatg gaggcggata aagttgcagg accacttctg 12780
cgctcggccc ttccggctgg ctggtttatt gctgataaat ctggagccgg tgagcgtggg 12840
tctcgcggta tcattgcagc actggggcca gatggtaagc cctcccgtat cgtagttatc 12900
tacacgacgg ggagtcaggc aactatggat gaacgaaata gacagatcgc tgagataggt 12960
gcctcactga ttaagcattg gtaaccgatt ctaggtgcat tggcgcagaa aaaaatgcct 13020
gatgcgacgc tgcgcgtctt atactcccac atatgccaga ttcagcaacg gatacggctt 13080
ccccaacttg cccacttcca tacgtgtcct ccttaccaga aatttatcct taagatcgtt 13140
taaactcgac tctggctcta tcgaatctcc gtcgtttcga gcttacgcga acagccgtgg 13200
cgctcatttg ctcgtcgggc atcgaatctc gtcagctatc gtcagcttac ctttttggca 13260
gcgatcgcgg ctcccgacat cttggaccat tagctccaca ggtatcttct tccctctagt 13320
ggtcataaca gcagcttcag ctacctctca attcaaaaaa cccctcaaga cccgtttaga 13380
ggccccaagg ggttatgcta tcaatcgttg cgttacacac acaaaaaacc aacacacatc 13440
catcttcgat ggatagcgat tttattatct aactgctgat cgagtgtagc cagatctagt 13500
aatcaattac ggggtcatta gttcatagcc catatatgga gttccgcgtt acataactta 13560
cggtaaatgg cccgcctggc tgaccgccca acgacccccg cccattgacg tcaataatga 13620
cgtatgttcc catagtaacg ccaataggga ctttccattg acgtcaatgg gtggagtatt 13680
tacggtaaac tgcccacttg gcagtacatc aagtgtatca tatgccaagt acgcccccta 13740
ttgacgtcaa tgacggtaaa tggcccgcct ggcattatgc ccagtacatg accttatggg 13800
actttcctac ttggcagtac atctacgtat tagtcatcgc tattaccatg ctgatgcggt 13860
tttggcagta catcaatggg cgtggatagc ggtttgactc acggggattt ccaagtctcc 13920
accccattga cgtcaatggg agtttgtttt ggcaccaaaa tcaacgggac tttccaaaat 13980
gtcgtaacaa ctccgcccca ttgacgcaaa tgggcggtag gcgtgtacgg tgggaggtct 14040
atataagcag agctggttta gtgaaccgtc agatcagatc tttgtcgatc ctaccatcca 14100
ctcgacacac ccgccagcgg ccgc 14124

<210> SEQ ID NO 46
<211> LENGTH: 13439
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 46
taatacgact cactataggg agaagtactg ccaccatggg caagaagcaa aatcgcaaga 60
cggggaattc caagacacaa tccgctagcc caccacctaa agagcgttct agctcccctg 120
ctactgagca gtcctggatg gaaaacgact tcgatgaact ccgggaagag ggatttaggc 180
gatccaacta ttcagaactc cgcgaagata tccagacaaa ggggaaggaa gtcgagaatt 240
tcgagaagaa cctcgaggag tgcatcaccc gtatcacaaa cactgagaaa tgtctcaaag 300
aactcatgga acttaagaca aaagccaggg agcttcgaga ggagtgtcgg agtctgagat 360
ccaggtgtga ccagctcgag gagcgcgtga gcgcgatgga agacgagatg aacgagatga 420
aaagagaggg caaattcagg gagaagcgca ttaagaggaa cgaacagagt ctgcaggaga 480
tttgggatta cgtcaagagg cctaacctgc ggttgatcgg cgtccccgag agcgacgtag 540
aaaacgggac taaactggag aatacacttc aagacatcat tcaagaaaat tttccaaacc 600
tggctcggca agctaatgtg caaatccaag agatccaacg cacaccccag cggtatagct 660
ctcggcgtgc cacccctagg catattatcg tgcgctttac taaggtggag atgaaagaga 720

```
agatgctgcg agccgctcgg gaaaagggaa gggtgacttt gaagggcaaa cctattcggc    780
tgacggttga ccttagcgcc gagacactcc aggcacgccg ggaatggggc cccatcttta    840
atatcctgaa ggagaagaac ttccagccac gaatctctta ccctgcaaag ttgagtttta    900
tctccgaggg tgagattaag tatttcatcg ataaacagat gctgcgagac ttcgtgacaa    960
ctcgcccagc tctcaaggaa ctgctcaaag aggctcttaa tatggagcgc aataatagat   1020
atcaaccctt gcagaaccac gcaaagatgg gaagcggaca gtgtactaat tatgctctct   1080
tgaaattggc tggagatgtt gagagcaacc ctggacctat gaccggctct aactcacata   1140
tcaccatcct tacacttaac attaacggcc tcaactcagc tatcaagcgc catcggctgg   1200
ccagctggat caaatcacag gatccaagcg tttgttgcat ccaagagacc cacctgacct   1260
gtagagatac tcaccgcctc aagatcaagg gatggcgaaa gatttatcag gcgaacggta   1320
agcagaagaa agccggagtc gcaattctgg tctcagacaa gacggatttc aagcccacca   1380
aaattaagcg tgataaggaa ggtcactata ttatggtgaa aggcagcata cagcaggaag   1440
aacttaccat attgaacatc tacgcgccaa acaccggcgc acctcgcttt atcaaacagg   1500
tcctgtccga tctgcagcga gatctggatt ctcatacgtt gattatgggt gatttcaata   1560
caccattgag caccctggat cgcagcacca ggcaaaaggt aaataaagac acgcaagagc   1620
tcaatagcgc actgcatcag gcagatctca ttgatattta tcgcactctt catcctaaga   1680
gtaccgagta cacattcttc agcgccccac atcatacata ctcaaagatc gatcatatcg   1740
tcggctcaaa ggctctgctg tcaaagtgca agcgcacaga gataattaca aattacctgt   1800
cagatcatag cgcgatcaag ctcgagctga gaatcaagaa cctgacccag agccggagta   1860
ccacttggaa gcttaataac ctgctgctca acgattattg ggtccacaat gagatgaagg   1920
cagagattaa aatgttcttc gaaacaaatg agaataagga tactacctat caaaaccttt   1980
gggatgcctt taaggccgtc tgcagaggca agttcatcgc cctcaacgcc tataaaagaa   2040
aacaagagag atctaagatc gatactctca cctctcagct gaaggagttg gagaaacagg   2100
aacagaccca ctccaaggcg tcaagacggc aggagatcac aaagattcgc gccgagttga   2160
aagagatcga aacccaaaag actcttcaga aaattaacga gtctcgtagt tggttcttcg   2220
agcggattaa taagatagac agacctctgg cacgactgat taagaagaag cgcgaaaaga   2280
accagattga taccatcaag aacgacaagg gcgacatcac tactgacccg accgagatcc   2340
agaccactat tcgggagtat tataagcatt tgtatgctaa caagcttgag aacctggaag   2400
agatggacac ttttctggat acctatactc tgccacggct taatcaagag gaagtcgagt   2460
ccctcaaccg cccaattaca ggaagcgaga ttgtggccat aattaactcc ctgccgacaa   2520
agaaatctcc tggtccggac gggtttacag ctgagtttta tcaacggtat atggaagagc   2580
ttgtaccgtt tctgctcaag ctctttcagt ctatagaaaa ggaaggcatc ttgcccaatt   2640
ccttctacga agcttctata atacttattc ccaaaccagg acgcgatacc acaaagaagg   2700
aaaacttccg gcccattagt ctcatgaata tcgacgctaa aatattgaac aagattctcg   2760
ccaacagaat ccaacaacat attaagaaat tgatacatca cgaccaggtg gggtttatac   2820
ctggcatgca gggctggttt aacatccgga agagtattaa cgtcattcaa cacattaata   2880
gagctaagga taagaatcat atgatcatct ctatagacgc ggaaaaggca ttcgataaga   2940
ttcagcagcc atttatgctc aagactctga acaaactcgg catcgacgga acatatttta   3000
agattattcg cgcaatttac gataagccga ctgctaacat tatccttaac ggccaaaagc   3060
```

```
tcgaggcctt tccgctcaag actggaaccc gccaaggctg tcccctctcc ccgcttttgt   3120
ttaatattgt actcgaggtg ctggctaggg ctattcgtca agagaaagag attaaaggga   3180
tacagctcgg gaaggaagag gtcaagcttt ccttgttcgc cgatgatatg attgtgtacc   3240
tggagaatcc tattgtgtct gctcagaacc ttcttaaact tatttctaac tttagcaagg   3300
tcagcggcta taagattaac gtccagaaat ctcaggcctt tctgtacaca aataatcgac   3360
agaccgaatc ccagataatg ggtgagcttc cgtttgtcat agccagcaaa aggataaagt   3420
atctcggaat ccagctgaca cgagacgtta aagatttgtt taaggaaaat tacaagcctc   3480
tcctgaaaga gattaaggaa gatactaata agtggaagaa tatcccctgt tcatgggttg   3540
gcagaatcaa catagtgaag atggcaatac ttcctaaagt gatatatcgc tttaacgcca   3600
tcccaattaa actgcctatg accttcttta cggagctcga gaaaacaacc cttaaattta   3660
tatggaatca aaagagagca agaatagcga agtccatctt gagccagaag aataaggccg   3720
gtgggattac tttgcctgat tttaagttgt attataaagc cacagtaact aagacagcct   3780
ggtattggta tcagaataga gacatcgacc agtggaatcg gaccgaacca tcagagataa   3840
tgccccacat ctataattac cttatattcg ataagccaga aaagaataaa cagtggggca   3900
aagacagcct cttcaacaag tggtgttggg agaattggct ggccatatgc cggaaactca   3960
agctcgaccc ctttcttaca ccctacacta aaatcaacag taggtggatc aaggacttga   4020
atgtcaagcc aaagactata aagacactgg aagagaatct tgggatcaca atacaagata   4080
taggcgtcgg caaagatttt atgtcaaaga cgcccaaggc catggccact aaggataaga   4140
ttgataagtg ggaccttatt aagctcaaaa gcttctgtac tgccaaggag accacgatca   4200
gagttaatag gcagcccact acatgggaaa agattttcgc cacttattca tcagataagg   4260
ggttgataag cagaatatat aacgagctga agcagatcta caagaagaaa acgaataatc   4320
ccatcaagaa gtgggcaaaa gatatgaaca ggcattttag caaagaggat atctacgccg   4380
cgaagaagca tatgaagaag tgtagttcaa gcttggccat tcgtgagatg cagattaaga   4440
cgaccatgcg ataccacctt accccagtga ggatggcaat tatcaagaaa tctggcaata   4500
atagatgttg gcggggctgt ggcgagattg gcaccctgct ccattgctgg tgggattgca   4560
agctggtgca gccgctttgg aaatcagtct ggcgctttct gagggacctc gagcttgaga   4620
ttcccttcga tcccgcaatt cccttgctcg gaatctatcc taacgaatac aagagctgtt   4680
gttacaagga tacgtgtacc cggatgttca tcgcggcctt gtttacgata gctaagacgt   4740
ggaatcagcc taagtgcccc acaatgatcg attggatcaa gaaaatgtgg catatttata   4800
ccatggagta ttacgcagca attaagaatg acgaatttat ttccttcgtt gggacctgga   4860
tgaagctgga gactattatt ctgagcaagc tgtctcagga gcaaaagaca aagcatagaa   4920
tcttctctct cattggtggt aacgactaca aagacgatga cgacaagtaa agcgcttcta   4980
gaagttgtct cctcctgcac tgactgactg atacaatcga tttctggatc cgcaggccta   5040
atcaacctct ggattacaaa atttgtgaaa gattgactgg tattcttaac tatgttgctc   5100
cttttacgct atgtggatac gctgctttaa tgcctttgta tcatgctatt gcttcccgta   5160
tggctttcat tttctcctcc ttgtataaat cctggttgct gtctctttat gaggagttgt   5220
ggcccgttgt caggcaacgt ggcgtggtgt gcactgtgtt tgctgacgca acccccactg   5280
gttggggcat tgccaccacc tgtcagctcc tttccgggac tttcgctttc cccctcccta   5340
ttgccacggc ggaactcatc gccgcctgcc ttgcccgctg ctggacaggg gctcggctgt   5400
tgggcactga caattccgtg gtgttgtcgg ggaagctgac gtcctttcca tggctgctcg   5460
```

```
cctgtgttgc cacctggatt ctgcgcggga cgtccttctg ctacgtccct tcggccctca   5520
atccagcgga ccttccttcc cgcgaacaaa cgacccaaca cccgtgcgtt ttattctgtc   5580
tttttattgc cgatcccctc agaagaactc gtcaagaagg cgatagaagg cgatgcgctg   5640
cgaatcggga gcggcgatac cgtaaagcac gaggaagcgg tcagcccatt cgccgccaag   5700
ctcttcagca atatcacggg tagccaacgc tatgtcctga tagcggtcgg ccgctttact   5760
tgtacagctc gtccatgccg agagtgatcc cggcggcggt cacgaactcc agcaggacca   5820
tgtgatcgcg cttctcgttg gggtctttgc tcagggcgga ctgggtgctc aggtagtggt   5880
tgtcgggcag cagcacgggg ccgtcgccga tgggggtgtt ctgctggtag tggtcggcca   5940
ggtgagtcca ggagatgttt cagcactgtt gcctttagtc tcgaggcaac ttagacaact   6000
gagtattgat ctgagcacag cagggtgtga gctgtttgaa gatactgggg ttgggggtga   6060
agaaactgca gaggactaac tgggctgaga cccagtggca atgttttagg gcctaaggaa   6120
tgcctctgaa aatctagatg gacaactttg actttgagaa aagagaggtg gaaatgagga   6180
aaatgacttt tctttattag atttcggtag aaagaacttt catctttccc ctatttttgt   6240
tattcgtttt aaaacatcta tctggaggca ggacaagtat ggtcattaaa aagatgcagg   6300
cagaaggcat atattggctc agtcaaagtg gggaactttg gtggccaaac atacattgct   6360
aaggctattc ctatatcagc tggacacata taaaatgctg ctaatgcttc attacaaact   6420
tatatccttt aattccagat gggggcaaag tatgtccagg ggtgaggaac aattgaaaca   6480
tttgggctgg agtagatttt gaaagtcagc tctgtgtgtg tgtgtgtgtg tgtgtgtgtg   6540
agagcgtgtg tttcttttaa cgttttcagc ctacagcata cagggttcat ggtggcaaga   6600
agataacaag atttaaatta tggccagtga ctagtgctgc aagaagaaca actacctgca   6660
tttaatggga aagcaaaatc tcaggctttg agggaagtta acataggctt gattctgggt   6720
ggaagctggg tgtgtagtta tctggaggcc aggctggagc tctcagctca ctatgggttc   6780
atctttattg tctcctttca tctcaacagc tgcacgctgc cgtcctcgat gttgtggcgg   6840
atcttgaagt tcaccttgat gccgttcttc tgcttgtcgg ccatgatata gacgttgtgg   6900
ctgttgtagt tgtactccag cttgtgcccc aggatgttgc cgtcctcctt gaagtcgatg   6960
cccttcagct cgatgcggtt caccagggtg tcgccctcga acttcacctc ggcgcgggtc   7020
ttgtagttgc cgtcgtcctt gaagaagatg gtgcgctcct ggacgtagcc ttcgggcatg   7080
gcggacttga agaagtcgtg ctgcttcatg tggtcggggt agcggctgaa gcactgcacg   7140
ccgtaggtca gggtggtcac gagggtgggc cagggcacgg gcagcttgcc ggtggtgcag   7200
atgaacttca gggtcagctt gccgtaggtg gcatcgccct cgccctcgcc ggacacgctg   7260
aacttgtggc cgtttacgtc gccgtccagc tcgaccagga tgggcaccac cccggtgaac   7320
agctcctcgc ccttgctcac catggtggcg aattcgaagc ttgagcacga gatctgagtc   7380
cggtaggcct agcggatctg acggttcact aaaccagctc tgcttatata gacctcccac   7440
cgtacacgcc taccgcccat ttgcgtcaat ggggcggagt tgttacgaca ttttggaaag   7500
tcccgttgat tttggtgcca aaacaaactc ccattgacgt caatggggtg gagacttgga   7560
aatccccgtg agtcaaaccg ctatccacgc ccattgatgt actgccaaaa ccgcatcacc   7620
atggtaatag cgatgactaa tacgtagatg tactgccaag taggaaagtc ccataaggtc   7680
atgtactggg cataatgcca ggcgggccat ttaccgtcat tgacgtcaat agggggcgta   7740
cttggcatat gatacacttg atgtactgcc aagtgggcag tttaccgtaa atactccacc   7800
```

cattgacgtc aatggaaagt ccctattggc gttactatgg gaacatacgt cattattgac 7860
gtcaatgggc gggggtcgtt gggcggtcag ccaggcgggc catttaccgt aagttatgta 7920
acgggcctgc tgccggctct gcggcctctt ccgcgtcttc gccttcgccc tcagacgagt 7980
cggatctccc tttgggccgc ctccccgcct gtctagcttg actgactgag atacagcgta 8040
ccttcagctc acagacatga taagatacat tgatgagttt ggacaaacca caactagaat 8100
gcagtgaaaa aaatgcttta tttgtgaaat ttgtgatgct attgctttat ttgtaaccat 8160
tataagctgc aataaacaag ttaacaacaa caattgcatt cattttatgt ttcaggttca 8220
gggggaggtg tgggaggttt tttaaagcaa gtaaaacctc tacaaatgtg gtattggccc 8280
atctctatcg gtatcgtagc ataacccctt ggggcctcta aacgggtctt gaggggtttt 8340
ttgtgcccct cgggccggat tgctatctac cggcattggc gcagaaaaaa atgcctgatg 8400
cgacgctgcg cgtcttatac tcccacatat gccagattca gcaacggata cggcttcccc 8460
aacttgccca cttccatacg tgtcctcctt accagaaatt tatccttaag gtcgtcagct 8520
atcctgcagg cgatctctcg atttcgatca agacattcct ttaatggtct tttctggaca 8580
ccactagggg tcagaagtag ttcatcaaac tttcttccct ccctaatctc attggttacc 8640
ttgggctatc gaaacttaat taagcgatct gcatctcaat tagtcagcaa ccatagtccc 8700
gcccctaact ccgcccatcc cgcccctaac tccgcccagt tccgcccatt ctccgcccca 8760
tcgctgacta atttttttta tttatgcaga ggccgaggcc gcctcggcct ctgagctatt 8820
ccagaagtag tgaggaggct tttttggagg cctaggcttt tgcaaaggag gtagccaaca 8880
tgattgaaca agatggattg cacgcaggtt ctcccgccgc ttgggtggag aggctattcg 8940
gctatgactg ggcacaacag acaatcggct gctctgatgc cgccgtgttc cggctgtcag 9000
cgcaggggcg cccggttctt tttgtcaaga ccgacctgtc cggtgccctg aatgaactcc 9060
aggacgaggc agcgcggcta tcgtggctgg ccacgacggg cgttccttgc gcagctgtgc 9120
tcgacgttgt cactgaagcg ggaagggact ggctgctatt gggcgaagtg ccggggcagg 9180
atctcctgtc atctcacctt gctcctgccg agaaagtatc catcatggct gatgcaatgc 9240
ggcggctgca tacgcttgat ccggctacct gcccattcga ccaccaagcg aaacatcgca 9300
tcgagcgagc acgtactcgg atggaagccg gtcttgtcga tcaggatgat ctggacgaag 9360
agcatcaggg gctcgcgcca gccgaactgt tcgccaggct caaggcgcgg atgcccgacg 9420
gcgaggatct cgtcgtgacc cacggcgatg cctgcttgcc gaatatcatg gtggaaaatg 9480
gccgcttttc tggattcatc gactgtggcc ggctgggtgt ggcggaccgc tatcaggaca 9540
tagcgttggc tacccgtgat attgctgaag agcttggcgg cgaatgggct gaccgcttcc 9600
tcgtgcttta cggtatcgcc gctcccgatt cgcagcgcat cgccttctat cgccttcttg 9660
acgagttctt ctagtatgta agccctgtgc cttctagttg ccagccatct gttgtttgcc 9720
cctcccccgt gccttccttg accctggaag gtgccactcc cactgtcctt tcctaataaa 9780
atgaggaaat tgcatcgcat tgtctgagta ggtgtcattc tattctgggg ggtggggtgg 9840
ggcaggacag caagggggag gattgggaag acaatagcag gcatgctggg gatgcggtgg 9900
gctctatggt taattaacca gtcaagtcag ctacttggcg agatcgactt gtctgggttt 9960
cgactacgct cagaattgcg tcagtcaagt tcgatctggt ccttgctatt gcacccgttc 10020
tccgattacg agtttcattt aaatcatgtg agcaaaaggc cagcaaaagg ccaggaaccg 10080
taaaaaggcc gcgttgctgg cgtttttcca taggctccgc ccccctgacg agcatcacaa 10140
aaatcgacgc tcaagtcaga ggtggcgaaa cccgacagga ctataaagat accaggcgtt 10200

```
tccccctgga agctccctcg tgcgctctcc tgttccgacc ctgccgctta ccggatacct  10260
gtccgccttt ctcccttcgg gaagcgtggc gctttctcat agctcacgct gtaggtatct  10320
cagttcggtg taggtcgttc gctccaagct gggctgtgtg cacgaacccc ccgttcagcc  10380
cgaccgctgc gccttatccg gtaactatcg tcttgagtcc aacccggtaa gacacgactt  10440
atcgccactg gcagcagcca ctggtaacag gattagcaga gcgaggtatg taggcggtgc  10500
tacagagttc ttgaagtggt ggcctaacta cggctacact agaagaacag tatttggtat  10560
ctgcgctctg ctgaagccag ttaccttcgg aaaaagagtt ggtagctctt gatccggcaa  10620
acaaaccacc gctggtagcg gtggtttttt tgtttgcaag cagcagatta cgcgcagaaa  10680
aaaaggatct caagaagatc ctttgatctt ttctacgggg tctgacgctc agtggaacga  10740
aaactcacgt taagggattt tggtcatgag attatcaaaa aggatcttca cctagatcct  10800
tttaaattaa aaatgaagtt ttaaatcaat ctaaagtata tatgagtaaa cttggtctga  10860
cagttaccaa tgcttaatca gtgaggcacc tatctcagcg atctgtctat ttcgttcatc  10920
catagttgca tttaaatttc cgaactctcc aaggccctcg tcggaaaatc ttcaaacctt  10980
tcgtccgatc catcttgcag gctacctctc gaacgaacta tcgcaagtct cttggccggc  11040
cttgcgcctt ggctattgct tggcagcgcc tatcgccagg tattactcca atcccgaata  11100
tccgagatcg ggatcacccg agagaagttc aacctacatc ctcaatcccg atctatccga  11160
gatccgagga atatcgaaat cggggcgcgc ctggtgtacc gagaacgatc ctctcagtgc  11220
gagtctcgac gatccatatc gttgcttggc agtcagccag tcggaatcca gcttgggacc  11280
caggaagtcc aatcgtcaga tattgtactc aagcctggtc acggcagcgt accgatctgt  11340
ttaaacctag atattgatag tctgatcggt caacgtataa tcgagtccta gcttttgcaa  11400
acatctatca agagacagga tcagcaggag gctttcgcat gagtattcaa catttccgtg  11460
tcgcccttat tccctttttt gcggcatttt gccttcctgt ttttgctcac ccagaaacgc  11520
tggtgaaagt aaaagatgct gaagatcagt tgggtgcgcg agtgggttac atcgaactgg  11580
atctcaacag cggtaagatc cttgagagtt ttcgccccga agaacgtttt ccaatgatga  11640
gcacttttaa agttctgcta tgtggcgcgg tattatcccg tattgacgcc gggcaagagc  11700
aactcggtcg ccgcatacac tattctcaga atgacttggt tgagtattca ccagtcacag  11760
aaaagcatct tacggatggc atgacagtaa gagaattatg cagtgctgcc ataaccatga  11820
gtgataacac tgcggccaac ttacttctga caacgattgg aggaccgaag gagctaaccg  11880
ctttttttgca caacatgggg gatcatgtaa ctcgccttga tcgttgggaa ccggagctga  11940
atgaagccat accaaacgac gagcgtgaca ccacgatgcc tgtagcaatg gcaacaacct  12000
tgcgtaaact attaactggc gaactactta ctctagcttc ccggcaacag ttgatagact  12060
ggatggaggc ggataaagtt gcaggaccac ttctgcgctc ggcccttccg gctggctggt  12120
ttattgctga taaatctgga gccggtgagc gtgggtctcg cggtatcatt gcagcactgg  12180
ggccagatgg taagccctcc cgtatcgtag ttatctacac gacggggagt caggcaacta  12240
tggatgaacg aaatagacag atcgctgaga taggtgcctc actgattaag cattggtaac  12300
cgattctagg tgcattggcg cagaaaaaaa tgcctgatgc gacgctgcgc gtcttatact  12360
cccacatatg ccagattcag caacggatac ggcttcccca acttgcccac ttccatacgt  12420
gtcctcctta ccagaaattt atccttaaga tcgtttaaac tcgactctgg ctctatcgaa  12480
tctccgtcgt ttcgagctta cgcgaacagc cgtggcgctc atttgctcgt cgggcatcga  12540
```

```
atctcgtcag ctatcgtcag cttacctttt tggcagcgat cgcggctccc gacatcttgg  12600

accattagct ccacaggtat cttcttccct ctagtggtca taacagcagc ttcagctacc  12660

tctcaattca aaaaacccct caagacccgt ttagaggccc caaggggtta tgctatcaat  12720

cgttgcgtta cacacacaaa aaaccaacac acatccatct tcgatggata gcgattttat  12780

tatctaactg ctgatcgagt gtagccagat ctagtaatca attacggggt cattagttca  12840

tagcccatat atggagttcc gcgttacata acttacggta aatggcccgc ctggctgacc  12900

gcccaacgac ccccgcccat tgacgtcaat aatgacgtat gttcccatag taacgccaat  12960

agggactttc cattgacgtc aatgggtgga gtatttacgg taaactgccc acttggcagt  13020

acatcaagtg tatcatatgc caagtacgcc ccctattgac gtcaatgacg gtaaatggcc  13080

cgcctggcat tatgcccagt acatgacctt atgggacttt cctacttggc agtacatcta  13140

cgtattagtc atcgctatta ccatgctgat gcggttttgg cagtacatca atgggcgtgg  13200

atagcggttt gactcacggg gatttccaag tctccacccc attgacgtca atgggagttt  13260

gttttggcac caaaatcaac gggactttcc aaaatgtcgt aacaactccg ccccattgac  13320

gcaaatgggc ggtaggcgtg tacggtggga ggtctatata agcagagctg gtttagtgaa  13380

ccgtcagatc agatctttgt cgatcctacc atccactcga cacacccgcc agcggccgc   13439


<210> SEQ ID NO 47
<211> LENGTH: 13436
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

taatacgact cactataggg agaagtactg ccaccatggg caagaagcaa aatcgcaaga     60

cggggaattc caagacacaa tccgctagcc caccacctaa agagcgttct agctcccctg    120

ctactgagca gtcctggatg gaaaacgact tcgatgaact ccgggaagag ggatttaggc    180

gatccaacta ttcagaactc cgcgaagata tccagacaaa ggggaaggaa gtcgagaatt    240

tcgagaagaa cctcgaggag tgcatcaccc gtatcacaaa cactgagaaa tgtctcaaag    300

aactcatgga acttaagaca aaagccaggg agcttcgaga ggagtgtcgg agtctgagat    360

ccaggtgtga ccagctcgag gagcgcgtga gcgcgatgga agacgagatg aacgagatga    420

aaagagaggg caaattcagg gagaagcgca ttaagaggaa cgaacagagt ctgcaggaga    480

tttgggatta cgtcaagagg cctaacctgc ggttgatcgg cgtccccgag agcgacgtag    540

aaaacgggac taaactggag aatacacttc aagacatcat tcaagaaaat tttccaaacc    600

tggctcggca agctaatgtg caaatccaag agatccaacg cacaccccag cggtatagct    660

ctcggcgtgc cacccctagg catattatcg tgcgctttac taaggtggag atgaaagaga    720

agatgctgcg agccgctcgg gaaaagggaa gggtgacttt gaagggcaaa cctattcggc    780

tgacggttga ccttagcgcc gagacactcc aggcacgccg ggaatggggc cccatcttta    840

atatcctgaa ggagaagaac ttccagccac gaatctctta ccctgcaaag ttgagtttta    900

tctccgaggg tgagattaag tatttcatcg ataaacagat gctgcgagac ttcgtgacaa    960

ctcgcccagc tctcaaggaa ctgctcaaag aggctcttaa tatggagcgc aataatagat   1020

atcaaccctt gcagaaccac gcaaagatgg gaagcggagc tactaacttc agcctgctga   1080

agcaggctgg agacgtggag gagaaccctg gacctatgac cggctctaac tcacatatca   1140
```

-continued

```
ccatccttac acttaacatt aacggcctca actcagctat caagcgccat cggctggcca   1200
gctggatcaa atcacaggat ccaagcgttt gttgcatcca agagacccac ctgacctgta   1260
gagatactca ccgcctcaag atcaagggat ggcgaaagat ttatcaggcg aacggtaagc   1320
agaagaaagc cggagtcgca attctggtct cagacaagac ggatttcaag cccaccaaaa   1380
ttaagcgtga taaggaaggt cactatatta tggtgaaagg cagcatacag caggaagaac   1440
ttaccatatt gaacatctac gcgccaaaca ccggcgcacc tcgctttatc aaacaggtcc   1500
tgtccgatct gcagcgagat ctggattctc atacgttgat tatgggtgat ttcaatacac   1560
cattgagcac cctggatcgc agcaccaggc aaaaggtaaa taaagacacg caagagctca   1620
atagcgcact gcatcaggca gatctcattg atatttatcg cactcttcat cctaagagta   1680
ccgagtacac attcttcagc gccccacatc atacatactc aaagatcgat catatcgtcg   1740
gctcaaaggc tctgctgtca aagtgcaagc gcacagagat aattacaaat tacctgtcag   1800
atcatagcgc gatcaagctc gagctgagaa tcaagaacct gacccagagc cggagtacca   1860
cttggaagct taataacctg ctgctcaacg attattgggt ccacaatgag atgaaggcag   1920
agattaaaat gttcttcgaa acaaatgaga ataaggatac tacctatcaa aacctttggg   1980
atgcctttaa ggccgtctgc agaggcaagt tcatcgccct caacgcctat aaaagaaaac   2040
aagagagatc taagatcgat actctcacct ctcagctgaa ggagttggag aaacaggaac   2100
agacccactc caaggcgtca agacggcagg agatcacaaa gattcgcgcc gagttgaaag   2160
agatcgaaac ccaaaagact cttcagaaaa ttaacgagtc tcgtagttgg ttcttcgagc   2220
ggattaataa gatagacaga cctctggcac gactgattaa gaagaagcgc gaaaagaacc   2280
agattgatac catcaagaac gacaagggcg acatcactac tgacccgacc gagatccaga   2340
ccactattcg ggagtattat aagcatttgt atgctaacaa gcttgagaac ctggaagaga   2400
tggacacttt tctggatacc tatactctgc cacggcttaa tcaagaggaa gtcgagtccc   2460
tcaaccgccc aattacagga agcgagattg tggccataat taactccctg ccgacaaaga   2520
aatctcctgg tccggacggg tttacagctg agttttatca acggtatatg gaagagcttg   2580
taccgtttct gctcaagctc tttcagtcta tagaaaagga aggcatcttg cccaattcct   2640
tctacgaagc ttctataata cttattccca aaccaggacg cgataccaca aagaaggaaa   2700
acttccggcc cattagtctc atgaatatcg acgctaaaat attgaacaag attctcgcca   2760
acagaatcca acaacatatt aagaaattga tacatcacga ccaggtgggg tttatacctg   2820
gcatgcaggg ctggtttaac atccggaaga gtattaacgt cattcaacac attaatagag   2880
ctaaggataa gaatcatatg atcatctcta tagacgcgga aaaggcattc gataagattc   2940
agcagccatt tatgctcaag actctgaaca aactcggcat cgacggaaca tattttaaga   3000
ttattcgcgc aatttacgat aagccgactg ctaacattat ccttaacggc caaaagctcg   3060
aggcctttcc gctcaagact ggaacccgcc aaggctgtcc cctctccccg cttttgttta   3120
atattgtact cgaggtgctg gctagggcta ttcgtcaaga gaaagagatt aaagggatac   3180
agctcgggaa ggaagaggtc aagctttcct tgttcgccga tgatatgatt gtgtacctgg   3240
agaatcctat tgtgtctgct cagaaccttc ttaaacttat ttctaacttt agcaaggtca   3300
gcggctataa gattaacgtc cagaaatctc aggcctttct gtacacaaat aatcgacaga   3360
ccgaatccca gataatgggt gagcttccgt ttgtcatagc cagcaaaagg ataaagtatc   3420
tcggaatcca gctgacacga gacgttaaag atttgtttaa ggaaaattac aagcctctcc   3480
tgaaagagat taaggaagat actaataagt ggaagaatat cccctgttca tgggttggca   3540
```

```
gaatcaacat agtgaagatg gcaatacttc ctaaagtgat atatcgcttt aacgccatcc   3600
caattaaact gcctatgacc ttctttacgg agctcgagaa aacaaccctt aaatttatat   3660
ggaatcaaaa gagagcaaga atagcgaagt ccatcttgag ccagaagaat aaggccggtg   3720
ggattacttt gcctgatttt aagttgtatt ataaagccac agtaactaag acagcctggt   3780
attggtatca gaatagagac atcgaccagt ggaatcggac cgaaccatca gagataatgc   3840
cccacatcta taattacctt atattcgata agccagaaaa gaataaacag tggggcaaag   3900
acagcctctt caacaagtgg tgttgggaga attggctggc catatgccgg aaactcaagc   3960
tcgacccctt tcttacaccc tacactaaaa tcaacagtag gtggatcaag gacttgaatg   4020
tcaagccaaa gactataaag acactggaag agaatcttgg gatcacaata caagatatag   4080
gcgtcggcaa agattttatg tcaaagacgc ccaaggccat ggccactaag gataagattg   4140
ataagtggga ccttattaag ctcaaaagct tctgtactgc caaggagacc acgatcagag   4200
ttaataggca gcccactaca tgggaaaaga ttttcgccac ttattcatca gataaggggt   4260
tgataagcag aatatataac gagctgaagc agatctacaa gaagaaaacg aataatccca   4320
tcaagaagtg ggcaaaagat atgaacaggc attttagcaa agaggatatc tacgccgcga   4380
agaagcatat gaagaagtgt agttcaagct tggccattcg tgagatgcag attaagacga   4440
ccatgcgata ccaccttacc ccagtgagga tggcaattat caagaaatct ggcaataata   4500
gatgttggcg gggctgtggc gagattggca ccctgctcca ttgctggtgg gattgcaagc   4560
tggtgcagcc gctttggaaa tcagtctggc gctttctgag ggacctcgag cttgagattc   4620
ccttcgatcc cgcaattccc ttgctcggaa tctatcctaa cgaatacaag agctgttgtt   4680
acaaggatac gtgtacccgg atgttcatcg cggccttgtt tacgatagct aagacgtgga   4740
atcagcctaa gtgccccaca atgatcgatt ggatcaagaa aatgtggcat atttatacca   4800
tggagtatta cgcagcaatt aagaatgacg aatttatttc cttcgttggg acctggatga   4860
agctggagac tattattctg agcaagctgt ctcaggagca aaagacaaag catagaatct   4920
tctctctcat tggtggtaac gactacaaag acgatgacga caagtaaagc gcttctagaa   4980
gttgtctcct cctgcactga ctgactgata caatcgattt ctggatccgc aggcctaatc   5040
aacctctgga ttacaaaatt tgtgaaagat tgactggtat tcttaactat gttgctcctt   5100
ttacgctatg tggatacgct gctttaatgc ctttgtatca tgctattgct tcccgtatgg   5160
ctttcatttt ctcctccttg tataaatcct ggttgctgtc tctttatgag gagttgtggc   5220
ccgttgtcag gcaacgtggc gtggtgtgca ctgtgtttgc tgacgcaacc cccactggtt   5280
ggggcattgc caccacctgt cagctccttt ccgggacttt cgctttcccc ctccctattg   5340
ccacggcgga actcatcgcc gcctgccttg cccgctgctg gacaggggct cggctgttgg   5400
gcactgacaa ttccgtggtg ttgtcgggga agctgacgtc ctttccatgg ctgctcgcct   5460
gtgttgccac ctggattctg cgcgggacgt ccttctgcta cgtcccttcg gccctcaatc   5520
cagcggacct tccttcccgc gaacaaacga cccaacaccc gtgcgtttta ttctgtcttt   5580
ttattgccga tcccctcaga agaactcgtc aagaaggcga tagaaggcga tgcgctgcga   5640
atcgggagcg gcgataccgt aaagcacgag gaagcggtca gcccattcgc cgccaagctc   5700
ttcagcaata tcacgggtag ccaacgctat gtcctgatag cggtcggccg ctttacttgt   5760
acagctcgtc catgccgaga gtgatcccgg cggcggtcac gaactccagc aggaccatgt   5820
gatcgcgctt ctcgttgggg tctttgctca gggcggactg ggtgctcagg tagtggttgt   5880
```

cgggcagcag cacggggccg tcgccgatgg gggtgttctg ctggtagtgg tcggccaggt 5940
gagtccagga gatgtttcag cactgttgcc tttagtctcg aggcaactta gacaactgag 6000
tattgatctg agcacagcag ggtgtgagct gtttgaagat actggggttg gggtgaaga 6060
aactgcagag gactaactgg gctgagaccc agtggcaatg ttttagggcc taaggaatgc 6120
ctctgaaaat ctagatggac aactttgact ttgagaaaag agaggtggaa atgaggaaaa 6180
tgacttttct ttattagatt tcggtagaaa gaactttcat ctttccccta tttttgttat 6240
tcgttttaaa acatctatct ggaggcagga caagtatggt cattaaaaag atgcaggcag 6300
aaggcatata ttggctcagt caaagtgggg aactttggtg gccaaacata cattgctaag 6360
gctattccta tatcagctgg acacatataa aatgctgcta atgcttcatt acaaacttat 6420
atcctttaat tccagatggg ggcaaagtat gtccaggggt gaggaacaat tgaaacattt 6480
gggctggagt agattttgaa agtcagctct gtgtgtgtgt gtgtgtgtgt gtgtgtgaga 6540
gcgtgtgttt cttttaacgt tttcagccta cagcatacag ggttcatggt ggcaagaaga 6600
taacaagatt taaattatgg ccagtgacta gtgctgcaag aagaacaact acctgcattt 6660
aatgggaaag caaaatctca ggctttgagg gaagttaaca taggcttgat tctgggtgga 6720
agctgggtgt gtagttatct ggaggccagg ctggagctct cagctcacta tgggttcatc 6780
tttattgtct cctttcatct caacagctgc acgctgccgt cctcgatgtt gtggcggatc 6840
ttgaagttca ccttgatgcc gttcttctgc ttgtcggcca tgatatagac gttgtggctg 6900
ttgtagttgt actccagctt gtgccccagg atgttgccgt cctccttgaa gtcgatgccc 6960
ttcagctcga tgcggttcac cagggtgtcg ccctcgaact tcacctcggc gcgggtcttg 7020
tagttgccgt cgtccttgaa gaagatggtg cgctcctgga cgtagccttc gggcatggcg 7080
gacttgaaga agtcgtgctg cttcatgtgg tcggggtagc ggctgaagca ctgcacgccg 7140
taggtcaggg tggtcacgag ggtgggccag ggcacgggca gcttgccggt ggtgcagatg 7200
aacttcaggg tcagcttgcc gtaggtggca tcgccctcgc cctcgccgga cacgctgaac 7260
ttgtggccgt ttacgtcgcc gtccagctcg accaggatgg gcaccacccc ggtgaacagc 7320
tcctcgccct tgctcaccat ggtggcgaat tcgaagcttg agcacgagat ctgagtccgg 7380
taggcctagc ggatctgacg gttcactaaa ccagctctgc ttatatagac ctcccaccgt 7440
acacgcctac cgcccatttg cgtcaatggg gcggagttgt tacgacattt tggaaagtcc 7500
cgttgatttt ggtgccaaaa caaactccca ttgacgtcaa tggggtggag acttggaaat 7560
ccccgtgagt caaaccgcta tccacgccca ttgatgtact gccaaaaccg catcaccatg 7620
gtaatagcga tgactaatac gtagatgtac tgccaagtag gaaagtccca taaggtcatg 7680
tactgggcat aatgccaggc gggccattta ccgtcattga cgtcaatagg gggcgtactt 7740
ggcatatgat acacttgatg tactgccaag tgggcagttt accgtaaata ctccacccat 7800
tgacgtcaat ggaaagtccc tattggcgtt actatgggaa catacgtcat tattgacgtc 7860
aatgggcggg ggtcgttggg cggtcagcca ggcgggccat ttaccgtaag ttatgtaacg 7920
ggcctgctgc cggctctgcg gcctcttccg cgtcttcgcc ttcgccctca gacgagtcgg 7980
atctcccttt gggccgcctc cccgcctgtc tagcttgact gactgagata cagcgtacct 8040
tcagctcaca gacatgataa gatacattga tgagtttgga caaaccacaa ctagaatgca 8100
gtgaaaaaaa tgctttattt gtgaaatttg tgatgctatt gctttatttg taaccattat 8160
aagctgcaat aaacaagtta acaacaacaa ttgcattcat tttatgtttc aggttcaggg 8220
ggaggtgtgg gaggtttttt aaagcaagta aaacctctac aaatgtggta ttggcccatc 8280
tctatcggta tcgtagcata accccttggg gcctctaaac gggtcttgag ggtttttttg 8340
tgcccctcgg gccggattgc tatctaccgg cattggcgca gaaaaaaatg cctgatgcga 8400
cgctgcgcgt cttatactcc cacatatgcc agattcagca acggatacgg cttccccaac 8460
ttgcccactt ccatacgtgt cctccttacc agaaatttat ccttaaggtc gtcagctatc 8520
ctgcaggcga tctctcgatt tcgatcaaga cattccttta atggtctttt ctggacacca 8580
ctaggggtca gaagtagttc atcaaacttt cttccctccc taatctcatt ggttaccttg 8640
ggctatcgaa acttaattaa gcgatctgca tctcaattag tcagcaacca tagtcccgcc 8700
cctaactccg cccatcccgc ccctaactcc gcccagttcc gcccattctc cgccccatcg 8760
ctgactaatt ttttttattt atgcagaggc cgaggccgcc tcggcctctg agctattcca 8820
gaagtagtga ggaggctttt ttggaggcct aggcttttgc aaaggaggta gccaacatga 8880
ttgaacaaga tggattgcac gcaggttctc cggccgcttg ggtggagagg ctattcggct 8940
atgactgggc acaacagaca atcggctgct ctgatgccgc cgtgttccgg ctgtcagcgc 9000
aggggcgccc ggttcttttt gtcaagaccg acctgtccgg tgccctgaat gaactccagg 9060
acgaggcagc gcggctatcg tggctggcca cgacgggcgt tccttgcgca gctgtgctcg 9120
acgttgtcac tgaagcggga agggactggc tgctattggg cgaagtgccg gggcaggatc 9180
tcctgtcatc tcaccttgct cctgccgaga aagtatccat catggctgat gcaatgcggc 9240
ggctgcatac gcttgatccg gctacctgcc cattcgacca ccaagcgaaa catcgcatcg 9300
agcgagcacg tactcggatg gaagccggtc ttgtcgatca ggatgatctg gacgaagagc 9360
atcaggggct cgcgccagcc gaactgttcg ccaggctcaa ggcgcggatg cccgacggcg 9420
aggatctcgt cgtgacccac ggcgatgcct gcttgccgaa tatcatggtg gaaaatggcc 9480
gcttttctgg attcatcgac tgtggccggc tgggtgtggc ggaccgctat caggacatag 9540
cgttggctac ccgtgatatt gctgaagagc ttggcggcga atgggctgac cgcttcctcg 9600
tgctttacgg tatcgccgct cccgattcgc agcgcatcgc cttctatcgc cttcttgacg 9660
agttcttcta gtatgtaagc cctgtgcctt ctagttgcca gccatctgtt gtttgcccct 9720
cccccgtgcc ttccttgacc ctggaaggtg ccactcccac tgtcctttcc taataaaatg 9780
aggaaattgc atcgcattgt ctgagtaggt gtcattctat tctggggggt ggggtggggc 9840
aggacagcaa gggggaggat tgggaagaca atagcaggca tgctggggat gcggtgggct 9900
ctatggttaa ttaaccagtc aagtcagcta cttggcgaga tcgacttgtc tgggtttcga 9960
ctacgctcag aattgcgtca gtcaagttcg atctggtcct tgctattgca cccgttctcc 10020
gattacgagt ttcatttaaa tcatgtgagc aaaaggccag caaaaggcca ggaaccgtaa 10080
aaaggccgcg ttgctggcgt ttttccatag gctccgcccc cctgacgagc atcacaaaaa 10140
tcgacgctca agtcagaggt ggcgaaaccc gacaggacta taaagatacc aggcgtttcc 10200
ccctggaagc tccctcgtgc gctctcctgt tccgaccctg ccgcttaccg gatacctgtc 10260
cgcctttctc ccttcgggaa gcgtggcgct ttctcatagc tcacgctgta ggtatctcag 10320
ttcggtgtag gtcgttcgct ccaagctggg ctgtgtgcac gaaccccccg ttcagcccga 10380
ccgctgcgcc ttatccggta actatcgtct tgagtccaac ccggtaagac acgacttatc 10440
gccactggca gcagccactg gtaacaggat tagcagagcg aggtatgtag gcggtgctac 10500
agagttcttg aagtggtggc ctaactacgg ctacactaga agaacagtat ttggtatctg 10560
cgctctgctg aagccagtta ccttcggaaa aagagttggt agctcttgat ccggcaaaca 10620

```
aaccaccgct ggtagcggtg gtttttttgt ttgcaagcag cagattacgc gcagaaaaaa  10680
aggatctcaa gaagatcctt tgatcttttc tacggggtct gacgctcagt ggaacgaaaa  10740
ctcacgttaa gggattttgg tcatgagatt atcaaaaagg atcttcacct agatcctttt  10800
aaattaaaaa tgaagtttta aatcaatcta aagtatatat gagtaaactt ggtctgacag  10860
ttaccaatgc ttaatcagtg aggcacctat ctcagcgatc tgtctatttc gttcatccat  10920
agttgcattt aaatttccga actctccaag gccctcgtcg gaaaatcttc aaacctttcg  10980
tccgatccat cttgcaggct acctctcgaa cgaactatcg caagtctctt ggccggcctt  11040
gcgccttggc tattgcttgg cagcgcctat cgccaggtat tactccaatc ccgaatatcc  11100
gagatcggga tcacccgaga gaagttcaac ctacatcctc aatcccgatc tatccgagat  11160
ccgaggaata tcgaaatcgg ggcgcgcctg gtgtaccgag aacgatcctc tcagtgcgag  11220
tctcgacgat ccatatcgtt gcttggcagt cagccagtcg gaatccagct tgggacccag  11280
gaagtccaat cgtcagatat tgtactcaag cctggtcacg gcagcgtacc gatctgttta  11340
aacctagata ttgatagtct gatcggtcaa cgtataatcg agtcctagct tttgcaaaca  11400
tctatcaaga gacaggatca gcaggaggct ttcgcatgag tattcaacat ttccgtgtcg  11460
cccttattcc cttttttgcg gcattttgcc ttcctgtttt tgctcaccca gaaacgctgg  11520
tgaaagtaaa agatgctgaa gatcagttgg gtgcgcgagt gggttacatc gaactggatc  11580
tcaacagcgg taagatcctt gagagttttc gccccgaaga acgctttcca atgatgagca  11640
cttttaaagt tctgctatgt ggcgcggtat tatcccgtat tgacgccggg caagagcaac  11700
tcggtcgccg catacactat tctcagaatg acttggttga gtattcacca gtcacagaaa  11760
agcatcttac ggatggcatg acagtaagag aattatgcag tgctgccata accatgagtg  11820
ataacactgc ggccaactta cttctgacaa cgattggagg accgaaggag ctaaccgctt  11880
ttttgcacaa catgggggat catgtaactc gccttgatcg ttgggaaccg gagctgaatg  11940
aagccatacc aaacgacgag cgtgacacca cgatgcctgt agcaatggca acaaccttgc  12000
gtaaactatt aactggcgaa ctacttactc tagcttcccg gcaacagttg atagactgga  12060
tggaggcgga taaagttgca ggaccacttc tgcgctcggc ccttccggct ggctggttta  12120
ttgctgataa atctggagcc ggtgagcgtg ggtctcgcgg tatcattgca gcactggggc  12180
cagatggtaa gccctcccgt atcgtagtta tctacacgac ggggagtcag gcaactatgg  12240
atgaacgaaa tagacagatc gctgagatag gtgcctcact gattaagcat tggtaaccga  12300
ttctaggtgc attggcgcag aaaaaaatgc ctgatgcgac gctgcgcgtc ttatactccc  12360
acatatgcca gattcagcaa cggatacggc ttccccaact tgcccacttc catacgtgtc  12420
ctccttacca gaaatttatc cttaagatcg tttaaactcg actctggctc tatcgaatct  12480
ccgtcgtttc gagcttacgc gaacagccgt ggcgctcatt tgctcgtcgg gcatcgaatc  12540
tcgtcagcta tcgtcagctt acctttttgg cagcgatcgc ggctcccgac atcttggacc  12600
attagctcca caggtatctt cttccctcta gtggtcataa cagcagcttc agctacctct  12660
caattcaaaa aacccctcaa gacccgttta gaggccccaa ggggttatgc tatcaatcgt  12720
tgcgttacac acacaaaaaa ccaacacaca tccatcttcg atggatagcg attttattat  12780
ctaactgctg atcgagtgta gccagatcta gtaatcaatt acggggtcat tagttcatag  12840
cccatatatg gagttccgcg ttacataact tacggtaaat ggcccgcctg gctgaccgcc  12900
caacgacccc cgcccattga cgtcaataat gacgtatgtt cccatagtaa cgccaatagg  12960
gactttccat tgacgtcaat gggtggagta tttacggtaa actgcccact tggcagtaca  13020
```

```
tcaagtgtat catatgccaa gtacgccccc tattgacgtc aatgacggta aatggcccgc  13080

ctggcattat gcccagtaca tgaccttatg ggactttcct acttggcagt acatctacgt  13140

attagtcatc gctattacca tgctgatgcg gttttggcag tacatcaatg ggcgtggata  13200

gcggtttgac tcacggggat ttccaagtct ccaccccatt gacgtcaatg ggagtttgtt  13260

ttggcaccaa aatcaacggg actttccaaa atgtcgtaac aactccgccc cattgacgca  13320

aatgggcggt aggcgtgtac ggtgggaggt ctatataagc agagctggtt tagtgaaccg  13380

tcagatcaga tctttgtcga tcctaccatc cactcgacac acccgccagc ggccgc      13436
```

```
<210> SEQ ID NO 48
<211> LENGTH: 13433
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

taatacgact cactataggg agaagtactg ccaccatggg caagaagcaa aatcgcaaga     60

cggggaattc caagacacaa tccgctagcc caccacctaa agagcgttct agctcccctg    120

ctactgagca gtcctggatg gaaaacgact tcgatgaact ccgggaagag ggatttaggc    180

gatccaacta ttcagaactc cgcgaagata tccagacaaa ggggaaggaa gtcgagaatt    240

tcgagaagaa cctcgaggag tgcatcaccc gtatcacaaa cactgagaaa tgtctcaaag    300

aactcatgga acttaagaca aaagccaggg agcttcgaga ggagtgtcgg agtctgagat    360

ccaggtgtga ccagctcgag gagcgcgtga gcgcgatgga agacgagatg aacgagatga    420

aaagagaggg caaattcagg gagaagcgca ttaagaggaa cgaacagagt ctgcaggaga    480

tttgggatta cgtcaagagg cctaacctgc ggttgatcgg cgtccccgag agcgacgtag    540

aaaacgggac taaactggag aatacacttc aagacatcat tcaagaaaat tttccaaacc    600

tggctcggca agctaatgtg caaatccaag agatccaacg cacaccccag cggtatagct    660

ctcggcgtgc cacccctagg catattatcg tgcgctttac taaggtggag atgaaagaga    720

agatgctgcg agccgctcgg gaaaagggaa gggtgacttt gaagggcaaa cctattcggc    780

tgacggttga ccttagcgcc gagacactcc aggcacgccg ggaatggggc cccatcttta    840

atatcctgaa ggagaagaac ttccagccac gaatctctta ccctgcaaag ttgagtttta    900

tctccgaggg tgagattaag tatttcatcg ataaacagat gctgcgagac ttcgtgacaa    960

ctcgcccagc tctcaaggaa ctgctcaaag aggctcttaa tatggagcgc aataatagat   1020

atcaaccctt gcagaaccac gcaaagatgg gaagcggaga gggcagagga agtctgctaa   1080

catgcggtga cgtcgaggag aatcctggac ctatgaccgg ctctaactca catatcacca   1140

tccttacact taacattaac ggcctcaact cagctatcaa gcgccatcgg ctggccagct   1200

ggatcaaatc acaggatcca agcgtttgtt gcatccaaga gacccacctg acctgtagag   1260

atactcaccg cctcaagatc aagggatggc gaaagattta tcaggcgaac ggtaagcaga   1320

agaaagccgg agtcgcaatt ctggtctcag acaagacgga tttcaagccc accaaaatta   1380

agcgtgataa ggaaggtcac tatattatgg tgaaaggcag catacagcag gaagaactta   1440

ccatattgaa catctacgcg ccaaacaccg gcgcacctcg ctttatcaaa caggtcctgt   1500

ccgatctgca gcgagatctg gattctcata cgttgattat gggtgatttc aatacaccat   1560

tgagcaccct ggatcgcagc accaggcaaa aggtaaataa agacacgcaa gagctcaata   1620
```

```
gcgcactgca tcaggcagat ctcattgata tttatcgcac tcttcatcct aagagtaccg   1680
agtacacatt cttcagcgcc ccacatcata catactcaaa gatcgatcat atcgtcggct   1740
caaaggctct gctgtcaaag tgcaagcgca cagagataat tacaaattac ctgtcagatc   1800
atagcgcgat caagctcgag ctgagaatca agaacctgac ccagagccgg agtaccactt   1860
ggaagcttaa taacctgctg ctcaacgatt attgggtcca caatgagatg aaggcagaga   1920
ttaaaatgtt cttcgaaaca aatgagaata aggatactac ctatcaaaac ctttgggatg   1980
cctttaaggc cgtctgcaga ggcaagttca tcgccctcaa cgcctataaa agaaaacaag   2040
agagatctaa gatcgatact ctcacctctc agctgaagga gttggagaaa caggaacaga   2100
cccactccaa ggcgtcaaga cggcaggaga tcacaaagat tcgcgccgag ttgaaagaga   2160
tcgaaaccca aaagactctt cagaaaatta acgagtctcg tagttggttc ttcgagcgga   2220
ttaataagat agacagacct ctggcacgac tgattaagaa gaagcgcgaa aagaaccaga   2280
ttgataccat caagaacgac aagggcgaca tcactactga cccgaccgag atccagacca   2340
ctattcggga gtattataag catttgtatg ctaacaagct tgagaacctg gaagagatgg   2400
acacttttct ggatacctat actctgccac ggcttaatca agaggaagtc gagtccctca   2460
accgcccaat tacaggaagc gagattgtgg ccataattaa ctccctgccg acaaagaaat   2520
ctcctggtcc ggacgggttt acagctgagt tttatcaacg gtatatggaa gagcttgtac   2580
cgtttctgct caagctcttt cagtctatag aaaaggaagg catcttgccc aattccttct   2640
acgaagcttc tataatactt attcccaaac caggacgcga taccacaaag aaggaaaact   2700
tccggcccat tagtctcatg aatatcgacg ctaaaatatt gaacaagatt ctcgccaaca   2760
gaatccaaca acatattaag aaattgatac atcacgacca ggtggggttt atacctggca   2820
tgcagggctg gtttaacatc cggaagagta ttaacgtcat tcaacacatt aatagagcta   2880
aggataagaa tcatatgatc atctctatag acgcggaaaa ggcattcgat aagattcagc   2940
agccatttat gctcaagact ctgaacaaac tcggcatcga cggaacatat tttaagatta   3000
ttcgcgcaat ttacgataag ccgactgcta acattatcct taacggccaa aagctcgagg   3060
cctttccgct caagactgga acccgccaag gctgtcccct ctccccgctt ttgtttaata   3120
ttgtactcga ggtgctggct agggctattc gtcaagagaa agagattaaa gggatacagc   3180
tcgggaagga agaggtcaag ctttccttgt tcgccgatga tatgattgtg tacctggaga   3240
atcctattgt gtctgctcag aaccttctta aacttatttc taactttagc aaggtcagcg   3300
gctataagat taacgtccag aaatctcagg cctttctgta cacaaataat cgacagaccg   3360
aatcccagat aatgggtgag cttccgtttg tcatagccag caaaaggata aagtatctcg   3420
gaatccagct gacacgagac gttaaagatt tgtttaagga aaattacaag cctctcctga   3480
aagagattaa ggaagatact aataagtgga agaatatccc ctgttcatgg gttggcagaa   3540
tcaacatagt gaagatggca atacttccta aagtgatata tcgctttaac gccatcccaa   3600
ttaaactgcc tatgaccttc tttacggagc tcgagaaaac aacccttaaa tttatatgga   3660
atcaaaagag agcaagaata gcgaagtcca tcttgagcca gaagaataag gccggtggga   3720
ttactttgcc tgattttaag ttgtattata aagccacagt aactaagaca gcctggtatt   3780
ggtatcagaa tagagacatc gaccagtgga atcggaccga accatcagag ataatgcccc   3840
acatctataa ttaccttata ttcgataagc cagaaaagaa taaacagtgg ggcaaagaca   3900
gcctcttcaa caagtggtgt tgggagaatt ggctggccat atgccggaaa ctcaagctcg   3960
```

```
acccctttct tacaccctac actaaaatca acagtaggtg gatcaaggac ttgaatgtca   4020
agccaaagac tataaagaca ctggaagaga atcttgggat cacaatacaa gatataggcg   4080
tcggcaaaga ttttatgtca aagacgccca aggccatggc cactaaggat aagattgata   4140
agtgggacct tattaagctc aaaagcttct gtactgccaa ggagaccacg atcagagtta   4200
ataggcagcc cactacatgg gaaaagattt tcgccactta ttcatcagat aaggggttga   4260
taagcagaat atataacgag ctgaagcaga tctacaagaa gaaaacgaat aatcccatca   4320
agaagtgggc aaaagatatg aacaggcatt ttagcaaaga ggatatctac gccgcgaaga   4380
agcatatgaa gaagtgtagt tcaagcttgg ccattcgtga gatgcagatt aagacgacca   4440
tgcgatacca ccttacccca gtgaggatgg caattatcaa gaaatctggc aataatagat   4500
gttggcgggg ctgtggcgag attggcaccc tgctccattg ctggtgggat tgcaagctgg   4560
tgcagccgct ttggaaatca gtctggcgct ttctgaggga cctcgagctt gagattccct   4620
tcgatcccgc aattcccttg ctcggaatct atcctaacga atacaagagc tgttgttaca   4680
aggatacgtg tacccggatg ttcatcgcgg ccttgtttac gatagctaag acgtggaatc   4740
agcctaagtg ccccacaatg atcgattgga tcaagaaaat gtggcatatt tataccatgg   4800
agtattacgc agcaattaag aatgacgaat ttatttcctt cgttgggacc tggatgaagc   4860
tggagactat tattctgagc aagctgtctc aggagcaaaa gacaaagcat agaatcttct   4920
ctctcattgg tggtaacgac tacaaagacg atgacgacaa gtaaagcgct tctagaagtt   4980
gtctcctcct gcactgactg actgatacaa tcgatttctg gatccgcagg cctaatcaac   5040
ctctggatta caaaatttgt gaaagattga ctggtattct taactatgtt gctcctttta   5100
cgctatgtgg atacgctgct ttaatgcctt tgtatcatgc tattgcttcc cgtatggctt   5160
tcattttctc ctccttgtat aaatcctggt tgctgtctct ttatgaggag ttgtggcccg   5220
ttgtcaggca acgtggcgtg gtgtgcactg tgtttgctga cgcaaccccc actggttggg   5280
gcattgccac cacctgtcag ctcctttccg ggactttcgc tttccccctc cctattgcca   5340
cggcggaact catcgccgcc tgccttgccc gctgctggac aggggctcgg ctgttgggca   5400
ctgacaattc cgtggtgttg tcggggaagc tgacgtcctt tccatggctg ctcgcctgtg   5460
ttgccacctg gattctgcgc gggacgtcct tctgctacgt cccttcggcc ctcaatccag   5520
cggaccttcc ttcccgcgaa caaacgaccc aacacccgtg cgttttattc tgtcttttta   5580
ttgccgatcc cctcagaaga actcgtcaag aaggcgatag aaggcgatgc gctgcgaatc   5640
gggagcggcg ataccgtaaa gcacgaggaa gcggtcagcc cattcgccgc caagctcttc   5700
agcaatatca cgggtagcca acgctatgtc ctgatagcgg tcggccgctt tacttgtaca   5760
gctcgtccat gccgagagtg atcccggcgg cggtcacgaa ctccagcagg accatgtgat   5820
cgcgcttctc gttggggtct ttgctcaggg cggactgggt gctcaggtag tggttgtcgg   5880
gcagcagcac ggggccgtcg ccgatggggg tgttctgctg gtagtggtcg gccaggtgag   5940
tccaggagat gtttcagcac tgttgccttt agtctcgagg caacttagac aactgagtat   6000
tgatctgagc acagcagggt gtgagctgtt tgaagatact ggggttgggg gtgaagaaac   6060
tgcagaggac taactgggct gagacccagt ggcaatgttt tagggcctaa ggaatgcctc   6120
tgaaaatcta gatggacaac tttgactttg agaaaagaga ggtggaaatg aggaaaatga   6180
cttttcttta ttagatttcg gtagaaagaa ctttcatctt tcccctattt ttgttattcg   6240
ttttaaaaca tctatctgga ggcaggacaa gtatggtcat taaaaagatg caggcagaag   6300
gcatatattg gctcagtcaa agtggggaac tttggtggcc aaacatacat tgctaaggct   6360
```

attcctatat cagctggaca catataaaat gctgctaatg cttcattaca aacttatatc 6420
ctttaattcc agatgggggc aaagtatgtc caggggtgag gaacaattga aacatttggg 6480
ctggagtaga ttttgaaagt cagctctgtg tgtgtgtgtg tgtgtgtgtg tgtgagagcg 6540
tgtgtttctt ttaacgtttt cagcctacag catacagggt tcatggtggc aagaagataa 6600
caagatttaa attatggcca gtgactagtg ctgcaagaag aacaactacc tgcatttaat 6660
gggaaagcaa aatctcaggc tttgagggaa gttaacatag gcttgattct gggtggaagc 6720
tgggtgtgta gttatctgga ggccaggctg gagctctcag ctcactatgg gttcatcttt 6780
attgtctcct ttcatctcaa cagctgcacg ctgccgtcct cgatgttgtg gcggatcttg 6840
aagttcacct tgatgccgtt cttctgcttg tcggccatga tatagacgtt gtggctgttg 6900
tagttgtact ccagcttgtg ccccaggatg ttgccgtcct ccttgaagtc gatgcccttc 6960
agctcgatgc ggttcaccag ggtgtcgccc tcgaacttca cctcggcgcg ggtcttgtag 7020
ttgccgtcgt ccttgaagaa gatggtgcgc tcctggacgt agccttcggg catggcggac 7080
ttgaagaagt cgtgctgctt catgtggtcg gggtagcggc tgaagcactg cacgccgtag 7140
gtcagggtgg tcacgagggt gggccagggc acgggcagct tgccggtggt gcagatgaac 7200
ttcagggtca gcttgccgta ggtggcatcg ccctcgccct cgccggacac gctgaacttg 7260
tggccgttta cgtcgccgtc cagctcgacc aggatgggca ccaccccggt gaacagctcc 7320
tcgcccttgc tcaccatggt ggcgaattcg aagcttgagc acgagatctg agtccggtag 7380
gcctagcgga tctgacggtt cactaaacca gctctgctta tatagacctc ccaccgtaca 7440
cgcctaccgc ccatttgcgt caatggggcg gagttgttac gacattttgg aaagtcccgt 7500
tgattttggt gccaaaacaa actcccattg acgtcaatgg ggtggagact tggaaatccc 7560
cgtgagtcaa accgctatcc acgcccattg atgtactgcc aaaaccgcat caccatggta 7620
atagcgatga ctaatacgta gatgtactgc caagtaggaa agtcccataa ggtcatgtac 7680
tgggcataat gccaggcggg ccatttaccg tcattgacgt caataggggg cgtacttggc 7740
atatgataca cttgatgtac tgccaagtgg gcagtttacc gtaaatactc cacccattga 7800
cgtcaatgga aagtccctat tggcgttact atgggaacat acgtcattat tgacgtcaat 7860
gggcgggggt cgttgggcgg tcagccaggc gggccattta ccgtaagtta tgtaacgggc 7920
ctgctgccgg ctctgcggcc tcttccgcgt cttcgccttc gccctcagac gagtcggatc 7980
tccctttggg ccgcctcccc gcctgtctag cttgactgac tgagatacag cgtaccttca 8040
gctcacagac atgataagat acattgatga gtttggacaa accacaacta gaatgcagtg 8100
aaaaaaatgc tttatttgtg aaatttgtga tgctattgct ttatttgtaa ccattataag 8160
ctgcaataaa caagttaaca acaacaattg cattcatttt atgtttcagg ttcaggggga 8220
ggtgtgggag gtttttaaa gcaagtaaaa cctctacaaa tgtggtattg gcccatctct 8280
atcggtatcg tagcataacc ccttggggcc tctaaacggg tcttgagggg tttttgtgc 8340
ccctcgggcc ggattgctat ctaccggcat tggcgcagaa aaaaatgcct gatgcgacgc 8400
tgcgcgtctt atactcccac atatgccaga ttcagcaacg gatacggctt ccccaacttg 8460
cccacttcca tacgtgtcct ccttaccaga aatttatcct taaggtcgtc agctatcctg 8520
caggcgatct ctcgatttcg atcaagacat tcctttaatg gtcttttctg gacaccacta 8580
ggggtcagaa gtagttcatc aaactttctt ccctccctaa tctcattggt taccttgggc 8640
tatcgaaact taattaagcg atctgcatct caattagtca gcaaccatag tcccgcccct 8700

```
aactccgccc atcccgcccc taactccgcc cagttccgcc cattctccgc cccatcgctg   8760
actaattttt tttatttatg cagaggccga ggccgcctcg gcctctgagc tattccagaa   8820
gtagtgagga ggcttttttg gaggcctagg cttttgcaaa ggaggtagcc aacatgattg   8880
aacaagatgg attgcacgca ggttctcccg ccgcttgggt ggagaggcta ttcggctatg   8940
actgggcaca acagacaatc ggctgctctg atgccgccgt gttccggctg tcagcgcagg   9000
ggcgcccggt tctttttgtc aagaccgacc tgtccggtgc cctgaatgaa ctccaggacg   9060
aggcagcgcg gctatcgtgg ctggccacga cgggcgttcc ttgcgcagct gtgctcgacg   9120
ttgtcactga agcgggaagg gactggctgc tattgggcga agtgccgggg caggatctcc   9180
tgtcatctca ccttgctcct gccgagaaag tatccatcat ggctgatgca atgcggcggc   9240
tgcatacgct tgatccggct acctgcccat tcgaccacca agcgaaacat cgcatcgagc   9300
gagcacgtac tcggatggaa gccggtcttg tcgatcagga tgatctggac gaagagcatc   9360
aggggctcgc gccagccgaa ctgttcgcca ggctcaaggc gcggatgccc gacggcgagg   9420
atctcgtcgt gacccacggc gatgcctgct tgccgaatat catggtggaa aatggccgct   9480
tttctggatt catcgactgt ggccggctgg gtgtggcgga ccgctatcag gacatagcgt   9540
tggctacccg tgatattgct gaagagcttg gcggcgaatg ggctgaccgc ttcctcgtgc   9600
tttacggtat cgccgctccc gattcgcagc gcatcgcctt ctatcgcctt cttgacgagt   9660
tcttctagta tgtaagccct gtgccttcta gttgccagcc atctgttgtt tgcccctccc   9720
ccgtgccttc cttgaccctg gaaggtgcca ctcccactgt cctttcctaa taaaatgagg   9780
aaattgcatc gcattgtctg agtaggtgtc attctattct ggggggtggg gtggggcagg   9840
acagcaaggg ggaggattgg gaagacaata gcaggcatgc tggggatgcg gtgggctcta   9900
tggttaatta accagtcaag tcagctactt ggcgagatcg acttgtctgg gtttcgacta   9960
cgctcagaat tgcgtcagtc aagttcgatc tggtccttgc tattgcaccc gttctccgat  10020
tacgagtttc atttaaatca tgtgagcaaa aggccagcaa aaggccagga accgtaaaaa  10080
ggccgcgttg ctggcgtttt tccataggct ccgcccccct gacgagcatc acaaaaatcg  10140
acgctcaagt cagaggtggc gaaacccgac aggactataa agataccagg cgtttccccc  10200
tggaagctcc ctcgtgcgct ctcctgttcc gaccctgccg cttaccggat acctgtccgc  10260
ctttctccct tcgggaagcg tggcgctttc tcatagctca cgctgtaggt atctcagttc  10320
ggtgtaggtc gttcgctcca agctgggctg tgtgcacgaa ccccccgttc agcccgaccg  10380
ctgcgcctta tccggtaact atcgtcttga gtccaacccg gtaagacacg acttatcgcc  10440
actggcagca gccactggta acaggattag cagagcgagg tatgtaggcg gtgctacaga  10500
gttcttgaag tggtggccta actacggcta cactagaaga acagtatttg gtatctgcgc  10560
tctgctgaag ccagttacct tcggaaaaag agttggtagc tcttgatccg gcaaacaaac  10620
caccgctggt agcggtggtt tttttgtttg caagcagcag attacgcgca gaaaaaaagg  10680
atctcaagaa gatcctttga tcttttctac ggggtctgac gctcagtgga acgaaaactc  10740
acgttaaggg attttggtca tgagattatc aaaaaggatc ttcacctaga tccttttaaa  10800
ttaaaaatga agttttaaat caatctaaag tatatatgag taaacttggt ctgacagtta  10860
ccaatgctta atcagtgagg cacctatctc agcgatctgt ctatttcgtt catccatagt  10920
tgcatttaaa tttccgaact ctccaaggcc ctcgtcggaa aatcttcaaa cctttcgtcc  10980
gatccatctt gcaggctacc tctcgaacga actatcgcaa gtctcttggc cggccttgcg  11040
ccttggctat tgcttggcag cgcctatcgc caggtattac tccaatcccg aatatccgag  11100
```

```
atcgggatca cccgagagaa gttcaaccta catcctcaat cccgatctat ccgagatccg  11160
aggaatatcg aaatcggggc gcgcctggtg taccgagaac gatcctctca gtgcgagtct  11220
cgacgatcca tatcgttgct tggcagtcag ccagtcggaa tccagcttgg gacccaggaa  11280
gtccaatcgt cagatattgt actcaagcct ggtcacggca gcgtaccgat ctgtttaaac  11340
ctagatattg atagtctgat cggtcaacgt ataatcgagt cctagctttt gcaaacatct  11400
atcaagagac aggatcagca ggaggctttc gcatgagtat tcaacatttc cgtgtcgccc  11460
ttattccctt ttttgcggca ttttgccttc ctgtttttgc tcacccagaa acgctggtga  11520
aagtaaaaga tgctgaagat cagttgggtg cgcgagtggg ttacatcgaa ctggatctca  11580
acagcggtaa gatccttgag agttttcgcc ccgaagaacg ctttccaatg atgagcactt  11640
ttaaagttct gctatgtggc gcggtattat cccgtattga cgccgggcaa gagcaactcg  11700
gtcgccgcat acactattct cagaatgact tggttgagta ttcaccagtc acagaaaagc  11760
atcttacgga tggcatgaca gtaagagaat tatgcagtgc tgccataacc atgagtgata  11820
acactgcggc caacttactt ctgacaacga ttggaggacc gaaggagcta accgcttttt  11880
tgcacaacat gggggatcat gtaactcgcc ttgatcgttg ggaaccggag ctgaatgaag  11940
ccataccaaa cgacgagcgt gacaccacga tgcctgtagc aatggcaaca accttgcgta  12000
aactattaac tggcgaacta cttactctag cttcccggca acagttgata gactggatgg  12060
aggcggataa agttgcagga ccacttctgc gctcggccct tccggctggc tggtttattg  12120
ctgataaatc tggagccggt gagcgtgggt ctcgcggtat cattgcagca ctggggccag  12180
atggtaagcc ctcccgtatc gtagttatct acacgacggg gagtcaggca actatggatg  12240
aacgaaatag acagatcgct gagataggtg cctcactgat taagcattgg taaccgattc  12300
taggtgcatt ggcgcagaaa aaaatgcctg atgcgacgct gcgcgtctta tactcccaca  12360
tatgccagat tcagcaacgg atacggcttc cccaacttgc ccacttccat acgtgtcctc  12420
cttaccagaa atttatcctt aagatcgttt aaactcgact ctggctctat cgaatctccg  12480
tcgtttcgag cttacgcgaa cagccgtggc gctcatttgc tcgtcgggca tcgaatctcg  12540
tcagctatcg tcagcttacc tttttggcag cgatcgcggc tcccgacatc ttggaccatt  12600
agctccacag gtatcttctt ccctctagtg gtcataacag cagcttcagc tacctctcaa  12660
ttcaaaaaac ccctcaagac ccgtttagag gccccaaggg gttatgctat caatcgttgc  12720
gttacacaca caaaaaacca acacacatcc atcttcgatg gatagcgatt ttattatcta  12780
actgctgatc gagtgtagcc agatctagta atcaattacg gggtcattag ttcatagccc  12840
atatatggag ttccgcgtta cataacttac ggtaaatggc ccgcctggct gaccgcccaa  12900
cgacccccgc ccattgacgt caataatgac gtatgttccc atagtaacgc caatagggac  12960
tttccattga cgtcaatggg tggagtattt acggtaaact gcccacttgg cagtacatca  13020
agtgtatcat atgccaagta cgccccctat tgacgtcaat gacggtaaat ggcccgcctg  13080
gcattatgcc cagtacatga ccttatggga ctttcctact tggcagtaca tctacgtatt  13140
agtcatcgct attaccatgc tgatgcggtt ttggcagtac atcaatgggc gtggatagcg  13200
gtttgactca cggggatttc caagtctcca ccccattgac gtcaatggga gtttgttttg  13260
gcaccaaaat caacgggact ttccaaaatg tcgtaacaac tccgccccat tgacgcaaat  13320
gggcggtagg cgtgtacggt gggaggtcta tataagcaga gctggtttag tgaaccgtca  13380
gatcagatct ttgtcgatcc taccatccac tcgacacacc cgccagcggc cgc         13433
```

<210> SEQ ID NO 49
<211> LENGTH: 9241
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49
taatacgact cactataggg agaagtactg ccaccatggg caagaagcaa aatcgcaaga 60
cggggaattc caagacacaa tccgctagcc caccacctaa agagcgttct agctcccctg 120
ctactgagca gtcctggatg gaaaacgact tcgatgaact ccgggaagag ggatttaggc 180
gatccaacta ttcagaactc cgcgaagata tccagacaaa ggggaaggaa gtcgagaatt 240
tcgagaagaa cctcgaggag tgcatcaccc gtatcacaaa cactgagaaa tgtctcaaag 300
aactcatgga acttaagaca aaagccaggg agcttcgaga ggagtgtcgg agtctgagat 360
ccaggtgtga ccagctcgag gagcgcgtga gcgcgatgga agacgagatg aacgagatga 420
aaagagaggg caaattcagg gagaagcgca ttaagaggaa cgaacagagt ctgcaggaga 480
tttgggatta cgtcaagagg cctaacctgc ggttgatcgg cgtccccgag agcgacgtag 540
aaaacgggac taaactggag aatacacttc aagacatcat tcaagaaaat tttccaaacc 600
tggctcggca agctaatgtg caaatccaag agatccaacg cacaccccag cggtatagct 660
ctcggcgtgc caccccctagg catattatcg tgcgctttac taaggtggag atgaaagaga 720
agatgctgcg agccgctcgg gaaaagggaa gggtgacttt gaagggcaaa cctattcggc 780
tgacggttga ccttagcgcc gagacactcc aggcacgccg ggaatggggc cccatcttta 840
atatcctgaa ggagaagaac ttccagccac gaatctctta ccctgcaaag ttgagtttta 900
tctccgaggg tgagattaag tatttcatcg ataaacagat gctgcgagac ttcgtgacaa 960
ctcgcccagc tctcaaggaa ctgctcaaag aggctcttaa tatggagcgc aataatagat 1020
atcaaccctt gcagaaccac gcaaagatgt gagacagccg tcagaccatc aagactagga 1080
agaaactgca tcaactaatg agcaaaaatca ccagctaaca tcatagtata catgaccggc 1140
tctaactcac atatcaccat ccttacactt aacattaacg gcctcaactc agctatcaag 1200
cgccatcggc tggccagctg gatcaaatca caggatccaa gcgtttgttg catccaagag 1260
acccacctga cctgtagaga tactcaccgc ctcaagatca agggatggcg aaagatttat 1320
caggcgaacg gtaagcagaa gaaagccgga gtcgcaattc tggtctcaga caagacggat 1380
ttcaagccca ccaaaattaa gcgtgataag gaaggtcact atattatggt gaaaggcagc 1440
atacagcagg aagaacttac catattgaac atctacgcgc caaacaccgg cgcacctcgc 1500
tttatcaaac aggtcctgtc cgatctgcag cgagatctgg attctcatac gttgattatg 1560
ggtgatttca atacaccatt gagcaccctg gatcgcagca ccaggcaaaa ggtaaataaa 1620
gacacgcaag agctcaatag cgcactgcat caggcagatc tcattgatat ttatcgcact 1680
cttcatccta agagtaccga gtacacattc ttcagcgccc cacatcatac atactcaaag 1740
atcgatcata tcgtcggctc aaaggctctg ctgtcaaagt gcaagcgcac agagataatt 1800
acaaattacc tgtcagatca tagcgcgatc aagctcgagc tgagaatcaa gaacctgacc 1860
cagagccgga gtaccacttg gaagcttaat aacctgctgc tcaacgatta ttgggtccac 1920
aatgagatga aggcagagat taaaatgttc ttcgaaacaa atgagaataa ggatactacc 1980
tatcaaaacc tttgggatgc ctttaaggcc gtctgcagag gcaagttcat cgccctcaac 2040

```
gcctataaaa gaaaacaaga gagatctaag atcgatactc tcacctctca gctgaaggag   2100
ttggagaaac aggaacagac ccactccaag gcgtcaagac ggcaggagat cacaaagatt   2160
cgcgccgagt tgaaagagat cgaaacccaa aagactcttc agaaaattaa cgagtctcgt   2220
agttggttct tcgagcggat taataagata gacagacctc tggcacgact gattaagaag   2280
aagcgcgaaa agaaccagat tgataccatc aagaacgaca agggcgacat cactactgac   2340
ccgaccgaga tccagaccac tattcgggag tattataagc atttgtatgc taacaagctt   2400
gagaacctgg aagagatgga cacttttctg gatacctata ctctgccacg gcttaatcaa   2460
gaggaagtcg agtccctcaa ccgcccaatt acaggaagcg agattgtggc cataattaac   2520
tccctgccga caaagaaatc tcctggtccg gacgggttta cagctgagtt ttatcaacgg   2580
tatatggaag agcttgtacc gtttctgctc aagctctttc agtctataga aaaggaaggc   2640
atcttgccca attccttcta cgaagcttct ataatactta ttcccaaacc aggacgcgat   2700
accacaaaga aggaaaactt ccggcccatt agtctcatga atatcgacgc taaaatattg   2760
aacaagattc tcgccaacag aatccaacaa catattaaga aattgataca tcacgaccag   2820
gtggggttta tacctggcat gcagggctgg tttaacatcc ggaagagtat taacgtcatt   2880
caacacatta atagagctaa ggataagaat catatgatca tctctataga cgcggaaaag   2940
gcattcgata agattcagca gccatttatg ctcaagactc tgaacaaact cggcatcgac   3000
ggaacatatt ttaagattat tcgcgcaatt tacgataagc cgactgctaa cattatcctt   3060
aacggccaaa agctcgaggc ctttccgctc aagactggaa cccgccaagg ctgtcccctc   3120
tccccgcttt tgtttaatat tgtactcgag gtgctggcta gggctattcg tcaagagaaa   3180
gagattaaag ggatacagct cgggaaggaa gaggtcaagc tttccttgtt cgccgatgat   3240
atgattgtgt acctggagaa tcctattgtg tctgctcaga accttcttaa acttatttct   3300
aactttagca aggtcagcgg ctataagatt aacgtccaga aatctcaggc ctttctgtac   3360
acaaataatc gacagaccga atcccagata atgggtgagc ttccgtttgt catagccagc   3420
aaaaggataa agtatctcgg aatccagctg acacgagacg ttaaagattt gtttaaggaa   3480
aattacaagc ctctcctgaa agagattaag gaagatacta ataagtggaa gaatatcccc   3540
tgttcatggg ttggcagaat caacatagtg aagatggcaa tacttcctaa agtgatatat   3600
cgctttaacg ccatcccaat taaactgcct atgaccttct ttacggagct cgagaaaaca   3660
acccttaaat ttatatggaa tcaaaagaga gcaagaatag cgaagtccat cttgagccag   3720
aagaataagg ccggtgggat tactttgcct gattttaagt tgtattataa agccacagta   3780
actaagacag cctggtattg gtatcagaat agagacatcg accagtggaa tcggaccgaa   3840
ccatcagaga taatgcccca catctataat taccttatat tcgataagcc agaaaagaat   3900
aaacagtggg gcaaagacag cctcttcaac aagtggtgtt gggagaattg gctggccata   3960
tgccggaaac tcaagctcga cccctttctt acaccctaca ctaaaatcaa cagtaggtgg   4020
atcaaggact tgaatgtcaa gccaaagact ataaagacac tggaagagaa tcttgggatc   4080
acaatacaag atataggcgt cggcaaagat tttatgtcaa agacgcccaa ggccatggcc   4140
actaaggata agattgataa gtgggacctt attaagctca aaagcttctg tactgccaag   4200
gagaccacga tcagagttaa taggcagccc actacatggg aaaagatttt cgccacttat   4260
tcatcagata aggggttgat aagcagaata tataacgagc tgaagcagat ctacaagaag   4320
aaaacgaata atcccatcaa gaagtgggca aaagatatga acaggcattt tagcaaagag   4380
gatatctacg ccgcgaagaa gcatatgaag aagtgtagtt caagcttggc cattcgtgag   4440
```

atgcagatta agacgaccat gcgataccac cttaccccag tgaggatggc aattatcaag 4500
aaatctggca ataatagatg ttggcggggc tgtggcgaga ttggcaccct gctccattgc 4560
tggtgggatt gcaagctggt gcagccgctt tggaaatcag tctggcgctt tctgagggac 4620
ctcgagcttg agattccctt cgatcccgca attcccttgc tcggaatcta tcctaacgaa 4680
tacaagagct gttgttacaa ggatacgtgt acccggatgt tcatcgcggc cttgtttacg 4740
atagctaaga cgtggaatca gcctaagtgc cccacaatga tcgattggat caagaaaatg 4800
tggcatattt ataccatgga gtattacgca gcaattaaga atgacgaatt tatttccttc 4860
gttgggacct ggatgaagct ggagactatt attctgagca agctgtctca ggagcaaaag 4920
acaaagcata gaatcttctc tctcattggt ggtaacgctt ctaactttac tcagttcgtt 4980
ctcgtcgaca atggcggaac tggcgacgtg actgtcgccc caagcaactt cgctaacggg 5040
atcgctgaat ggatcagctc taactcgcgt tcacaggctt acaaagtaac ctgtagcgtt 5100
cgtcagagct ctgcgcagaa tcgcaaatac accatcaaag tcgaggtgcc taaaggcgcc 5160
tggcgttcgt acttaaatat ggaactaacc attccaattt tcgccacgaa ttccgactgc 5220
gagcttattg ttaaggcaat gcaaggtctc ctaaaagatg gaaacccgat tccctcagca 5280
atcgcagcaa actccggcat ctacgccatg gccagcaact tcacccagtt cgtgctggtg 5340
gacaacggcg gcaccggcga cgtgaccgtg gcccccagca acttcgccaa cggcatcgcc 5400
gagtggatca gcagcaacag cagaagccag gcctacaagg tgacctgcag cgtgagacag 5460
agcagcgccc agaacagaaa gtacaccatc aaggtggagg tgcccaaggg cgcctggaga 5520
agctacctga acatggagct gaccatcccc atcttcgcca ccaacagcga ctgcgagctg 5580
atcgtgaagg ccatgcaggg cctgctgaag gacggcaacc ccatccccag cgccatcgcc 5640
gccaacagcg gcatctacga ctacaaagac gatgacgaca agtaaagcaa cctacaaacg 5700
ggtggaggat caccccaccc gacacttcac aatcaagggg tacaatacac aagggtggag 5760
gaacacccca ccctccagac acattacaca gaaatccaat caaacagaag caccatcagg 5820
gcttctgcta ccaaatttat ctcaaaaaac tacaacaagg aatcaccatc agggattccc 5880
tgtgcaatat acgtcaaacg agggccacga cgggaggacg atcacgcctc ccgaatatcg 5940
gcatgtctgg ctttcgaatt cagtgcgtgg agcatcagcc cacgcagcca atcagagtcg 6000
aatacaagtc gactttcgcg aagagcatca gccttcgcgc cattcttaca caaaccacac 6060
tctcccctac aggaacagca tcagcgttcc tgcccagtac ccaactcaag aaaatttatg 6120
tccccatgca gcatcagcgc atgggcccca agaatacatc cccaacaaaa tcacatccga 6180
gcaccaacag ggctcggagt gttgtttctt gtccaactgg acaaaccctc catggaccat 6240
caggccatgg actctcacca acaagacaaa aactactctt ctcgaagcag catcagcgct 6300
tcgaaacact cgagcataca ttgtgcctat ttcttgggtg gacgatcacg ccacccatgc 6360
tctcacgaat ttcaaaacac ggacaaggac gagcaccacc agggctcgtc gttccacgtc 6420
caatacgatt acttaccttt cgggatcacg atcacggatc ccgcagctac atcacttcca 6480
ctcaggacat tcaagcatgc acgatcacgg catgctccac aagtctcaac cacagaaact 6540
accaaatggg ttcagcacca gcgaacccac tcctacctca aacctcttcc cacaaaactg 6600
gcaagcagga tcaccgcttg cccattccaa cataccaaat caaaaacaat tactggtaca 6660
gcatcagcgt accagcccac atctctcact actatcaaaa accaaaccgt tcagcaacag 6720
cgaacggtac acacggaaaa atcaactggt ttacaaatac gaaagacgat cacgctttcg 6780
tccagcgcaa actattacga aaaacatccg acgggaagag caacagcctt cccgcggcgg 6840
aaaacctcac aaaaacacga caaacggatg cacgaacacg gcatccgccg acaacccaca 6900
aacttacaac caggcaaacg gtgcaggatc accgcaccgt acatcaaaca cctcagatct 6960
catgcttcta gaagttgtct cctcctgcac tgactgactg atacaatcga tttctggatc 7020
cgcaggccta atcaacctct ggattacaaa atttgtgaaa gattgactgg tattcttaac 7080
tatgttgctc cttttacgct atgtggatac gctgctttaa tgcctttgta tcatgctatt 7140
gcttcccgta tggctttcat tttctcctcc ttgtataaat cctggttgct gtctctttat 7200
gaggagttgt ggcccgttgt caggcaacgt ggcgtggtgt gcactgtgtt tgctgacgca 7260
acccccactg gttggggcat tgccaccacc tgtcagctcc tttccgggac tttcgctttc 7320
cccctcccta ttgccacggc ggaactcatc gccgcctgcc ttgcccgctg ctggacaggg 7380
gctcggctgt tgggcactga caattccgtg gtgttgtcgg ggaagctgac gtcctttcca 7440
tggctgctcg cctgtgttgc cacctggatt ctgcgcggga cgtccttctg ctacgtccct 7500
tcggccctca atccagcgga ccttccttcc cgctgagaga cacaaaaaat tccaacacac 7560
tattgcaatg aaaataaatt tcctttatta gccagaagtc agatgctcaa ggggcttcat 7620
gatgtcccca taatttttgg cagagggaaa aagatctcag tggtatttgt gagccagggc 7680
attggccttc tgataggcag cctgcacctg aggagtgcgg ccgctttact tgtacagctc 7740
gtccatgccg agagtgatcc cggcggcggt cacgaactcc agcaggacca tgtgatcgcg 7800
cttctcgttg gggtctttgc tcagggcgga ctgggtgctc aggtagtggt tgtcgggcag 7860
cagcacgggg ccgtcgccga tgggggtgtt ctgctggtag tggtcggcga gctgcacgct 7920
gccgtcctcg atgttgtggc ggatcttgaa gttcaccttg atgccgttct tctgcttgtc 7980
ggccatgata tagacgttgt ggctgttgta gttgtactcc agcttgtgcc ccaggatgtt 8040
gccgtcctcc ttgaagtcga tgcccttcag ctcgatgcgg ttcaccaggg tgtcgccctc 8100
gaacttcacc tcggcgcggg tcttgtagtt gccgtcgtcc ttgaagaaga tggtgcgctc 8160
ctggacgtag ccttcgggca tggcggactt gaagaagtcg tgctgcttca tgtggtcggg 8220
gtagcggctg aagcactgca cgccgtaggt cagggtggtc acgagggtgg gccagggcac 8280
gggcagcttg ccggtggtgc agatgaactt cagggtcagc ttgccgtagg tggcatcgcc 8340
ctcgccctcg ccggacacgc tgaacttgtg gccgtttacg tcgccgtcca gctcgaccag 8400
gatgggcacc accccggtga acagctcctc gcccttgctc accatggtgg cgggatctga 8460
cggttcacta aaccagctct gcttatatag acctcccacc gtacacgcct accgcccatt 8520
tgcgtcaatg gggcggagtt gttacgacat tttggaaagt cccgttgatt ttggtgccaa 8580
aacaaactcc cattgacgtc aatggggtgg agacttggaa atccccgtga gtcaaaccgc 8640
tatccacgcc cattgatgta ctgccaaaac cgcatcacca tggtaatagc gatgactaat 8700
acgtagatgt actgccaagt aggaaagtcc cataaggtca tgtactgggc ataatgccag 8760
gcgggccatt taccgtcatt gacgtcaata gggggcgtac ttggcatatg atacacttga 8820
tgtactgcca agtgggcagt ttaccgtaaa tactccaccc attgacgtca atggaaagtc 8880
cctattggcg ttactatggg aacatacgtc attattgacg tcaatgggcg ggggtcgttg 8940
ggcggtcagc caggcgggcc atttaccgta agttatgtaa cgggcctgct gccggctctg 9000
cggcctcttc cgcgtcttcg ccttcgccct cagacgagtc ggatctccct ttgggccgcc 9060
tccccgcctg tctagcttga ctgactgaga tacagcgtac cttcagctca cagacatgat 9120
aagatacatt gatgagtttg gacaaaccac aactagaatg cagtgaaaaa aatgctttat 9180
ttgtgaaatt tgtgatgcta ttgctttatt tgtaaccatt ataagctgca ataaacaagt 9240
t 9241

<210> SEQ ID NO 50
<211> LENGTH: 7309
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50
taatacgact cactataggg agaagtactg ccaccatggg caagaagcaa aatcgcaaga 60
cggggaattc caagacacaa tccgctagcc caccacctaa agagcgttct agctcccctg 120
ctactgagca gtcctggatg gaaaacgact tcgatgaact ccgggaagag ggatttaggc 180
gatccaacta ttcagaactc cgcgaagata tccagacaaa ggggaaggaa gtcgagaatt 240
tcgagaagaa cctcgaggag tgcatcaccc gtatcacaaa cactgagaaa tgtctcaaag 300
aactcatgga acttaagaca aaagccaggg agcttcgaga ggagtgtcgg agtctgagat 360
ccaggtgtga ccagctcgag gagcgcgtga gcgcgatgga agacgagatg aacgagatga 420
aaagagaggg caaattcagg gagaagcgca ttaagaggaa cgaacagagt ctgcaggaga 480
tttgggatta cgtcaagagg cctaacctgc ggttgatcgg cgtccccgag agcgacgtag 540
aaaacgggac taaactggag aatacacttc aagacatcat tcaagaaaat tttccaaacc 600
tggctcggca agctaatgtg caaatccaag agatccaacg cacaccccag cggtatagct 660
ctcggcgtgc cacccctagg catattatcg tgcgctttac taaggtggag atgaaagaga 720
agatgctgcg agccgctcgg gaaaagggaa gggtgacttt gaagggcaaa cctattcggc 780
tgacggttga ccttagcgcc gagacactcc aggcacgccg ggaatggggc cccatcttta 840
atatcctgaa ggagaagaac ttccagccac gaatctctta ccctgcaaag ttgagtttta 900
tctccgaggg tgagattaag tatttcatcg ataaacagat gctgcgagac ttcgtgacaa 960
ctcgcccagc tctcaaggaa ctgctcaaag aggctcttaa tatggagcgc aataatagat 1020
atcaaccctt gcagaaccac gcaaagatgt gagacagccg tcagaccatc aagactagga 1080
agaaactgca tcaactaatg agcaaaatca ccagctaaca tcatagtata catggtcata 1140
ggaacttaca tttcgattat taccttaaac gtgaatgggt taaatgcccc aaccaagaga 1200
catcggctgg ctgaatggat tcagaaacag gacccctata tttgctgtct gcaggagacc 1260
cacttccgtc ctcgcgacac atacagactg aaagtgaggg gctggaaaaa gatcttccat 1320
gccaatggaa atcaaaagaa agctggagtg gctattctca tctcagataa aattgacttc 1380
aaaataaaga atgttactcg agataaggag ggacactaca taatgatcca ggggtccatc 1440
caagaagagg atataactat tattaatatt tatgcaccca acattggcgc ccctcagtac 1500
atcaggcagc tgcttacagc tatcaaggag gaaatcgaca gtaacacgat tatcgtgggg 1560
gactttaaca ccagccttac tccgatggat agatcatcca aaatgaaaat aaataaggaa 1620
acagaggctc ttaatgacac cattgaccag atagatctga ttgatatata taggacattc 1680
catccaaaaa ctgccgatta cactttcttc agcagtgcgc atggaacctt ctccaggata 1740
gatcacatct tgggtcacaa aagtagcctc agtaagttta agaaaattga aatcattagc 1800
agcatctttt ctgaccataa cgctatgcgc ctggagatga atcacaggga gaagaacgta 1860
aagaagacaa acacctggag gctgaacaat acgctgctaa ataaccaaga gatcactgag 1920

```
gaaatcaaac aggaaataaa aaaatacttg gagacaaatg acaatgaaaa cacgaccacc   1980
cagaacttgt gggatgcagc taaagcggtt ctgagaggga agtttatagc tattcaagcc   2040
taccttaaga aacaggaaaa atctcaagtg aacaatttga ccttacacct aaagaaactg   2100
gagaaggagg agcagaccaa acccaaagtg agcaggagga aagaaatcat caagatcaga   2160
gccgaaatca atgaaataga aactaagaag acaattgcca agatcaataa aactaaatcc   2220
tggttctttg agaagatcaa caaaattgat aagccattag ccagactcat caagaaaaag   2280
agggagagga ctcagatcaa taagatcaga aatgagaaag gggaagttac aaccgacacc   2340
gcggagattc agaacatcct gagagactac tacaagcaac tttatgccaa taaaatggac   2400
aacctggaag aaatggacaa attcctggaa aggtataacc ttccccggct gaaccaggag   2460
gagactgaaa atatcaaccg cccaatcaca agtaatgaga ttgagactgt gattaagaat   2520
cttccaacta acaaaagtcc cggccccgat ggcttcacag gtgaattcta tcagaccttt   2580
cgggaggagt tgacacccat ccttctcaag ctcttccaaa aaattgcaga ggagggcaca   2640
ctcccgaact cattctatga ggccaccatc accctgatcc caaagcccga caaggacact   2700
acaaagaaag aaaattaccg accaatttcc ctgatgaata tcgatgccaa gatcctcaac   2760
aaaatcttgg caaacagaat ccagcagcac attaagagga tcatacacca cgatcaggtg   2820
ggctttatcc cggggatgca aggattcttc aatatccgca aatcaatcaa tgtgatccac   2880
catattaaca agttgaagaa gaagaaccat atgatcatct ccatcgatgc agagaaagct   2940
tttgacaaaa ttcaacaccc atttatgatc aaaactctcc agaaggtggg catcgagggg   3000
acctacctca acataattaa ggccatctat gataagccca cagccaacat cattctcaat   3060
ggtgaaaagc tgaaggcatt tcctctgcgg tccggaacga gacagggatg tcctctctct   3120
cctcttctgt tcaacatcgt tctggaagtc ctagccaccg ctatccgcga ggaaaaggaa   3180
attaaaggca tacagattgg aaaggaagag gtaaaactgt ctctgtttgc ggatgatatg   3240
atactgtaca tagagaatcc taaaactgcc acccggaagc tgttggagct aattaatgag   3300
tatggtaagg tcgccggtta caagattaat gctcagaagt ctcttgcttt cctgtacact   3360
aatgatgaaa agtctgaacg ggaaattatg gagacactcc cctttaccat tgcaaccaaa   3420
cgtattaaat accttggcat taacctgcct aaggagacaa aagacctgta tgctgaaaac   3480
tataagacac tgatgaaaga gattaaagat gataccaacc ggtggcggga tatcccatgt   3540
tcttggattg gcagaatcaa cattgtgaag atgagcatcc tgcccaaggc catctacaga   3600
ttcaatgcca tccctatcaa attacctatg gcattttttta cggagctgga acagatcatc   3660
ttaaaatttg tgtggcgcca caagcggccc cgaatcgcca aagcggtctt gaggcagaag   3720
aatggcgctg gggaatccg actccctgac ttcagattgt actacaaagc taccgtcatc   3780
aagacaatct ggtactggca caagaacaga aacatcgatc agtggaacaa gatcgaaagc   3840
cctgagatta acccccgcac ctatggtcaa ctgatctatg acaaaggggg caaggatata   3900
caatggcgca aggacagcct cttcaataag tggtgctggg aaaactggac agccacctgc   3960
aagcgtatga agctggagta ctccctgaca ccatacacaa aaataaactc aaagtggatt   4020
cgagacctca atattcggct ggacactata aaactcctgg aggagaacat tgggcgtaca   4080
ctctttgaca ttaatcatag caagatcttt ttcgatcccc ctcctcgtgt aatggaaata   4140
aaaacaaaaa taaacaagtg ggatctgatg aaacttcaga gcttttgcac cgcaaaggag   4200
accataaaca agacgaagcg ccaaccctca gaatgggaga aaatatttgc gaatgagtct   4260
```

acggacaaag gcttaatctc caaaatatat aagcagctca ttcagctcaa tatcaaggaa 4320
acaaacaccc cgatccaaaa gtgggcagag gacctaaatc ggcatttctc caaggaagac 4380
atccagacgg ccacgaagca catgaagcga tgctcaactt ccctgattat tcgcgaaatg 4440
cagatcaaga ctactatgcg ctatcacctc actcctgttc ggatgggcat catccggaaa 4500
tctacaaaca acaagtgctg gagagggtgt ggcgaaaagg gaaccctctt gcattgttgg 4560
tgggagtgta agttgatcca gccactatgg cggaccatat ggaggttcct taaaaaactg 4620
aagattgagc tgccatatga cccagcaatc ccactgctgg gcatataccc ggagaaaacc 4680
gtgattcaga aagacacttg cacccgaatg ttcattgcag cattgtttac aatagccagg 4740
tcatggaagc agcctaagtg cccctcgaca gacgagtgga tcaagaagat gtggtacatt 4800
tatactatgg aatattacag cgccatcaaa cgcaacgaaa ttgggtcttt tctggagacg 4860
tggatggatc tagagactgt catccagagt gaggtaagtc agaaagagaa gaacaaatat 4920
cgtattttaa cgcatatttg tggaacctgg aagaatggta cagatgagcc ggtctgccga 4980
accgagattg agacccagat ggactacaaa gacgatgacg acaagtgaag cgcttctaga 5040
agttgtctcc tcctgcactg actgactgat acaatcgatt tctggatccg caggcctaat 5100
caacctctgg attacaaaat ttgtgaaaga ttgactggta ttcttaacta tgttgctcct 5160
tttacgctat gtggatacgc tgctttaatg cctttgtatc atgctattgc ttcccgtatg 5220
gctttcattt tctcctcctt gtataaatcc tggttgctgt ctctttatga ggagttgtgg 5280
cccgttgtca ggcaacgtgg cgtggtgtgc actgtgtttg ctgacgcaac ccccactggt 5340
tggggcattg ccaccacctg tcagctcctt tccgggactt tcgctttccc cctccctatt 5400
gccacggcgg aactcatcgc cgcctgcctt gcccgctgct ggacaggggc tcggctgttg 5460
ggcactgaca attccgtggt gttgtcgggg aagctgacgt cctttccatg gctgctcgcc 5520
tgtgttgcca cctggattct gcgcgggacg tccttctgct acgtcccttc ggccctcaat 5580
ccagcggacc ttccttcccg ctgagagaca caaaaaattc caacacacta ttgcaatgaa 5640
aataaatttc ctttattagc cagaagtcag atgctcaagg ggcttcatga tgtccccata 5700
atttttggca gagggaaaaa gatctcagtg gtatttgtga gccagggcat tggccttctg 5760
ataggcagcc tgcacctgag gagtgcggcc gctttacttg tacagctcgt ccatgccgag 5820
agtgatcccg gcggcggtca cgaactccag caggaccatg tgatcgcgct tctcgttggg 5880
gtctttgctc agggcggact gggtgctcag gtagtggttg tcgggcagca gcacggggcc 5940
gtcgccgatg ggggtgttct gctggtagtg gtcggcgagc tgcacgctgc cgtcctcgat 6000
gttgtggcgg atcttgaagt tcaccttgat gccgttcttc tgcttgtcgg ccatgatata 6060
gacgttgtgg ctgttgtagt tgtactccag cttgtgcccc aggatgttgc cgtcctcctt 6120
gaagtcgatg cccttcagct cgatgcggtt caccagggtg tcgccctcga acttcacctc 6180
ggcgcgggtc ttgtagttgc cgtcgtcctt gaagaagatg gtgcgctcct ggacgtagcc 6240
ttcgggcatg gcggacttga agaagtcgtg ctgcttcatg tggtcggggt agcggctgaa 6300
gcactgcacg ccgtaggtca gggtggtcac gagggtgggc cagggcacgg gcagcttgcc 6360
ggtggtgcag atgaacttca gggtcagctt gccgtaggtg gcatcgccct cgccctcgcc 6420
ggacacgctg aacttgtggc cgtttacgtc gccgtccagc tcgaccagga tgggcaccac 6480
cccggtgaac agctcctcgc ccttgctcac catggtggcg ggatctgacg gttcactaaa 6540
ccagctctgc ttatatagac ctcccaccgt acacgcctac cgcccatttg cgtcaatggg 6600
gcggagttgt tacgacattt tggaaagtcc cgttgatttt ggtgccaaaa caaactccca 6660
ttgacgtcaa tggggtggag acttggaaat ccccgtgagt caaaccgcta tccacgccca 6720
ttgatgtact gccaaaaccg catcaccatg gtaatagcga tgactaatac gtagatgtac 6780
tgccaagtag gaaagtccca taaggtcatg tactgggcat aatgccaggc gggccattta 6840
ccgtcattga cgtcaatagg gggcgtactt ggcatatgat acacttgatg tactgccaag 6900
tgggcagttt accgtaaata ctccacccat tgacgtcaat ggaaagtccc tattggcgtt 6960
actatgggaa catacgtcat tattgacgtc aatgggcggg ggtcgttggg cggtcagcca 7020
ggcgggccat ttaccgtaag ttatgtaacg ggcctgctgc cggctctgcg gcctcttccg 7080
cgtcttcgcc ttcgccctca gacgagtcgg atctcccttt gggccgcctc cccgcctgtc 7140
tagcttgact gactgagata cagcgtacct tcagctcaca gacatgataa gatacattga 7200
tgagtttgga caaaccacaa ctagaatgca gtgaaaaaaa tgctttattt gtgaaatttg 7260
tgatgctatt gctttatttg taaccattat aagctgcaat aaacaagtt 7309

<210> SEQ ID NO 51
<211> LENGTH: 19
<212> TYPE: DNA
<213> ORGANISM: Unknown
<220> FEATURE:
<223> OTHER INFORMATION: Description of Unknown: transposon end sequence

<400> SEQUENCE: 51
agatgtgtat aagagacag 19

<210> SEQ ID NO 52
<211> LENGTH: 19
<212> TYPE: DNA
<213> ORGANISM: Unknown
<220> FEATURE:
<223> OTHER INFORMATION: Description of Unknown: transposon end sequence

<400> SEQUENCE: 52
ctgtctctta tacacatct 19

<210> SEQ ID NO 53
<211> LENGTH: 338
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Met Gly Lys Lys Gln Asn Arg Lys Thr Gly Asn Ser Lys Thr Gln Ser
1 5 10 15

Ala Ser Pro Pro Pro Lys Glu Arg Ser Ser Ser Pro Ala Thr Glu Gln
20 25 30

Ser Trp Met Glu Asn Asp Phe Asp Glu Leu Arg Glu Glu Gly Phe Arg
35 40 45

Arg Ser Asn Tyr Ser Glu Leu Arg Glu Asp Ile Gln Thr Lys Gly Lys
50 55 60

Glu Val Glu Asn Phe Glu Lys Asn Leu Glu Glu Cys Ile Thr Arg Ile
65 70 75 80

Thr Asn Thr Glu Lys Cys Leu Lys Glu Leu Met Glu Leu Lys Thr Lys
85 90 95

Ala Arg Glu Leu Arg Glu Glu Cys Arg Ser Leu Arg Ser Arg Cys Asp

```
            100                 105                 110

Gln Leu Glu Glu Arg Val Ser Ala Met Glu Asp Glu Met Asn Glu Met
        115                 120                 125

Lys Arg Glu Gly Lys Phe Arg Glu Lys Arg Ile Lys Arg Asn Glu Gln
    130                 135                 140

Ser Leu Gln Glu Ile Trp Asp Tyr Val Lys Arg Pro Asn Leu Arg Leu
145                 150                 155                 160

Ile Gly Val Pro Glu Ser Asp Val Glu Asn Gly Thr Lys Leu Glu Asn
                165                 170                 175

Thr Leu Gln Asp Ile Ile Gln Glu Asn Phe Pro Asn Leu Ala Arg Gln
            180                 185                 190

Ala Asn Val Gln Ile Gln Glu Ile Gln Arg Thr Pro Gln Arg Tyr Ser
        195                 200                 205

Ser Arg Arg Ala Thr Pro Arg His Ile Ile Val Arg Phe Thr Lys Val
    210                 215                 220

Glu Met Lys Glu Lys Met Leu Arg Ala Ala Arg Glu Lys Gly Arg Val
225                 230                 235                 240

Thr Leu Lys Gly Lys Pro Ile Arg Leu Thr Val Asp Leu Ser Ala Glu
                245                 250                 255

Thr Leu Gln Ala Arg Arg Glu Trp Gly Pro Ile Phe Asn Ile Leu Lys
            260                 265                 270

Glu Lys Asn Phe Gln Pro Arg Ile Ser Tyr Pro Ala Lys Leu Ser Phe
        275                 280                 285

Ile Ser Glu Gly Glu Ile Lys Tyr Phe Ile Asp Lys Gln Met Leu Arg
    290                 295                 300

Asp Phe Val Thr Thr Arg Pro Ala Leu Lys Glu Leu Leu Lys Glu Ala
305                 310                 315                 320

Leu Asn Met Glu Arg Asn Asn Arg Tyr Gln Pro Leu Gln Asn His Ala
                325                 330                 335

Lys Met
```

<210> SEQ ID NO 54
<211> LENGTH: 1017
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
atgggcaaga agcaaaatcg caagacgggg aattccaaga cacaatccgc tagcccacca     60

cctaaagagc gttctagctc ccctgctact gagcagtcct ggatggaaaa cgacttcgat    120

gaactccggg aagagggatt taggcgatcc aactattcag aactccgcga agatatccag    180

acaaagggga aggaagtcga gaatttcgag aagaacctcg aggagtgcat cacccgtatc    240

acaaacactg agaaatgtct caaagaactc atggaactta agacaaaagc cagggagctt    300

cgagaggagt gtcggagtct gagatccagg tgtgaccagc tcgaggagcg cgtgagcgcg    360

atggaagacg agatgaacga gatgaaaaga gagggcaaat tcagggagaa gcgcattaag    420

aggaacgaac agagtctgca ggagatttgg gattacgtca agaggcctaa cctgcggttg    480

atcggcgtcc ccgagagcga cgtagaaaac gggactaaac tggagaatac acttcaagac    540

atcattcaag aaaatttcc aaacctggct cggcaagcta atgtgcaaat ccaagagatc    600

caacgcacac cccagcggta tagctctcgg cgtgccaccc ctaggcatat tatcgtgcgc    660
```

```
tttactaagg tggagatgaa agagaagatg ctgcgagccg ctcgggaaaa gggaagggtg    720

actttgaagg gcaaacctat tcggctgacg gttgacctta gcgccgagac actccaggca    780

cgccgggaat ggggccccat ctttaatatc ctgaaggaga agaacttcca gccacgaatc    840

tcttaccctg caaagttgag ttttatctcc gagggtgaga ttaagtattt catcgataaa    900

cagatgctgc gagacttcgt gacaactcgc ccagctctca aggaactgct caaagaggct    960

cttaatatgg agcgcaataa tagatatcaa cccttgcaga accacgcaaa gatgtga      1017
```

<210> SEQ ID NO 55
<211> LENGTH: 1275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Met Thr Gly Ser Asn Ser His Ile Thr Ile Leu Thr Leu Asn Ile Asn
1               5                   10                  15

Gly Leu Asn Ser Ala Ile Lys Arg His Arg Leu Ala Ser Trp Ile Lys
            20                  25                  30

Ser Gln Asp Pro Ser Val Cys Cys Ile Gln Glu Thr His Leu Thr Cys
        35                  40                  45

Arg Asp Thr His Arg Leu Lys Ile Lys Gly Trp Arg Lys Ile Tyr Gln
    50                  55                  60

Ala Asn Gly Lys Gln Lys Lys Ala Gly Val Ala Ile Leu Val Ser Asp
65                  70                  75                  80

Lys Thr Asp Phe Lys Pro Thr Lys Ile Lys Arg Asp Lys Glu Gly His
                85                  90                  95

Tyr Ile Met Val Lys Gly Ser Ile Gln Gln Glu Glu Leu Thr Ile Leu
            100                 105                 110

Asn Ile Tyr Ala Pro Asn Thr Gly Ala Pro Arg Phe Ile Lys Gln Val
        115                 120                 125

Leu Ser Asp Leu Gln Arg Asp Leu Asp Ser His Thr Leu Ile Met Gly
    130                 135                 140

Asp Phe Asn Thr Pro Leu Ser Thr Leu Asp Arg Ser Thr Arg Gln Lys
145                 150                 155                 160

Val Asn Lys Asp Thr Gln Glu Leu Asn Ser Ala Leu His Gln Ala Asp
                165                 170                 175

Leu Ile Asp Ile Tyr Arg Thr Leu His Pro Lys Ser Thr Glu Tyr Thr
            180                 185                 190

Phe Phe Ser Ala Pro His His Thr Tyr Ser Lys Ile Asp His Ile Val
        195                 200                 205

Gly Ser Lys Ala Leu Leu Ser Lys Cys Lys Arg Thr Glu Ile Ile Thr
    210                 215                 220

Asn Tyr Leu Ser Asp His Ser Ala Ile Lys Leu Glu Leu Arg Ile Lys
225                 230                 235                 240

Asn Leu Thr Gln Ser Arg Ser Thr Thr Trp Lys Leu Asn Asn Leu Leu
                245                 250                 255

Leu Asn Asp Tyr Trp Val His Asn Glu Met Lys Ala Glu Ile Lys Met
            260                 265                 270

Phe Phe Glu Thr Asn Glu Asn Lys Asp Thr Thr Tyr Gln Asn Leu Trp
        275                 280                 285

Asp Ala Phe Lys Ala Val Cys Arg Gly Lys Phe Ile Ala Leu Asn Ala
    290                 295                 300
```

```
Tyr Lys Arg Lys Gln Glu Arg Ser Lys Ile Asp Thr Leu Thr Ser Gln
305                 310                 315                 320

Leu Lys Glu Leu Glu Lys Gln Glu Gln Thr His Ser Lys Ala Ser Arg
                325                 330                 335

Arg Gln Glu Ile Thr Lys Ile Arg Ala Glu Leu Lys Glu Ile Glu Thr
            340                 345                 350

Gln Lys Thr Leu Gln Lys Ile Asn Glu Ser Arg Ser Trp Phe Phe Glu
        355                 360                 365

Arg Ile Asn Lys Ile Asp Arg Pro Leu Ala Arg Leu Ile Lys Lys Lys
    370                 375                 380

Arg Glu Lys Asn Gln Ile Asp Thr Ile Lys Asn Asp Lys Gly Asp Ile
385                 390                 395                 400

Thr Thr Asp Pro Thr Glu Ile Gln Thr Thr Ile Arg Glu Tyr Tyr Lys
                405                 410                 415

His Leu Tyr Ala Asn Lys Leu Glu Asn Leu Glu Glu Met Asp Thr Phe
            420                 425                 430

Leu Asp Thr Tyr Thr Leu Pro Arg Leu Asn Gln Glu Glu Val Glu Ser
        435                 440                 445

Leu Asn Arg Pro Ile Thr Gly Ser Glu Ile Val Ala Ile Ile Asn Ser
    450                 455                 460

Leu Pro Thr Lys Lys Ser Pro Gly Pro Asp Gly Phe Thr Ala Glu Phe
465                 470                 475                 480

Tyr Gln Arg Tyr Met Glu Glu Leu Val Pro Phe Leu Leu Lys Leu Phe
                485                 490                 495

Gln Ser Ile Glu Lys Glu Gly Ile Leu Pro Asn Ser Phe Tyr Glu Ala
            500                 505                 510

Ser Ile Ile Leu Ile Pro Lys Pro Gly Arg Asp Thr Thr Lys Lys Glu
        515                 520                 525

Asn Phe Arg Pro Ile Ser Leu Met Asn Ile Asp Ala Lys Ile Leu Asn
    530                 535                 540

Lys Ile Leu Ala Asn Arg Ile Gln Gln His Ile Lys Lys Leu Ile His
545                 550                 555                 560

His Asp Gln Val Gly Phe Ile Pro Gly Met Gln Gly Trp Phe Asn Ile
                565                 570                 575

Arg Lys Ser Ile Asn Val Ile Gln His Ile Asn Arg Ala Lys Asp Lys
            580                 585                 590

Asn His Met Ile Ile Ser Ile Asp Ala Glu Lys Ala Phe Asp Lys Ile
        595                 600                 605

Gln Gln Pro Phe Met Leu Lys Thr Leu Asn Lys Leu Gly Ile Asp Gly
    610                 615                 620

Thr Tyr Phe Lys Ile Ile Arg Ala Ile Tyr Asp Lys Pro Thr Ala Asn
625                 630                 635                 640

Ile Ile Leu Asn Gly Gln Lys Leu Glu Ala Phe Pro Leu Lys Thr Gly
                645                 650                 655

Thr Arg Gln Gly Cys Pro Leu Ser Pro Leu Leu Phe Asn Ile Val Leu
            660                 665                 670

Glu Val Leu Ala Arg Ala Ile Arg Gln Glu Lys Glu Ile Lys Gly Ile
        675                 680                 685

Gln Leu Gly Lys Glu Glu Val Lys Leu Ser Leu Phe Ala Asp Asp Met
    690                 695                 700

Ile Val Tyr Leu Glu Asn Pro Ile Val Ser Ala Gln Asn Leu Leu Lys
705                 710                 715                 720
```

```
Leu Ile Ser Asn Phe Ser Lys Val Ser Gly Tyr Lys Ile Asn Val Gln
                725                 730                 735

Lys Ser Gln Ala Phe Leu Tyr Thr Asn Asn Arg Gln Thr Glu Ser Gln
            740                 745                 750

Ile Met Gly Glu Leu Pro Phe Val Ile Ala Ser Lys Arg Ile Lys Tyr
        755                 760                 765

Leu Gly Ile Gln Leu Thr Arg Asp Val Lys Asp Leu Phe Lys Glu Asn
    770                 775                 780

Tyr Lys Pro Leu Leu Lys Glu Ile Lys Glu Asp Thr Asn Lys Trp Lys
785                 790                 795                 800

Asn Ile Pro Cys Ser Trp Val Gly Arg Ile Asn Ile Val Lys Met Ala
                805                 810                 815

Ile Leu Pro Lys Val Ile Tyr Arg Phe Asn Ala Ile Pro Ile Lys Leu
            820                 825                 830

Pro Met Thr Phe Phe Thr Glu Leu Glu Lys Thr Thr Leu Lys Phe Ile
        835                 840                 845

Trp Asn Gln Lys Arg Ala Arg Ile Ala Lys Ser Ile Leu Ser Gln Lys
    850                 855                 860

Asn Lys Ala Gly Gly Ile Thr Leu Pro Asp Phe Lys Leu Tyr Tyr Lys
865                 870                 875                 880

Ala Thr Val Thr Lys Thr Ala Trp Tyr Trp Tyr Gln Asn Arg Asp Ile
                885                 890                 895

Asp Gln Trp Asn Arg Thr Glu Pro Ser Glu Ile Met Pro His Ile Tyr
            900                 905                 910

Asn Tyr Leu Ile Phe Asp Lys Pro Glu Lys Asn Lys Gln Trp Gly Lys
        915                 920                 925

Asp Ser Leu Phe Asn Lys Trp Cys Trp Glu Asn Trp Leu Ala Ile Cys
    930                 935                 940

Arg Lys Leu Lys Leu Asp Pro Phe Leu Thr Pro Tyr Thr Lys Ile Asn
945                 950                 955                 960

Ser Arg Trp Ile Lys Asp Leu Asn Val Lys Pro Lys Thr Ile Lys Thr
                965                 970                 975

Leu Glu Glu Asn Leu Gly Ile Thr Ile Gln Asp Ile Gly Val Gly Lys
            980                 985                 990

Asp Phe Met Ser Lys Thr Pro Lys  Ala Met Ala Thr Lys  Asp Lys Ile
        995                 1000                 1005

Asp Lys  Trp Asp Leu Ile Lys  Leu Lys Ser Phe Cys  Thr Ala Lys
    1010                 1015                 1020

Glu Thr  Thr Ile Arg Val Asn  Arg Gln Pro Thr Thr  Trp Glu Lys
    1025                 1030                 1035

Ile Phe  Ala Thr Tyr Ser Ser  Asp Lys Gly Leu Ile  Ser Arg Ile
    1040                 1045                 1050

Tyr Asn  Glu Leu Lys Gln Ile  Tyr Lys Lys Lys Thr  Asn Asn Pro
    1055                 1060                 1065

Ile Lys  Lys Trp Ala Lys Asp  Met Asn Arg His Phe  Ser Lys Glu
    1070                 1075                 1080

Asp Ile  Tyr Ala Ala Lys Lys  His Met Lys Lys Cys  Ser Ser Ser
    1085                 1090                 1095

Leu Ala  Ile Arg Glu Met Gln  Ile Lys Thr Thr Met  Arg Tyr His
    1100                 1105                 1110

Leu Thr  Pro Val Arg Met Ala  Ile Ile Lys Lys Ser  Gly Asn Asn
    1115                 1120                 1125

Arg Cys  Trp Arg Gly Cys Gly  Glu Ile Gly Thr Leu  Leu His Cys
```

```
    1130                1135                1140

Trp Trp  Asp Cys Lys Leu Val  Gln Pro Leu Trp Lys  Ser Val Trp
    1145                1150                1155

Arg Phe  Leu Arg Asp Leu Glu  Leu Glu Ile Pro Phe  Asp Pro Ala
    1160                1165                1170

Ile Pro  Leu Leu Gly Ile Tyr  Pro Asn Glu Tyr Lys  Ser Cys Cys
    1175                1180                1185

Tyr Lys  Asp Thr Cys Thr Arg  Met Phe Ile Ala Ala  Leu Phe Thr
    1190                1195                1200

Ile Ala  Lys Thr Trp Asn Gln  Pro Lys Cys Pro Thr  Met Ile Asp
    1205                1210                1215

Trp Ile  Lys Lys Met Trp His  Ile Tyr Thr Met Glu  Tyr Tyr Ala
    1220                1225                1230

Ala Ile  Lys Asn Asp Glu Phe  Ile Ser Phe Val Gly  Thr Trp Met
    1235                1240                1245

Lys Leu  Glu Thr Ile Ile Leu  Ser Lys Leu Ser Gln  Glu Gln Lys
    1250                1255                1260

Thr Lys  His Arg Ile Phe Ser  Leu Ile Gly Gly Asn
    1265                1270                1275
```

<210> SEQ ID NO 56
<211> LENGTH: 3828
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
atgaccggct ctaactcaca tatcaccatc cttacactta acattaacgg cctcaactca     60

gctatcaagc gccatcggct ggccagctgg atcaaatcac aggatccaag cgtttgttgc    120

atccaagaga cccacctgac ctgtagagat actcaccgcc tcaagatcaa gggatggcga    180

aagatttatc aggcgaacgg taagcagaag aaagccggag tcgcaattct ggtctcagac    240

aagacggatt tcaagcccac caaaattaag cgtgataagg aaggtcacta tattatggtg    300

aaaggcagca tacagcagga agaacttacc atattgaaca tctacgcgcc aaacaccggc    360

gcacctcgct ttatcaaaca ggtcctgtcc gatctgcagc gagatctgga ttctcatacg    420

ttgattatgg gtgatttcaa tacaccattg agcaccctgg atcgcagcac caggcaaaag    480

gtaaataaag acacgcaaga gctcaatagc gcactgcatc aggcagatct cattgatatt    540

tatcgcactc ttcatcctaa gagtaccgag tacacattct tcagcgcccc acatcataca    600

tactcaaaga tcgatcatat cgtcggctca aaggctctgc tgtcaaagtg caagcgcaca    660

gagataatta caaattacct gtcagatcat agcgcgatca agctcgagct gagaatcaag    720

aacctgaccc agagccggag taccacttgg aagcttaata acctgctgct caacgattat    780

tgggtccaca atgagatgaa ggcagagatt aaaatgttct tcgaaacaaa tgagaataag    840

gatactacct atcaaaacct ttgggatgcc tttaaggccg tctgcagagg caagttcatc    900

gccctcaacg cctataaaag aaaacaagag agatctaaga tcgatactct cacctctcag    960

ctgaaggagt tggagaaaca ggaacagacc cactccaagg cgtcaagacg gcaggagatc   1020

acaaagattc gcgccgagtt gaaagagatc gaaacccaaa agactcttca gaaaattaac   1080

gagtctcgta gttggttctt cgagcggatt aataagatag acagacctct ggcacgactg   1140

attaagaaga agcgcgaaaa gaaccagatt gataccatca agaacgacaa gggcgacatc   1200
```

actactgacc cgaccgagat ccagaccact attcgggagt attataagca tttgtatgct 1260
aacaagcttg agaacctgga agagatggac acttttctgg atacctatac tctgccacgg 1320
cttaatcaag aggaagtcga gtccctcaac cgcccaatta caggaagcga gattgtggcc 1380
ataattaact ccctgccgac aaagaaatct cctggtccgg acgggtttac agctgagttt 1440
tatcaacggt atatggaaga gcttgtaccg tttctgctca agctctttca gtctatagaa 1500
aaggaaggca tcttgcccaa ttccttctac gaagcttcta taatacttat tcccaaacca 1560
ggacgcgata ccacaaagaa ggaaaacttc cggcccatta gtctcatgaa tatcgacgct 1620
aaaatattga acaagattct cgccaacaga atccaacaac atattaagaa attgatacat 1680
cacgaccagg tggggtttat acctggcatg cagggctggt ttaacatccg gaagagtatt 1740
aacgtcattc aacacattaa tagagctaag gataagaatc atatgatcat ctctatagac 1800
gcggaaaagg cattcgataa gattcagcag ccatttatgc tcaagactct gaacaaactc 1860
ggcatcgacg gaacatattt taagattatt cgcgcaattt acgataagcc gactgctaac 1920
attatcctta acggccaaaa gctcgaggcc tttccgctca agactggaac ccgccaaggc 1980
tgtcccctct ccccgctttt gtttaatatt gtactcgagg tgctggctag ggctattcgt 2040
caagagaaag agattaaagg gatacagctc gggaaggaag aggtcaagct ttccttgttc 2100
gccgatgata tgattgtgta cctggagaat cctattgtgt ctgctcagaa ccttcttaaa 2160
cttatttcta actttagcaa ggtcagcggc tataagatta acgtccagaa atctcaggcc 2220
tttctgtaca caaataatcg acagaccgaa tcccagataa tgggtgagct tccgtttgtc 2280
atagccagca aaaggataaa gtatctcgga atccagctga cacgagacgt taaagatttg 2340
tttaaggaaa attacaagcc tctcctgaaa gagattaagg aagatactaa taagtggaag 2400
aatatcccct gttcatgggt tggcagaatc aacatagtga agatggcaat acttcctaaa 2460
gtgatatatc gctttaacgc catcccaatt aaactgccta tgaccttctt tacggagctc 2520
gagaaaacaa cccttaaatt tatatggaat caaaagagag caagaatagc gaagtccatc 2580
ttgagccaga agaataaggc cggtgggatt actttgcctg attttaagtt gtattataaa 2640
gccacagtaa ctaagacagc ctggtattgg tatcagaata gagacatcga ccagtggaat 2700
cggaccgaac catcagagat aatgccccac atctataatt accttatatt cgataagcca 2760
gaaaagaata aacagtgggg caaagacagc ctcttcaaca agtggtgttg ggagaattgg 2820
ctggccatat gccggaaact caagctcgac ccctttctta caccctacac taaaatcaac 2880
agtaggtgga tcaaggactt gaatgtcaag ccaaagacta taaagacact ggaagagaat 2940
cttgggatca caatacaaga tataggcgtc ggcaaagatt ttatgtcaaa gacgcccaag 3000
gccatggcca ctaaggataa gattgataag tgggacctta ttaagctcaa aagcttctgt 3060
actgccaagg agaccacgat cagagttaat aggcagccca ctacatggga aaagattttc 3120
gccacttatt catcagataa ggggttgata agcagaatat ataacgagct gaagcagatc 3180
tacaagaaga aaacgaataa tcccatcaag aagtgggcaa aagatatgaa caggcatttt 3240
agcaaagagg atatctacgc cgcgaagaag catatgaaga agtgtagttc aagcttggcc 3300
attcgtgaga tgcagattaa gacgaccatg cgataccacc ttaccccagt gaggatggca 3360
attatcaaga aatctggcaa taatagatgt tggcggggct gtggcgagat tggcaccctg 3420
ctccattgct ggtgggattg caagctggtg cagccgcttt ggaaatcagt ctggcgcttt 3480
ctgagggacc tcgagcttga gattcccttc gatcccgcaa ttcccttgct cggaatctat 3540

```
cctaacgaat acaagagctg ttgttacaag gatacgtgta cccggatgtt catcgcggcc   3600

ttgtttacga tagctaagac gtggaatcag cctaagtgcc ccacaatgat cgattggatc   3660

aagaaaatgt ggcatattta taccatggag tattacgcag caattaagaa tgacgaattt   3720

atttccttcg ttgggacctg gatgaagctg gagactatta ttctgagcaa gctgtctcag   3780

gagcaaaaga caaagcatag aatcttctct ctcattggtg gtaactaa               3828
```

<210> SEQ ID NO 57
<211> LENGTH: 1290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Met Val Ile Gly Thr Tyr Ile Ser Ile Ile Thr Leu Asn Val Asn Gly
1               5                   10                  15

Leu Asn Ala Pro Thr Lys Arg His Arg Leu Ala Glu Trp Ile Gln Lys
            20                  25                  30

Gln Asp Pro Tyr Ile Cys Cys Leu Gln Glu Thr His Phe Arg Pro Arg
        35                  40                  45

Asp Thr Tyr Arg Leu Lys Val Arg Gly Trp Lys Lys Ile Phe His Ala
    50                  55                  60

Asn Gly Asn Gln Lys Lys Ala Gly Val Ala Ile Leu Ile Ser Asp Lys
65                  70                  75                  80

Ile Asp Phe Lys Ile Lys Asn Val Thr Arg Asp Lys Glu Gly His Tyr
                85                  90                  95

Ile Met Ile Gln Gly Ser Ile Gln Glu Glu Asp Ile Thr Ile Ile Asn
            100                 105                 110

Ile Tyr Ala Pro Asn Ile Gly Ala Pro Gln Tyr Ile Arg Gln Leu Leu
        115                 120                 125

Thr Ala Ile Lys Glu Glu Ile Asp Ser Asn Thr Ile Ile Val Gly Asp
    130                 135                 140

Phe Asn Thr Ser Leu Thr Pro Met Asp Arg Ser Ser Lys Met Lys Ile
145                 150                 155                 160

Asn Lys Glu Thr Glu Ala Leu Asn Asp Thr Ile Asp Gln Ile Asp Leu
                165                 170                 175

Ile Asp Ile Tyr Arg Thr Phe His Pro Lys Thr Ala Asp Tyr Thr Phe
            180                 185                 190

Phe Ser Ser Ala His Gly Thr Phe Ser Arg Ile Asp His Ile Leu Gly
        195                 200                 205

His Lys Ser Ser Leu Ser Lys Phe Lys Lys Ile Glu Ile Ile Ser Ser
    210                 215                 220

Ile Phe Ser Asp His Asn Ala Met Arg Leu Glu Met Asn His Arg Glu
225                 230                 235                 240

Lys Asn Val Lys Lys Thr Asn Thr Trp Arg Leu Asn Asn Thr Leu Leu
                245                 250                 255

Asn Asn Gln Glu Ile Thr Glu Glu Ile Lys Gln Glu Ile Lys Lys Tyr
            260                 265                 270

Leu Glu Thr Asn Asp Asn Glu Asn Thr Thr Thr Gln Asn Leu Trp Asp
        275                 280                 285

Ala Ala Lys Ala Val Leu Arg Gly Lys Phe Ile Ala Ile Gln Ala Tyr
    290                 295                 300

Leu Lys Lys Gln Glu Lys Ser Gln Val Asn Asn Leu Thr Leu His Leu
```

```
305                 310                 315                 320

Lys Lys Leu Glu Lys Glu Glu Gln Thr Lys Pro Lys Val Ser Arg Arg
                325                 330                 335

Lys Glu Ile Ile Lys Ile Arg Ala Glu Ile Asn Glu Ile Glu Thr Lys
            340                 345                 350

Lys Thr Ile Ala Lys Ile Asn Lys Thr Lys Ser Trp Phe Phe Glu Lys
        355                 360                 365

Ile Asn Lys Ile Asp Lys Pro Leu Ala Arg Leu Ile Lys Lys Lys Arg
    370                 375                 380

Glu Arg Thr Gln Ile Asn Lys Ile Arg Asn Glu Lys Gly Glu Val Thr
385                 390                 395                 400

Thr Asp Thr Ala Glu Ile Gln Asn Ile Leu Arg Asp Tyr Tyr Lys Gln
                405                 410                 415

Leu Tyr Ala Asn Lys Met Asp Asn Leu Glu Glu Met Asp Lys Phe Leu
            420                 425                 430

Glu Arg Tyr Asn Leu Pro Arg Leu Asn Gln Glu Glu Thr Glu Asn Ile
        435                 440                 445

Asn Arg Pro Ile Thr Ser Asn Glu Ile Glu Thr Val Ile Lys Asn Leu
    450                 455                 460

Pro Thr Asn Lys Ser Pro Gly Pro Asp Gly Phe Thr Gly Glu Phe Tyr
465                 470                 475                 480

Gln Thr Phe Arg Glu Glu Leu Thr Pro Ile Leu Leu Lys Leu Phe Gln
                485                 490                 495

Lys Ile Ala Glu Glu Gly Thr Leu Pro Asn Ser Phe Tyr Glu Ala Thr
            500                 505                 510

Ile Thr Leu Ile Pro Lys Pro Asp Lys Asp Thr Thr Lys Lys Glu Asn
        515                 520                 525

Tyr Arg Pro Ile Ser Leu Met Asn Ile Asp Ala Lys Ile Leu Asn Lys
    530                 535                 540

Ile Leu Ala Asn Arg Ile Gln Gln His Ile Lys Arg Ile Ile His His
545                 550                 555                 560

Asp Gln Val Gly Phe Ile Pro Gly Met Gln Gly Phe Phe Asn Ile Arg
                565                 570                 575

Lys Ser Ile Asn Val Ile His His Ile Asn Lys Leu Lys Lys Lys Asn
            580                 585                 590

His Met Ile Ile Ser Ile Asp Ala Glu Lys Ala Phe Asp Lys Ile Gln
        595                 600                 605

His Pro Phe Met Ile Lys Thr Leu Gln Lys Val Gly Ile Glu Gly Thr
    610                 615                 620

Tyr Leu Asn Ile Ile Lys Ala Ile Tyr Asp Lys Pro Thr Ala Asn Ile
625                 630                 635                 640

Ile Leu Asn Gly Glu Lys Leu Lys Ala Phe Pro Leu Arg Ser Gly Thr
                645                 650                 655

Arg Gln Gly Cys Pro Leu Ser Pro Leu Leu Phe Asn Ile Val Leu Glu
            660                 665                 670

Val Leu Ala Thr Ala Ile Arg Glu Glu Lys Glu Ile Lys Gly Ile Gln
        675                 680                 685

Ile Gly Lys Glu Glu Val Lys Leu Ser Leu Phe Ala Asp Asp Met Ile
    690                 695                 700

Leu Tyr Ile Glu Asn Pro Lys Thr Ala Thr Arg Lys Leu Leu Glu Leu
705                 710                 715                 720

Ile Asn Glu Tyr Gly Lys Val Ala Gly Tyr Lys Ile Asn Ala Gln Lys
                725                 730                 735
```

```
Ser Leu Ala Phe Leu Tyr Thr Asn Asp Glu Lys Ser Glu Arg Glu Ile
            740                 745                 750

Met Glu Thr Leu Pro Phe Thr Ile Ala Thr Lys Arg Ile Lys Tyr Leu
        755                 760                 765

Gly Ile Asn Leu Pro Lys Glu Thr Lys Asp Leu Tyr Ala Glu Asn Tyr
    770                 775                 780

Lys Thr Leu Met Lys Glu Ile Lys Asp Asp Thr Asn Arg Trp Arg Asp
785                 790                 795                 800

Ile Pro Cys Ser Trp Ile Gly Arg Ile Asn Ile Val Lys Met Ser Ile
                805                 810                 815

Leu Pro Lys Ala Ile Tyr Arg Phe Asn Ala Ile Pro Ile Lys Leu Pro
            820                 825                 830

Met Ala Phe Phe Thr Glu Leu Glu Gln Ile Ile Leu Lys Phe Val Trp
        835                 840                 845

Arg His Lys Arg Pro Arg Ile Ala Lys Ala Val Leu Arg Gln Lys Asn
    850                 855                 860

Gly Ala Gly Gly Ile Arg Leu Pro Asp Phe Arg Leu Tyr Tyr Lys Ala
865                 870                 875                 880

Thr Val Ile Lys Thr Ile Trp Tyr Trp His Lys Asn Arg Asn Ile Asp
                885                 890                 895

Gln Trp Asn Lys Ile Glu Ser Pro Glu Ile Asn Pro Arg Thr Tyr Gly
            900                 905                 910

Gln Leu Ile Tyr Asp Lys Gly Gly Lys Asp Ile Gln Trp Arg Lys Asp
        915                 920                 925

Ser Leu Phe Asn Lys Trp Cys Trp Glu Asn Trp Thr Ala Thr Cys Lys
    930                 935                 940

Arg Met Lys Leu Glu Tyr Ser Leu Thr Pro Tyr Thr Lys Ile Asn Ser
945                 950                 955                 960

Lys Trp Ile Arg Asp Leu Asn Ile Arg Leu Asp Thr Ile Lys Leu Leu
                965                 970                 975

Glu Glu Asn Ile Gly Arg Thr Leu Phe Asp Ile Asn His Ser Lys Ile
            980                 985                 990

Phe Phe Asp Pro Pro Pro Arg Val  Met Glu Ile Lys Thr  Lys Ile Asn
        995                 1000                1005

Lys Trp  Asp Leu Met Lys Leu  Gln Ser Phe Cys Thr  Ala Lys Glu
    1010                 1015                 1020

Thr Ile  Asn Lys Thr Lys Arg  Gln Pro Ser Glu Trp  Glu Lys Ile
    1025                 1030                 1035

Phe Ala  Asn Glu Ser Thr Asp  Lys Gly Leu Ile Ser  Lys Ile Tyr
    1040                 1045                 1050

Lys Gln  Leu Ile Gln Leu Asn  Ile Lys Glu Thr Asn  Thr Pro Ile
    1055                 1060                 1065

Gln Lys  Trp Ala Glu Asp Leu  Asn Arg His Phe Ser  Lys Glu Asp
    1070                 1075                 1080

Ile Gln  Thr Ala Thr Lys His  Met Lys Arg Cys Ser  Thr Ser Leu
    1085                 1090                 1095

Ile Ile  Arg Glu Met Gln Ile  Lys Thr Thr Met Arg  Tyr His Leu
    1100                 1105                 1110

Thr Pro  Val Arg Met Gly Ile  Ile Arg Lys Ser Thr  Asn Asn Lys
    1115                 1120                 1125

Cys Trp  Arg Gly Cys Gly Glu  Lys Gly Thr Leu Leu  His Cys Trp
    1130                 1135                 1140
```

```
Trp Glu  Cys Lys Leu Ile Gln  Pro Leu Trp Arg Thr  Ile Trp Arg
    1145                 1150                 1155

Phe Leu  Lys Lys Leu Lys Ile  Glu Leu Pro Tyr Asp  Pro Ala Ile
    1160                 1165                 1170

Pro Leu  Leu Gly Ile Tyr Pro  Glu Lys Thr Val Ile  Gln Lys Asp
    1175                 1180                 1185

Thr Cys  Thr Arg Met Phe Ile  Ala Ala Leu Phe Thr  Ile Ala Arg
    1190                 1195                 1200

Ser Trp  Lys Gln Pro Lys Cys  Pro Ser Thr Asp Glu  Trp Ile Lys
    1205                 1210                 1215

Lys Met  Trp Tyr Ile Tyr Thr  Met Glu Tyr Tyr Ser  Ala Ile Lys
    1220                 1225                 1230

Arg Asn  Glu Ile Gly Ser Phe  Leu Glu Thr Trp Met  Asp Leu Glu
    1235                 1240                 1245

Thr Val  Ile Gln Ser Glu Val  Ser Gln Lys Glu Lys  Asn Lys Tyr
    1250                 1255                 1260

Arg Ile  Leu Thr His Ile Cys  Gly Thr Trp Lys Asn  Gly Thr Asp
    1265                 1270                 1275

Glu Pro  Val Cys Arg Thr Glu  Ile Glu Thr Gln Met
    1280                 1285                 1290
```

```
<210> SEQ ID NO 58
<211> LENGTH: 3873
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

atggtcatag gaacatacat atcgataatt accttaaacg tgaatggatt aaatgcccca     60

accaaaagac atagactggc tgaatggata caaaaacaag acccatatat atgctgtcta    120

caagagaccc acttcagacc tagggacaca tacagactga aagtgagggg atggaaaaag    180

atattccatg caaatggaaa tcaaaagaaa gctggagtag ctatactcat atcagataaa    240

atagacttta aaataaagaa tgttacaaga gacaaggaag gacactacat aatgatccag    300

ggatcaatcc aagaagaaga tataacaatt ataaatatat atgcacccaa cataggagca    360

cctcaataca taaggcaact gctaacagct ataaaagagg aaatcgacag taacacaata    420

atagtggggg actttaacac ctcacttaca ccaatggaca gatcatccaa aatgaaaata    480

aataaggaaa cagaagcttt aaatgacaca atagaccaga tagatttaat tgatatatat    540

aggacattcc atccaaaaac agcagattac acgttcttct caagtgcgca cggaacattc    600

tccaggatag atcacatctt gggtcacaaa tcaagcctca gtaaatttaa gaaaattgaa    660

atcatatcaa gcatcttttc tgaccacaac gctatgagat tagaaatgaa tcacagggaa    720

aaaaacgtaa aaaagacaaa cacatggagg ctaaacaata cgttactaaa taaccaagag    780

atcactgaag aaatcaaaca ggaaataaaa aaatacctag agacaaatga caatgaaaac    840

acgacgaccc aaaacctatg ggatgcagca aaagcggttc taagagggaa gtttatagct    900

atacaagcct acctaaagaa acaagaaaaa tctcaagtaa acaatctaac cttacaccta    960

aagaaactag agaaagaaga acaaacaaaa cccaaagtta gcagaaggaa agaaatcata   1020

aagatcagag cagaaataaa tgaaatagaa acaaagaaaa caatagcaaa gatcaataaa   1080

actaaaagtt ggttctttga gaagataaac aaaattgata agccattagc cagactcatc   1140
```

```
aagaaaaaga gggagaggac tcaaatcaat aaaatcagaa atgaaaaagg agaagttaca   1200
acagacaccg cagaaataca aaacatccta agagactact acaagcaact ttatgccaat   1260
aaaatggaca acctggaaga aatggacaaa ttcttagaaa ggtataacct tccaagactg   1320
aaccaggaag aaacagaaaa tatcaacaga ccaatcacaa gtaatgaaat tgaaactgtg   1380
attaaaaatc ttccaacaaa caaaagtcca ggaccagatg gcttcacagg tgaattctat   1440
caaacattta gagaagagct aacacccatc cttctcaaac tcttccaaaa aattgcagaa   1500
gaaggaacac tcccaaactc attctatgag gccaccatca ccctgatacc aaaaccagac   1560
aaagacacta caaaaaaaga aaattacaga ccaatatcac tgatgaatat agatgcaaaa   1620
atcctcaaca aaatactagc aaacagaatc caacaacaca ttaaaaggat catacaccac   1680
gatcaagtgg gatttatccc agggatgcaa ggattcttca atatacgcaa atcaatcaat   1740
gtgatacacc atattaacaa attgaagaag aaaaaccata tgatcatctc aatagatgca   1800
gaaaaagctt ttgacaaaat tcaacaccca tttatgataa aaactctcca gaaagtgggc   1860
atagagggaa cctacctcaa cataataaag gccatatatg acaaacccac agcaaacatc   1920
attctcaatg gtgaaaaact gaaagcattt cctctaagat caggaacgag acaaggatgt   1980
ccactctcac cactattatt caacatagtt ctggaagtcc tagccacggc aatcagagaa   2040
gaaaaagaaa taaaaggaat acaaattgga aaagaagaag taaaactgtc actgtttgcg   2100
gatgacatga tactatacat agagaatcct aaaactgcca ccagaaaact gctagagcta   2160
attaatgaat atggtaaagt tgcaggttac aaaattaatg cacagaaatc tcttgcattc   2220
ctatacacta atgatgaaaa atctgaaaga gaaattatgg aaacactccc atttaccatt   2280
gcaacaaaaa gaataaaata cctaggaata aacctaccta aggagacaaa agacctgtat   2340
gcagaaaact ataagacact gatgaaagaa attaaagatg ataccaacag atggagagat   2400
ataccatgtt cttggattgg aagaatcaac attgtgaaaa tgagtatact acccaaagca   2460
atctacagat tcaatgcaat ccctatcaaa ttaccaatgg catttttttac ggagctagaa   2520
caaatcatct taaaatttgt atggagacac aaaagacccc gaatagccaa agcagtcttg   2580
aggcaaaaaa atggagctgg aggaatcaga ctccctgact tcagactata ctacaaagct   2640
acagtaatca agacaatatg gtactggcac aaaaacagaa acatagatca atggaacaag   2700
atagaaagcc cagagattaa cccacgcacc tatggtcaac taatctatga caaaggaggc   2760
aaagatatac aatggagaaa agacagtctc ttcaataagt ggtgctggga aaactggaca   2820
gccacatgta aaagaatgaa attagaatac tccctaacac catacacaaa aataaactca   2880
aaatggatta gagacctaaa tataagactg gacactataa aactcttaga ggaaaacata   2940
ggaagaacac tctttgacat aaatcacagc aagatctttt tcgatccacc tcctagagta   3000
atggaaataa aaacaaaaat aaacaagtgg gacctaatga aacttcaaag cttttgcaca   3060
gcaaaggaaa ccataaacaa gacgaaaaga caaccctcag aatgggagaa aatatttgca   3120
aatgaatcaa cggacaaagg attaatctcc aaaatatata aacagctcat tcagctcaat   3180
atcaaagaaa caaacacccc aatccaaaaa tgggcagaag acctaaatag acatttctcc   3240
aaagaagaca tacagacggc cacgaagcac atgaaaagat gctcaacatc actaattatt   3300
agagaaatgc aaatcaaaac tacaatgagg tatcacctca ctcctgttag aatgggcatc   3360
atcagaaaat ctacaaacaa caaatgctgg agagggtgtg gagaaaaggg aaccctcttg   3420
cactgttggt gggaatgtaa attgatacag ccactatgga gaacaatatg gaggttcctt   3480
aaaaaactaa aaatagaatt accatatgac ccagcaatcc cactactggg catataccca   3540
```

gagaaaaccg taattcaaaa agacacatgc acccgaatgt tcattgcagc actatttaca 3600
atagccaggt catggaagca acctaaatgc ccatcgacag acgaatggat aaagaagatg 3660
tggtacatat atacaatgga atattactca gccataaaaa ggaacgaaat tgggtcattt 3720
ttagagacgt ggatggatct agagactgtc atacagagtg aagtaagtca gaaagagaaa 3780
aacaaatatc gtatattaac gcatatatgt ggaacctgga aaaatggtac agatgaaccg 3840
gtctgcagga cagaaattga gacacaaatg taa 3873

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Pro Ala Ala Lys Arg Val Lys Leu Asp
1 5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Asp Tyr Lys Asp Asp Asp Asp Lys
1 5

<210> SEQ ID NO 61
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

Ala Ser Asn Phe Thr Gln Phe Val Leu Val Asp Asn Gly Gly Thr Gly
1 5 10 15

Asp Val Thr Val Ala Pro Ser Asn Phe Ala Asn Gly Ile Ala Glu Trp
20 25 30

Ile Ser Ser Asn Ser Arg Ser Gln Ala Tyr Lys Val Thr Cys Ser Val
35 40 45

Arg Gln Ser Ser Ala Gln Asn Arg Lys Tyr Thr Ile Lys Val Glu Val
50 55 60

Pro Lys Gly Ala Trp Arg Ser Tyr Leu Asn Met Glu Leu Thr Ile Pro
65 70 75 80

Ile Phe Ala Thr Asn Ser Asp Cys Glu Leu Ile Val Lys Ala Met Gln
85 90 95

Gly Leu Leu Lys Asp Gly Asn Pro Ile Pro Ser Ala Ile Ala Ala Asn
100 105 110

Ser Gly Ile Tyr Ala Met Ala Ser Asn Phe Thr Gln Phe Val Leu Val
115 120 125

Asp Asn Gly Gly Thr Gly Asp Val Thr Val Ala Pro Ser Asn Phe Ala
130 135 140

```
Asn Gly Ile Ala Glu Trp Ile Ser Ser Asn Ser Arg Ser Gln Ala Tyr
145                 150                 155                 160

Lys Val Thr Cys Ser Val Arg Gln Ser Ser Ala Gln Asn Arg Lys Tyr
                165                 170                 175

Thr Ile Lys Val Glu Val Pro Lys Gly Ala Trp Arg Ser Tyr Leu Asn
            180                 185                 190

Met Glu Leu Thr Ile Pro Ile Phe Ala Thr Asn Ser Asp Cys Glu Leu
        195                 200                 205

Ile Val Lys Ala Met Gln Gly Leu Leu Lys Asp Gly Asn Pro Ile Pro
    210                 215                 220

Ser Ala Ile Ala Ala Asn Ser Gly Ile Tyr
225                 230


<210> SEQ ID NO 62
<211> LENGTH: 9
<212> TYPE: PRT
<213> ORGANISM: Unknown
<220> FEATURE:
<223> OTHER INFORMATION: Description of Unknown: "LAGLIDADG" family
      motif peptide

<400> SEQUENCE: 62

Leu Ala Gly Leu Ile Asp Ala Asp Gly
1               5


<210> SEQ ID NO 63
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
            100                 105                 110

Thr Val Thr Val
        115


<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
```

```
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95

Thr Phe Gly Gly Gly Thr Lys Leu Glu Ile Lys
            100                 105


<210> SEQ ID NO 65
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Leu Tyr Cys Arg Arg Leu Lys Ile Gln Val Arg Lys Ala Ala Ile Thr
1               5                   10                  15

Ser Tyr Glu Lys Ser Asp Gly Val Tyr Thr Gly Leu Ser Thr Arg Asn
            20                  25                  30

Gln Glu Thr Tyr Glu Thr Leu Lys His Glu Lys Pro Pro
        35                  40                  45


<210> SEQ ID NO 66
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Tyr Glu Asp Met Arg Gly Ile Leu Tyr Ala Ala Pro Gln Leu Arg Ser
1               5                   10                  15

Ile Arg Gly Gln Pro Gly Pro Asn His Glu Glu Asp Ala Asp Ser Tyr
            20                  25                  30

Glu Asn Met
        35


<210> SEQ ID NO 67
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Lys Val Ala Lys Lys Pro Thr Asn Lys Ala Pro His Pro Lys Gln Glu
1               5                   10                  15

Pro Gln Glu Ile Asn Phe Pro Asp Asp Leu Pro Gly Ser Asn Thr Ala
            20                  25                  30

Ala Pro Val Gln Glu Thr Leu His Gly Cys Gln Pro Val Thr Gln Glu
        35                  40                  45
```

```
Asp Gly Lys Glu Ser Arg Ile Ser Val Gln Glu Arg Gln
    50                  55                  60


<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Tyr Ile Trp Ala Pro Leu Ala Gly Thr Cys Gly Val Leu Leu Leu
1               5                   10                  15

Ser Leu Val Ile Thr
            20


<210> SEQ ID NO 69
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp
    50                  55                  60


<210> SEQ ID NO 70
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
            100                 105                 110

Thr Val Thr Val Ser Ser Gly Gly Gly Gly Ser Gly Gly Gly Gly Ser
        115                 120                 125
```

```
Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Asp Ile Asn Ser Tyr Leu Ser Trp Phe Gln Gln Lys Pro Gly Lys Ala
                165                 170                 175

Pro Lys Thr Leu Ile Tyr Arg Ala Asn Arg Leu Glu Ser Gly Val Pro
            180                 185                 190

Ser Arg Phe Ser Gly Ser Gly Ser Gly Thr Asp Tyr Thr Leu Thr Ile
        195                 200                 205

Ser Ser Leu Gln Tyr Glu Asp Phe Gly Ile Tyr Tyr Cys Gln Gln Tyr
    210                 215                 220

Asp Glu Ser Pro Trp Thr Phe Gly Gly Gly Thr Lys Leu Glu Ile Lys
225                 230                 235                 240

Ser Gly Gly Gly Gly Ser Gly Ala Leu Ser Asn Ser Ile Met Tyr Phe
                245                 250                 255

Ser His Phe Val Pro Val Phe Leu Pro Ala Lys Pro Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Ile Tyr Ile Trp Ala Pro Leu Ala Gly Thr Cys
305                 310                 315                 320

Gly Val Leu Leu Leu Ser Leu Val Ile Thr Leu Tyr Cys Arg Arg Leu
                325                 330                 335

Lys Ile Gln Val Arg Lys Ala Ala Ile Thr Ser Tyr Glu Lys Ser Asp
            340                 345                 350

Gly Val Tyr Thr Gly Leu Ser Thr Arg Asn Gln Glu Thr Tyr Glu Thr
        355                 360                 365

Leu Lys His Glu Lys Pro Pro Gln Gly Ser Gly Ser Tyr Glu Asp Met
    370                 375                 380

Arg Gly Ile Leu Tyr Ala Ala Pro Gln Leu Arg Ser Ile Arg Gly Gln
385                 390                 395                 400

Pro Gly Pro Asn His Glu Glu Asp Ala Asp Ser Tyr Glu Asn Met
                405                 410                 415
```

<210> SEQ ID NO 71
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80
```

```
Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Asp Ile Asn Ser Tyr Leu Ser Trp Phe Gln Gln Lys Pro Gly Lys Ala
                165                 170                 175

Pro Lys Thr Leu Ile Tyr Arg Ala Asn Arg Leu Glu Ser Gly Val Pro
            180                 185                 190

Ser Arg Phe Ser Gly Ser Gly Ser Gly Thr Asp Tyr Thr Leu Thr Ile
        195                 200                 205

Ser Ser Leu Gln Tyr Glu Asp Phe Gly Ile Tyr Tyr Cys Gln Gln Tyr
    210                 215                 220

Asp Glu Ser Pro Trp Thr Phe Gly Gly Gly Thr Lys Leu Glu Ile Lys
225                 230                 235                 240

Ser Gly Gly Gly Gly Ser Gly Ala Leu Ser Asn Ser Ile Met Tyr Phe
                245                 250                 255

Ser His Phe Val Pro Val Phe Leu Pro Ala Lys Pro Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Ile Tyr Ile Trp Ala Pro Leu Ala Gly Thr Cys
305                 310                 315                 320

Gly Val Leu Leu Leu Ser Leu Val Ile Thr Leu Tyr Cys Arg Leu Lys
                325                 330                 335

Ile Gln Val Arg Lys Ala Ala Ile Thr Ser Tyr Glu Lys Ser Asp Gly
            340                 345                 350

Val Tyr Thr Gly Leu Ser Thr Arg Asn Gln Glu Thr Tyr Glu Thr Leu
        355                 360                 365

Lys His Glu Lys Pro Pro Gln Lys Lys Val Ala Lys Lys Pro Thr Asn
    370                 375                 380

Lys Ala Pro His Pro Lys Gln Glu Pro Gln Glu Ile Asn Phe Pro Asp
385                 390                 395                 400

Asp Leu Pro Gly Ser Asn Thr Ala Ala Pro Val Gln Glu Thr Leu His
                405                 410                 415

Gly Cys Gln Pro Val Thr Gln Glu Asp Gly Lys Glu Ser Arg Ile Ser
            420                 425                 430

Val Gln Glu Arg Gln
        435
```

```
<210> SEQ ID NO 72
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 72

```
Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Asp Ile Asn Ser Tyr Leu Ser Trp Phe Gln Gln Lys Pro Gly Lys Ala
                165                 170                 175

Pro Lys Thr Leu Ile Tyr Arg Ala Asn Arg Leu Glu Ser Gly Val Pro
            180                 185                 190

Ser Arg Phe Ser Gly Ser Gly Ser Gly Thr Asp Tyr Thr Leu Thr Ile
        195                 200                 205

Ser Ser Leu Gln Tyr Glu Asp Phe Gly Ile Tyr Tyr Cys Gln Gln Tyr
    210                 215                 220

Asp Glu Ser Pro Trp Thr Phe Gly Gly Gly Thr Lys Leu Glu Ile Lys
225                 230                 235                 240

Ser Gly Gly Gly Gly Ser Gly Ala Leu Ser Asn Ser Ile Met Tyr Phe
                245                 250                 255

Ser His Phe Val Pro Val Phe Leu Pro Ala Lys Pro Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Ile Tyr Ile Trp Ala Pro Leu Ala Gly Thr Cys
305                 310                 315                 320

Gly Val Leu Leu Leu Ser Leu Val Ile Thr Leu Tyr Cys Arg Arg Leu
                325                 330                 335

Lys Ile Gln Val Arg Lys Ala Ala Ile Thr Ser Tyr Glu Lys Ser Asp
            340                 345                 350

Gly Val Tyr Thr Gly Leu Ser Thr Arg Asn Gln Glu Thr Tyr Glu Thr
        355                 360                 365

Leu Lys His Glu Lys Pro Pro Gln Lys Lys Val Ala Lys Lys Pro Thr
    370                 375                 380

Asn Lys Ala Pro His Pro Lys Gln Glu Pro Gln Glu Ile Asn Phe Pro
385                 390                 395                 400

Asp Asp Leu Pro Gly Ser Asn Thr Ala Ala Pro Val Gln Glu Thr Leu
                405                 410                 415
```

```
His Gly Cys Gln Pro Val Thr Gln Glu Asp Gly Lys Glu Ser Arg Ile
            420                 425                 430

Ser Val Gln Glu Arg Gln
        435


<210> SEQ ID NO 73
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Arg Asn Lys Lys Ile Leu Lys Glu Asp Glu Leu Leu Ser Glu Thr
1               5                   10                  15

Gln Gln Ala Ala Phe His Gln Ile Ala Met Glu Pro Phe Glu Ile Asn
            20                  25                  30

Val Pro Lys Pro Lys Arg Arg Asn Gly Val Asn Phe
        35                  40


<210> SEQ ID NO 74
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Glu Gln Trp Asp His Phe His Asn Gln Gln Glu Asp Thr Asp Ser
1               5                   10                  15

Cys Ser Glu Ser Val Lys Phe Asp Ala Arg Ser Met Thr Ala Leu Leu
            20                  25                  30

Pro Pro Asn Pro Lys Asn Ser Pro Ser Leu Gln Glu Lys Leu Lys Ser
        35                  40                  45

Phe Lys
    50


<210> SEQ ID NO 75
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Ala Ala Pro Ala Ala Ala Pro Ala Lys Gln Glu Ala Ala Ala Pro
1               5                   10                  15

Ala Pro Ala Ala Lys Ala Glu Ala Pro Ala Ala Ala Pro Ala Ala Lys
            20                  25                  30

Ala


<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
```

<222> LOCATION: (1)..(20)
<223> OTHER INFORMATION: This sequence may encompass 1-4 “Gly Gly Gly Gly Ser” repeating units
<220> FEATURE:
<223> OTHER INFORMATION: See specification as filed for detailed description of substitutions and preferred embodiments

<400> SEQUENCE: 76

Gly Gly Gly Gly Ser Gly Gly Gly Gly Ser Gly Gly Gly Gly Ser Gly
1 5 10 15

Gly Gly Gly Ser
20

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Gly Gly Gly Gly Gly Gly
1 5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Gly Gly Gly Gly Gly Gly Gly Gly
1 5

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(20)
<223> OTHER INFORMATION: This sequence may encompass 1-4 “Glu Ala Ala Ala Lys” repeating units
<220> FEATURE:
<223> OTHER INFORMATION: See specification as filed for detailed description of substitutions and preferred embodiments

<400> SEQUENCE: 79

Glu Ala Ala Ala Lys Glu Ala Ala Ala Lys Glu Ala Ala Ala Lys Glu
1 5 10 15

Ala Ala Ala Lys
20

<210> SEQ ID NO 80
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 80

```
cuaggaaucu ggaaguaccg aggaaacucg guacuuccug uguccuag                48


<210> SEQ ID NO 81
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81

auauggaaga uccuggggaa cugggaucuu ccuaagu                            37


<210> SEQ ID NO 82
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(17)
<223> OTHER INFORMATION: Dihydrouridine
<220> FEATURE:
<221> NAME/KEY: modified_base
<222> LOCATION: (37)..(37)
<223> OTHER INFORMATION: a, c, t, g or u
<220> FEATURE:
<221> NAME/KEY: modified_base
<222> LOCATION: (39)..(39)
<223> OTHER INFORMATION: Pseudouridine
<220> FEATURE:
<221> NAME/KEY: modified_base
<222> LOCATION: (55)..(55)
<223> OTHER INFORMATION: Pseudouridine

<400> SEQUENCE: 82

gcgcauuuag cucagnnggg agagcgccag acugaananc uggagcuccu gugtncgauc     60

cacagaauuc gcacca                                                   76


<210> SEQ ID NO 83
<211> LENGTH: 203
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (66)..(185)
<223> OTHER INFORMATION: a, c, u or g
<220> FEATURE:
<223> OTHER INFORMATION: See specification as filed for detailed
      description of substitutions and preferred embodiments

<400> SEQUENCE: 83

gcuggguuuu uccuuguucg caccggacac cuccagugac cagacggcaa gguuuuuauc     60

ccagunnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnaaaaa aaaaaaaaaa aaa                                          203


<210> SEQ ID NO 84
<211> LENGTH: 93
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 84

gaagguuuuu cuuuuccuga gaaaacaaca cguauuguuu ucucagguuu ugcuuuuugg     60

ccuuuuucua gcuuaaaaaa aaaaaaagca aaa                                  93


<210> SEQ ID NO 85
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85

ggaagguuuu ucuuuuccug aggcgaaagu cucagguuuu gcuuuuuggc cuuucuuaaa     60

aaaaaaaaaa gcaaaa                                                     76
```